US009512491B2

(12) United States Patent
Kaneko et al.

(10) Patent No.: US 9,512,491 B2
(45) Date of Patent: Dec. 6, 2016

(54) DETECTION OF DIGESTIVE ORGAN CANCER, GASTRIC CANCER, COLORECTAL CANCER, PANCREATIC CANCER, AND BILIARY TRACT CANCER BY GENE EXPRESSION PROFILING

(71) Applicant: NATIONAL UNIVERSITY CORPORATION KANAZAWA UNIVERSITY, Ishikawa (JP)

(72) Inventors: Shuichi Kaneko, Ishikawa (JP); Masao Honda, Ishikawa (JP); Yoshio Sakai, Ishikawa (JP); Taro Yamashita, Ishikawa (JP)

(73) Assignee: KUBIX INC., Nonoichi-Shi, Ishikawa (JP)

( * ) Notice: Subject to any disclaimer, the term of this patent is extended or adjusted under 35 U.S.C. 154(b) by 46 days.

(21) Appl. No.: 14/551,674

(22) Filed: Nov. 24, 2014

(65) Prior Publication Data
US 2015/0133335 A1    May 14, 2015

Related U.S. Application Data

(62) Division of application No. 13/391,858, filed as application No. PCT/JP2010/063122 on Aug. 3, 2010, now Pat. No. 8,932,990.

(30) Foreign Application Priority Data

Aug. 24, 2009    (JP) .................................. 2009-193702

(51) Int. Cl.
C07H 21/04    (2006.01)
C12Q 1/68     (2006.01)

(52) U.S. Cl.
CPC ....... *C12Q 1/6886* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 5,474,796 A | 12/1995 | Brennan |
| 2005/0014165 A1 | 1/2005 | Lee et al. |
| 2005/0181516 A1 | 8/2005 | Dressman et al. |
| 2005/0260572 A1 | 11/2005 | Kato et al. |
| 2006/0269921 A1 | 11/2006 | Segara et al. |
| 2007/0065844 A1 | 3/2007 | Golub et al. |
| 2010/0086537 A1 | 4/2010 | Sooknanan et al. |
| 2012/0036101 A1 | 2/2012 | Rosenberg et al. |
| 2012/0040849 A1 | 2/2012 | Valles et al. |

FOREIGN PATENT DOCUMENTS

| JP | 2005-523727 A | 8/2005 |
| JP | 2005-304497 A | 11/2005 |
| JP | 2007-074916 A | 3/2007 |
| JP | 2007-236253 A | 9/2007 |
| WO | 2004/091548 A2 | 10/2004 |
| WO | 2007/081740 A2 | 7/2007 |
| WO | 2007/147265 A1 | 12/2007 |
| WO | 2008/036765 A2 | 3/2008 |
| WO | 2008/147205 A1 | 12/2008 |
| WO | 2009/002175 A1 | 12/2008 |
| WO | 2009/032915 A2 | 3/2009 |
| WO | 2009/126271 A1 | 10/2009 |

OTHER PUBLICATIONS

Shimoji, Takashi, et al., "Genetic diagnosis of digestive tract cancer", separate volume, Igaku no Ayumi, 2006, partial English translation of the key points on p. 1.
Sasaki, Yasushi, et al., "Gene Diagnosis for Gastrointestinal Tract: Tailor-made Medicine Based on Individual Gene/Molecule, Progress of Tumor Marker", Mebio, 2002, partial English translation of the point section on p. 82.
Toyota et al., Epigenetic Silencing of MicroRNA-34b/c and B-Cell Translocation Gene 4 is Associated with CpG Island Methylation in Colorectal Cancer, Cancer Research, 2008, vol. 68, No. 11, pp. 4123-3132.
Raslova et al., Interrelation between polyploidization and megakaryocyte differentiation: a gene profiling approach, Blood, 2007, vol. 109, No. 8, pp. 3225-3234.
Office Action for corresponding U.S. Appl. No. 14/551,651 issued Sep. 11, 2015.
Office Action for corresponding U.S. Appl. No. 14/551,651 issued Mar. 7, 2016.
"Whole Human Genome Microarray Kit 4×44k", Agilent Technologies, 2007, Version 2.0, pp. 1-13.

(Continued)

*Primary Examiner* — Jeanine A Goldberg
(74) *Attorney, Agent, or Firm* — Lucas & Mercanti LLP

(57) ABSTRACT

The present invention provides a method and a reagent for detecting a digestive organ cancer, gastric cancer, colorectal cancer, pancreatic cancer, or biliary tract cancer patient by analyzing genes with expression levels (in peripheral blood) that vary in association with digestive organ cancer, gastric cancer, colorectal cancer, pancreatic cancer, or biliary tract cancer cases, compared with normal healthy subjects. Specifically, the method for detecting a digestive organ cancer, gastric cancer, colorectal cancer, pancreatic cancer, or biliary tract cancer patient based on expression profiles comprises obtaining the expression profile of at least one gene selected from the group consisting of probes corresponding to genes with expression levels (in peripheral blood) that vary in digestive organ cancer, gastric cancer, colorectal cancer, pancreatic cancer, and biliary tract cancer cases, compared with normal healthy subjects. The reagent for detecting digestive organ cancer, gastric cancer, colorectal cancer, pancreatic cancer, or biliary tract cancer contains nucleotides or partial sequences thereof consisting of the nucleotide sequence of at least one gene selected from the group consisting of probes with expression levels that vary in digestive organ cancer, gastric cancer, colorectal cancer, pancreatic cancer, or biliary tract cancer, or nucleotides containing sequences complementary thereto.

5 Claims, 220 Drawing Sheets

(56) References Cited

OTHER PUBLICATIONS

"Safety Data Sheet Whole Human Genome Kit-4×44k", Agilent Technologies, 2013, pp. 1-8.
"Specification for Whole Human Genome Microarray Kit 4×44k", Agilent Technologies, 1 page.
Extended European Search Report dated Jul. 1, 2015, which is issued by European Patent Office for a related European Application No. EP15157502.4 (5 pgs.).
Extended European Search Report dated Jul. 3, 2015, which is issued by European Patent Office for a related European Application No. EP15157500.8 (5 pgs.).
Extended European Search Report dated Jul. 1, 2015, which is issued by European Patent Office for a related European Application No. EP15157499.3 (5 pgs.).
Antonio Jimeno, et al., "Dual mitogen-activated protein kinase and epidermal growth factor receptor inhibition in biliary and pancreatic cancer," Molecular Cancer Therapeutics, vol. 6, No. 3, Mar. 1, 2007, pp. 1079-1088.
George Miller, et al., "Genome wide analysis and clinical correlation of chromosomal and transcriptional mutations in cancers of the biliary tract," Journal of Experimental & Clinical Cancer Research, vol. 28, No. 62, Jan. 1, 2009, (13 pgs.).
Jun, Lu, et al: "Micro RNA expression profiles classify human cancers", Nature: International Weekly Journal of Science, Nature Publishing Group, United Kingdom, vol. 435. No. 7043, Jun. 9, 2005. pp. 834-838.
Marshall, et al., "A blood-based biomarker panel for stratifying current risk for colorectal cancer", International Journal of Cancer, 126, Mar. 1, 2010, pp. 1177-1186.
Malati T., "Tumour markers: An overview", Indian Journal of Clinical Biochemistry, 2007, 22(2), pp. 17-31.
Honda, Masao, et al., "Shokaki Gan to Idenshi Ijo", Biotherapy, 2007, vol. 21, pp. 153 to 159.
Shimoji, Takashi, et al., "Shokaki Gan no Idenshi Shindan", separate volume, Igaku no Ayunni, 2006, 1st edition, 1st print, pp. 252 to 255.
Hansel, D.E., et al., "Identification of novel cellular targets in biliary tract cancers using global gene expression technology", Am. J. Pathol., 2003, vol. 163, pp. 217-229.
Karamitopoulou, E., et al., "Clinical significance of cell cycle- and apoptosisrelated markers in biliary tract cancer: a tissue microarray-based approach revealing a distinctive immunophenotype for intrahepatic and extrahepatic cholangiocarcinomas", Am. J. Clin. Pathol., 2008, vol. 130, pp. 780-786.
Sasaki, Yasushi, et al., "Shokaki Shokakan no Idenshi Shindanho Idenshi Bunshi no Kosei ni Motozuita Tailor Made Iryo Shuyo Marker no Shinpo", Mebio, 2002, vol. 19, pp. 77 to 82.
Yokozaki, Hiroshi, "Shokudo Gan, I Gan no Akuseido o Kitei suru Bunshi Joho no Haaku to sore o Oyo shita Seiken Shindanho no Kakuritsu", Ministry of Health, Labour and Welfare Gan Kenkyu Joseikin ni yoru Kenkyu Hokokushu, Heisei 17 Nendo (2005), pp. 607 to 610.
Yasui, Wataru, "I Gan no Bunshi Byorigakuteki Shindan", Japanese Journal of Cancer and Chemotherapy, 2005, vol. 32, pp. 427 to 431.
Kawaguchi, K., et al., "Differential gene alteration among hepatoma cell lines demonstrated by cDNA microarray-based comparative genomic hybridization", Biochem. Biophys. Res. Commun., 2005, vol. 329, pp. 370 to 380.

Fig. 1-1

| No | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P100292 | ZNF598 | TGAATCTTTTTATGAGAGAAGGTGAATCTGGGATCTGAAATTGCCTCTGACCTTTTATAA | SEQ ID NO: 1 | Homo sapiens mRNA for FLJ00086 protein, partial cds. [AK024487] |
| 2 | A_23_P100664 | ZBTB4 | GTATTTGAGCTGGGAATTTGAATATTGTGAGTTTCAGATGTTGGAATTTGGATTTTG | SEQ ID NO: 2 | Homo sapiens zinc finger and BTB domain containing 4 (ZBTB4), mRNA [NM_020899] |
| 3 | A_23_P100779 | UBTF | CAGGACCGGTGCAGCATATAAAGAGTACATCTCGAATAAACGTAAGAGGATGACCAAGGTG | SEQ ID NO: 3 | Homo sapiens upstream binding transcription factor, RNA polymerase I (UBTF), transcript variant 1, mRNA [NM_014233] |
| 4 | A_23_P101308 | ENST00000221462 | TAGTTCCCTTTTTCCGGTCGGTCCTGCGATGAGCTGAGGCAGAGCCATGAGAATCTGGTC | SEQ ID NO: 4 | Homo sapiens hypothetical protein LOC284352, mRNA (cDNA clone IMAGE:4779950), with apparent retained intron. [BC039061] |
| 5 | A_23_P101332 | FLJ12949 | ACAGGTCTGCACCCAGAAGTACTATCTGCTGCAGAGATGTCTCGATCTGTGGCAGGGA | SEQ ID NO: 5 | Homo sapiens hypothetical protein FLJ12949 (FLJ12949), transcript variant 1, mRNA [NM_023009] |
| 6 | A_23_P101551 | BCAT2 | TCCGTACGAATGACTCACGTGAAGTGCAATACGAAGAAATAAAAGGCCAGCGGGCGGGTGCTG | SEQ ID NO: 6 | Homo sapiens branched chain aminotransferase 2, mitochondrial (BCAT2), mRNA [NM_001190] |
| 7 | A_23_P102404 | CCT7 | GGGGTACGATGGTATGGAGAGTAGAACATCAACAAGGAGGACATTGCTGACAACTTTGAGCTT | SEQ ID NO: 7 | Homo sapiens chaperonin containing TCP1, subunit 7 (eta) (CCT7), transcript variant 1, mRNA [NM_006429] |
| 8 | A_23_P102508 | SLC5A6 | TTTTCTCTGCTTGCCAATCTGTTTTTAAAGGATCAGAGGCTCGTAGGAAGCAGGATCA | SEQ ID NO: 8 | Homo sapiens solute carrier family 5 (sodium-dependent vitamin transporter), member 6 (SLC5A6), mRNA [NM_021095] |
| 9 | A_23_P102973 | DGCR14 | TGGGTCATAGACGCTTCACAGAGCCTGAGGGCAGCTGCACACCCAGCAGAGGACTCCA | SEQ ID NO: 9 | Homo sapiens DiGeorge syndrome critical region gene 14 (DGCR14), mRNA [NM_022719] |
| 10 | A_23_P102994 | PIK4CA | AAGATGGAGGCCACACGGCTTGAAGTGGTTCATGGAGATGTGTGTCCGAGGCTAGGTGGCT | SEQ ID NO: 10 | Homo sapiens phosphatidylinositol 4-kinase, catalytic, alpha polypeptide (PIK4CA), transcript variant 1, mRNA [NM_002650] |
| 11 | A_23_P103104 | MFNG | CCAATTGTCATGATGCTTTTTGCTCATTGGAGCTTTCTTGCTGTTAGGGGCTACCAT | SEQ ID NO: 11 | Homo sapiens MFNG O-fucosylpeptide 3-beta-N-acetylglucosaminyltransferase (MFNG), mRNA [NM_002405] |
| 12 | A_23_P103942 | DNAJC11 | CTGTAACATTCATCTGCATTTTTAAAAAAGGTTTCTGTGACGGCCCCAACGGGCCGGAGCC | SEQ ID NO: 12 | Homo sapiens DnaJ (Hsp40) homolog, subfamily C, member 11 (DNAJC11), mRNA [NM_018198] |
| 13 | A_23_P103868 | AKR7A3 | ACAGGCTGTGGGCGCGGCTTCTTCTTTGGGAATACCTGGGCACAGAGATGTAGAGGAATCGCTACTG | SEQ ID NO: 13 | Homo sapiens aldo-keto reductase family 7, member A3 (aflatoxin aldehyde reductase) (AKR7A3), mRNA [NM_012067] |
| 14 | A_23_P104641 | C11orf2 | ACTGCCACTTCTGCAGGTCTACCTGTGCGGGTTTTGTGGGCGACGAAGAACTGCGCACT | SEQ ID NO: 14 | Homo sapiens chromosome 11 open reading frame 2 (C11orf2), mRNA [NM_013265] |
| 15 | A_23_P106532 | CHST14 | AAGGGCTTTCAGGTTGTGAGTGTGGCTGGATATCTGGGTGGCATTTTCTGATGGATTT | SEQ ID NO: 15 | Homo sapiens dermatan 4 sulfotransferase 1 (D4ST1), mRNA [NM_130468] |
| 16 | A_23_P106575 | GOT2 | CTATTGCAGATTTTCATCCACATTCTAGTGCTTGATTGACCATGAACTCCAATCGGAG | SEQ ID NO: 16 | Homo sapiens glutamic-oxaloacetic transaminase 2, mitochondrial (aspartate aminotransferase 2) (GOT2), nuclear gene encoding mitochondrial protein, mRNA [NM_002080] |

Fig. 1-2

| No. | Probe ID No. | Symbols of genes | Sequence | SEQ ID NO: | Descriptions of genes (letters and numbers within [ ] indicates GenBank accession No.) |
|---|---|---|---|---|---|
| 17 | A_23_P106887 | FUS | TATTGACTGGTTTGATGGTAAAGAATTCTCGGGAAATCGTATCAAGGTGTCATTTGGTAC | SEQ ID NO: 17 | Homo sapiens fusion (involved in t(12;16) in malignant liposarcoma) (FUS), mRNA [NM_004960] |
| 18 | A_23_P106973 | SEPT9 | AGGGTCTGTTCCTCAATGGCCGTTTTGGTACGGTGCCTCCGAGAAATTTGTCTTTTGTAT | SEQ ID NO: 18 | Homo sapiens septin 9 (SEPT9), mRNA [NM_006640] |
| 19 | A_23_P1072 | ATP1A1 | TGCCCTGGAATGGGTGTTGGTCTTAGGATGTATCCCCTCAAACCTACGTGGTGGTTCTGT | SEQ ID NO: 19 | Homo sapiens ATPase, Na+/K+ transporting, alpha 1 polypeptide (ATP1A1), transcript variant 1, mRNA [NM_000701] |
| 20 | A_23_P108376 | THADA | CTGTGTGGAGGAGCATGGCATCAGGTGGAAGAAGTAACCTGTTTGAAAAAGCAGAAGTCAA | SEQ ID NO: 20 | Homo sapiens thyroid adenoma associated (THADA), transcript variant 1, mRNA [NM_022065] |
| 21 | A_23_P109901 | KIAA0406 | TGATGGAACGGTGCATCCACTTGTTGTCGAGATAAAAATCTGCAAATCCGGCTGAAGGTCT | SEQ ID NO: 21 | Homo sapiens KIAA0406 (KIAA0406), mRNA [NM_014657] |
| 22 | A_23_P110062 | EIF2B5 | CATTGAGGACTTCTTCCTAGAGCATGAAAGTCTTGGTATTCCATGGCCAAGGTACTGAT | SEQ ID NO: 22 | Homo sapiens eukaryotic translation initiation factor 2B, subunit 5 epsilon, 82kDa (EIF2B5), mRNA [NM_003907] |
| 23 | A_23_P111745 | ZMIZ2 | TGGGTGAGCGTCAGATTCAGCTCTGTGTAAAGATTCTCTAGGGGCTGCCCTCCCAAGT | SEQ ID NO: 23 | Homo sapiens zinc finger, MIZ-type containing 2 (ZMIZ2), transcript variant 1, mRNA [NM_031449] |
| 24 | A_23_P112406 | GTF3C5 | AGCTGACGGTAGGCGTGGCTGTGACATGCGTGTGGTGGTGCGTGTGGTCCTGAGGGGTT | SEQ ID NO: 24 | Homo sapiens general transcription factor IIIC, polypeptide 5, 63kDa (GTF3C5), mRNA [NM_012087] |
| 25 | A_23_P113026 | PARN | GAGTGTGGGCTGTGAAATCTGCAAAAAGAGGCTGACATTCCAGCTGCTGTGATGATGAATT | SEQ ID NO: 25 | Homo sapiens poly(A)-specific ribonuclease (deadenylation nuclease) (PARN), mRNA [NM_002582] |
| 26 | A_23_P113184 | FTO | TTGGGGCATGACCGAGCCTATGGTTGGCATACTCCCTCTTTTCTCGTTTTTTCATTA | SEQ ID NO: 26 | Homo sapiens fatso (FTO), mRNA [NM_001080432] |
| 27 | A_23_P116840 | C12orf44 | CTGGGGCAGATGTCCTTGGAGTTCTACCAGAAGAAGAAGTCTCGCTGGCCATTCTCAGAC | SEQ ID NO: 27 | Homo sapiens chromosome 12 open reading frame 44 (C12orf44), mRNA [NM_021934] |
| 28 | A_23_P119095 | PPP1R13L | AGTCACTGCTGACCACCATCTCTCCCAGCAGTCTTGGGGTCTGGGTGGGAAACATTGGTCT | SEQ ID NO: 28 | Homo sapiens protein phosphatase 1, regulatory (inhibitor) subunit 13 like (PPP1R13L), mRNA [NM_006663] |
| 29 | A_23_P119907 | ANKZF1 | GACAAATCAACACGGTAATGAGTTCCGAAAGGTTCATGGAGAAGAATCCAGATGCCTACGAT | SEQ ID NO: 29 | Homo sapiens ankyrin repeat and zinc finger domain containing 1 (ANKZF1), transcript variant 1, mRNA [NM_018089] |
| 30 | A_23_P120146 | TGFBRAP1 | AAATCCCTTTTGGAGCGTGTGTTTGTTAGATACCCAAATGGTGGTCTTGTGGAGAGCGA | SEQ ID NO: 30 | Homo sapiens transforming growth factor, beta receptor associated protein 1 (TGFBRAP1), mRNA [NM_004257] |
| 31 | A_23_P120915 | ANKRD54 | ACCTTGTATGGCCAAAAGGGGCTTTGCAGATGTAATGAAGTTAAGGATCTTGGGCAGGAA | SEQ ID NO: 31 | Homo sapiens ankyrin repeat domain 54 (ANKRD54), mRNA [NM_138797] |
| 32 | A_23_P120921 | ANKRD54 | TTTTCCTCCCAGTCATTGAAACACCCAAAACTATTATACCGGAGGGTGTAATAGTTTTGCT | SEQ ID NO: 32 | Homo sapiens ankyrin repeat domain 54 (ANKRD54), mRNA [NM_138797] |
| 33 | A_23_P120942 | XRCC6 | TTTATGTTTTTGAGGGTTTCTGTTTGCCATGGTGATGGTGTAGCCCTCCCACTTTGCTGTT | SEQ ID NO: 33 | Homo sapiens X-ray repair complementing defective repair in Chinese hamster cells 6 (Ku autoantigen, 70kDa) (XRCC6), mRNA [NM_001469] |

Fig. 1-3

| No. | Probe ID No. | Symbols of genes | Sequence | SEQ ID NO: | Descriptions of genes (letters and numbers within [ ] indicates GenBank accession No.) |
|---|---|---|---|---|---|
| 34 | A_23_P120947 | XRCC6 | GCAAGATGAAGGCTATCGTTGAGAAGGCTTGGCTTCAGATACAGAAGTGACAGGTTTGAGA | SEQ ID NO: 34 | Homo sapiens X-ray repair complementing defective repair in Chinese hamster cells 6 (Ku autoantigen, 70kDa) (XRCC6), mRNA [NM_001469] |
| 35 | A_23_P121499 | WFS1 | GTGACCTTTCTGAGTCGACATGGGTGTGGCAGGGTAGACTAGGAGGTTCCGGTGTGTGGAA | SEQ ID NO: 35 | Homo sapiens Wolfram syndrome 1 (wolframin) (WFS1), mRNA [NM_006005] |
| 36 | A_23_P122116 | DDX41 | GGGGCCTCGGGAAACACAGGCATGGCCAGTACCTTCATCAACAAAGCGTGTGAGAGTCA | SEQ ID NO: 36 | Homo sapiens DEAD (Asp-Glu-Ala-Asp) box polypeptide 41 (DDX41), mRNA [NM_016222] |
| 37 | A_23_P122579 | DAXX | CAGAGAGCGGGTTGACCACGTGTCTAGAGATGAGCAGGGATGGTCTCTTGTACTTCCT | SEQ ID NO: 37 | Homo sapiens death-associated protein 6 (DAXX), mRNA [NM_001350] |
| 38 | A_23_P122650 | LOC649233 | CCACCGCGTGGTGGAAAGATGGTGAGGACTTCAATCTTGGTGATGCCCTGGACAGCAGTAA | SEQ ID NO: 38 | PREDICTED: Homo sapiens similar to Keratin, type I cytoskeletal 18 (Cytokeratin-18) (CK-18) (Keratin-18) (K18) (LOC649233), mRNA [XR_018843] |
| 39 | A_23_P122876 | TAF6 | TTGCTTCGTTCGATGTCACTTTCTTTTAGATATTGTAGAGGGAGTTTCTCAGAATAAAAG | SEQ ID NO: 39 | Homo sapiens TAF6 RNA polymerase II, TATA box binding protein (TBP)-associated factor, 80kDa (TAF6), transcript variant 1, mRNA [NM_005641] |
| 40 | A_23_P124044 | DEAF1 | GGAGGTAAAGAAGAAGTTGCTGGACAAGTCATTAAGACAGAGTTAAGCGAATGGTGCCCTGG | SEQ ID NO: 40 | Homo sapiens deformed epidermal autoregulatory factor 1 (Drosophila) (DEAF1), mRNA [NM_021008] |
| 41 | A_23_P124522 | DCAKD | TAGCCGAAACTTGCGTGGGTTTTCCTACTAGAGACTGTCAAGGCCTCTAGGGACAGGGACAGT | SEQ ID NO: 41 | Homo sapiens dephospho-CoA kinase domain containing (DCAKD), mRNA [NM_024819] |
| 42 | A_23_P126669 | USP21 | ACAAAGCCGGAAGTCCTGTATAGCAGGTGTATGGCCTTTGCAACCACTCAGGCAGGGTCC | SEQ ID NO: 42 | Homo sapiens ubiquitin specific peptidase 21 (USP21), transcript variant 1, mRNA [NM_012475] |
| 43 | A_23_P126790 | SARS | CAGGACTGCAAGAACTGATCGCCTTTGTGAAGCCTGCGGCGGATTGAGCAGGAGCCATCAA | SEQ ID NO: 43 | Homo sapiens seryl-tRNA synthetase (SARS), mRNA [NM_006513] |
| 44 | A_23_P127079 | PPRC1 | ACCGGGAAGAGTTTGAGCCAGCACCTGTAAAGAGCAAATTTGATTCTCTTGACTTTGACA | SEQ ID NO: 44 | Homo sapiens peroxisome proliferator-activated receptor gamma, coactivator-related 1 (PPRC1), mRNA [NM_015062] |
| 45 | A_23_P127394 | CRY2 | AGATGGTTGCAGCAAAATGCACTTTATAGAGATTTTCTATTGGTGGGAAGGTGTGTTC | SEQ ID NO: 45 | Homo sapiens cryptochrome 2 (photolyase-like) (CRY2), mRNA [NM_021117] |
| 46 | A_23_P127525 | ETS1 | CCTGGTGAGACTTCCAAGGACAGACCCGTTGGTTGGAGTCTGAAATTTGAATTGTTATT | SEQ ID NO: 46 | Homo sapiens v-ets erythroblastosis virus E26 oncogene homolog 1 (avian) (ETS1), mRNA [NM_005238] |
| 47 | A_23_P127793 | EML3 | TGCAAGCAGGTGAAGAATGGCTATGAGAGGCCGAGACCGGGGAAATGGGCTACCTAGACCTGT | SEQ ID NO: 47 | Homo sapiens echinoderm microtubule associated protein like 3 (EML3), mRNA [NM_153265] |
| 48 | A_23_P129678 | SETD1A | GGTGACGAGATGGTCATCGAATACGTGGGTCAGAACATCGGTCAGATGGTGGCGGACATG | SEQ ID NO: 48 | Homo sapiens SET domain containing 1A (SETD1A), mRNA [NM_014712] |
| 49 | A_23_P130149 | ENO3 | CTCGGAGGGTCTGGCCAAATAGAAGCGAAGTCATGAGGATCGAGGAGGCTCTTGGGAGACAA | SEQ ID NO: 49 | Homo sapiens enolase 3 (beta, muscle) (ENO3), transcript variant 1, mRNA [NM_001976] |
| 50 | A_23_P13033 | RBM4 | TTACGGCATGAGAGGTGAGTTGTCCCAAGGCTTCCCAGGCCCAGATGGAATTCTCTACGA | SEQ ID NO: 50 | Homo sapiens RNA binding motif protein 4 (RBM4), mRNA [NM_002896] |
| 51 | A_23_P130455 | MZF1 | GTGTGGCAAGGCTTGGGCCAGGGCCCAAGCGTCACGCAGGCATGTGCCCACGGCACCGACG | SEQ ID NO: 51 | Homo sapiens myeloid zinc finger 1 (MZF1), transcript variant 2, mRNA [NM_198055] |

Fig. 1-4

| No. | Probe ID No. | Symbols of genes | Sequence | SEQ ID NO: | Descriptions of genes (letters and numbers within [ ] indicates GenBank accession No.) |
|---|---|---|---|---|---|
| 52 | A_23_P130753 | DBP | GACGAGACCTTTGACCCTCGAAAGAGAATGGCTTCTCAGAAGAGGAACTTAAGCCGCAAGCA | SEQ ID NO: 52 | Homo sapiens D site of albumin promoter (albumin D-box) binding protein (DBP), mRNA [NM_001352] |
| 53 | A_23_P131826 | ASCC3L1 | CTTTTGGGTAAAGGAGAAGTTGAGCCTGAATTAGGAATGTGTACATTGTAGGAATCCTGGT | SEQ ID NO: 53 | Homo sapiens activating signal cointegrator 1 complex subunit 3-like 1 (ASCC3L1), mRNA [NM_014014] |
| 54 | A_23_P13338 | INTS5 | TAAAGCCACCCAAGTTTGTCCAGTGACAGAAATCAGCAGGAAGTGATCTATAACACGCAGA | SEQ ID NO: 54 | Homo sapiens integrator complex subunit 5 (INTS5), mRNA [NM_030628] |
| 55 | A_23_P135104 | MRPS2 | TTGTCAATCTAAATGGCTTTCAGGTGGGCGGCTTCCTTGGCTACCTGGTTCCAGGGGGCT | SEQ ID NO: 55 | Homo sapiens mitochondrial ribosomal protein S2 (MRPS2), nuclear gene encoding mitochondrial protein, mRNA [NM_016034] |
| 56 | A_23_P135634 | MAGED1 | TTGAGTGAGATGTTGGATATTGGTATCAATCGCAGTAGTCTTTCCGCTGTGTGAGCTGAA | SEQ ID NO: 56 | Homo sapiens NRAGE mRNA, complete cds. [AF217963] |
| 57 | A_23_P135914 | SF3B3 | TTAATTGGTTTTCTTGTAAATACAGTTTTTGTAGAATGTTATGTCTGTGGAGGAAGGAGG | SEQ ID NO: 57 | Homo sapiens splicing factor 3b, subunit 3, 130kDa (SF3B3), mRNA [NM_012426] |
| 58 | A_23_P135977 | CKAP5 | AAGTCCTCATAGTTTAAAATGGCTCAGCAGGCCTAGTATACAAACTGGTTGTATGTA | SEQ ID NO: 58 | Homo sapiens cytoskeleton associated protein 5 (CKAP5), transcript variant 1, mRNA [NM_001008938] |
| 59 | A_23_P137073 | ZMYM3 | GGGTTTCGTGACCCATCCCGGCATAGAGCCTCTTGTTCCTAGGCATGACCTAGGGGAAA | SEQ ID NO: 59 | Homo sapiens zinc finger, MYM-type 3 (ZMYM3), transcript variant 1, mRNA [NM_005096] |
| 60 | A_23_P137423 | IGSF8 | CCTTACTCGCCAGGTGCTTCATGAAGAACGGCGTCGAAAACGGTGATCCCTTACTCGCCAGGT | SEQ ID NO: 60 | Homo sapiens immunoglobulin superfamily, member 8 (IGSF8), mRNA [NM_052868] |
| 61 | A_23_P137715 | POGK | GGGAGGTTAAACATTTTACAAGAGGCTAATTTGGGTTCCTTCCTTGGAGCCATAGTTAC | SEQ ID NO: 61 | Homo sapiens pogo transposable element with KRAB domain (POGK), mRNA [NM_017542] |
| 62 | A_23_P138058 | NOC2L | TCACTGCCCAAGTCGTTTGAAAATTGTTCCTTTGAAGTCACATTTTCTTTTAA | SEQ ID NO: 62 | Homo sapiens nucleolar complex associated 2 homolog (S. cerevisiae) (NOC2L), mRNA [NM_015658] |
| 63 | A_23_P13855 | ATN1 | CTGCCCCGTTGGTGTGATTATTTCATCTGTTAGATAGATGTGGGTGTTTTGGTAAGCATCGTGT | SEQ ID NO: 63 | Homo sapiens atrophin 1 (ATN1), transcript variant 1, mRNA [NM_001007026] |
| 64 | A_23_P141180 | TOM1L2 | GCTACTGAAAAGAAGAATGTTGAATGTGGGGTTGGTGTCCACTCGCCTAGAAGTTT | SEQ ID NO: 64 | Homo sapiens target of myb1-like 2 (chicken) (TOM1L2), transcript variant 3, mRNA [NM_001029968] |
| 65 | A_23_P141484 | C17orf63 | ATTCTGTAGTGATCTGAAGCAGATGTGAGTGAAGACCAGTTTAAGTTATGTGTTGGCAAG | SEQ ID NO: 65 | Homo sapiens chromosome 17 open reading frame 63 (C17orf63), transcript variant 2, mRNA [NM_018182] |
| 66 | A_23_P141779 | CXXC1 | GTGTACGGCCAAGTATGAGAGAGAGCGAGACGTCCTTGGGTCCATGTACCCCACACCATTGA | SEQ ID NO: 66 | Homo sapiens CXXC finger 1 (PHD domain) (CXXC1), mRNA [NM_014593] |
| 67 | A_23_P142018 | PRPF31 | TCAAGGGGCGAGAAGAGTGGGGTTATGTCCAGCCTGAATGACTGGTGTGTCCAAGGTGCCT | SEQ ID NO: 67 | Homo sapiens PRPF31 pre-mRNA processing factor 31 homolog (S. cerevisiae) (PRPF31), mRNA [NM_015629] |
| 68 | A_23_P142272 | PAF1 | AAATTGCTCGGAGTAGAACTGAAGCTGAAGAACAGAAAGGCTAGCAAGGGCTATGAGGAAA | SEQ ID NO: 68 | Homo sapiens Paf1, RNA polymerase II associated factor, homolog (S. cerevisiae) (PAF1), mRNA [NM_019088] |
| 69 | A_23_P143560 | KLHL22 | ACAAGAATGTCCAAGGATTTCGAGGAGAAGTCCCGATGCTGGAAGGTATGACGCACGGGACA | SEQ ID NO: 69 | Homo sapiens kelch-like 22 (Drosophila) (KLHL22), mRNA [NM_032775] |

Fig. 1-5

| No. | Probe ID No. | Symbols of genes | Sequence | SEQ ID NO: | Descriptions of genes (letters and numbers within [ ] indicates GenBank accession No.) |
|---|---|---|---|---|---|
| 70 | A_23_P144202 | EEFSEC | GTTGATGTCTTCAGTCGTCCTGCTCCAGAATAACTTTGACCAGGAGGCCTATACTGGACTCTTT | SEQ ID NO: 70 | Homo sapiens eukaryotic elongation factor, selenocysteine-tRNA-specific (EEFSEC), mRNA [NM_021937] |
| 71 | A_23_P145289 | GNL1 | AACACCCGTGGTGTGCCTGGGACATCTGTGAAGCCTGGGCAGAGAAACGTGTTACAAGA | SEQ ID NO: 71 | Homo sapiens guanine nucleotide binding protein-like 1 (GNL1), mRNA [NM_005275] |
| 72 | A_23_P145835 | EPHB6 | CAAGCAAAGTTCTCCAAGTTTGGCCTCTGTGTACCTCAGTGATGTGGCTCAGCTCAGCCTA | SEQ ID NO: 72 | Homo sapiens EPH receptor B6 (EPHB6), mRNA [NM_004445] |
| 73 | A_23_P146637 | OPRS1 | ATTTGAAGAAATGCTTGAAGTCAGGGTCGTTCCATTCCAGAAAGACCCCCATTCTTGCTTTG | SEQ ID NO: 73 | Homo sapiens opioid receptor, sigma 1 (OPRS1), transcript variant 1, mRNA [NM_005866] |
| 74 | A_23_P147641 | TCEA2 | ATCGAGGAATGCATCTTCCGGGACGTTGGAAACACAGAGATGAAGTATAAGAAGGGTGTA | SEQ ID NO: 74 | Homo sapiens transcription elongation factor A (SII), 2 (TCEA2), transcript variant 1, mRNA [NM_003195] |
| 75 | A_23_P148473 | IL2RG | CTTTCGTGTTTGCAATTGGAAGCCGTGGTTATCTCTGTTGGCTCCATGGGATTGATTATCA | SEQ ID NO: 75 | Homo sapiens interleukin 2 receptor, gamma (severe combined immunodeficiency) (IL2RG), mRNA [NM_000206] |
| 76 | A_23_P150256 | RBM14 | GATGGTGAGCAGGGCACAGTCCCACTTCCCGTCTGTCCCAAGTAGGTGGTGTTAGAAAACCT | SEQ ID NO: 76 | Homo sapiens RNA binding motif protein 14 (RBM14), mRNA [NM_006328] |
| 77 | A_23_P150403 | VPS11 | ACGAGATCTCCATGACTGATCAATTGCAAGGATCAGGTCAGGTGCTCCAATGAGAGGTTTTCGTT | SEQ ID NO: 77 | Homo sapiens vacuolar protein sorting 11 homolog (S. cerevisiae) (VPS11), mRNA [NM_021729] |
| 78 | A_23_P150852 | FAM62A | GCCTTTGCCTCGACCAAAGAAGAAGAAGGGTATGTCCCTTACTGCACGGGCCGTTTATCGTT | SEQ ID NO: 78 | Homo sapiens family with sequence similarity 62 (C2 domain containing), member A (FAM62A), mRNA [NM_015292] |
| 79 | A_23_P150931 | LMBR1L | AGAGTTGGGACCAGGAGGCTGGCGTTTTGCATACTAACTGTGGCCTCAGCATGGGGTA | SEQ ID NO: 79 | Homo sapiens limb region 1 homolog (mouse)-like (LMBR1L), mRNA [NM_018113] |
| 80 | A_23_P151426 | FOXO1 | GAGCGTTAGTGAGCAGGTTACAGTTAAAAGTTACTTCAGATTGTCTGACAGGAGGAAGTGA | SEQ ID NO: 80 | Homo sapiens forkhead box O1A (FOXO1A), mRNA [NM_002015] |
| 81 | A_23_P15247 | C16orf5 | GTGAAATGACAGACCCTGGTAGCTAAGAAGAAGCTTGTCCCTTTGAGTCAGTGTGCAGA | SEQ ID NO: 81 | Homo sapiens chromosome 16 open reading frame 5 (C16orf5), mRNA [NM_013399] |
| 82 | A_23_P152818 | MYST2 | CAAAGTTGGCACTTTCCCCTTTTGATGCTGCATATTAACTGGTTAATTATACTGCGAGA | SEQ ID NO: 82 | Homo sapiens MYST histone acetyltransferase 2 (MYST2), mRNA [NM_007067] |
| 83 | A_23_P152992 | AK125672 | GGGCAAGAAAGCAAGAAGACCCTGGTCTCCACCAAAAATAAGTAATTAATTTTTTAAAAGAGAGA | SEQ ID NO: 83 | Homo sapiens cDNA FLJ43684 fis, clone TBAES2001492. [AK125672] |
| 84 | A_23_P153892 | XRCC1 | CGATACGTCACAGCGTTCAATGGGAGGCTCGAGGACTATATGAGTGACCGGGTTCAGTTT | SEQ ID NO: 84 | Homo sapiens X-ray repair complementing defective repair in Chinese hamster cells 1 (XRCC1), mRNA [NM_006297] |
| 85 | A_23_P154962 | KIAA1666 | TTGTGATAACTATGGCAGGTATACGGAGGAAGCGGCCTTTTCTGTGGGGAATGTGTGTTT | SEQ ID NO: 85 | Homo sapiens KIAA1666 protein, mRNA (cDNA clone IMAGE:4927837), complete cds. [BC035246] |
| 86 | A_23_P155027 | MORC2 | GCACCTTGGTTTGACTTACACGGGAACGATTTGTGTTTTGGAGGAAAAGATACCCTGATTC | SEQ ID NO: 86 | Homo sapiens MORC family CW-type zinc finger 2 (MORC2), mRNA [NM_014941] |
| 87 | A_23_P155257 | FOXP1 | CAAGCAGAGATCCAGATTTTGACCATGAGAGAGATTACGAAGAAGATGAACCAGTAAACGAGGA | SEQ ID NO: 87 | Homo sapiens forkhead box P1 (FOXP1), transcript variant 1, mRNA [NM_032682] |

Fig. 1-6

| No. | Probe ID No. | Symbols of genes | Sequence | SEQ ID NO: | Descriptions of genes (letters and numbers within [ ] indicates GenBank accession No.) |
|---|---|---|---|---|---|
| 88 | A_23_P15603 | MRM1 | CCAGCGCAGGGGACCGTTGGTCTTGAACCAGTGATTGCCTGTGGCAAATGTGTGTATGA | SEQ ID NO: 88 | Homo sapiens mitochondrial rRNA methyltransferase 1 homolog (S. cerevisiae) (MRM1), mRNA [NM_024864] |
| 89 | A_23_P158897 | BE531123 | TAGGAACATGAATACCTTACAAAGCTGAAAGCTGAAAGTGGAAGTTGCCCAAAGGGTTTGGGTAT | SEQ ID NO: 89 | BE531123 601278493F1 NIH_MGC_39 Homo sapiens cDNA clone IMAGE:3610487 5', mRNA sequence [BE531123] |
| 90 | A_23_P1594 | VEGFB | TGTCTCAGTTTCTTAAGCACTCTGTGCAAGTAAGGATGTTAGAAGTGGCTCTTCCTCCCT | SEQ ID NO: 90 | Homo sapiens vascular endothelial growth factor B (VEGFB), mRNA [NM_003377] |
| 91 | A_23_P161257 | PDCD11 | CAGGAGAGACCCAGCTAGTTGTTGAAGGCAGTTCTTTTTTGTCTTGGTCATGAGGGAATT | SEQ ID NO: 91 | RRP5 protein homolog (Programmed cell death protein 11). [Source:Uniprot/SWISSPROT:Acc:Q14690] [ENST00000369797] |
| 92 | A_23_P16143 | GTF2F1 | ACCTGACACGGAAGCCCATGACCACTAAGGACCTGCTGAAAAAGTTGGAGACCAAGAAGA | SEQ ID NO: 92 | Homo sapiens general transcription factor IIF, polypeptide 1, 74kDa (GTF2F1), mRNA [NM_002096] |
| 93 | A_23_P161552 | ZNF289 | TGGATGAATGAATTCCTTGCAGGATGGCTACGGTTCCTACTGTGATCCGAGCTCTGTGTACTCAGG | SEQ ID NO: 93 | Homo sapiens zinc finger protein 289, ID1 regulated (ZNF289), mRNA [NM_032389] |
| 94 | A_23_P161918 | CCDC86 | AAAATACAGACAATAGAACCAAAGTCGGTGCCCTCGAGGAGCTTTCATTCTGATGGACGAGAA | SEQ ID NO: 94 | Homo sapiens coiled-coil domain containing 86 (CCDC86), mRNA [NM_024093] |
| 95 | A_23_P162120 | NUMA1 | AGGAGAAAGCAGGTCCAGGTTCTAGTAAACAGAGGGTGACCGGGGCCAGTGGATGGCCTTCA | SEQ ID NO: 95 | Homo sapiens nuclear mitotic apparatus protein 1 (NUMA1), mRNA [NM_006185] |
| 96 | A_23_P162374 | DDX54 | CTATCAGAAGTGGAAGTGGAACAGAGAAACAGAGAAAATTGATGATCGTGACTCGGACGAAGAAGGGGC | SEQ ID NO: 96 | Homo sapiens DEAD (Asp-Glu-Ala-Asp) box polypeptide 54 (DDX54), mRNA [NM_024072] |
| 97 | A_23_P162525 | UTP20 | GTAGGCAATGGATCTTGGGAATAGACAAGGTAAAGCCGTATCTCCAATGATCATAGCTCCT | SEQ ID NO: 97 | Homo sapiens UTP20, small subunit (SSU) processome component, homolog (yeast) (UTP20), mRNA [NM_014503] |
| 98 | A_23_P163258 | PARP6 | GACCCGAAGATACAGAAGGAAATCATGCGTGTGATCGGAACTCAGGTTACACAAACTGA | SEQ ID NO: 98 | Homo sapiens poly (ADP-ribose) polymerase family, member 6 (PARP6), mRNA [NM_020214] |
| 99 | A_23_P164718 | SNRPA | TCACGAACCTGCCAGAGGAGGACAAGGAACTGCTGCATGCTTTCAATCAGTTCC | SEQ ID NO: 99 | Homo sapiens small nuclear ribonucleoprotein polypeptide A (SNRPA), mRNA [NM_004596] |
| 100 | A_23_P166280 | THC2614148 | GTCAGGGGAGTTCTGAGCTTGGACCCTTATCTCCCAGAAATCGTGGAAGCGTGGCTGGTCT | SEQ ID NO: 100 | G59686_HUMAN (G59686) Androgen-regulated short-chain dehydrogenase/reductase 1 variant (Fragment), partial (7%) [THC2614148] |
| 101 | A_23_P166491 | RUTBC3 | ATTCCGTCTGGTCTGTCTGTAAGAGGTTCAGGTTGGATGAAGATGGCAAAGTTCCTGACCC | SEQ ID NO: 101 | Homo sapiens RUN and TBC1 domain containing 3 (RUTBC3), mRNA [NM_015705] |
| 102 | A_23_P166609 | DHX30 | CGTCACATATAGGACCGAAATGGAGGTTCACTGTGAAGCATCACCAAGTCGACGATTAACAGGGA | SEQ ID NO: 102 | Homo sapiens DEAH (Asp-Glu-Ala-His) box polypeptide 30 (DHX30), transcript variant 2, mRNA [NM_014966] |
| 103 | A_23_P166826 | DCP1A | CATTCTCAGTGATAATGGAGGTTTCACTGTGAAGCATCACCAAGCAGATCCTTGTTTTGAC | SEQ ID NO: 103 | Homo sapiens DCP1 decapping enzyme homolog A (S. cerevisiae) (DCP1A), mRNA [NM_018403] |
| 104 | A_23_P167093 | IDUA | ACATACGGAGATCCAGTTCTGTCTCAGGAGGGTAAGGGGTAGACCCCGGTCAGGAGGAGCA | SEQ ID NO: 104 | Homo sapiens iduronidase, alpha-L- (IDUA), mRNA [NM_000203] |
| 105 | A_23_P168541 | C7orf26 | TGGAGGGAAGAGTCCAGCCTCTGCCGAGAGCCTGCTGCGTGGATTTTAAAAGATGCCGA | SEQ ID NO: 105 | Homo sapiens chromosome 7 open reading frame 26 (C7orf26), mRNA [NM_024067] |
| 106 | A_23_P171366 | USP11 | AGTTTGATGACAACAAGGGTCTCCCGTGTGAATGAGAATACAGATCGAGTCAAGGCAGCCT | SEQ ID NO: 106 | Homo sapiens ubiquitin specific peptidase 11 (USP11), mRNA [NM_004651] |

Fig. 1-7

| No. | Probe ID No. | Symbols of genes | Sequence | SEQ ID NO: | Descriptions of genes (letters and numbers within [ ] indicates GenBank accession No.) |
|---|---|---|---|---|---|
| 107 | A_23_P18205 | RAD54L2 | GAGGTTGGGTTCAGCTCCAATGATGATGAGGATAAAGAAGGATGATGTGATAGAGGTCACT | SEQ ID NO: 107 | Homo sapiens RAD54-like 2 (S. cerevisiae) (RAD54L2), mRNA [NM_015106] |
| 108 | A_23_P203489 | TMEM63A | CTCCTGGGGATTCTGGGGAATGGGATGCAACTTAAGACTTGTGCCTGAGAAGGCTCCTCC | SEQ ID NO: 108 | Homo sapiens transmembrane protein 63A (TMEM63A), mRNA [NM_014698] |
| 109 | A_23_P202156 | NFKB2 | GGCCACGACGCCCTCTTGACCTGACTGCAGCAGCAAGGTGAAGAGCCTTGCTGTAAATGCT | SEQ ID NO: 109 | Homo sapiens nuclear factor of kappa light polypeptide gene enhancer in B-cells 2 (p49/p100) (NFKB2), transcript variant 2, mRNA [NM_002502] |
| 110 | A_23_P202708 | MADD | GTGTCCTTGAGACATTTGTGTTGGTTCGTTGTCGTTGTTGGCGTGGGTTATAACTGTGTCC | SEQ ID NO: 110 | Homo sapiens MAP-kinase activating death domain (MADD), transcript variant 4, mRNA [NM_003682] |
| 111 | A_23_P203406 | GANAB | GCCTTTGAGGGGCCACTTAAGGATGGAGAAATCAGTTGTGGTTTCAGTGAATCATGGTCACCT | SEQ ID NO: 111 | Homo sapiens glucosidase, alpha; neutral AB (GANAB), transcript variant 2, mRNA [NM_198334] |
| 112 | A_23_P203488 | SMPD1 | GTGTACCAAATAGATGGAAACTACTCCGGGAGGTCTCAGGTGGTCCTGACGCATGAGACC | SEQ ID NO: 112 | Homo sapiens sphingomyelin phosphodiesterase 1, acid lysosomal (acid sphingomyelinase) (SMPD1), transcript variant 1, mRNA [NM_000543] |
| 113 | A_23_P203737 | INTS4 | ACCATTCCCTTCAGCAAGCCTGTAAAAGTTTATATAATGGGAAATCGTGAAGGCGCTAA | SEQ ID NO: 113 | Homo sapiens integrator complex subunit 4 (INTS4), mRNA [NM_033547] |
| 114 | A_23_P203819 | GOLGA3 | TCTCACAGGATCCGGAGGGAAGTGTTAGAGGGTCTGGAAAATTCAGTGGTTTTCAGTT | SEQ ID NO: 114 | Homo sapiens golgi autoantigen, golgin subfamily a, 3 (GOLGA3), mRNA [NM_005895] |
| 115 | A_23_P20427 | RHOBTB2 | AGGAGGTATGAATCCCAGTCCGGAGGGAACCTAGGTCTTTAAAGTCTGGGGAAGGCTGGGATTC | SEQ ID NO: 115 | Homo sapiens Rho-related BTB domain containing 2 (RHOBTB2), mRNA [NM_015178] |
| 116 | A_23_P204364 | NCL1 | GGCAGAGTTCAGAATTGTCCACTGTACCTCTGTCACAAAGACCCAAGCTTCCTCCAGCTT | SEQ ID NO: 116 | Homo sapiens nucleolar protein 1, 120kDa (NCL1), transcript variant 1, mRNA [NM_006170] |
| 117 | A_23_P204641 | MYO9A | TGAAAGGAAAAGGCTTTGGGGTTTATTTTGGGAATAGTTAGGAGGCTAGGGTAGAATATAATT | SEQ ID NO: 117 | Homo sapiens myosin IXA (MYO9A), mRNA [NM_006901] |
| 118 | A_23_P20722 | SNAPC4 | ATGGCGTGTTCCCCAAGTGCAAGCTGCAGACTTGGAGGAATAAAGTTCTGTTTTAATTG | SEQ ID NO: 118 | Homo sapiens small nuclear RNA activating complex, polypeptide 4, 190kDa (SNAPC4), mRNA [NM_003086] |
| 119 | A_23_P207319 | MAP3K14 | CAGGAGTCACGTAGCATTAAATCAGGTGTGAATCGTGAAGCGGGGGTGTCTGCTAGCCTCAAC | SEQ ID NO: 119 | Homo sapiens mitogen-activated protein kinase kinase kinase 14 (MAP3K14), mRNA [NM_003954] |
| 120 | A_23_P207736 | AK023077 | TTCGTTAATTCTTGGGCAGTGGTGAGCACGAGATGAGCTTTGTGTGCAGGGTTATGCACTGTT | SEQ ID NO: 120 | Homo sapiens cDNA FLJ13015 fis, clone NT2RP3000622. [AK023077] |
| 121 | A_23_P20793 | A_23_P20793 | TGCCCCTTCCATAGGTGGGGGTTTGTAGGGTCTTGTTGGTTCTGGTGTCTGCAGGTT | SEQ ID NO: 121 | |
| 122 | A_23_P208358 | RPL28 | CACCATCAACAAGAATGCTCGGGGCACGGTCAGCAGGCATCAGAGACATGATCGGCAAGAA | SEQ ID NO: 122 | Homo sapiens ribosomal protein L28 (RPL28), mRNA [NM_000991] |
| 123 | A_23_P208551 | LPHN1 | TCGGTATCTGGGGAGCAGATTTTGGGTGTGGAATCTCCCTGGGATCGTCCTGGGCTT | SEQ ID NO: 123 | Homo sapiens latrophilin 1 (LPHN1), transcript variant 1, mRNA [NM_001008701] |
| 124 | A_23_P208582 | A_23_P208582 | CTATTGTCCGTGGGACTTCCTGCTGCATCAGTAGCCAGTGAGCCCAGAGATCCTAC | SEQ ID NO: 124 | |
| 125 | A_23_P208961 | MUM1 | CATTGTGGGTTCCTGAGAGTAGGACAATTGCCCATGGTTTGTGGGAATCACGCCCCCT | SEQ ID NO: 125 | Homo sapiens melanoma associated antigen (mutated) 1 (MUM1), mRNA [NM_032853] |
| 126 | A_23_P210319 | DTNB | CAGAGGCACATTCCTCTCGATGCTTCCACCCGGACACCTGACCAGGCTTGCAGGCTGGCA | SEQ ID NO: 126 | Homo sapiens dystrobrevin, beta (DTNB), transcript variant 4, mRNA [NM_183360] |

Fig. 1-8

| No. | Probe ID No. | Symbols of genes | Sequence | SEQ ID NO: | Descriptions of genes (letters and numbers within [ ] indicates GenBank accession No.) |
|---|---|---|---|---|---|
| 127 | A_23_P210643 | TH1L | ATGGTTCACCTGCTGAGTCGAGTCGGAGGTTATGTAGTCGTGTGTCAGTTACATCCGAAAGTGT | SEQ ID NO: 127 | Homo sapiens TH1-like (Drosophila) (TH1L), transcript variant 1, mRNA [NM_198976] |
| 128 | A_23_P211878 | FLNB | GCCCCAGCCAACTTCATGGGTCACTTTTGTGGAAATAATGATCTGTACAGACAGGACA | SEQ ID NO: 128 | Homo sapiens filamin B, beta (actin binding protein 278) (FLNB), mRNA [NM_001457] |
| 129 | A_23_P214567 | TRIM26 | ATTATCTGATGATTGGTCCTGTGAGGGGAGTTTAAGAATGCAGAACATGCTCTTG | SEQ ID NO: 129 | Homo sapiens tripartite motif-containing 26 (TRIM26), mRNA [NM_003449] |
| 130 | A_23_P214638 | EHMT2 | GGTCTTCATGGTGCACCAAGACCTGCGATTTCCACGGATCGGCTTCTTCAGTTCCGAGACA | SEQ ID NO: 130 | Homo sapiens euchromatic histone-lysine N-methyltransferase 2 (EHMT2), transcript variant NG36/69a, mRNA [NM_006709] |
| 131 | A_23_P1495 | FCGBP | TCAGTCATCCACCAGGAACGAAGAATTCCTGAAGAAGAAGACCTGGTCCCTCTGGAGGTTGGG | SEQ ID NO: 131 | Homo sapiens Fc fragment of IgG binding protein (FCGBP), mRNA [NM_003890] |
| 132 | A_23_P215175 | ABCF2 | GAGGGTGGTATGATCGTGGTCAGCCATGACTTCAGACTCATTCAGCAGGTTGCACAGGGA | SEQ ID NO: 132 | Homo sapiens ATP-binding cassette, sub-family F (GCN20), member 2 (ABCF2), nuclear gene encoding mitochondrial protein, transcript variant 2, mRNA [NM_005692] |
| 133 | A_23_P215449 | BAZ1B | CAAGTCCTAGAAACATGAGAATCAAGCCTCTTAATTTTAAACTGCGCAATGTGGGTCTGC | SEQ ID NO: 133 | Homo sapiens bromodomain adjacent to zinc finger domain 1B (BAZ1B), mRNA [NM_024083] |
| 134 | A_23_P1640 | CHD3 | GTCCAATGGGCGGCTCTGGGAACCACACAGACCCCCACACTACGTGGGTCTTGATGTTCAATATCGGCGA | SEQ ID NO: 134 | Homo sapiens chromodomain helicase DNA binding protein 3 (CHD3), transcript variant 1, mRNA [NM_001005273] |
| 135 | A_23_P217028 | USP20 | GGGAAGGGGCTCTGGGACCAGACGGCCCACACTACGTGGGTCTTTGTTTCTATCAGTCTTT | SEQ ID NO: 135 | Homo sapiens ubiquitin specific peptidase 20 (USP20), transcript variant 1, mRNA [NM_001008563] |
| 136 | A_23_P218086 | TPCN1 | TCTAGAAAACCCATTCTGTCTCTGGATCTGTAGGACATTACTAAAACAGGCTGTGCTT | SEQ ID NO: 136 | Homo sapiens mRNA for KIAA1169 protein, partial cds. [AB032995] |
| 137 | A_23_P218215 | AA601902 | AACCCTTAGTATCCGACAGATTCTGTGTTTGCAAATGTATCTAGTCGGTAAAATATATCTG | SEQ ID NO: 137 | AA601902 np02b01.s1 NCI_CGAP_Pr2 Homo sapiens cDNA clone IMAGE:1115113 similar to contains Alu repetitive element., mRNA sequence [AA601902] |
| 138 | A_23_P218654 | ZGPAT | GTCCCATCTGGACACGTTACTTGCCACCTGGCAGTGTCTTGGGCATTTCCTTGGCAAGGA | SEQ ID NO: 138 | Homo sapiens zinc finger, CCCH-type with G patch domain (ZGPAT), transcript variant 1, mRNA [NM_032527] |
| 139 | A_23_P218751 | GNB1L | GGAGTCCCCGCTGTCTTCATGAGGTTGGTATTTCGTTTTGTGGAGTGCCTCATGCAGAGGA | SEQ ID NO: 139 | Homo sapiens guanine nucleotide binding protein (G protein), beta polypeptide 1-like (GNB1L), mRNA [NM_053004] |
| 140 | A_23_P23411 | PRCC | GCAAGAGGAACCGACGGGACAGAGAAGAAAATCAACTTTGTGGAGATCAAAGGTGATGACCAGC | SEQ ID NO: 140 | Homo sapiens papillary renal cell carcinoma (translocation-associated) (PRCC), transcript variant 1, mRNA [NM_005973] |
| 141 | A_23_P23894 | RIPK5 | AGGGCCAAGGTATCGGTTTAGCAAAAAAGTGTCAGATGTGTAAAAGCTGAGGAATGTG | SEQ ID NO: 141 | Homo sapiens receptor interacting protein kinase 5 (RIPK5), transcript variant 1, mRNA [NM_015375] |
| 142 | A_23_P24068 | BMS1 | TCATGAAAGAAAAGATCCTTGCAGCTGCTGGATGCTCTGAGTACGGTGGATAGTCAGAAGAT | SEQ ID NO: 142 | Homo sapiens BMS1 homolog, ribosome assembly protein (yeast) (BMS1), mRNA [NM_014753] |
| 143 | A_23_P251259 | GTF2H4 | TCTGGGCAAGGATTACTCTGTGGAAGGTATGAGTCATTGTGTTGAAGTTCCTGCAAGCA | SEQ ID NO: 143 | Homo sapiens general transcription factor IIH, polypeptide 4, 52kDa (GTF2H4), mRNA [NM_001517] |

Fig. 1-9

| No. | Probe ID No. | Symbols of genes | Sequence | SEQ ID NO: | Descriptions of genes (letters and numbers within [ ] indicate GenBank accession No.) |
|---|---|---|---|---|---|
| 144 | A_23_P251660 | ABCF1 | CCCACTCTGTGATTGGATGCATTTCTCTGAAAGACTTGTTTGTTCTG CTTCTTCATATAA | SEQ ID NO: 144 | Homo sapiens ATP-binding cassette, sub-family F (GCN20), member 1 (ABCF1), transcript variant 2, mRNA [NM_001090] |
| 145 | A_23_P252642 | BBS5 | GAAAAGATTGAGAAATCGGATGGTTGCCGTGTCGTGTGTAGAAAGA AGTAGACATGGGAGA | SEQ ID NO: 145 | Homo sapiens Bardet-Biedl syndrome 5 (BBS5), mRNA [NM_152384] |
| 146 | A_23_P25346 | ACAD10 | CAGAGAGGAGGACAGCTTCTATGTCATAAAGGTCACAAATGGTG GATCACAGGGATCGT | SEQ ID NO: 146 | Homo sapiens acyl-Coenzyme A dehydrogenase family, member 10 (ACAD10), mRNA [NM_025247] |
| 147 | A_23_P255569 | DUS1L | AAAGTGTGACCAGTGTGTGGAAACCCAAAGGGAACAGATGTGTGTT CAGCCGTGTGCAGCGG | SEQ ID NO: 147 | Homo sapiens dihydrouridine synthase 1-like (S. cerevisiae) (DUS1L), mRNA [NM_022156] |
| 148 | A_23_P256021 | LAS1L | AGACAACCTGGGAGGAGACAGCCTGGATCAGCCACACTCAGTTGG TCCACGACAGGGGAA | SEQ ID NO: 148 | Homo sapiens LAS1-like (S. cerevisiae) (LAS1L), mRNA [NM_031206] |
| 149 | A_23_P257155 | ATXN7 | TGGTGAACAGGAGTGATTCTAGTGTTTTCTTGGGCCATTCATTC ACCAGTCCAATGAAC | SEQ ID NO: 149 | Homo sapiens ataxin 7 (ATXN7), mRNA [NM_000333] |
| 150 | A_23_P258124 | ZNF346 | AAGCTGGGGATCTGCTTTATGTGTGAGAGAACGTGTTCTGGCTGTT ATGTAAAGGAGTGCA | SEQ ID NO: 150 | Homo sapiens zinc finger protein 346 (ZNF346), mRNA [NM_012279] |
| 151 | A_23_P258190 | AKR1B1 | GTGATCGCCAAGTGTGTGACACCAGACGCATTGCTGAGAAACTTT AAGGTCTTTGACTTT | SEQ ID NO: 151 | Homo sapiens aldo-keto reductase family 1, member B1 (aldose reductase) (AKR1B1), mRNA [NM_001628] |
| 152 | A_23_P26375 | ACD | CCAAAGAGGACTCGTGATGGTTCTGGGTCCAGTATGAGTATGAG GGACCCTGCAGGTCC | SEQ ID NO: 152 | Homo sapiens adrenocortical dysplasia homolog (mouse) (ACD), transcript variant 2, mRNA [NM_022914] |
| 153 | A_23_P26610 | TP53 | GTGTCAGGGATGTTTGGAGGATGTAAGAAATGTTCTTGCAGTTAA GGGTTAGTTTACAAT | SEQ ID NO: 153 | Homo sapiens tumor protein p53 (Li-Fraumeni syndrome) (TP53), mRNA [NM_000546] |
| 154 | A_23_P27894 | SAFB2 | CAGGGTTCGGTCGAACTTGGGGGATCTTTTAAAAGCAAAGTAAA TCCTCCCACCATGTT | SEQ ID NO: 154 | Homo sapiens scaffold attachment factor B2 (SAFB2), mRNA [NM_014649] |
| 155 | A_23_P28857 | SIRPG | TCCCATGGATCGCCTTGAGAGACTTGACGGTAAACCACAGAGCGTC CAGGTTCTCAAGAGT | SEQ ID NO: 155 | Homo sapiens signal-regulatory protein gamma (SIRPG), transcript variant 2, mRNA [NM_080816] |
| 156 | A_23_P300150 | NFATC1 | AGCCTTTCTCAGGGGACTGTCATTGAAAAGGAAAGGAAAGTTTGATGTC TGTGTCAGGTGTCTT | SEQ ID NO: 156 | Homo sapiens nuclear factor of activated T-cells, cytoplasmic, calcineurin-dependent 1 (NFATC1), transcript variant 3, mRNA [NM_172387] |
| 157 | A_23_P300714 | SORBS3 | ACGCAGCACCTTCTTAGCGATCCTAGGCCTGGCAAAGAGCTCTGGCC CCAAGGGTCCTCTT | SEQ ID NO: 157 | Homo sapiens sorbin and SH3 domain containing 3 (SORBS3), transcript variant 1, mRNA [NM_005775] |
| 158 | A_23_P300826 | C6orf136 | TACAAGCGTGACAAAGACGAAGGCATTACCGGGAGCGGTATGATGCGTAC TCCACTTTCTACCTG | SEQ ID NO: 158 | Homo sapiens chromosome 6 open reading frame 136 (C6orf136), mRNA [NM_145029] |
| 159 | A_23_P309803 | ZNF777 | TGTAGGGCCATCTAGTTGGGGATAGAAGTTTATAATTACCTTT GGATACTGTGTTGT | SEQ ID NO: 159 | Homo sapiens zinc finger protein 777 (ZNF777), mRNA [NM_015694] |
| 160 | A_23_P309850 | RPUSD2 | GCTTGTAAAAGAGAGGCTGCTCATACTTGCTACCTCCTCCAGTGGG AATTTGAGAACTTT | SEQ ID NO: 160 | Homo sapiens RNA pseudouridylate synthase domain containing 2 (RPUSD2), mRNA [NM_152260] |
| 161 | A_23_P310331 | RANBP3 | GGCCCATGTGTTTTGGAACATTTATGTAAGATTGTCATATGAAAT GTATTTGGGAACTAC | SEQ ID NO: 161 | Homo sapiens RAN binding protein 3 (RANBP3), transcript variant RANBP3-a, mRNA [NM_003624] |
| 162 | A_23_P311740 | PARC | CTGCCGGTGTCATAAGGGAGGGGATTCCCAGCGCTGTAGTGCTT CCTGTTTGCTGAATA | SEQ ID NO: 162 | Homo sapiens p53-associated parkin-like cytoplasmic protein (PARC), mRNA [NM_015089] |

Fig. 1-10

| No. | Probe ID No. | Symbols of genes | Sequence | SEQ ID NO: | Descriptions of genes (letters and numbers within [ ] indicates GenBank accession No.) |
|---|---|---|---|---|---|
| 163 | A_23_P312179 | ALMS1 | GAGATTGTGAAGGTGCGAAAAACACAGTCGAGATGTTGGGATAACTTTCCCAACTGCA | SEQ ID NO: 163 | Homo sapiens Alstrom syndrome 1 (ALMS1), mRNA [NM_015120] |
| 164 | A_23_P3128 | YLPM1 | AAGAGAAGAAGGATGCAGATAGGAAAAGGGCCATAGGTTTGTGCTCGGACAGACTCGA | SEQ ID NO: 164 | Homo sapiens YLP motif containing 1, mRNA (cDNA clone IMAGE:3835909), complete cds. [BC023570] |
| 165 | A_23_P31477 | NUDCD3 | AAGTGATGCAGTGGTGTGAGAATGCCCTAGACCTGTTATTTGGGAGACTTTGAGAGTCAT | SEQ ID NO: 165 | Homo sapiens NudC domain containing 3 (NUDCD3), mRNA [NM_015332] |
| 166 | A_23_P31489 | URG4 | GAGGAAGTGACCTCACAGAACCCAGTCGAGAGATGTTACCAAGAAATACACAGCCCCAGGG | SEQ ID NO: 166 | Homo sapiens up-regulated gene 4 (URG4), transcript variant 1, mRNA [NM_017920] |
| 167 | A_23_P315252 | AK097322 | CATCGTGGGTCAATAGTACTTGCCGGAGTACTCTTAAAACTAGGCGGCTATGGTATAAT | SEQ ID NO: 167 | Homo sapiens cDNA FLJ40003 fis, clone STOMA2003716. [AK097322] |
| 168 | A_23_P315378 | ATG16L1 | GTGTGTTTCCAGTTTATACTCTTTGTCGAAAACTCAGTTTCAAAATATTGCAAATGGGAC | SEQ ID NO: 168 | Homo sapiens cDNA FLJ10035 fis, clone HEMBA1000919. [AK000897] |
| 169 | A_23_P315843 | NCOA5 | GCCCCGATGGGATCTACCAGAGAGGCATTACTGAGGATCTGAAGCTAAATCTTTCAACTCTCCCAGTC | SEQ ID NO: 169 | Homo sapiens nuclear receptor coactivator 5 (NCOA5), mRNA [NM_020967] |
| 170 | A_23_P316472 | DNHD1 | TAAGCTGCAGAGCAGGAGGAACACTGTGATGGATCTGCCTTTACCCACCAAGGCTCACCCCAG | SEQ ID NO: 170 | Homo sapiens dynein heavy chain domain 1 (DNHD1), mRNA [NM_144666] |
| 171 | A_23_P319270 | AZI1 | GATGCCCATGGGCTAAGCACCGTGGCTGCAATTTAACAGTAAAGGAGGCCGTTGTTTTGA | SEQ ID NO: 171 | Homo sapiens 5-azacytidine induced 1 (AZI1), transcript variant 1, mRNA [NM_014984] |
| 172 | A_23_P320304 | AFAR3 | AGGGTGCCCAAGGCTTTCTGTCAACTCTTTTGCTCTGTCTCCCGCTTTGTGTAATTTAGAA | SEQ ID NO: 172 | Homo sapiens aflatoxin B1 aldehyde reductase 3 (AFAR3), mRNA [NM_201252] |
| 173 | A_23_P320837 | DKFZP434A0131 | GCTCTGAGTCCCATCATGTTGGGAAAGTGGTTGAACCTCACCGGTGAAACGGGACAGT | SEQ ID NO: 173 | Homo sapiens mRNA; cDNA DKFZp434A0131 (from clone DKFZp434A0131). [AL137492] |
| 174 | A_23_P32125 | PMPCA | CCGGTTCCGGTGCCGTGTTAGTTTGGACGAGAATTTAGTCTAAAAAGCTGTGTGGTTGTAT | SEQ ID NO: 174 | Homo sapiens peptidase (mitochondrial processing) alpha (PMPCA), nuclear gene encoding mitochondrial protein, mRNA [NM_015160] |
| 175 | A_23_P32136 | DHX30 | ACCGTTACACACGGTTAGGAGTGCTTAGGAGGCGGATGGCTGAGGTATTCATGGCAGTCAAGTCGAAT | SEQ ID NO: 175 | Homo sapiens DEAH (Asp-Glu-Ala-His) box polypeptide 30 (DHX30), transcript variant 3, mRNA [NM_138614] |
| 176 | A_23_P325093 | GGTL3 | TGGGCCGAGCTTAGGAGTGTGCTTGGCAAACCCTGTGCAAGGGGTCAACAACCCAACAT | SEQ ID NO: 176 | Homo sapiens gamma-glutamyltransferase-like 3 (GGTL3), mRNA [NM_178026] |
| 177 | A_23_P326142 | NAG8 | GTGTTGGGATTAGGAGTGGAATGAGGAATAGTTAGGACGACAAGAGATTTGGCTCGTT | SEQ ID NO: 177 | Homo sapiens nasopharyngeal carcinoma associated gene protein-8 (NAG8), mRNA [NM_014411] |
| 178 | A_23_P329133 | GOT2 | TCAACTCCATCGTATCCGAGATTATTTAAGAATGAAGAACATAATTTTCTGCTGATGCCG | SEQ ID NO: 178 | Human mitochondrial aspartate aminotransferase mRNA, complete cds. [M22632] |
| 179 | A_23_P329212 | ETS1 | GTCAACTCCAGCCTATCCAGAATCCGGCTATACCTGGATTACTTCATTAGCTATGGTATT | SEQ ID NO: 179 | Homo sapiens v-ets erythroblastosis virus E26 oncogene homolog 1 (avian) (ETS1), mRNA [NM_005238] |
| 180 | A_23_P332042 | RECQL5 | CTTTCTGGTTGCAAAGACCTCTTTTGACCTGAGCGGGTGTCATGGCTGGGTTTTTCTG | SEQ ID NO: 180 | Homo sapiens RecQ protein-like 5 (RECQL5), transcript variant 1, mRNA [NM_004259] |
| 181 | A_23_P336015 | NOC2L | GGAATTTAAAGAGCTCTTTGACCTGAAGAGCTCTGAAGAGGACGACACTGAGGGATTCTC | SEQ ID NO: 181 | Homo sapiens nucleolar complex associated 2 homolog (S. cerevisiae) (NOC2L), mRNA [NM_015658] |

Fig. 1-11

| No. | Probe ID No | Symbols of genes | Sequence | SEQ ID NO: | Description of genes (letters and numbers within [ ] indicates GenBank accession No.) |
|---|---|---|---|---|---|
| 182 | A_23_P336218 | MGC27345 | TGAGTGACTGCTTGTTGAATCAGATAGTAACAAACATTTATTTG TAGTCTGGTTGTGTC | SEQ ID NO: 182 | Homo sapiens hypothetical protein MGC27345, mRNA (cDNA clone MGC:27345 IMAGE:4670552), complete cds. [BC024231] |
| 183 | A_23_P336513 | GEMIN5 | AGACCTTGGCAGAAATGATCCGACAACACCAAAGAGTCAACTCT GTAAATCCACAGCAA | SEQ ID NO: 183 | Homo sapiens gem (nuclear organelle) associated protein 5 (GEMIN5), mRNA [NM_015465] |
| 184 | A_23_P339095 | SPTBN1 | AGTGGGATAGTTCAAAAGGAAGAACGAAGTTTCCCAAAAGGGTTTGC CAGCTGAACAGGGAT | SEQ ID NO: 184 | Homo sapiens spectrin, beta, non-erythrocytic 1 (SPTBN1), transcript variant 2, mRNA [NM_178313] |
| 185 | A_23_P342131 | CYBASC3 | GCTGACGGCTCTGAGCTGCTGTGTTTCGTATTGTGCGTCTGTGTC TGCATGTATTGTGAC | SEQ ID NO: 185 | Homo sapiens cytochrome b, ascorbate dependent 3 (CYBASC3), mRNA [NM_153611] |
| 186 | A_23_P34496 | TMEM39B | CCTCATCCGTCTTCAGCAACTACTATGCCTTCTTGAGCTGCTCCG GGATCCGGTTGGTATT | SEQ ID NO: 186 | Homo sapiens transmembrane protein 39B (TMEM39B), mRNA [NM_018056] |
| 187 | A_23_P349310 | TNRC6A | CGTGCCCTCTGCTAGTATGCCTATGATGTTGCGCTACCTTATTGTGGT ATCGTGGAGTTTTAA | SEQ ID NO: 187 | Homo sapiens trinucleotide repeat containing 6A (TNRC6A), mRNA [NM_014494] |
| 188 | A_23_P3502 | NHN1 | AGTTGACATGTTGAATAAGCGGGTGATAAGGAAGCAGGAAGC GCTATGAACCATCAG | SEQ ID NO: 188 | Homo sapiens conserved nuclear protein NHN1 (NHN1), mRNA [NM_144604] |
| 189 | A_23_P356565 | KIAA0409 | TGAAGACAAAGTGTGATAAAAACGTTCTGGCTCAGAGCTTGGTACT GAAGGCTTCTTGGTT | SEQ ID NO: 189 | Homo sapiens KIAA0409 (KIAA0409), mRNA [NM_015324] |
| 190 | A_23_P359174 | BC069659 | CCAGGGTGGCATACTAGGGGTAAAGAAAAATTTTGTAATAGCAACA GTGGTTTAGGATTT | SEQ ID NO: 190 | Homo sapiens cDNA clone IMAGE:7262526, with apparent retained intron [BC069659] |
| 191 | A_23_P36076 | SSRP1 | AATGCAGGATCGAAATGCTCATCTTACTTTGGGGACCTTAAGGAT GTAGCTGGTGCTTGT | SEQ ID NO: 191 | Homo sapiens structure specific recognition protein 1 (SSRP1), mRNA [NM_003146] |
| 192 | A_23_P36140 | B3GAT3 | AGAGACAGTCTTCTGAGCCACCTGTGGATCCAAGGAGCGTGGAGC CACGGGCTGCCAACCT | SEQ ID NO: 192 | Homo sapiens beta-1,3-glucuronyltransferase 3 (glucuronosyltransferase I) (B3GAT3), mRNA [NM_012200] |
| 193 | A_23_P36157 | WDR74 | TAGAGACCAGCTATGGAAGAGTACCCACTAACAGAGCCATGACCGTCA CTCCGGAGGCAAC | SEQ ID NO: 193 | Homo sapiens WD repeat domain 74 (WDR74), mRNA [NM_018093] |
| 194 | A_23_P364537 | DDX51 | CCTCCTTCCAGAGCAGTGTTTGTCACTGGATCCTGTATGTGAGGA AAGGAATCGCCAGT | SEQ ID NO: 194 | Homo sapiens DEAD (Asp-Glu-Ala-Asp) box polypeptide 51 (DDX51), mRNA [NM_175066] |
| 195 | A_23_P367676 | SIN3A | CGTTGGAACTGTTTGTATCTGCCTCTTTAGTAGTCTACCTTAGTG CCATCCACCAGCTTT | SEQ ID NO: 195 | Homo sapiens SIN3 homolog A, transcription regulator (yeast) (SIN3A), mRNA [NM_015477] |
| 196 | A_23_P368996 | LRRC56 | CAAACGAACATTTCCAGGCTGTCTCAGGTGTACAGACAAATGGGTTTAC TTTGTAGGGCAGGT | SEQ ID NO: 196 | Homo sapiens leucine rich repeat containing 56 (LRRC56), mRNA [NM_198075] |
| 197 | A_23_P371765 | C21orf56 | CAACATGCCCGAGAAGAATCGAGCAGACCTCCACCAAGTCTGTGGA GGGCTCCGTGGACGA | SEQ ID NO: 197 | Homo sapiens chromosome 21 open reading frame 56 (C21orf56), mRNA [NM_032261] |
| 198 | A_23_P37205 | NDRG2 | CGTTTGGGTGCACTAACTTTGGTAGGTCAGTGCATCTAGAGTG GGACTGGGAGGGAG | SEQ ID NO: 198 | Homo sapiens NDRG family member 2 (NDRG2), transcript variant 1, mRNA [NM_201535] |
| 199 | A_23_P372255 | ITPKB | TCAGTTGTATTTAGCTTTGAGTTTCTCTGCATGTGTCCACCCAA GTGTATATAACCCAG | SEQ ID NO: 199 | Homo sapiens inositol 1,4,5-trisphosphate 3-kinase B (ITPKB), mRNA [NM_002221] |
| 200 | A_23_P38219 | PRPF8 | CCAGAACACAGAGAAGGGCAACAACAACGCGAAGGGCTACCTGCCTTG ACAGTATGAGAGGGT | SEQ ID NO: 200 | Homo sapiens PRP8 pre-mRNA processing factor 8 homolog (S. cerevisiae) (PRPF8), mRNA [NM_006445] |

Fig. 1-12

| No. | Probe ID No. | Symbols of genes | Sequence | SEQ ID NO: | Descriptions of genes (letters and numbers within [ ] indicates GenBank accession No.) |
|---|---|---|---|---|---|
| 201 | A_23_P383060 | SLC5A6 | GAAATAGGGATGGAAGTCGCATCCGTGGGAAAAAGATAATGGCTTCTGATTCAACATAGC | SEQ ID NO: 201 | Homo sapiens solute carrier family 5 (sodium-dependent vitamin transporter), member 6 (SLC5A6), mRNA [NM_021095] |
| 202 | A_23_P384698 | LOC442075 | CAGGTCACTTGACAAGGAGATACAAAAGTATCAGTTCATGATAGGGAAAC | SEQ ID NO: 202 | Homo sapiens cDNA FLJ35033 fis, clone OCBBF2016590, weakly similar to CELL SURFACE ANTIGEN 114/A10 PRECURSOR [AK092352] |
| 203 | A_23_P3849 | TRAP1 | ACTCATCAGGAAACTGGGGACGTTTACAGCAGAGGCTGATCAAATTCTTCATTGACCA | SEQ ID NO: 203 | Homo sapiens TNF receptor-associated protein 1 (TRAP1), mRNA [NM_016292] |
| 204 | A_23_P38876 | LIPE | GGGGAGAGCGGCAGCACACACCGGTCAGGGAGACCGGTGGACCTGCACGCCACCGGTGCCTT | SEQ ID NO: 204 | Homo sapiens lipase, hormone-sensitive (LIPE), mRNA [NM_005357] |
| 205 | A_23_P388780 | DMAP1 | GATACCAAGTATATTGATGCTGGGGACCAAGCAGGGCGGGGAAGGAACAGCTTGAGGGTCTGTA | SEQ ID NO: 205 | Homo sapiens DNA methyltransferase 1 associated protein 1 (DMAP1), transcript variant 1, mRNA [NM_019100] |
| 206 | A_23_P389914 | CCDC101 | CAACAAGTATGAGGTAGATGACATGGCCAGCCTGAGGCGACACGCGTGAGGCG | SEQ ID NO: 206 | Homo sapiens coiled-coil domain containing 101 (CCDC101), mRNA [NM_138414] |
| 207 | A_23_P389907 | ATXN2 | TTTCAGAGTCGGGCAAGTCCCAGGTAGCGCAGCTCTGCTTGCCGAAAACTGGAAGTTATTATTTTT | SEQ ID NO: 207 | Homo sapiens ataxin 2 (ATXN2), mRNA [NM_002973] |
| 208 | A_23_P39034 | SMARCA4 | CTGGCATCAGTAGAGATGTGTAACAGGATTAACTGTCTTAAAGAGAGAGAGAGAATTCC | SEQ ID NO: 208 | Homo sapiens SWI/SNF related, matrix associated, actin dependent regulator of chromatin, subfamily a, member 4 (SMARCA4), mRNA [NM_003072] |
| 209 | A_23_P39040 | SMARCA4 | AAGGAGCGCATTGCCAACCACAAGTGCCAACGGAGCCTCAACGAGCTAGAGAAGGAGGTCATG | SEQ ID NO: 209 | Homo sapiens SWI/SNF related, matrix associated, actin dependent regulator of chromatin, subfamily a, member 4 (SMARCA4), mRNA [NM_003072] |
| 210 | A_23_P391275 | DSCR1L2 | TAAATATGATTTACTCGTGCTGTTCCAAATTGGGACCAGAGAGAAATATGAAGTTC | SEQ ID NO: 210 | Homo sapiens Down syndrome critical region gene 1-like 2 (DSCR1L2), mRNA [NM_013441] |
| 211 | A_23_P3921 | FLJ11710 | CCTGATTCATGATTGAAGTACATTACCATAAATGCTATACATCCATGCATTGGATGTTA | SEQ ID NO: 211 | Homo sapiens cDNA FLJ11710 fis, clone HEMBA1005149. [AK021772] |
| 212 | A_23_P392501 | TNRC6C | GGTTGTGACTGCTTTGGGGAGGCTGGGGTTTCGGCTGCCACCTGTTTACAGAGGTTT | SEQ ID NO: 212 | Homo sapiens cDNA FLJ31859 fis, clone NT2RP7001231. [AK056421] |
| 213 | A_23_P393401 | LOC339047 | CAATGACTTTCTTTACCCGCGTAGCTCTCGGCAGTACTCAGTGGAAGGGTGATATTATGA | SEQ ID NO: 213 | Homo sapiens hypothetical protein LOC339047, mRNA (cDNA clone IMAGE:4184431), complete cds. [BC008179] |
| 214 | A_23_P394917 | SRCAP | TGGTGGCTGAATTCAGGATGACGTCGGACTTAGCAGATAGCGGGCAGGGGGGGTTGGAAT | SEQ ID NO: 214 | Homo sapiens Snf2-related CBP activator protein (SRCAP), mRNA [NM_006662] |
| 215 | A_23_P39844 | IMMT | GGCTTGTGAGGCCAATCAAAATAATGTTTGATGTCTACTAGTGTTGATTTTGCCCTGG | SEQ ID NO: 215 | Homo sapiens inner membrane protein, mitochondrial (mitofilin) (IMMT), mRNA [NM_006839] |
| 216 | A_23_P40049 | CAD | CCTGACACTGATGTGTCTACAGACTGAATCCAGAAGGAACGATTTGGCTGTAGCCAG | SEQ ID NO: 216 | Homo sapiens carbamoyl-phosphate synthetase 2, aspartate transcarbamylase, and dihydroorotase (CAD), mRNA [NM_004341] |
| 217 | A_23_P401084 | ZNF575 | CTTTGGGAGATCTCAAACATGGACGTGGAGCTGTGGTTTGAGAGCGGTGGGCTCTGCTT | SEQ ID NO: 217 | Homo sapiens zinc finger protein 575 (ZNF575), mRNA [NM_174945] |

Fig. 1-13

| No. | Probe ID No. | Symbols of genes | Sequence | SEQ ID NO: | Descriptions of genes (letters and numbers within [ ] indicates GenBank accession No.) |
|---|---|---|---|---|---|
| 218 | A_23_P40194 | DDX27 | CATGTCTGTCAATCTCGGTTCTTGCTGATTAGGTTTCAATATGAGTATATTAAATGGAAGT | SEQ ID NO: 216 | Homo sapiens DEAD (Asp-Glu-Ala-Asp) box polypeptide 27 (DDX27), mRNA [NM_017895] |
| 219 | A_23_P406105 | GCN1L1 | TCTGGGAGGGGTATAGGTTTGAAAGGCTGTTTGAAAGAGGAATGTTTAATAAAGGCTTT | SEQ ID NO: 217 | Homo sapiens GCN1 general control of amino-acid synthesis 1-like 1 (yeast) (GCN1L1), mRNA [NM_006836] |
| 220 | A_23_P407601 | C8orf6 | GTGTCCTAGGTTAGTGTAGCAGAGAATTCTATTCTCAGATAAGAGTTCCGTGTCGGCTGAA | SEQ ID NO: 220 | Homo sapiens mRNA for hypothetical protein (C8orf6 gene), [AJ307469] |
| 221 | A_23_P407684 | ZNF598 | TGTCTGCACAGACGGAGTTCTGCAACCGCGAGAAGCCTCTGACGACCAAGTCCAAGAAGA | SEQ ID NO: 221 | Homo sapiens zinc finger protein 598 (ZNF598), mRNA [NM_178167] |
| 222 | A_23_P40989 | USP13 | TGAGATGGAGAATAATGCCAATGAAACATTATTCTGAGGCAAGGCCAAGGAGCTAG | SEQ ID NO: 222 | Homo sapiens ubiquitin specific peptidase 13 (isopeptidase T-3) (USP13), mRNA [NM_003940] |
| 223 | A_23_P41021 | NISCH | TAATTTGACTGTCTCGGCAGAGAATGTGAACATGTGTGTGTTGTGTTAATTCTTTCTC | SEQ ID NO: 223 | Homo sapiens nischarin (NISCH), mRNA [NM_007184] |
| 224 | A_23_P410653 | MLLT6 | AACACCAGACTGTTGTCTACCAGATGCAGGAGATCCAGCAGAAACGGGAGCTGCAGC | SEQ ID NO: 224 | Homo sapiens myeloid/lymphoid or mixed-lineage leukemia (trithorax homolog, Drosophila); translocated to, 6 (MLLT6), mRNA [NM_005937] |
| 225 | A_23_P411246 | TMC8 | GTCTGACGGTGTGCTCTCCCAGACCAGGTGTGAGGCAAGTTGGAAGCATCCACAGGCGTCGGG | SEQ ID NO: 225 | Homo sapiens transmembrane channel-like 8 (TMC8), mRNA [NM_152468] |
| 226 | A_23_P41755 | PURA | GAACTCCATCACCGTGCGCTGCGGTGTGGGCAAGTTCGGGAGTACACCCTCTGCAAGTA | SEQ ID NO: 226 | Homo sapiens purine-rich element binding protein A (PURA), mRNA [NM_005859] |
| 227 | A_23_P422305 | SFXN4 | GATTTTAACCGTCAAGGGCAATTTGATACTGAGAGGTTAAGGGGACAGAGTTCGAATCA | SEQ ID NO: 227 | Homo sapiens cDNA FLJ37976 fis, clone CTONG2010148, [AK095295] |
| 228 | A_23_P423457 | SERINC5 | TTTTGGTTCTTTAAACTTCGTCGTTGGGGGCCATGTGCTGAGGAGGTTCTTCATTCGA | SEQ ID NO: 228 | Homo sapiens serine incorporator 5 (SERINC5), mRNA [NM_178276] |
| 229 | A_23_P425932 | VTI1A | TACCTCAAAAATAGAACAAGAGAGTCCATCCATGTGCAGGATGACTGTCAAGGTCACTGA | SEQ ID NO: 229 | Vesicle transport through interaction with t-SNAREs homolog 1A (Vesicle transport v-SNARE protein Vti1-like 2) (Vti1-rp2). [Source:Uniprot/SWISSPROT;Acc:Q96AJ9] [ENST00000369399] |
| 230 | A_23_P431418 | U2AF2 | TGAAGACGATGGGCACGAGGAGTGAGCAGCCCGACAGAGCAGACAGCCGGAGCAGCAACCTGGAA | SEQ ID NO: 230 | Homo sapiens U2 small nuclear RNA auxiliary factor 2 (U2AF2), transcript variant 1, mRNA [NM_007279] |
| 231 | A_23_P45108 | QRICH1 | GAAAGGCTTGGACTCTGAAAAGAAATGTGGCGCCCTTTCCATCTTCAAGAGAGAATGGAAT | SEQ ID NO: 231 | Homo sapiens glutamine-rich 1 (QRICH1), transcript variant 1, mRNA [NM_017730] |
| 232 | A_23_P48964 | VPS33B | CCTCACAGCCCTGGAACAGTTAAAGTGAGGCAAGCTGGTGACCGACGAGGCTGCAGGAAAGAT | SEQ ID NO: 232 | Homo sapiens vacuolar protein sorting 33 homolog B (yeast) (VPS33B), mRNA [NM_018668] |
| 233 | A_23_P4922 | LOC374920 | GAGAGTCTCCAGCAGGGAGGGGAAGGGGAATTGTTTGGACTATTGTTCAGGATTGGAATAAA | SEQ ID NO: 233 | Homo sapiens hypothetical protein LOC374920 (LOC374920), mRNA [NM_199341] |
| 234 | A_23_P49327 | ZNF174 | AATCACAAAACTGTGACTTACAAGGAAAGCACGAGGGCGTTGAGGAATGATGATGCA | SEQ ID NO: 234 | Homo sapiens zinc finger protein 174 (ZNF174), transcript variant 1, mRNA [NM_003450] |
| 235 | A_23_P4944 | CALM3 | CTCACTGCCCAGGTCGATCAAGTTTCCTGGGACCTGCCAGGTTTGAGAATCTGT | SEQ ID NO: 235 | Homo sapiens calmodulin 3 (phosphorylase kinase, delta) (CALM3), mRNA [NM_005184] |

Fig. 1-14

| No. | Probe ID No. | Symbols of genes | Sequence | SEQ ID NO: | Descriptions of genes (letters and numbers within [ ] indicate GenBank accession No.) |
|---|---|---|---|---|---|
| 236 | A_23_P49900 | PELP1 | TGAGTGTCCCCAAAGGTGCAGGCAGAACCCGAACCCCGGGGTGCTTTTGGAAGT | SEQ ID NO: 236 | Homo sapiens proline, glutamic acid and leucine rich protein 1 (PELP1), mRNA [NM_014389] |
| 237 | A_23_P50020 | COG1 | GCATGACAAGCACTCGAAAGGCTAAATCAACCAGAAACATGAAACAAAAGGTCAGGTTG | SEQ ID NO: 237 | Homo sapiens component of oligomeric golgi complex 1 (COG1), mRNA [NM_018714] |
| 238 | A_23_P501795 | SURF5 | CCATCATTCCGAGTGATCATCTCTGTTTGCTGCCTTCCTGGGCAGCCAGGTGCAAGAAAG | SEQ ID NO: 238 | Homo sapiens surfeit 5 (SURF5), transcript variant b, mRNA [NM_133640] |
| 239 | A_23_P501887 | DHPS | GCTGATGCCCATTCTGGACCGAGATGGTGATGGAGCAGAAACAGAGAGGGTGAAAGTGGAC | SEQ ID NO: 239 | Homo sapiens deoxyhypusine synthase (DHPS), transcript variant 3, mRNA [NM_013407] |
| 240 | A_23_P502196 | IDH3B | CATGTGAAGTCACTTCGTGGGTATATAGACTCGGCACAACAATGTAGACCTGGTGATGATT | SEQ ID NO: 240 | Homo sapiens isocitrate dehydrogenase 3 (NAD+) beta (IDH3B), nuclear gene encoding mitochondrial protein, transcript variant 2, mRNA [NM_174855] |
| 241 | A_23_P50472 | ALDH16A1 | CTGTGGCTGCCATGGGGGGAGCTGATGGCTGAGCGGCCACCTACTGCATTTTGGACACCTCA | SEQ ID NO: 241 | Homo sapiens aldehyde dehydrogenase 16 family, member A1 (ALDH16A1), mRNA [NM_153329] |
| 242 | A_23_P51639 | KIAA0467 | GGTTCCAATCCGCAGCTCTGGCTTTGAAGCACTTGTGGCCACGGTCAAGTCCCTTTGCTCT | SEQ ID NO: 242 | Homo sapiens KIAA0467 (KIAA0467), mRNA [NM_015284] |
| 243 | A_23_P53015 | TUT1 | CATATAGAACAGGCAACCAAGAGAACCGCGGTCAAGAATCCCAGGCTACAACTGGGGAGTCCTCT | SEQ ID NO: 243 | Homo sapiens terminal uridylyl transferase 1, U6 snRNA-specific (TUT1), mRNA [NM_022830] |
| 244 | A_23_P53541 | CHD4 | TGCTGAGTGACTGAAAGCTGATGTGACTCGACTCCCAGGCTACCATTGCCCGAATTGCCC | SEQ ID NO: 244 | Homo sapiens chromodomain helicase DNA binding protein 4 (CHD4), mRNA [NM_001273] |
| 245 | A_23_P55091 | FTSJ3 | GAGTCAGAGGTCATTCAAGTCGTGGCACTCAAGGATGAAGAAGGACCAAGAGCAGAGC | SEQ ID NO: 245 | Homo sapiens FtsJ homolog 3 (E. coli) (FTSJ3), mRNA [NM_017647] |
| 246 | A_23_P553 | TARS2 | GTCCCAAATGCCAAGAAGAAATTTCTGAGCGTTTGTACATGATGAGGCAAAAACCTGCGA | SEQ ID NO: 246 | Homo sapiens threonyl-tRNA synthetase 2, mitochondrial (putative) (TARS2), mRNA [NM_025150] |
| 247 | A_23_P55948 | PRR12 | TGTCTCTTGCCTGTTTCTTGGGGTTCTACGCCCTTCATGGACAGTGAAGAGAGAGTCACTGTACACA | SEQ ID NO: 247 | Homo sapiens mRNA for KIAA1205 protein, partial cds. [AB033031] |
| 248 | A_23_P56127 | C12orf61 | GTCAGTTATTCCTGGTACGCCTCATGCATCGCTGTTAAGGACCCTCGGGAGCGAAAACCCACCAAGA | SEQ ID NO: 248 | Homo sapiens hypothetical protein FLJ12886 (FLJ12886), mRNA [NM_019108] |
| 249 | A_23_P57296 | GGTL3 | CGAAGGACCAAGAAGTTCATCATCGCTGTTAAGGACCCTCGGAGCCCAGATGCAGGTGGA | SEQ ID NO: 249 | Homo sapiens gamma-glutamyltransferase-like 3 (GGTL3), mRNA [NM_178026] |
| 250 | A_23_P57819 | TATDN2 | TACTTTCTCTCTAGGATTTAGATTTATGATTATCTCATTATGTCGTTGGCACAGTGAAACCTCACC | SEQ ID NO: 250 | Homo sapiens TatD DNase domain containing 2 (TATDN2), mRNA [NM_014760] |
| 251 | A_23_P586 | DMAP1 | CTGCTGAGCCGGGCAGTGAGTGACTGAAACCCGGACTTGGTCCTGACCCCAAGGAGACCATCAT | SEQ ID NO: 251 | Homo sapiens DNA methyltransferase 1 associated protein 1 (DMAP1), transcript variant 1, mRNA [NM_019100] |
| 252 | A_23_P60180 | ABL1 | AGGCCCTAAGTTTACGGTCATCACCCTAAAGTTGTACGTTTATTTTCTGATAGAAATGGTT | SEQ ID NO: 252 | Homo sapiens v-abl Abelson murine leukemia viral oncogene homolog 1 (ABL1), transcript variant a, mRNA [NM_005157] |
| 253 | A_23_P60657 | KIAA0460 | TTTATAACGAAAAGGGGGCTCTCTTCGAAAGTAAGAAATCACATACGGCTTACGTTTACTATTG | SEQ ID NO: 253 | Homo sapiens KIAA0460 (KIAA0460), mRNA [NM_015203] |
| 254 | A_23_P61268 | C8orf30A | TGAAGGAGCTTAGCTTGTTGTTCTTGTTGGGAATTCACAATGGCTCACTCCACACCCTAAAACT | SEQ ID NO: 254 | Homo sapiens chromosome 8 open reading frame 30A (C8orf30A), mRNA [NM_016458] |

Fig. 1-15

| No | Probe ID No. | Symbols of genes | Sequence | SEQ ID NO. | Descriptions of genes (letters and numbers within [ ] indicates GenBank accession No.) |
|---|---|---|---|---|---|
| 255 | A_23_P6223 | SFRS15 | AAATGACCGGGAACGGGTATGGGAACGGTAATGATGATAGAGATAATAGTAACCGTGACAG | SEQ ID NO: 255 | Homo sapiens splicing factor, arginine/serine-rich 15 (SFRS15), mRNA [NM_020706] |
| 256 | A_23_P62868 | EXOSC10 | TGGGAAACAAAAGCATGTCGTTGCAACTGGAAAGTCAGACGAGGGTTCAGGTACAACT | SEQ ID NO: 256 | Homo sapiens exosome component 10 (EXOSC10), transcript variant 1, mRNA [NM_001001998] |
| 257 | A_23_P63128 | OBSCN | CCTCGCTTCAGCGCGTGGGGGGATTCTTCCCCTCATTGTTGCATTGTTTGCATTAATATGAAT | SEQ ID NO: 257 | Homo sapiens cDNA FLJ14124 fis, clone MAMMA1002498 [AK024186] |
| 258 | A_23_P63281 | MGC10334 | GAACCACGGGTGAAGTCAAGGTCACAGGGTCCCGGGGGTGTGGAGGGTGGATCCTTTCTGCTTTTCTGCGC | SEQ ID NO: 258 | Homo sapiens hypothetical protein MGC10334 (MGC10334), mRNA [NM_001029985] |
| 259 | A_23_P64770 | DEX23 | AGTGGAATCTTACTGTCATCGTGGAACAGGGTGTTTCGTGTTTGGATGGTAAAGGAAGTTGA | SEQ ID NO: 259 | Homo sapiens DEAD (Asp-Glu-Ala-Asp) box polypeptide 23 (DDX23), mRNA [NM_004818] |
| 260 | A_23_P65797 | KLHL25 | GACGTGCCATGGTGCTTTGGCAAAAGTTGTTGTTGGTTTTATCAGTTTTCTAACTTAATA | SEQ ID NO: 260 | Homo sapiens kelch-like 25 (Drosophila) (KLHL25), mRNA [NM_022480] |
| 261 | A_23_P68390 | CIB2 | TGTGGCTCCAAGCTCCCAAGGACAGTGCCAGGCTGTGGGGTTTACACCACAAATAT | SEQ ID NO: 261 | Homo sapiens calcium and integrin binding family member 2 (CIB2), mRNA [NM_006383] |
| 262 | A_23_P68367 | GEMIN4 | AAAGAAAATAGTTCTTGGGTATTTGTAACGTACAAAGTATCATAAAAATTCCTCTCTT | SEQ ID NO: 262 | Homo sapiens gem (nuclear organelle) associated protein 4 (GEMIN4), mRNA [NM_015721] |
| 263 | A_23_P6802 | RRP9 | CCGATGGTGGAGAATCAAAAGAGGCTCGGAATTCTGTCTGGCATCATGCCACTCCGCAGGGT | SEQ ID NO: 263 | Homo sapiens RRP9, small subunit (SSU) processome component, homolog (yeast) (RRP9), mRNA [NM_004704] |
| 264 | A_23_P68087 | ATIC | GCAGAGAAAGGAATGGGTTGAGAAACTGACTGAAGTTTGTATGAGCTCTAGCGCCTTC | SEQ ID NO: 264 | Homo sapiens 5-aminoimidazole-4-carboxamide ribonucleotide formyltransferase/IMP cyclohydrolase (ATIC), mRNA [NM_004044] |
| 265 | A_23_P71146 | POLD2 | CTCCGGTGAGAGCAGCGAGGAAGTTTCTGCTCGGAGGACTATTGTTTGGCTGACCTTGCTCC | SEQ ID NO: 265 | Homo sapiens polymerase (DNA directed), delta 2, regulatory subunit 50kDa (POLD2), mRNA [NM_006230] |
| 266 | A_23_P71889 | ODF2 | AAGATCCTTAAAGATGAGATGAACAAGAGATTGAGGAGGCAGGAAGGCAGTTGCAGTCT | SEQ ID NO: 266 | Homo sapiens outer dense fiber of sperm tails 2 (ODF2), transcript variant 2, mRNA [NM_153437] |
| 267 | A_23_P73160 | ENST00000354261 | TGGTTGTTCATTAGAGTCTCGTGGAGTATTTGTTAAAAATAACAGATTCACATTCAGTAGAG | SEQ ID NO: 267 | Leucine-rich repeat and calponin homology domain-containing protein 3 precursor. [Source:Uniprot/SWISSPROT;Acc:Q96I18] [ENST00000354261] |
| 268 | A_23_P73604 | CXorf34 | ACTGGATTACAAGGTGATTCAAGCCATTCGAAACTTGAGGGGCATCCACACCGCTAGTTTT | SEQ ID NO: 268 | Homo sapiens chromosome X open reading frame 34 (CXorf34), mRNA [NM_024917] |
| 269 | A_23_P74269 | SRM | TGCTATTACCAGCTCATGAAGACAGAGCCCTCAAGGAAGATGGTGTCCTCGCTGCCAGGGC | SEQ ID NO: 269 | Homo sapiens spermidine synthase (SRM), mRNA [NM_003132] |
| 270 | A_23_P74653 | NUDC | GGGCAGGCCAGCCATCATTGATGGGAGGCTCTACAATGAAGGTGAAGGTGGAGAGAGGCTGT | SEQ ID NO: 270 | Homo sapiens nuclear distribution gene C homolog (A. nidulans) (NUDC), mRNA [NM_006600] |
| 271 | A_23_P75609 | CEP164 | TTTCTAACCTGTGCCATCGGGTATATTCATGGGCATTGTTTCCATCTGTCTTTTCTAACCTGTGCCA | SEQ ID NO: 271 | Homo sapiens centrosomal protein 164kDa (CEP164), mRNA [NM_014956] |
| 272 | A_23_P77437 | PRMT7 | AGAAAATGTTGAAGGGTAAGCACTTGAAGATAAAATTAACATGATAGAGAAACGGCCG | SEQ ID NO: 272 | Homo sapiens protein arginine methyltransferase 7 (PRMT7), mRNA [NM_019023] |

Fig. 1-16

| No. | Probe ID No. | Symbols of genes | Sequence | SEQ ID NO: | Descriptions of genes (letters and numbers within [ ] indicates GenBank accession No.) |
|---|---|---|---|---|---|
| 273 | A_23_P77440 | NFATC3 | GTCTCAGTTACAACCTATTACATATGGTCCTTCACATTCAGGGTC TGGTACAAGAGGTTG | SEQ ID NO: 273 | Homo sapiens nuclear factor of activated T-cells, cytoplasmic, calcineurin-dependent 3 (NFATC3), transcript variant 4, mRNA [NM_173164] |
| 274 | A_23_P77562 | PKD1 | CCTGCACCGTCTCACTGTGTCTCGTGTCAGTAATTTATATGGT GTTAAAATGTGTATA | SEQ ID NO: 274 | Homo sapiens polycystic kidney disease 1 (autosomal dominant) (PKD1), transcript variant 1, mRNA [NM_001009944] |
| 275 | A_23_P78170 | MYBBP1A | CTGGCACGGGAAAAAAGGGAAGGGTGTCTTTGGTCATCAGGAGTCCC AGGCTGCTTGGAGT | SEQ ID NO: 275 | Homo sapiens MYB binding protein (P160) 1a (MYBBP1A), mRNA [NM_014520] |
| 276 | A_23_P78191 | C17orf68 | TGCCTGTTGTTCTCTGATTGAACCAAGGACTCCAGATTCAGAAA CTGCTACTCCACTAT | SEQ ID NO: 276 | Homo sapiens chromosome 17 open reading frame 68 (C17orf68), mRNA [NM_025099] |
| 277 | A_23_P78665 | FARSA | CCTGGAGCGCCCAACGATGATCAAATATGGCATCAACAATATCCG GGAGCTGGTGGGGCA | SEQ ID NO: 277 | Homo sapiens phenylalanyl-tRNA synthetase, alpha subunit (FARSA), mRNA [NM_004461] |
| 278 | A_23_P79927 | NOL5A | GCCACATACTGCCGTCTCTTGCCCAGTTTATTGGAAAACCGAAGGGAA GTGAATGAGGACAAG | SEQ ID NO: 278 | Homo sapiens nucleolar protein 5A (56kDa with KKE/D repeat) (NOL5A), mRNA [NM_006392] |
| 279 | A_23_P80129 | RRP1 | CTCCGCCTGTGCCTGTGATGACCTTGGGCCAGAAGGTCAAACTGC GAAGACTGAAACTGT | SEQ ID NO: 279 | Homo sapiens DNA segment on chromosome 21 (unique) 2056 expressed sequence (D21S2056E), mRNA [NM_003683] |
| 280 | A_23_P80136 | RRP1 | TGAATGAACTGGACGACAACGAGGATGAGGAGGTGGCGTCGGACAGTG ATGAGTCCTCGAGG | SEQ ID NO: 280 | Homo sapiens DNA segment on chromosome 21 (unique) 2056 expressed sequence (D21S2056E), mRNA [NM_003683] |
| 281 | A_23_P84782 | THAP4 | GAGAGGGAATGACTGAGGATGTTCAGGTCAGGTACGAAGAAGGTGA CCCCGTAAACCTAGA | SEQ ID NO: 281 | Homo sapiens THAP domain containing 4 (THAP4), mRNA [NM_015963] |
| 282 | A_23_P8848 | RC74 | ACAGTCTTGGTTTCGTTTACTTGGCTACGAGTGCTGCTGTACGCAATA AGATGATGATCCCAA | SEQ ID NO: 282 | Homo sapiens integrator complex subunit 9 (RC74), mRNA [NM_018250] |
| 283 | A_23_P89835 | THC2619205 | AGCTATACATTCTTCTTTCTGGTCCCATCTTAAACGTCTTCTGTT GTGTGCAGCCCAGA | SEQ ID NO: 283 | MARE2_HUMAN (Q15555) Microtubule-associated protein RP/EB family member 2 (APC-binding protein EB2) (End-binding protein 2) (EB2), partial (87%) [THC2619205] |
| 284 | A_23_P89884 | TRIM28 | AGTTTGCCCAGGAATGTGGCCGGCATGTCAAGGAATTGAACAAGT TAACTGAGGACAAGG | SEQ ID NO: 284 | Homo sapiens tripartite motif-containing 28 (TRIM28), mRNA [NM_005762] |
| 285 | A_23_P90089 | GCDH | GAATGGGATTTCTCAGGAGTATCACGTTGATCGGCCACGCCATGAA CCTGGAGCGCGTGAA | SEQ ID NO: 285 | Homo sapiens glutaryl-Coenzyme A dehydrogenase (GCDH), nuclear gene encoding mitochondrial protein, transcript variant 2, mRNA [NM_013976] |
| 286 | A_23_P91328 | NOL5A | GAGGTTCCTCAGGAGGAATGGAATGGAGGACCCATCTCTCTTTC TCCAACACAGAAAAA | SEQ ID NO: 286 | Homo sapiens nucleolar protein 5A (56kDa with KKE/D repeat) (NOL5A), mRNA [NM_006392] |
| 287 | A_23_P93318 | DKFZP434A0131 | TTTGAATGAGAGTCTCATCTTGGGTAGGCAGGATGGCGCAACAAC TGGGGAGGTGGAGGT | SEQ ID NO: 287 | Homo sapiens mRNA; cDNA DKFZp434A0131 (from clone DKFZp434A0131). [AL137492] |
| 288 | A_23_P9415 | ACO1 | AATTATACCAGTGTTAAGTGACATAGATAAGAACTTTGACACTT GAAATCAGAAGCAGTG | SEQ ID NO: 288 | Homo sapiens aconitase 1, soluble (ACO1), mRNA [NM_002197] |
| 289 | A_23_P9416 | ACO1 | TACCCTCTTATTGTTCCTTCTTTACGCTGTGCTGCAATGAAAACCTTGG TCTTGAGGGTCATTT | SEQ ID NO: 289 | Homo sapiens aconitase 1, soluble (ACO1), mRNA [NM_002197] |

Fig. 1-17

| No. | Probe ID No. | Symbols of genes | Sequence | SEQ ID NO: | Descriptions of genes (letters and numbers within [ ] indicates GenBank accession No.) |
|---|---|---|---|---|---|
| 290 | A_23_P9426 | GOLGA2 | CGTTCTCAGTCAACCCGTTACCGTTAGCGCTTACAGTAGCAAGGCATAGAGCCCCTGCTCTAAGCGGGGT | SEQ ID NO: 290 | Homo sapiens golgi autoantigen, golgin subfamily a 2 (GOLGA2), mRNA [NM_004486] |
| 291 | A_23_P96853 | FAF1 | GGGTTTCCTGGCCAGGAAGACCAAGGTGCAGAATTGTCTTGATTTTGTAGCTTCCAAAGGATT | SEQ ID NO: 291 | Homo sapiens Fas (TNFRSF6) associated factor 1 (FAF1), mRNA [NM_007051] |
| 292 | A_23_P97274 | SCAMP3 | TGCCAGCTTTCGAAGAAGGGCAGCAAGAGATTTGGTGCTGGTGTCTTCTGAAACCGTGCGGT | SEQ ID NO: 292 | Homo sapiens secretory carrier membrane protein 3 (SCAMP3), transcript variant 2, mRNA [NM_052837] |
| 293 | A_23_P97736 | NCDN | GCTTGCTTGAAGGGACCCAGAGTCTTGTTGTTTGGGCCGGAGATCTTAAACCTTTGTCGTGTTG | SEQ ID NO: 293 | Homo sapiens neurochondrin (NCDN), transcript variant 3, mRNA [NM_014284] |
| 294 | A_23_P9823 | MLXIP | TCTTGTTCTAGAGGTTTTGTTTGTTTGGAATCTTGCCTGATGAATCCAGCCAGAACCAAGG | SEQ ID NO: 294 | Homo sapiens MLX interacting protein (MLXIP), mRNA [NM_014938] |
| 295 | A_23_P98252 | ARL2 | TGGCGGGCATGCAGTGGCTCCTGGATGAGAGCGGGCATTTCCAGGCGGCATTTTCAGAGGTGACTGAA | SEQ ID NO: 295 | Homo sapiens ADP-ribosylation factor-like 2 (ARL2), mRNA [NM_001667] |
| 296 | A_23_P98845 | DCHS1 | GTTGCTCAGTCACCTGTGACCAGGTCCAATGTGGGGAGAAATATGAAGGAGGTAGCAGCC | SEQ ID NO: 296 | Homo sapiens dachsous 1 (Drosophila) (DCHS1), mRNA [NM_003737] |
| 297 | A_23_P100234 | MORC2 | TGAATTCAGATGAGCTAATATCTTTTCGTCTGAAGGAGTAGTTCAAGCAATATGAAGTAG | SEQ ID NO: 297 | Homo sapiens MORC family CW-type zinc finger 2 (MORC2), mRNA [NM_014941] |
| 298 | A_24_P101402 | NOL5A | GGCTGGCAAGAAGGTTCGAAGAAGAAGCCACCTCGTGGGTTGGCAGAAGTTGCATAAAGCATGCAGGAAGAATTA | SEQ ID NO: 298 | Homo sapiens nucleolar protein 5A (56kDa with KKE/D repeat) (NOL5A), mRNA [NM_006392] |
| 299 | A_24_P101426 | A_24_P101426 | GTTTATGAGGTGGGAGCAAAGCCACGTCAGGATCCGGATGATGAA | SEQ ID NO: 299 | |
| 300 | A_24_P102512 | CABIN1 | CTCGTAGGGTGATATTTCTGGGGGAGATAAATCCAAGAAAGGGGTAAAACGGAAGAAGA | SEQ ID NO: 300 | Homo sapiens calcineurin binding protein 1 (CABIN1), mRNA [NM_012295] |
| 301 | A_24_P105933 | VIPR1 | TCTGATAGGAATGTGAAAGGCACGGACTGTTACTGCTAAGCTTTTGTGTATGCTAACCAGCC | SEQ ID NO: 301 | Homo sapiens vasoactive intestinal peptide receptor 1 (VIPR1), mRNA [NM_004624] |
| 302 | A_24_P110719 | ZNF236 | AGTTCTACAGAGAGACTGCTCATGTTTAACGCGCGACAGTTTTTTCAGACGTTAGCTCTCAA | SEQ ID NO: 302 | Homo sapiens zinc finger protein 236 (ZNF236), mRNA [NM_007345] |
| 303 | A_24_P119337 | AK054562 | GCTTGCAGTTAGGACCACAGCTAAAAGGTTAATGTCCACGGTGGTGTTGACCAAGCCGT | SEQ ID NO: 303 | Homo sapiens mRNA for FLJ00054 protein, partial cds. [AK054562] |
| 304 | A_24_P127701 | LOC441616 | CCAAGCTGATGGATAGTGAGACGGGAGACTGGTGCAGCAGATCGGGCGCTCTAGACAGCAACAT | SEQ ID NO: 304 | PREDICTED: Homo sapiens similar to Protein C11orf2 (Another new gene 2 protein) (LOC441616), mRNA [XM_001129767] |
| 305 | A_24_P128001 | ZNF395 | GAATTCTTTGCTTCTAAAGCTCTTGCAGAAAGGACTGTGAGGCAAGATGAATTTACTTTTC | SEQ ID NO: 305 | Homo sapiens zinc finger protein 395 (ZNF395), mRNA [NM_018660] |
| 306 | A_24_P128057 | MBNL1 | AGAATATTGGTGCAAACTATCTGTGATTGGTTATCTCTATCATGCATTGCTTCACAA | SEQ ID NO: 306 | Homo sapiens muscleblind-like (Drosophila), mRNA (cDNA clone IMAGE:3935812), partial cds. [BC005296] |
| 307 | A_24_P142269 | HIRIP3 | GAGAGGAAGAAGACCGCTCTTCCAAGGAGGTCGAGGAAAGGCAGGACACAGAGGCTGCT | SEQ ID NO: 307 | Homo sapiens HIRA interacting protein 3 (HIRIP3), mRNA [NM_003609] |
| 308 | A_24_P142963 | PIK4CA | TCACTCCATGTTTGGACACGGGTGCCCTGTTTTCGGGGGCAGACAATCAAGGTCTTGA | SEQ ID NO: 308 | Homo sapiens phosphatidylinositol 4-kinase, catalytic, alpha polypeptide (PIK4CA), transcript variant 1, mRNA [NM_002650] |

Fig. 1-18

| No. | Probe ID No. | Symbols of genes | Sequence | SEQ ID NO: | Descriptions of genes (letters and numbers within [ ] indicates GenBank accession No.) |
|---|---|---|---|---|---|
| 309 | A_24_P144601 | POU5F1 | AACAATGAAAATCTTCAGGAGATATGCAAAGGAGAAACCCTCGTGCAGGGCGGAAAGAGA | SEQ ID NO: 309 | Homo sapiens POU domain, class 5, transcription factor 1 (POU5F1), transcript variant 1, mRNA [NM_002701] |
| 310 | A_24_P145047 | ZNF609 | ACTATTTAAACGGTGCCTGGGCAGTTAGGAGGGATGGTTTTAGGAATGAGCGGAAAACTACC | SEQ ID NO: 310 | Homo sapiens zinc finger protein 609 (ZNF609), mRNA [NM_015042] |
| 311 | A_24_P147910 | SEPT9 | GTCGCATCACGGCACGTGAGGAAAGGCGTGGGGATGAAGCTGACAGGATTGACAG | SEQ ID NO: 311 | Homo sapiens septin 9 (SEPT9), mRNA [NM_006640] |
| 312 | A_24_P153587 | CRY2 | CACCACAGTGCTGCCAGTGAGGACAGCGTGACACCCAGCCAGGGAAACGATTCTAGTCTTT | SEQ ID NO: 312 | Homo sapiens cryptochrome 2 (photolyase-like) (CRY2), mRNA [NM_021117] |
| 313 | A_24_P166042 | IMPDH2 | TTGGACTCTTCCGAGGGAAATTCCATCTTCCAGATCAATATGATGAAGTACATGAAAGAG | SEQ ID NO: 313 | Homo sapiens IMP (inosine monophosphate) dehydrogenase 2 (IMPDH2), mRNA [NM_000884] |
| 314 | A_24_P166645 | REPIN1 | CCCGTTGGGTAGGCACCCAGAGTTGGAGAGACCCGTCTGGTGGTTAATACTTCCAATGCTCTT | SEQ ID NO: 314 | Homo sapiens replication initiator 1 (REPIN1), transcript variant 2, mRNA [NM_014374] |
| 315 | A_24_P169645 | A_24_P169645 | AAGTTGTCGTGAAGAGGTTATTTATGAGTTGGACAAATGGGCATCTCTGTCTCTTTCCT | SEQ ID NO: 315 | |
| 316 | A_24_P171345 | PUM1 | GAGCACGGTCGTCCTGAGGATAAAAGCAAAATTGTAGGAGAAATCCGAGGCAATGTAGTT | SEQ ID NO: 316 | Homo sapiens pumilio homolog 1 (Drosophila) (PUM1), transcript variant 2, mRNA [NM_014676] |
| 317 | A_24_P181108 | WDR74 | TGGGTTGCAGTGCCACGGTTCAAAGCCTACTAGCCTCCTGTGGCTTGAACAGAGTCTT | SEQ ID NO: 317 | Homo sapiens WD repeat domain 74 (WDR74), mRNA [NM_018093] |
| 318 | A_24_P185158 | FAM134C | GCCCGTAGCTGAAATCATGTGATGTGAGAGAAACCTAAACATGGTAGTTGATTCTAAAC | SEQ ID NO: 318 | Homo sapiens hypothetical protein LOC162427 (LOC162427), mRNA [NM_178126] |
| 319 | A_24_P191067 | CLSTN1 | ACCGACATAGCACTTGGTCTTAGTTACATGTAAAATTTTAGATTTCTAAACAGGTGGG | SEQ ID NO: 319 | Homo sapiens calsyntenin 1 (CLSTN1), transcript variant 1, mRNA [NM_001009566] |
| 320 | A_24_P193570 | CNOT1 | AGAGTTCCTTTGTGATTACGATTATGGGTTCTGATGTGATCCCACCTAATTGTATCGA | SEQ ID NO: 320 | Homo sapiens CCR4-NOT transcription complex, subunit 1 (CNOT1), transcript variant 1, mRNA [NM_016284] |
| 321 | A_24_P196298 | MLL | GCAACTTGAACATCCTCAGCAGTCTCCAATGGCAAATGTTCTAAGGAAAAATTCCAG | SEQ ID NO: 321 | Homo sapiens myeloid/lymphoid or mixed-lineage leukemia (trithorax homolog, Drosophila) (MLL), mRNA [NM_005933] |
| 322 | A_24_P209694 | RING1 | GAAATTCTGGAAGGTGTCCCGGGCCATGGAGCGTGTCCTATGGTGGCAGCAAGGATCCAAA | SEQ ID NO: 322 | Homo sapiens ring finger protein 1 (RING1), mRNA [NM_002931] |
| 323 | A_24_P2093 | XAB2 | ACGTGGAAGGACTTTGAGGTCGGGATGGCAATGACGACAGCATCAAGGAAATGCTGGGT | SEQ ID NO: 323 | Homo sapiens XPA binding protein 2 (XAB2), mRNA [NM_020196] |
| 324 | A_24_P212764 | A_24_P212764 | CTCCCGCACTTGTGGCCAGACAGGGAGTCTAGACCAGGTTGTCCGTGGGAGATTGACAC | SEQ ID NO: 324 | |
| 325 | A_24_P213175 | A_24_P213175 | TTTCCCTGAGAGGTCACAGTACAATGTTTGTTTCAGAAGCCCCATTTGCACAGGTTTTCA | SEQ ID NO: 325 | |
| 326 | A_24_P214841 | POU5F1 | AATCTTCAGGAGATATGCAAAGCAGAAACCCTCGTGCAGGCGCCGAAAGAGAAAGGGAACC | SEQ ID NO: 326 | Homo sapiens POU domain, class 5, transcription factor 1 (POU5F1), transcript variant 1, mRNA [NM_002701] |

Fig. 1-19

| No. | Probe ID No. | Symbols of genes | Sequence | SEQ ID NO. | Descriptions of genes (letters and numbers within [ ] indicates GenBank accession No.) |
|---|---|---|---|---|---|
| 327 | A_24_P216067 | PAF1 | GACGATGCGACTCTGATGATGAGGAGGAGGAGGCCCAAGGTGGCAGTGACAATGAT | SEQ ID NO: 327 | Homo sapiens Paf1, RNA polymerase II associated factor, homolog (S. cerevisiae) (PAF1), mRNA [NM_019088] |
| 328 | A_24_P221658 | AW172589 | GGAGGTGCTGGGATGTCTGATTATATCTGATTTCTGAGCTCTGGGGATGGAGGTCTGTCTG | SEQ ID NO: 328 | xj79h10.x1 Soares_NFL_T_GBC_S1 Homo sapiens cDNA clone IMAGE:2663491 3' similar to TR:Q13116 Q13116 MEMBRANE PROTEIN-LIKE PROTEIN ;, mRNA sequence [AW172589] |
| 329 | A_24_P224926 | MFNG | AGACAATGATCCAACAGGCTATTCCCTGGAGCATCTGGTTCTGTGTACAAAAATTAAATGCTTA | SEQ ID NO: 329 | Homo sapiens MFNG O-fucosylpeptide 3-beta-N-acetylglucosaminyltransferase (MFNG), mRNA [NM_002405] |
| 330 | A_24_P231132 | ACVR2B | CTGTCAGCAATGTGGACCTGCCCCTGCCCCCTAAAGAGTCAAGCATCTAAGCCCAGGACATAGTG | SEQ ID NO: 330 | Homo sapiens activin A receptor, type IIB (ACVR2B), mRNA [NM_001106] |
| 331 | A_24_P231173 | PERQ1 | CCCTACTTGGGTTCGTGTCGGCGCATTTTGGGTTTTGTAACAGTTTTGTCTTTTGGGTTT | SEQ ID NO: 331 | Homo sapiens PERQ amino acid rich, with GYF domain 1 (PERQ1), mRNA [NM_022574] |
| 332 | A_24_P235131 | TRIAD3 | TCCAGTATCCCCCATGTGAAGGTCAGTTCCCTTCTCATGGAGTCAGCTGAGGATCAGGTC | SEQ ID NO: 332 | Homo sapiens TRIAD3 protein (TRIAD3), transcript variant 1, mRNA [NM_207111] |
| 333 | A_24_P238215 | DKFZP586P0123 | TTGAAAACAGATTCCCCATCTGGAATTTTGAACAGGAGTCAAGGCTATCGAAAGAGC | SEQ ID NO: 333 | Homo sapiens hypothetical protein DKFZP586P0123, mRNA [NM_015531] |
| 334 | A_24_P241862 | RANBP3 | TGCTCAGAGTCAATGACATGGCGTCCACGGATGAGGGCACAGTACAGTCCCGACTAGTGA | SEQ ID NO: 334 | Homo sapiens RAN binding protein 3 (RANBP3), transcript variant RANBP3-b, mRNA [NM_007320] |
| 335 | A_24_P244575 | TPCN1 | CCCTTGGGAAAGGAACACATTATTGAGACTCACTGTGATTCCCCGGGAGTCAGAGTGG | SEQ ID NO: 335 | Homo sapiens mRNA for KIAA1169 protein, partial cds. [AB032895] |
| 336 | A_24_P245246 | PIP5K2B | TTTGAGACCGTCGTTACTGTTTGAAAAATGGCATGCATGTTACGATGAATGTCAAGCTGAGG | SEQ ID NO: 336 | Homo sapiens phosphatidylinositol-4-phosphate 5-kinase, type II, beta (PIP5K2B), mRNA [NM_003559] |
| 337 | A_24_P248053 | TOP1MT | GCAGGAGAAGACTTTGAATTCTAACGACGAGCCGTGTTGAAAGTTCTTTTGTATGTGTGT | SEQ ID NO: 337 | Homo sapiens topoisomerase (DNA) I, mitochondrial (TOP1MT), nuclear gene encoding mitochondrial protein, mRNA [NM_052963] |
| 338 | A_24_P250333 | SNRPA | CAGCTCGGGATGCGCCTGGAGGGGTTTAAGATCACGCAGAACAACGCCATGAAGATGTCGT | SEQ ID NO: 338 | Homo sapiens small nuclear ribonucleoprotein polypeptide A (SNRPA), mRNA [NM_004596] |
| 339 | A_24_P251688 | ABCF3 | TTGGGGACAGCCTATTCCCAAATGTCTATGGTTTTGACTGGAGCATCTTCTGCACAA | SEQ ID NO: 339 | Homo sapiens ATP-binding cassette, sub-family F (GCN20), member 3 (ABCF3), mRNA [NM_018358] |
| 340 | A_24_P252130 | PPARD | GCTGAGGATACAGGCTCTTCTCAGTGTCTGAACAATGTCCAAAATTGAAATGTATATTTT | SEQ ID NO: 340 | Homo sapiens peroxisome proliferator-activated receptor delta (PPARD), mRNA [NM_006238] |
| 341 | A_24_P254437 | THC2563227 | GGGAGGGCACTGTCTCTCTTTTTCTCTCATTTTAAAATGAAGTGTTGTTGCCTTTGTAT | SEQ ID NO: 341 | CA312433 UI-CF-FN0-afk-i-18-0-UI s1 UI-CF-FN0 Homo sapiens cDNA clone UI-CF-FN0-afk-i-18-0-UI 3', mRNA sequence [CA312433] |
| 342 | A_24_P256063 | LOC442249 | CTCAGGAGGATTCGAAGATCATGGGACATCCAGGCCCAATATAACGAGCTGTCTCGGA | SEQ ID NO: 342 | PREDICTED: Homo sapiens hypothetical LOC442249 (LOC442249), mRNA [XR_019231] |
| 343 | A_24_P258846 | NFATC1 | CTCTGGTTGGTTGAGATCCCGGCCATTTCGGAATGAGGATAACCAGCCCCCGTTCACGTCA | SEQ ID NO: 343 | Homo sapiens nuclear factor of activated T-cells, cytoplasmic, calcineurin-dependent 1 (NFATC1), transcript variant 1, mRNA [NM_172390] |

Fig. 1-20

| No. | Probe ID No. | Symbols of genes | Sequence | SEQ ID NO: | Descriptions of genes (letters and numbers within [ ] indicates GenBank accession No.) |
|---|---|---|---|---|---|
| 344 | A_24_P26170 | VPRBP | GGACACTGACAGCTCTGACAAGCTCTGATTTGGAAGATGACATCATCTTATCTCTGAATGA | SEQ ID NO: 344 | Homo sapiens Vpr (HIV-1) binding protein (VPRBP), mRNA [NM_014703] |
| 345 | A_24_P266728 | SF1 | GCTTCCTTTTATGTTTGTTTAATCCAAATGTCTGAATGTTTTGCAGTGTGTAGGAGGT | SEQ ID NO: 345 | Homo sapiens splicing factor 1 (SF1), transcript variant 1, mRNA [NM_004630] |
| 346 | A_24_P267452 | CD3EAP | ACAGTGAAGCAGGAACAGATTAACACTGAGCCTCAGAAGACACAGTCCTGTCCGCGACC | SEQ ID NO: 346 | Homo sapiens CD3e molecule, epsilon associated protein (CD3EAP), mRNA [NM_012099] |
| 347 | A_24_P272594 | MAPKBP1 | GTCCTGTTTTTAACGTGCCCGTTTGTACTGATGTATGAACTTGTCAATAACAGAATTGT | SEQ ID NO: 347 | Homo sapiens mitogen activated protein kinase binding protein 1 (MAPKBP1), mRNA [NM_014994] |
| 348 | A_24_P273823 | NPAT | TGCCATTAGCCGCGATACCACCATAAGAGAAAGTCAATCAGAAAAGAAAGTTCTGCAAC | SEQ ID NO: 348 | Homo sapiens nuclear protein, ataxia-telangiectasia locus (NPAT), mRNA [NM_002519] |
| 349 | A_24_P294931 | PPP2R5D | TGACAGACATGGAAGGGACCACCCTGGGCGTGACTGCTTTCTGTGGTGTTGGTTCGGAA | SEQ ID NO: 349 | Homo sapiens protein phosphatase 2, regulatory subunit B', delta isoform (PPP2R5D), transcript variant 2, mRNA [NM_180876] |
| 350 | A_24_P29641 | NSUN5C | CAATAAAGAGCCAGTGCACTGGGTGCCTGCTGTCTGAAGAACCAAGGAGAGATCTTGCCTTG | SEQ ID NO: 350 | Homo sapiens NOL1/NOP2/Sun domain family, member 5C (NSUN5C), transcript variant 2, mRNA [NM_148936] |
| 351 | A_24_P298360 | LTBP3 | CTGCTGTTGGGGAAGCCCGGAAGATGAGGAGAGGTTCAGAGGAGGATTCAGACGAGTGT | SEQ ID NO: 351 | Homo sapiens latent transforming growth factor beta binding protein 3 (LTBP3), mRNA [NM_021070] |
| 352 | A_24_P307103 | tcag7.1017 | ATGTTTGGATGAATGCATGATGATGAGCCAGAAGAGGAGCTGGACGGCTGAGGAGAC | SEQ ID NO: 352 | Homo sapiens similar to Williams Beuren syndrome chromosome region 19 (MGC57359), mRNA [NM_001004351] |
| 353 | A_24_P312325 | C8orf15 | CTTGTTCAATGTGACTACTTTAGTTGCCTGTCCAATATGAAGTAGAAAAGACAGATTTCTG | SEQ ID NO: 353 | Homo sapiens chromosome 8 open reading frame 15 (C8orf15), mRNA [NM_001033662] |
| 354 | A_24_P315564 | LOC646253 | AGCAGATCAGGAGCTCTAGACAGCAACATGCAAACCCTGGTCTATGAGAACTACAATAAGT | SEQ ID NO: 354 | PREDICTED: Homo sapiens similar to Protein C1orf2 (Another new gene 2 protein) (LOC646253), mRNA [XM_001130995] |
| 355 | A_24_P316414 | BC014346 | TAACCGTTGGGGTCGTTTGGGAGTAGAAGTTTAGCTTTGAATAATTTAAGGGCCTGGCCGTA | SEQ ID NO: 355 | Homo sapiens, clone IMAGE:4042963, mRNA, partial cds. [BC014346] |
| 356 | A_24_P317827 | C9orf127 | AGCCTTCCGAAGACAGGAATGGTTGGCAGGGAGGAGACAAAGGCCCTGTCAGGACGAGCAT | SEQ ID NO: 356 | Homo sapiens chromosome 9 open reading frame 127 (C9orf127), transcript variant 1, mRNA [NM_001042590] |
| 357 | A_24_P321093 | SPOCK2 | CTGGAAGAAGCTTAACCATGTGTTGTTCAAAGAACCGGTTCTTGCTTGCTTGGTCTGGAAGT | SEQ ID NO: 357 | Homo sapiens sparc/osteonectin, cwcv and kazal-like domains proteoglycan (testican) 2 (SPOCK2), mRNA [NM_014767] |
| 358 | A_24_P322847 | POLR3H | ACATGCCTGGGTGCTGGGTGCTGATGAGTGATTAGTGTCTTCTGTCACAGGGTGCCTGGAGA | SEQ ID NO: 358 | Homo sapiens polymerase (RNA) III (DNA directed) polypeptide H (22.9kD) (POLR3H), transcript variant 4, mRNA [NM_001018511] |
| 359 | A_24_P32295 | C19orf36 | TTAAGGTGTCTGGAGCCCCCACTTGGCCAACCTGACCTTGGAAGATGCTGCTGAGTGT | SEQ ID NO: 359 | Homo sapiens chromosome 19 open reading frame 36 (C19orf36), transcript variant 3, mRNA [NM_001039846] |
| 360 | A_24_P323626 | FLJ45055 | ATTGAGGAAGAACGGCACCGAAAGCAAGAAGAAGCTCGTGCTCTCGTAAAGCCGGAAGGCAA | SEQ ID NO: 360 | Homo sapiens hypothetical protein LOC644128, mRNA (cDNA clone IMAGE:6158500). [BC064933] |

Fig. 1-21

| No. | Probe ID No. | Symbols of genes | Sequence | SEQ ID NO: | Descriptions of genes (letters and numbers within [ ] indicate GenBank accession No.) |
|---|---|---|---|---|---|
| 361 | A_24_P32646 | LOC648644 | AGATCTGTACCCTCTGCAAGAGGCAAAGGGTGCTGGATCCTGCCCACTGTGTACCATGGCA | SEQ ID NO: 361 | PREDICTED: Homo sapiens similar to Aflatoxin B1 aldehyde reductase member 2 (AFB1-AR 1) (Aldoketoreductase 7) (LOC648644), mRNA [XR_018390] |
| 362 | A_24_P327815 | STIP1 | CACCAAACTGGTGGAGTTGCAGCTGGCAGTCAAGGACTGTGAGGAATGTATCCAGCTGGA | SEQ ID NO: 362 | Homo sapiens stress-induced-phosphoprotein 1 (Hsp70/Hsp90-organizing protein) (STIP1), mRNA [NM_006819] |
| 363 | A_24_P329939 | VPS11 | CGTCATCAGGGAGTAGGTGGTCCAAAAACTACAGAAGACAGAGCCAGCAGATTGCACAGGA | SEQ ID NO: 363 | Homo sapiens vacuolar protein sorting 11 homolog (S. cerevisiae) (VPS11), mRNA [NM_021729] |
| 364 | A_24_P335356 | PUS1 | CCTGGAGTTTGCGCTGATCAGGGTGAAGGGCCAGAGCTCATGATGCATCAGATGCGGAA | SEQ ID NO: 364 | Homo sapiens pseudouridylate synthase 1 (PUS1), transcript variant 1, mRNA [NM_025215] |
| 365 | A_24_P338992 | EDC3 | TTGGCCAAAATCTGAGGAGCAGTCTAGGCTTACAGGCTTTTTGGTAGGTAGGTCTGGCTG | SEQ ID NO: 365 | Homo sapiens enhancer of mRNA decapping 3 homolog (S. cerevisiae) (EDC3), mRNA [NM_025083] |
| 366 | A_24_P340891 | LOC402149 | CTACGTGCGGGACATGATCAACAGAGAACGCTGGAGGGCAAACTCAGCAGCATCAGATAGCAT | SEQ ID NO: 366 | PREDICTED: Homo sapiens similar to ribosomal protein L28 (LOC402149), mRNA [XR_019242] |
| 367 | A_24_P349002 | POM121 | AGCTAAATTAATGAACCATATTTTAAAATGCTATTTTCGAAACAGGAGCCCTCTGGCAG | SEQ ID NO: 367 | Homo sapiens POM121 membrane glycoprotein (rat) (POM121), mRNA [NM_172020] |
| 368 | A_24_P360644 | ENST00000320547 | CATGTAGACCAGATATTTGAAAGGGGAGGAGACCGATGGCTAGAGGTGTAATGTGCAGGTTGTT | SEQ ID NO: 368 | Uncharacterized protein KIAA0515. [Source:Uniprot/SWISSPROT;Acc:Q5JS25] [ENST00000320547] |
| 369 | A_24_P356 | AAK1 | GCGGCTATGTTCGAATTGTTTATGAAGTGATCATTAGTGAGAGTGGCCACAGTAT | SEQ ID NO: 369 | AP2-associated protein kinase 1 (EC 2.7.11.1) (Adaptor-associated kinase 1). [Source:Uniprot/SWISSPROT;Acc:Q2M2I8] [ENST00000360555] |
| 370 | A_24_P364970 | DHX33 | ATTTAATTATCAGAAGCAAGTAATGTTTCCCCAGATAATATTTTGCCCTAGAAGACAGAGCCG | SEQ ID NO: 370 | Homo sapiens DEAH (Asp-Glu-Ala-His) box polypeptide 33 (DHX33), mRNA [NM_020162] |
| 371 | A_24_P369263 | MMS19L | TTCTACTCGAAGGACCCCAAGTCATGAGTGTTCAGGTGGACACCGTGCGTGAGCAAGTTTC | SEQ ID NO: 371 | Homo sapiens MMS19-like (MET18 homolog, S. cerevisiae) (MMS19L), mRNA [NM_022362] |
| 372 | A_24_P371670 | HNRPA0 | ACTTCTCCAGTTTGGCACCGTGGAAAAGGCCGAGATTATTGCCGACAAGCAGTCGGGCA | SEQ ID NO: 372 | Homo sapiens heterogeneous nuclear ribonucleoprotein A0 (HNRPA0), mRNA [NM_006805] |
| 373 | A_24_P372613 | APBB1 | AAACCTGTTTGGGGTAGATGTGATTAATGGGGGCCTCGAGTCAGTCCTGTCTCCAGCAGGC | SEQ ID NO: 373 | Homo sapiens amyloid beta (A4) precursor protein-binding, family B, member 1 (Fe65) (APBB1), transcript variant 1, mRNA [NM_001164] |
| 374 | A_24_P373312 | NFATC3 | GAACCAAGAATCGAGAGGCGTAACTTTGCAACCATTGGTCTGCAGGAGATGACTTTAGAT | SEQ ID NO: 374 | Homo sapiens nuclear factor of activated T-cells, cytoplasmic, calcineurin-dependent 3 (NFATC3), transcript variant 4, mRNA [NM_173164] |
| 375 | A_24_P375592 | PHF20 | GCAGGGGAGCCATTTGAAAACAAAATGTTAAAATGCCAAGATTTGTGTTTAATTCTAGGTAC | SEQ ID NO: 375 | Homo sapiens cDNA FLJ33479 fis, clone BRAMY2002739. [AK090798] |
| 376 | A_24_P376422 | BC035371 | GAGCCAAGTTTGCATTTTGACAGCGATCTCAGACTGCTCTGGACTCTGAAGTTGGAGAGG | SEQ ID NO: 376 | Homo sapiens HSPC047 protein, mRNA (cDNA clone MGC:34358 IMAGE:5178752), complete cds. [BC035371] |

Fig. 1-22

| No. | Probe ID No. | Symbols of genes | Sequence | SEQ ID NO: | Descriptions of genes (letters and numbers within [ ] indicates GenBank accession No.) |
|---|---|---|---|---|---|
| 377 | A_24_P382765 | NHP2L1 | TACGTGTTCAAGTGATCAAGGGGTTTCATTTGCTCTTGGGGGATAGGTATCATTTGGGG | SEQ ID NO: 377 | Homo sapiens NHP2 non-histone chromosome protein 2-like 1 (S. cerevisiae) (NHP2L1), transcript variant 1, mRNA [NM_005008] |
| 378 | A_24_P384779 | PRKAG2 | CCATTAAATCACAGGCTGAGGCAGGAGAAATGGTGAGGGACAATAGCAAAATGGAAATACACAA | SEQ ID NO: 378 | Homo sapiens cDNA FLJ90194 fis, clone MAMMA1001284. [AK074675] |
| 379 | A_24_P389038 | WDR46 | TAGAGCCACCAGGTGAAGATGTTTGAGTTGGAGGGACGTAGAAGCCTCTGAGCAGTTGGGA | SEQ ID NO: 379 | Homo sapiens WD repeat domain 46 (WDR46), mRNA [NM_005452] |
| 380 | A_24_P388944 | CCDC86 | TTCTCCAGATGCTTCAGGACAAGAGCGGTGCGCACATCGTGGGAGCGGAAGATGAAGGAA | SEQ ID NO: 380 | Homo sapiens coiled-coil domain containing 86 (CCDC86), mRNA [NM_024098] |
| 381 | A_24_P391526 | MAGED1 | GCTGAGATTCATTGCAGAGAGGTTCAGAAAAGAGAGCCGGTGGTGACTGGACTGCACAGTTCAT | SEQ ID NO: 381 | Homo sapiens melanoma antigen family D, 1 (MAGED1), transcript variant 1, mRNA [NM_001005333] |
| 382 | A_24_P396197 | PRKCSH | AGGGGTCGCTGAAGGACATGGAGGAGTGCATCAGGAAACGTGGAGCAAGGAGATTTCTTTTG | SEQ ID NO: 382 | Homo sapiens protein kinase C substrate 80K-H (PRKCSH), transcript variant 1, mRNA [NM_002743] |
| 383 | A_24_P399365 | NUDT16L1 | GCCAGCTCCTGCTTTGCCCTCAAGGTGCTCAACATGATGCCGAGGAGAAGCTGGTTGAGG | SEQ ID NO: 383 | Homo sapiens nudix (nucleoside diphosphate linked moiety X)-type motif 16-like 1 (NUDT16L1), mRNA [NM_032349] |
| 384 | A_24_P40910 | RPS28 | GCGGCGGCCATGATGCTCCTGCACGCCGGTGTGCAGCGTATCAAGCTGGCCAGGGTCACCAAGG | SEQ ID NO: 384 | Homo sapiens ribosomal protein S28 (RPS28), mRNA [NM_001031] |
| 385 | A_24_P401521 | A_24_P401521 | CAACGTAAGTATCTCCTGGCTATGGTCAGCGTATTTTAAGCCGGGGGCCAGACGGTTCCTCCTG | SEQ ID NO: 385 | |
| 386 | A_24_P401637 | AK095727 | CGGGGGGCTGTCCCTTCTTACAAGGTCGGTCATGGCATATTTGATCTGGCGTTGCCAG | SEQ ID NO: 386 | Homo sapiens cDNA FLJ38408 fis, clone FEBRA2009029. [AK095727] |
| 387 | A_24_P405621 | NISCH | TGAAGTCGAGTGAGGAGTTGTTGTCCCCAGTGGTGAGAGCAGAGAGAGAAGCTCATCTCGCT | SEQ ID NO: 387 | Homo sapiens nischarin (NISCH), mRNA [NM_007184] |
| 388 | A_24_P409881 | LOC338756 | TGAAGGAGGTCCTCAGGAGAAACAGAGACCCATCTATCTTTGTCCAAAGCCAAGAAA | SEQ ID NO: 388 | PREDICTED: Homo sapiens similar to nucleolar protein 5A (LOC338756), mRNA [XM_291989] |
| 389 | A_24_P412976 | TMEM143 | TTATTGGTCTATCAATTTCTCCGGTCTCGTGTCCAAAGTAATAAATCATGTTTAATAAG | SEQ ID NO: 389 | Homo sapiens transmembrane protein 143 (TMEM143), mRNA [NM_018273] |
| 390 | A_24_P416289 | KIAA0195 | GGGGTAAGGCAGAGCAGACCCATTTCTGAACAGGGGGAGTTTGTAATCATGAATGTTCCAGGTTT | SEQ ID NO: 390 | Homo sapiens KIAA0195 (KIAA0195), mRNA [NM_014730] |
| 391 | A_24_P42136 | KRT18 | GCTCACAGAGGCTGAGAACAATACAGTCCAGTCGTCTTTGGAGATCGACCTGGAAGTCGTTGAGAAA | SEQ ID NO: 391 | Homo sapiens keratin 18 (KRT18), transcript variant 1, mRNA [NM_000224] |
| 392 | A_24_P42569 | BC030138 | AGCTTTGCTTGCTGATGAACAGTTCGACAGTGTTTGAGGTAAGGTAGTTTTTGTAATTACT | SEQ ID NO: 392 | Homo sapiens cDNA clone IMAGE:4335164, partial cds. [BC030138] |
| 393 | A_24_P44514 | CIB1 | GAACAGGAGAAGACCT | SEQ ID NO: 393 | Homo sapiens calcium and integrin binding 1 (calmyrin) (CIB1), mRNA [NM_006384] |
| 394 | A_24_P44891 | TNPO2 | GATGGTGCTCAAGAACGTGGTCGGAAATCATTAAGGAGAGCCGACACACCCAAGACAGTGCT | SEQ ID NO: 394 | Homo sapiens transportin 2 (importin 3, karyopherin beta 2b) (TNPO2), mRNA [NM_013433] |
| 395 | A_24_P460763 | AK022443 | GTGAGTAGCAGGCTACTTAAGATGGGTAGTGGGCTCAAATGTGAAATGGTATTGGGAGAT | SEQ ID NO: 395 | Homo sapiens cDNA FLJ12381 fis, clone MAMMA1002566. [AK022443] |

Fig. 1-23

| No. | Probe ID No. | Symbols of genes | Sequence | SEQ ID NO: | Descriptions of genes (letters and numbers within [ ] indicates GenBank accession No.) |
|---|---|---|---|---|---|
| 396 | A_24_P477127 | PKD1 | CCAGATAGGCAAGAACATCACGGAGACTCTGGTGTCCCTGAGGGTCGACAGTGTGGATGA | SEQ ID NO: 396 | Homo sapiens polycystic kidney disease 1 (autosomal dominant) (PKD1), transcript variant 2, mRNA [NM_000296] |
| 397 | A_24_P481783 | LOC390595 | GCATCTAGGCCAATGCCAGAGCCTGGCAACCATCCTAACTGTATTATTAAAGCCAAGTA | SEQ ID NO: 397 | Homo sapiens cDNA FLJ13740 fis, clone PLACE3000199 [AK023802] |
| 398 | A_24_P51360 | LARS | GAAAAGAGAAATAGAGCTGTATGGTTGCCCCCCTGATTTTCCAGATGAAGAAGGAAGA | SEQ ID NO: 398 | Homo sapiens leucyl-tRNA synthetase (LARS), mRNA [NM_020117] |
| 399 | A_24_P529786 | AK091744 | GATACATAACAGGGAATACAAATATTATCACATAGCGTGAATATTATTTGTGAATATTGAA | SEQ ID NO: 399 | Homo sapiens cDNA FLJ34425 fis, clone HHDPC2006297 [AK091744] |
| 400 | A_24_P348264 | AL512741 | AAGAATTGAGTTAGAACTGCCGTATAATGTAATGCAGAATATTCCAATAATGCCTAGG | SEQ ID NO: 400 | Homo sapiens mRNA; cDNA DKFZp667N064 (from clone DKFZp667N064) [AL512741] |
| 401 | A_24_P55719 | SURF5 | CTCAAGCCTTTGCGAAGCTAATGACCTGCCTGTGCGAAGCTTACGGGAGGCTGGACCT | SEQ ID NO: 401 | Homo sapiens surfeit 5 (SURF5), transcript variant b, mRNA [NM_133640] |
| 402 | A_24_P55971 | VEGFB | CAGTGGGCAGCCAGCCAAGTCGGGATGGAGATGGTGATGATCCGGTACCCAGCAGTCAGCT | SEQ ID NO: 402 | Homo sapiens vascular endothelial growth factor B (VEGFB), mRNA [NM_003377] |
| 403 | A_24_P5743 | ALDH16A1 | CTTGCACGAAGAGGTCCAGGACGATGTGGTATTTCGGATCAGCGCAGGGTTCCCAGTTTGT | SEQ ID NO: 403 | Homo sapiens aldehyde dehydrogenase 16 family, member A1 (ALDH16A1), mRNA [NM_153329] |
| 404 | A_24_P583330 | THC2657163 | GTAAGGAGTCTCATTATAATTTGTTGATGATAGTTTAAGTATAATGGGTATGCCATTAGGG | SEQ ID NO: 404 | |
| 405 | A_24_P592421 | AL050185 | TTTTTCTATACCCCTTTCATAGGACACGGTAATGAGATGCATATCATTTAAAAGCCCTGA | SEQ ID NO: 405 | Homo sapiens mRNA; cDNA DKFZp536A0423 (from clone DKFZp536A0423) [AL050185] |
| 406 | A_24_P598516 | AK021595 | CTGAGTTCCTGATGATGTTCCTGCAGTTATCCTTTTCCTTATGATTTAAAGTGTTTAGG | SEQ ID NO: 406 | Homo sapiens cDNA FLJ11533 fis, clone HEMBA1002679 [AK021595] |
| 407 | A_24_P611114 | hCG_1730474 | CTTTGTTATCAGGTAGAGTCGGCATGGCATGTTCATGGGCTAAGGACATGAGATTACTAGGCAAAT | SEQ ID NO: 407 | Homo sapiens cDNA FLJ10133 fis, clone HEMBA1003067 [AK000995] |
| 408 | A_24_P63608 | NOLA2 | ATTGAGGTATACTGCCATCTCCCAGTCATGTGAGGACCCAAATTTGGGTATGTGTAT | SEQ ID NO: 408 | Homo sapiens nucleolar protein family A, member 2 (H/ACA small nucleolar RNPs) (NOLA2), transcript variant 1, mRNA [NM_017838] |
| 409 | A_24_P636318 | LOC130074 | GGAAACTGCATGTTTCAGAAAGTTGTCTCTTTTTCCTAGTCATTATTGAAGAAGAGAG | SEQ ID NO: 409 | Homo sapiens mRNA; cDNA (LOC130074), mRNA [XM_001009993] |
| 410 | A_24_P636390 | AF009267 | TTGGATATACACTGTCTGTACGTGTGCGAAGTCCTGGAGTCGTGTGGGTGCTCATCAGCAG | SEQ ID NO: 410 | Homo sapiens clone FBA1 Cri-du-chat region mRNA, [AF009267] |
| 411 | A_24_P6381 | SERINC5 | GGTCATTTATGACGAAGAAGCCACCGTCTACATCTACTCCTAGTTCAGTCGTGTT | SEQ ID NO: 411 | Homo sapiens serine incorporator 5 (SERINC5), mRNA [NM_178276] |
| 412 | A_24_P65941 | C21orf96 | ATTGGGACTTCTCCCCAGGATGCTACTGTTTCCACCAATTCTCTAAACTTTGTAGGTGTAGGAGAA | SEQ ID NO: 412 | Homo sapiens cDNA FLJ20856 fis, clone ADKA01509, [AK024509] |
| 413 | A_24_P662427 | AK022109 | GAAGGCCCTACCCTAAGGCATGTTTCCACCAATTCTCTAAACTTTTCTTTTCTGATAGTC | SEQ ID NO: 413 | Homo sapiens cDNA FLJ12047 fis, clone HEMBB1001983, [AK022109] |
| 414 | A_24_P664995 | AK055641 | TAAGCATTTATGTGTTTCGATAACTAACTGACATGATGTGGAGACCTGATTCTCCCCCTGTT | SEQ ID NO: 414 | Homo sapiens cDNA FLJ31079 fis, clone NSYRA2001595, [AK055641] |
| 415 | A_24_P67784 | KIAA1666 | GGAAACTGAAGAGAGTCCCAGTGTGAGTCGAAAGATGATGATAGCAGCTCTGGACTATG | SEQ ID NO: 415 | Homo sapiens KIAA1666 protein, mRNA (cDNA clone IMAGE:4827837), complete cds, [BC035246] |

Fig. 1-24

| No. | Probe ID No. | Symbols of genes | Sequence | SEQ ID NO: | Descriptions of genes (letters and numbers within [ ] indicates GenBank accession No.) |
|---|---|---|---|---|---|
| 416 | A_24_P677890 | BC016384 | CCTTTGTAGGAGTTCCAGGTTTTTCAGAAGTGGTGAATCCATGGCTTGGCATTCCT | SEQ ID NO: 416 | Homo sapiens, clone IMAGE:4703872, mRNA. [BC016384] |
| 417 | A_24_P690273 | AK024900 | TAGCTGTGTGAGATAGTAGTATTGATGGTGAGAGGTGAATAGTAAAATATCTTGGAGGTA | SEQ ID NO: 417 | Homo sapiens cDNA: FLJ21247 fis, clone COL01205. [AK024900] |
| 418 | A_24_P69784 | PACS1 | AAGTTCCCTGACTGAAGACCTATCAGAAGTTTATTCCGTTGATTGGGGTGGTGAAGGTG | SEQ ID NO: 418 | Homo sapiens phosphofurin acidic cluster sorting protein 1 (PACS1), mRNA [NM_018026] |
| 419 | A_24_P700170 | A_24_P700170 | ACGGGCTGAACATCATCTCTAAGCTGGAGTGTGTGAACGAGAGGTGATTGGATCCGGTCAGC | SEQ ID NO: 419 | |
| 420 | A_24_P708901 | BF895757 | TCTGGGGCTCTGGAGAGTGACAACAACACAGCGCTTTGGCTTTCTAAGAAGTTGATCTAC | SEQ ID NO: 420 | BF895757 RC3-MT0162-221100-012-h03 MT0162 Homo sapiens cDNA, mRNA sequence [BF895757] |
| 421 | A_24_P713185 | THC2595309 | AATATGACTAGCTTACACAATAGGTCACATAGTAGAGATACTGTTTACGGAGTCCACTTA | SEQ ID NO: 421 | HLMITCSEQ Hylobates lar complete mitochondrial DNA sequence, partial (3%) [THC2595309] |
| 422 | A_24_P713312 | THC2639056 | TTTATATGTCGGATGCTCCATGTTAAGGATTAAGAGGGTAATTAATAGTAATGTATGTGGA | SEQ ID NO: 422 | ALU8_HUMAN (P39195) Alu subfamily SX sequence contamination warning entry, partial (10%) [THC2639056] |
| 423 | A_24_P728115 | AK024937 | ACTCGATAGTACTAGTACTACTAGTTTAGTGAGTTTGAAATCTGTTGGAGAGCTATGTAAGTACCA | SEQ ID NO: 423 | Homo sapiens cDNA: FLJ21284 fis, clone COL01911 [AK024937] |
| 424 | A_24_P782337 | AK026477 | AGTCAAAGACCTTGCTGGTGACAATGTAAGTTGTTAGGATTCGTGAATGGAAGTTATA | SEQ ID NO: 424 | Homo sapiens cDNA: FLJ22824 fis, clone KAIA3991. [AK026477] |
| 425 | A_24_P801451 | EHMT2 | AAATGGGGCCATCGGACGAAGAGGAAGAATCATTCTGCCGGGACGTGGGTGGGGGCTATGA | SEQ ID NO: 425 | Homo sapiens euchromatic histone-lysine N-methyltransferase 2 (EHMT2), transcript variant NG36/69a, mRNA [NM_006709] |
| 426 | A_24_P83183 | WHSC2 | GACACTTTTGGGACTCAAGGTTACATTTTGAATGTAGTAAGTAAATTAACCAAAAAAGT | SEQ ID NO: 426 | Homo sapiens Wolf-Hirschhorn syndrome candidate 2 (WHSC2), mRNA [NM_005663] |
| 427 | A_24_P84984 | TTC3 | TGCGCGTTCAAGCCAGTCTACAGTCTCCAAAAAGCGTTCAATAGTATATAAGCACCTGTCAGT | SEQ ID NO: 427 | Homo sapiens tetratricopeptide repeat domain 3 (TTC3), transcript variant 1, mRNA [NM_003316] |
| 428 | A_24_P85283 | POLR3A | AAGATGAACCTTTGGAGTTCTGGACAAGATCAAAGCAGTCTTCCGGTGTC | SEQ ID NO: 428 | Homo sapiens polymerase (RNA) III (DNA directed) polypeptide A, 155kDa (POLR3A), mRNA [NM_007055] |
| 429 | A_24_P87763 | EEF2 | CATGTTTGGTCAAGGCCTATCTGCCCGTCAAGCAGTGCTTTGGCTTCACCGGTGACCT | SEQ ID NO: 429 | Homo sapiens eukaryotic translation elongation factor 2 (EEF2), mRNA [NM_001961] |
| 430 | A_24_P87824 | ZMYND8 | GAGGTCAGCTAGGAAAAGCAAGAGAGTGGGCTCGACCGGTTGACCTTCTGGCTCCAGAGA | SEQ ID NO: 430 | Homo sapiens zinc finger, MYND-type containing 8 (ZMYND8), transcript variant 2, mRNA [NM_012408] |
| 431 | A_24_P883109 | AL833452 | GGGCAACTAGTCATCTACTAGTTAGCTTAGTAAGGTAAGGATTAAATCTAAGAAATAGGA | SEQ ID NO: 431 | Homo sapiens mRNA; cDNA DKFZp686E08116 (from clone DKFZp686E08116). [AL833452] |
| 432 | A_24_P898583 | TRIM26 | TTGACGACGATTGTCTCAGAGCTGCCCACTTTGTGTGTGCAGATGCTGCCTAGTCAGA | SEQ ID NO: 432 | Homo sapiens tripartite motif-containing 26 (TRIM26), mRNA [NM_003449] |
| 433 | A_24_P910490 | BX099367 | AGGGGCAGAGTTGCAGACAGCCTGGGGTACGAGAGTGACAGCCTGTCTGTAGAAAAGTA | SEQ ID NO: 433 | BX099367 Soares_fetal_liver_spleen_1NFLS_S1 Homo sapiens cDNA clone IMAGp998O05977, mRNA sequence [BX099367] |
| 434 | A_24_P914102 | A_24_P914102 | TTAGTAGACCCTAGATTTCTGTACAAATGTAAAATGTATTTTAGTGTTGAAAATCAG | SEQ ID NO: 434 | |

Fig. 1-25

| No. | Probe ID No. | Symbols of genes | Sequence | SEQ ID NO. | Descriptions of genes (letters and numbers within [ ] indicates GenBank accession No.) |
|---|---|---|---|---|---|
| 435 | A_24_P916606 | AA435826 | GGAAATGGTCTTCGGGTGGACGATCAACGACAACCAGTGGGTGACCTTCCAGAAAGTGGT | SEQ ID NO: 435 | AA435826 zt80a02.s1 Soares_testis_NHT Homo sapiens cDNA clone IMAGE:728819 3' similar to TR:G790819 G790819 POLYCYSTIC KIDNEY DISEASE-ASSOCIATED PROTEIN. ; mRNA sequence [AA435826] |
| 436 | A_24_P921402 | THC2484646 | AGTGTTGGGCATCCACTTCAGTAGAATTTGAGGTGAGCAAATATGATGAATCATTCCAGAAA | SEQ ID NO: 436 | |
| 437 | A_24_P925884 | SIRT3 | GGAAATTGGTGAACCTAGGAAAACGTGTTGAATTGTAAAAAGAATGAAGTTAGTTTGTAACGC | SEQ ID NO: 437 | Homo sapiens sirtuin (silent mating type information regulation 2 homolog) 3 (S. cerevisiae) (SIRT3), transcript variant 1, mRNA [NM_012239] |
| 438 | A_24_P924462 | PRKCZ | GCATGAGATGAAAGATGATATTTTAATTGTATCATTGAGGCATAGTCTTTCGAACGACAGC | SEQ ID NO: 438 | Homo sapiens mRNA, chromosome 1 specific transcript KIAA0505. [AB007974] |
| 439 | A_24_P92952 | ARID1A | ATCACCGTTGATGAACTGATGATTGGTTTCAGAAGTCATTTGTGATGTACTGTTTTTGATTGG | SEQ ID NO: 439 | Homo sapiens AT rich interactive domain 1A (SWI-like) (ARID1A), transcript variant 1, mRNA [NM_006015] |
| 440 | A_24_P930062 | CXXC5 | GGGCTTTCCCATCAACCCAAGCGTGTTGATTATGAGCCGCGGCAGGTGTGTTCCTGGCGG | SEQ ID NO: 440 | Homo sapiens CXXC finger 5 (CXXC5), mRNA [NM_016463] |
| 441 | A_24_P930337 | THC2503773 | AGCAAGTGGATGACCGACACCCAAAATAGAGTTGAAGAATGTAATTTAAAATGTAGCATAG | SEQ ID NO: 441 | |
| 442 | A_24_P930391 | AK022351 | AAGTGGGTTTAATTTCCTTTTCATGAAAGGAAAGATTAGGTTTGATGCAAACACTTGGTC | SEQ ID NO: 442 | Homo sapiens cDNA FLJ12299 fis, clone MAMMA1001788. [AK022351] |
| 443 | A_24_P930707 | THC2663601 | ATGTTAGTTACTGGCTTGGCATGTGTACCCACACAGCTGGTTTGCACAGTTTAAAAGAA | SEQ ID NO: 443 | BX098637 BX098637 Soares fetal liver spleen 1NFLS Homo sapiens cDNA clone IMAGp998F16386 ; IMAGE:200047. mRNA sequence [BX098637] |
| 444 | A_24_P932418 | AP2A2 | CGGGCGTGCAGAGGGGCCCTCAGTGTGGCACTCCTGGTCAAAGAAAAATAAAGGCTAGAA | SEQ ID NO: 444 | Homo sapiens adaptor-related protein complex 2, alpha 2 subunit (AP2A2), mRNA [NM_012305] |
| 445 | A_24_P933514 | AK094334 | CGTAGGTGACACTGTAGGAATTTCCTTAGGTGGCCATTATATACTACGGTGAACTGTGGC | SEQ ID NO: 445 | Homo sapiens cDNA FLJ37015 fis, clone BRACE2010208. [AK094334] |
| 446 | A_24_P934861 | A_24_P934861 | GGAAGGTATCAACGACCAGCCAAATTCGAGTTGTGGGAAAATAGTGGACCAGATGGTCGCATGG | SEQ ID NO: 446 | |
| 447 | A_24_P935682 | AY358248 | AGTCAGTAATCAGCATTCAATCAATATGAGGCTCTAACATGATGGTTGAAGTTATGCAAC | SEQ ID NO: 447 | Homo sapiens clone DNA166629 MRSS6228 (UNQ6228) mRNA, complete cds. [AY358248] |
| 448 | A_24_P93703 | LOC440104 | GGGTGGGCACTAATTCCTCGTTAACCAGAACTTTGTTCGAGGAGCTGACCCATTCTAACT | SEQ ID NO: 448 | Homo sapiens cDNA FLJ36942 fis, clone BRACE2005518. [AK094261] |
| 449 | A_24_P940310 | ENST00000270201 | AGGGTGACCTCCCATCCAGGGCTGTATCTCAGTGTAGTTGATTTATATCCATAGCCCAA | SEQ ID NO: 449 | Nucleolar preribosomal-associated protein 1 (Fragment). [Source:Uniprot/SWISSPROT:Acc:Q60287] [ENST00000270201] |
| 450 | A_24_P940551 | FLJ38723 | TTCCAGTTACCCCTTTAGCCTTACAGTAGCCAAAATAAGACGCGTATCTAGTGAGGGAGA | SEQ ID NO: 450 | Homo sapiens hypothetical protein FLJ38723 (FLJ38723), mRNA [NM_173605] |
| 451 | A_24_P942604 | SMC1A | GGGGTGACAAGATAAGCGCAGGCGTCTAGAGGCTGGCTTTGGATCATGAACCGATTTTCAAGTTT | SEQ ID NO: 451 | Homo sapiens structural maintenance of chromosomes 1A (SMC1A), mRNA [NM_006306] |

Fig. 1-26

| No. | Probe ID No. | Symbols of genes | Sequence | SEQ ID NO: | Descriptions of genes (letters and numbers within [ ] indicates GenBank accession No.) |
|---|---|---|---|---|---|
| 452 | A_24_P942893 | TEX261 | GATGCAGTGGCTCTCCATTGCCACTCTGATTCCTCGTTCTTTTG GTCACAGAGAAAGGG | SEQ ID NO: 452 | Homo sapiens testis expressed 261 (TEX261), mRNA [NM_144582] |
| 453 | A_24_P945262 | AK097139 | ACAGTCTGTGTATACCGTGGTCAGAGTGTGGCTGAGAAGACATG AGATGGTAAAGAATT | SEQ ID NO: 453 | Homo sapiens cDNA FLJ39820 fis, clone SPLEN2010625 [AK097139] |
| 454 | A_24_P96234 | QTRT1 | TGCCGAAGGAGAAGCCCCGATATCTGATGGGAGGGTTGGCTATCCGA CTGATCTGGTAGTCT | SEQ ID NO: 454 | Homo sapiens queuine tRNA-ribosyltransferase 1 (tRNA-guanine transglycosylase) (QTRT1), mRNA [NM_031209] |
| 455 | A_24_P96325 | ZGPAT | CCAGGTGGCTCGGAATGTGTTTGACTTCCTCAATGAAAAGCTGGAA GGTCAGGGCTCCTGGG | SEQ ID NO: 455 | Homo sapiens zinc finger, CCCH-type with G patch domain (ZGPAT), transcript variant 1, mRNA [NM_032527] |
| 456 | A_32_P10633 | BC022417 | GTTGATGTTTAAACAGGAGCTCCACGAGTTCAGCCCTGTGTG CATTCCTCATGTAT | SEQ ID NO: 456 | Homo sapiens cDNA clone IMAGE:4243762, partial cds [BC022417] |
| 457 | A_32_P111394 | THC2643957 | GAATACAGTGTTCCTTTTCATCCCATATTTGACTGAACGTAAGAC ACATCAATTATAAGG | SEQ ID NO: 457 | |
| 458 | A_32_P112546 | LOC649344 | AGGGAGGTCACTATGCAGGGTAGCACTGGGAACAGGAGAGCCAACC TGAGGCTCAGGCCTA | SEQ ID NO: 458 | PREDICTED: Homo sapiens similar to Keratin, type II cytoskeletal 8 (Cytokeratin-8) (CK-8) (Keratin-8) (K8) (LOC649344), mRNA [XR_018597] |
| 459 | A_32_P116967 | THC2713256 | AAACATTAGGTAGGAGGTTGTAGAGGATATATATTTAGGGTCATGAT GTCCTTCTGTTGGC | SEQ ID NO: 459 | BE147120 PM2-HT0224-221099-001-B10 HT0224 Homo sapiens cDNA, mRNA sequence [BE147120] |
| 460 | A_32_P118220 | AK091308 | GAATTGTACACACTGTGGGGTTTGGGAGGTGGATATTAATATCAT TATGGGCTTTCTCAC | SEQ ID NO: 460 | Homo sapiens cDNA FLJ33939 fis, clone DFNES2006944 [AK091308] |
| 461 | A_32_P11899 | C12orf65 | AAGGACTACCGTGGACTGGACTGGATTCCTTGGATGAGAATGAACTCGAA GAGGAGTTTGTGAAA | SEQ ID NO: 461 | Homo sapiens chromosome 12 open reading frame 65 (C12orf65), mRNA [NM_152269] |
| 462 | A_32_P120454 | THC2642550 | ACACAATGAGAATGACTGGACTGGATGCTTCATCTGTTTATTGGAAGCT CAGGACAGGGTATGA | SEQ ID NO: 462 | |
| 463 | A_32_P121755 | THC2672892 | AAACCCTCCTGCTCCAGGTGGTTCCCGCTGGCATTGTAGCGTGG GATTCCGAGGCCAGA | SEQ ID NO: 463 | Q2TXF9_ASPOR (Q2TXF9) Predicted protein, partial (5%) [THC2672892] |
| 464 | A_32_P124493 | LOC642626 | AAAGAAAAGAGGGGTTAGAGATCATTGGACATGAGAAATATTCCC AGCAGTAACCACTTC | SEQ ID NO: 464 | Homo sapiens cDNA FLJ39589 fis, clone SKMUS2008607 [AK096908] |
| 465 | A_32_P124538 | THC2758091 | AGTTAGGGTTGGTCTTGATTCCCGAAGAGCGTCTCATCTAACCAG GTCTTAAACCAGAC | SEQ ID NO: 465 | |
| 466 | A_32_P125589 | THC2649341 | CGCTCTATCCCTTGCTTTAGCCTTTTGAATGAAAGTGAGATGTCT CATCAGCTCAGATAG | SEQ ID NO: 466 | |
| 467 | A_32_P12703 | THC2697162 | TTGAAAGGGAAAGAGTATAGAGGGGGAAGTGCCAGACTAAACGAATC CTAAGTAAATAGGGT | SEQ ID NO: 467 | |
| 468 | A_32_P127583 | THC2650423 | AGAGAGGCCTTCTATGTACATGACGTGTTCGTCCGTTAGCTAGAT TAGTTCATCCAACTG | SEQ ID NO: 468 | |
| 469 | A_32_P131294 | BM854107 | AGTAGGGAAAAAAGGTTTGTTCCTTAATTAGAGGTAGTGTGGGAAA TGCTGCACTTGTGC | SEQ ID NO: 469 | K-EST0136406 S22SNU16n1 Homo sapiens cDNA clone S22SNU16n1-145-F11 5', mRNA sequence [BM854107] |
| 470 | A_32_P136586 | BF928446 | CTGCCCAAATGGTGAGAATAAAAAGGAAAGCATTCTGGGCTTTCAG GTTTTTTCAAAGTCAC | SEQ ID NO: 470 | BF928446 IL2-NT0200-061200-269-F07 NT0200 Homo sapiens cDNA, mRNA sequence [BF928446] |

Fig. 1-27

| No. | Probe ID No. | Symbols of genes | Sequence | SEQ ID NO. | Descriptions of genes (letters and numbers within [ ] indicate GenBank accession No.) |
|---|---|---|---|---|---|
| 471 | A_32_P:38178 | BE835321 | AGATTTGCCTTAATCCCAGACAGTATGAGATACAATTCTGGGACTTTGTTGGTAACC | SEQ ID NO: 471 | BE835321 RC5-FN0022-300600-022-G12 FN0022 Homo sapiens cDNA, mRNA sequence [BE835321] |
| 472 | A_32_P:145385 | AK001118 | CCGGAATTAACAGTCGAGGAGGAAGCTTAAATTTCCAGCTTTTTGATTCTCAGGAAATGAAGAT | SEQ ID NO: 472 | Homo sapiens cDNA FLJ10256 fis, clone HEMBB1000G370. [AK001118] |
| 473 | A_32_P:146844 | THC2639689 | CCTGTGGGCTGATCCAGACTGAGAGTTGAAGTTTGTGTGCATCATCATGTGCATTAA | SEQ ID NO: 473 | |
| 474 | A_32_P:51244 | AK022268 | GTAGTCAGATGTCAGAGAGTTATTTCATGTGTAACGTTTTGAACTGTTGATGTCTT | SEQ ID NO: 474 | Homo sapiens cDNA FLJ12206 fis, clone MAMMA1000941. [AK022268] |
| 475 | A_32_P:151544 | KRT18 | GAGGAGTTCATTCTTGGTGATGCCTTGGACAGCAGCAAACTCCATGCAAACGATCCAAAAG | SEQ ID NO: 475 | Homo sapiens keratin 18 (KRT18), transcript variant 1, mRNA [NM_000224] |
| 476 | A_32_P:155091 | ATXN2L | GAGTGACGCTGTGTGAGAGACAAGAGATGCCCGCATGAGGATGGCTGGACAAGAGTTTTA | SEQ ID NO: 476 | Homo sapiens ataxin 2-like (ATXN2L), transcript variant B, mRNA [NM_145714] |
| 477 | A_32_P:155416 | PRNPIP | TAGATCCAAAGGTCAAGTCAATTTTGTCACCTGTGGAGACTGGGACTTAAAAGTCATGC | SEQ ID NO: 477 | Homo sapiens prion protein interacting protein (PRNPIP), mRNA [NM_024066] |
| 478 | A_32_P:155841 | AL079294 | CCTTCGTGTTTATATACCTGGAGTTCTTCTTGTTAAGGAAGAATGGAAATGCAAA | SEQ ID NO: 478 | Homo sapiens mRNA full length insert cDNA clone EUROIMAGE 362780 [AL079294] |
| 479 | A_32_P:156171 | THC2634329 | TCGTATGTGGAGTCTGATTTAAGGGGTATAAGGCCTGTGTCTTCCTACCCAATAGAGGTT | SEQ ID NO: 479 | |
| 480 | A_32_P:159176 | THC2744561 | CAGAAGAAGATAGAGGAGCACATGTCACCAAAGACAAGTGACCTAACTCTTAAATCAT | SEQ ID NO: 480 | |
| 481 | A_32_P:162395 | THC2673084 | AAGGTGCTTTATTTGTGGGCAAATAGTAGTAGGTATTAGATACGTTGGTAGGCCAAGAA | SEQ ID NO: 481 | |
| 482 | A_32_P:163458 | hcag7.1017 | AGATGTCGATTTCAGGAGGAGTCTGAATGCTAATGGCAGACATCAGGAAGGAGG | SEQ ID NO: 482 | Homo sapiens similar to Williams Beuren syndrome chromosome region 19 (MGC57359), mRNA [NM_0010043511] |
| 483 | A_32_P:164573 | THC2611661 | AGCTGTTTTCTATTAACACTCAGGAGTACTCTGAGACGTTGAAATTTTCAGTGCAAATGCAAAATC | SEQ ID NO: 483 | RRT2_SPIMX (P42544) Chloroplast 30S ribosomal protein S12, partial (11%) [THC2611661] |
| 484 | A_32_P:16452 | THC2567672 | GGCCAGAAGAATGGGAGGACAGTGATGAGGAATAATTTTCAGTCTTTATCATTTTATAT | SEQ ID NO: 484 | W18193 IMAGE:20964 Soares infant brain 1NIB Homo sapiens cDNA clone IMAGE:20964, mRNA sequence [W18193] |
| 485 | A_32_P:165990 | AK094623 | GTGGGGACACAGAGAGTGAGCATTCTTGCCATGGGTGATTAATTTTGGGCCTCAGTTT | SEQ ID NO: 485 | Homo sapiens cDNA FLJ37304 fis, clone BRAMY2018070. [AK094623] |
| 486 | A_32_P:166356 | THC2655727 | GTCGTCGTTGGATTTTAGCCACAGTGAAAACAAGGGTGAATTGCTTAATGGTTGCAATGGTG | SEQ ID NO: 486 | |
| 487 | A_32_P:167863 | THC2697442 | AGGTAATTGGGGGTATGAGTTCAGTCACTTTTGAAATATTGGAAGTAAATTGTCTCATT | SEQ ID NO: 487 | |
| 488 | A_32_P:169316 | A_32_P169316 | AGGAAGTGGAAGCATAGTCTTAGCGCAGCTAGATGCAAAGCAGGTGTTTTGAATATAAC | SEQ ID NO: 488 | |
| 489 | A_32_P:70811 | KIAA1509 | CAGTGTGAGGAGGAAAGAGGGAGTTCATTGAAGAGAATCAAACAGAGTGGACATTGACGACCCAG | SEQ ID NO: 489 | Homo sapiens KIAA1509 (KIAA1509), mRNA [NM_0010804141] |
| 490 | A_32_P:176609 | ZNF609 | ATGATGGCTCTGATGGACGCCTCAGTGATGATGGAATGAAACAAGCAATGATGCCTTTGATT | SEQ ID NO: 490 | Homo sapiens zinc finger protein 609 (ZNF609), mRNA [NM_015042] |

Fig. 1-28

| No. | Probe ID No. | Symbols of genes | Sequence | SEQ ID NO: | Descriptions of genes (letters and numbers within [ ] indicates GenBank accession No.) |
|---|---|---|---|---|---|
| 491 | A_32_P179526 | ZBTB20 | TTGAAGTTGGAAATCCAAGGGAATCTAAAACCGACCAGATGTTTCTGCTGCTGGAAAGG | SEQ ID NO: 491 | Homo sapiens zinc finger and BTB domain containing 20, mRNA (cDNA clone IMAGE:4291354), partial cds. [BC010934] |
| 492 | A_32_P181564 | THC2606490 | TTATAAGTGCCGTTAATATCTCCAGTATCTCCAGAGAGAATTTTGTCTTGAAGGTTGGC | SEQ ID NO: 492 | |
| 493 | A_32_P184039 | A_32_P184039 | ATCATTGTTAGTCTTGGCCAAAAATAGTTGTTATGATGATGGGTAATAACTGACCAGC | SEQ ID NO: 493 | |
| 494 | A_32_P185361 | AL109784 | GGAAGGCTGTTTGCTGAATAAGACAAAGATACAGACAGATGAAAGTAAAGGATGTGGGCGT | SEQ ID NO: 494 | Homo sapiens mRNA full length insert cDNA clone EUROIMAGE 122871. [AL109784] |
| 495 | A_32_P187304 | A_32_P187304 | ATAAATGAGAGAACATTCAGATAGAACAAAGGTGTGATGGAGGCTCTCACCAGCTTAACC | SEQ ID NO: 495 | |
| 496 | A_32_P192545 | TCEAL6 | ATTTGCCAGGGCGAATGCTTAAGCTTAAGCTGATATATTTTGCTTTAGATGTGAATGTCG | SEQ ID NO: 496 | Homo sapiens transcription elongation factor A (SII)-like 6 (TCEAL6), mRNA [NM_001006938] |
| 497 | A_32_P194072 | DKFZP434B0335 | ATGGGGCTCAGGGGCGTCTTCTTACCAGTGTGCAGTGAGCAATTCTCAGAGGAGGAGTTGAAA | SEQ ID NO: 497 | Homo sapiens DKFZP434B0335 protein (DKFZP434B0335), mRNA [NM_015395] |
| 498 | A_32_P196297 | THC2652466 | CCTTTCACAAGACTGTAAGCCTTACCCAAGACATTAATTTTTGCCCATAGGGGCGTGTT | SEQ ID NO: 498 | Q9BHM3_PARTE (Q9BHM3) Cyclophilin-RNA interacting protein, partial (4%) [THC2652466] |
| 499 | A_32_P198845 | THC2651047 | GCCAACCAATCCAACAACTGTCTTCACTTGACAGTGACAGTGCTTCATAGGTAACATTAAGC | SEQ ID NO: 499 | |
| 500 | A_32_P199917 | BM684461 | ATATGTTAAGAGTCTAAACATTCAAGAGACGAGGCAAGAAAGCCAGTGCAGCATGTGA | SEQ ID NO: 500 | UI-E-EJ0-aip-o-14-0-UI.s1 UI-E-EJ0-aip-o-14-0-UI 3', mRNA sequence [BM684461] |
| 501 | A_32_P200429 | A_32_P200429 | GGAGCAGGCAGTTCACATCTGGACCATTCTTAGCACAGGAAGGCAACTCATTAAAGATGTTA | SEQ ID NO: 501 | |
| 502 | A_32_P203815 | SPECC1L | GATTGCCTTTTGCCTGGTGTCAATAGGATCGTTAGGAGACAGTGTGGGCTTAGGAATGACTA | SEQ ID NO: 502 | Homo sapiens SPECC1-like (SPECC1L), mRNA [NM_015330] |
| 503 | A_32_P204565 | A_32_P204565 | CAAGGATCAGATGATACAGCGGGATGTGTGTTTCAGTGTGAGTGAGAAAGATTGTTCCAGTGA | SEQ ID NO: 503 | |
| 504 | A_32_P205323 | tcag7.1017 | TCATCTAGAAGAAGCGGTGGACGATTCTTGACAGAGCTGAATACAGTGATGACGTTGTCCTC | SEQ ID NO: 504 | Homo sapiens similar to Williams Beuren syndrome chromosome region 19 (MGC573599), mRNA [NM_001004351] |
| 505 | A_32_P208039 | AL049390 | TTTCATGTTTGAGCATTCAGATTGGGCTTTATTTCTCAAGGCATGTGCAAAACGTCACAA | SEQ ID NO: 505 | Homo sapiens mRNA; cDNA DKFZp586O1318 (from clone DKFZp586O1318) [AL049390] |
| 506 | A_32_P209582 | THC2663167 | CAATGTAAAGCCAGAATATCAACGTCGTTTTGTCAAGATTTTCAAACCTATTTTGGCTGAT | SEQ ID NO: 506 | ALU1_HUMAN (P39188) Alu subfamily J sequence contamination warning entry, partial (5%) [THC2663167] |
| 507 | A_32_P211048 | A_32_P211048 | GTTCACAAAACACCGTAGGTATTCAGTTCATATTGGAATGAATGAGAAAATGAGACAG | SEQ ID NO: 507 | |
| 508 | A_32_P213609 | THC2663555 | GATTTGTTCCAGTGTTGGAGGCCTTTTAATGAAAATTCTCAACACCTACACTTGGAAAAA | SEQ ID NO: 508 | |
| 509 | A_32_P214054 | THC2755661 | GGCTTATGTCGTTTGTTTAACAGTTGGGGTTTGGCTTCCATAGCAATGATTTCAAAT | SEQ ID NO: 509 | |

Fig. 1-29

| No. | Probe ID No. | Symbols of genes | Sequence | SEQ ID NO. | Descriptions of genes (letters and numbers within [ ] indicates GenBank accession No.) |
|---|---|---|---|---|---|
| 510 | A_32_P216122 | AK130891 | TTCTTCCTCTATATGTTTGGGAGGCATTCAATGAAGAATTGAGTAC ACATATATGGGTC | SEQ ID NO: 510 | Homo sapiens cDNA FLJ27381 fis, clone UBA07680. [AK130891] |
| 511 | A_32_P220567 | | GGAAAGTGAAAAATAGTTCCTATGGTGGAAGGTGGGGGTGAGAG ATAGCTCGTCTGAAA | SEQ ID NO: 511 | |
| 512 | A_32_P220580 | AK124352 | ACCAGGAGAATCAGGACTACTATCTTTTGGGAAATATAAGCTGGGTCC TTATGATGAGTCGG | SEQ ID NO: 512 | Homo sapiens cDNA FLJ42361 fis, clone UTERU2025366. [AK124352] |
| 513 | A_32_P224622 | SLC25A23 | CTTACATTCTGCACTTCATAGTTGGATTCTGAGGTTAGGATCATC TGGAGACCGCATGGA | SEQ ID NO: 513 | Homo sapiens solute carrier family 25 (mitochondrial carrier; phosphate carrier), member 23 (SLC25A23), mRNA [NM_024103] |
| 514 | A_32_P225525 | AA971667 | GGCAAATGCTGGTCCTTTTTCGAGAGAATGAAAAGCATCTTTTAA ATCATCCTCATTTT | SEQ ID NO: 514 | AA971667 op85c06.s1 Soares_NFL_T_GBC_S1 Homo sapiens cDNA clone IMAGE:1583626 3', mRNA sequence [AA971667] |
| 515 | A_32_P227110 | THC2512148 | TAAAGAAATCGTTTTGATTCAGCGCCACTGTGTATTGATAATGGCT TATTTATTACAATCA | SEQ ID NO: 515 | |
| 516 | A_32_P227657 | BX114900 | GTCGCAGAGCCTGAAGACAGAAGCTTCCTGAAGACTTAGTCAGCGCGTC TTTGACGGTAAGGAC | SEQ ID NO: 516 | BX114900 Soares_fetal_liver_spleen_1NFLS_S1 Homo sapiens cDNA clone IMAGp998L191010, mRNA sequence [BX114900] |
| 517 | A_32_P232851 | THC2645586 | CTTTGAAAAGGATATCCTTCACATTCGTTTTCCAGAAAATTGAGG TCACTGACTTATTTC | SEQ ID NO: 517 | Q9P3E1_HUMAN (Q9P3E1) Related to rna-binding protein fus/tls, partial (5%) [THC2645586] |
| 518 | A_32_P234661 | THC2650029 | AACGAAGAATGGTAAGTAAGGTCAGGGTTTGATTTGTCCTTGCCA GCAAAAACACTTAGG | SEQ ID NO: 518 | Q98PH0_PSEPK (Q98PH0) Dipeptide ABC transporter, permease protein, partial (5%) [THC2650029] |
| 519 | A_32_P29442 | AI911989 | ATAGTTAGATGTGGGACATGAGCTAGTGTTTGTAGATGTGACAG ACCTTGTTCTGTGGAT | SEQ ID NO: 519 | AI911989 wd78e07.x1 NCI_CGAP_Lu24 Homo sapiens cDNA clone IMAGE:2337732 3', mRNA sequence [AI911989] |
| 520 | A_32_P3342 | THC2676548 | TATAGCATTTTCTGAAGATCATGTTGTAGTCTTGTTCGTGTAGA TGATTTGGTCAACAG | SEQ ID NO: 520 | ALU7_HUMAN (P39194) Alu subfamily SQ sequence contamination warning entry, partial (19%) [THC2676548] |
| 521 | A_32_P38782 | BX113029 | CATCGTGAGTGGTAGAAGTCCAGTGCCCTTCTCTACCCACAGCC ACTCACACACCCAG | SEQ ID NO: 521 | BX113029 Soares_fetal_liver_spleen_1NFLS_S1 Homo sapiens cDNA clone IMAGp998E061010, mRNA sequence [BX113029] |
| 522 | A_32_P402521 | PRPF8 | GTCCTCGTGGAACTACAACTTCATGGGTGTTCGGCATGACCCCAA CATGAAATATGAGCT | SEQ ID NO: 522 | Homo sapiens PRP8 pre-mRNA processing factor 8 homolog (S. cerevisiae) (PRPF8), mRNA [NM_006445] |
| 523 | A_32_P40673 | A_32_P40673 | CATCACACTTGATATTAGGACAGCCTACGTACTTGTTGAGTGTC ACAGCCTGATATGTA | SEQ ID NO: 523 | |
| 524 | A_32_P430359 | DDX54 | CCTGAGTGCCTCAGGGTTTGGGAATGAATGGAATTTTAAAGTAATAAA TCTTTATTGAGGAGT | SEQ ID NO: 524 | Homo sapiens DEAD (Asp-Glu-Ala-Asp) box polypeptide 54 (DDX54), mRNA [NM_024072] |
| 525 | A_32_P43878 | DB111455 | ATGTGAGAAAGGTTCTTTAAGGTTTTAAGGAGAAGTTCGAATGTG AGCTCTTACTTGGGA | SEQ ID NO: 525 | DB111455 THYMU2 Homo sapiens cDNA clone THYMU2015028 5', mRNA sequence [DB111455] |
| 526 | A_32_P46404 | AK092468 | CTCTATGCCCAACCTGCTTTTTGGATAAATACTTATGATTCAGCC AAGAGGAAAAGGCACT | SEQ ID NO: 526 | Homo sapiens cDNA FLJ35149 fis, clone PLACE6010485. [AK092468] |
| 527 | A_32_P514790 | UNK | AGCACGAAAGGGCTTTCAATGAATTAAGTGAAAAACTTTTTCCTTT TTTCAAAAATGCAA | SEQ ID NO: 527 | Homo sapiens unkempt homolog (Drosophila) (UNK), mRNA [NM_001080419] |

Fig. 1-30

| No. | Probe ID No | Symbols of genes | Sequence | SEQ ID NO: | Descriptions of genes (letters and numbers within [ ] indicates GenBank accession No.) |
|---|---|---|---|---|---|
| 528 | A_32_P52206 | TYW1 | GAGGAAGCATGCATTGATTTTCGATTTGGCAAAACTTACCTGAAGT GGTATGAGAGATGCG | SEQ ID NO:528 | Homo sapiens tRNA-yW synthesizing protein 1 homolog (S. cerevisiae) (TYW1), mRNA [NM_018264] |
| 529 | A_32_P55161 | CENTG2 | AAAGAAGGGTTACAGATCATTGGCACATGGACAAAATATTCCGACCAGT AAACACTTCGATTAA | SEQ ID NO:529 | Homo sapiens centaurin, gamma 2 (CENTG2), transcript variant 1 mRNA [NM_001037131] |
| 530 | A_32_P5542 | AF131782 | GAGGCTCTTACGGATCTAACTTCGAGTTAAGGTGGGAGGAAATGTCTT ATAAATAAACAACAG | SEQ ID NO:530 | Homo sapiens clone 24941 mRNA sequence. [AF131782] |
| 531 | A_32_P55427 | THC2701763 | CACTTTATGCCTATCCTGTAAAACAAACAAAGTAGAAATTGAGAGAGTA GATTCCATAGCTTGG | SEQ ID NO:531 | Q9F8M7_CARHY (Q9F8M7) DTDP-glucose 4,6-dehydratase (Fragment), partial (11%) [THC2701763] |
| 532 | A_32_P55987 | THC2639487 | GAAAGAACCCAGTGCTGGTGTAAGGAAGTGTAATAGCTGCTCAGTA CATAGTAAATGCTAT | SEQ ID NO:532 | Q7G6E4_AMOGA (Q7G6E4) ENSANGP00000015281 (Fragment), partial (6%) [THC2639487] |
| 533 | A_32_P57140 | JMJD1C | GAGTGGCTTAAAGTTTATGAAGAATTTTCAACTTCTTGGTGGAA TACCACTTAATCTGG | SEQ ID NO:533 | Homo sapiens jumonji domain containing 1C (JMJD1C), transcript variant 1, mRNA [NM_032776] |
| 534 | A_32_P6415 | TNRC6B | GCATAGAGGTTTAATCAAACTCCCATATGTTGAAATTGCTCCTCA TATTACTCGTTTTAC | SEQ ID NO:534 | Homo sapiens trinucleotide repeat containing 6B (TNRC6B), transcript variant 1, mRNA [NM_015088] |
| 535 | A_32_P65067 | THC2618074 | CCCCCAAAGTGAATTTAAACTTGACTTATTTATGCCGTTGTGAT AGGAAGCCAGAAT | SEQ ID NO:535 | |
| 536 | A_32_P6972 | THC2621771 | AGGAACCTGATTGTGGAGAAGTTCGTAATGCAGTAGGAGCAACAAGTGACAG TGATGAAGCCAGAAT | SEQ ID NO:536 | |
| 537 | A_32_P70875 | CD239706 | GTTTGTTTCAGAAGTTGGTAATATGGAGAAAGAAGAATCCAGGGTGGTGATGGCTG TTTTGTTATTTACTG | SEQ ID NO:537 | FNPBXF03 FNP Homo sapiens cDNA, mRNA sequence [CD239706] |
| 538 | A_32_P71171 | A_32_P71171 | TCTAGATAGTAATAGGAAAGCAAGAAATCCAGGGTTGGTGATGGCTG GAGGGAGTCATTGAA | SEQ ID NO:538 | |
| 539 | A_32_P718498 | MLLT6 | CCAACCAGCTATTTCGCCAGTGTAGAGTGGGCAATTCTCAGCTTCA AAGAGTCCGACCTG | SEQ ID NO:539 | Homo sapiens myeloid/lymphoid or mixed-lineage leukemia (trithorax homolog, Drosophila); translocated to, 6 (MLLT6), mRNA [NM_005937] |
| 540 | A_32_P749354 | MGC11102 | GTTTTGTGTTTTGGCTGCTGGTGTCTATTGGATGTGATATGTTAT GGATGTGATGTGTTA | SEQ ID NO:540 | Homo sapiens hypothetical protein MGC11102 (MGC11102), mRNA [NM_032325] |
| 541 | A_32_P79103 | BM932034 | GTGGTACAGAATGAAAATGGCATTTAGGAAGGTTGAGTGAGAGG TGCGAGTGGGGGATA | SEQ ID NO:541 | UI-E-EJ1-ajl-k-24-0-UI rI UI-E-EJ1 Homo sapiens cDNA clone UI-E-EJ1-ajl-k-24-0-UI 5', mRNA sequence [BM932034] |
| 542 | A_32_P81357 | FAH-D2A | CAACACGAACCACGATGTATTCAAGACAGCAGGAGGACCTGATAGGCTG GGTGTCCAGTTTGT | SEQ ID NO:542 | Homo sapiens fumarylacetoacetate hydrolase domain containing 2A (FAHD2A), mRNA [NM_016044] |
| 543 | A_32_P8251 | KIAA1542 | TCGGGTTCCTGGGGTGACACCTGGTCTGTCACCTGTGTTGGTCA CAGTTGAAAAGTGGAA | SEQ ID NO:543 | Homo sapiens CID-binding SR-like protein rA9 (KIAA1542), mRNA [NM_020901] |
| 544 | A_32_P83453 | LOC647768 | TTTTCTCTTGGGATGTCGCCGTTTTGTTGTGATTGACAACTGTAT TGCATTGAAGAAAGT | SEQ ID NO:544 | PREDICTED: Homo sapiens similar to Tetratricopeptide repeat protein 3 (TPR repeat protein 3) (TPR repeat protein B) (LOC647768), mRNA [XR_018202] |
| 545 | A_32_P84289 | C1orf93 | ACACAGTGGAACGTGTCTGCGAAGGCCGGCAGGTTCTGCAGCGACCC CAGTACCGTGTGGGT | SEQ ID NO:545 | Homo sapiens chromosome 1 open reading frame 93 (C1orf93), mRNA [NM_152371] |
| 546 | A_32_P86 | LOC728411 | TCGTCGACGAGGTCTCTGGGATGCTCTGGTTATATCTGATTTGTGACC TCTGGGCATGGGAGGT | SEQ ID NO:546 | Homo sapiens, clone IMAGE:4590099, mRNA [BC048193] |

Fig. 1-31

| No. | Probe ID No. | Symbols of genes | Sequence | SEQ ID NO: | Descriptions of genes (letters and numbers within [ ] indicates GenBank accession No.) |
|---|---|---|---|---|---|
| 547 | A_32_P88626 | PHACTR4 | TGAAGCCTGAGAGGAAGGCTCAGGATGTGACATGTTCTTCCTTTTG CTCACAAGTCATCAT | SEQ ID NO: 547 | Homo sapiens phosphatase and actin regulator 4 (PHACTR4), transcript variant 2, mRNA [NM_023923] |
| 548 | A_32_P88987 | AK022346 | ATGGAAGTTACTACCGCAGGGTTAGGAAAAGGTCAGGTTTATATA AAGTGGGGTTCCTTT | SEQ ID NO: 548 | Homo sapiens cDNA FLJ12284 fis, clone MAMMA1001757. [AK022346] |
| 549 | A_32_P90468 | A_32_P90468 | AAGCCAGGAATAATTTCTATCTCATGCTACGTAACTGCTGGAAG TTATGATGAGACCCT | SEQ ID NO: 549 | |
| 550 | A_32_P91328 | THC2641595 | GTTAGCGCAATAATGTCATTGAAGTCTTTAAGTCTGTAGCGTGACTC TAAGGCCAGGGTTCA | SEQ ID NO: 550 | |
| 551 | A_32_P92783 | STIP1 | CCAGGCACTCAGGCGAACACTTAAAGAATCGTGTAATCGCAAAGAA GATCCAGAAGCTGAT | SEQ ID NO: 551 | Homo sapiens stress-induced-phosphoprotein 1 (Hsp70/Hsp90-organizing protein) (STIP1), mRNA [NM_006819] |
| 552 | A_32_P97305 | THC2681839 | AATATGCACACACAAACTAAAGAAAAGGATGTCACTTGAGCACGAC AGCTTCCTGCGGCGT | SEQ ID NO: 552 | |
| 553 | A_32_P98847 | POLRMT | AGCAGAAGAAGGCGTTGCCGCCCAACTTCATCCACTGGCTGGACT CGTACACATGATGC | SEQ ID NO: 553 | Homo sapiens polymerase (RNA) mitochondrial (DNA directed) (POLRMT), nuclear gene encoding mitochondrial protein, mRNA [NM_005035] |
| 554 | A_32_P98940 | THC2745659 | AAGAGTATTCCAAGATAGCAAAGGTGTGTTGTTTTAGCAGGTG TATTTCAGCTAGTTA | SEQ ID NO: 554 | |
| 555 | A_32_P98097 | TNPO1 | AAATTGGAGGCATTTCCTGAGCAGTTTCCTCTTCCCTTAAAAAG ACCGTTCGAGGTG | SEQ ID NO: 555 | Homo sapiens transportin 1 (TNPO1), transcript variant 1, mRNA [NM_002270] |
| 556 | A_23_P102235 | SNRPG | ACAACAGAACAATATTGGAAATGGTGGTAATACGAGGAAATAGTAT CATGATGTTAGAAGC | SEQ ID NO: 556 | Homo sapiens small nuclear ribonucleoprotein polypeptide G (SNRPG), mRNA [NM_003096] |
| 557 | A_23_P108835 | YPEL5 | AAAGTGACTTCTGAGTACAGTTAAGTTCCTTCCTATTTGCCACTCGG GCTGTTGGTTAGAAG | SEQ ID NO: 557 | Homo sapiens yippee-like 5 (Drosophila) (YPEL5), mRNA [NM_016061] |
| 558 | A_23_P110704 | SLU7 | CGTCTCTTCCTTGGACAGTAGGACGTAGAGAAGACCATCCAAGA TAGATGCAGGTGATA | SEQ ID NO: 558 | Homo sapiens SLU7 splicing factor homolog (S. cerevisiae) (SLU7), mRNA [NM_006425] |
| 559 | A_23_P111583 | CD36 | GTTTGGGTTAATGACAGCTGGGACCATTGGTGATGAGAAGGCAAAC ATGTCAGAAGTCAA | SEQ ID NO: 559 | Homo sapiens CD36 molecule (thrombospondin receptor) (CD36), transcript variant 2, mRNA [NM_001001547] |
| 560 | A_23_P115872 | CEP55 | GTAAACCAAAAGTTTAAATTTCTCAGGTTTTGTGAACATGCTT ACCAGTGGGCTACTG | SEQ ID NO: 560 | Homo sapiens centrosomal protein 55kDa (CEP55), mRNA [NM_018131] |
| 561 | A_23_P117852 | KIAA0101 | TACTGCTGCCATTTTATTGGTGTTTGATTATTGGAATGGTGCCA TATGTCACTCCTTC | SEQ ID NO: 561 | Homo sapiens KIAA0101 (KIAA0101), transcript variant 1, mRNA [NM_014736] |
| 562 | A_23_P118061 | CKLF | GCACAAGCCCGTGAACCATATATTGTTATCACTGGATTGAAGTC ACGTATGTTATT | SEQ ID NO: 562 | Homo sapiens chemokine-like factor (CKLF), transcript variant 4, mRNA [NM_181641] |
| 563 | A_23_P118150 | ARL6IP1 | TTCAGATTTTCAGCTGACTGACATTAGTAGTATAGTAGGTTAAG ACTCAGTGTGTATGAC | SEQ ID NO: 563 | Homo sapiens ADP-ribosylation factor-like 6 interacting protein 1 (ARL6IP1), mRNA [NM_015161] |
| 564 | A_23_P119992 | VRK2 | TTTAAGTTTCCAGCTCTTCACCGAAATGTTGTATTCTTATTCAG TGTTCCTTGCAGAG | SEQ ID NO: 564 | Homo sapiens vaccinia related kinase 2 (VRK2), mRNA [NM_006296] |

Fig. 1-32

| No. | Probe ID No. | Symbols of genes | Sequence | SEQ ID NO: | Descriptions of genes [labels and numbers within [ ] indicates GenBank accession No.] |
|---|---|---|---|---|---|
| 565 | A_23_P120316 | MTHFD2 | AGGATTATTGCTTGCTATTAGTACTGATTTATGTATGTACCGT TCAGTAAGTTGTCCG | SEQ ID NO: 565 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 566 | A_23_P120644 | A_23_P120644 | GGCTTTGTTGTAGGAGGCAATGACTGTTGTTATATATCATGTATGGAG AATTCTGGGCAAAAC | SEQ ID NO: 566 | |
| 567 | A_23_P121253 | TNFSF10 | GCAACAATCCATCTCTGAAGTAGTGTATCACAGTAGTAGCCTCCA GGTTTCCTTAAGGGA | SEQ ID NO: 567 | Homo sapiens tumor necrosis factor (ligand) superfamily, member 10 (TNFSF10), mRNA [NM_003810] |
| 568 | A_23_P121622 | SULT1B1 | GAAATAGAGATTGTCGTAGTTGATTGAAACGAGGGGCAGTTATGA ATTGATTTGGGCAAT | SEQ ID NO: 568 | Homo sapiens mRNA for ST1B2, complete cds [D89479] |
| 569 | A_23_P122007 | C5orf30 | ATCAGATTTGCGTTGGGCTGGGAAATGTTCGCTGTGTATATTT TAAAGTAAATTGCAG | SEQ ID NO: 569 | Homo sapiens chromosome 5 open reading frame 30 (C5orf30), mRNA [NM_033211] |
| 570 | A_23_P123608 | JAK2 | GGATAACATGCCTGGATGAAAGAAATGACCCTTGATTGTGAGACCA AAGTAGATTTACAGA | SEQ ID NO: 570 | Homo sapiens Janus kinase 2 (a protein tyrosine kinase) (JAK2), mRNA [NM_004972] |
| 571 | A_23_P124823 | THC2510119 | GGAAGAGAGATTCGTAAGTTCACGGAGTGTTGAAGATTCATGAA AAATTTGTTCCTTAT | SEQ ID NO: 571 | BC000359 SPC18 protein {Homo sapiens} (exp=1; wgp=0; cg=0), partial (77%) [THC2510119] |
| 572 | A_23_P126057 | SCP2 | ACATTGGCAAATAGGGTGGGATAGATTTGTTTGTTAATGGGTGTGG ACCAATCCTGTTTT | SEQ ID NO: 572 | Homo sapiens sterol carrier protein 2 (SCP2), transcript variant 1, mRNA [NM_002979] |
| 573 | A_23_P127195 | PRPF18 | TGAGTGTGTACCTGATGTAAGTGTCTTTGATTGGTTTTTAAGAACTTTGT TGGCTTCATTTCAT | SEQ ID NO: 573 | Homo sapiens PRP18 pre-mRNA processing factor 18 homolog (S. cerevisiae) (PRPF18), mRNA [NM_003675] |
| 574 | A_23_P128192 | PFDN5 | CACCTGCATTGCTCAGCTCAAAGTGTACAGAGCAAGTATGGTGGA AGCCAAGGACTGTGT | SEQ ID NO: 574 | Homo sapiens prefoldin subunit 5 (PFDN5), transcript variant 1, mRNA [NM_002624] |
| 575 | A_23_P128384 | VPS29 | CAGGTAATTGGAGGATGATGTGAAAGTAGAACGGAATACAAA AAACCTTAAAGCCAG | SEQ ID NO: 575 | Homo sapiens vacuolar protein sorting 29 homolog (S. cerevisiae) (VPS29), transcript variant 2, mRNA [NM_057180] |
| 576 | A_23_P128447 | LRRK2 | GCACAAAAGAATAGAATCTTGGCTTGACCGTTTGGGCAGATCAATCT TCGACATGAAGTGCA | SEQ ID NO: 576 | Homo sapiens leucine-rich repeat kinase 2 (LRRK2), mRNA [NM_198578] |
| 577 | A_23_P130089 | IFT20 | TGGCCAGTTTCAGAAAATAGTTGGTGGTTTAATTGAGGTTGTTGA TGAACTTGCAAAAGA | SEQ ID NO: 577 | Homo sapiens intraflagellar transport 20 homolog (Chlamydomonas) (IFT20), mRNA [NM_174887] |
| 578 | A_23_P130293 | ANKRD12 | TCAGGATTTAGAAGAATCCAGGAGTTTATGTTCCCCTTGTTGTATG TTAACGACGACTTTG | SEQ ID NO: 578 | Homo sapiens ankyrin repeat domain 12 (ANKRD12), mRNA [NM_015208] |
| 579 | A_23_P130444 | ZNF701 | CTCCTTGCAGAATATGATAACGTTCATTTTGAGGTAATAGTTAC AATGGGGTGAGCAC | SEQ ID NO: 579 | Homo sapiens zinc finger protein 701 (ZNF701), mRNA [NM_018260] |
| 580 | A_23_P13065 | ZDHHC13 | GATACAATCTTGGATTCATGGAGAAACCTGGCAGATTCTTTCAGT GTGGCTGCTTTGGCT | SEQ ID NO: 580 | Homo sapiens zinc finger, DHHC-type containing 13 (ZDHHC13), transcript variant 1, mRNA [NM_019028] |
| 581 | A_23_P132863 | ENST00000306024 | AGGTAAATGGTATTTTCATTTTTGTGAAGCTCTCCAATAAATATG ACACGAAGATGCA | SEQ ID NO: 581 | U6 snRNA-associated Sm-like protein LSm3 [Source:Uniprot/SWISSPROT;Acc:P62310] [ENST00000306024] |
| 582 | A_23_P132936 | SPCS3 | GAATGTCAGTTTGACCCTGTCGTTGGAACGTCGTACCAAATGCTGG AATTACCACCTTGT | SEQ ID NO: 582 | Homo sapiens signal peptidase complex subunit 3 homolog (S. cerevisiae) (SPCS3), mRNA [NM_021928] |

Fig. 1-33

| No. | Probe ID No. | Symbols of genes | Sequence | SEQ ID NO: | Descriptions of genes (letters and numbers within [ ] indicates GenBank accession No.) |
|---|---|---|---|---|---|
| 583 | A_23_P133436 | FAM105A | TCAGCATGCAAGGAATTAGGACCTTTTGTTCGAGGATTAGAGGTAGCACTGGATGCAGCCAT | SEQ ID NO: 583 | Homo sapiens family with sequence similarity 105, member A (FAM105A), mRNA [NM_019018] |
| 584 | A_23_P133646 | FAM8A1 | AGTTCGGCGCGAATTAGAAAATGAGTGTTTAGATTCAAGTGACGGTAAAAGGATTTGTT | SEQ ID NO: 584 | Homo sapiens family with sequence similarity 8, member A1 (FAM8A1), mRNA [NM_016255] |
| 585 | A_23_P134247 | RHEB | GTGGATGTTTTTGGAAGGATAATTTTGGAGGAGAAAAATGGAGGGGCCAGCTTCACAA | SEQ ID NO: 585 | Homo sapiens Ras homolog enriched in brain (RHEB), mRNA [NM_005614] |
| 586 | A_23_P13701 | TMBIM4 | TGCACATGCGAATGGCGCTTTCTGAGAAAAGTCTACAGGATTCTTCTCTCCAGGTTCTCT | SEQ ID NO: 586 | Homo sapiens transmembrane BAX inhibitor motif containing 4 (TMBIM4), mRNA [NM_016056] |
| 587 | A_23_P137616 | SAT1 | GAAATAATAGAATGAGGACGGATTCCAAAGCTTTATTACCAGTGGCGTTGTTGCATGTTT | SEQ ID NO: 587 | Homo sapiens spermidine/spermine N1-acetyltransferase 1 (SAT1), mRNA [NM_002970] |
| 588 | A_23_P138308 | CD58 | AACCTGTATCCCAAGCAGCGGTCATTGAAGACAGATATGCACTTATACGCATACGATT | SEQ ID NO: 588 | Homo sapiens CD58 molecule (CD58), mRNA [NM_001779] |
| 589 | A_23_P138507 | CDC2 | CCCATGTGAAAAACTTGGATGAAAATGGCTTGGATTTGGTCTCGAAAATGTTAATCTATG | SEQ ID NO: 589 | Homo sapiens cell division cycle 2, G1 to S and G2 to M (CDC2), transcript variant 1, mRNA [NM_001786] |
| 590 | A_23_P140301 | PSMA3 | TGAACTAGAACTCAGCTGGGTTGGTGAATTAACTAATGAAGACATGAAATGTTCCAAA | SEQ ID NO: 590 | Homo sapiens proteasome (prosome, macropain) subunit, alpha type, 3 (PSMA3), transcript variant 1, mRNA [NM_002788] |
| 591 | A_23_P140423 | NDUFB1 | GGATGTTATTTAGACAGAAGAGTGTTCTGCAAGTGCATGATGAACGGCTAAGTGCCTTCCGGAACAAGAGTATG | SEQ ID NO: 591 | Homo sapiens NADH dehydrogenase (ubiquinone) 1 beta subcomplex, 1, 7kDa (NDUFB1), mRNA [NM_004545] |
| 592 | A_23_P142560 | ZEB2 | CTTTTAATCTCTGTTTCTGCAAGTGCCATCCTTGTACAGTGTTAAGAGGTAACATGGGT | SEQ ID NO: 592 | Homo sapiens zinc finger E-box binding homeobox 2 (ZEB2), mRNA [NM_014795] |
| 593 | A_23_P144145 | DCUN1D1 | TCTTTAGTGAATATCATCTGGATATCTCTGTAAGTCAATTGTGTTCTTACAGTCCCTG | SEQ ID NO: 593 | Homo sapiens RP42 protein mRNA, complete cds. [AF292100] |
| 594 | A_23_P144224 | TLOC1 | ATGGGATTGTGAAGACGGATGAGGAAGAAGGGAAAATGATGGAGAAACAGCTCAAATGTTGAG | SEQ ID NO: 594 | Homo sapiens translocation protein 1 (TLOC1), mRNA [NM_003262] |
| 595 | A_23_P14564 | GPR65 | AACAAGTTTAAATTGTTGGTGATCGAATTCGTGTACTGTTTTGTAACCGAAACAGGAAG | SEQ ID NO: 595 | Homo sapiens G protein-coupled receptor 65 (GPR65), mRNA [NM_003608] |
| 596 | A_23_P145777 | NDUFA4 | ACGGCTGCTTTAGAATGAAGGTCTTCCAGAAGCCACATCGGCACAATTTTCCAGTTAACCA | SEQ ID NO: 596 | Homo sapiens NADH dehydrogenase (ubiquinone) 1 alpha subcomplex, 4, 9kDa (NDUFA4), nuclear gene encoding mitochondrial protein, mRNA [NM_002489] |
| 597 | A_23_P14734 | RPS27L | TACAAGATCACCACGGTTTTCAGGCATGCTCAGACAGTGGTTGTTGTGTAGGTTGTTCA | SEQ ID NO: 597 | Homo sapiens ribosomal protein S27-like (RPS27L), mRNA [NM_015920] |
| 598 | A_23_P147404 | A_23_P147404 | CTGGGTGAACATGAAATTGATTAGATGTTGTTGGATGGTGAGCAGCGTCCCTCTCATGTG | SEQ ID NO: 598 | |
| 599 | A_23_P148273 | RP11-217H1.1 | GGTCGAGAGATATATAGACACTGAGTAGTGAAAATTGAAAAGGAAATCGTGTGTGT | SEQ ID NO: 599 | Homo sapiens cDNA FLJ14142 (DKFZp564K142), mRNA [NM_032121] |
| 600 | A_23_P148297 | SH3BGRL | ATAAACAAGGTTGGCGATCATTTCCAAGAATTGGTTTCCCTTGAGTTTTTGCTAAAACAA | SEQ ID NO: 600 | Homo sapiens SH3 domain binding glutamic acid-rich protein like (SH3BGRL), mRNA [NM_003022] |
| 601 | A_23_P149992 | GALNACT-2 | CATGGTTGGTTCAGAATAGAATGAAGCAATAGGCATGGTTGTTTTGTTTTTCTTGCTTTCAATTTTC | SEQ ID NO: 601 | Homo sapiens chondroitin sulfate GalNAcT-2 (GALNACT-2), mRNA [NM_018590] |

Fig. 1-34

| No. | Probe ID No. | Symbols of genes | Sequence | SEQ ID NO: | Descriptions of genes (letters and numbers written [ ] indicates GenBank accession No.) |
|---|---|---|---|---|---|
| 602 | A_23_P152002 | BCL2A1 | TGTAACGATATTTGCATTTGAAGGTATTCTCATCAAGCAAACTTCT ACGACAAGCAAATTGC | SEQ ID NO: 602 | Homo sapiens BCL2-related protein A1 (BCL2A1), mRNA [NM_004049] |
| 603 | A_23_P154235 | NMI | CCATGTTTCTGAATCTTCTTTGTTCAAATGGTGCTGCATGTTTCAACTCACAATAAGTG | SEQ ID NO: 603 | Homo sapiens N-myc (and STAT) interactor (NMI), mRNA [NM_004688] |
| 604 | A_23_P154832 | ATP5J | TACAAATCTAAGCGAGCAGAGACATCTGGAGGAGACCGTGTTGATCGTAGTTCAGAGTATCAGCAA | SEQ ID NO: 604 | Homo sapiens ATP synthase, H+ transporting, mitochondrial F0 complex, subunit F6 (ATP5J), nuclear gene encoding mitochondrial protein, transcript variant 1, mRNA [NM_001003703] |
| 605 | A_23_P15564 | AMZ2 | AAACCGTTGGAAGCCTTTAAGGAATGGAAAGAGTGGATAATAAAATGGCTGGCTGTTGTG | SEQ ID NO: 605 | Homo sapiens archaemetzincins-2 (AMZ2), transcript variant 1, mRNA [NM_016627] |
| 606 | A_23_P155677 | HIP2 | GATTTTGGGGTCTATAGAGATTGCTTTATTGGATAGTTGAAGTCATTTGTTGGTTGCACTT | SEQ ID NO: 606 | Homo sapiens huntingtin interacting protein 2 (HIP2), mRNA [NM_005339] |
| 607 | A_23_P155765 | HMGB2 | TAAAAATGCAGGTTGTAGCTTTTGATGGGCTACTCATACAGTTAGATTTTACAGCTTC | SEQ ID NO: 607 | Homo sapiens high-mobility group box 2 (HMGB2), mRNA [NM_002129] |
| 608 | A_23_P155815 | NCAPG | AAGTTAGGAAAGACGATGGAGGTGGAATCCTTTAAGATTATGTCCAGTTATTTGGTTTAA | SEQ ID NO: 608 | Homo sapiens non-SMC condensin I complex, subunit G (NCAPG), mRNA [NM_022346] |
| 609 | A_23_P157452 | POLR2K | GGAATGTCTTCACTTATACTTGGATTTGGCTCTCTTCCCATTTGTGATTGTTGTATAGCTT | SEQ ID NO: 609 | Homo sapiens polymerase (RNA) II (DNA directed) polypeptide K, 7.0kDa (POLR2K), mRNA [NM_005034] |
| 610 | A_23_P159839 | C16ALT1C1 | TCCAAATACAGATGCATGTGATGCATGTATGGGGTATACCGCCTTAGGGCATTTGGGCATAT | SEQ ID NO: 610 | Homo sapiens C16ALT1-specific chaperone 1 (C16ALT1C1), transcript variant 1, mRNA [NM_152692] |
| 611 | A_23_P163216 | ATP9B4 | ATCAGTGTATTTTCCATAAAAGTGATTCGGGGCATATTTGTGTGAAAACCTCAGTTCTGTGA | SEQ ID NO: 611 | Homo sapiens ATPase, Class I, type 8B, member 4 (ATP9B4), mRNA [NM_024837] |
| 612 | A_23_P163402 | SF3B14 | CATGTGATCACCTATCGGGATGTTTGTAACAGATACCTTGTGTTTGTACTATA | SEQ ID NO: 612 | Homo sapiens splicing factor 3B, 14 kDa subunit (SF3B14), mRNA [NM_016047] |
| 613 | A_23_P165819 | A_23_P165819 | AGGCATGTTGTTTGAAGTGTGGAGTTGTAAGTCTGCCTGGAGTATGGACAAGCACACAAT | SEQ ID NO: 613 | |
| 614 | A_23_P168592 | CCDC126 | GGGGAGTATCAGATAGGAGTTGAAAACTCACCTTGTGTGGTCATCCACTGTGGATTATA | SEQ ID NO: 614 | Homo sapiens coiled-coil domain containing 126 (CCDC126), mRNA [NM_138771] |
| 615 | A_23_P169576 | EXOC6 | ATGCTGAAATCTTCCCTTTCGCCTTTTCAGGATTTTAGGCCTGTAAGAAAGTATGCCTGATTC | SEQ ID NO: 615 | Homo sapiens exocyst complex component 6 (EXOC6), transcript variant 2, mRNA [NM_001013848] |
| 616 | A_23_P170233 | CSTA | AACTGCCTACTGAGTGCTGATCATCCTTGCTGATAAATATAACCATCAATAAAGAAGGATTCT | SEQ ID NO: 616 | Homo sapiens cystatin A (stefin A) (CSTA), mRNA [NM_005213] |
| 617 | A_23_P17287 | IAH1 | TGGGAGATGGAGACCATTAGGCAATCACAGGAGCGAAATCTGCTTGTTATCTACAAGAA | SEQ ID NO: 617 | Homo sapiens isoamyl acetate-hydrolyzing esterase 1 homolog (S. cerevisiae) (IAH1), mRNA [NM_001039613] |
| 618 | A_23_P18325 | PDCD10 | CCAAACGGACTAATTCATCAAACGAAGTTAATACTTCAGACCTTCAAACTGTGGCCTGAA | SEQ ID NO: 618 | Homo sapiens programmed cell death 10 (PDCD10), transcript variant 1, mRNA [NM_007217] |
| 619 | A_23_P200507 | CNIH4 | TGGTTGAAGTGAGGCTACACTACAGTGCAGAGTTGAGGAGCCAGAGAGTTCTTAAATCAT | SEQ ID NO: 619 | Homo sapiens cornichon homolog 4 (Drosophila) (CNIH4), mRNA [NM_014184] |

Fig. 1-35

| No. | Probe ID No. | Symbols of genes | Sequence | SEQ ID NO. | Descriptions of genes (letters and numbers within [ ] indicates GenBank accession No.) |
|---|---|---|---|---|---|
| 620 | A_23_P20758 | CD46 | CTCATGAGTGGAAGTGCAAGTGTGGCTTAGCTAATATTGCAATGTGGCTTG AATCTAGCTAGCATC | SEQ ID NO: 620 | Homo sapiens CD46 molecule, complement regulatory protein (CD46), transcript variant a, mRNA [NM_002389] |
| 621 | A_23_P201918 | ABCB10 | CATGGATGAGGCTAGACCCTAAGAAGTAATTAAGTCAATGTAAAT CAAATGGAAGTTTTC | SEQ ID NO: 621 | Homo sapiens ATP-binding cassette, sub-family B (MDR/TAP), member 10 (ABCB10), nuclear gene encoding mitochondrial protein, mRNA [NM_012089] |
| 622 | A_23_P202750 | C11orf54 | TGCAGAAGTTTCTGTATGCATTGGTCAACCAAAAGAGAGCGGCATTC CATTGGGCGAGATTA | SEQ ID NO: 622 | Homo sapiens chromosome 11 open reading frame 54 (C11orf54), mRNA [NM_014039] |
| 623 | A_23_P202978 | CASP1 | CTGTTCGTGTGATGTGGAAGGGAAATTTCCGGCAAGGTTCGATTTTC ATTTGAGCAGCCAGA | SEQ ID NO: 623 | Homo sapiens caspase 1, apoptosis-related cysteine peptidase (interleukin 1, beta, convertase) (CASP1), transcript variant alpha, mRNA [NM_033292] |
| 624 | A_23_P20384 | LSM1 | TGAGTGAAAGTGACAATCCTGGGCACCTCAGCGATTTGATCACAGA GTGTAGAGTTTTGAA | SEQ ID NO: 624 | Homo sapiens LSM1 homolog, U6 small nuclear RNA associated (S. cerevisiae) (LSM1), mRNA [NM_014462] |
| 625 | A_23_P204550 | SCYL2 | TGTGACTTCCGTGACTGCTACTACCTTCATATTTCATTTCAAATTGAA ACTTCTGAGGTTGCA | SEQ ID NO: 625 | Homo sapiens SCY1-like 2 (S. cerevisiae) (SCYL2), mRNA [NM_017988] |
| 626 | A_23_P205281 | C14orf2 | TGATAAGAAGTAAGGGTTTGAAAGGTTCAGGGCGTGCTCCTGG TCATCAGTAACCAGA | SEQ ID NO: 626 | Homo sapiens chromosome 14 open reading frame 2 (C14orf2), mRNA [NM_004894] |
| 627 | A_23_P205768 | ARPP-19 | GGGCAATATTTGCCCATTCTCGTCGTGAATTTATGTAACTTATGTGACTCAGTGC TTAACAGCTGCCGTT | SEQ ID NO: 627 | Homo sapiens cyclic AMP phosphoprotein, 19 kD (ARPP-19), mRNA [NM_006628] |
| 628 | A_23_P206396 | CKLF | ATTATCAAGTCAGTGGTAACAACAGTATTCATGGTCATGTATGT GTGTTGGCACTGATA | SEQ ID NO: 628 | Homo sapiens chemokine-like factor (CKLF), transcript variant 1, mRNA [NM_016951] |
| 629 | A_23_P207445 | MAP2K6 | ACAGACTCAATAGAAAAGTCATCTTTGAGATAATTAACGCTGGGT CTCAGAGAAGTTTGT | SEQ ID NO: 629 | Homo sapiens mitogen-activated protein kinase kinase 6 (MAP2K6), mRNA [NM_002758] |
| 630 | A_23_P20882 | ATP6V1G1 | AGGTCCTTCCACTTTTTGGAGAGTAGCCAATCTAGGTTTTTTGTA CAGACTTAGAAATTA | SEQ ID NO: 630 | Homo sapiens ATPase, H+ transporting, lysosomal 13kDa, V1 subunit G1 (ATP6V1G1), mRNA [NM_004888] |
| 631 | A_23_P208866 | GMFG | CTCCAAGAAAAGTTGTGTTCTTCGTTGATGTCTGGGCTGGGGA CTGAATTCCTGATGT | SEQ ID NO: 631 | Homo sapiens glia maturation factor, gamma (GMFG), mRNA [NM_004877] |
| 632 | A_23_P210274 | PREI3 | GGATAGATGCGTAGGATTACAGAATATTTCACATGCTTAT TTTCATCATCGGCAG | SEQ ID NO: 632 | Homo sapiens preimplantation protein 3 (PREI3), transcript variant 1, mRNA [NM_015387] |
| 633 | A_23_P211840 | UBE1C | GCCACGCTAGAGGGAAAAAATAGAACAGACTTACTTACAGTCGGTA ACCTCTATTGAAGAA | SEQ ID NO: 633 | Homo sapiens ubiquitin-activating enzyme E1C (UBA3) homolog, yeast) (UBE1C), transcript variant 1, mRNA [NM_003968] |
| 634 | A_23_P212706 | ATG3 | AAGACATCAGTCAGGATCATGTGAAGACAGTGACCATTGAAA ATCACCCTCATGTGC | SEQ ID NO: 634 | Homo sapiens ATG3 autophagy related 3 homolog (S. cerevisiae) (ATG3), mRNA [NM_022488] |
| 635 | A_23_P213247 | FBXL5 | ATGAAGGTGATTGGTTCTCTTTACACATTAAGACTGTACCAAGCT TTGCAGATCTTTTGC | SEQ ID NO: 635 | Homo sapiens F-box and leucine-rich repeat protein 5 (FBXL5), transcript variant 2, mRNA [NM_033535] |
| 636 | A_23_P213638 | PANK3 | TGTATATAGGCAGTGTAAATCCTTAAATGAATACAGGCGTGA TTATTGAGCTTGGTC | SEQ ID NO: 636 | Homo sapiens pantothenate kinase 3 (PANK3), mRNA [NM_024594] |
| 637 | A_23_P217236 | HMGB3 | GACCTGTTGACTGTGCAGGGGCATCCATTTAGCTTCAGGTTGTC TTGTTTCTGTATATA | SEQ ID NO: 637 | Homo sapiens high-mobility group box 3 (HMGB3), mRNA [NM_005342] |

Fig. 1-36

| No. | Probe ID No. | Symbols of genes | Sequence | SEQ ID NO: | Descriptions of genes (letters and numbers within [ ] indicates GenBank accession No.) |
|---|---|---|---|---|---|
| 638 | A_23_P22671 | SYBL1 | CAAACCGAATACGGTCAGCAGTCAACTCCAGGGGTTTGGGCTTGAT TCCTGTTGAATAATA | SEQ ID NO: 638 | Homo sapiens synaptobrevin-like 1 (SYBL1), mRNA [NM_005638] |
| 639 | A_23_P24515 | ACAT1 | CAGGATTGTTGGTCATTTGAGTCATGGCTTGAAGCAAGGAGAATA GGGTGTTGGCAGTAT | SEQ ID NO: 639 | Homo sapiens acetyl-Coenzyme A acetyltransferase 1 (acetoacetyl Coenzyme A thiolase) (ACAT1), nuclear gene encoding mitochondrial protein, mRNA [NM_000019] |
| 640 | A_23_P250642 | SELT | GGAAGATAGTGTTTCAGTGCTGGCATATTTTGGAATTGTGCACAT TCATGGAGTGCAATA | SEQ ID NO: 640 | Homo sapiens selenoprotein T (SELT), mRNA [NM_016275] |
| 641 | A_23_P250904 | UBQLN1 | CTTTGAGAAAGATCTCCCAGCAAAAGTGCGGTTAGTCAGGTTTG TTGAAAATACAGTAG | SEQ ID NO: 641 | Homo sapiens ubiquilin 1 (UBQLN1), transcript variant 1, mRNA [NM_013438] |
| 642 | A_23_P251421 | CDCA7 | ATTACTTGCATATGTAAACCATTGCTGTGGGATTCAATGTTTGA TGCATAATTGGACGT | SEQ ID NO: 642 | Homo sapiens cell division cycle associated 7 (CDCA7), transcript variant 1, mRNA [NM_031942] |
| 643 | A_23_P251945 | DCTN4 | ACACGTTTGCATAGAACTACACACATGTCATCGTTTATGGCAGGT AGCTGGTATTATTC | SEQ ID NO: 643 | Homo sapiens dynactin 4 (p62) (DCTN4), mRNA [NM_016221] |
| 644 | A_23_P252145 | C1GALT1 | ATATGTCATATATATGAGGAACTTGTGTTTTTTAAAATGGTGGCC AGGTAGAGGAACTAG | SEQ ID NO: 644 | Homo sapiens core 1 synthase, glycoprotein-N-acetylgalactosamine 3-beta-galactosyltransferase, 1 (C1GALT1), mRNA [NM_020156] |
| 645 | A_23_P252371 | RBBP8 | GGGCAAGAGCAAGGACAGTAGACGTTGAAACAGAGAAACAGAAGAT GAAGGACAGTTTTT | SEQ ID NO: 645 | Homo sapiens retinoblastoma binding protein 8 (RBBP8), transcript variant 1, mRNA [NM_002894] |
| 646 | A_23_P253524 | CENPE | CTGAGTGCAAAAGTCAGTAGACTCCTGTTGTCAGTGCTGTGGAG ATCCAGCATTCCTTA | SEQ ID NO: 646 | Homo sapiens centromere protein E, 312kDa (CENPE), mRNA [NM_001813] |
| 647 | A_23_P255223 | VBP1 | TGAAGGTCAGGGATTGTTGCTGAAAGAGAATTTATGACTGGGAAA GAATCTTGATTCCCT | SEQ ID NO: 647 | Homo sapiens von Hippel-Lindau binding protein 1 (VBP1), mRNA [NM_003372] |
| 648 | A_23_P256231 | FBXO30 | GCCTTTTAAAGTTTTGCTGAAGGATGTGTCGTTAGGATAGG ACAGACATTAACTT | SEQ ID NO: 648 | Homo sapiens F-box protein 30 (FBXO30), mRNA [NM_032145] |
| 649 | A_23_P256868 | DCP2 | CCGTGGGCATGGTAATGGACATTGGCAAGTTCCCGTTTTGATCGGAG CCTTTTTGAGTTTCA | SEQ ID NO: 649 | Homo sapiens DCP2 decapping enzyme homolog (S. cerevisiae) (DCP2), mRNA [NM_152624] |
| 650 | A_23_P25735 | PSMA6 | TAGGAGAGAAGAGACTAAACATTGTCGTTAGTTACGAGATGCGTG ATGCCACTTACCTGT | SEQ ID NO: 650 | Homo sapiens proteasome (prosome, macropain) subunit, alpha type, 6 (PSMA6), mRNA [NM_002791] |
| 651 | A_23_P258814 | ENST00000328644 | GGAAGGTGTGGCAATGTGTGCAGGCTGCTCTCTCATTATAAAGT GATTTATGACAAAGA | SEQ ID NO: 651 | DPH3 homolog B (CSL-type zinc finger-containing protein 1). [Source:Uniprot/SWISSPROT;Acc:Q9H4G8] [ENST00000328644] |
| 652 | A_23_P259272 | WSB2 | AACGTTACATGACTGCTGTTGAGAAGAAGTTGAGGAATTTCCTCTACCA CGTTTGTTGCTTGAA | SEQ ID NO: 652 | Homo sapiens WD repeat and SOCS box-containing 2 (WSB2), mRNA [NM_018639] |
| 653 | A_23_P259521 | WDR41 | TTGGCAGTTTAAGATTATTTCAAAAATTAGAGGAAGAATGGTGAC TTATAGGTTGGTGTC | SEQ ID NO: 653 | Homo sapiens WD repeat domain 41 (WDR41), mRNA [NM_018268] |
| 654 | A_23_P2705 | P2RY5 | TCTGTATTGCTGTTTGCAAGTGTTGTTTGACCCTATAGTTTACT ACTTTAGATCGGACA | SEQ ID NO: 654 | Homo sapiens purinergic receptor P2Y, G-protein coupled, 5 (P2RY5), mRNA [NM_005767] |
| 655 | A_23_P26664 | KIAA1212 | GGACTTCTATGATAGAGGACGAACTAAGCCTGAGTTTTTGAGAC CTGGTCCTCGAAAAA | SEQ ID NO: 655 | Homo sapiens KIAA1212 (KIAA1212), mRNA [NM_018084] |
| 656 | A_23_P29005 | SAMSN1 | CTCTGGTTCTATATCTCATCAGGAGAATTCAGATAATGGCAAAGA GGATCGGAGTGTGA | SEQ ID NO: 656 | Homo sapiens SAM domain, SH3 domain and nuclear localization signals 1 (SAMSN1), mRNA [NM_022136] |

Fig. 1-37

| No. | Probe ID No. | Symbols of genes | Sequence | SEQ ID NO: | Descriptions of genes (letters and numbers within [ ] indicates GenBank accession No.) |
|---|---|---|---|---|---|
| 657 | A_23_P30369 | FLJ31033 | AGATTGTTTAAGTCCCTACAGTTTGTTTATTCTAAATGATCAAGAGTACACTTGGTGG | SEQ ID NO: 657 | Homo sapiens cDNA FLJ13691 fis, clone PLACE2000014, weakly similar to HYPOTHETICAL HELICASE C28H8.3 IN CHROMOSOME III [AK023743] |
| 658 | A_23_P30338 | CCNH | ACGTCTCAAAGAATCCAAACATGAGGAGGAAGAATTGGACTGATGACGACCTGGTAGAAT | SEQ ID NO: 658 | Homo sapiens cyclin H (CCNH), mRNA [NM_001239] |
| 659 | A_23_P304287 | PSMC2 | GATCCAGACAGTGATGAAGGCCAGGAGGAGATTGGATAGAAAAATTGAATTTAAGTTGGCCGAT | SEQ ID NO: 659 | Homo sapiens proteasome (prosome, macropain) 26S subunit, ATPase, 2 (PSMC2), mRNA [NM_002803] |
| 660 | A_23_P305759 | ABHD3 | AGTCCTAGACTGAAGTCAGTAGGAATTGGAAGTATGTGTCTAAATTCTGTGGATGATGTT | SEQ ID NO: 660 | Homo sapiens abhydrolase domain containing 3 (ABHD3), mRNA [NM_138340] |
| 661 | A_23_P307940 | CAPZA2 | CTACAAGATTGGCAAGAGATGGAAGATGCATAAGATGAACATTGGATGACCGGAATCATT | SEQ ID NO: 661 | Homo sapiens capping protein (actin filament) muscle Z-line, alpha 2 (CAPZA2), mRNA [NM_006136] |
| 662 | A_23_P31097 | OSTM1 | ACTGAAAATGTGCTGGGGTTTGTTCTGCTGTGACTGTTTATGCTGCTGGAACGTTAGGACT | SEQ ID NO: 662 | Homo sapiens osteopetrosis associated transmembrane protein 1 (OSTM1), mRNA [NM_014028] |
| 663 | A_23_P31315 | CBX3 | GCGTTGGAAGAGTTGTTGGGGGTTTTTTGCATCCATAGCACTGGTTAGTTTGAACAAAATA | SEQ ID NO: 663 | Homo sapiens chromobox homolog 3 (HP1 gamma homolog, Drosophila) (CBX3), transcript variant 2, mRNA [NM_016587] |
| 664 | A_23_P314202 | PAPD4 | TCTGTGTAGAAGAAGGTTTGTTTGATGGAACAAATACAGCCAGAGCACTGCACGAAAAGCAGA | SEQ ID NO: 664 | Homo sapiens PAP associated domain containing 4 (PAPD4), mRNA [NM_173797] |
| 665 | A_23_P316601 | RIT1 | TGGTTGCTTGCTCTTTCACTTAACTGATAAGAGGGACAATGCCTACTAGGAAGTTTTTAATGA | SEQ ID NO: 665 | Homo sapiens Ras-like without CAAX 1 (RIT1), mRNA [NM_006912] |
| 666 | A_23_P31671 | UQCRB | AGGCCATAAGAAGACTTCCTGCTGAGAACTTTATAATGACAGGATGTTTGCATAAGAGGG | SEQ ID NO: 666 | Homo sapiens ubiquinol-cytochrome c reductase binding protein (UQCRB), mRNA [NM_006294] |
| 667 | A_23_P324633 | C9orf72 | TTTGTGGATTTAGTCGCTGGGATTCAGTCTGTAGAAATGTGTAATAGTTCTGTAGTCG | SEQ ID NO: 667 | Homo sapiens chromosome 9 open reading frame 72 (C9orf72), transcript variant 1, mRNA [NM_018325] |
| 668 | A_23_P32577 | DACH1 | AATATTAATGCTAGTTGTTGTTCTATATTATAACCAGATTGTCTGCCGTCTATGGAAGCCCTTGG | SEQ ID NO: 668 | Homo sapiens dachshund homolog 1 (Drosophila) (DACH1), transcript variant 1, mRNA [NM_080759] |
| 669 | A_23_P326170 | CALM2 | TAAACTTGTTTAGGCACTTAAAATCTGCTTATGGCACAATTGCCTCAAAATCCATTCC | SEQ ID NO: 669 | Homo sapiens calmodulin 2 (phosphorylase kinase, delta) (CALM2), mRNA [NM_001743] |
| 670 | A_23_P328511 | HSBP1 | TTTCTTGAACATCGTATCTTCACATCTTGGACGTTGGTCAGTTGTGCTATTCATTATTAA | SEQ ID NO: 670 | Homo sapiens heat shock factor binding protein 1 (HSBP1), mRNA [NM_001537] |
| 671 | A_23_P329198 | OBFC2A | ACATGTCATAAGTGGTACCGACTTCCCGTTTTTACTGTAGGGTGGATAACTCTTAGGAATT | SEQ ID NO: 671 | Homo sapiens oligonucleotide/oligosaccharide-binding fold containing 2A (OBFC2A), mRNA [NM_001031716] |
| 672 | A_23_P339480 | HAT1 | AACATGAACAGCTGGAAGAGAGAGTTTCAGGAACTAGTAGTGGAAGATTACCGGCGTGTTATG | SEQ ID NO: 672 | Homo sapiens histone acetyltransferase 1 (HAT1), transcript variant 1, mRNA [NM_003642] |
| 673 | A_23_P339557 | MLSTD2 | GGGCCAATAGTAAATCTAACCTCCAATCATCTTTATACATTACTGGATGCGTAAGCC | SEQ ID NO: 673 | Homo sapiens male sterility domain containing 2 (MLSTD2), mRNA [NM_032228] |
| 674 | A_23_P344973 | MYL6 | GCTATGAGGATTATGTGGAAGGAACTTCGGGTGTTTGACAAGGAAGGAAATGGCACCGTCA | SEQ ID NO: 674 | Homo sapiens myosin, light chain 6, alkali, smooth muscle and non-muscle (MYL6), transcript variant 1, mRNA [NM_079423] |
| 675 | A_23_P345691 | PSMA2 | GCCTGGAAGCTACAGCAATGGGAAAGAACTATGTGAATGGGAAGACTTTTCCTTGAGAAA | SEQ ID NO: 675 | Homo sapiens proteasome (prosome, macropain) subunit, alpha type, 2 (PSMA2), mRNA [NM_002787] |

Fig. 1-38

| No. | Probe ID No. | Symbols of genes | Sequence | SEQ ID NO: | Descriptions of genes [letters and numbers within { } indicates GenBank accession No.] |
|---|---|---|---|---|---|
| 676 | A_23_P346606 | CCPG1 | TATGGTCGGACTAATGGAAGACAAATGGCAAATGTTGAAAATAGAATTTGGGCAATTACCT | SEQ ID NO: 676 | Homo sapiens cell cycle progression 1 (CCPG1), transcript variant 2, mRNA [NM_020739] |
| 677 | A_23_P34628 | GTF2B | TGTTAGAATCAGACAAGTCGTATAGAGTGATGTATCCTCGAGGGCCAGATCTGTTTCGTAG | SEQ ID NO: 677 | Homo sapiens general transcription factor IIB (GTF2B), mRNA [NM_001514] |
| 678 | A_23_P351903 | TMEM167 | AAACTGGATTGTTGGGTATATTTTGGAAGTGTGCCAGAATTGGTGAACGGAAGAGTCTT | SEQ ID NO: 678 | Homo sapiens transmembrane protein 167 (TMEM167), mRNA [NM_174099] |
| 679 | A_23_P355067 | TMCO1 | AACTCAAGAAGTCTTTATTTTCTATCATCGTTGTAGACACACACATCAAGAGAGTGGCAA | SEQ ID NO: 679 | Homo sapiens transmembrane and coiled-coil domains 1 (TMCO1), mRNA [NM_019026] |
| 680 | A_23_P355244 | SAMD9 | TCAGTGGAGGAAGATTTTCCGTTGCTTGTGGATAAAATTTAAGTCCATAACTTATAAGC | SEQ ID NO: 680 | Homo sapiens sterile alpha motif domain containing 9 (SAMD9), mRNA [NM_017654] |
| 681 | A_23_P357995 | ZBTB8OS | ATCAATTGGGTGGGGAAGAAGATTTCATTGTCCAAGCACCGTCAGGGAACAGAAGTCAA | SEQ ID NO: 681 | Homo sapiens zinc finger and BTB domain containing 8 opposite strand (ZBTB8OS), mRNA [NM_178547] |
| 682 | A_23_P371266 | DNM3 | ACTGTCTTCTTGGGAGTTTCAGGATTTCTTAATGCTGATATATGGACTGTTAGAATGGAA | SEQ ID NO: 682 | Homo sapiens dynamin 3 (DNM3), mRNA [NM_015569] |
| 683 | A_23_P37441 | B2M | TTGTCTTTCAGCAAGGACTGGTGTTTGTTCTATCGTCTTGTAGACAGGAATTCACCCCCACT | SEQ ID NO: 683 | Homo sapiens beta-2-microglobulin (B2M), mRNA [NM_004048] |
| 684 | A_23_P37535 | RAB8B | AGCGTTTCCGTATTTCAGCACAACATGTTAGAGTCATATATTTGACACTTTGTCGTGAAG | SEQ ID NO: 684 | Homo sapiens RAB8B, member RAS oncogene family (RAB8B), mRNA [NM_016530] |
| 685 | A_23_P378722 | SAT1 | CCATGTACTATTTTACGTATGACCCGTGGATTGGCAAGTTATGTATGTGAGGACTCT | SEQ ID NO: 685 | Homo sapiens spermidine/spermine N1-acetyltransferase 1 (SAT1), mRNA [NM_002970] |
| 686 | A_23_P380848 | TXNL5 | ATGTGGAAATGTTGTCTGTGAAGATTAAGAATTTAGGATGGCAATCATGTCTTGATGT | SEQ ID NO: 686 | Homo sapiens thioredoxin-like 5 (TXNL5), mRNA [NM_032731] |
| 687 | A_23_P389118 | TMEM16F | TATGTTGAGAGGGGAAGAGTAAAATGTATGAGCAGCTTAACTGAAGTAGAACTATTCATGATGC | SEQ ID NO: 687 | Homo sapiens transmembrane protein 16F (TMEM16F), mRNA [NM_001025356] |
| 688 | A_23_P406355 | FAM76B | AAACTGTTGGAAACAAAGTTCAGGCCAAAAGAGAAGAAGTACTCAAACAGGTGGAGGATTAT | SEQ ID NO: 688 | Homo sapiens family with sequence similarity 76, member B (FAM76B), mRNA [NM_144664] |
| 689 | A_23_P41114 | CSTA | AAACAAATGAGACTTATGGAAAAATTGGAAGGTGTGCAGTATAAAACTCAAGTTGTTGCTG | SEQ ID NO: 689 | Homo sapiens cystatin A (stefin A) (CSTA), mRNA [NM_005213] |
| 690 | A_23_P412392 | SEC22B | GTTTTTGATGGCCTTTTAAAGAAGAGTCCAGTATGTGAAGGTTAATTGCTGTGCAGA | SEQ ID NO: 690 | Homo sapiens SEC22 vesicle trafficking protein homolog B (S. cerevisiae) (SEC22B), mRNA [NM_004892] |
| 691 | A_23_P412980 | SNX13 | CCCGATGTCAAGCAAGAATGGCGTTGGTTTGTTCCATTTCAAAGTAATCAGGATTCTCCA | SEQ ID NO: 691 | Homo sapiens sorting nexin 13 (SNX13), mRNA [NM_015132] |
| 692 | A_23_P41645 | ELL2 | TGTCTTTCAAAGTGCTGCCAGTTGAAAAGGGAAGCATTATGTTTACAAATCTGTTTTGA | SEQ ID NO: 692 | Homo sapiens elongation factor, RNA polymerase II, 2 (ELL2), mRNA [NM_012081] |
| 693 | A_23_P419239 | ETNK1 | GGGCTTTGGGACTGAAGTTACTGAAGAAGGAGGTAGAAATACTCTTCATTCAAGTCAATGA | SEQ ID NO: 693 | Homo sapiens ethanolamine kinase 1 (ETNK1), transcript variant 1, mRNA [NM_018638] |
| 694 | A_23_P422794 | NSMCE2 | CATTTCGGATGATTGAGTGCAGGCAAAGCGGAAGAAAAAGGCCTATTCGCGTCAAAT | SEQ ID NO: 694 | Homo sapiens non-SMC element 2, MMS21 homolog (S. cerevisiae) (NSMCE2), mRNA [NM_173685] |
| 695 | A_23_P424080 | YIPF4 | AAAGCATTGTTTTTAAGAATTGTGTCGATATTCACGTAAAAACTTGTGGGAAAAGCACC | SEQ ID NO: 695 | Homo sapiens Yip1 domain family, member 4 (YIPF4), mRNA [NM_032312] |

Fig. 1-39

| No. | Probe ID No. | Symbols of genes | Sequence | SEQ ID NO: | Descriptions of genes (letters and numbers within [ ] indicates GenBank accession No.) |
|---|---|---|---|---|---|
| 696 | A_23_P42514 | C6orf62 | TCGTTTGGAGTAAAACTAGTGCTTACGGAGTTTCCAATTGTATTTA GCTTGTGGTTGGAAT | SEQ ID NO: 696 | Uncharacterized protein C6orf62 (HBV X-transactivated gene 12 protein). [Source:Uniprot/SWISSPROT:Acc:Q9GZU0] [ENST00000378119] |
| 697 | A_23_P42949 | FLJ25416 | GCTTGGTCACGTGGAATTGTTTTCATAAAAGTCACCTGAACGCAA TTCGTGAACTTTTAA | SEQ ID NO: 697 | Homo sapiens hypothetical protein FLJ25416 (FLJ25416), mRNA [NM_145018] |
| 698 | A_23_P42975 | PRKAR2B | GCCACATTTTAGAACAGTGTTAACATTTTTGCAAAACCTTCTTGTAGGAAAAGAGAGC | SEQ ID NO: 698 | Homo sapiens protein kinase, cAMP-dependent, regulatory, type II, beta (PRKAR2B), mRNA [NM_002736] |
| 699 | A_23_P43049 | DCTN6 | AAATACATTTGAAGTCATCCCCTGAGAATACGGTGATCTATGGTGC AGAGTGCTTCGTCG | SEQ ID NO: 699 | Homo sapiens dynactin 6 (DCTN6), mRNA [NM_006571] |
| 700 | A_23_P434768 | NUP50 | TATAATCTCAGGTTGTATTAGTTTTTGAATGCTCCCATGGAGGAA GTGTAAGAATCCATG | SEQ ID NO: 700 | Homo sapiens nucleoporin 50kDa (NUP50), transcript variant 2, mRNA [NM_007172] |
| 701 | A_23_P434809 | S100A8 | AAAGCCAATGAAGAAAGCACAGAAGAGTAGCTGAGTTACTGGGCCG AGAGGCTGGGGCCT | SEQ ID NO: 701 | Homo sapiens S100 calcium binding protein A8 (S100A8), mRNA [NM_002964] |
| 702 | A_23_P43946 | CIP29 | AAAGAGCAGAGCGGCGTTGGGATTGGCTGATGAAAAGTTCGTGATA CTTTGTTCTCCAG | SEQ ID NO: 702 | Homo sapiens cytokine induced protein 29 kDa (CIP29), mRNA [NM_033082] |
| 703 | A_23_P44768 | TBK1 | TCTACTCGAGTGGGGCTAAATAAGTTATTTCTGTGACCGCCTA GTGAAATATTTTA | SEQ ID NO: 703 | Homo sapiens TANK-binding kinase 1 (TBK1), mRNA [NM_013254] |
| 704 | A_23_P48697 | CCPG1 | AAGTCAAGAAGAGCTCATATATATATAATTCTAATGTCCCACCTATGT CCATTCGATGTACCA | SEQ ID NO: 704 | Homo sapiens cell cycle progression restoration 8 protein (CPR8) mRNA, complete cds. [AF011794] |
| 705 | A_23_P500381 | HTR7 | TAACTCCATTGAAGATTGCTTCTTACGGAGACATGGGAAAAGTA CCGTTTCCTGCTAAAGGG | SEQ ID NO: 705 | Homo sapiens 5-hydroxytryptamine (serotonin) receptor 7 (adenylate cyclase-coupled) (HTR7), transcript variant d, mRNA [NM_019859] |
| 706 | A_23_P50108 | NDC80 | AAAGTGGGAAATAACTTGCAACGTCGTTGTTAGAGATGGTTGCTACA CATGTTGGGTGTGTA | SEQ ID NO: 706 | Homo sapiens NDC80 homolog, kinetochore complex component (S. cerevisiae) (NDC80), mRNA [NM_006101] |
| 707 | A_23_P51009 | NDUFB3 | CCGCAATGAAGGATAAGGTTGGAGAATACATGGGTGGCTTTGACTTCTTTAAAGGTCATTCCTTTCTGATGT | SEQ ID NO: 707 | Homo sapiens NADH dehydrogenase (ubiquinone) 1 beta subcomplex, 3, 12kDa (NDUFB3), mRNA [NM_002491] |
| 708 | A_23_P51487 | GBP3 | AATCCTAAAGGATAAGGTAGTGTTCCTGATTGTTAAAGGTCAT ACTTGAAATCCTGCC | SEQ ID NO: 708 | Homo sapiens guanylate binding protein 3 (GBP3), mRNA [NM_018284] |
| 709 | A_23_P51572 | TSNAX | GAATGGGGACATTGATACCCCCTTTGAAGTGAGCCAGTTTTTACG TCAGGTTTATGATGG | SEQ ID NO: 709 | Homo sapiens translin-associated factor X (TSNAX), mRNA [NM_005999] |
| 710 | A_23_P5389 | LOC84661 | TACCTGGATCAGACAGTTGTGCCTATCTTATTACAGGGACTTGGT GTGGTGCAAAGGAA | SEQ ID NO: 710 | Homo sapiens dpy-30-like protein (LOC84661), mRNA [NM_032574] |
| 711 | A_23_P58390 | C4orf32 | TAATACTAACTATTTAGTATACGTGCAGTACTGTACATGTGCACA CTGGTGTTAATAGGG | SEQ ID NO: 711 | Homo sapiens chromosome 4 open reading frame 32 (C4orf32), mRNA [NM_152400] |
| 712 | A_23_P58396 | PDGFC | CATGAATATTTATGTACAGAAGAATATGTCTCTTAACCAGTTCAG TTATTGTACTGTGCC | SEQ ID NO: 712 | Homo sapiens platelet derived growth factor C (PDGFC), mRNA [NM_016205] |
| 713 | A_23_P59921 | SUB1 | CAGATTGGGAAATGAGGTACGTTAGTGTTCGCGATTTAAAGGC AAAGTGGTAATTGAT | SEQ ID NO: 713 | Homo sapiens SUB1 homolog (S. cerevisiae) (SUB1), mRNA [NM_006713] |

Fig. 1-40

| No. | Probe ID No. | Symbols of genes | Sequence | SEQ ID NO: | Descriptions of genes [letters and numbers within [ ] indicates GenBank accession No.) |
|---|---|---|---|---|---|
| 714 | A_23_P60248 | TXN | GGAGAAAAGGTGGGTGAATTTTGTGAGGGAATAAGGAAAAGCTTGAAGCCACCATTAAT | SEQ ID NO: 714 | Homo sapiens thioredoxin (TXN), mRNA [NM_003329] |
| 715 | A_23_P63655 | ATP5C1 | AGAGAGGCTGAAAGCAGCTCGAATATAGGGATTGGGATCTTTAGGTGTGTATGAAAAAGCT | SEQ ID NO: 715 | Homo sapiens ATP synthase, H+ transporting, mitochondrial F1 complex, gamma polypeptide 1 (ATP5C1), nuclear gene encoding mitochondrial protein, transcript variant 2, mRNA [NM_005174] |
| 716 | A_23_P63896 | FAS | ATGTCTATCCACAGGGTAAGGCACTCTATGAATGAATAGAAGAAGCTATGACGTTTTGC | SEQ ID NO: 716 | Homo sapiens Fas (TNF receptor superfamily, member 6) (FAS), transcript variant 1, mRNA [NM_000043] |
| 717 | A_23_P64129 | HTATIP2 | AAAGTCAGCATGTTTTGATTGTTTGTTTAGTATCGTCAGGCATCCATTCGAATCGAAGA | SEQ ID NO: 717 | Homo sapiens HIV-1 Tat interactive protein 2, 30kDa (HTATIP2), mRNA [NM_006410] |
| 718 | A_23_P65262 | RP11-298P3.3 | AGCCAAGAGCTTAAGCAGCACGTGAGTACGGTTCCCTGAGGCTACCATTATCAAGGGTTT | SEQ ID NO: 718 | Human BRCA2 region, mRNA sequence CG016 [U50529] |
| 719 | A_23_P69193 | DPH3 | TGCTGTTGTGTAAGAGTGTGGATTCTTGTATCAACTGCTGATATCATCTTCAGGAAGCA | SEQ ID NO: 719 | Homo sapiens DPH3, KTI11 homolog (S. cerevisiae) (DPH3), transcript variant 1, mRNA [NM_206831] |
| 720 | A_23_P69908 | GLRX | CTGATAAAAGTTAGAGCCCCTACACGAAGAGTGTATCGTGAAAGAGCTCCTACACTTT | SEQ ID NO: 720 | Homo sapiens glutaredoxin (thioltransferase) (GLRX), mRNA [NM_002064] |
| 721 | A_23_P69958 | AP3S1 | GATGACAAGTGGAGCATTCGTTAATTCCTTCTGCTATATGTCACACAGTTGTTATTTGAA | SEQ ID NO: 721 | Homo sapiens adaptor-related protein complex 3, sigma 1 subunit (AP3S1), mRNA [NM_001284] |
| 722 | A_23_P70290 | TMEM30A | ATCTTCTGCCTGCAAGTCAAGCACATGTAAAGCACATGTAAGTGCTTAATGGAGACTGTTTTCATTGTTG | SEQ ID NO: 722 | Homo sapiens transmembrane protein 30A (TMEM30A), mRNA [NM_018247] |
| 723 | A_23_P71117 | SLC25A40 | AGCCAAAGAAGAATGGCTTAGGCAAGAGTGTTAGGCAAGAGTTACCATTATTCTCTGAGAATG | SEQ ID NO: 723 | Homo sapiens solute carrier family 25, member 40 (SLC25A40), mRNA [NM_018843] |
| 724 | A_23_P74799 | SLC25A24 | GATTCTGTATCTTTTGGAAAAAAGCCGAGAGTTGAAGATAGTATACAGTGTGGTAGTAGTG | SEQ ID NO: 724 | Homo sapiens solute carrier family 25 (mitochondrial carrier; phosphate carrier), member 24 (SLC25A24), transcript variant 2, mRNA [NM_213651] |
| 725 | A_23_P75028 | REEP3 | AGAAACGACGACAAGTGTATTTTTAGTCATCTACACGTGAAATATGCCAAGACAGATTAT | SEQ ID NO: 725 | Homo sapiens receptor accessory protein 3 (REEP3), mRNA [NM_001330] |
| 726 | A_23_P76480 | BF213736 | AAATGAACAGAGGACAAATGGGTAGAATGGAGGTACAATTTACCAAATCGTTTGGCATGACAGG | SEQ ID NO: 726 | BF213736 601847628F1 NIH_MGC_55 Homo sapiens cDNA clone IMAGE:4078519 5', mRNA sequence [BF213738] |
| 727 | A_23_P76799 | BAZ1A | TACGACATGAATGAATCCAATGTTATACCTTGAAGTGGTACCAGTGGTGGGTGCAGGT | SEQ ID NO: 727 | Homo sapiens bromodomain adjacent to zinc finger domain, 1A (BAZ1A), transcript variant 1, mRNA [NM_013448] |
| 728 | A_23_P77073 | SPPL2A | ATGTTCAGCAGCTGGTTCTTCTTACATATAGTATGTTTCGTACAGTTGCTATGCTATTG | SEQ ID NO: 728 | Homo sapiens signal peptide peptidase-like 2A (SPPL2A), mRNA [NM_032802] |
| 729 | A_23_P77145 | RAB11A | TATAGAATATATAGTCAGTTAAATCTTTGTTTCAGTATGTCTGAAGAGTACAGTGAGAGG | SEQ ID NO: 729 | Homo sapiens RAB11A, member RAS oncogene family (RAB11A), mRNA [NM_004663] |
| 730 | A_23_P78092 | EVI2A | GCTAATTCAGACACTTGGAAAAGAACAAAAACAGCTCACAGGACGCAACGTAGTAGTGATGCAA | SEQ ID NO: 730 | Homo sapiens ecotropic viral integration site 2A (EVI2A), transcript variant 1, mRNA [NM_001003927] |

Fig. 1-41

| No | Probe ID No | Symbols of genes | Sequence | SEQ ID NO. | Descriptions of genes (letters and numbers within [ ] indicates GenBank accession No.) |
|---|---|---|---|---|---|
| 731 | A_23_P79199 | DBI | TGCTCACCATACGGCTCTAACAGATTAGGGGCTAAAACGATTACTGACTTGCTTGAGTA | SEQ ID NO: 731 | Homo sapiens diazepam binding inhibitor (GABA receptor modulator, acyl-Coenzyme A binding protein) (DBI), transcript variant 1, mRNA [NM_020548] |
| 732 | A_23_P81212 | MRPS18C | ATGGGGTTTATGCAGTTACATAGAAGGATCCTGCATATCTCAAGGACCCTAAAGTTGT | SEQ ID NO: 732 | Homo sapiens mitochondrial ribosomal protein S18C (MRPS18C), nuclear gene encoding mitochondrial protein, mRNA [NM_016067] |
| 733 | A_23_P81612 | SRP19 | AGGAAAGAAAAAGAAGTAACGTAGTATCAGGATCAAGTATGTGGTACTACTGTAAGAGAC | SEQ ID NO: 733 | Homo sapiens signal recognition particle 19kDa (SRP19), mRNA [NM_003135] |
| 734 | A_23_P81690 | COX7A2 | AGCTCTGTATGGACGACTTATCTGATAAATAACCGAGCTCTGTTTGGGGATCAATATTT | SEQ ID NO: 734 | Homo sapiens cytochrome c oxidase subunit VIIa polypeptide 2 (liver) (COX7A2), mRNA [NM_001865] |
| 735 | A_23_P82674 | GBAS | TTACAAGTGTACCGAATAACTGAAATGTTTAACTCACTCGATTTGTAAGCAGTCCAC | SEQ ID NO: 735 | Homo sapiens glioblastoma amplified sequence (GBAS), mRNA [NM_001483] |
| 736 | A_23_P82748 | ENY2 | CATTGTCTGGTCAGCATGGCAGGCTTTAAGATTGAATTAGATTGTGTGTTGGTTTTA | SEQ ID NO: 736 | Homo sapiens enhancer of yellow 2 homolog (Drosophila) (ENY2), mRNA [NM_020189] |
| 737 | A_23_P83073 | HIATL1 | AAACAACTCAAGCATTCTGGTGGCAACATAGAGATTGTAGGCTGCTTGCTAAGAAAGTTAT | SEQ ID NO: 737 | Homo sapiens hippocampus abundant transcript-like 1 (HIATL1), mRNA [NM_032258] |
| 738 | A_23_P83175 | PTPLAD2 | CATCCTTTTTGTGGTGATCACCAGTCAAGAGGAAGTCCAAGAGAATATGTGGTGTGT | SEQ ID NO: 738 | Homo sapiens protein tyrosine phosphatase-like A domain containing 2 (PTPLAD2), mRNA [NM_001010915] |
| 739 | A_23_P83278 | CHMP5 | CATTGTCTATTTTCTGGGACTCATTGCTTGGGAATGGTTTCTTCGTAG | SEQ ID NO: 739 | Homo sapiens chromatin modifying protein 5 (CHMP5), mRNA [NM_016410] |
| 740 | A_23_P83414 | PPP1CB | AAATAGCCACATTGTCCAATCCAGTGATTTAATCATACAGTTTGACTGGGGCAAGTTTA | SEQ ID NO: 740 | Homo sapiens protein phosphatase 1, catalytic subunit, beta isoform (PPP1CB), transcript variant 1, mRNA [NM_002709] |
| 741 | A_23_P86403 | KIF5B | AACACAACTAGAGTGCAATTTGGCATCTTAGGAGGGAAAAAGGACAGTTACAAGTGTG | SEQ ID NO: 741 | Homo sapiens kinesin family member 5B (KIF5B), mRNA [NM_004521] |
| 742 | A_23_P86653 | SRGN | AGGACTTGGGTCAACATGGATTAGAAGAGGATTTTATGTTATAAAGAGAATTTCCAC | SEQ ID NO: 742 | Homo sapiens serglycin (SRGN), mRNA [NM_002727] |
| 743 | A_23_P92842 | SAR1B | TAATCTGCACATCACCCCAGCGCCATTTGTAAAGAGCAACTTTCCAGCAGTACATTTGAAG | SEQ ID NO: 743 | Homo sapiens SAR1 gene homolog B (S. cerevisiae) (SAR1B), transcript variant 2, mRNA [NM_016103] |
| 744 | A_23_P94230 | LY96 | TGAAGTCTATTTCTGGGAGCCCAGAAGAAAATGCTCTTTTGCTTGGAGTTTGTCATCCTACA | SEQ ID NO: 744 | Homo sapiens lymphocyte antigen 96 (LY96), mRNA [NM_015364] |
| 745 | A_23_P94533 | CTSL1 | AAGAGATAGGATCATGGTGTGTGGCGGTTGGTTGGCTAGGAGTTTGAAAGCAACAGAATCAGATA | SEQ ID NO: 745 | Homo sapiens cathepsin L1 (CTSL1), transcript variant 1, mRNA [NM_001912] |
| 746 | A_23_P94932 | C2orf25 | TCTGTTGATGAGCTTGGATGCTGTAAAGTGATTCGTCATAGTCTCTGGGTACCCATGTA | SEQ ID NO: 746 | Homo sapiens chromosome 2 open reading frame 25 (C2orf25), mRNA [NM_015762] |
| 747 | A_23_P95130 | SLC37A3 | TTGAGGGATAGGTAATTTGCATTCGGTTAGGGAGATATTTTCAACCTCTTGCTTTATACT | SEQ ID NO: 747 | Homo sapiens solute carrier family 37 (glycerol-3-phosphate transporter), member 3 (SLC37A3), transcript variant 1, mRNA [NM_207113] |
| 748 | A_23_P95382 | TIMM8B | TTGTTACTAAGCAGATTTAAGGGTCAGTGGGGCAAGGCTATCAACGCATTGTCAGAATCAG | SEQ ID NO: 748 | Homo sapiens translocase of inner mitochondrial membrane 8 homolog B (yeast) (TIMM8B), mRNA [NM_012459] |

Fig. 1-42

| No. | Probe ID No. | Symbols of genes | Sequence | SEQ ID NO: | Descriptions of genes (letters and numbers within [ ] indicates GenBank accession No.) |
|---|---|---|---|---|---|
| 749 | A_24_P101859 | LOC392221 | GGTTCAGTGGAGGAAGTAATGGTGAGGCGTGGAAAACTTGACATCACTTACCAGGAGGATG | SEQ ID NO: 749 | PREDICTED: Homo sapiens similar to Coiled-coil-helix-coiled-helix domain-containing protein 2 (HCV NS2 trans-regulated protein) (MS2TP) (LOC392221), mRNA [XM_373252] |
| 750 | A_24_P103886 | IDI1 | GGTTCGGTCCTTCAAAACAGTGTTAATTAACTTTCATATTAGGAGATTAAACTAGCAGAG | SEQ ID NO: 750 | Homo sapiens isopentenyl-diphosphate delta isomerase 1 (IDI1), mRNA [NM_004508] |
| 751 | A_24_P105164 | RP11-217H1.1 | GGAATAATGTGTGTGGCTGGTATTGGAGTTGTTGTATTATCTTCAGTTGGAATGCTCTCT | SEQ ID NO: 751 | Homo sapiens implantation-associated protein (DKFZp564K142), mRNA [NM_032121] |
| 752 | A_24_P105648 | BX111927 | TTATGAGATGCTTCAGTTCAAATAACAGTGGAGTAATTCACCTATATCTAAAAGAGTGCC | SEQ ID NO: 752 | BX111927 Soares multiple sclerosis_2NbHMSP Homo sapiens cDNA clone IMAGp998G05619, mRNA sequence [BX111927] |
| 753 | A_24_P11045 | THC2785765 | CCACCAGAAACGTAGACGTGATTTTCATGACAAATACGGGTAGGAACACAAGTGGGAATAG | SEQ ID NO: 753 | COX7B HUMAN (P24311) Cytochrome c oxidase polypeptide VIIb, mitochondrial precursor, partial (78%) [THC2785765] |
| 754 | A_24_P110591 | A_24_P110591 | TGATGGAACTATAACAACAGAATCAGGAAGTGTAATGAGGGTCTCTTGGGCAGAATCCCAC | SEQ ID NO: 754 | |
| 755 | A_24_P111737 | ATP11B | GGTCCTGTCAAGTGGTTCTGGTTTGGTTTGGCATAATCCTCATGGTTGTTACATGTCATT | SEQ ID NO: 755 | Homo sapiens ATPase, Class VI, type 11B (ATP11B), mRNA [NM_014616] |
| 756 | A_24_P114249 | GALNT3 | ATTTCAAATGCAGAATAGTGACTCATTTAAAGCTAAATTTGTTACTGATTCAATTATA | SEQ ID NO: 756 | Homo sapiens UDP-N-acetyl-alpha-D-galactosamine:polypeptide N-acetylgalactosaminyltransferase 3 (GalNAc-T3) (GALNT3), mRNA [NM_004482] |
| 757 | A_24_P114617 | CHMP2B | GGCTAATTGAAATATGTAGTCTTATTTTAGACACGGGTGTGTTAAAAGAGACCAGAGTTTT | SEQ ID NO: 757 | Homo sapiens chromatin modifying protein 2B (CHMP2B), mRNA [NM_014043] |
| 758 | A_24_P115774 | BIRC2 | GATACCATTTTGGTTAAAGGAAATGGTGCGGCCCAAATCTTCAAAAGTGTGTAAAAGAA | SEQ ID NO: 758 | Homo sapiens baculoviral IAP repeat-containing 2 (BIRC2), mRNA [NM_001166] |
| 759 | A_24_P119141 | PROS1 | AGGAGCACCAGGAATCTTAGTTCTTGGCAGCTGCAGTCGTCGAAGATGAGACATCAGATTA | SEQ ID NO: 759 | Homo sapiens protein S (alpha) (PROS1), mRNA [NM_000313] |
| 760 | A_24_P12149 | CLINT1 | TTAACTTGCAAGGGGTTCCTTGCGTGTTTATCCCTGTAGGGATCATTTAAGTCAGGAACA | SEQ ID NO: 760 | Homo sapiens clathrin interactor 1 (CLINT1), mRNA [NM_014666] |
| 761 | A_24_P123652 | RAP2B | GGAATAAGTTCCTGGATTATAAGTATAAAGGGAACCGAGAATTAATTTGGAGATCATCAC | SEQ ID NO: 761 | Homo sapiens RAP2B, member of RAS oncogene family (RAP2B), mRNA [NM_002886] |
| 762 | A_24_P124992 | PSMA4 | AAAGTCCCTTTGGTGTTTCATTGGTGTACATTGGCTGGGATAAGCACTATGGGTTTCAG | SEQ ID NO: 762 | Homo sapiens proteasome (prosome, macropain) subunit, alpha type, 4 (PSMA4), mRNA [NM_002789] |
| 763 | A_24_P126741 | ENST00000309178 | AGGGTCCAACCACACTAGACAAGATTGAAGATTAGTTGCAACAGGTCAGAGGAGGAGAAT | SEQ ID NO: 763 | |
| 764 | A_24_P131392 | FAM82A | CTATGCCTGGTTATTCTAATCCAATTACATGTAGTTAGGAAAAGTGTTATACTGATCTT | SEQ ID NO: 764 | Homo sapiens family with sequence similarity 82, member A (FAM82A), mRNA [NM_144713] |
| 765 | A_24_P137372 | ATP2C1 | TCGGTTGAGAAGGTTTTCAGACTGAGAGCCTAAGGAATACTGAGTCTGTGTTCTTTT | SEQ ID NO: 765 | Homo sapiens ATPase, Ca++ transporting, type 2C, member 1 (ATP2C1), transcript variant 2, mRNA [NM_001001487] |

Fig. 1-43

| No. | Probe ID No. | Symbols of genes | Sequence | SEQ ID NO: | Descriptions of genes (letters and numbers within [ ] indicates GenBank accession No.) |
|---|---|---|---|---|---|
| 766 | A_24_P143827 | PCMT1 | GGATGAATTGTAAAAGGAACATCAGGTTGACCAGTATAAAATTACAGTGGATTGCTCATC | SEQ ID NO: 766 | Homo sapiens protein-L-isoaspartate (D-aspartate) O-methyltransferase (PCMT1), mRNA [NM_005389] |
| 767 | A_24_P146670 | SLK | TGTGGTTGCTGGTGTGGTGTAATTATTAATGAAATGTTCACTCGTAGTCCTTATGAGCT | SEQ ID NO: 767 | Homo sapiens STE20-like kinase (yeast) (SLK), mRNA [NM_014720] |
| 768 | A_24_P152385 | THC2736233 | CAAACAGCTCACAGTCCAAGGAAGCTGTGTTGAATGTTTGAGAGGTCAGTGGGGTGTGGAT | SEQ ID NO: 768 | ATP5L_PONPY (Q5RFH0) ATP synthase subunit g, mitochondrial (ATPase subunit g), partial (91%) [THC2736233] |
| 769 | A_24_P157415 | ATP11B | GTGTACTGTAAGACAGGCTGTAAAGTTAGCCATATAAAATGCAAGGGTATATCATATATAG | SEQ ID NO: 769 | Homo sapiens ATPase, Class VI, type 11B (ATP11B), mRNA [NM_014616] |
| 770 | A_24_P169976 | LOC652912 | TTCGTTCTGTCTGTGAGTATCACCCAAAAAACCAAAGGAGAACATCCTGTCCAGTCCACTA | SEQ ID NO: 770 | PREDICTED: Homo sapiens similar to High mobility group protein B1 (High mobility group protein 1) (HMG-1) (Amphoterin) (Heparin-binding protein p30) (LOC652912), mRNA [XR_019552] |
| 771 | A_24_P175187 | SAMD9 | CAAGCAGGATACAGTAATCAAGTAATGCAAAATGTAAATTTGCCTAATAAAATTATGGATATGGGCAG | SEQ ID NO: 771 | Homo sapiens sterile alpha motif domain containing 9 (SAMD9), mRNA [NM_017654] |
| 772 | A_24_P175188 | SAMD9 | TGCCAATGTACTGCGTAAGCTAAGCATACAACGCTATGTTTTGAACAAAACACCAGCAGATA | SEQ ID NO: 772 | Homo sapiens sterile alpha motif domain containing 9 (SAMD9), mRNA [NM_017654] |
| 773 | A_24_P175519 | TXN | AAGTAGATGTGGATGAATGACTGTCAGGATGTGCTTCAGAGTGTGAAGTCAAATGCACGCAA | SEQ ID NO: 773 | Homo sapiens thioredoxin (TXN), mRNA [NM_003329] |
| 774 | A_24_P175989 | VPS29 | GAGAGGAGACTTCGATGAGAATTATCCAGAAGACAGAAAGTTGTGACTGTTGGACA | SEQ ID NO: 774 | Homo sapiens vacuolar protein sorting 29 homolog (S. cerevisiae) (VPS29), transcript variant 2, mRNA [NM_057180] |
| 775 | A_24_P177634 | A_24_P177634 | CATTCATTCCAGGCTCTCTCATGGGACCAGAAATCTGATAAATGAGTTCTTCTTGGGGGATCAA | SEQ ID NO: 775 | |
| 776 | A_24_P180424 | TMEM30A | CAATGTGTATGCACATTGTCTTTAGTTAAGGCACCAATTGTTTTGGTTGGTTTTCCTAAG | SEQ ID NO: 776 | Homo sapiens transmembrane protein 30A (TMEM30A), mRNA [NM_018247] |
| 777 | A_24_P186862 | CHMP5 | TGAGAATTTAGAAGACAGCTAGTGAACAGTTAGGTGAACAGTTGGGATGGCTGAAATCCGAAGAGC | SEQ ID NO: 777 | Homo sapiens chromatin modifying protein 5 (CHMP5), mRNA [NM_016410] |
| 778 | A_24_P195327 | LOC391040 | ACAGGTTAACAATGCTTAAGAAGCTTAGGTGAACAGTTAAGCGTTAGAAGAAGCTTGGAGCAGTA | SEQ ID NO: 778 | PREDICTED: Homo sapiens similar to basic transcription factor 3-like 4 (LOC391040), mRNA [XR_019253] |
| 779 | A_24_P200162 | HIGD1A | TATTCGATGTATCGGGAATTCTGGGCAAAAGCTAAGCGTTAGAAGAAGATGCTGCTT | SEQ ID NO: 779 | Homo sapiens HIG1 domain family, member 1A (HIGD1A), mRNA [NM_014056] |
| 780 | A_24_P20120 | KIAA1212 | TTGGACAATGAAAAATGCCTTAAAAGGAATGCATATGGATAAAGTTGGACTTATAAGACCC | SEQ ID NO: 780 | Homo sapiens KIAA1212 (KIAA1212), mRNA [NM_018084] |
| 781 | A_24_P201702 | CLEC2B | ATTGAATTCAAGTAAGTAATAGAACTTCCAGTCAACTGCCAGCCTAACTATAATTGACA | SEQ ID NO: 781 | Homo sapiens C-type lectin domain family 2, member B (CLEC2B), mRNA [NM_005127] |
| 782 | A_24_P209204 | C6orf62 | GGTTGGCATAGTTTATTGGAGTAAATCTGAATGCTACTCGTTGGAGTAAGAGTAGT | SEQ ID NO: 782 | Homo sapiens chromosome 6 open reading frame 62 (C6orf62), mRNA [NM_030939] |
| 783 | A_24_P211351 | ENST00000370395 | GTGTGGATTCTTTCGATCAACTGCTGATTCATCTTCAGGAAGCAAGAGATAACATGA | SEQ ID NO: 783 | DPH3 homolog B (CSL-type zinc finger-containing protein 1). [Source:Uniprot/SWISSPROT;Acc:Q9H4G8] [ENST00000370395] |

Fig. 1-44

| No. | Probe ID No. | Symbols of genes | Sequence | SEQ ID NO: | Descriptions of genes (letters and numbers within [ ] indicates GenBank accession No.) |
|---|---|---|---|---|---|
| 784 | A_24_P216654 | SOAT1 | CGCAGTAATGTTCTGCAGAACAGTATTGTAATTGTAATGGAATCATTAACCTGCTAACTAG | SEQ ID NO: 784 | Homo sapiens sterol O-acyltransferase (acyl-Coenzyme A: cholesterol acyltransferase) 1 (SOAT1), transcript variant 688113, mRNA [NM_003101] |
| 785 | A_24_P223124 | FNDC3B | CTCAGTGTTGGACAATACATTCCAAGCTTTCAACTCTAGGAGAAAAAGAAAATACATGTTT | SEQ ID NO: 785 | Homo sapiens fibronectin type III domain containing 3B (FNDC3B), mRNA [NM_022763] |
| 786 | A_24_P23245 | NDUFA6 | TTCTGGTCATTAAGGCAAAGATCGAACTGGAAGAAACAATTAAAGTATGGAAGGAGCGGA | SEQ ID NO: 786 | Homo sapiens NADH dehydrogenase (ubiquinone) 1 alpha subcomplex, 6, 14kDa (NDUFA6), nuclear gene encoding mitochondrial protein, mRNA [NM_002490] |
| 787 | A_24_P234214 | HNRPLL | AGAGGTGTCACACACGTTAATAATGTCAAATTATTGGGAAAAGAGTTAAIGTTTGCGTG | SEQ ID NO: 787 | Homo sapiens heterogeneous nuclear ribonucleoprotein L-like (HNRPLL), mRNA [NM_138394] |
| 788 | A_24_P240065 | VPS24 | GACCATGAGGGAGTTGTGCAAAGAAATGATGAAGGCTGGGATCATAGAGGAGATGTTAGA | SEQ ID NO: 788 | Homo sapiens vacuolar protein sorting 24 homolog (S. cerevisiae) (VPS24), transcript variant 1, mRNA [NM_016079] |
| 789 | A_24_P247608 | PCMT1 | GTATGGTTGGATGTACTGGCAAAAGTCATAGGAAATTGATCACATTAAAGAGCTAGTAGATG | SEQ ID NO: 789 | Homo sapiens protein-L-isoaspartate (D-aspartate) O-methyltransferase (PCMT1), mRNA [NM_005389] |
| 790 | A_24_P255314 | SRP14P1 | TATCGATGGAGAAAAGAAGAAGATGAGCACTGTGTGGTGAACTCCAAGGAAGTGAGTAAGTTTCA | SEQ ID NO: 790 | Homo sapiens signal recognition particle 14kDa (homologous Alu RNA binding protein) pseudogene 1 (SRP14P1) on chromosome 12 [NR_002273] |
| 791 | A_24_P263524 | TXNDC9 | TGACTCACCACGAGAAACTTTAGAATGGAGGGCTCAGTTGTTGTGACATTCTTAATTACAG | SEQ ID NO: 791 | Homo sapiens thioredoxin domain containing 9 (TXNDC9), mRNA [NM_005783] |
| 792 | A_24_P278460 | MLSTD2 | ACCCATGGACAATATGGTTAGGATTAGAGGAAGGAAGTCCTTAGTTACACTTCTTGTCTG | SEQ ID NO: 792 | Homo sapiens male sterility domain containing 2 (MLSTD2), mRNA [NM_032228] |
| 793 | A_24_P283320 | PCMT1 | CAAAATGTAACCATACGATGTCGCACAATCAATAAGGTTTCCAAGGAACAACATCAGTG | SEQ ID NO: 793 | Homo sapiens protein-L-isoaspartate (D-aspartate) O-methyltransferase (PCMT1), mRNA [NM_005389] |
| 794 | A_24_P320284 | DHFR | GTCGTGTGATGTGCAGGAGGGCATTAAGTACAAATTTGAAGTATATGAGAAGAAT | SEQ ID NO: 794 | Homo sapiens dihydrofolate reductase (DHFR), mRNA [NM_000791] |
| 795 | A_24_P320328 | SUB1 | CACAAAAAGCGTGTAAAGAAACAAAAGACAGGTGAGACTTCGAGAGCCCTGTCATCTTCCA | SEQ ID NO: 795 | Homo sapiens SUB1 homolog (S. cerevisiae) (SUB1), mRNA [NM_006713] |
| 796 | A_24_P322353 | PSTPIP2 | AGAATCTTTCCCTTGCTAGACCCCAGAATTTTAAATGCATCCGTCTTACACTTTCACAAA | SEQ ID NO: 796 | Homo sapiens proline-serine-threonine phosphatase interacting protein 2 (PSTPIP2), mRNA [NM_024430] |
| 797 | A_24_P324506 | A_24_P324506 | GCAAATAAGGCAGCTAATTGCAAATAGAAGTATGGCATATTTCGTGACATGTGTGT | SEQ ID NO: 797 | |
| 798 | A_24_P324886 | DOCK4 | ATTTTCCGTGTTTTGTTGGGAAGGCTGATTTTAGTTTAAGCATGTTTGTTTGGTAGC | SEQ ID NO: 798 | Homo sapiens dedicator of cytokinesis 4 (DOCK4), mRNA [NM_014705] |
| 799 | A_24_P325176 | KIAA1109 | TGATCCAGTAGGTGTTGATTATTCTTGAAAAATTGGGCTTTCATCAAGCTAGGAGTA | SEQ ID NO: 799 | Homo sapiens KIAA1109, mRNA (cDNA clone IMAGE:3924668), complete cds, [BC108274] |
| 800 | A_24_P32766 | LOC730556 | ACAAGCAGCAGGAGCCTTGCTTCTATGAAGGCAGTTTCTGGAGTGTGCCCAGAACCAGGGTGA | SEQ ID NO: 800 | PREDICTED: Homo sapiens similar to Coiled-coil-helix-coiled-coil-helix domain-containing protein 2 (HCV NS2 trans-regulated protein) (NS2TP) (LOC730556), mRNA [XR_015322] |

Fig. 1-45

| No. | Probe ID No | Symbols of genes | Sequence | SEQ ID NO: | Descriptions of genes (letters and numbers within [ ] indicates GenBank accession No.) |
|---|---|---|---|---|---|
| 801 | A_24_P351451 | OPA1 | TTTTGGGTATAGAGGGCATGGCTGCTATCACCGGCAAATAGTTTAAGGCAAGAAGTTAGA | SEQ ID NO: 801 | Homo sapiens optic atrophy 1 (autosomal dominant) (OPA1), nuclear gene encoding mitochondrial protein, transcript variant 8, mRNA [NM_130837] |
| 802 | A_24_P256601 | HEXIM1 | CATGAAGCCCATGAAATTATTTGTAGACTTGTATGTACATTTTCTGGGAGAAGGTTCA | SEQ ID NO: 802 | Homo sapiens hexamethylene bis-acetamide inducible 1 (HEXIM1), mRNA [NM_006460] |
| 803 | A_24_P362540 | DDEF2 | TGGTGCTATTGTGCAGTAACTAATAGTACTCTTACGAGAGGAGAAATTATATTAACGACC | SEQ ID NO: 803 | Homo sapiens development and differentiation enhancing factor 2 (DDEF2), mRNA [NM_003887] |
| 804 | A_24_P362646 | TXNDC9 | CTCCACATTCAGGTGTAAAATACTAGACAGACATGTGGCAATATTGTCCAAGAAACAGGT | SEQ ID NO: 804 | Homo sapiens thioredoxin domain containing 9 (TXNDC9), mRNA [NM_005783] |
| 805 | A_24_P379379 | CAPZA1 | ACCAGTTTCAGGCTAAAACTTCTGGAATGGTCGTTGGAGATCAGAGTGGAAGTTCACCA | SEQ ID NO: 805 | Homo sapiens capping protein (actin filament) muscle Z-line, alpha 1 (CAPZA1), mRNA [NM_006135] |
| 806 | A_24_P388810 | SRP19 | GTTGTATGCAGCAGAAATGATAGCTAAAGTAAAACAAGGACACAAAAACAGGAGGTGC | SEQ ID NO: 806 | Homo sapiens signal recognition particle 19kDa (SRP19), mRNA [NM_003135] |
| 807 | A_24_P39378 | CCPG1 | TACTTTTGTCGCTGGAACGAACTTGATCAGTTCATCAATAAGTTTTTCGTAAACGGTGT | SEQ ID NO: 807 | Homo sapiens cell cycle progression 1 (CCPG1), transcript variant 1, mRNA [NM_004748] |
| 808 | A_24_P400760 | LOC643454 | TCCATGTAGACAAGGTTCACAGTATTGTTGGAGAAATAATGGGGGGAATGGTATTGGAGA | SEQ ID NO: 808 | PREDICTED: Homo sapiens similar to AP-3 complex subunit sigma-1 (Adapter-related protein complex 3 sigma-1 subunit) (Sigma-adaptin 3a) (AP-3 complex sigma-3A subunit) (Sigma-3A-adaptin) (LOC643454), mRNA [XR_016772] |
| 809 | A_24_P405298 | PPP1CB | GTATTAGGTTAGGTCACGACAAAGGTTTATCTGAGGTGATTAAATAACTGCTGATTGGAG | SEQ ID NO: 809 | Homo sapiens protein phosphatase 1, catalytic subunit, beta isoform (PPP1CB), mRNA [NM_002709] |
| 810 | A_24_P409410 | A_24_P409410 | ACCAGCTAATATATGGATGGGCTCTGGAGAGAAAAGCTGGTATCAAGGTGCC | SEQ ID NO: 810 | |
| 811 | A_24_P414256 | CCDC72 | TCTTTGGTCCTTGTTCTCACCGTAAATTTGTTATCACCTGAATTAAACCAACTCATTTGA | SEQ ID NO: 811 | Homo sapiens HSPC330 mRNA, partial cds. [AF161448] |
| 812 | A_24_P417281 | TXNDC10 | ATGATGAGTGATTCTTGGGAAGATAAATGTTAATGTTCCAATAGTCAAGCTTGTTTTGC | SEQ ID NO: 812 | Homo sapiens thioredoxin domain containing 10 (TXNDC10), mRNA [NM_019022] |
| 813 | A_24_P50753 | NUDT4 | AACAGAAATAAGTAGTTTTGTGAATGAGCTGCAGACAACAAAGTAGAAAGTGTCGTGCATG | SEQ ID NO: 813 | Homo sapiens nudix (nucleoside diphosphate linked moiety X)-type motif 4 (NUDT4), transcript variant 2, mRNA [NM_199040] |
| 814 | A_24_P53080 | ETFA | TGCTGTTGATGCTGGCTTTGTTCCCAATGACATGGAAGTTGGACAGACGGGAAAAATAGT | SEQ ID NO: 814 | Homo sapiens electron-transfer-flavoprotein, alpha polypeptide (glutaric aciduria II) (ETFA), nuclear gene encoding mitochondrial protein, mRNA [NM_000126] |
| 815 | A_24_P548415 | BC092452 | TATTTCTATGGAAATGCTTGCAAACATGGAAACAATGCATTTGGCCCAGTGCTTTTGTGG | SEQ ID NO: 815 | Homo sapiens cDNA clone IMAGE:30325617 [BC092452] |
| 816 | A_24_P561223 | THC2697551 | TTATGCCCAGTTAGATACAAGGATGCTGGCATATTTCAGGGACCCTAAAGTTTATAACAT | SEQ ID NO: 816 | ALU1_HUMAN (P39188) Alu subfamily J sequence contamination warning entry, partial (8%) [THC2697551] |

Fig. 1-46

| No. | Probe ID No. | Symbols of genes | Sequence | SEQ ID NO: | Description of genes (letters and numbers within [ ] indicates GenBank accession No.) |
|---|---|---|---|---|---|
| 817 | A_24_P56130 | MYL6 | CCAAGAGTGATGAGATGAATGTGAAGGTGGTGGACTTTGAGGCAGT TTCTGCCGACGCTGC | SEQ ID NO: 817 | Homo sapiens myosin, light chain 6, alkali, smooth muscle and non-muscle (MYL6), transcript variant 2, mRNA [NM_079423] |
| 818 | A_24_P587882 | A_24_P587882 | GTGAAATGTGTGGTATTAGGACTGAGAAGAGAGAAATCCAT TCTGTATGATGAGCA | SEQ ID NO: 818 | |
| 819 | A_24_P675386 | BX109843 | ACCTGAAATGCACTTTTAAATGTTTGCGTTATATCCAAGTGTTTA CTTGTATCCATGAACC | SEQ ID NO: 819 | BX109843 Soares placenta Nb2HP Homo sapiens cDNA clone IMAGp998B14208, mRNA sequence [BX109843] |
| 820 | A_24_P584186 | U52054 | GCTTGACTAACGCCAGATTAGTTCAAGAGCTTTAATGTGATCTT GTGTGTCATGAAGC | SEQ ID NO: 820 | Human S6 H-3 mRNA expressed in chromosome 6-suppressed melanoma cells. [U52054] |
| 821 | A_24_P703614 | A_24_P703614 | AAGAACATTACCCGAATCGAGTCGCACTGTAAGTCATCAGTAGC AGCTTTGTGTGTG | SEQ ID NO: 821 | |
| 822 | A_24_P724040 | SNRPB2 | ATCGCTCAGGTGCTCGATTACCCTCCAAAGTATATATTTATCGTTA ATAAGTAGCAGAAG | SEQ ID NO: 822 | Homo sapiens small nuclear ribonucleoprotein polypeptide B" (SNRPB2), transcript variant 1, mRNA [NM_003092] |
| 823 | A_24_P745670 | A_24_P745670 | GGTAAAACAGAGATGAATACATTCCAAGTTCAAATTTGAAGAT CCCAAATCTGAAGTC | SEQ ID NO: 823 | |
| 824 | A_24_P787947 | YPEL2 | AAGGTAAAGCCTAGAAGAACTATGAAAGGTATTGTCATGTTACC AAATTCTATCTGCGC | SEQ ID NO: 824 | Homo sapiens yippee-like 2 (Drosophila) (YPEL2), mRNA [NM_001005404] |
| 825 | A_24_P79413 | SEC11A | GTTTCGTTACTGGATGTTTGGAGTAGAAGATGGTGTGGTCATTGG TGGAATGGAACAG | SEQ ID NO: 825 | Homo sapiens SEC11 homolog A (S. cerevisiae) (SEC11A), mRNA [NM_014300] |
| 826 | A_24_P81965 | RAP2A | TTCTTTGATGTTGCAACTTTTTGGTTCTTTTAAACTGTGATAGT GATGGTAACTGATGG | SEQ ID NO: 826 | Homo sapiens RAP2A, member of RAS oncogene family (RAP2A), mRNA [NM_021033] |
| 827 | A_24_P859859 | THC2553238 | TTTAACCAGAGAGGTCTGCACCCTTTTCTGATATACTGGAGGACAC TCGGTGTGTAGCAAT | SEQ ID NO: 827 | I305349A cystic fibrosis antigen. [Homo sapiens] (exp=-1; wgp=0; cg=0), partial (65%) [THC2553238] |
| 828 | A_24_P879563 | LOC220906 | TCTAGTTCGAAGGAAAAATTCCAGGGGTTTTCTACAGTTCGGTGG TGCGTCATCTGAAAT | SEQ ID NO: 828 | Homo sapiens hypothetical protein LOC220906, mRNA (cDNA clone IMAGE:4837455). [BC045318] |
| 829 | A_24_P920181 | YIPF6 | AAGTGTTAAAAGTCAACGTTAATCATTAAGGTGTTTTGCCTCAA AGTCTTTTGCCTCTG | SEQ ID NO: 829 | Protein YIPF6 (YIP1 family member 6). [Source:Uniprot/SWISSPROT:Acc:Q96EC8] [ENST00000374643] |
| 830 | A_24_P941699 | PCGF5 | TGGTATATTCAAGTCAACAGCTTCTAAGGATAGGACTAGTTTCATG TCTAGTAATACAGTG | SEQ ID NO: 830 | Homo sapiens polycomb group ring finger 5 (PCGF5), mRNA [NM_032373] |
| 831 | A_24_P95029 | TAX1BP1 | TGCTTTGATTCCAAGCTTTGATGTTCACAAGAAGTGTCCCCTCTGT GAGTTAATGTTTCCT | SEQ ID NO: 831 | Homo sapiens Tax1 (human T-cell leukemia virus type I) binding protein 1 (TAX1BP1), transcript variant 1, mRNA [NM_006024] |
| 832 | A_32_P100338 | THC2586959 | AATTAGAGAAACATTCTGTGTTTCATAAGGATGGCAATGGCTA TATTAGTAGTGTAGA | SEQ ID NO: 832 | 1PKQ_D Chain D, Crystal Structure Of The Ef3-Cam Complexed With Pmeapp. [Homo sapiens] (exp=-1; cg=0), partial (70%) [THC2586959] |
| 833 | A_32_P10100 | A_32_P10100 | TATGAGGAAATAGTATCATCAIGTTAGAAGGCCTTGGAATGAGTAT AAATAATGGCTGGTC | SEQ ID NO: 833 | |
| 834 | A_32_P10424 | AX721252 | AAATTTGTCAGGAAGGAGATGGAAGCTGTAGATGTGCACAAGTGA TACCAGGGTCAACAA | SEQ ID NO: 834 | Sequence 212 from Patent WO0220754 [AX721252] |

Fig. 1-47

| No. | Probe ID No. | Symbols of genes | Sequence | SEQ ID NO: | Descriptions of genes (letters and numbers within [ ] indicates GenBank accession No.) |
|---|---|---|---|---|---|
| 835 | A_32_P131377 | REEP5 | CATCACTAAAGAAGGAAGCCAAGAAAAGGCTACGGTGAATTTACTGGGTGAAGAAAAGAAGAGCAG | SEQ ID NO: 835 | Homo sapiens receptor accessory protein 5 (REEP5), mRNA [NM_005669] |
| 836 | A_32_P136402 | THOC7 | AGCTGGAATTGAGACCGAAACAGTTTCATGTTCTTCTTAGTACCATCCATGAACTTCAGC | SEQ ID NO: 836 | Homo sapiens THO complex 7 homolog (Drosophila) (THOC7), mRNA [NM_025075] |
| 837 | A_32_P143323 | CR613267 | AGAGAGCTCAAACAATGGGGTTTATGCCAGTTACATACAAGGATCCTGCATATTTCAGGG | SEQ ID NO: 837 | full-length cDNA clone CS0DL011YP14 of B cells (Ramos cell line) Cot 25-normalized of Homo sapiens (human) [CR613267] |
| 838 | A_32_P147603 | THC2499508 | GCGTTGAGCTCGGAGGAGGAAAAATATCTAAAAATTCCCGGCTCGCCGTAGGGGTCCTGTGGTTT | SEQ ID NO: 838 | |
| 839 | A_32_P147747 | THC2575761 | TTGATACGCTCTGATTCTGATGAGACAAACGGCAATTTGGGTTCTGCAGGTACATAGAAGTTG | SEQ ID NO: 839 | HUMRPL7Y ribosomal protein L7 [Homo sapiens] (exp=-1; wgp=0; cg=0), partial (40%) [THC2575761] |
| 840 | A_32_P154830 | OSTM1 | GTTGGTAAATGTTAGTTATATTCGGACTAGTATTTTCTAATGTTTCTGGGATATGCTCCC | SEQ ID NO: 840 | Homo sapiens osteopetrosis associated transmembrane protein 1 (OSTM1), mRNA [NM_014028] |
| 841 | A_32_P159651 | PCAF | GAGTGGTGTCTAGATTTGTAATGAAGAATCATGATACAGTTGGATTAAGTATCTTGGAC | SEQ ID NO: 841 | Homo sapiens p300/CBP-associated factor (PCAF), mRNA [NM_003884] |
| 842 | A_32_P161432 | CBWD2 | GAAGGAAAACCTGATGGCCTTATCAATGAAGCTACTAGACAAGTTGCTTTGGCAGATGCC | SEQ ID NO: 842 | Homo sapiens COBW domain containing 2 (CBWD2), mRNA [NM_172003] |
| 843 | A_32_P162250 | ARHGAP18 | AAGTCCTGAATAAGTCTACGTGGAAGAATTATTCTTCTGGGTGAAAAAGTTTTGTTTGTG | SEQ ID NO: 843 | Homo sapiens Rho GTPase activating protein 18 (ARHGAP18), mRNA [NM_033515] |
| 844 | A_32_P162416 | BE218351 | GTCTATTTCAAATTCAGGTTGTCCACTAGGTCAGTTTTACAGGAGATGGTCTTTTTAACAT | SEQ ID NO: 844 | hv37eG8.x1 NCI_CGAP_Lu24 Homo sapiens cDNA clone IMAGE:3175622 3', mRNA sequence [BE218351] |
| 845 | A_32_P165713 | CIP29 | AAAGCAAGAATCTTATCGCACGAGACTCCAGGCATATGTTGAAGAACATGCTGAAGAGGAGGG | SEQ ID NO: 845 | Homo sapiens cytokine induced protein 29 kDa (CIP29), mRNA [NM_033082] |
| 846 | A_32_P171163 | ENST00000368149 | TCCTTAGTCAGTTTTAAATCTCAGGCAGCTAGATTTTTATTTGTTTTCTGTGTGTGTAGAG | SEQ ID NO: 846 | Rho GTPase-activating protein 18 (MacGAP). [Source:Uniprot/SWISSPROT;Acc:Q8N392] [ENST00000368149] |
| 847 | A_32_P17504 | THC2698682 | ATGTCTATGCTGTTTCAGTATGCTGAAATATTCCCAGGCGTTTCCCCTGATGCCCAAA | SEQ ID NO: 847 | |
| 848 | A_32_P195387 | DKFZP779L1068 | ATATAAGCTTGGAATTCTATTGTAATTATGTTGTTGTGGCTGCTTGTAGTATCAGTTGGC | SEQ ID NO: 848 | Homo sapiens cDNA clone IMAGE:5555490. [BC110326] |
| 849 | A_32_P200724 | FAM19A2 | AGAACAAAGTAATTTTCTGAAGGGAAGGCTGCAGAATATGGAAAACATATATTGGAGCTAC | SEQ ID NO: 849 | Homo sapiens mRNA; cDNA DKFZp781P0552 (from clone DKFZp781P0552). [CR749367] |
| 850 | A_32_P205550 | RPL26L1 | AGGTAGTTCGAGGGACACTACAAAAGGTCAGCAAGGTAATCCAGGGTAGAGAA | SEQ ID NO: 850 | Homo sapiens ribosomal protein L26-like 1 (RPL26L1), mRNA [NM_016093] |
| 851 | A_32_P205553 | RPL26L1 | TCGGAATGTCTGGAACATTTCATTTCCTGTTTGTTACCTGTGGCTCTGTAAATCTACT | SEQ ID NO: 851 | Homo sapiens ribosomal protein L26-like 1 (RPL26L1), mRNA [NM_016093] |
| 852 | A_32_P206541 | LOC642123 | TTAGAGAAGCGCCCATACCTGGTAGAGCATGTACCATGTTAGATGCTTAAATAACTCCAC | SEQ ID NO: 852 | Homo sapiens cDNA FLJ46681 fis, clone UTERU3015647, moderately similar to Embigin precursor. [AK128714] |
| 853 | A_32_P267231 | AI630435 | TTGTTGGCTTTTTGTTAAGGGTTTCTGGAACAGCAGGAAGGTCCTTGTTCTTCTTCTTCT | SEQ ID NO: 853 | AI630435 ad10b05.y1 Hembase: Erythroid Progenitor Cells (LCB ad library) Homo sapiens cDNA clone ad10b05 random, mRNA sequence [AI630435] |

Fig. 1-48

| No. | Probe ID No. | Symbols of genes | Sequence | SEQ ID NO: | Descriptions of genes (letters and numbers within [ ] indicates GenBank accession No.) |
|---|---|---|---|---|---|
| 854 | A_32_P223189 | SUMO1P3 | GAATGAGGAAGAAGATGATTGAGGTTTATCAGGAACAAATCGGGAGGTCATTCAACAG | SEQ ID NO: 854 | Homo sapiens SUMO1 pseudogene 3 (SUMO1P3) on chromosome 1 [NR_002190] |
| 855 | A_32_P224666 | CAPZA2 | AATGCTGTTTGAGATTCTGAAATTAAATGAAAATACTTATTTCAGAAATGCATTTAATG | SEQ ID NO: 855 | Homo sapiens capping protein (actin filament) muscle Z-line, alpha 2 (CAPZA2), mRNA [NM_006136] |
| 856 | A_32_P2333 | SUB1 | AGGAAGAAAAGGTATTTCTTTAAATCAGAAGAACATGGAGCCCAGCTGACAGAACAGATTTC | SEQ ID NO: 856 | Homo sapiens SUB1 homolog (S. cerevisiae) (SUB1), mRNA [NM_006713] |
| 857 | A_32_P26895 | KIAA1600 | AATTCTTGGTGCTCCGTGGAGAAACTCTTCAGATGGTCATTGTGTACCTACTCTCTCTT | SEQ ID NO: 857 | KIAA1600 (KIAA1600), mRNA [Source:RefSeq_dna:Acc:NM_020940] [ENST00000369248] |
| 858 | A_32_P30004 | AF086044 | ATTTCTCTTTCTAAAGGGGAGTAACTTTTTAAACCCTTCCTGATTTTAGCGTGGCAATGT | SEQ ID NO: 858 | Homo sapiens full length insert cDNA clone YX74D05. [AF086044] |
| 859 | A_32_P32250 | C10orf84 | CAAAAAGGAGGTTGAAAATTCACAGGCTGCCGAAAAAAAGAAGAAACTTGCATGGGGGTT | SEQ ID NO: 859 | Homo sapiens chromosome 10 open reading frame 84 (C10orf84), mRNA [NM_022063] |
| 860 | A_32_P32315 | A_32_P32315 | AAAGTGGGAAGATACGGATTCAAGTGCTGGGATTCTCGTGTTTGGAAAAGGTCAGTCCTCA | SEQ ID NO: 860 | |
| 861 | A_32_P43217 | PSMA6 | TTGTTGTTAGTTAGCAGATCGGTGATGCCACTTACGTGTGTGTTTGGTAACAACAAACA | SEQ ID NO: 861 | Homo sapiens proteasome (prosome, macropain) subunit, alpha type, 6 (PSMA6), mRNA [NM_002791] |
| 862 | A_32_P44394 | AIM2 | GAAGGAGATAAGGTTCGACTTACATTGTTCACACTGTCAAAAAATGGAGAAAACTACAG | SEQ ID NO: 862 | Homo sapiens absent in melanoma 2 (AIM2), mRNA [NM_004833] |
| 863 | A_32_P62342 | GLT8D3 | TGTGATGTAAGTGATGTAACCATTGACAATGTCTATGTGTGCCTTTATACATTTCATCTCTG | SEQ ID NO: 863 | Homo sapiens glycosyltransferase 8 domain containing 3, mRNA (cDNA clone MGC:21651 IMAGE:4508330), complete cds. [BC039145] |
| 864 | A_32_P73222 | AA631847 | TTTGTTTGTTTTGGACAATGTCATAAGAACTTAGGTGTTAGAGCACGAACCCCTGAAAG | SEQ ID NO: 864 | np61b02.s1 NCI_CGAP_Br2 Homo sapiens cDNA clone IMAGE:1130763 3' similar to TR:G971838 G971838 60S RIBOSOMAL PROTEIN L34 ; mRNA sequence [AA631847] |
| 865 | A_32_P81765 | TMEM167 | CCTCAGTAGTGTCACTACAATATTACATTGTGAAATGTTATTCTGTTGTATCAGATAGG | SEQ ID NO: 865 | Homo sapiens transmembrane protein 167 (TMEM167), mRNA [NM_174909] |
| 866 | A_32_P82424 | LOC647252 | ATTGGATGCTGAGCTAGTCAAGTATAAGGAGGATCAAGATGAGAGGGGCTCCTACAAA | SEQ ID NO: 866 | PREDICTED: Homo sapiens similar to Charged multivesicular body protein 5 (Chromatin-modifying protein 5) (SNF7 domain-containing protein 2) (hVps60) (Vacuolar protein sorting 60) (Vps60) (LOC647252), mRNA [XR_019210] |
| 867 | A_32_P89738 | THC2544977 | GGAGAATAAGTCATTCTCGGTTCTTGCCGTTTTCAGATAAAAAGTATATTGTCTTG | SEQ ID NO: 867 | |
| 868 | A_32_P95397 | ITGB1 | GTCTTACTTGAGTTAGTGGCATAACAGAGACCACTGTATGTTTACTTCTCACGCATTTGAGT | SEQ ID NO: 868 | Homo sapiens integrin, beta 1 (fibronectin receptor, beta polypeptide, antigen CD29 includes MDF2, MSK12) (ITGB1), transcript variant 1A, mRNA [NM_002211] |

Fig. 2

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P407601 | C8orf6 | GTCTGCTAGGTTAGTGTAGGAGAGATTCTATTCTGAGATAAGAGCTTCCCTGTCGGGCTGAA | SEQ ID NO: 220 | Homo sapiens mRNA for hypothetical protein (C8orf6 gene). [AJ307469] |
| 2 | A_32_P209582 | THC2663167 | GAATGATAAAGCCAGAATACAACGTGCTTTTGTCAAGATTTCAAACCTATTTGGCTGAT | SEQ ID NO: 506 | ALU1_HUMAN (P39188) Alu subfamily J sequence contamination warning entry, partial (5%) [THC2663167] |
| 3 | A_32_P213509 | THC2663555 | GATTTGTTCCAGTGTTGGAGCGGTTTTAATGAAAATGTCAACACCTACAGACTGGAAAAA | SEQ ID NO: 508 | |
| 4 | A_32_P40673 | A_32_P40673 | CATCACGTTGATATTAGGACAGCCTACGTACTTGTTGAGTGTCACAGCCTGATATGTA | SEQ ID NO: 523 | |
| 5 | A_32_P71171 | A_32_P71171 | TGTAGATAGTAATAGGAAAACGAAGAATCCAGCCTGGTGATGGTCGAGGGAGTGATTGA | SEQ ID NO: 536 | |
| 6 | A_32_P98940 | THC2745859 | AAGAGTATTCCCAAGATAGGCAAAGGTGTGTTGTTTTAGGAAGGTGTATTTCAGCTAGTTA | SEQ ID NO: 554 | |
| 7 | A_23_P123608 | JAK2 | GGATAACATGGCTGGATGCAAGAAATGAGCTTCATTCGACACGAAAGTAGATTTACAGA | SEQ ID NO: 570 | Homo sapiens Janus kinase 2 (a protein tyrosine kinase) (JAK2), mRNA [NM_004972] |
| 8 | A_23_P138507 | CDC2 | CCCATGTCAAAAACTTGGATGCAAAATGGCTTGGATTTGCTCTGAAAAATGTTAATGTATG | SEQ ID NO: 589 | Homo sapiens cell division cycle 2, G1 to S and G2 to M (CDC2), transcript variant 1, mRNA [NM_001786] |
| 9 | A_23_P14734 | RPS27L | TAGAAGATCACCACGGTTTCAGGCATGCTCAGACAGTGGTCTTTGTGTAGGTTGTTCA | SEQ ID NO: 597 | Homo sapiens ribosomal protein S27-like (RPS27L), mRNA [NM_015920] |
| 10 | A_23_P152002 | BCL2A1 | GTTAAGCATATTTGCATTTGAAGGTATTGCATCGATCAAGAAACTGTAGGAGCAAATTGC | SEQ ID NO: 602 | Homo sapiens BCL2-related protein A1 (BCL2A1), mRNA [NM_004049] |
| 11 | A_23_P18325 | PDCD10 | CCAAGCGATGAATTCATCAAACCAACTTAATACTTCAGAGCTTGAAAACTGTGGGCTGAA | SEQ ID NO: 619 | Homo sapiens programmed cell death 10 (PDCD10), transcript variant 1, mRNA [NM_007217] |
| 12 | A_23_P2705 | P2RY5 | TGTGTATTTGCTGTTTGCAAGTGTTGTTTGAGCGTATAGTTTACTACTTTACATGGGACA | SEQ ID NO: 654 | Homo sapiens purinergic receptor P2Y, G-protein coupled, 5 (P2RY5), mRNA [NM_005767] |
| 13 | A_23_P41114 | CSTA | AAACAATGAGAATTATGGAAAATTGAAAGCTGTGCAGTTAGTCTGAAGTTGTTGCTG | SEQ ID NO: 689 | Homo sapiens cystatin A (stefin A) (CSTA), mRNA [NM_005213] |
| 14 | A_23_P434609 | S100A8 | AAAGGCATGAAGAAAGCCAGAAGAGTAGCTGAGTTAGTGGGGCCAGAGGCTGGGGCGCT | SEQ ID NO: 701 | Homo sapiens S100 calcium binding protein A8 (S100A8), mRNA [NM_002964] |
| 15 | A_23_P76480 | BF213738 | AATCGAACAAGGACACATGGGATGGGATGGAAGCTACATTTACCAAATCGTTGGACAGG | SEQ ID NO: 726 | BF213738 601847628F1 NIH_MGC_55 Homo sapiens cDNA clone IMAGE:4078519 5', mRNA sequence [BF213738] |
| 16 | A_23_P94230 | LY96 | TGAAGGTATTTCTGGAGCCCAGAGAAAATGTCTCTTTGCTTGGAGTTTGTCATCCTACA | SEQ ID NO: 744 | Homo sapiens lymphocyte antigen 96 (LY96), mRNA [NM_015364] |
| 17 | A_24_P124992 | PSMA4 | AAACGTCCCCTTTGGTGTTTGATTGCTGTACATGGGTGGGATAAGCACTGATGGGTTGCAG | SEQ ID NO: 762 | Homo sapiens proteasome (prosome, macropain) subunit, alpha type, 4 (PSMA4), mRNA [NM_002789] |
| 18 | A_24_P126741 | ENST00000369178 | AGCCTCCACCACCTAACAAGATTCAAGATTACTTGGAACAGCGTGACAGGAGCGAGAAT | SEQ ID NO: 763 | |
| 19 | A_24_P201702 | CLEC2B | ATTGGATTCAAGTAAGTAAATACAACTGTTGCACTCAACATGCCGACCTAACTATAATTGACA | SEQ ID NO: 781 | Homo sapiens C-type lectin domain family 2, member B (CLEC2B), mRNA [NM_005127] |
| 20 | A_24_P320328 | SUB1 | GAGAAAAACCTGTAAAGAACAAAAGAGAAGGAGCTTGAGAGGCCCGTGTCATCTCTA | SEQ ID NO: 795 | Homo sapiens SUB1 homolog (S. cerevisiae) (SUB1), mRNA [NM_006713] |
| 21 | A_32_P200724 | FAM19A2 | AGAACAAAGTAATTTTCTGAAGGAAGGTGCAGAATATGGAAAACATATATTGGGAGCTAC | SEQ ID NO: 849 | Homo sapiens mRNA; cDNA DKFZp781P0552 (from clone DKFZp781P0552). [CR749367] |

Fig. 3-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P12343 | GSTM3 | AAGTTGTTTTGTTTGAAGTCCGTCCGGTAAGGGGTCAGCAGGTCTTG CTTTGCTCTTTTCAAT | SEQ ID NO:869 | Homo sapiens glutathione S-transferase M3 (brain) (GSTM3), mRNA [NM_000849] |
| 2 | A_23_P143247 | TSHZ2 | CCCAAGAAGAGCGTATGCAAATCTCTAAGTTTACGGGGACTCTGAA TGACCACTATCAGTCA | SEQ ID NO:870 | Homo sapiens teashirt family zinc finger 2 (TSHZ2), mRNA [NM_173485] |
| 3 | A_23_P146325 | DDEF1IT1 | TGGAAAGTGAAGTGAAGGAGATTTTGTCATACAGGCAGTAAGTGC CAGAACTGACTTGAAC | SEQ ID NO:871 | Homo sapiens DDEF1 intronic transcript 1 (DDEF1IT1) on chromosome 8 [NR_002765] |
| 4 | A_23_P14853 | LTK | AAGTTTGATCTTGGGCCCAGAGGCCGGCCTTACACACACCCGAG GTGTCCATGGAGCA | SEQ ID NO:872 | Homo sapiens leukocyte tyrosine kinase (LTK), transcript variant 1, mRNA [NM_002344] |
| 5 | A_23_P20566 | TPM2 | GGAGTATTCCACCAAAGAAGAATAAATATGAAGAGGAGAATCAAAC TGTTGGAGAGAAGCT | SEQ ID NO:873 | Homo sapiens tropomyosin 2 (beta) (TPM2), transcript variant 2, mRNA [NM_213674] |
| 6 | A_23_P315378 | ATG16L1 | CTGTGTTTCCACTTATACTCTTTGTCCAAAACTCAGTTTCAAA ATATTTGCAATAGGAC | SEQ ID NO:874 | Homo sapiens cDNA FLJ10035 fis, clone HEMBA1000919. [AK000897] |
| 7 | A_23_P339095 | SPTBN1 | AGTGGATACTTCAAAAGGAGAAGAACAAGTTTCCAAAACGGTTTG CCAAGTGAACAGGGAT | SEQ ID NO:875 | Homo sapiens spectrin, beta, non-erythrocytic 1 (SPTBN1), transcript variant 2, mRNA [NM_178313] |
| 8 | A_23_P344531 | SYNPO | TCCTCTGCTGTGAAGATGAAGAAGGTGCTCTTACTCAGTTAATG ATGAGTGAGTATATTT | SEQ ID NO:876 | Synaptopodin. [Source:Uniprot/SWISSPROT;Acc:Q8N3V7] [ENST00000307662] |
| 9 | A_23_P359174 | BC069659 | CCAGGGGTGCATACTAGGGTAAAGAAAAATTTTGTAATAGGAAGC AGTGGTTTGGGATTTT | SEQ ID NO:877 | Homo sapiens cDNA clone IMAGE:7262526 with apparent retained intron. [BC069659] |
| 10 | A_23_P359870 | C8orf15 | CTGAGGTTATAATTTCACTTAACATTGTCGAGGCATTGGCATTTTG GTTTAGTCGAAGT | SEQ ID NO:878 | Homo sapiens mRNA for hypothetical protein (C8orf16). [AJ312226] |
| 11 | A_23_P379147 | KRT74 | ATGTCTGGTGAGAATGCATCCTGTGAGGCATCTGTGATGCAG CAGTAGCAGCTACGAC | SEQ ID NO:879 | Homo sapiens keratin 74 (KRT74), mRNA [NM_175053] |
| 12 | A_23_P3921 | FLJ11710 | CCTGATTCATGATTGAAGTACCATTAGGATAAATGCTATACATC CATGCATTGGATGTTA | SEQ ID NO:880 | Homo sapiens cDNA FLJ11710 fis, clone HEMBA1005149. [AK021772] |
| 13 | A_23_P407601 | C8orf6 | GTCTCCTACGTTACTGTAGGAGAGATTCTATTCTCAGATAAGAC TTCGGTGTCGGGTGAA | SEQ ID NO:881 | Homo sapiens mRNA for hypothetical protein (C8orf6 gene). [AJ307469] |
| 14 | A_23_P86222 | PLD4 | TGAAAGCTTCATCGTCGCCGGTGGGGAACCATTCGAACATGGCA TTCAGAGGGTGAACC | SEQ ID NO:882 | Homo sapiens phospholipase D family, member 4 (PLD4), mRNA [NM_138790] |
| 15 | A_24_P126857 | MBNL1 | AGAATATTGCTCGAACGACTATCTGTAGATTGGTTATCTCTATC ATGCATTGCTTCACAA | SEQ ID NO:883 | Homo sapiens muscleblind-like (Drosophila), mRNA (cDNA clone IMAGE:3935812), partial cds. [BC005296] |
| 16 | A_24_P312325 | C8orf15 | CTTGTCAATGTGACTACTTTAGTTGCCTGTCCAATATGAAGTA GAAAAGCAGTTCTG | SEQ ID NO:884 | Homo sapiens chromosome 8 open reading frame 15 (C8orf15), mRNA [NM_001033662] |
| 17 | A_24_P350136 | LOC652370 | CCAGCTACCACCACCTGCTGGAAGATGAGGACTTCAAATGTTAGG GATGCGGTGGAAGCA | SEQ ID NO:885 | PREDICTED: Homo sapiens similar to Keratin, type 1 cytoskeletal 18 (Cytokeratin-18) (CK-18) (Keratin-18) (K18) (LOC652370), mRNA [XR_019330] |
| 18 | A_24_P360499 | DDEF1IT1 | TGTTTCTTTAATGTAGCGGAGGTCGTACTTCAGATTTAAGT TTGAAATGTAGGCATAG | SEQ ID NO:886 | Homo sapiens DDEF1 intronic transcript 1 (DDEF1IT1) on chromosome 8 [NR_002765] |
| 19 | A_24_P460763 | AK022443 | GTAGTAGCAGGCTAGTTAAGAATGCCTAGTGGGTCTAAATGTCA AATGGTATTGGGAGAT | SEQ ID NO:887 | Homo sapiens cDNA FLJ12381 fis, clone MAMMA1002566. [AK022443] |
| 20 | A_24_P491923 | THC2491622 | CTTCTTGTTTCAATAAAGTAGAAGTAGCATGCATCGATGGT GTTTAGTAGGGTATGA | SEQ ID NO:888 | |

Fig. 3-2

| No. | Probe ID No | Symbols of genes | Sequence | SEQ ID NO. | Descriptions of genes (letters and numbers within [ ] indicates GenBank accession No.) |
|---|---|---|---|---|---|
| 21 | A_24_P348264 | AL512741 | AAGAATTGAGTTAGAACTGCGCTATAATGTAATGCAGAATATTT CGGAATAATGCCTAGG | SEQ ID NO: 889 | Homo sapiens mRNA; cDNA DKFZp667N064 (from clone DKFZp667N064) [AL512741] |
| 22 | A_24_P558141 | A_24_P558141 | AACCCTGTGTGTGGGATAAGCGTCTCTAGATTTCGGATGAGGT GTGCTGATCAAAACTAA | SEQ ID NO: 890 | |
| 23 | A_24_P642771 | AK024956 | ATTCTCCATATATTTTAGTGTTGTTCTATTTGGCTAGAAAGACAA AACAAGGGGAATCTGG | SEQ ID NO: 891 | Homo sapiens cDNA FLJ21303 fis, clone COL02107. [AK024956] |
| 24 | A_24_P693321 | AK123481 | ATCAGAACTATGCAAGATAATGCAATGCTACAATGTCAAAATTT TAGTTTAAAAGTGGAA | SEQ ID NO: 892 | Homo sapiens cDNA FLJ41467 fis, clone BRTHA2004350. [AK123481] |
| 25 | A_24_P69784 | PACS1 | AAGTTCCCTGATGAAGACTGGTATCAGAGAATTTATTGGTTGAT TGGGTGGTGAAGGTG | SEQ ID NO: 893 | Homo sapiens phosphofurin acidic cluster sorting protein 1 (PACS1), mRNA [NM_018026] |
| 26 | A_24_P713312 | THC2639056 | TTTATATGGTCGGATGCTCCATGTTAGGATTAAGGGGTAATTAA TAGTAATGTATGTGGA | SEQ ID NO: 894 | ALUB_HUMAN (P39195) Alu subfamily SX sequence contamination warning entry, partial (10%) [THC2639056] |
| 27 | A_24_P728115 | AK024937 | ACTGGATAGTCACTACTTTTAGTGAGTTGAAATCTGTTTGGAG AGCTATGTAAGTAGCA | SEQ ID NO: 895 | Homo sapiens cDNA FLJ21284 fis, clone COL01911. [AK024937] |
| 28 | A_24_P792389 | THC2671169 | ATGCTAACGGTGGAGACTAAGGCATACAAGTATGACTAGAATTG CCAGGTACACATTAGA | SEQ ID NO: 896 | |
| 29 | A_24_P79855 | ENST00000390643 | AAACCATTGGTCCCTTTACCCAGGGAAGGACTCAAGAAGCGGA ACGTGATAGGAGATGG | SEQ ID NO: 897 | Homo sapiens hypothetical protein DKFZp566H0824, mRNA (cDNA clone MGC:129790 IMAGE:40021976), complete cds. [BC104430] |
| 30 | A_24_P883109 | AL833452 | GGGCAACTAGTGATCTCACTAGTTAGGTTAGCGCGGTTAAAGCGGGTGTTTGAGTAC AATCTAAGAAAATAGCA | SEQ ID NO: 898 | Homo sapiens mRNA; cDNA DKFZp686E08116 (from clone DKFZp686E08116). [AL833452] |
| 31 | A_24_P896649 | THC2635386 | AATGTAGCATGAGTGTTGCACGGGTTTCTCACAAATGTAAAATGTTATTT TCTAAAGTAGTTTCT | SEQ ID NO: 899 | |
| 32 | A_24_P914102 | A_24_P914102 | TTAGTAGAGCCTAGATTTTCTCTACAAATGTAAAATGTTATTT TAGTGTTGAAAATCAG | SEQ ID NO: 900 | |
| 33 | A_24_P928025 | DKFZp547E087 | TGTTATGAACATAGTTCAGTTCATGTTAAGTCTCCATTTAAATACAAGC TGAAATACCAAAGTTA | SEQ ID NO: 901 | Homo sapiens cDNA FLJ30147 fis, clone BRACE2000266. [AK054709] |
| 34 | A_24_P930337 | THC2503773 | AGCAAGTGGAACGCGACACGCAAAATATGACTTGAAGAATGTAAT TTAAAATGTAGCATAG | SEQ ID NO: 902 | |
| 35 | A_24_P930391 | AK023351 | AAGTGGGTTTAATTTCCTTTTCATGAAAGGAAAGATTAGCTTTC ATGCAAAGCACTTGGTG | SEQ ID NO: 903 | Homo sapiens cDNA FLJ12289 fis, clone MAMMA1001783. [AK022351] |
| 36 | A_24_P931364 | AK022052 | TGGCCATCTGGAGTATAGTTTGGTTTGGAAGTCATTGCTTTGTAGTAAG GCATTATTTTCCTGGT | SEQ ID NO: 904 | Homo sapiens cDNA FLJ12000 fis, clone HEMBB1001531. [AK022052] |
| 37 | A_24_P933514 | AK094334 | CGTTATCCACCCTTTAGTGATAATTCCTTAGGTGGCCATATTATATA CTACGTGAACTCTGGC | SEQ ID NO: 905 | Homo sapiens cDNA FLJ37015 fis, clone BRACE2010208. [AK094334] |
| 38 | A_24_P933546 | A_24_P933546 | CACCTGCCACCTTTATACTTTATGCTTTATACCTGCAGAAGTATAA CCTAACGGAAGAAATG | SEQ ID NO: 906 | |
| 39 | A_24_P934861 | A_24_P934861 | GGAAGGTATCAACGAGGCAAATTCGAGTTTCTGGGAAATAGTGGAC CAGATCGTGTCCATGG | SEQ ID NO: 907 | |
| 40 | A_24_P935682 | AY358246 | AGTCAGTAATCAGCATTCAATCAATGAATATGGTCTAACACATGC TTGACAGTTATGCAAAC | SEQ ID NO: 908 | Homo sapiens clone DNA166629 MRSS6228 (UNQ6228) mRNA, complete cds. [AY358246] |

Fig. 3-3

| No. | Probe ID No | Symbols of genes | Sequence | SEQ ID NO: | Descriptions of genes (letters and numbers within [ ] indicates GenBank accession No.) |
|---|---|---|---|---|---|
| 41 | A_32_P105940 | A_32_P105940 | GTGCCAAGGTAAGCTACCACTTTGGTTTTATTTCAAGCACAACATGAAAATAAGGATTC | SEQ ID NO: 909 | |
| 42 | A_32_P116997 | TH-C2719256 | AAACATTAGGTAGCAGCTGTAGAGGATATATTTAGGGTCATGATGTCGTTGTTGTTGGG | SEQ ID NO: 910 | BE147120 PM2-HT0224-221099-001-b10 HT0224 Homo sapiens cDNA, mRNA sequence [BE147120] |
| 43 | A_32_P120454 | TH-C2642550 | ACACAATGAGATGCTGGACTGGTTCATCTGTTTATTGGCAAGCTCAGGACGAGGTATGA | SEQ ID NO: 911 | |
| 44 | A_32_P121978 | A_32_P121978 | CAGATTAGACCCACCTCATAATGAGTCTTGATTGCACTTCAGATTGTCTTGATGGGGAC | SEQ ID NO: 912 | |
| 45 | A_32_P12703 | TH-C2697162 | TTGAAGGAAAGAGTATAGGGGGAAGTGCCAGAGACTAAACGAATCCTAAGTAAATATAGGGT | SEQ ID NO: 913 | |
| 46 | A_32_P131294 | BM854107 | AGTAGGGAAAAGGTTGTTTCCTTAATAGAGGTAGTGTGGGAAATGCTAGCACTTGTGC | SEQ ID NO: 914 | K-EST0136406 S22SNU16n1 Homo sapiens cDNA clone S22SNU16n1-145-F11 5', mRNA sequence [BM854107] |
| 47 | A_32_P132936 | TH-C2673888 | AAATGGAAGTATTGACCAGATTAAAGAGGTGGTTAAGTCATGGCCATGAATGAATTACCA | SEQ ID NO: 915 | Q65549 9ALPH (Q65549) Glycoprotein C, partial (4%) [THC2673888] |
| 48 | A_32_P145385 | AK001118 | CCCGAATTAACACTCGAGGAAGGTTAAATTCCAGGTTTTTGTGTGATTCTCAGGAAATGAAT | SEQ ID NO: 916 | Homo sapiens cDNA FLJ10256 fis, clone HEMBB1000870. [AK001118] |
| 49 | A_32_P146844 | TH-C2639689 | CCTGTGGGCTGATTCCAGACTGAGAGTGAAGTGAAGTTTTGTGTGGACATCATGTGCATTAA | SEQ ID NO: 917 | |
| 50 | A_32_P147969 | AL080232 | TAATGAGCTCTTTCGGCATGAAGGCAAGAAGTGTCCAGAAGACCTCTGGAGAATTCTT | SEQ ID NO: 918 | Homo sapiens mRNA; cDNA DKFZp586A061 (from clone DKFZp586A061) [AL080232] |
| 51 | A_32_P151244 | AK022268 | GTAGTCAGAATGTGAGAGAACTATTCATGTGTAACCTTTTGAACTGTTCAGTGTTCTT | SEQ ID NO: 919 | Homo sapiens cDNA FLJ12206 fis, clone MAMMA1000941. [AK022268] |
| 52 | A_32_P164573 | TH-C2611661 | AGTCGTTTCTATTAACACTGAAGTAGTCTCGAGAGGTTGGAAATTTCAAGTCCAAAATC | SEQ ID NO: 920 | RPT2_SPIMX (P42344) Chloroplast 30S ribosomal protein S12, partial (11%) [THC2611661] |
| 53 | A_32_P167863 | TH-C2697442 | ATGAATTGGGGGTATGAGTTCAGTGAGTTTGAAGTATATGTATATGGGACTAAATTCTCTCATT | SEQ ID NO: 921 | |
| 54 | A_32_P184039 | A_32_P184039 | ATGATTGTTAGTTGTTGGGCAAAAATAGTTGTTATGTATCATGCGTAATAACTGACCAGC | SEQ ID NO: 922 | |
| 55 | A_32_P184330 | AK130741 | TGTGACGGTTGTGACGGAGTTGTCGAGTGGTCACATGAGTTGTTACATGAGTCCCCTCTA | SEQ ID NO: 923 | Homo sapiens cDNA FLJ27231 fis, clone SYN06240. [AK130741] |
| 56 | A_32_P194372 | AK129547 | AGACCAGAGAAACATAGACGGATGATATTTGGACCAAGCATAGGTTAAAACTAGGGCAGG | SEQ ID NO: 924 | Homo sapiens cDNA FLJ26036 fis, clone PRS00145. [AK129547] |
| 57 | A_32_P204565 | A_32_P204565 | GAGGATGAGATGATCAGGGGGATGTGTTTCAGTGTGATGGAAAGATTGTTCCAGTGA | SEQ ID NO: 925 | |
| 58 | A_32_P208039 | AL049390 | TTTCATGTTTGAAGATTGAGATTGGGGTTTATTTCTCAAGGGATGTGCAAACCTCACAA | SEQ ID NO: 926 | Homo sapiens mRNA; cDNA DKFZp586O1318 (from clone DKFZp586O1318) [AL049390] |
| 59 | A_32_P209562 | TH-C2663167 | CAATGTAAAGCCAGAATTCAAGCTGCTTTTGTCAAGATTTTGAAACCTATTTGGCTGAT | SEQ ID NO: 927 | ALU1_HUMAN (P39188) Alu subfamily J sequence contamination warning entry, partial (5%) [THC2663167] |
| 60 | A_32_P211048 | A_32_P211048 | GTTCACAAAAACACCTAGTAGGTATTCAGTTCATATTGGAATGAATGAAGAAAATGAGGAC | SEQ ID NO: 928 | |
| 61 | A_32_P213509 | TH-C2663555 | GATTTGTTCCAGTGTTGGAGCCCTTTTAATGAAAATTCTCAACAGCTAGACTGGAGAAAA | SEQ ID NO: 929 | |

Fig. 3-4

| No. | Probe ID No. | Symbols of genes | Sequence | SEQ ID NO. | Descriptions of genes, letters and numbers within [ ] indicates GenBank accession No.) |
|---|---|---|---|---|---|
| 62 | A_32_P216122 | AK130891 | TGTTCCTGTATATGTTTTGGGAGGGATTCATGAAGAATTGAGGTACACATATATGGGTC | SEQ ID NO: 930 | Homo sapiens cDNA FLJ27381 fis, clone UBA07680. [AK130891] |
| 63 | A_32_P224638 | THC2731042 | ACACCAGTGTAACTGCTAGCCTAATGAGCCATGGAAAACAAAATAGCTCAATCTGTTGTAAC | SEQ ID NO: 931 | Q4SSA7_TETNG (Q4SSA7) Chromosome 11 SCAF14479, whole genome shotgun sequence. (Fragment), partial (5%) [THC2731042] |
| 64 | A_32_P227110 | THC2512148 | TAAAACAAATCCTTTGATTCAGCCAGTGTGTGTATTGATAATGGCTTATTTATTACAATCA | SEQ ID NO: 932 | |
| 65 | A_32_P232851 | THC2645586 | CTTGAAAAGGATATGGTTCACATTGGTTCTCAGAAAATTGAGGTGACTGAGTTATTTG | SEQ ID NO: 933 | Q9P3E1_NEUCR (Q9P3E1) Related to rna-binding protein fus/tls, partial (5%) [THC2645586] |
| 66 | A_32_P25243 | THC2658826 | GGCTCTGGGCACCATTGGAAGAGTGACGATATAAATGACAAGTGATTTATTTGTTTTCA | SEQ ID NO: 934 | |
| 67 | A_32_P33304 | ANK3 | TGTTGGAATACCGGCGGGGGTGATCTGTGTCTTTTATAAACGTCAGGTGATTAAAGGAAAGATGA | SEQ ID NO: 935 | Homo sapiens cDNA FLJ4903 fis, clone BRAMY3035184, highly similar to Mus musculus ankyrin 3, epithelial (Ank3). [AK126851] |
| 68 | A_32_P3342 | THC2678548 | TATAGCATTTCTGAAGATCATGTTGTACTGTTCTTGGTCTAGATGATTTGGTCAACAG | SEQ ID NO: 936 | ALU7_HUMAN (P39194) Alu subfamily SQ sequence contamination warning entry, partial (19%) [THC2678548] |
| 69 | A_32_P40673 | A_32_P40673 | CATCAGACTTGATATTAGGAGAGCCTACTACTTGTTTGAGTGTCACAGCCTGATATGTA | SEQ ID NO: 937 | |
| 70 | A_32_P41099 | THC2658419 | AGGGGCAGAAAATATTTGGGTTCCTCGGTTTATTAGTAAAGTGTCTTTGGACTATTGTCTG | SEQ ID NO: 938 | |
| 71 | A_32_P42976 | THC2713078 | CTTATTCCTTTCGTTTTGTGGTGTCAACCTGGGAACTATGTTGGGCTCATTCTTTCTGGCTA | SEQ ID NO: 939 | |
| 72 | A_32_P43878 | DB111455 | ATGTGAGAAATATTTCTTTTAAGGTTTAATGACCAAGTTCCATGTGAGCTGTTACTTGGGA | SEQ ID NO: 940 | DB111455 THYMU2 Homo sapiens cDNA clone THYMU2015028 5', mRNA sequence. [DB111455] |
| 73 | A_32_P5542 | AF131782 | GAGGCTCTAGGATCTAGCTTCCACTAACTGGGAGGAAAATGTCTTATAAATAAACAACAG | SEQ ID NO: 941 | Homo sapiens clone 24941 mRNA sequence. [AF131782] |
| 74 | A_32_P60551 | BU567566 | GGAGAAGTACAAGCTTTAGGGCTGTATCTATTCATCTCTATTCCTAGTAGATAAAATTTAGCC | SEQ ID NO: 942 | AGENCOURT_10399416 NIH_MGC_82 Homo sapiens cDNA clone IMAGE:6614194 5', mRNA sequence [BU567566] |
| 75 | A_32_P65067 | THC2618574 | CCCCCAAAGTGAATTTAAACTTGACTTATTTATGCGGTTCTCATAGCAACAGGAAAACT | SEQ ID NO: 943 | |
| 76 | A_32_P67209 | BU726029 | CTCCACTGTATATTTATGTGCACCTAGGTGCAGGTGACCACTGCTATTGTTCGAGAGAAG | SEQ ID NO: 944 | UI-E-C1C-aac-g-02-0-UI.s1 UI-E-C10 Homo sapiens cDNA clone UI-E-C10-aac-g-02-0-UI 3', mRNA sequence [BU726029] |
| 77 | A_32_P70875 | CD239706 | GTTGTTTGAGAAGTTGGTAATGCAGTGCGTAGGAGTAGGAGAACAAAGTGACAGTTTCTTATTTACTG | SEQ ID NO: 945 | FNP6XF03 FNP Homo sapiens cDNA, mRNA sequence [CD239706] |
| 78 | A_32_P71171 | A_32_P71171 | TCTAGATAGTATAGGAAAACCAAGAAATCCAGGCTGGTGATGGCTGGAGGGAGGTGATTGAA | SEQ ID NO: 946 | |
| 79 | A_32_P79103 | BM932034 | GTGCTACAGAATGAAAATAGCATTTTAGGAAGGTTGACTCAGAAGGTGCGAGTGGGGCATA | SEQ ID NO: 947 | UI-E-EJI-aji-k-24-0-UI.r1 UI-E-EJI Homo sapiens cDNA clone UI-E-EJI-aji-k-24-0-UI 5', mRNA sequence [BM932034] |
| 80 | A_32_P89987 | AK022346 | ATGGGAAGTTAGTACCGCAGGCTTACCAAAAGTCAGGTTTATATAAAGTCGGGTTCCTTT | SEQ ID NO: 948 | Homo sapiens cDNA FLJ12284 fis, clone MAMMA1001757. [AK022346] |

Fig. 3-5

| No. | Probe ID No. | Symbols of genes | Sequence | SEQ ID NO. | Descriptions of genes (letters and numbers within [ ] indicates GeneBank accession No.) |
|---|---|---|---|---|---|
| 81 | A_32_P89087 | AL134462 | TTGATGGAAGCTTCTAGTGAAGCGGAGGACGGATAAACAGTAAAGG GACAAATAGGATTAGT | SEQ ID NO: 948 | DKFZp547J085_r1 547 (synonym: hfbr1) Homo sapiens cDNA clone DKFZp547J085 5', mRNA sequence [AL134462] |
| 82 | A_32_P90468 | A_32_P90468 | AAGGCAGGAATAATTTGTATCTCATGGTAGGTAACTCCTGGAA GTTATCGAGACCCT | SEQ ID NO: 949 | |
| 83 | A_32_P91328 | THC2641595 | GTTAGCGGCAATAATGTCATTGAAGTCTTAACTGTAGGCTGACT CTAAGGCCAGGGTTCA | SEQ ID NO: 950 | |
| 84 | A_32_P98940 | THC2745869 | AAGAGTATTCCAAGATAGCAAAAGGTGTGTTGTTTTTAGCAGGT GTATTTCAGCTAGTTA | SEQ ID NO: 951 | |
| 85 | A_23_P102060 | SSFA2 | GTATCATCGAAATAATGGGCCCATGACTTGAATGAATAGAAAT GAATAAGGTGGTGTTT | SEQ ID NO: 952 | Homo sapiens sperm specific antigen 2 (SSFA2), mRNA [NM_006751] |
| 86 | A_23_P102235 | SNRPG | ACACAGAACAAATATGGAATGGTGGTAACGAGGAAATAGTA TCATCATGTAGGAAGG | SEQ ID NO: 953 | Homo sapiens small nuclear ribonucleoprotein polypeptide G (SNRPG), mRNA [NM_003096] |
| 87 | A_23_P104054 | C1orf9 | TAAATTTCTTCCTGTCTGCACAATTAGCTATTCAGAGCAAGAA GGCGTGATTTATAGA | SEQ ID NO: 954 | Homo sapiens chromosome 1 open reading frame 9 (C1orf9), transcript variant 2, mRNA [NM_016227] |
| 88 | A_23_P106131 | KTN1 | ATGTCTTCAGCGGTTTCTACTTTGTGAGAAACACTGAACAGAGTT TTGTCTTTGGTTGTTT | SEQ ID NO: 955 | Homo sapiens kinectin 1 (kinesin receptor) (KTN1), transcript variant 1, mRNA [NM_182926] |
| 89 | A_23_P106145 | ERO1L | ACTGAGGGTTTGGGCA ATGTGTTCGTTGTTTAAATGTCCGTCTGTGGAGAAAAGGCTTCAG | SEQ ID NO: 956 | Homo sapiens ERO1-like (S. cerevisiae) (ERO1L), mRNA [NM_014584] |
| 90 | A_23_P108835 | YPEL5 | AAAGTGACTCTGACTGAGTAGAGTTAAGTTCCTCCTATTTCGCACTG GGCTGTTGGTTAGAAAG | SEQ ID NO: 957 | Homo sapiens yippee-like 5 (Drosophila) (YPEL5), mRNA [NM_016061] |
| 91 | A_23_P109774 | ZBTB11 | GCCTCTCCCAGTTGCTTTAAAAATGGCTTAAGGAATAAGAAAT AAATGTGATAGGTGTG | SEQ ID NO: 958 | Homo sapiens zinc finger and BTB domain containing 11 (ZBTB11), mRNA [NM_014415] |
| 92 | A_23_P110362 | MAP2K1IP1 | ACTGAGAAGGAGAGTTCTTAATGTGACAGTGGGTTGA GTGGTACCTTATCT | SEQ ID NO: 959 | Homo sapiens mitogen-activated protein kinase kinase 1 interacting protein 1 (MAP2K1IP1), mRNA [NM_021970] |
| 93 | A_23_P110611 | ZH2C2 | CTCTGAAAGGAGAGCTTTCAGTGTTGGACTCTTGAAACCAG GTCTTGAAFACTTAA | SEQ ID NO: 960 | Homo sapiens zinc finger, H2C2 domain containing (ZH2C2), mRNA [NM_017676] |
| 94 | A_23_P110704 | SLU7 | CCTGCTTCGTTGGACAGTAGCAAGTAGTCAGAAGACATCGAAG ATAGATGCAGGTGATA | SEQ ID NO: 961 | Homo sapiens SLU7 splicing factor homolog (S. cerevisiae) (SLU7), mRNA [NM_006425] |
| 95 | A_23_P110811 | COX7C | AGGCTCTGGAAGTGGATGGATAGAAACTAGAAGTCATATGCCAATGTAG ATATGTTTGTCAATAA | SEQ ID NO: 962 | Homo sapiens cytochrome c oxidase subunit VIIc (COX7C), nuclear gene encoding mitochondrial protein, mRNA [NM_001867] |
| 96 | A_23_P114616 | ANKRD13C | GTCTCAAGAATGATCTGTCAAGTTTTTTGTATGTGTTTAACTCATATTCAGGAGTAGC TTAAAGTTTTTCAGG | SEQ ID NO: 963 | Homo sapiens mRNA; cDNA DKFZp566D1346 (from clone DKFZp566D1346). [AL136717] |
| 97 | A_23_P11652 | USP1 | GGTGGCATGGACTAATTTGTATCTGTTAACTCATATTCGCAC GATCGTATATAGTAC | SEQ ID NO: 964 | Homo sapiens ubiquitin specific peptidase 1 (USP1), transcript variant 1, mRNA [NM_003368] |
| 98 | A_23_P11685 | PLA2G4A | GAAATGGCAGGAGTTCTGATGCTGAGGGAGTTTGCAATGCAT GACAACTGGATTTAAA | SEQ ID NO: 965 | Homo sapiens phospholipase A2, group IVA (cytosolic, calcium-dependent) (PLA2G4A), mRNA [NM_024420] |

Fig. 3-6

| No. | Probe ID No. | Symbols of genes | Sequence | SEQ ID NO. | Descriptions of genes (letters and numbers within [ ] indicates GenBank accession No.) |
|---|---|---|---|---|---|
| 99 | A_23_P117163 | RCBTB1 | AAGTGAAGGAGGAGTTGTGATATTAGATTAGTAAGTGATTTGTA TGAATATGTGTGGCAC | SEQ ID NO: 967 | Homo sapiens regulator of chromosome condensation (RCC1) and BTB (POZ) domain containing protein 1 (RCBTB1), mRNA [NM_018191] |
| 100 | A_23_P117721 | RPS17 | AATTAGTGTGGTGAGGTGTCAGGGTTGGATGCAGGAGATTATTGA AGTAGATCCTGCACACT | SEQ ID NO: 968 | Homo sapiens ribosomal protein S17 (RPS17), mRNA [NM_001021] |
| 101 | A_23_P117852 | KIAA0101 | TAGTGCTGGGCATTTTTATTGGTGTTTGATTATTGGAATGGTGCC ATATGTCACTCCTTC | SEQ ID NO: 969 | Homo sapiens KIAA0101 (KIAA0101), transcript variant 1, mRNA [NM_014736] |
| 102 | A_23_P118516 | FAM18B | TATTCGTGTAGATTGTTTCAGGAGAAAGTTTTCGTTCCTATGGT AAGAGTGAGGACTTTG | SEQ ID NO: 970 | Homo sapiens family with sequence similarity 18, member B (FAM18B), mRNA [NM_016078] |
| 103 | A_23_P120046 | BAZ2B | TATTTGCTGAAGGTAATGATAGTAAGCTATACAGTGTGTACAGTA ATTATGCTGTAGGAAAG | SEQ ID NO: 971 | Homo sapiens bromodomain adjacent to zinc finger domain, 2B (BAZ2B), mRNA [NM_013450] |
| 104 | A_23_P120319 | MTHFD2 | AGGATTATTGGTTGGTATTAGTAGTCATTTTATGTATGTTACCC TTCAGTAAGTTCTCCC | SEQ ID NO: 972 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 105 | A_23_P1206 | RPS24 | TTTGGATTCAGAACTCATTTGGTGGTGGGAAGACAAACTGGGTT TGGCATGATTTATGAT | SEQ ID NO: 973 | Homo sapiens ribosomal protein S24 (RPS24), transcript variant 2, mRNA [NM_001026] |
| 106 | A_23_P121386 | IFT57 | TGGAACACACACTACTCCAATCAAAGCTGAAGAGAAGTCAAAG ATGACTAGGAACATGC | SEQ ID NO: 974 | Homo sapiens intraflagellar transport 57 homolog (Chlamydomonas) (IFT57), mRNA [NM_018010] |
| 107 | A_23_P121622 | SULT1B1 | GAAATAGGACATTGGTCGTGTAGTTGATTGAAAACCAGGGGCAGTTATG AATCATTTGGGCAAT | SEQ ID NO: 975 | Homo sapiens mRNA for ST1B2, complete cds. [D89479] |
| 108 | A_23_P121825 | FLJ13611 | CATGTGTTACTGTTACAAAACTTCTCTCTCCATGTAATGACAG TAGTTACTGAGCAAAG | SEQ ID NO: 976 | Homo sapiens hypothetical protein FLJ13611 (FLJ13611), mRNA [NM_024941] |
| 109 | A_23_P121875 | C5orf26 | TTAAAACATGTTGGCTTAGGCTACAGATAGCACTTTACTGAAGTAGTATTT TTGGTATCCTAGCC | SEQ ID NO: 977 | Homo sapiens chromosome 5 open reading frame 26 (C5orf26), mRNA [NM_022483] |
| 110 | A_23_P122007 | C5orf30 | ATGAGAATTTGTGGTTGGGGTGGAAATGTTTCGCTGTTGTATATT TTAAAGTAAATTGCAC | SEQ ID NO: 978 | Homo sapiens chromosome 5 open reading frame 30 (C5orf30), mRNA [NM_033211] |
| 111 | A_23_P122174 | XRCC4 | AAAAGCAAACTGATGTCTCTGGGTTGGGTTCAGCTGCTGTAAGTA AAGATGATTCCATTAT | SEQ ID NO: 979 | Homo sapiens X-ray repair complementing defective repair in Chinese hamster cells 4 (XRCC4), transcript variant 3, mRNA [NM_022550] |
| 112 | A_23_P123315 | BC067244 | GTTCCAAATCACTCGGTTTGGAGGGGGGTGGATACATGCTCATTT TCTGTACATGATGCAT | SEQ ID NO: 980 | Homo sapiens cDNA clone IMAGE:4807381, partial cds. [BC067244] |
| 113 | A_23_P123343 | NUDCD1 | GGGCTGCTTTGTAGTGGAAAAGTATTGAGTGGTACCTGGAGGT CTGACAGTTATACTG | SEQ ID NO: 981 | Homo sapiens NudC domain containing 1 (NUDCD1), mRNA [NM_032869] |
| 114 | A_23_P123608 | JAK2 | GGATAACAATGGGTGGATGAAAGAAATGAGCTTCATTCTGAGACC AAAGTAGATTACAGA | SEQ ID NO: 982 | Homo sapiens Janus kinase 2 (a protein tyrosine kinase) (JAK2), mRNA [NM_004972] |
| 115 | A_23_P127579 | PTS | GTGGTTTATAAAGGAGAAATAGGTATTGGGGTTAGCATTGCACAA AGCCCAGTTCTTCT | SEQ ID NO: 983 | Homo sapiens 6-pyruvoyltetrahydropterin synthase (PTS), mRNA [NM_000317] |
| 116 | A_23_P128060 | ZNF26 | ATCGGTCCATTGCTCAGCTACAGCTGAGGCATTTACCAGTTGTTGGA TAATGGTAATGTCTTT | SEQ ID NO: 984 | Homo sapiens zinc finger protein 26 (ZNF26), mRNA [NM_019591] |
| 117 | A_23_P128192 | PFDN5 | CAGGTCCATTGCTCAGCTCAAGTGTACAGACCCAAAGTGGTATGTGT AAGGCAAGGAGTGTGT | SEQ ID NO: 985 | Homo sapiens prefoldin subunit 5 (PFDN5), transcript variant 1, mRNA [NM_002624] |

Fig. 3-7

| No. | Probe ID No. | Symbols of genes | Sequence | SEQ ID NO: | Descriptions of genes (letters and numbers within [ ] indicates GenBank accession No.) |
|---|---|---|---|---|---|
| 118 | A_23_P128930 | PSMC6 | GAACAAGGAAGATTAGAGATACGTGAAAATCCATGCAGGTCCCATTACAAAGCATTGGTGAA | SEQ ID NO: 966 | Homo sapiens proteasome (prosome, macropain) 26S subunit, ATPase, 6 (PSMC6), mRNA [NM_002806] |
| 119 | A_23_P130444 | ZNF701 | GTGGTTGGAGAATATGATAACGGTTCATTTTGAGGTAATAGTTACAAATGCGGTGAGCAC | SEQ ID NO: 967 | Homo sapiens zinc finger protein 701 (ZNF701), mRNA [NM_018260] |
| 120 | A_23_P133375 | SLC25A46 | GAGTGGTTAGGAAGTTAATTCTGCATACATTTATAGAGTTTGGTTTGGTTTCCTAGTTGTG | SEQ ID NO: 968 | Homo sapiens solute carrier family 25, member 46 (SLC25A46), mRNA [NM_138773] |
| 121 | A_23_P133648 | FAM8A1 | AGTTGGGCGGAATTAGAAATGAGTGTTTTTAGATTCAAGTGACGGTAAAAGGATTTGTT | SEQ ID NO: 969 | Homo sapiens family with sequence similarity 8, member A1 (FAM8A1), mRNA [NM_016255] |
| 122 | A_23_P134786 | PHF20L1 | AGTTGTGTGGGCCGAGTGCTACATACCCAGGTATCCGTAAGTGTGATGCGTTGTTTTA | SEQ ID NO: 970 | Homo sapiens PHD finger protein 20-like 1 (PHF20L1), transcript variant 1, mRNA [NM_016018] |
| 123 | A_23_P135494 | CLIC4 | GTCGTCAAGCCGTAATGTTGAACAGAATTGGAGTATTTTCTTTATAATTCTTGAACAGG | SEQ ID NO: 971 | Homo sapiens chloride intracellular channel 4 (CLIC4), mRNA [NM_013943] |
| 124 | A_23_P135499 | CLIC4 | GTTCGTTTTTGATGTAGTAGCAGTATATTCTATACAGTCGTTGTGTTTTTACTAGGAC | SEQ ID NO: 972 | Homo sapiens chloride intracellular channel 4 (CLIC4), mRNA [NM_013943] |
| 125 | A_23_P13822 | STYK1 | AGGGTTAGTTCAGTCTTTAAGCAGGGCTAGAAAAGAATGTAATCTGATATGGAAGGA | SEQ ID NO: 973 | Homo sapiens serine/threonine/tyrosine kinase 1 (STYK1), mRNA [NM_018423] |
| 126 | A_23_P138308 | CD58 | AAGGTGTATCCGAAGGACGGGTCATTCAAGCACAGATATGCACTTATACCATACCATT | SEQ ID NO: 974 | Homo sapiens CD58 molecule (CD58), mRNA [NM_001779] |
| 127 | A_23_P140069 | FBXL3 | TAAGCGGAAGTGGAATACAATTAATTCTTAAAGCCGCTCTCTTTCAGTAGTGTGACTTTTAGA | SEQ ID NO: 975 | Homo sapiens F-box and leucine-rich repeat protein 3 (FBXL3), mRNA [NM_012158] |
| 128 | A_23_P140301 | PSMA3 | TGAACTAGAAGCTAGGCTGGGTTGGTGAATTAACTAATGGAAGACATGAAATTGTTCCAAA | SEQ ID NO: 976 | Homo sapiens proteasome (prosome, macropain) subunit, alpha type, 3 (PSMA3), transcript variant 1, mRNA [NM_002788] |
| 129 | A_23_P141549 | RPS7 | GTCAAACTAGAAGAGAAGTAGGCAGCGGGCTGGCCTCATAAAGGTTCATTGGAGAAAGACAGGAGAACAAT | SEQ ID NO: 977 | Homo sapiens ribosomal protein S7 (RPS7), mRNA [NM_001011] |
| 130 | A_23_P143956 | RPL22L1 | ATTGGCTTCGGAGTTGGTTCGATCTGACAAGGAGAGACCTACGAAGTTCGTTACTTCCGAGATTA | SEQ ID NO: 978 | Homo sapiens ribosomal protein L22-like 1, mRNA (cDNA clone IMAGE:4865966), [BC049823] |
| 131 | A_23_P144224 | TLOC1 | ATGGGATTGTGAAGAGGATGAAGGAGGCAAAATGATGGAGAAACACTAAATGTTCAC | SEQ ID NO: 979 | Homo sapiens translocation protein 1 (TLOC1), mRNA [NM_003262] |
| 132 | A_23_P144497 | RPS3A | CCAAATCCGGAAGAAGATGATGGAAATCATGACCGGAGAGGTGCAGACAAATGATTTGAA | SEQ ID NO: 980 | Homo sapiens ribosomal protein S3A (RPS3A), mRNA [NM_001006] |
| 133 | A_23_P144684 | ANKRD32 | AAACTTGTAGAAAACTTGGAAATAAACCATTGGACAGATTTCAGTAATGTGTAGAATTGACTC | SEQ ID NO: 981 | Homo sapiens ankyrin repeat domain 32 (ANKRD32), mRNA [NM_032290] |
| 134 | A_23_P145397 | CCNC | TAGTGGACCACTTGGAAATAAACCATTGGACACAGATTTCAGTAATGTCTTCAGTGGAACAC | SEQ ID NO: 982 | Homo sapiens cyclin C (CCNC), transcript variant 1, mRNA [NM_005190] |
| 135 | A_23_P14564 | GPR65 | AACAAGTTTAAATTGTGTTGCTTGATCCAATTCTGCTACTGTTTTGTAACCGAAACAGGAAG | SEQ ID NO: 983 | Homo sapiens G protein-coupled receptor 65 (GPR65), mRNA [NM_003608] |
| 136 | A_23_P145777 | NDUFA4 | ACGCTGGTTTAGAATGAAGGTGTTCCAGAAGGACCACATCGGACAATTTCCACTTAACCA | SEQ ID NO: 984 | Homo sapiens NADH dehydrogenase (ubiquinone) 1 alpha subcomplex, 4, 9kDa (NDUFA4), nuclear gene encoding mitochondrial protein, mRNA [NM_002489] |
| 137 | A_23_P146347 | FAM29A | TTGGACAACAAGCTCAAGGCAATGGGAAGGATTTTGATTTGTTGAGTAATGTGTAAGG | SEQ ID NO: 985 | Homo sapiens family with sequence similarity 29, member A (FAM29A), mRNA [NM_017645] |

Fig. 3-8

| No. | Probe ID No. | Symbols of genes | Sequence | SEQ ID NO: | Descriptions of genes (letters and numbers within [ ] indicates GenBank accession No.) |
|---|---|---|---|---|---|
| 138 | A_23_P14708 | SUHW4 | TCTTGTACCTCCATAGAAGTGTTAGCGTGCAGGGCTGTAAGGTTACCTTAATTAAACTT | SEQ ID NO: 1006 | Homo sapiens suppressor of hairy wing homolog 4 (Drosophila) (SUHW4), transcript variant 1, mRNA [NM_017661] |
| 139 | A_23_P14734 | RPS27L | TACAAGACTACCACCAGGTTTCAGCGATGGTCGAGACAGTGGTTGTTTGTGTAGGTTGTTCA | SEQ ID NO: 1007 | Homo sapiens ribosomal protein S27-like (RPS27L), mRNA [NM_015920] |
| 140 | A_23_P147404 | A_23_P147404 | TGGGGTGAAGATGAAATTGATTAGAATTTGTTGGATGGTGAGCAGGCTGCCTGTCATGTG | SEQ ID NO: 1008 | |
| 141 | A_23_P149775 | ARHGAP12 | TGTATAATAAAACAGAGAGGGTTTGGAAGGTTTTGTTACAGGGAGGATGGTCTGTTGAAGAT | SEQ ID NO: 1009 | Homo sapiens Rho GTPase activating protein 12 (ARHGAP12), mRNA [NM_018287] |
| 142 | A_23_P149892 | GALNACT-2 | CATGGTGGTTGAGAATAGAGAGGAATAAGGATAAGGATGGTTTTGTTTGTTTGGCTTTCAATTTC | SEQ ID NO: 1010 | Homo sapiens chondroitin sulfate GalNAcT-2 (GALNACT-2), mRNA [NM_018590] |
| 143 | A_23_P150129 | SAPS3 | TTACCTTGTTAACAAGGATCACGAATGAACATTTCAGAGGAATCTGCATATTTAAGAGAC | SEQ ID NO: 1011 | Homo sapiens SAPS domain family, member 3 (SAPS3), mRNA [NM_018312] |
| 144 | A_23_P151018 | LEMD3 | CCCCATCTTGTACCTGTTGCAAGAGTGAATGTAAAAATAGTTGTGGGCATTTTAAAAGG | SEQ ID NO: 1012 | Homo sapiens LEM domain containing 3 (LEMD3), mRNA [NM_014319] |
| 145 | A_23_P152002 | BCL2A1 | TGTAACCATATTTGCATTTGAAGGTATTGCTGATCAAGAAGTTCTACGAGCAGCAAATTGC | SEQ ID NO: 1013 | Homo sapiens BCL2-related protein A1 (BCL2A1), mRNA [NM_004049] |
| 146 | A_23_P154330 | TXNDC9 | CTCAGTTCTTAAATATGTGGGAAGGTGTGTGGAGATTGCTCTATTTTGAGATTGACTTTATC | SEQ ID NO: 1014 | Homo sapiens thioredoxin domain containing 9 (TXNDC9), mRNA [NM_005783] |
| 147 | A_23_P154367 | STK17B | TACCAATGGGCATGAACTGTTTGAGATTGCTGTGTTAGCACTTTTTCTTTGACTCA | SEQ ID NO: 1015 | Homo sapiens serine/threonine kinase 17b (STK17B), mRNA [NM_004226] |
| 148 | A_23_P155765 | HMGB2 | TAAAAATGCAGTTGTAGCTTTTGATGGGTACTACTAGAAGTTAGATTTTACAGCTTC | SEQ ID NO: 1016 | Homo sapiens high-mobility group box 2 (HMGB2), mRNA [NM_002129] |
| 149 | A_23_P155815 | NCAPG | AAGTTAGGAAGACGATGGAGGTGGAATCCTTTAAGATATGTCCAGTATTTGCTTTAA | SEQ ID NO: 1017 | Homo sapiens non-SMC condensin I complex, subunit G (NCAPG), mRNA [NM_022346] |
| 150 | A_23_P156355 | TMEM161B | AGGGTTGAGCCTGCCATATTTGTTTTATTCTGTGATCCTAAGCTAGTTCCTTTTAATAGG | SEQ ID NO: 1018 | Homo sapiens transmembrane protein 161B (TMEM161B), mRNA [NM_153354] |
| 151 | A_23_P156842 | EEF1E1 | AAGAAAAAGCAATCGTTCAGCAGTGGTTAGAATACAGGGTCAGTCAAGTAGATGGGCAGT | SEQ ID NO: 1019 | Homo sapiens eukaryotic translation elongation factor 1 epsilon 1 (EEF1E1), mRNA [NM_004280] |
| 152 | A_23_P157449 | POLR2K | GGTCTCTCTTGTTCTTGTCAAAATATGTTCTTGTACAGAGTAGTCACCATTTAAGTGTGGTTGA | SEQ ID NO: 1020 | Homo sapiens polymerase (RNA) II (DNA directed) polypeptide K, 7.0kDa (POLR2K), mRNA [NM_005034] |
| 153 | A_23_P157452 | POLR2K | GGAATGTCTTCACTTACTTGGATTTGGTCTGTCTCCCATTTGTGATTGTTATAGGTT | SEQ ID NO: 1021 | Homo sapiens polymerase (RNA) II (DNA directed) polypeptide K, 7.0kDa (POLR2K), mRNA [NM_005034] |
| 154 | A_23_P159650 | COX7B | CAAATACGGTAATGCTGTATTAGCTATGGAGCCACTTTCTGTATTGTTACATGGACATA | SEQ ID NO: 1022 | Homo sapiens cytochrome c oxidase subunit VIIb (COX7B), nuclear gene encoding mitochondrial protein, mRNA [NM_001866] |
| 155 | A_23_P159839 | C1GALT1C1 | TCCAAATCAGATGCATGTGATGATGTATGGGGTATAGCGCCTTAGGGCATTTGGGCATAT | SEQ ID NO: 1023 | Homo sapiens C1GALT1-specific chaperone 1 (C1GALT1C1), transcript variant 1, mRNA [NM_152692] |
| 156 | A_23_P160466 | SLC19A2 | CTTGGTATGTGGCCACATTTATAGAAATGCTGAACTCAATGTGCAAGTTGTAGTTGTATGCA | SEQ ID NO: 1024 | Homo sapiens solute carrier family 19 (thiamine transporter), member 2 (SLC19A2), mRNA [NM_006996] |

Fig. 3-9

| No. | Probe ID No. | Symbols of genes | Sequence | SEQ ID NO: | Descriptions of genes (letters and numbers within [ ] indicates GenBank accession No.) |
|---|---|---|---|---|---|
| 157 | A_23_P161091 | ZMYM1 | GAGGTATTTTTCCTAAGTGGTATTGTAGGGTGTATACTGTGTTCAGGTTGTGTCTGTG | SEQ ID NO: 1025 | Homo sapiens zinc finger, MYM-type 1 (ZMYM1), mRNA [NM_024772] |
| 158 | A_23_P162279 | CCDC91 | AGTACAGGATATATGAAAATGTTTTCCCAGTATTTCAGAATGTAGTTAATTCACAGGCAGG | SEQ ID NO: 1026 | Homo sapiens coiled-coil domain containing 91 (CCDC91), mRNA [NM_018318] |
| 159 | A_23_P162596 | ACTR6 | TTAACGGCTCAGTGGACAGTTTTCCTTAGAAGGTAGTTTTGTGTGACTGTGACTAAACT | SEQ ID NO: 1027 | Homo sapiens ARP6 actin-related protein 6 homolog (yeast) (ACTR6), mRNA [NM_022496] |
| 160 | A_23_P162866 | HSP90AA1 | CTGGGTATTGATGAAGAATGAACGCTACGCTGATGATACCAGTGGTGTGTAACTGAAGAA | SEQ ID NO: 1028 | Homo sapiens heat shock protein 90kDa alpha (cytosolic), class A member 1 (HSP90AA1), transcript variant 2, mRNA [NM_005348] |
| 161 | A_23_P163113 | PRPF39 | TAGTAATAGGGGGAAAATGTCAATTAGTAGGTTACCACAGATACTGTTTCCTACCATTTA | SEQ ID NO: 1029 | Homo sapiens PRPF39 pre-mRNA processing factor 39 homolog (S. cerevisiae) (PRPF39), mRNA [NM_017922] |
| 162 | A_23_P163216 | ATP8B4 | ATCAGTGTATTTTCATAAAGTGATTCCGGGCATATTTGTGTGAAAAGCTCAGTTCTGTCA | SEQ ID NO: 1030 | Homo sapiens ATPase, Class I, type 8B, member 4 (ATP8B4), mRNA [NM_024837] |
| 163 | A_23_P167828 | RWDD1 | GAGGATGCTGAAAGAAGAAGGTGGAGGTAGATGAGTCTTTGTTCGAAGAAATGGATGACTTG | SEQ ID NO: 1031 | Homo sapiens RWD domain containing 1 (RWDD1), transcript variant 2, mRNA [NM_016104] |
| 164 | A_23_P16817 | CLK1 | ATGGAAAGGATTCTTGGACGTCTACCAAAAACATATGATACAGAAAAGCAGGAAAACGTAAA | SEQ ID NO: 1032 | Homo sapiens CDC-like kinase 1 (CLK1), transcript variant 1, mRNA [NM_004071] |
| 165 | A_23_P168656 | GTPBP10 | AATTTGTGGATTTCTGATACAAATGTCTCTACTGAGCCACCACAAGCATGCTGTTACT | SEQ ID NO: 1033 | Homo sapiens GTP-binding protein 10 (putative) (GTPBP10), transcript variant 2, mRNA [NM_033107] |
| 166 | A_23_P168974 | SDCBP | GGAAAACGAACAAGTTCATCTTGAGAATTTATACAGACTGGTCGAGAACAAGCATCCTCAG | SEQ ID NO: 1034 | Homo sapiens cDNA FLJ46804 fis, clone TRACH3032570, highly similar to Homo sapiens syndecan binding protein (syntenin), (SDCBP). [AK128645] |
| 167 | A_23_P169050 | MRPS28 | GAGCAACAACAGATACAACTGTACTAGAAGGGTAGTAATGCAGTTCTCTTGGGAATCCAAGAGA | SEQ ID NO: 1035 | Homo sapiens mitochondrial ribosomal protein S28 (MRPS28), nuclear gene encoding mitochondrial protein, mRNA [NM_014018] |
| 168 | A_23_P169576 | EXOC6 | ATGGTGAATCTTGGGTTTTGTTAGTGATCATATGTCAGGCTAATATTAGTAACTATGCCTCATTC | SEQ ID NO: 1036 | Homo sapiens exocyst complex component 6 (EXOC6), transcript variant 2, mRNA [NM_001013848] |
| 169 | A_23_P17021 | SCRN3 | GTCAAAGTTAGTTCTTAGTGATGATGAATGGTCTTAGTGATCAGTGCA | SEQ ID NO: 1037 | Homo sapiens secernin 3 (SCRN3), mRNA [NM_024583] |
| 170 | A_23_P170233 | CSTA | AACTGGCTACTGAGTGATGATGATGCTTGCTGATAATAACCATGAATAAAGAAGAACATTCT | SEQ ID NO: 1038 | Homo sapiens cystatin A (stefin A) (CSTA), mRNA [NM_005213] |
| 171 | A_23_P18325 | PDCD10 | CCAACCGACTAATTCATCGAAACGAACCAACTTAATACTTCAGAGGTTGAAAACTGTGGCCTGAA | SEQ ID NO: 1039 | Homo sapiens programmed cell death 10 (PDCD10), transcript variant 1, mRNA [NM_007217] |
| 172 | A_23_P18422 | MRPL3 | CAGTAGAAAACCATATGGGAACTATAGTGCAAGGTATTTGGGTAAAGAAACCATTTGTA | SEQ ID NO: 1040 | Homo sapiens mitochondrial ribosomal protein L3 (MRPL3), nuclear gene encoding mitochondrial protein, mRNA [NM_007208] |
| 173 | A_23_P18598 | PI4K2B | AGGGTTAAAACGAATGTCACGACTGGGCTTAAGCTGGGTAATTTGTGGGTCTAGGCCTTTT | SEQ ID NO: 1041 | Homo sapiens phosphatidylinositol 4-kinase type 2 beta (PI4K2B), mRNA [NM_018323] |
| 174 | A_23_P200030 | FPGT | TAAAAATTGGTAAACATAGAAGTAACTGTCCACAACCGTCAGTTATGATAGTTATGTGCG | SEQ ID NO: 1042 | Homo sapiens fucose-1-phosphate guanylyltransferase (FPGT), mRNA [NM_003838] |

Fig. 3-10

| No. | Probe ID No. | Symbols of genes | Sequence | SEQ ID NO: | Descriptions of genes (letters and numbers within [ ] indicates GenBank accession No.) |
|---|---|---|---|---|---|
| 175 | A_23_P202298 | AGL | TAGATTTTTAACAGGTGTCATTTGAGTAAACGTTTCGGTAGAAT GCTTCATCACTTCAGTG | SEQ ID NO: 1043 | Homo sapiens amylo-1, 6-glucosidase, 4-alpha-glucanotransferase (glycogen debranching enzyme, glycogen storage disease type III) (AGL), transcript variant 4, mRNA [NM_000028] |
| 176 | A_23_P203493 | LBR | GAGCCCTTTATCAATACAGATGGTGGAATTTCTGGATATCAGCTA CAGTTGTTTTAAGT | SEQ ID NO: 1044 | Homo sapiens lamin B receptor (LBR), transcript variant 1, mRNA [NM_002296] |
| 177 | A_23_P200507 | CNIH4 | TGGTTGAAGTCAGCCTACAGTACAGGTTGCACAGTTGAAGAGCCAG AGACTTCTAAATCAT | SEQ ID NO: 1045 | Homo sapiens cornichon homolog 4 (Drosophila) (CNIH4), mRNA [NM_014184] |
| 178 | A_23_P203955 | A_23_P203955 | AGACCATGATTGAACCTCACATTGATGTCAAGACCACCGATGGT TATTGTTTCATCTAC | SEQ ID NO: 1046 | |
| 179 | A_23_P201619 | NEK7 | TGAAGGGCAAAGAGGAAGTCACTGTTAAAGGACTCTGTGCCATCT TACAACCTTGGATGAA | SEQ ID NO: 1047 | Serine/threonine-protein kinase Nek7 (EC 2.7.11.1) (NimA-related protein kinase 7). [Source:Uniprot/SWISSPROT;Acc:Q8IDX7] [ENST00000367385] |
| 180 | A_23_P201918 | ABCB10 | CATGGATGAGAGCTAGACCCTAAGAAGTAATTAAGTCAATGTAAA TCAAATGGAAGTTTTG | SEQ ID NO: 1048 | Homo sapiens ATP-binding cassette, sub-family B (MDR/TAP), member 10 (ABCB10), nuclear gene encoding mitochondrial protein, mRNA [NM_012089] |
| 181 | A_23_P201951 | ARID4B | ATGTTTAGAGGTTTGAATTAGGCTAAAAGGTCTTGCAGTGGCTT TTCATGGCCCTTCAAA | SEQ ID NO: 1049 | Homo sapiens AT rich interactive domain 4B (RBP1-like) (ARID4B), transcript variant 1, mRNA [NM_016374] |
| 182 | A_23_P202225 | RRM2B | TGCTCGTTTGTAAAAAGTTAAAGATTTGAAAGAGAATCTCATAT TCCCAGGCATTAGGA | SEQ ID NO: 1050 | Homo sapiens ribonucleotide reductase M2 B (TP53 inducible) (RRM2B), mRNA [NM_015713] |
| 183 | A_23_P202496 | NOC3L | ACAGCTATTCCGACATATGTAGGAGTGGCCTAAGAAATGCGTGTT TCAGTGAGTCATGAAT | SEQ ID NO: 1051 | Homo sapiens nucleolar complex associated 3 homolog (S. cerevisiae) (NOC3L), mRNA [NM_022451] |
| 184 | A_23_P202637 | SAPS3 | TGATTATTCCTACAAGTGAAACACTAGACATATTTGGAGTGTATA TGCCTTGTGTTTGGG | SEQ ID NO: 1052 | Homo sapiens SAPS domain family, member 3 (SAPS3), mRNA [NM_018312] |
| 185 | A_23_P203498 | TRIM22 | GTACATAAGAATGTATCACTAAGTAATGTATGCGTTCAGAATGTG TTGGTTTACCAGTGAC | SEQ ID NO: 1053 | Homo sapiens tripartite motif-containing 22 (TRIM22), mRNA [NM_006074] |
| 186 | A_23_P203645 | CREBZF | TCTGTTGGAGTATTTTCTTCCTTAGGTCAATAGTTTCCTGAT TATTTGAAAATTGTGGG | SEQ ID NO: 1054 | Homo sapiens CREB/ATF bZIP transcription factor (CREBZF), mRNA [NM_010396181] |
| 187 | A_23_P204197 | FLJ22028 | CTATAAGGTTGTACTGCGGGGAAAAATACAATGGACAGGGGTTAG GTCAGATCATGAATT | SEQ ID NO: 1055 | Homo sapiens hypothetical protein FLJ22028 (FLJ22028), mRNA [NM_024854] |
| 188 | A_23_P204269 | USP15 | GACCAGGATAAATGAGGTATGTTGATCATGGGCTTGGCTTTGATTATAT CTTGATATTAAAGCTG | SEQ ID NO: 1056 | Homo sapiens ubiquitin specific peptidase 15 (USP15), mRNA [NM_006313] |
| 189 | A_23_P204564 | PPP1R12A | GTATAAGATGTTAGATCTGTAATCTTGACATTCATTTTAGCAG GTACTGAGTGATGCTG | SEQ ID NO: 1057 | Homo sapiens protein phosphatase 1, regulatory (inhibitor) subunit 12A (PPP1R12A), mRNA [NM_002480] |
| 190 | A_23_P205027 | ABHD13 | ATTTGTGCAGAAGATAAAGAATGTCCTTTAGAAGGTGTTA TGTGTGTACCTGTCTG | SEQ ID NO: 1058 | Homo sapiens abhydrolase domain containing 13 (ABHD13), mRNA [NM_032859] |
| 191 | A_23_P205336 | C14orf129 | CAATTCATTGCCAGACTTCATTGGAATGCTTGTTTTGATGATGT ATGTTCATTCTCAGGCT | SEQ ID NO: 1059 | Homo sapiens chromosome 14 open reading frame 129 (C14orf129), mRNA [NM_016472] |

Fig. 3-11

| No. | Probe ID No. | Symbols of genes | Sequence | SEQ ID NO: | Descriptions of genes (letters and numbers within [ ] indicates GenBank accession No.) |
|---|---|---|---|---|---|
| 192 | A_23_P205646 | MAP4K5 | CTAATGTAGCAGGGGGAAGTATTTAATTGGCGATGATATGTATTTTACTTATATACTTAGCC | SEQ ID NO:1060 | Homo sapiens mitogen-activated protein kinase kinase kinase kinase 5 (MAP4K5), transcript variant 2, mRNA [NM_198794] |
| 193 | A_23_P20606 | NIPSNAP3A | GTAAGTACCACTTCAAAAAATAGTTCGTTTACTTTCTGCATGGTATTCAGTGTGTGTC | SEQ ID NO:1061 | Homo sapiens nipsnap homolog 3A (C. elegans) (NIPSNAP3A), mRNA [NM_015469] |
| 194 | A_23_P207299 | LOC51136 | CCAAAACAGGCAATTTGAAATTAGAACTAGTGGTTTTAGAGAACTGAGGTATTCTTCCTG | SEQ ID NO:1062 | Homo sapiens PTD016 protein (LOC51136), mRNA [NM_016125] |
| 195 | A_23_P207999 | PMAIP1 | TTAGAGAATGTTCTAGTGTTTTGCCGAAGATTACCGGCTGGCCTACTGTGAAGGGAGAT | SEQ ID NO:1063 | Homo sapiens phorbol-12-myristate-13-acetate-induced protein 1 (PMAIP1), mRNA [NM_021127] |
| 196 | A_23_P208238 | ZNF137 | CCATACTGGAGCATAAATCTTACAAATGTTAAGTGTGGCAAGGTCTTCAGTCTCTGGGC | SEQ ID NO:1064 | Homo sapiens zinc finger protein 137 (ZNF137), mRNA [NM_003438] |
| 197 | A_23_P209032 | ZNF302 | TCAGAAAAATGTATACTGGGCAAAAGTTGTATGAAGGTGGTGAAGATGGGAGACTTTAG | SEQ ID NO:1065 | Homo sapiens zinc finger protein 302 (ZNF302), transcript variant 1, mRNA [NM_018443] |
| 198 | A_23_P209879 | ATF2 | TCATGTAAACGGTTAACAAGCTTAGGAAGGTTAGCAAAACTTTCAATGTAAATCAGTCTG | SEQ ID NO:1066 | Homo sapiens cDNA FLJ46699 fis, clone UTERU3022588, highly similar to Cyclic-AMP-dependent transcription factor ATF-2. [AK128731] |
| 199 | A_23_P210274 | PREI3 | GGATCAGTATGCGGTAGGATTTACAGAATATATTTGAGTTATGGTTATTTTCATCATCGGCAG | SEQ ID NO:1067 | Homo sapiens preimplantation protein 3 (PREI3), transcript variant 1, mRNA [NM_015387] |
| 200 | A_23_P210829 | PCMTD2 | TGCTGGGCACCTTATACCAGAATTCAGTATAATACACTAGTTTCTGTTTCAAACAGATA | SEQ ID NO:1068 | Homo sapiens protein-L-isoaspartate (D-aspartate) O-methyltransferase domain containing 2 (PCMTD2), mRNA [NM_018257] |
| 201 | A_23_P211840 | UBE1C | GCCACCCTAGAGAGGGAAAAAATAGAACACTTTAGTTAGAGTCGGTAAGCTCTATTCAAGAA | SEQ ID NO:1069 | Homo sapiens ubiquitin-activating enzyme E1C (UBA3 homolog, yeast) (UBE1C), transcript variant 1, mRNA [NM_003968] |
| 202 | A_23_P212728 | TBC1D23 | TGTACCCTGTTAACAGCCAGTCATTTTGATTTACTTATGGAAATCAAGTGAATAAAAGGG | SEQ ID NO:1070 | Homo sapiens TBC1 domain family, member 23, mRNA (cDNA clone MGC:8800 IMAGE:3847561), complete cds. [BC020955] |
| 203 | A_23_P2129 | TMEM126B | CATATGCATCATATGGGTACACTTCCATTTTTGTCTAGTGTTGTTACTGACGAAGCTTTTG | SEQ ID NO:1071 | Homo sapiens transmembrane protein 126B (TMEM126B), mRNA [NM_018480] |
| 204 | A_23_P213661 | HSPPD1 | GTATGTAAGTTTTGTTTGTGAAAATGTAGTTAATGTAGTGCACTGTGGAGGTCATAAGG | SEQ ID NO:1072 | Homo sapiens histidine acid phosphatase domain containing 1 (HSPPD1), mRNA [NM_015216] |
| 205 | A_23_P215751 | NDUFA5 | TAAAAGTGGAGTCACTCACTAAATAGTTTGCAGTACGTTTCTAATATAAGTATAGGTTGGGTATG | SEQ ID NO:1073 | Homo sapiens NADH dehydrogenase (ubiquinone) 1 alpha subcomplex, 5, 13kDa (NDUFA5), nuclear gene encoding mitochondrial protein, mRNA [NM_005000] |
| 206 | A_23_P21734 | TAF9 | CATGGTTGTGATTTGTTCCCTGAACGCTGGTTCTGTCATATAGTTTTTGTGCTGAGAACAGAT | SEQ ID NO:1074 | Homo sapiens TAF9 RNA polymerase II, TATA box binding protein (TBP)-associated factor, 32kDa (TAF9), transcript variant 3, mRNA [NM_001015891] |
| 207 | A_23_P217384 | AP1S2 | AAAGGTTGCTCTCTTCACGTAGTATTATGTGTAAAGTCATTGTTTAAACGACGAATGTTC | SEQ ID NO:1075 | Homo sapiens adaptor-related protein complex 1, sigma 2 subunit (AP1S2), mRNA [NM_003916] |
| 208 | A_23_P217564 | ACSL4 | GTTATAGGTTCCTTAGAAAACACATAATTAACACGTTAAGGTTGGGTGCTGGTAATTCTTTG | SEQ ID NO:1076 | Homo sapiens acyl-CoA synthetase long-chain family member 4 (ACSL4), transcript variant 1, mRNA [NM_004458] |

Fig. 3-12

| No. | Probe ID No. | Symbols of genes | Sequence | SEQ ID NO. | Descriptions of genes (letters and numbers within [ ] indicates GenBank accession No.) |
|---|---|---|---|---|---|
| 209 | A_23_P218928 | C4orf18 | CAGATGAGTTCATTGGTTGTGTAGATGTGTTTCAGAGGTAGGTACAGAGAATGTTTG | SEQ ID NO: 1077 | Homo sapiens chromosome 4 open reading frame 18 (C4orf18), transcript variant 2, mRNA [NM_016613] |
| 210 | A_23_P219072 | SAMD9 | AACCTACCTCCGAGATTAGTAAAGCCAGTTGAAAAACTAAAAGATCAGTTCGAGAAGTCT | SEQ ID NO: 1078 | Homo sapiens sterile alpha motif domain containing 9 (SAMD9), mRNA [NM_017654] |
| 211 | A_23_P22671 | SYBL1 | CAAACGGAATACGGCTTGGAGGGAGTAGAGAGGTTGAAAATCTCATTTCCTGTTGAATAATA | SEQ ID NO: 1079 | Homo sapiens synaptobrevin-like 1 (SYBL1), mRNA [NM_005638] |
| 212 | A_23_P23765 | ITGB3BP | AGTATAGAGGCTTGGAGGGAGTAGAGAGGTTGAAAATCTCATTGGAAATGTCGTGTGCA | SEQ ID NO: 1080 | Homo sapiens integrin beta 3 binding protein (beta3-endonexin) (ITGB3BP), mRNA [NM_014288] |
| 213 | A_23_P23960 | BLOC1S2 | GAGTAAACTGGAGGACTGTGGCTATTCCTGAACCTCTTGAGACAGAATCCGTCAGAAT | SEQ ID NO: 1081 | Homo sapiens biogenesis of lysosome-related organelles complex-1, subunit 2 (BLOC1S2), transcript variant 2, mRNA [NM_031342] |
| 214 | A_23_P24365 | ANKRD49 | GGGCACTGCTTGTATGTCTCAAGTTCACAGGAAATGTGATTTTGTAAGGTCTCAT | SEQ ID NO: 1082 | Homo sapiens ankyrin repeat domain 49 (ANKRD49), mRNA [NM_017704] |
| 215 | A_23_P250002 | HACE1 | TAAGCAGTCATTGTTGTTTGCAGTAGTAATGTTTGAGAGAGATGTAAGTTGAAAGTTTGGTA | SEQ ID NO: 1083 | Homo sapiens HECT domain and ankyrin repeat containing, E3 ubiquitin protein ligase 1 (HACE1), mRNA [NM_020771] |
| 216 | A_23_P250600 | ST3GAL6 | ATGTCACGAAGTTCAGGTAGTGGTTTAAATAGAAGTTTCTGACGTCAAGAAGTCGTTT | SEQ ID NO: 1084 | Homo sapiens ST3 beta-galactoside alpha-2,3-sialyltransferase 6 (ST3GAL6), mRNA [NM_006100] |
| 217 | A_23_P250930 | CRBN | TGATGTATTGAGAATTCAGCTCCTTAAAATAGGAGCAGTGCTATCCAGGCAACTTCGGCTGTGA | SEQ ID NO: 1085 | Homo sapiens cereblon (CRBN), mRNA [NM_016302] |
| 218 | A_23_P250994 | ANAPC10 | GATTCATTGCCTTAACTGACAATCATAAGAAGCCAACTCGGTACATTCATGATACAGAT | SEQ ID NO: 1086 | Homo sapiens anaphase promoting complex subunit 10 (ANAPC10), mRNA [NM_014885] |
| 219 | A_23_P251421 | CDCA7 | ATTTACTTGGATATGTAAACGCATTGGTCCATTGCAATGTTGATGCATAATTGGACCT | SEQ ID NO: 1087 | Homo sapiens cell division cycle associated 7 (CDCA7), transcript variant 1, mRNA [NM_031942] |
| 220 | A_23_P251937 | CPEB4 | GTATGTCAGTTAATTGTACTACTTGGGTGAATTGAATATAGTTTTTACTGTGTATGGGG | SEQ ID NO: 1088 | Homo sapiens cytoplasmic polyadenylation element binding protein 4 (CPEB4), mRNA [NM_030627] |
| 221 | A_23_P252145 | C1GALT1 | ATATGTGTATATATATGAGGAACTGTGTTTTAAATGGTGGCCAGGTAGGAAGTAG | SEQ ID NO: 1089 | Homo sapiens core 1 synthase, glycoprotein-N-acetylgalactosamine 3-beta-galactosyltransferase, 1 (C1GALT1), mRNA [NM_020156] |
| 222 | A_23_P252201 | EAF2 | CAGGATTCGTCATAATAGATGCCAGTACATAATAGATTTCGAGACAACAGTGCCTTCTCGAT | SEQ ID NO: 1090 | Homo sapiens ELL associated factor 2 (EAF2), mRNA [NM_018456] |
| 223 | A_23_P252371 | RBBP8 | GGCAAGGAGGAGGAGACAGATAGACGTTGAAACAGAAACAGAAGGATGAAGGACAGTTTTT | SEQ ID NO: 1091 | Homo sapiens retinoblastoma binding protein 8 (RBBP8), transcript variant 1, mRNA [NM_002894] |
| 224 | A_23_P253412 | MRPL50 | GAAAAGTTTTGAGAGGGACTGTCAACTTGGGTTAAGACAGGAGGAGATTGCAGTTCA | SEQ ID NO: 1092 | Homo sapiens mitochondrial ribosomal protein L50 (MRPL50), nuclear gene encoding mitochondrial protein, mRNA [NM_019051] |
| 225 | A_23_P254472 | C6orf211 | TTCATTCAATAGCTTGTTTGTTTCATTTGCACGGCCCTTGTATTTGATTGAGGTGTAGAATGG | SEQ ID NO: 1093 | Homo sapiens chromosome 6 open reading frame 211 (C6orf211), mRNA [NM_024573] |
| 226 | A_23_P254702 | DEK | TTTTTATTTAACTGCTTTTGCCATATAACATGCTGATATTACTGGAAACCTAGCCAGG | SEQ ID NO: 1094 | Homo sapiens DEK oncogene (DNA binding) (DEK), mRNA [NM_003472] |
| 227 | A_23_P254733 | MLF1IP | GCTTAGCTTGTGAAACTGTACGTTATAAATGATCAATGTTTGCAAAGAAGTTATGGGC | SEQ ID NO: 1095 | Homo sapiens MLF1 interacting protein (MLF1IP), mRNA [NM_024629] |

Fig. 3-13

| No. | Probe ID No | Symbols of genes | Sequence | SEQ ID NO: | Descriptions of genes (letters and numbers within ( ) indicates GenBank accession No.) |
|---|---|---|---|---|---|
| 228 | A_23_P254756 | CD164 | TTAGTTTTTAGTTGAGTTGTGTAGGATTAATTCGAAAATAGGGAG AATTCGATTCCTCGGCA | SEQ ID NO: 1095 | Homo sapiens CD164 molecule, sialomucin (CD164), mRNA [NM_006016] |
| 229 | A_23_P28503 | FNDC3A | ATACTTGCCATTTGAGCCTCACTGCAAAATTAGTCGAAGAAGA AAACAATTTTAATGT | SEQ ID NO: 1097 | Homo sapiens fibronectin type III domain containing 3A (FNDC3A), transcript variant 2, mRNA [NM_014923] |
| 230 | A_23_P255663 | MANEA | AAAGAGTCTGTACATCTCAGAGTTCAGTCGGCAATTTCTTGG CCATGCATGTAGAAGC | SEQ ID NO: 1098 | Homo sapiens mannosidase, endo-alpha (MANEA), mRNA [NM_024641] |
| 231 | A_23_P256251 | FBXO30 | GCCTTTAAAGTTTTGCTGAAGAATGTGTCGTGGTTAGGAATAC CAGAAGCATTAAGCTT | SEQ ID NO: 1099 | Homo sapiens F-box protein 30 (FBXO30), mRNA [NM_032145] |
| 232 | A_23_P256342 | SNX13 | ATTAGGCAGGTGAATGATCCTTGAAACATCTCTTCAGGTGTGG AGAAAGAGAGAAATG | SEQ ID NO: 1100 | Homo sapiens sorting nexin 13 (SNX13), mRNA [NM_015132] |
| 233 | A_23_P25638 | C13orf7 | GTTGCATTCGAGGGGAGTTTTGTTTTGAGTAGTATGTTCTTGT TTGCATGTCCTGTC | SEQ ID NO: 1101 | Homo sapiens chromosome 13 open reading frame 7 (C13orf7), mRNA [NM_024546] |
| 234 | A_23_P25735 | PSMA6 | TAGGAGAGAGAGGTAAACATTGTCGTTAGTTTACCAGATCCGT GATGCCACTTACCTGT | SEQ ID NO: 1102 | Homo sapiens proteasome (prosome, macropain) subunit, alpha type, 6 (PSMA6), mRNA [NM_002791] |
| 235 | A_23_P257911 | USP16 | GTACTTGTGTTTTAATATATCTGGGTGATGGATCAACACACATC AATAAAGTGACTTACC | SEQ ID NO: 1103 | Homo sapiens ubiquitin specific peptidase 16 (USP16), transcript variant 1, mRNA [NM_006447] |
| 236 | A_23_P258108 | LOC731224 | GTGAGGCCAGGTGTTGCTGTTGAATCGAAGCCAGAAAGA TGAGTCAATCCTTAAA | SEQ ID NO: 1104 | PREDICTED: Homo sapiens similar to 60S ribosomal protein L9 (LOC731224), mRNA [XR_015767] |
| 237 | A_23_P259054 | SNX14 | CATCAGACTTCTGTTTGATGGCTTACAGCACCACTACTCAAGA AGGAGCTGACTTATGT | SEQ ID NO: 1105 | Homo sapiens sorting nexin 14 (SNX14), transcript variant 1, mRNA [NM_153816] |
| 238 | A_23_P259594 | AKAP7 | GAAGATAAGCTCGAGGTGTTATGGTATCGGTTGGCATCTGAAGCT TGTTTGCAGTCGTTCT | SEQ ID NO: 1106 | Homo sapiens A kinase (PRKA) anchor protein 7 (AKAP7), transcript variant gamma, mRNA [NM_016377] |
| 239 | A_23_P26021 | COPS2 | TGCTTTTTCTTGATCAACTGGTTTGTGTTGGCTGCATTTAC CGAAGAAAAGAGCTT | SEQ ID NO: 1107 | Homo sapiens COP9 constitutive photomorphogenic homolog subunit 2 (Arabidopsis) (COPS2), mRNA [NM_004236] |
| 240 | A_23_P2705 | P2RY5 | TCTGTATTGCTGTTTCCAACTGTTGTTTGACCGTATAGTTTAC TACTTTACATCGGACA | SEQ ID NO: 1108 | Homo sapiens purinergic receptor P2Y, G-protein coupled, 5 (P2RY5), mRNA [NM_005767] |
| 241 | A_23_P28169 | ARL6IP6 | GGAAAGCAAATAATGCCTACTACTCCGACTTTATAGAAGCTAC TTTAAATCAGAATAT | SEQ ID NO: 1109 | Homo sapiens ADP-ribosylation-like factor 6 interacting protein 6 (ARL6IP6), mRNA [NM_152522] |
| 242 | A_23_P29005 | SAMSN1 | CTCTGGTTGCTATATCTGATCATCAGGAAATTCAGATAATGGCAAAG AGGATCTGGAGTCTGA | SEQ ID NO: 1110 | Homo sapiens SAM domain, SH3 domain and nuclear localization signals 1 (SAMSN1), mRNA [NM_022136] |
| 243 | A_23_P302550 | RGS18 | GAGTCTTAAGGCCCTAAGGGATTTGGGGATCTGGCACATTGGTTCA TATTCAGAAAGTGTTA | SEQ ID NO: 1111 | Homo sapiens regulator of G-protein signaling 18 (RGS18), mRNA [NM_130782] |
| 244 | A_23_P30307 | CRSP9 | CAATTGTACTGGACAAGAATGAACATCAAAGAGAAAATTCAGGTC ATAGGAGAGATCAGAT | SEQ ID NO: 1112 | Homo sapiens cofactor required for Sp1 transcriptional activation, subunit 9, 33kDa (CRSP9), mRNA [NM_004270] |
| 245 | A_23_P360280 | STX7 | GTCTGATGTTACGGGGGAGAGTGTAGCACCTCAAGATTTAGTAAAATGTTAA CATAATTTGAAGAAG | SEQ ID NO: 1113 | Homo sapiens syntaxin 7 (STX7), mRNA [NM_003569] |
| 246 | A_23_P365060 | PBEF1 | TGCCTGTGGCTGTATATGCACCTCAAGATTTAAGGAGAATAAT GTTTTTAGAGAGAATT | SEQ ID NO: 1114 | Homo sapiens pre-B-cell colony enhancing factor 1 (PBEF1), mRNA [NM_005746] |

Fig. 3-14

| No. | Probe ID No | Symbols of genes | Sequence | SEQ ID NO: | Descriptions of genes (letters and numbers within [ ] indicates GenBank accession No.) |
|---|---|---|---|---|---|
| 247 | A_23_P305723 | MIER1 | TGATGTATTTGAAATAGAAGTTCACGATCTGGAATTCAGTTCAACACAAGTTGTTGAGC | SEQ ID NO: 1115 | Homo sapiens mesoderm induction early response 1 homolog (Xenopus laevis) (MIER1), transcript variant 1, mRNA [NM_020948] |
| 248 | A_23_P306890 | POLI | TCAATAACGGAGTAAAGTAAAGTGTTCCAACATAAAGCAAGAATAGTTGCAAGAAGTAAATTCTGG | SEQ ID NO: 1116 | Homo sapiens polymerase (DNA directed) iota (POLI), mRNA [NM_007195] |
| 249 | A_23_P307940 | CAPZA2 | GTACAAGATTGGCAAAGAGATGGACAATGCATAAGACAGAAGATGCATGACCGGATGATT | SEQ ID NO: 1117 | Homo sapiens capping protein (actin filament) muscle Z-line, alpha 2 (CAPZA2), mRNA [NM_006136] |
| 250 | A_23_P308800 | GLS | CGGAAGAAGAGATAAGATAGCTGCGAAATGGTCTCTTTTGTTGGGAGAGTAAAGAAAGAAAAAACTTGC | SEQ ID NO: 1118 | Homo sapiens glutaminase C mRNA, complete cds. [AF158555] |
| 251 | A_23_P309956 | KIAA0776 | TTTTTCATTTGTGAAAATGGTCTCTTTGTTGGGACAGTAAAGAACAGTTTTATTGTTT | SEQ ID NO: 1119 | Homo sapiens KIAA0776 (KIAA0776), mRNA [NM_015323] |
| 252 | A_23_P31097 | OSTM1 | AGTGAAAATGTGCTGCGGTTTGTGTGTGTGACTGTTTATGGTGCTGGAACTTAGGACT | SEQ ID NO: 1120 | Homo sapiens osteopetrosis associated transmembrane protein 1 (OSTM1), mRNA [NM_014028] |
| 253 | A_23_P312246 | CCDC82 | GGCTTTATAACAGATGACTGTCAAGTGAATGAGCCTGTTGATATCCTGTCAGTTTAGTCAA | SEQ ID NO: 1121 | Homo sapiens coiled-coil domain containing 82 (CCDC82), mRNA [NM_024725] |
| 254 | A_23_P314191 | ZDHHC17 | TGGATACTTTTTAGGAAATAAGGAAACTTAATTGTCAGCACTGAACATGAATTACTTCCTTGG | SEQ ID NO: 1122 | Homo sapiens zinc finger, DHHC-type containing 17 (ZDHHC17), mRNA [NM_015336] |
| 255 | A_23_P314591 | NFYB | GGAGGGCATTTACTAACCAGTTACCAGCGTGGCTTAATAACGACCAGACGGTCAACAAGAAA | SEQ ID NO: 1123 | Homo sapiens nuclear transcription factor Y, beta (NFYB), mRNA [NM_006166] |
| 256 | A_23_P31671 | UQCRB | AAGGCATAAGAAGACTTCCTGAGAAGAACGTTTATAATGACAGAGGATGTTCGCATTAAGAGGG | SEQ ID NO: 1124 | Homo sapiens ubiquinol-cytochrome c reductase binding protein (UQCRB), mRNA [NM_006294] |
| 257 | A_23_P31702 | PXMP3 | CTTCTCTGTCGGCATGGTGTTTTGGCTGAATTTGTGAATTTTCTGTAGCAGTTATCAATGTCCAG | SEQ ID NO: 1125 | Homo sapiens peroxisomal membrane protein 3, 35kDa (Zellweger syndrome) (PXMP3), transcript variant 1, mRNA [NM_000318] |
| 258 | A_23_P317347 | ESCO1 | GCTAATTTTAAAAGGGGTGAACTATACTTGAAAGAAAACCCCTATAGAAAAGGAAAGCTC | SEQ ID NO: 1126 | Homo sapiens establishment of cohesion 1 homolog 1 (S. cerevisiae) (ESCO1), mRNA [NM_052911] |
| 259 | A_23_P3204 | MAPK6 | AACGTGCTCAGTTGTGTATATGGAATTTGTATTTTGGAGGTGCTTGCATCTATCTAGAAAGAA | SEQ ID NO: 1127 | Homo sapiens mitogen-activated protein kinase 6 (MAPK6), mRNA [NM_002748] |
| 260 | A_23_P324633 | C9orf72 | TTTGTTGGAATTTAGTCCCTGGGATTCAGTGTGTAGAAATGTGTAATTAGTTCTCTATAGTGC | SEQ ID NO: 1128 | Homo sapiens chromosome 9 open reading frame 72 (C9orf72), transcript variant 1, mRNA [NM_018325] |
| 261 | A_23_P325501 | MORC3 | CATGCATAAAATACTATGCTTATTGGGCATGTTTGTTGGATGAAGTATATGGCTAATTTTAAAGAGATGGC | SEQ ID NO: 1129 | Homo sapiens MORC family CW-type zinc finger 3 (MORC3), mRNA [NM_015358] |
| 262 | A_23_P327022 | MDFIC | TTATGATTTGTTAATGTAAAATGTTTTGTTGAAGATATATGGCTATCAGTGACTAAGTGGTA | SEQ ID NO: 1130 | Homo sapiens MyoD family inhibitor domain containing (MDFIC), mRNA [NM_199072] |
| 263 | A_23_P329198 | OBFC2A | ACATGTCATAAGTGGTACCGCACTTCCCGTTTTACTGTAGGGTGGATAACTCTTAGGATT | SEQ ID NO: 1131 | Homo sapiens oligonucleotide/oligosaccharide-binding fold containing 2A (OBFC2A), mRNA [NM_001031716] |
| 264 | A_23_P33045 | RPL26 | TACAAAGGTCAGACAAATTGGCAAAGTAGTCCAGGTTACAAGGCGGAAATATGTTATCTAC | SEQ ID NO: 1132 | Homo sapiens ribosomal protein L26 (RPL26), mRNA [NM_000987] |
| 265 | A_23_P332439 | NUPL1 | ATTGAAATGTTGAATGTATTGAATGTGTGTCAAGGTACAACAGCGGTGGGTTTGTAAATGTC | SEQ ID NO: 1133 | Homo sapiens KIAA0410 mRNA, partial cds. [AB007870] |
| 266 | A_23_P339490 | HAT1 | AACATGAACAGCTGAAGAGAGTTTCAGGAACTAGTGGAACATTACCGGCGTGTTATTG | SEQ ID NO: 1134 | Homo sapiens histone acetyltransferase 1 (HAT1), transcript variant 1, mRNA [NM_003642] |

Fig. 3-15

| No. | Probe ID No. | Symbols of genes | Sequence | SEQ ID NO: | Descriptions of genes (letters and numbers within [ ] indicates GenBank accession No.) |
|---|---|---|---|---|---|
| 267 | A_23_P34307 | PIGK | ATTCATTCAGAGTGTCTATTGTTGGAGGACTTACATTGTAGG AAATGTTTGCTTGG | SEQ ID NO: 1135 | Homo sapiens phosphatidylinositol glycan anchor biosynthesis, class K (PIGK), mRNA [NM_005482] |
| 268 | A_23_P347059 | MOBKL1A | CTAGAAGGGGAAAAATCATCTAAGTTATGAAATCCAAACATAGGC GGTATATTACAAAGTG | SEQ ID NO: 1136 | Homo sapiens MOB1, Mps One Binder kinase activator-like 1A (yeast) (MOBKL1A), mRNA [NM_173468] |
| 269 | A_23_P347198 | SP3 | GAGCAGGTCAAATTTAAAGAGGTTACGTTATTGTAGGTTAAAGTG TATATAACAAGTGTGG | SEQ ID NO: 1137 | Homo sapiens Sp3 transcription factor (SP3), transcript variant 1, mRNA [NM_003111] |
| 270 | A_23_P349083 | FCHO2 | GTGAAATGGTTAAAGCTCTGCACTTGTCTTAGTTACCACAGTCTT CATACCAAGTATTGGG | SEQ ID NO: 1138 | Homo sapiens FCH domain only 2 (FCHO2), mRNA [NM_138782] |
| 271 | A_23_P351467 | CMAH | GGTTACATTTGTGGATCACTACATAGGCAGAGATTCAAAAATATTT TACTTGTTCCATCGAC | SEQ ID NO: 1139 | Homo sapiens cytidine monophosphate-N-acetylneuraminic acid hydroxylase (CMP-N-acetylneuraminate monooxygenase) (CMAH) on chromosome 6 [NR_002174] |
| 272 | A_23_P353704 | RP5-1022P6.2 | TGTCTCTCACTACCTATTACACACACTGTTGCTTCGTGGTTTGTT TTGTATGTGCGTGTGT | SEQ ID NO: 1140 | Homo sapiens hypothetical protein KIAA1434 (KIAA1434), mRNA [NM_019593] |
| 273 | A_23_P354894 | ZNF567 | ACCTAAGAGTTAGCACTTCCGGTTAGGCTATAACATCAAAACGTTAG TTTTTGGATGTTTTCA | SEQ ID NO: 1141 | Homo sapiens zinc finger protein 567 (ZNF567), mRNA [NM_152603] |
| 274 | A_23_P355067 | TMCO1 | AAGTCAAGAGAACTCTTTATTTCTATCATTCTTTCTAGAGACACA CACATCAGACTGGCAA | SEQ ID NO: 1142 | Homo sapiens transmembrane and coiled-coil domains 1 (TMCO1), mRNA [NM_019026] |
| 275 | A_23_P355244 | SAMD9 | CACTGGAGAAGAATTTCGGTTGCTCTGCAATAAAATTTAAG TCCATAAGTTATAAGC | SEQ ID NO: 1143 | Homo sapiens sterile alpha motif domain containing 9 (SAMD9), mRNA [NM_017654] |
| 276 | A_23_P356122 | ZNF451 | TTTTACCTGCTTAGACTTTTATGTGTGAGTGTATGGTCTCCTGGT TAAAGGGAATGGTGTC | SEQ ID NO: 1144 | Homo sapiens zinc finger protein 451 (ZNF451), transcript variant 2, mRNA [NM_015555] |
| 277 | A_23_P356125 | KIAA1468 | GCACTGCTTTTAATTACTGGTGTATATTTGTTGATTTCGAGTT AGAAGTGTGGTGATAG | SEQ ID NO: 1145 | Homo sapiens KIAA1468 (KIAA1468), mRNA [NM_020854] |
| 278 | A_23_P357811 | MBNL1 | ATGCTTTCAAACCCTCATGACTGACAAAAACTTCCATGGGGCCAA AATCGGCTGAAGATCA | SEQ ID NO: 1146 | Homo sapiens muscleblind-like (Drosophila) (MBNL1), transcript variant 1, mRNA [NM_021038] |
| 279 | A_23_P358470 | CCDC111 | ATGAAGCGTGTATGTAAAGAGAAGCGAAGACTGTCTTTGAAGTGTGACTGTTTG CGATTACGTGCTGAAG | SEQ ID NO: 1147 | Homo sapiens coiled-coil domain containing 111 (CCDC111), mRNA [NM_152683] |
| 280 | A_23_P364107 | C14orf106 | AAGGAGACAGATTCGTATTTTCAACGTGGAGTACATGTATTTTCT TTGTAAAGTAAGCTTCC | SEQ ID NO: 1148 | Homo sapiens chromosome 14 open reading frame 106 (C14orf106), mRNA [NM_018353] |
| 281 | A_23_P36776 | PUS7L | GGGCTTGACTTCAACATCGTGTTAAAATGGGCACATGTTAAGCATTGG CTACCTCATAGGATTA | SEQ ID NO: 1149 | Homo sapiens pseudouridylate synthase 7 homolog (S. cerevisiae)-like (PUS7L), mRNA [NM_031292] |
| 282 | A_23_P371266 | DNM3 | ACTGTGTTCTTGGCACTTTCAGGATTTCTTAATGCTGATATATG GACTCTTAAGAATGGAA | SEQ ID NO: 1150 | Homo sapiens dynamin 3 (DNM3), mRNA [NM_015569] |
| 283 | A_23_P37275 | CGRRF1 | GAGGAAGATAAAAGAAGCGGAAAGACTGTCTTTGAAGAGACATGGTAA CAGTGAAAAGTAGACT | SEQ ID NO: 1151 | Homo sapiens cell growth regulator with ring finger domain 1 (CGRRF1), mRNA [NM_006568] |
| 284 | A_23_P37441 | B2M | TTGCTTTCTTCAGGAAGGACTGGTCTTTCTATCTCTTGTACTACAC TGAATTCAGGGGCACT | SEQ ID NO: 1152 | Homo sapiens beta-2-microglobulin (B2M), mRNA [NM_004048] |
| 285 | A_23_P37636 | FAM96A | CTTGAACCTGACTAGATAGGTGTTTTAAAGAGGCCACTGGGCTGTAA TTGTTTGATATATTTG | SEQ ID NO: 1153 | Homo sapiens family with sequence similarity 96, member A (FAM96A), transcript variant 1, mRNA [NM_032231] |

Fig. 3-16

| No. | Probe ID No. | Symbols of genes | Sequence | SEQ ID NO: | Descriptions of genes (letters and numbers within [ ] indicates GenBank accession No.) |
|---|---|---|---|---|---|
| 286 | A_23_P38275 | THC2504576 | TCTCGCCAAAATGAAGTTTAATGGCTTTGTGAGTTCGACCGAAGGAAGAATGGCAAAAG | SEQ ID NO: 1154 | Homo sapiens (P61257) 60S ribosomal protein L26, complete [THC2504576] |
| 287 | A_23_P384056 | CCDC14 | TAGGTCAGTATGCATCTTCGCTTCATGTAAGCAGCACGTTTTAACTGTTAGAAGGTGAATG | SEQ ID NO: 1155 | Homo sapiens coiled-coil domain containing 14 (CCDC14), mRNA [NM_022757] |
| 288 | A_23_P390734 | FGFR1OP2 | CCACCAGAATACAGAAGTGCTTAACATCAGTTGAAAACTAAATTTTCTTATGTGTGAG | SEQ ID NO: 1156 | Homo sapiens FGFR1 oncogene partner 2 (FGFR1OP2), mRNA [NM_015633] |
| 289 | A_23_P394276 | RWDD4A | TTGTTCAGGCTTATTATGGCTCATAGATTACAGAGAAATGGTAGTTACATGGCAATGA | SEQ ID NO: 1157 | Homo sapiens RWD domain containing 4A (RWDD4A), mRNA [NM_152682] |
| 290 | A_23_P394605 | SEC24A | GATTTATTTCTCTAATCAAAGATGCATAACAGCTATTATGTAGGGGAGGACCAAAATGTG | SEQ ID NO: 1158 | Homo sapiens SEC24 related gene family, member A (S. cerevisiae) (SEC24A), mRNA [NM_021982] |
| 291 | A_23_P396353 | NIN | ATCTTGCAGTGTGTAGTATTTTAATAATGCACTATTACCCAGGGCAGATATTATGAGAAAC | SEQ ID NO: 1159 | Homo sapiens ninein (GSK3B interacting protein) (NIN), transcript variant 2, mRNA [NM_020921] |
| 292 | A_23_P398073 | PPM1B | GGTTCAGTAAGTTTCATTTATAAACATTGGGCACGGTACAGAGTGATTGTCACATAAGG | SEQ ID NO: 1160 | Homo sapiens protein phosphatase 1B (formerly 2C), magnesium-dependent, beta isoform (PPM1B), transcript variant 2, mRNA [NM_177968] |
| 293 | A_23_P40059 | PMS1 | GATCCTGCTCTTACACGCAATGGTTCAAGATAAAATTGATAGGAGGAGTTTGAATTAGT | SEQ ID NO: 1161 | Homo sapiens PMS1 postmeiotic segregation increased 1 (S. cerevisiae) (PMS1), mRNA [NM_000534] |
| 294 | A_23_P405873 | C9orf72 | GAGAAGTAAGGAAGATCAGGTCCAGACTGTTCAAGATAAATTTCCAATGCTTACGTGGAGAAGTGATTGTGT | SEQ ID NO: 1162 | Homo sapiens chromosome 9 open reading frame 72 (C9orf72), transcript variant 2, mRNA [NM_145005] |
| 295 | A_23_P408455 | SLC25A36 | CCATTAAGCTACACACTGATTTTATGCTAGTCGTTGTAGAAAAGAAAATTCTGGTTTGAC | SEQ ID NO: 1163 | Homo sapiens mRNA; cDNA DKFZp564C053 (from clone DKFZp564C053). [AL049246] |
| 296 | A_23_P41114 | CSTA | AAACAAATAGAGAGTTGTGGTTGGAAAAATTGGAAGGGTGTGCAGATATAAAACTCAAGTTGTTGCTG | SEQ ID NO: 1164 | Homo sapiens cystatin A (stefin A) (CSTA), mRNA [NM_005213] |
| 297 | A_23_P413796 | CCDC5 | GCATGGATGCTTGTGTGTGCATCAGTCGTTAGTAGCACTATCAGAGAAACTGGCAAGAT | SEQ ID NO: 1165 | Homo sapiens coiled-coil domain containing 5 (spindle associated) (CCDC5), mRNA [NM_138443] |
| 298 | A_23_P41470 | FLJ20035 | TGTCCGTTAATGGCTATGGCACTGGATTTCTACAAACATGGTTCCTTGATAGGATTAGGCC | SEQ ID NO: 1166 | Homo sapiens hypothetical protein FLJ20035 (FLJ20035), mRNA [NM_017631] |
| 299 | A_23_P41512 | C4orf15 | TAAGGCTGTTAGTCTTGAAGATTGAAAATTACTGAAAACTGAATCTTTATTACGTGTCGT | SEQ ID NO: 1167 | Homo sapiens chromosome 4 open reading frame 15 (C4orf15), mRNA [NM_024511] |
| 300 | A_23_P41645 | ELL2 | TGTCTTTTCAAAGTGCTGCCAGTTGAAAAGGGAAGCATTATGTTTACAAATCTGTTTTGA | SEQ ID NO: 1168 | Homo sapiens elongation factor, RNA polymerase II, 2 (ELL2), mRNA [NM_012081] |
| 301 | A_23_P41664 | ENST00000334994 | TGGCTTGGAGCAGATTCGACTTCATAAACAAATTGTTCCTGAAAATGAGGCACAGGTCAT | SEQ ID NO: 1169 | Syndeurin [Source:Uniprot/SPTREMBL;Acc:Q7Z207] [ENST00000334994] |
| 302 | A_23_P421563 | LSM3 | CATAAGAGAAAAGCTGGCATAGATTTTGATATTAAGAAAATAATTCCGGGGGATTGTTCCACTC | SEQ ID NO: 1170 | Homo sapiens LSM3 homolog, U6 small nuclear RNA associated (S. cerevisiae) (LSM3), mRNA [NM_014463] |
| 303 | A_23_P422083 | TMEM55A | AAATTTATGGAATCAAGGTCTGCCACTGCGCCATGTTCAGTTTTGAAAAGAAATTGCTT | SEQ ID NO: 1171 | Homo sapiens transmembrane protein 55A (TMEM55A), mRNA [NM_018710] |
| 304 | A_23_P422794 | NSMCE2 | CATTGTTCGCATGATTGAGTCCAGGCAAAAGGGGAAGAAAAAGGCCTATTTGGGCTCGAAAT | SEQ ID NO: 1172 | Homo sapiens non-SMC element 2, MMS21 homolog (S. cerevisiae) (NSMCE2), mRNA [NM_173685] |

Fig. 3-17

| No. | Probe ID No. | Symbols of genes | Sequence | SEQ ID NO: | Descriptions of genes (letters and numbers without [ ] indicates GenBank accession No.) |
|---|---|---|---|---|---|
| 305 | A_23_P428468 | ENST00000369577 | AAACCTAGGGTCAGTTGGAAAAAACTTGAAGTAGATTCAAATGATCCAGATATGTCTGTT | SEQ ID NO: 1173 | Zinc finger protein 292 [Source:Uniprot/SWISSPROT:Acc:Q60281] [ENST00000369577] |
| 306 | A_23_P429491 | FLJ25416 | GGTTGGTCAGCTGAATTGTTTCATAAAAAGTCACCTGAACCCAATTGGTGAACTTTTAA | SEQ ID NO: 1174 | Homo sapiens hypothetical protein FLJ25416 (FLJ25416), mRNA [NM_145019] |
| 307 | A_23_P429975 | PRKAR2B | GCCACATTTTTAGAAGACAGTGTTTAACATTTTTGGAAAACCTTGTTGTAGGAAAAGAGAGG | SEQ ID NO: 1175 | Homo sapiens protein kinase, cAMP-dependent, regulatory, type II, beta (PRKAR2B), mRNA [NM_002736] |
| 308 | A_23_P430161 | EXOC8 | AAGTACAGGATTTTCTTCAGGTAAAATGCTGTGTGTTCGAATTACAGTTGTAGCTGAAGGA | SEQ ID NO: 1176 | Homo sapiens exocyst complex component 8 (EXOC8), mRNA [NM_175876] |
| 309 | A_23_P434809 | S100A8 | AAAGCCATGAAGAAAGGACACAAAGAAGTAGCTGAGTTACTGGGCCCAGAGGCTGGGCCCCT | SEQ ID NO: 1177 | Homo sapiens S100 calcium binding protein A8 (S100A8), mRNA [NM_002964] |
| 310 | A_23_P443946 | CIP29 | AAAGAGGAGAGCCTTTGGGATTGCCTGATGAAAAGTTCGTGATAGTTCTCTGTTCTCCAG | SEQ ID NO: 1178 | Homo sapiens cytokine induced protein 29 kDa (CIP29), mRNA [NM_033082] |
| 311 | A_23_P44257 | COMMD8 | ACATTTTACTTCTGTGGCCTTGTATGTTTGGAAACAATTGGTCTGATAAAAATAGGTGTG | SEQ ID NO: 1179 | Homo sapiens COMM domain containing 8 (COMMD8), mRNA [NM_017345] |
| 312 | A_23_P4462 | A_23_P4462 | GGTCTCGAAAAGCAGGGAATACCATATTTTCGGGATTAGGGGTTATTAAGGTCTGTATA | SEQ ID NO: 1180 | |
| 313 | A_23_P44768 | TBK1 | TCTAGTCTGAGTGGGCTAAATAAGTTATTTTCTGACGGCTACTGGAAATATTTTTA | SEQ ID NO: 1181 | Homo sapiens TANK-binding kinase 1 (TBK1), mRNA [NM_013254] |
| 314 | A_23_P44974 | MRPL13 | ATGGGTAAAACAAGTCGTACAGTCAGGACCTGTTTATGTGCCGAATCAGTGTGGGGA | SEQ ID NO: 1182 | Homo sapiens mitochondrial ribosomal protein L13 (MRPL13), nuclear gene encoding mitochondrial protein, mRNA [NM_014078] |
| 315 | A_23_P46396 | PTBP2 | AACCAGGTGGGACCAAAGTTTATGTGCCTTAATTTTCAGTCAGGAAGACGTTGCATTGTAATTAT | SEQ ID NO: 1183 | Homo sapiens polypyrimidine tract binding protein 2 (PTBP2), mRNA [NM_021190] |
| 316 | A_23_P48166 | TWF1 | TGGAGGAGGACCATAGGTGAAGCTGTTATTTCAGTCAGGAAGACTACCTGTCGATGAAGGT | SEQ ID NO: 1184 | Homo sapiens twinfilin, actin-binding protein, homolog 1 (Drosophila) (TWF1), mRNA [NM_002822] |
| 317 | A_23_P48897 | CCPG1 | AAGTCAGGAGGAGGCTCATATATAATTCTAATGTCAGACTAAGACATTCTGCATTCCAGTACCA | SEQ ID NO: 1185 | Homo sapiens cell cycle progression restoration 3 protein (CCPG1), mRNA complete cds. [AF011794] |
| 318 | A_23_P501080 | ZNF92 | GAATATTAAGTGCTACTTGAGGTAGCATGGTCAGAGTAAGACATTCTTTGCAGTATAGTCAG | SEQ ID NO: 1186 | Homo sapiens zinc finger protein 92 (ZNF92), transcript variant 1, mRNA [NM_007139] |
| 319 | A_23_P50195 | A_23_P50195 | CCTCACAAGTGTGATGATTGTGGGGAAGGTTTAGTTCATGTTGACCGGTCTTAGAGATC | SEQ ID NO: 1187 | |
| 320 | A_23_P502425 | MRPL47 | GTTCGACATCTTGCTGAAGCCAAAAGTCAAGTCTGTGTAAGATGCTGAACTATTAA | SEQ ID NO: 1188 | Homo sapiens mitochondrial ribosomal protein L47 (MRPL47), nuclear gene encoding mitochondrial protein, transcript variant 1, mRNA [NM_020409] |
| 321 | A_23_P502797 | WDFY1 | GTAACAGTTTACTTGGTTGTTCCATTCGTGAATATGCAGGCTAATTTGTACAGATAGGGAT | SEQ ID NO: 1189 | Homo sapiens WD repeat and FYVE domain containing 1 (WDFY1), mRNA [NM_020830] |
| 322 | A_23_P502832 | RBM12 | CTGGCAGTTCTATAGTAGTGGAGACTTAGAAACCAAACACAACAAAATGGCTTGTTGCC | SEQ ID NO: 1190 | Homo sapiens RNA binding motif protein 12 (RBM12), transcript variant 1, mRNA [NM_006047] |
| 323 | A_23_P50907 | ITGAV | AAAGAGTGATTAAGTGAGGTATTACCCCTAAATGGTCCATTCTGCATTGTATTTCAGG | SEQ ID NO: 1191 | Homo sapiens integrin, alpha V (vitronectin receptor, alpha polypeptide, antigen CD51) (ITGAV), mRNA [NM_002210] |

Fig. 3-18

| No. | Probe ID No. | Symbols of genes | Sequence | SEQ ID NO. | Descriptions of genes (letters and numbers within [ ] indicates GenBank accession No.) |
|---|---|---|---|---|---|
| 324 | A_23_P51009 | NDUFB3 | CCGCAATGAAGGTTGGAGAGATACATGGGTGCCTTTGCAAAGAGTGTTTCCTTTCTGATGT | SEQ ID NO: 1192 | Homo sapiens NADH dehydrogenase (ubiquinone) 1 beta subcomplex, 3, 12kDa (NDUFB3), mRNA [NM_002491] |
| 325 | A_23_P51317 | CCDC76 | CCGTTGTTGTTATAAGTTTATGTCAAGTAAGGTAGTTGTTTAAGTTAGTTACCCATGTGGG | SEQ ID NO: 1193 | Homo sapiens coiled-coil domain containing 76 (CCDC76), mRNA [NM_019083] |
| 326 | A_23_P51487 | GBP3 | AATGGTAAAGCATAAGTTAGTCTTTTGGTGATTGTTAAAGGTCATACTGAAATCCTGGG | SEQ ID NO: 1194 | Homo sapiens guanylate binding protein 3 (GBP3), mRNA [NM_018284] |
| 327 | A_23_P53666 | NFYB | TGGGTCATATTGTGCATACCATTTGTAACCTGCTTTTTCACTTAACAATATATTGGG | SEQ ID NO: 1195 | Homo sapiens nuclear transcription factor Y, beta (NFYB), mRNA [NM_006166] |
| 328 | A_23_P53957 | C14orf112 | TTATACTTCCGAGGTATTGGATCGTGTGGATGAAAGTAAGAATGTTGGGCAGCTATATTTT | SEQ ID NO: 1196 | Homo sapiens chromosome 14 open reading frame 112 (C14orf112), mRNA [NM_016468] |
| 329 | A_23_P5611 | RIF1 | ATGTATTCTTGGCTGCTGATGCGTGGTTTTCAGGAAATTTAATATCTTACTGAGATGTG | SEQ ID NO: 1197 | Homo sapiens RAP1 interacting factor homolog (yeast) (RIF1), mRNA [NM_018151] |
| 330 | A_23_P56380 | ZC3H15 | GTGCAAGCCAAGATAGGTAAGGAAGTGTATCTGGGTTCCATCTTTCTTGGTTTCATTTGGGCATGTGG | SEQ ID NO: 1198 | Homo sapiens zinc finger CCCH-type containing 15 (ZC3H15), mRNA [NM_018471] |
| 331 | A_23_P56734 | HNMT | CCTTTTGTGCACCATGGATATATCTGACTGCTTTATTGAATGGTAATGAAAATGGAGACCT | SEQ ID NO: 1199 | Homo sapiens histamine N-methyltransferase (HNMT) transcript variant 1, mRNA [NM_006895] |
| 332 | A_23_P56759 | KRCC1 | GATATCCGTGTTGATAGGAGTTTTCTTATGTGTAAGGTTGTTTAAGTTGTAACAAAGGC | SEQ ID NO: 1200 | Homo sapiens lysine-rich coiled-coil 1 (KRCC1), mRNA [NM_016161] |
| 333 | A_23_P58877 | GOPC | AAGGTTCATGTGATTCATGTGTAAGAATGCACAGTATTTGAGATCCTGATTATGTAATCC | SEQ ID NO: 1201 | Homo sapiens golgi associated PDZ and coiled-coil motif containing (GOPC), transcript variant 1, mRNA [NM_020399] |
| 334 | A_23_P58898 | CASP8AP2 | ATCTATTTGTTATTACTGAGTGAGTCTGTAATTTCAGATCACCATGTTCAGCTTGTGC | SEQ ID NO: 1202 | Homo sapiens CASP8 associated protein 2 (CASP8AP2), mRNA [NM_012115] |
| 335 | A_23_P59912 | SLC35A1 | ATGATCAGTGCGGTATATGTGCAAACAACAACAAACAAACAAGAAGCTATCTGAGTGAAGTGG | SEQ ID NO: 1203 | Homo sapiens solute carrier family 35 (CMP-sialic acid transporter), member A1 (SLC35A1), mRNA [NM_006416] |
| 336 | A_23_P59637 | DOCK4 | TTTGGGAGTGCAGCAGTTGAAATTGTTGAATTTATCATGTGTGTGTGTATTCTGAAGGAG | SEQ ID NO: 1204 | Homo sapiens dedicator of cytokinesis 4 (DOCK4), mRNA [NM_014705] |
| 337 | A_23_P59921 | SUB1 | CAGAATTGGGAAAATGAGGGTACGTTAGTGTTGGGGATTTTAAGGCAAAGTGCTAATTGAT | SEQ ID NO: 1205 | Homo sapiens SUB1 homolog (S. cerevisiae) (SUB1), mRNA [NM_006713] |
| 338 | A_23_P60565 | ZNF354A | AAACCAAAGCTCATCCGAAGAATACAATCCTTGAGAGAGATGTAATAAATGTAATGGATGTG | SEQ ID NO: 1206 | Homo sapiens zinc finger protein 354A (ZNF354A), mRNA [NM_005649] |
| 339 | A_23_P61674 | CLK4 | GAAAGTAGGTGCAGTTTGTGCATTGTGACAGTTTGTTAATAAACCAGACACACCTTA | SEQ ID NO: 1207 | Homo sapiens CDC-like kinase 4 (CLK4), mRNA [NM_020666] |
| 340 | A_23_P62890 | GBP1 | CAAAGATGCATTTAGCTGTATGTCAACTCAGGAAATGTCATAAGCTGGTACCACTCAGGA | SEQ ID NO: 1208 | Homo sapiens guanylate binding protein 1, interferon-inducible, 67kDa (GBP1), mRNA [NM_002053] |
| 341 | A_23_P63190 | NRAS | ATGAAGTCTGAGATGCTGAGATACGTCGTGTGACCTAGTCCAACATTACCTTTGAGATGAAAGCTATATCTATTGG | SEQ ID NO: 1209 | Homo sapiens neuroblastoma RAS viral (v-ras) oncogene homolog (NRAS), mRNA [NM_002524] |
| 342 | A_23_P63205 | DR1 | TCCAACTAGAATGGCCTAGAGTCCAACATTACCTTTGAGATGACATTATGTCTCGATA | SEQ ID NO: 1210 | Homo sapiens down-regulator of transcription 1, TBP-binding (negative cofactor 2) (DR1), mRNA [NM_001938] |

Fig. 3-19

| No. | Probe ID No. | Symbols of genes | Sequence | SEQ ID NO: | Descriptions of genes (letters and numbers within [ ] indicates GenBank accession No.) |
|---|---|---|---|---|---|
| 343 | A_23_P63343 | UTS2 | AGAATCTGGAAACCATAAGAGAAACGTGAGACTCCTGATTGTTCTGGAAATACTGTGTC | SEQ ID NO: 1211 | Homo sapiens urotensin 2 (UTS2), transcript variant 1, mRNA [NM_021995] |
| 344 | A_23_P63655 | ATP5C1 | AGAGAGGTGAAACCAGCTCGAATATATGGATCTTTAGCTCTGTATGAAAAAGCT | SEQ ID NO: 1212 | Homo sapiens ATP synthase, H+ transporting, mitochondrial F1 complex, gamma polypeptide 1 (ATP5C1), nuclear gene encoding mitochondrial protein, transcript variant 2, mRNA [NM_005174] |
| 345 | A_23_P63789 | ZWINT | TCAAAGAATTCAGAGATTGGCTTTTGTGATCGACTACTATTGTATGTTTTGTTCATTGACCTC | SEQ ID NO: 1213 | Homo sapiens ZW10 interactor (ZWINT), transcript variant 4, mRNA [NM_001005414] |
| 346 | A_23_P63896 | FAS | ATGCTATCCACAGGGTAAGCGGCAGTGTATGAATCAATACAAGAAGGTATGAGGTTTTGC | SEQ ID NO: 1214 | Homo sapiens Fas (TNF receptor superfamily, member 6) (FAS), transcript variant 1, mRNA [NM_000043] |
| 347 | A_23_P65262 | RP11-298P3.3 | AGGCAAGAGCTTAAGAAGCACTGACTACCGTTCCGTTGAGGCTACCATTATCACAAGGGTTT | SEQ ID NO: 1215 | Human BRCA2 region, mRNA sequence CG016 [U50529] |
| 348 | A_23_P65768 | C15orf15 | TGGTGCATTGCCATCTACATAATATCAGATATACGGATGTTAGATTGCATCTCAGTGTT | SEQ ID NO: 1216 | Homo sapiens chromosome 15 open reading frame 15 (C15orf15), mRNA [NM_016304] |
| 349 | A_23_P66260 | ZNF267 | TGTGATGAATGTGGTAAACGTTCAGGCTATAGCTCACACACATCGGAGAAGT | SEQ ID NO: 1217 | Homo sapiens zinc finger protein 267 (ZNF267), transcript variant 498723, mRNA [NM_003414] |
| 350 | A_23_P67992 | C1D | AATGAATAATGAGCTTATGAAGTAATGGCTATCATGTAGGCTGAAATTATAGGTACATCTGTT | SEQ ID NO: 1218 | Homo sapiens nuclear DNA-binding protein (C1D), transcript variant 1, mRNA [NM_006333] |
| 351 | A_23_P68472 | DPM1 | CTATTGGGGAGGTCGAGTTCCAATATCATTGTGGATCGTGTTTTATGGTGAATCCAAGTTGGGAG | SEQ ID NO: 1219 | Homo sapiens dolichyl-phosphate mannosyltransferase polypeptide 1, catalytic subunit (DPM1), mRNA [NM_003859] |
| 352 | A_23_P69791 | C4orf16 | GGCTCCATTGATTTTATTAAGGGTTGGCTTTACGTTGTAGTACGAAATGGATTATTGCATTT | SEQ ID NO: 1220 | Homo sapiens chromosome 4 open reading frame 16 (C4orf16), mRNA [NM_018569] |
| 353 | A_23_P69908 | GLRX | CTGAATAAAACTTACAGGCGCCCTAGAGACAAGAGTGTATCGTGAAAGAGGCTGAGAGTT | SEQ ID NO: 1221 | Homo sapiens glutaredoxin (thioltransferase) (GLRX), mRNA [NM_002064] |
| 354 | A_23_P70047 | MATR3 | GCAACAGACAGAAGTAGTTGTAGAGATTGAGTTCCTAAGCTACTTAAGACAAGTTGCAC | SEQ ID NO: 1222 | Homo sapiens matrin 3 (MATR3), transcript variant 1, mRNA [NM_199189] |
| 355 | A_23_P70318 | ENPP4 | TGTTTTTGGATGTCTCCTTCTTGTGCCCATATCTGATAAGCTTTATGGATTATTGCATTT | SEQ ID NO: 1223 | Homo sapiens ectonucleotide pyrophosphatase/phosphodiesterase 4 (putative function) (ENPP4), mRNA [NM_014936] |
| 356 | A_23_P70328 | CENPQ | GAATTGGCTTAGAGTTTCGTCTGAAATCCCAAATTCTTGGGTGAAAAGAATATATCCCTCAAATGCTTCAC | SEQ ID NO: 1224 | Homo sapiens centromere protein Q (CENPQ), mRNA [NM_018132] |
| 357 | A_23_P7066 | RPL9 | GGTCTGCTTGTTGAAATCCAAAGTTCTTGGGTGAACTTTCGGATGA | SEQ ID NO: 1225 | Homo sapiens ribosomal protein L9 (RPL9), transcript variant 1, mRNA [NM_000661] |
| 358 | A_23_P70938 | STARD3NL | GGATTATGTGTATGGGCTCAAGTGTTGGACTTGCAAAAGGGGAAGAAAGGAATTGGGAAT | SEQ ID NO: 1226 | Homo sapiens STARD3 N-terminal like (STARD3NL), mRNA [NM_032016] |
| 359 | A_23_P71433 | UBE2W | CATGAGCCGTACTGCCTAAACACTATTCATTTATTATGTTTGGAAACCCCGTAAACAT | SEQ ID NO: 1227 | Homo sapiens ubiquitin-conjugating enzyme E2W (putative) (UBE2W), transcript variant 1, mRNA [NM_001001481] |
| 360 | A_23_P71727 | CKS2 | GATAAAAGTTCTTCCAGTTCAGTTTTTGTTAAGTGCCTCTTTGAGTTTAGTTAGTGAAACAGT | SEQ ID NO: 1228 | Homo sapiens CDC28 protein kinase regulatory subunit 2 (CKS2), mRNA [NM_001827] |

Fig. 3-20

| No. | Probe ID No. | Symbols of genes | Sequence | SEQ ID NO: | Descriptions of genes (letters and numbers within [ ] indicates GenBank accession No.) |
|---|---|---|---|---|---|
| 361 | A_23_P72503 | KLHL2 | TTTTTGATATTTAACAATGCTTAACACTTTAAATGGCAGTTCTG AGGAATGGCACCTGGTG | SEQ ID NO:1229 | Homo sapiens kelch-like 2, Mayven (Drosophila) (KLHL2), mRNA [NM_007246] |
| 362 | A_23_P72568 | SNX4 | AAGTCAGTAATGAGCCTAAATTACTCTGGTGGTGTGCTACA CATGCATTTCAGGGT | SEQ ID NO:1230 | Homo sapiens sorting nexin 4 (SNX4), mRNA [NM_003794] |
| 363 | A_23_P72282 | ELMOD2 | TTCAACTAGCTTTCTCTGGGGGAAAAGTACCACTTGGACATT AAAGGAATTGGGATTT | SEQ ID NO:1231 | ELM0 domain-containing protein 2 [Source:Uniprot/SWISSPROT;Acc:Q8IZ81] [ENST00000323570] |
| 364 | A_23_P73114 | PROS1 | CCAGAAGAAATTTTAACAAAAGGACAAGCCAGAGAGGATATAGT GAATATGGTATGCATTG | SEQ ID NO:1232 | Homo sapiens protein S (alpha) (PROS1), mRNA [NM_000313] |
| 365 | A_23_P73577 | DYNLT3 | TGTTTCTTTATGCTGGCTGGCTTTTGTGCCCTGGAAGATCATAAT AGTGAGGAAAATATAC | SEQ ID NO:1233 | Dynein light chain Tctex-type 3 (T-complex-associated testis-expressed 1-like) (Protein 91/23). [Source:Uniprot/SWISSPROT;Acc:P51808] [ENST00000378578] |
| 366 | A_23_P73835 | MOSPD1 | TATGTGGAGATGATTTTCACCTTTAAACTGTAAGGCAAGTGTA AGAAACTCTGATAGC | SEQ ID NO:1234 | Homo sapiens motile sperm domain containing 1 (MOSPD1), mRNA [NM_019556] |
| 367 | A_23_P74001 | S100A12 | TGAAGGGTTTTTACCCAGCAATGTCCTCAATGAAGGGTCTTTTCT TTCCCTCACCAAAACC | SEQ ID NO:1235 | Homo sapiens S100 calcium binding protein A12 (S100A12), mRNA [NM_005621] |
| 368 | A_23_P74799 | SLC25A24 | GATTCTGTATCTTTTGGAAAAAAGCCGAGAGTTGAAGATAGTAT ATTTCTGGTAGTACTG | SEQ ID NO:1236 | Homo sapiens solute carrier family 25 (mitochondrial carrier; phosphate carrier), member 24 (SLC25A24), transcript variant 2, mRNA [NM_213651] |
| 369 | A_23_P7543 | ZFYVE16 | TCTGCCTCAGCATTATCTAATGATCTTGATAGTGCTCTGATAC CTGTGATCCATGGTGG | SEQ ID NO:1237 | Homo sapiens zinc finger, FYVE domain containing 16 (ZFYVE16), mRNA [NM_014733] |
| 370 | A_23_P76159 | EEA1 | TATTGTCTTAGACTTGTGATCATTGATGTAGTTGTGCCTTACTTTG TGAAAAGGTTAGCTC | SEQ ID NO:1238 | Homo sapiens early endosome antigen 1 (EEA1), mRNA [NM_003566] |
| 371 | A_23_P76480 | BF213736 | AAATCCAACAGGACAATGGGTAGATGGAGCTACATTACCAAAT CGTTTGGGATGACAGG | SEQ ID NO:1239 | BF213736 601847628F1 NIH_MGC_55 Homo sapiens cDNA clone IMAGE:4078519 5., mRNA sequence [BF213736] |
| 372 | A_23_P76598 | EFHA1 | AAAGTACTTGAGACGAAAGGGAGGATCAATTCCAGACATCTTCA TGTTGGTAATAGGCTA | SEQ ID NO:1240 | Homo sapiens EF-hand domain family, member A1 (EFHA1), mRNA [NM_152726] |
| 373 | A_23_P76799 | BAZ1A | TACACATGAATGAATGAATCCAATCTTATAACCTTGAAGTGCTGTACC AGTGCTGCGTGCAGGT | SEQ ID NO:1241 | Homo sapiens bromodomain adjacent to zinc finger domain, 1A (BAZ1A), transcript variant 1, mRNA [NM_013448] |
| 374 | A_23_P76951 | TXNDC1 | ATTTCTGTAATGTCCCCTTCTTCTAGGGTCTGTTGGTGTGTGA ATCCATTAGATTTACA | SEQ ID NO:1242 | Homo sapiens thioredoxin domain containing 1 (TXNDC1), mRNA [NM_030755] |
| 375 | A_23_P78018 | ABCA5 | ACTGGAGAACCAAGAAGGAGTTGAAATTTTCTAAGCTCCTTA ATTGAAAATGGTGTGGT | SEQ ID NO:1243 | Homo sapiens ATP-binding cassette, sub-family A (ABC1), member 5 (ABCA5), transcript variant 1, mRNA [NM_018672] |
| 376 | A_23_P78092 | EVI2A | GCTGAATCAGACACTTGGAAAAGAACAAAACAGCTCACAGGACC CAACCTAGTGATGCAA | SEQ ID NO:1244 | Homo sapiens ecotropic viral integration site 2A (EVI2A), transcript variant 1, mRNA [NM_001003927] |

Fig. 3-21

| No. | Probe ID No. | Symbols of genes | Sequence | SEQ ID NO: | Descriptors of genes (letters and numbers within [ ] indicates GenBank accession No.) |
|---|---|---|---|---|---|
| 377 | A_23_P79199 | DBI | TGGTCAACGATAGGGGTGTAACAGATTAGGGGGTAAAAGGATTAGTGACTTCCTTGAGTA | SEQ ID NO: 1245 | Homo sapiens diazepam binding inhibitor (GABA receptor modulator, acyl-Coenzyme A binding protein) (DBI), transcript variant 1, mRNA [NM_020548] |
| 378 | A_23_P81212 | MRPS18C | ATGGGGTTTATGCAGTTACATACAAGGATCCTGCATATCTCAAGGACCGCTAAAGTTTGT | SEQ ID NO: 1246 | Homo sapiens mitochondrial ribosomal protein S18C (MRPS18C), nuclear gene encoding mitochondrial protein, mRNA [NM_016067] |
| 379 | A_23_P81248 | TAF7 | TGGGTAGTTGGAATATGTTTCGTATGAATAGTGTTTTGGGAGTTATTCAAAGCAGCTT | SEQ ID NO: 1247 | Homo sapiens TAF7 RNA polymerase II, TATA box binding protein (TBP)-associated factor, 55kDa (TAF7), mRNA [NM_005642] |
| 380 | A_23_P82947 | BU507302 | TCTGTTTGGTTAATGTCAGCTGGCTTGAACATTCAGCAGTTTATAAATTGGTTAATTTGTC | SEQ ID NO: 1248 | AGENCOURT_10309688 NIH_MGC_71 Homo sapiens cDNA clone IMAGE:6901220 5', mRNA sequence [BU507302] |
| 381 | A_23_P6241 | FBX05 | GATAGCAACAGAAATATCAACTTCTGGAGTCTATTAAATGTGTTGTCAGCTTCTAAAGC | SEQ ID NO: 1249 | Homo sapiens F-box protein 5 (FBXO5), mRNA [NM_012177] |
| 382 | A_23_P83175 | PTPLAD2 | CATCCTTTTTGTGGTGATCACCAGTCAAGAGGAAGTCAAGAGACGAAGATGCAAGAGAAATATGGGTGTGT | SEQ ID NO: 1250 | Homo sapiens protein tyrosine phosphatase-like A domain containing 2 (PTPLAD2), mRNA [NM_0010109151] |
| 383 | A_23_P83278 | CHMP5 | CATTGCTCTTTATTTTTCCATTAAGGAGCTCATTGCTTGGGAAATGGTTCTTGGTAG | SEQ ID NO: 1251 | Homo sapiens chromatin modifying protein 5 (CHMP5), mRNA [NM_016410] |
| 384 | A_23_P84070 | LARP7 | TGATTTGCTAGAAGGGGATACAGGAATTGCCATGCTAGATTTAAGACTCCTGAGGATGCTCA | SEQ ID NO: 1252 | Homo sapiens La ribonucleoprotein domain family, member 7 (LARP7), transcript variant 1, mRNA [NM_016648] |
| 385 | A_23_P86653 | SRGN | AGGAGTTGGGTCAACATGGATTCAGTGGTGCCTAATGACTCTCTATTAGGAAATATTCTGAAGAGGATTTCCCAC | SEQ ID NO: 1253 | Homo sapiens serglycin (SRGN), mRNA [NM_002727] |
| 386 | A_23_P87769 | C12orf48 | GTAAGAAATATGTCAGTGCTCCTAATGACTCTCTATTAGGAAATATTCTGGCATATACTTCTGTTT | SEQ ID NO: 1254 | Homo sapiens chromosome 12 open reading frame 48 (C12orf48), mRNA [NM_017915] |
| 387 | A_23_P87879 | CD69 | TGTGCAATATGTCATGTGCGGCAAATCTCTATTAGGAAATATTCTGTAATCTTCAGACCTAG | SEQ ID NO: 1255 | Homo sapiens CD69 molecule (CD69), mRNA [NM_001781] |
| 388 | A_23_P89145 | ZNF83 | GTATAATGAATGCATAGTGAGGAGGCATTTCTTGTTTTTTGTTCAAGGGTTAATAAGGCGGTTAGGCTAGA | SEQ ID NO: 1256 | Homo sapiens zinc finger protein 83 (ZNF83), mRNA [NM_018300] |
| 389 | A_23_P89755 | RNF138 | GTGACGGTGATATAGTGAGAAAGATTCTACCAACCACTGTTTCAGTAAGCGGTTAGGTAA | SEQ ID NO: 1257 | Homo sapiens ring finger protein 138 (RNF138), transcript variant 1, mRNA [NM_016271] |
| 390 | A_23_P89921 | ZNF180 | AGTGCATCATTTTACTACATAGATCTTCCAATTAGATAGCTTGTAATGTGTTCAGAGG | SEQ ID NO: 1258 | Homo sapiens zinc finger protein 180 (ZNF180), mRNA [NM_013256] |
| 391 | A_23_P9056 | RB1CC1 | TTCATTTCAAAGGGAGCATACCTTGTGCATTGGCATTGATGAGGGATATTAATTGG | SEQ ID NO: 1259 | Homo sapiens RB1-inducible coiled-coil 1 (RB1CC1), mRNA [NM_014781] |
| 392 | A_23_P91346 | BC008667 | GGGCTTAGGAGTGAGATTCTGGTTGGTACAGAAATGATCATGCTCATGAATTTTCAGATTT | SEQ ID NO: 1260 | Homo sapiens cDNA clone MGC:17708 IMAGE:3865595, complete cds. [BC008667] |
| 393 | A_23_P92410 | CASP3 | TGGCACCAAGTCTCACTGGCTGTGTCAGTACGTATGACATTCACGGGGAGATTTCTTCTTCCTGTCAAA | SEQ ID NO: 1261 | Homo sapiens caspase 3, apoptosis-related cysteine peptidase (CASP3), mRNA [NM_004346] |
| 394 | A_23_P92441 | MAD2L1 | TGTGTCTGAAAAATGGAAGAGTCGGGACGAAGAGTTTATTACCAATTCTGAGGAAGTCCG | SEQ ID NO: 1262 | Homo sapiens MAD2 mitotic arrest deficient-like 1 (yeast) (MAD2L1), mRNA [NM_002358] |

Fig. 3-22

| No. | Probe ID No. | Symbols of genes | Sequence | SEQ ID NO: | Descriptions of genes (letters and numbers within [ ] indicates GenBank accession No.) |
|---|---|---|---|---|---|
| 395 | A_23_P92842 | SAR1B | TAATCTGACATCACCCAGCGGCCATTTGTAAAGAGCAAGTTTCC AGGAGTACATTGAAG | SEQ ID NO:1263 | Homo sapiens SAR1 gene homolog B (S. cerevisiae) (SAR1B), transcript variant 2, mRNA [NM_016103] |
| 396 | A_23_P933 | RWDD3 | GGAATCGTTTTAGTAAAATAGCAGTGTTTTTGTTTGTTTTTGCAT TGGATTTGGGGAGTGG | SEQ ID NO:1264 | Homo sapiens RWD domain containing 3 (RWDD3), mRNA [NM_015485] |
| 397 | A_23_P94230 | LY96 | TGAAGGTATTTCTGGGAGCCCAGAAGAAACTAAAACATTCCGTTGATGGTCGAAG AGTTTGTCATCGTACA | SEQ ID NO:1265 | Homo sapiens lymphocyte antigen 96 (LY96), mRNA [NM_015364] |
| 398 | A_23_P94501 | ANXA1 | GGGTCTTTTGTGTGGAGGAAACTAAAACATTCCGTTGATGGTCGAAG CTATGATCAGAAGACT | SEQ ID NO:1266 | Homo sapiens annexin A1 (ANXA1), mRNA [NM_000700] |
| 399 | A_23_P94546 | GKAP1 | TACCAGGGTGCCAGAAAAGCGGAAAAGAAAAGCTGAATCGAACCA GTGTAGGTGATTACAT | SEQ ID NO:1267 | Homo sapiens G kinase anchoring protein 1 (GKAP1), mRNA [NM_025211] |
| 400 | A_23_P95130 | SLC37A3 | TTGAGGGATACCTAATTTGCATTCGGTTAGGGGATATTTTCAA CCCTTGGTTTTATACT | SEQ ID NO:1268 | Homo sapiens solute carrier family 37 (glycerol-3-phosphate transporter), member 3 (SLC37A3), transcript variant 1, mRNA [NM_207113] |
| 401 | A_23_P95594 | NAT1 | TCTTGGAGAGAAAGCTTGTGGCCAAACATGGTGATAGATTTT TACTATTTAGAATAAG | SEQ ID NO:1269 | Homo sapiens N-acetyltransferase 1 (arylamine N-acetyltransferase) (NAT1), mRNA [NM_000662] |
| 402 | A_23_P9574 | ECT2 | TAATAGTTAACTAGTATAGATTGTTTCTATGCCATGTATGTG CCACTTGTGAGAGTAG | SEQ ID NO:1270 | Homo sapiens epithelial cell transforming sequence 2 oncogene (ECT2), mRNA [NM_018098] |
| 403 | A_23_P96382 | TIMM8B | TTGTTACTAAGGACGATTTAAGGGCTAGTGGGGAAGGCTATCAA CCCATTGTCAGATCAG | SEQ ID NO:1271 | Homo sapiens translocase of inner mitochondrial membrane 8 homolog B (yeast) (TIMM8B), mRNA [NM_012459] |
| 404 | A_23_P98446 | SC5DL | TGTGAACAACCAGGACTTAATCTTATGCTTAAAATGCCAGATGT TGTTCGGGGGAGAAGT | SEQ ID NO:1272 | Homo sapiens sterol-C5-desaturase (ERG3 delta-5-desaturase homolog, S. cerevisiae)-like (SC5DL), transcript variant 2, mRNA [NM_001024961] |
| 405 | A_23_P99405 | ZMYM2 | GCTGGGTATTACCATGTAAATAATGTGTGAGTGAAAGTTGCCAT TATTCTATGTAGTGGT | SEQ ID NO:1273 | Homo sapiens zinc finger, MYM-type 2 (ZMYM2), mRNA [NM_003453] |
| 406 | A_23_P99693 | ZBTB1 | TATTAGTGTCTAAAAAACCCTAGAGTTACTCTCTTTTGGAACA TAAGGAGGTATACAGA | SEQ ID NO:1274 | Homo sapiens zinc finger and BTB domain containing 1 (ZBTB1), mRNA [NM_014950] |
| 407 | A_23_P99853 | KIAA1370 | CTTTTGTACTGTTGAAACCAGTTCATTGGAGACATGTTGCAATAG CAAAACCCCAGTTAG | SEQ ID NO:1275 | Homo sapiens KIAA1370 (KIAA1370), mRNA [NM_019600] |
| 408 | A_23_P99980 | HMGB1 | GGAATTCTTTCGATTTGACATTTGTTTATGTAATTTCAGGAGGAAT ACTGAACATCTGAGTC | SEQ ID NO:1276 | Homo sapiens high-mobility group box 1 (HMGB1), mRNA [NM_002128] |
| 409 | A_23_P99985 | HMGB1 | TGGGCCAGCTTTTCAAACAAAGATGCCACATTCAAAATAGGGTA TATTTCCTATATTAC | SEQ ID NO:1277 | Homo sapiens high-mobility group box 1 (HMGB1), mRNA [NM_002128] |
| 410 | A_24_P100387 | GK | TAAAAGGTTCTGTTTTGTTTGTTTGGAATGAATGACCAAGTAGCTTTATTGAC TGTTCTGATTGTGTG | SEQ ID NO:1278 | Homo sapiens glycerol kinase (GK), transcript variant 1, mRNA [NM_203391] |
| 411 | A_24_P105649 | BX111927 | | SEQ ID NO:1279 | BX111927 Soares_multiple_sclerosis_2NbHMSP Homo sapiens cDNA clone IMAGp998G05619, mRNA sequence [BX111927] |
| 412 | A_24_P105913 | THC26068573 | CTGTGTCTCTAGGAAATGCAACAATAGCAAAGGTCAATCTGAAA TATGGGCATGTTTGCC | SEQ ID NO:1280 | AY151366 NAP1 [Homo sapiens] (exp=-1; wgp=0; cg=0), partial (35%) [THC26065731] |
| 413 | A_24_P106306 | RPL26L1 | TGGCAAGGTAGTCCAGGTGTACAGAAAGAAATATGTCATGTACA TTCGAGCCGGGTGCAGCG | SEQ ID NO:1281 | Homo sapiens ribosomal protein L26-like 1 (RPL26L1), mRNA [NM_016093] |

Fig. 3-23

| No. | Probe ID No. | Symbols of genes | Sequence | SEQ ID NO: | Descriptions of genes (letters and numbers within [ ] indicates GenBank accession No.) |
|---|---|---|---|---|---|
| 414 | A_24_P107257 | LIN7C | TATTAGTGTGGGAGTGTGACTGAGGTCTTAAAGACTGAAAAGT TGGGGTTCATTTTCTG | SEQ ID NO: 1282 | Homo sapiens lin-7 homolog C (C. elegans) (LIN7C), mRNA [NM_018362] |
| 415 | A_24_P11045 | THC2785765 | CCAGCAGAAAGGTAGACGTGATTTCATGAGAGAAATACGGTAGCA ACACAAGTCGGAATAAG | SEQ ID NO: 1283 | COX7B_HUMAN (P24311) Cytochrome c oxidase polypeptide VIIb, mitochondrial precursor, partial (78%) [THC2785765] |
| 416 | A_24_P114249 | GALNT3 | ATTTCAAATGAGGAATACTTGACTCATTTAAAGCTAAATTTGT TACTGATTCAATTATA | SEQ ID NO: 1284 | Homo sapiens UDP-N-acetyl-alpha-D-galactosamine:polypeptide N-acetylgalactosaminyltransferase 3 (GalNAc-T3) (GALNT3), mRNA [NM_004482] |
| 417 | A_24_P115774 | BIRC2 | GATACCCATTTTGGTTAAAGGAAATGGTGGGCGGAACATCTTCAA AAAGTGTCTAAAAGAA | SEQ ID NO: 1285 | Homo sapiens baculoviral IAP repeat-containing 2 (BIRC2), mRNA [NM_001166] |
| 418 | A_24_P116766 | ZNF207 | TTTGTGAGAGGACGGTATAGGAGTGAAAATTAGCTTCTGAGTAAA TTTGTAATTTATGCGC | SEQ ID NO: 1286 | Homo sapiens mRNA; cDNA DKFZp761N202 (from clone DKFZp761N202). [AL834501] |
| 419 | A_24_P123521 | CLK4 | CGCAACGTCGAAAAACAGAGAATGCAAAGTGTGCAGTTGGAAG TGCAACGTATGATGAT | SEQ ID NO: 1287 | Homo sapiens CDC-like kinase 4 (CLK4), mRNA [NM_020666] |
| 420 | A_24_P124326 | IKZF5 | GCTAGAAGTTCTTGAACTTCAAGTTAAGGCTAGACATTTAGTTT GAAAAATTCGACTGG | SEQ ID NO: 1288 | Homo sapiens mRNA; cDNA DKFZp781B0249 (from clone DKFZp781B0249). [CR749800] |
| 421 | A_24_P124992 | PSMA4 | AAAAGTTCCCTTGGTGTTTCATTGCTGTACATTGGGTGGGATAA GCACTATGGCTTCAG | SEQ ID NO: 1289 | Homo sapiens proteasome (prosome, macropain) subunit, alpha type, 4 (PSMA4), mRNA [NM_002789] |
| 422 | A_24_P126741 | ENST00000309178 | AGCCTCGAACACGACCACAGTAACAAGATCAACACTAGTAGAATTG TCAGAGGACGGAGAAT | SEQ ID NO: 1290 | |
| 423 | A_24_P127181 | LOC442237 | AACTGAAATTTCCAGAGAAATCCAAGTGCAGCTAGTAGAATTG GAGAAAAAGTTCAGTG | SEQ ID NO: 1291 | PREDICTED: Homo sapiens similar to 40S ribosomal protein S7 (S8) (LOC442237), mRNA [XR_018963] |
| 424 | A_24_P127621 | A_24_P127621 | TCGAAGGAAGTACCACAACAAAGGCATTTCAATGGACTTCCGACA TTCTCAGAAATATAG | SEQ ID NO: 1292 | |
| 425 | A_24_P129232 | SERINC1 | CAGGTCAAGAATGATGGAAATGTTTTAGAATAAACTCTGCTT ATAGTATACTAGACGAG | SEQ ID NO: 1293 | Homo sapiens serine incorporator 1 (SERINC1), mRNA [NM_020755] |
| 426 | A_24_P132787 | RAB18 | TAAAAGCCTCAGATTCTAGTTGATTAGACTTCCTAGTCTACAT TACATGTGGTTGAAGG | SEQ ID NO: 1294 | Homo sapiens RAB18, member RAS oncogene family (RAB18), mRNA [NM_021252] |
| 427 | A_24_P133991 | ANKRD12 | TTTGGAATGGAGTATTGTAGTTGCCTGAAAAGGTTTCAGAAAAG AAAAAGGATGGTTAGT | SEQ ID NO: 1295 | Homo sapiens ankyrin repeat domain 12 (ANKRD12), mRNA [NM_015208] |
| 428 | A_24_P134392 | STCH | TGAGTAACTTATTTTGTATGAGGAATGTTTTGGTACGTGTGTTT CAGTCAAACCACTGAC | SEQ ID NO: 1296 | Homo sapiens stress 70 protein chaperone, microsome-associated, 60kDa (STCH), mRNA [NM_006948] |
| 429 | A_24_P135242 | A_24_P135242 | GATGCCAAGAAAAAGTGGCAACTAGTTTGTACGTGCAGAACGGA AACTGGCATTTGTCAT | SEQ ID NO: 1297 | |
| 430 | A_24_P135551 | LOC130865 | TAAGAGGATAGGTGTCCCTGTGGGATTGACCCAAAGTGGTTA TCACTAGAGCTAAAACT | SEQ ID NO: 1298 | PREDICTED: Homo sapiens similar to 60S ribosomal protein L26 (Silica-induced gene 20 protein) (SIG-20) (LOC130865), mRNA [XR_019454] |
| 431 | A_24_P139208 | USP25 | CAATATAGAGCAAGGTGATTATTGAAGAGAATGTCCAAAGTAGT | SEQ ID NO: 1299 | Homo sapiens ubiquitin specific peptidase 25 (USP25), mRNA [NM_013396] |
| 432 | A_24_P144383 | A_24_P144383 | GTGCGTTGAGGCCAAAGATGGTAAGAGAATGGTGGCTAAAAGAT GCAAGGCATTTTGAAGT | SEQ ID NO: 1300 | |

Fig. 3-24

| No. | Probe ID No | Symbols of genes | Sequence | SEQ ID NO: | Descriptions of genes (letters and numbers within [ ] indicates GenBank accession No.) |
|---|---|---|---|---|---|
| 433 | A_24_P144666 | LOC401975 | TGCGATGTCAAGAGTAATGATGGCTACTGTTTAATGTGTTCTGTGTTGGTTTTAGTCA | SEQ ID NO: 1301 | PREDICTED: Homo sapiens similar to ribosomal protein S3a (LOC401975), mRNA [XR_017247] |
| 434 | A_24_P148151 | TSNAX | AAAGTTGAGTTATATACTTGTACATACAAATGGAAATGCTTTTAGTAGTGATTATTTAGCA | SEQ ID NO: 1302 | Homo sapiens translin-associated factor X (TSNAX), mRNA [NM_005999] |
| 435 | A_24_P152753 | LOC285260 | TGTGTGATACCGAATCGTGTGTGGGATTATCCAGAAAGGATGAAGATTCACCAAATAAGGT | SEQ ID NO: 1303 | PREDICTED: Homo sapiens similar to ribosomal protein L31 (LOC285260), mRNA [XR_019376] |
| 436 | A_24_P153324 | LOC390413 | GAAGGTTAACAAGGTTCAATTAACATGCTGGGGATTGTGAGAACCATATATTCAGGGTA | SEQ ID NO: 1304 | PREDICTED: Homo sapiens similar to 60S ribosomal protein L7 (LOC390413), mRNA [XR_019341] |
| 437 | A_24_P153511 | OSBPL8 | CCTTGTCCATATAGACACAAAATTTGTGGAAGGCAGTTTTAACTTTCTGAAGAATATC | SEQ ID NO: 1305 | Homo sapiens oxysterol binding protein-like 6 (OSBPL8), transcript variant 1, mRNA [NM_020841] |
| 438 | A_24_P15765 | AK098605 | TCCAAGTCTGGCTAGTACGTGAATGGAAGAAAAGTTGGGAAGCATGTTGTCTTTATTG | SEQ ID NO: 1306 | Homo sapiens cDNA FLJ25739 fis, clone TST05834 [AK098605] |
| 439 | A_24_P161914 | LOC130726 | CTATACTGTTGGAAAACACTTCAAGAAATAACTTCCTGCGGCCATTGAAATTATCTTC | SEQ ID NO: 1307 | PREDICTED: Homo sapiens similar to 60S ribosomal protein L7 (LOC130726), mRNA [XR_019248] |
| 440 | A_24_P166816 | AK023645 | AAGATTGAATGAAGGAGTAATTCTGTTCTGTATAGGCAACTTAACTTCACTGTGGAA | SEQ ID NO: 1308 | Homo sapiens cDNA FLJ13563 fis, clone PLACE1009050 [AK023645] |
| 441 | A_24_P167063 | ZNF518 | AAAGAAAGCCATACATAGAATGGTCAAGGTATGTTCTTGCTATGCA CAATATACTTGTGTG | SEQ ID NO: 1309 | Homo sapiens zinc finger protein 518 (ZNF518), mRNA [NM_014803] |
| 442 | A_24_P168378 | RPS7 | AACTGAAATCTTTCCAGAAAATGCAAATCGGGCTAGTAAGTGAATTGGAGAAAAAAGTTCA | SEQ ID NO: 1310 | Homo sapiens ribosomal protein S7 (RPS7), mRNA [NM_001011] |
| 443 | A_24_P170025 | A_24_P170025 | TCCATGCTATTGTTGTCAGAGGGGAGTAGCGTGTATTAAAGTCGCCATTGATATGCTC | SEQ ID NO: 1311 | |
| 444 | A_24_P171873 | FBXO4 | GATTGCAGAGATTCAAAAGTGTCAAAAGTTGTAGATGGGTTGATCTATGTTGCAAATGC | SEQ ID NO: 1312 | Homo sapiens F-box protein 4 (FBXO4), transcript variant 1, mRNA [NM_012176] |
| 445 | A_24_P172481 | TRIM22 | TGCGCGGTTAAAAGATTGAACAAAGAGAAAAGTGTCAACTCATATGCAGGTTATCTAGGAA | SEQ ID NO: 1313 | Homo sapiens tripartite motif-containing 22 (TRIM22), mRNA [NM_006074] |
| 446 | A_24_P175059 | ATG5 | TTGCACAGAGACGGTGGTCTGAATGATTGATAGAGCACATTAAGAGTGTTATTCGTCGGTTC | SEQ ID NO: 1314 | Homo sapiens ATG5 autophagy related 5 homolog (S. cerevisiae) (ATG5), mRNA [NM_004849] |
| 447 | A_24_P175176 | PHF2 | AGAATTGAGGTTAACTTAGAGTGTTGGGAGTTGATTTATTAAGTACAGTATACCTCAAGAG | SEQ ID NO: 1315 | Homo sapiens putative homeodomain transcription factor 2 (PHF2), mRNA [NM_020432] |
| 448 | A_24_P175187 | SAMD9 | CAAGGAGCAGATACGTAATGAAATGTAATTTTCCCCTAATAAAATTATGGATATGGGGAGCAG | SEQ ID NO: 1316 | Homo sapiens sterile alpha motif domain containing 9 (SAMD9), mRNA [NM_017654] |
| 449 | A_24_P175188 | SAMD9 | TGCCAATGTACTGCCAGATTAACATACAAACCTATGTTTGAACAAAAAGAACCAGGGATA | SEQ ID NO: 1317 | Homo sapiens sterile alpha motif domain containing 9 (SAMD9), mRNA [NM_017654] |
| 450 | A_24_P179351 | TPT1 | GAACAGCAGCAGAAAGACTTCAAGCTTTTATGAGAGGGGGGTGCAGAACAAATCAAGCAG | SEQ ID NO: 1318 | Homo sapiens tumor protein, translationally-controlled 1 (TPT1), mRNA [NM_003295] |
| 451 | A_24_P180424 | TMEM30A | CAATGTGTATGCACATTCTGTTTAGTTAAGGCACCAATTGTTTTGGTTTTTCCTTAAG | SEQ ID NO: 1319 | Homo sapiens transmembrane protein 30A (TMEM30A), mRNA [NM_018247] |
| 452 | A_24_P183864 | IMPA1 | TCAGTTCGTTTGAGCTTGGCAGGTAAACAGAAGTAGGTCAAATCGTACATCGTAGAACTCGGTGTATTG | SEQ ID NO: 1320 | Homo sapiens inositol(myo)-1(or 4)-monophosphatase 1 (IMPA1), mRNA [NM_005536] |
| 453 | A_24_P186944 | LOC389404 | AGGAAGCCCTTGCGGAGGGGAACTTCAATCACATCGTAGAACTCAGTCTTCTTGGAAAGAAAAA | SEQ ID NO: 1321 | PREDICTED: Homo sapiens similar to 60S ribosomal protein L9 (LOC389404), mRNA [XR_018133] |

Fig. 3-25

| No. | Probe ID No. | Symbols of genes | Sequence | SEQ ID NO: | Descriptions of genes (letters and numbers within [ ] indicates GenBank accession No.) |
|---|---|---|---|---|---|
| 454 | A_24_P191417 | NAB1 | AAGTTGGTTAAGTACTATGTTATGTTTCTAGTCTTCGAAGCTTAGT GATAAGGTGGAAGGAC | SEQ ID NO: 1322 | Homo sapiens NGFI-A binding protein 1 (NAB1), mRNA [NM_005966] |
| 455 | A_24_P191833 | SFRS12 | AAGGACTTAGGAGTATGGGAGGTTATTGGTTTTATGTTTAAG GATACGTTTACTTGAG | SEQ ID NO: 1323 | Homo sapiens splicing factor, arginine/serine-rich 12 (SFRS12), transcript variant 2, mRNA [NM_139168] |
| 456 | A_24_P192556 | DNAJA4 | TATAGGAAGGTGTCTTCTTAGGTATGTACAAGGATTACTTTAAAG CATTTGAGTTTGGCTG | SEQ ID NO: 1324 | DnaJ homolog subfamily A member 1 (Heat shock 40 kDa protein 4) (DnaJ protein homolog 2) (HSJ-2) (HSD). [Source:Uniprot/SWISSPROT:Acc:P31689] [ENST00000330899] |
| 457 | A_24_P194313 | C21orf66 | ATTTAAATTAACGGTCTCAGTTAATTGTCCCGTGTAAACGATGT GTGAGTGTAAATTGT | SEQ ID NO: 1325 | Homo sapiens chromosome 21 open reading frame 66 (C21orf66), transcript variant 1, mRNA [NM_016631] |
| 458 | A_24_P199506 | RNF2 | AAACTGCTTAGATTTTGTTGATGACATTAGATTAGTAGTTGCAT TAAATAAGTAAATTCC | SEQ ID NO: 1326 | Homo sapiens ring finger protein 2 (RNF2), mRNA [NM_007212] |
| 459 | A_24_P201702 | CLEC2B | ATTGGAATTCAGTAAATACAACGTGTTCCAGTCAACATGCCGAC GTAAGTATAATTGACA | SEQ ID NO: 1327 | Homo sapiens C-type lectin domain family 2, member B (CLEC2B), mRNA [NM_005127] |
| 460 | A_24_P203909 | RPL34 | GAGGGGTTGGTGCTGTAAGACTTAAAGTTCTTATGAAATTGCC AAAACAAACAAACATG | SEQ ID NO: 1328 | Homo sapiens ribosomal protein L34 (RPL34), transcript variant 2, mRNA [NM_033625] |
| 461 | A_24_P208045 | EDEM3 | TTTAGAGGGGGTAGAATTTGAAATATTCAGCGGCGGTCGTTT TATGCACAAGGTCA | SEQ ID NO: 1329 | Homo sapiens ER degradation enhancer, mannosidase alpha-like 3 (EDEM3), mRNA [NM_025191] |
| 462 | A_24_P20996 | BC043173 | CTGAAAATGTTCATATATATGTTGAAGTGTCTCTTTATGT GAAGGCTGATTGC | SEQ ID NO: 1330 | Homo sapiens cDNA clone IMAGE:5287121. [BC043173] |
| 463 | A_24_P212864 | LOC646161 | ACAGAAGTACAACGTGCGATCCATGATCGAAAAGAATGATGAAG TTAGGCTGTGTACCAGG | SEQ ID NO: 1331 | PREDICTED: Homo sapiens similar to 60S ribosomal protein L26 (LOC646161), mRNA [XR_018048] |
| 464 | A_24_P213375 | A_24_P213375 | AAATTGTTCCATGATCAAAGTTTACCAGTTCAAAAAATGTCAT CTGTCTGTGTTGGTT | SEQ ID NO: 1332 | |
| 465 | A_24_P213783 | RPL31 | CTTTTGGTTAGGGATGTAGGTGTTACCAGTTTGGTTAGAGCTAGAG ACAGTCAATGTGGATG | SEQ ID NO: 1333 | Homo sapiens ribosomal protein L31 (RPL31), mRNA [NM_000993] |
| 466 | A_24_P221375 | A_24_P221375 | TAGTTGGTTAGGGATGTAGGTGTACCTAGGACTTGAAAATGTAGAGA GAGTCAATGTCATCC | SEQ ID NO: 1334 | |
| 467 | A_24_P222911 | SFRS7 | CAGAAAGTGAATGCAATGATATAGAGATGGTTTTTAAATGTCAGCTA TATTTAGCAACATCC | SEQ ID NO: 1335 | Homo sapiens splicing factor, arginine/serine-rich 7, 35kDa (SFRS7), mRNA [NM_001031684] |
| 468 | A_24_P225308 | ARID4B | GTTGAAAATGGTTCAAGTTATTCAAATTGTACAGGACTGTAA AGATTTGTTGACAGCA | SEQ ID NO: 1336 | Homo sapiens AT rich interactive domain 4B (RBP1-like) (ARID4B), transcript variant 1, mRNA [NM_016374] |
| 469 | A_24_P225468 | ANP32E | TCATCTTACGTGTGCAATCAAAATTAGAAGTACTTTGGTTTGAAAA CAAGACTTAGAGGGTC | SEQ ID NO: 1337 | Homo sapiens acidic (leucine-rich) nuclear phosphoprotein 32 family, member E (ANP32E), mRNA [NM_030920] |
| 470 | A_24_P225719 | PREI3 | GACTATTTCTTAGTCAATATTTATACTAAGGTAGTGACTGAGA TTTGGTTGATCTGGCTG | SEQ ID NO: 1338 | Homo sapiens preimplantation protein 3 (PREI3), transcript variant 1, mRNA [NM_015387] |
| 471 | A_24_P229066 | ENST00000678131 | AAGAAGCTCCAACAACAAGACAGGAGGTATGTGACCCATCTGAT GAAGCAGAATTCAGAGA | SEQ ID NO: 1339 | OTTHUMP00000016594. [Source:Uniprot/SPTREMBL:Acc:Q9NU98] [ENST00000678131] |

Fig. 3-26

| No. | Probe ID No. | Symbols of genes | Sequence | SEQ ID NO. | Descriptions of genes (letters and numbers within [ ] indicates GenBank accession No.) |
|---|---|---|---|---|---|
| 472 | A_24_P232856 | RPL9 | GAACCCTGGGAGGGACTTCAATCAGTCAATGTAGAAGTCAGCCTGTTGGAAAGAAAA | SEQ ID NO: 1340 | Homo sapiens ribosomal protein L9 (RPL9), transcript variant 1, mRNA [NM_000661] |
| 473 | A_24_P234792 | CSNK1G3 | GGGTTTTTGGATTGTACAGTGTTTATATGATCTGAACTCCTTATACAAGAAGGTGTG | SEQ ID NO: 1341 | Homo sapiens casein kinase 1, gamma 3 (CSNK1G3), transcript variant 1, mRNA [NM_004384] |
| 474 | A_24_P235429 | ABCA1 | CCAAAGAGGCCATGTGTCATGTAATACTGAAGCAGTTGATATGAGACATTAATTGTAC | SEQ ID NO: 1342 | Homo sapiens ATP-binding cassette, sub-family A (ABCA), member 1 (ABCA1), mRNA [NM_005502] |
| 475 | A_24_P236008 | SCYL2 | ATAGACTATGTACTTGTCTGGTTTGTTTGTTTTATTTTGGAATGGTTATAAGCCTCG | SEQ ID NO: 1343 | Homo sapiens mRNA for KIAA1360 protein, partial cds. [AB037781] |
| 476 | A_24_P242299 | ZRANB2 | GACTTTTTGAAAGTCTACCTTCTAAATTGCCCGACGATCTAGATTCTACATGTTACGAT | SEQ ID NO: 1344 | Homo sapiens zinc finger, RAN-binding domain containing 2 (ZRANB2), transcript variant 2, mRNA [NM_005455] |
| 477 | A_24_P243749 | PDK4 | ATTTGACATTGTGTGTAATTTCATGGTGGGCCTAGTGTTGTGGTGCTTGTGGTAATGGTA | SEQ ID NO: 1345 | Homo sapiens pyruvate dehydrogenase kinase, isozyme 4 (PDK4), mRNA [NM_002612] |
| 478 | A_24_P250922 | PTGS2 | TGAGATATTTAAGGTTGAATGTTGTCCTTAGGATAGGCCTATGTGCTAGCCGAGAAGA | SEQ ID NO: 1346 | Homo sapiens prostaglandin-endoperoxide synthase 2 (prostaglandin G/H synthase and cyclooxygenase) (PTGS2), mRNA [NM_000963] |
| 479 | A_24_P25326 | ZMYM6 | AGCACTATTTAAATCAGTGTCGTAACTCAGTTTGGATAAATGCAAAGACAAGTTACCC | SEQ ID NO: 1347 | Homo sapiens zinc finger, MYM-type 6 (ZMYM6), mRNA [NM_071167] |
| 480 | A_24_P255252 | A_24_P255252 | TGGACTACTGGAAGGATGGTGTGACTCCATATGTGATTTCTTGAGGATGATTTAGAGA | SEQ ID NO: 1348 | |
| 481 | A_24_P257151 | CLK1 | TATGGAAGTCTGTGAATTTTTGCACAGTATAATAAGTTGACTCAGACAGACTTAAAGGCTG | SEQ ID NO: 1349 | Homo sapiens CDC-like kinase 1 (CLK1), transcript variant 1, mRNA [NM_004071] |
| 482 | A_24_P263524 | TXNDC9 | TGACTTCACCACAGAAACTTAGAATGGGGGCTCAGTTGTTGTGAATTGTTAATTACAG | SEQ ID NO: 1350 | Homo sapiens thioredoxin domain containing 9 (TXNDC9), mRNA [NM_005783] |
| 483 | A_24_P265856 | SENP7 | TGTGTGTGTTGGGGGTACTTTAAAGGTGACTATGTTTGTACATGTAAGATAAC | SEQ ID NO: 1351 | Homo sapiens SUMO1/sentrin specific peptidase 7 (SENP7), transcript variant 1, mRNA [NM_020654] |
| 484 | A_24_P268786 | MYNN | TGGAGGATCATACTTTGGAGTGAACAGGATTGCATACAAAAAGTCCTTATCAGAAAC | SEQ ID NO: 1352 | Homo sapiens myoneurin (MYNN), mRNA [NM_018657] |
| 485 | A_24_P268917 | RAB33B | CGGAGAATCTAATGTAGTTCGGCTATTAATAAGAATGCATTATTGAAGTATATTGCAAAT | SEQ ID NO: 1353 | Homo sapiens RAB33B, member RAS oncogene family (RAB33B), mRNA [NM_031296] |
| 486 | A_24_P276583 | TMCO1 | CCTTCATTTTTGCTGTATATTCTGTACTATGTCGATTGGAGAGAAGATCAGAAGATTC | SEQ ID NO: 1354 | Homo sapiens transmembrane and coiled-coil domains 1 (TMCO1), mRNA [NM_019026] |
| 487 | A_24_P278008 | DCTN6 | CTATGAAAGGAAGCTCAACTCAGTAGGATAAAGAACTAAGAAGAGTGTATAACATGAAGATAAC | SEQ ID NO: 1355 | Homo sapiens dynactin 6 (DCTN6), mRNA [NM_006571] |
| 488 | A_24_P278460 | MLSTD2 | ACCCATGGAACAATATGCGTTAGGATACAGGAAGGAGTCCTTACTTACACTCTGTCTG | SEQ ID NO: 1356 | Homo sapiens male sterility domain containing 2 (MLSTD2), mRNA [NM_032228] |
| 489 | A_24_P280897 | LOC366532 | AGGAGTGTGAGAGCTGGGATAGCTCCTGGAAATACGATGAAAAAGA | SEQ ID NO: 1357 | PREDICTED: Homo sapiens similar to ribosomal protein L21 (LOC388532), mRNA [XM_001127035] |
| 490 | A_24_P285179 | THC2649313 | AGTGGGAATTTGAAATGCCATGTCGTATATAATTCTGGCATATTTGTTGGACATTTGGA | SEQ ID NO: 1358 | |

Fig. 3-27

| No. | Probe ID No. | Symbols of genes | Sequence | SEQ ID NO: | Descriptions of genes (letters and numbers within [ ] indicates GenBank accession No.) |
|---|---|---|---|---|---|
| 491 | A_24_P286054 | ZFYVE16 | GTGTATGTATCTGGCATGTAAGTAATTGAACAGTCTAAAATAACCAAATGGTAGAGGG | SEQ ID NO: 1359 | Zinc finger FYVE domain-containing protein 16 (Endofin) (Endosome-associated FYVE domain protein). [Source:Uniprot/SWISSPROT:Acc:Q7Z3T8] [ENST00000380248] |
| 492 | A_24_P287756 | NUDT21 | CCCAATAGTTAGTTCACTTGTTATACATGACTGATTATTTGGTTAAACTGGACTCATTTG | SEQ ID NO: 1360 | Homo sapiens nudix (nucleoside diphosphate linked moiety X)-type motif 21 (NUDT21), mRNA [NM_007006] |
| 493 | A_24_P288754 | PIGA | CTTTCTCTGGATACGTTAATTGTAACTGTCAGTTTGCACTGGTCGGTATATGGAAACAGATT | SEQ ID NO: 1361 | Homo sapiens phosphatidylinositol glycan anchor biosynthesis, class A (paroxysmal nocturnal hemoglobinuria) (PIGA), transcript variant 1, mRNA [NM_002641] |
| 494 | A_24_P290257 | A_24_P290257 | CCAATTGATTGAACATAGAACAAGCCAATTATACCATCCAGTCATTGAAGGACACCAAGA | SEQ ID NO: 1362 | |
| 495 | A_24_P295543 | BLOC1S2 | GTTTATTTGTATGTAGTCAGACATTGACATGCGATCAGTTTGGGAAATGTGATGAAAACA | SEQ ID NO: 1363 | Homo sapiens biogenesis of lysosome-related organelles complex-1, subunit 2 (BLOC1S2), transcript variant 2, mRNA [NM_001013342] |
| 496 | A_24_P298238 | A_24_P298238 | ATGCTTGAAGCAGAATAGACATTGAGGTTGTTTCAATTCAGGAAGCCACAACAGTTAAAAC | SEQ ID NO: 1364 | |
| 497 | A_24_P298604 | LOC731599 | GATGGAAATCAATGACCAAGAGGTGCGGCAAATGACTGAAAGAATTGGTCAATAAAATGAT | SEQ ID NO: 1365 | PREDICTED: Homo sapiens hypothetical protein LOC731599 (LOC731599), mRNA [XR_015536] |
| 498 | A_24_P306527 | ENST00000308989 | ACCGATCCGTCCGTGGTTATCCAGAAAATGTAATGAGGATGAAGATTCAGGAAATAAGT | SEQ ID NO: 1366 | PREDICTED: Homo sapiens similar to ribosomal protein L31 (LOC729005), mRNA [XM_001133428] |
| 499 | A_24_P306726 | TPT1 | GACCAGAAACAGTAAAACTTTTATGACAGGGGGTGGAAAACAAATCAAGGAGAATCTTG | SEQ ID NO: 1367 | Homo sapiens tumor protein, translationally-controlled 1 (TPT1), mRNA [NM_003295] |
| 500 | A_24_P309415 | TMEM123 | GTTTCCTCCTGCATTGGGTTTGAAGTAGTTTAGTTATGTGTTTTTCTGTGTATGTAAGTAG | SEQ ID NO: 1368 | Homo sapiens transmembrane protein 123 (TMEM123), mRNA [NM_052932] |
| 501 | A_24_P310894 | CAPZA1 | TGTATTATTTGTCCTTCATAGCTATCTATGCAATCCATACCACACAGTATCTCTGTATCAGGTAGTC | SEQ ID NO: 1369 | Homo sapiens capping protein (actin filament) muscle Z-line, alpha 1 (CAPZA1), mRNA [NM_006135] |
| 502 | A_24_P312417 | ZBTB26 | AGAGGAGAAGTGATTTTTAAAACCTTTATCATTGAGCATTTGTATTTATGGATGGGCAGG | SEQ ID NO: 1370 | Zinc finger and BTB domain-containing protein 26 (Zinc finger protein 481) (Zinc finger protein BIore). [Source:Uniprot/SWISSPROT:Acc:Q9HCK0] [ENST00000373635] |
| 503 | A_24_P315326 | LOC341412 | AAAGTCTATACTTGGTTACGAATGTACCGGTTACCGCTTCAAAAATGTACAGGGAAATG | SEQ ID NO: 1371 | AGENCOURT 10640955 NIH_MGC_126 Homo sapiens cDNA clone IMAGE:6723568 5', mRNA sequence [CA455253] |
| 504 | A_24_P316074 | LOC730902 | TATCAATGGTGTGAGCCCAAAGGTCAAAGGTGTTGGAGGTTCTTGCCTTGGTGAAATCTT | SEQ ID NO: 1372 | PREDICTED: Homo sapiens similar to 60S ribosomal protein L7 (LOC730902), mRNA [XR_015600] |
| 505 | A_24_P320328 | SUB1 | CAGAAAACCTGTAAAGAAACAAGAAAAAGACAGTGAGAGTTGAGAGTTGAGAGCCGTGTGTCATCTTCTA | SEQ ID NO: 1373 | Homo sapiens SUB1 homolog (S. cerevisiae) (SUB1), mRNA [NM_006713] |
| 506 | A_24_P321511 | GOLT1B | TTAGAGGAAGAAGTAGTATCTGCTAATGTAAGGAGACATGTATTTAACTCGTTTGTAGAC | SEQ ID NO: 1374 | Homo sapiens golgi transport 1 homolog B (S. cerevisiae) (GOLT1B), mRNA [NM_016072] |
| 507 | A_24_P324224 | A_24_P324224 | AAAGCTGTCTGGGCCAAAGAATAAGGAATTCCTATAGGCATGTGCCGGTTGTCCAGAAGA | SEQ ID NO: 1375 | |

Fig. 3-28

| No | Probe ID No. | Symbols of genes | Sequence | SEQ ID NO: | Descriptions of genes (Italics and numbers within [ ] indicates GenBank accession No.) |
|---|---|---|---|---|---|
| 508 | A_24_P324506 | A_24_P324506 | GCAATATAAGGGAGGTAATTGCAAATACAAGTATGGCTATTCCTGTGGAACATGCTGTGT | SEQ ID NO: 1376 | |
| 509 | A_24_P324581 | KIAA1466 | ATAATAGCTCATAGAATTGCTGTACCAACCAAGGCTAAAAAGAATTTAAGTAGGCC | SEQ ID NO: 1377 | Homo sapiens mRNA for KIAA1466 protein, partial cds. [AB040899] |
| 510 | A_24_P330397 | STRN3 | ATGGTGTAAGTAAGCATTTTTGTTGTGTAACATTTTGTTGTGTAAATGCATGATTAAGAACAATAAAGTATTTTTTC | SEQ ID NO: 1378 | Homo sapiens striatin, calmodulin binding protein 3 (STRN3), mRNA [NM_014574] |
| 511 | A_24_P33213 | A_24_P33213 | GACCATATATTACATGGGGGGTACCCAAAATGTGAAGTCAGTAAATGAACTTATCTACAAGG | SEQ ID NO: 1379 | |
| 512 | A_24_P333112 | A_24_P333112 | GGTCATCAGAATCAGAGGTATCAATGTGTGAGCCCAGAGGACCAAAGGTATGCAAGTT | SEQ ID NO: 1380 | |
| 513 | A_24_P334361 | FLJ20035 | GTGAAAATGAACAGCAGAACAGTTGTTCTCTTAGCCTTTGAACAAGTGAGTACAACTTTTTGGG | SEQ ID NO: 1381 | Homo sapiens hypothetical protein FLJ20035 (FLJ20035), mRNA [NM_017631] |
| 514 | A_24_P33607 | LOC652558 | TAAGAAATAATTGTTTGACAGAGCAACGGCTTTGATTGCTCATCTCTTGGTAAATATGG | SEQ ID NO: 1382 | PREDICTED: Homo sapiens similar to 60S ribosomal protein L7 (LOC652558), mRNA [XR_019386] |
| 515 | A_24_P349636 | LOC386401 | AGTTGCTTGACAGATAACACTTTGCATTGCTCGATCTGTTGGTAAATATAGCATGAAGTG | SEQ ID NO: 1383 | PREDICTED: Homo sapiens similar to 60S ribosomal protein L7 (LOC388401), mRNA [NM_016879] |
| 516 | A_24_P351435 | CRBN | GAAATGAAAGCAATTGGAAGACGAAAAGGTTCAAAGTCGTTGGAGGAAGAACACAGTCAGA | SEQ ID NO: 1384 | Homo sapiens cereblon (CRBN), mRNA [NM_016302] |
| 517 | A_24_P352445 | MRPL42 | TTTTTAGTGCATCACAATGACAAAGGGGTGGTTTTCTTTGAGCCAAGAAATGTGCTTTGC | SEQ ID NO: 1385 | Homo sapiens mitochondrial ribosomal protein L42 (MRPL42), nuclear gene encoding mitochondrial protein, transcript variant 3, mRNA [NM_172178] |
| 518 | A_24_P354257 | AK025305 | GAAAAACAAGATGTTTTTCTTAAGTGAAAGGACGTTTAATTTGCTGTAAGGGTACATCCTG | SEQ ID NO: 1386 | Homo sapiens cDNA: FLJ21652 fis, clone COL08582. [AK025305] |
| 519 | A_24_P354412 | AK091335 | TGTAGACTGAAGGAGTCTTCAAAACACGCCAGAGCATTAAATCTCACTGTGCGCTGCTCT | SEQ ID NO: 1387 | Homo sapiens cDNA FLJ34016 fis, clone FCBBF2002541. [AK091335] |
| 520 | A_24_P354954 | CCDC126 | AATGGAAGTCTTGAGGAGTGTTAGCCAGGTGTATATAATAAAAGGTACTTTTGTGTGCATT | SEQ ID NO: 1388 | Homo sapiens coiled-coil domain containing 126 (CCDC126), mRNA [NM_138771] |
| 521 | A_24_P357576 | KIAA1370 | TGCTGGATATGAAGCTCAAATCTTAGACTGAATCAGGAACGAAAGGTCAGTTTTTCACCAAG | SEQ ID NO: 1389 | Homo sapiens KIAA1370 (KIAA1370), mRNA [NM_019600] |
| 522 | A_24_P362646 | TXNDC9 | CTCCACATTGAGGTGTAAAATACTAGACAGATCTGGCATATTGTCCAAGAAAACACCT | SEQ ID NO: 1390 | Homo sapiens thioredoxin domain containing 9 (TXNDC9), mRNA [NM_005783] |
| 523 | A_24_P364807 | AYTL1 | TGTAACTCTTGTTTGTCAGGTAATGCTTGTCTCTCAAGAAGTTGTCAAGGCGTGTGTAA | SEQ ID NO: 1391 | Homo sapiens mRNA; cDNA DKFZp686H22112 (from clone DKFZp686H22112). [BX641069] |
| 524 | A_24_P365048 | C17orf42 | GGAACTAGTGGAAAAGAACGCTAGTGAAGGAGTTTCTCTTGGATTCATAGTGAAGGCGGAT | SEQ ID NO: 1392 | Homo sapiens chromosome 17 open reading frame 42 (C17orf42), mRNA [NM_024683] |
| 525 | A_24_P366165 | LOC391126 | ACTTCGAACGCAAATCAAAAATAGCAAAAAGGCATTCAATGCAGCCTTGCCACATTCACAGG | SEQ ID NO: 1393 | PREDICTED: Homo sapiens similar to ribosomal protein L26 (Silica-induced gene 20 protein) (SIG-20) (LOC391126), mRNA [XR_019504] |
| 526 | A_24_P366546 | RPL31P10 | CGGCTGTCGAGAAAACTGGTCAGGCATCAAGGGTATACATAAAAGCCCTATACTTTGGTTACC | SEQ ID NO: 1394 | |
| 527 | A_24_P367139 | A_24_P367139 | AGACCATGAAAACTGGTCAGGACATGAAGGATGAAGATTCAAATAAGCCTAAGAAGTATGTGAAAG | SEQ ID NO: 1395 | PREDICTED: Homo sapiens similar to ribosomal protein L31 (LOC390283), mRNA [XR_018695] |

Fig. 3-29

| No. | Probe ID No. | Symbols of genes | Sequence | SEQ ID NO. | Descriptions of genes (letters and numbers within [ ] indicates GenBank accession No.) |
|---|---|---|---|---|---|
| 528 | A_24_P367191 | LOC652890 | AGTTAACATGCTGAGGACTGTAGAGGCATATATTGGCTGTCGGT ACCCAAATCTGAAGTC | SEQ ID NO: 1396 | PREDICTED: Homo sapiens similar to 60S ribosomal protein L7 (LOC652890), mRNA [XR_019544] |
| 529 | A_24_P367199 | A_24_P367199 | TCTTATGCTGAGCACCAAGAGTGTGCCAAATGGAGAAGAGAGGTG TAATCATGACCTGAGA | SEQ ID NO: 1397 | |
| 530 | A_24_P367369 | A_24_P367369 | ATTTAAAGGTTGGATGTAGATTCTGTGGTCGAGGAATCCAAG TGAAGAAAGCATCTAA | SEQ ID NO: 1398 | |
| 531 | A_24_P371353 | C3orf63 | GTCAGTGCAAGAAGAAATGAGAAATTACTTCTTATCTGGTTATAGT GAAAGCTTGGATAGAG | SEQ ID NO: 1399 | Homo sapiens chromosome 3 open reading frame 63 (C3orf63), mRNA [NM_015224] |
| 532 | A_24_P374319 | RAP2C | ATTGTGTGTGATGTTCAAATAAAGTGGATCTACATTGATGTGA TTTATAGGTCAGACATG | SEQ ID NO: 1400 | Homo sapiens RAP2C, member of RAS oncogene family (RAP2C), mRNA [NM_021183] |
| 533 | A_24_P37519 | LZTFL1 | GCTAGGTAGAATTTGTACTTGTTTTCTTGGTAGGAGTTTGAAA TATTCTGTACAGTACG | SEQ ID NO: 1401 | Homo sapiens leucine zipper transcription factor-like 1 (LZTFL1), mRNA [NM_020347] |
| 534 | A_24_P375599 | LOC731681 | TGTATGTCACTTGGCCATCAAGTCGTTATCCAGAATGGGTCT CTTGTTGAAATCCGAA | SEQ ID NO: 1402 | PREDICTED: Homo sapiens similar to 60S ribosomal protein L9 (LOC731681), mRNA [XR_019544] |
| 535 | A_24_P375849 | ENST00000359659 | AAGAAGCTGTGCAACAAGAATAGCAGGCTATGTCACACATCGAT GAAGGGGATTCAGAGA | SEQ ID NO: 1403 | G6BT90 MOUSE (G6BT90) 1C, 11 days embryo whole body cDNA, RIKEN full-length enriched library, clone:2610021H19 product:ribosomal protein S17, full insert sequence. (Fragment), partial (96%) [THC2555910] |
| 536 | A_24_P381625 | PSMC6 | ATGAAAGCAGTCAGAAAAGTGGCTGACTGGATCCTGAGTC TAAATTGGACTACAAA | SEQ ID NO: 1404 | Homo sapiens proteasome (prosome, macropain) 26S subunit, ATPase, 6 (PSMC6), mRNA [NM_002806] |
| 537 | A_24_P383999 | RPS3A | TGGTTTTACTAAAAACGAACAATGAGATACAGAATACAGAAGAGCCTT ATGCCAGGAGCAACG | SEQ ID NO: 1405 | Homo sapiens ribosomal protein S3A (RPS3A), mRNA [NM_001006] |
| 538 | A_24_P384411 | A_24_P384411 | AGCAAATCAATAACGAGTGAAGCTTTGACAGATAATGCTTG ACAGGTCGATCTGTTG | SEQ ID NO: 1406 | |
| 539 | A_24_P384539 | LOC730452 | CAAGAAAAGCTGGCAACTTGTCTATGTACCCAAACCCAAATTG GCATTGTCATCAGGA | SEQ ID NO: 1407 | PREDICTED: Homo sapiens similar to 60S ribosomal protein L7 (LOC730452), mRNA [XM_001125895] |
| 540 | A_24_P387869 | PKN2 | TTGTCAGAGATCATTTATATTACCTTGGAAATTGTTTATTACC CAAGATCCTTTGGGAG | SEQ ID NO: 1408 | Homo sapiens protein kinase N2 (PKN2), mRNA [NM_006256] |
| 541 | A_24_P389612 | ARL5B | ATTAATGCATTCACATGATGAGTTCTTGAAAATGGTTCAAAAGGA TGTTTCCTGATGGTG | SEQ ID NO: 1409 | ADP-ribosylation factor-like protein 5B (ADP-ribosylation factor-like protein 8) [Source:Uniprot/SWISSPROT;Acc:Q96KG2] [ENST00000377275] |
| 542 | A_24_P392231 | LOC641784 | CCATCAATATTGACAAGTGGATCGATGGAGTGGGCAAGAAGGGT GCCCCTGCGGAACTCA | SEQ ID NO: 1410 | xr65h07.x1 NCI_CGAP_Ov26 Homo sapiens cDNA clone IMAGE:2764093 3' similar to gb:X69181 60S RIBOSOMAL PROTEIN L31 (HUMAN)., mRNA sequence [AW302767] |
| 543 | A_24_P39375 | CCPG1 | TAGTTTTTGTGGCTGGAAGGAAACTTGATCAGTTCCATCCATAATAAGT TTTTCCTAAAGGGTGT | SEQ ID NO: 1411 | Homo sapiens cell cycle progression 1 (CCPG1), transcript variant 1, mRNA [NM_004748] |
| 544 | A_24_P393811 | TMCO1 | AGATGACAGCCACAGCTGTTCCTTGCATTTCCTTGCATCGATATTCCT GTACTATGTCCATTCG | SEQ ID NO: 1412 | Homo sapiens transmembrane and coiled-coil domains 1 (TMCO1), mRNA [NM_019026] |

Fig. 3-30

| No. | Probe ID No. | Symbols of genes | Sequence | SEQ ID NO: | Descriptions of genes (letters and numbers within [ ] indicates GenBank accession No.) |
|---|---|---|---|---|---|
| 545 | A_24_P396720 | PPP1CB | TTGTTGAAGCAGTAGCTTCTACATTGGTTGACTTAGACCGTAAGCTTTTTAAGTTTCTC | SEQ ID NO: 1413 | Homo sapiens protein phosphatase 1, catalytic subunit, beta isoform (PPP1CB), transcript variant 1, mRNA [NM_002709] |
| 546 | A_24_P399942 | ATP11C | TGAGGATGTTACCTACTAAACTGAAAACATTCATTTCGATATCTACTTACACATACAGCAG | SEQ ID NO: 1414 | Homo sapiens ATPase, Class VI, type IIC (ATP11C), transcript variant 1, mRNA [NM_173694] |
| 547 | A_24_P40417 | FMR1 | TTGTGAGTTTGTTTCTTTGAATTTTCATTTACAGTTAGTTTTCCTTGCATACAAACAAG | SEQ ID NO: 1415 | Homo sapiens fragile X mental retardation 1 (FMR1), mRNA [NM_002024] |
| 548 | A_24_P405002 | PDIK1L | TGGTGGTAAGGGATACTTTGTCATTATGATGAAGTAAGTGTTAAGTGTCAGATAAAATAGC | SEQ ID NO: 1416 | Homo sapiens PDLIM1 interacting kinase 1 like (PDIK1L), mRNA [NM_152835] |
| 549 | A_24_P405298 | PPP1CB | GTATTAGGTTAGGTCAGAAAGGTTTTATGTGAGGTGATTAAATAAGTTGGTGATTGGAGG | SEQ ID NO: 1417 | Homo sapiens protein phosphatase 1, catalytic subunit, beta isoform (PPP1CB), transcript variant 1, mRNA [NM_002709] |
| 550 | A_24_P405430 | TIA1 | GGATTTTCTGTTGTTAAATCACAAAAATGATAGTCCCAAATCGTTCTTTATGAGG | SEQ ID NO: 1418 | Homo sapiens cDNA FLJ36425 fis, clone THYMU2011482. [AK093744] |
| 551 | A_24_P406034 | SLC35A1 | ATGACAGAGTATTTTGTCCTAGCAGGATAAAGACCTAGCTCTTTCTTACAAGAGGCAGAA | SEQ ID NO: 1419 | Homo sapiens solute carrier family 35 (CMP-sialic acid transporter), member A1 (SLC35A1), mRNA [NM_006416] |
| 552 | A_24_P409681 | A_24_P409681 | AGATGAGCTCGCTGCCGGCATTGAGATGCATTCTTGAAAAGGAACAGATGTTCATAAAC | SEQ ID NO: 1420 | |
| 553 | A_24_P414556 | TTC33 | TACTGAACATTTGGTATATTGTTTGAGTAATGGATGTTTGTTTTGTGTAATTTGTGA | SEQ ID NO: 1421 | Homo sapiens tetratricopeptide repeat domain 33 (TTC33), mRNA [NM_012382] |
| 554 | A_24_P414952 | TMEM168 | TTTTGACTGAAAGTCAGAGGATAGGAAACAAGTATTTCTCTGGTATACATGTAATG | SEQ ID NO: 1422 | Homo sapiens transmembrane protein 168 (TMEM168), mRNA [NM_022484] |
| 555 | A_24_P41551 | LOC641790 | AAGGAAGATGGGAAGCTCCTGATGTGCCATTCATATGAGGCACACAAAGTAGTCTGGAAA | SEQ ID NO: 1423 | PREDICTED: Homo sapiens similar to ribosomal protein L31 (LOC641790), mRNA [XR_018025] |
| 556 | A_24_P417281 | TXNDC10 | ATGATGAGTGATTCTTGGGAAGATAAATGTTAATGTTCCCAATAGTCAAGCTGTTTTGC | SEQ ID NO: 1424 | Homo sapiens thioredoxin domain containing 10 (TXNDC10), mRNA [NM_019022] |
| 557 | A_24_P418418 | RPS17 | GATGAACTTGAAAAGTTCAAAATGCCTCGGGGACCTCTTTGAATTTTTTCTGCAGTGCTGTATTATTT | SEQ ID NO: 1425 | Homo sapiens ribosomal protein S17 (RPS17), mRNA [NM_001021] |
| 558 | A_24_P418712 | A_24_P418712 | AGGGTCAACAAAGCGTGTCTGGGCCAAAGAAATAAGGAATATCGATACCATATCTGTGTTA | SEQ ID NO: 1426 | |
| 559 | A_24_P450172 | AK095515 | ATGCAGACTGAATAAAGCTACTTAAACCAGAGTAATTTGGGATATTAATCCTTAGGGTAC | SEQ ID NO: 1427 | Homo sapiens cDNA FLJ37832 fis, clone BRSSN2009630. [AK095151] |
| 560 | A_24_P487736 | CXorf23 | TGGATAGCTTACTATGTGTAAGCAAATCGATGGATTTTAAATGAAATTTTTAGGGCC | SEQ ID NO: 1428 | Homo sapiens chromosome X open reading frame 23 (CXorf23), mRNA [NM_198279] |
| 561 | A_24_P497226 | RPS6KB1 | TAACATTTATAGCACAAGTATTATCTCAGGTTATCCGGAATAACATCTGAAAGATGGG | SEQ ID NO: 1429 | Homo sapiens ribosomal protein S6 kinase, 70kDa, polypeptide 1 (RPS6KB1), mRNA [NM_003161] |
| 562 | A_24_P50437 | BC065737 | TGAGAGAATGATGAAGTTGCATTTAGAAAAATTCCTGATTACTGAAGATGTTCAGGGGAAAA | SEQ ID NO: 1430 | Homo sapiens cDNA clone IMAGE:30404477, partial cds. [BC065737] |
| 563 | A_24_P50472 | LOC649839 | TAAAAGTAGAAAAGAAGATTGTGCTGGGGCTTGAGTGTGCATTCAGCCCAACTGCAGAATCCAA | SEQ ID NO: 1431 | PREDICTED: Homo sapiens similar to large subunit ribosomal protein L36a (LOC649839), mRNA [XM_001129410] |

Fig. 3-31

| No. | Probe ID No. | Symbols of genes | Sequence | SEQ ID NO: | Descriptions of genes (letters and numbers within [ ] indicates GenBank accession No.) |
|---|---|---|---|---|---|
| 564 | A_24_P50554 | LOC391655 | TGAAGGGTTTAGATGTAGAATCTCTGGTCATTGAGTATAAGGGAGTAAACAAAGACCTA | SEQ ID NO: 1432 | PREDICTED: Homo sapiens similar to 60S ribosomal protein L17 (L23) (LOC391655), mRNA [XR_018405] |
| 565 | A_24_P50567 | A_24_P50567 | CGTTGTAATTCAAAAACTACCAGAACATGAATCGAATGGCATGGTTGCTCTGGACTA | SEQ ID NO: 1433 | |
| 566 | A_24_P58403 | ROCK1 | TTAGAGGTTGTTGGACTTTCATAAATTGAGTACAATGTTTGCATCAAATACTGCTAC | SEQ ID NO: 1434 | Homo sapiens Rho-associated, coiled-coil containing protein kinase 1 (ROCK1), mRNA [NM_005406] |
| 567 | A_24_P54178 | TMED5 | GCTCTGATATGCATTTGGATGATTAAGTTATGCTGTTCTTCATGTGAATGTGAAGACA | SEQ ID NO: 1435 | Homo sapiens transmembrane emp24 protein transport domain containing 5 (TMED5), mRNA [NM_016040] |
| 568 | A_24_P551028 | LOC339745 | TGGAGTTGAACAAATATTGAGTGCCTATCATATGAAGAGTAAGTCCTACTAGGAATGA | SEQ ID NO: 1436 | Homo sapiens hypothetical protein LOC339745 (LOC339745), mRNA [NM_001016664] |
| 569 | A_24_P561223 | THC2697551 | TTATGCCCAGTTACATACAAGGATGCTGGCATATATTCAGGGACCCTAAAGTTTATAACAT | SEQ ID NO: 1437 | ALU1_HUMAN (P39188) Alu subfamily J sequence contamination warning entry, partial (8%) [THC2697551] |
| 570 | A_24_P56240 | CPNE8 | TACAACTATGTGACTTAGTGCACAACACATGTGTGAAATAATCCTACTGTATATACTGAC | SEQ ID NO: 1438 | Homo sapiens copine VIII (CPNE8), mRNA [NM_153634] |
| 571 | A_24_P56252 | AF086032 | GTATCTAAAACTGAACAGCTAGTGTGCTATATTCATTTTATTGTAGTATTGAGCAGACC | SEQ ID NO: 1439 | Homo sapiens full length insert cDNA clone YW25G09. [AF086032] |
| 572 | A_24_P57837 | THC2567891 | AGAAATCGGGAAGAACCTCTTATGCCAGTACGAGGCAAATGGGGAAGAAGATGATGGAAA | SEQ ID NO: 1440 | Q6NXR8_HUMAN (Q6NXR8) Ribosomal protein S3a, partial (91%) [THC2567891] |
| 573 | A_24_P587938 | A_24_P587938 | CTTCAAAGAACAAAAGTGGAGATGCTGGCAACAGGGAGGACCAGATTAAGAGTCTTAT | SEQ ID NO: 1441 | |
| 574 | A_24_P606663 | LOC392030 | TGTGCAGGTTGCCCAGGAAAACGTAATGCGGGTGAAGATTGAGTATGCAGGCAAATAAGCTCCATACTTT | SEQ ID NO: 1442 | PREDICTED: Homo sapiens hypothetical LOC392030 (LOC392030), mRNA [XR_018063] |
| 575 | A_24_P62659 | TSPAN2 | CGGTTTTTGGAGTATAAGCTTTCCAAAAATATGGGTATGAGTAAAATTAGAGAATTCAGCAC | SEQ ID NO: 1443 | Homo sapiens tetraspanin 2 (TSPAN2), mRNA [NM_005725] |
| 576 | A_24_P62860 | STAM2 | GTGTATATGGTACTTGATCTACACTTAAGTGGAAAAATTAGGCAGTATTTGAAAGCTCAGT | SEQ ID NO: 1444 | Homo sapiens signal transducing adaptor molecule (SH3 domain and ITAM motif) 2 (STAM2), mRNA [NM_005843] |
| 577 | A_24_P630039 | AL049321 | AACATGAGACAATACAAAAGTTAGATTTTTGGACCATATTAAAACTGGAAGAAGACAGGGG | SEQ ID NO: 1445 | Homo sapiens mRNA; cDNA DKFZp564D156 (from clone DKFZp564D156). [AL049321] |
| 578 | A_24_P66125 | STAG2 | TAATCATTCCATGCGTTAATATGGTTGCAATACAGAGAATATCTTCAGAATGGGTGAATACC | SEQ ID NO: 1446 | Homo sapiens stromal antigen 2 (STAG2), transcript variant 4, mRNA [NM_006603] |
| 579 | A_24_P675947 | ENST00000389400 | CTTGATGGGAAGGTAGCAGTTCTGGAAAAAGCTACTGAGAAGAGACAGGTTCTAAAGTT | SEQ ID NO: 1447 | similar to 40S ribosomal protein S3a (v-fos transformation effector protein) (LOC391706), mRNA [Source:RefSeq_dna;Acc:XR_017186] [ENST00000389400] |
| 580 | A_24_P685729 | A_24_P685729 | TTGAAGGTTATGTTGATGTCAAGAGTATCAGTGATGATTTGCTTGTCTGTTTTTGTGTGG | SEQ ID NO: 1448 | |
| 581 | A_24_P688133 | AK124299 | TAGGCATATCTGAGGAAAATATGTTGTTTAGTGATATGCCCCAATAAGTGATTGATTTC | SEQ ID NO: 1449 | Homo sapiens cDNA FLJ42306 fis, clone TRACH2001646. [AK124299] |

Fig. 3-32

| No. | Probe ID No. | Symbols of genes | Sequence | SEQ ID NO. | Descriptions of genes (letters and numbers within [ ] indicates GenBank accession No.) |
|---|---|---|---|---|---|
| 582 | A_24_P6975 | LOC342994 | GGAAGACTTCGAGGGGTTCGTGCTGTAAGACGTAAGTTCTTATGAAATTGTCAAAAAGA | SEQ ID NO: 1450 | PREDICTED: Homo sapiens similar to ribosomal protein L34 (LOC342994), mRNA [XM_933484] |
| 583 | A_24_P703614 | | AAGAACATTACCGGAATGGAGGTCTGCACTGTAAGTCATGAGTAGCAGCTTTGTGTGTG | SEQ ID NO: 1451 | |
| 584 | A_24_P712350 | CHML | GTGTAGAAGACTATAAAAAGGGCTTTATAACTGATGTTTTGAGATACTCACTTTGAGTGG | SEQ ID NO: 1452 | Homo sapiens choroideremia-like (Rab escort protein 2) (CHML), mRNA [NM_001821] |
| 585 | A_24_P7181 | | TCATGGTCGGATTAAGTCAGACGTGATGTCTCCGTGCGACGATGGAAATGATCGTTAGTGA | SEQ ID NO: 1453 | |
| 586 | A_24_P75158 | PTAR1 | CCATTAGATTTGTTCTTATGTGACCATGACGAACAGCAGGTATAAAGTATTGTATTTCTG | SEQ ID NO: 1454 | Homo sapiens mRNA; cDNA DKFZp313P0917 (from clone DKFZp313P0917). [AL832663] |
| 587 | A_24_P755505 | | ATACAGAAGACCTTCTTTATGCTCAGCACCAGCAACAGAGAAAAGATAAAATGCTGAAGAAGCCCAA | SEQ ID NO: 1455 | |
| 588 | A_24_P76358 | LOC643981 | TTACTGAAGAATGTTCAGGGACAAAAACTGCGTAAGTTCGGGCATGGATCTTATTCGTGACA | SEQ ID NO: 1456 | PREDICTED: Homo sapiens similar to 40S ribosomal protein S3a (V-fos transformation effector protein) (LOC643981), mRNA [XR_016444] |
| 589 | A_24_P77681 | PAIP1 | AGCTGATGCAGATTACCAAGAGAGAATACGAAGAATTAGTTGAAAGAGAGGAGTTTTTCC | SEQ ID NO: 1457 | Homo sapiens poly(A) binding protein interacting protein 1 (PAIP1), transcript variant 1, mRNA [NM_006451] |
| 590 | A_24_P781846 | AK024092 | ACTTTTTATAGAATGTTCTATCGTGGTAGTACAAGGACTTTGTTACTTTGGCTGC | SEQ ID NO: 1458 | Homo sapiens cDNA FLJ14030 fis, clone HEMBA1004086. [AK024092] |
| 591 | A_24_P792734 | PSMC6 | AGAACGTTAACGGAGTTAGTCAAATCAAATGGATTTGATACTGCATAGAGTTAAA | SEQ ID NO: 1459 | Homo sapiens proteasome (prosome, macropain) 26S subunit, ATPase, 6 (PSMC6), mRNA [NM_002806] |
| 592 | A_24_P795230 | AK027541 | ACAAGTTCTAGGAGTTTGAACTTTGGGTCAAGATGTTAATTGGTTTAATGTAGGAAGGT | SEQ ID NO: 1460 | Homo sapiens cDNA FLJ14635 fis, clone NT2RP2001196. [AK027541] |
| 593 | A_24_P80915 | BCLAF1 | AACTGTGTCAATGATGGTAATGAGAGCAAAGTTGTACATTAAATTAAGGGTACCAGTTC | SEQ ID NO: 1461 | Homo sapiens BCL2-associated transcription factor 1 (BCLAF1), transcript variant 1, mRNA [NM_014739] |
| 594 | A_24_P81965 | RAP2A | TTCTTTGATGTTGCAACTTTGGGTTCGTTGTTTAAACTGTGATAGTCATGGTAACTGATGC | SEQ ID NO: 1462 | Homo sapiens RAP2A, member of RAS oncogene family (RAP2A), mRNA [NM_021033] |
| 595 | A_24_P82630 | SMCHD1 | TGTTTAATATATCAACACGTAAGAACAATTGAAATTTTCTTCTCAAGATTAATACTAGTCT | SEQ ID NO: 1463 | Homo sapiens mRNA for KIAA0650 protein, partial cds. [AB014550] |
| 596 | A_24_P83968 | LOC730887 | AGAAAGCCCAGCGAAGAACGTGGAACACGAGAGAGAAAGTTTTTCTGGTGTCTCTAAGAAGC | SEQ ID NO: 1464 | PREDICTED: Homo sapiens similar to 40S ribosomal protein S7 (S8) (LOC730887), mRNA [XR_015507] |
| 597 | A_24_P84408 | A_24_P84408 | AAGGTACATCCAGGAAGTGGTCATTGAGAAGTCATAGGCAGAGAAAAGATGGGGTGTTCTT | SEQ ID NO: 1465 | |
| 598 | A_24_P84808 | LOC729449 | GATTGCTTTGACAGATAACCGTTTGGATCGTCTTGGAAAATATGGCATCATCGTATGG | SEQ ID NO: 1466 | PREDICTED: Homo sapiens similar to 60S ribosomal protein L7 (LOC729449), mRNA [XR_015546] |
| 599 | A_24_P850187 | A_24_P850187 | TAAATGAAGTAATCTACAGCGGTGCTTATGGCAAAATGAATTGACTTGCAGCTTTCGTAC | SEQ ID NO: 1467 | |
| 600 | A_24_P859859 | THC2553238 | TTTAACGAGACGGTCTGCAGCCGTTTTTGCTGATATACTGAGGACACTGGGTCTCAGGAAT | SEQ ID NO: 1468 | T305349A cystic fibrosis antigen, [Homo sapiens] (exp=-1; wgp=0; cg=0), partial (6%) [THC2553238] |
| 601 | A_24_P867201 | AK029997 | CTGACATGTGATAAATATTTCAGTGACTTTCAGATTATTGCTGTTAGCGCTGTGTC | SEQ ID NO: 1469 | Homo sapiens cDNA FLJ12935 fis, clone NT2RP2004982. [AK029997] |

Fig. 3-33

| No | Probe ID No | Symbols of genes | Sequence | SEQ ID NO: | Descriptions of genes letters and numbers within [ ] indicates GenBank accession No.) |
|---|---|---|---|---|---|
| 602 | A_24_P886040 | DCP2 | CATTTGAACAGAGGTTTCATTGTGTTTCTAGATTTATGTTTGT AGTTGAACAGCAACTG | SEQ ID NO: 1470 | Homo sapiens DCP2 decapping enzyme homolog (S. cerevisiae) (DCP2), mRNA [NM_152624] |
| 603 | A_24_P890536 | CR627148 | AATTGCCTTCTTGTAACCGTAAGTATGGTGAAGCAGAATTGAAT TCTACAAAGTCTTTC | SEQ ID NO: 1471 | Homo sapiens mRNA; cDNA DKFZp779F2127 (from clone DKFZp779F2127). [CR627148] |
| 604 | A_24_P91852 | DYNLT3 | ATACATATACAGAGCGGAACCAATAAGTCATTCATTGAAATTTCGGACAG GAATAAGCTTAGCGTT | SEQ ID NO: 1472 | Homo sapiens dynein, light chain, Tctex-type 3 (DYNLT3), mRNA [NM_006520] |
| 605 | A_24_P91916 | NXT2 | AAGGATGCTTTCTTTGTAGTAGTACGTGATTGAAACTTACAGGTTTTAT TCTACTACTAGTGAGG | SEQ ID NO: 1473 | Homo sapiens nuclear transport factor 2-like export factor 2 (NXT2), mRNA [NM_018698] |
| 606 | A_24_P931282 | THC2726401 | GGAAATATTTCTCCTCTAATGCATGAAATCATGTTGAAGTAAT CTACTGGAGATTACAC | SEQ ID NO: 1474 | Q26195_PLAVI (Q26195) Pva1 protein, partial (14%) [THC2726401] |
| 607 | A_24_P935988 | BCAT1 | ATGGTCTGAAGGTTTTGTAGAAGCAGAATTAAACATCAAAATG GCTTTGTTACAACGAGA | SEQ ID NO: 1475 | Homo sapiens branched chain aminotransferase 1, cytosolic (BCAT1), mRNA [NM_005504] |
| 608 | A_24_P937095 | SLC30A1 | TTTGATGTAGCTCTACGGATACTATGTGGTAATGGCTATTTGTT TTACTAACAAGCTGTG | SEQ ID NO: 1476 | Zinc transporter 1 (ZnT-1) (Solute carrier family 30 member 1). [Source:Uniprot/SWISSPROT;Acc:Q9Y6M5] [ENST00000357000] |
| 609 | A_24_P940426 | QKI | AAGCTGTTTGAATGAGTCTTAAAAATTATACTACTGTTAAGTGGA CCAAGTTTGCTGAAGG | SEQ ID NO: 1477 | Homo sapiens quaking homolog, KH domain RNA binding (mouse) (QKI), transcript variant 4, mRNA [NM_206855] |
| 610 | A_24_P940725 | C6orf111 | AATTTATGATTAGTGAGTGGTCTAACAGTTTAAGGCATTGATAAC TTACAAGTAGAGTGGG | SEQ ID NO: 1478 | Splicing factor, arginine/serine-rich 130 (Serine-arginine-rich splicing regulatory protein 130) (SRrp130) (SR-rich protein) (SR-related protein). [Source:Uniprot/SWISSPROT;Acc:Q8IF01] [ENST00000369239] |
| 611 | A_24_P940778 | BDP1 | TCGGAGGGGAAATTGTCTATAAGTAGGCATTTATTTCATGATTG ATATGTGACAAGAAATC | SEQ ID NO: 1479 | Homo sapiens B double prime 1, subunit of RNA polymerase III transcription initiation factor IIIB (BDP1), mRNA [NM_018429] |
| 612 | A_24_P941643 | PLCB1 | ATGTAGTTGCAGTTTTGTGCCTTATGTATTTGGCCTTGTTGTTG TCGAATGTGTGAAATT | SEQ ID NO: 1480 | Homo sapiens phospholipase C, beta 1 (phosphoinositide-specific) (PLCB1), transcript variant 2, mRNA [NM_182734] |
| 613 | A_24_P941699 | PCGF5 | TGGTATATTCGAACTACAGCTTTCTAAGGATAGGACTAGTTTCAT GTCTAGAATACACTG | SEQ ID NO: 1481 | Homo sapiens polycomb group ring finger 5 (PCGF5), mRNA [NM_032373] |
| 614 | A_24_P944458 | INSIG2 | ATGTATTCGTCTATCGATTAGTGAATAGTTCAAGTCTGTTTAAG AGTGTATTGAGATGGC | SEQ ID NO: 1482 | Homo sapiens insulin induced gene 2 (INSIG2), mRNA [NM_016133] |
| 615 | A_24_P95029 | TAX1BP1 | TGCTTGATTCCAGGTTTGATGTTCACAAGAAGTGTCCCCTCTG TGAGTTAATGTTTCCT | SEQ ID NO: 1483 | Homo sapiens Tax1 (human T-cell leukemia virus type 1) binding protein 1 (TAX1BP1), transcript variant 2, mRNA [NM_006024] |
| 616 | A_24_P99046 | STK38L | GCTATCTGTCTTTTGTGATGTAGAAATAAATGAAGCCTGGAATGAATT TAGTCGAATAGAGGTCC | SEQ ID NO: 1484 | Homo sapiens serine/threonine kinase 38 like (STK38L), mRNA [NM_015000] |
| 617 | A_32_P10100 | A_32_P10100 | TATGAGGAAATAGTACATCATCATGTTAGAAGCATAATGAATGGCTGGTC | SEQ ID NO: 1485 | |

Fig. 3-34

| No. | Probe ID No. | Symbols of genes. | Sequence | SEQ ID NO: | Descriptions of genes (letters and numbers within [ ] indicates GenBank accession No.) |
|---|---|---|---|---|---|
| 618 | A_32_P10424 | AX721252 | AAATTTGTCAAGAAGGAGAATGGGAACTGTAGATGTGCACAACTGATACCAGGCTGAAGAA | SEQ ID NO: 1486 | Sequence 212 from Patent WO0220754. [AX721252] |
| 619 | A_32_P105397 | THC2642694 | TAAAATGCTACACAGTATTCTACCATGCAGGCTGAATGTATATACAGTAATTCTCTGG | SEQ ID NO: 1487 | Q6IDT1_HUMAN (Q6IDT1) Protein transactivated by hepatitis B virus E antigen, partial (11%) [THC2642694] |
| 620 | A_32_P106732 | FANCM | AATCAAGCTGCTCAAGAATGGGGTTTTCAAAGACGTCTCACAATATTAAATGCACTTCAAT | SEQ ID NO: 1488 | Homo sapiens Fanconi anemia, complementation group M (FANCM), mRNA [NM_020937] |
| 621 | A_32_P107372 | GBP1 | GGTACTGAGCAGAGTCGTTAAGGTAAAAGTCTTGGGAAATATTTGGGCATTGGTCTAGGCAA | SEQ ID NO: 1489 | Homo sapiens guanylate binding protein 1, interferon-inducible, 67kDa (GBP1), mRNA [NM_002053] |
| 622 | A_32_P109522 | C6orf113 | TAGAAGGATGCTGTTTCTCTAGAGGAGGAAACTTGGCAGGAGACGAAGGTTCTGAAGTCTTTA | SEQ ID NO: 1490 | Homo sapiens chromosome 6 open reading frame 113 (C6orf113), mRNA [NM_145062] |
| 623 | A_32_P113154 | LOC730861 | ACCAGCAGTCCAAGAATCTGTTTAAAGTTCAGAGTTAAAACAGTAGCAAATAAAAAGTCC | SEQ ID NO: 1491 | PREDICTED: Homo sapiens similar to 40S ribosomal protein S3a (V-fos transformation effector protein) (LOC730861), mRNA [XR_015591] |
| 624 | A_32_P113634 | ZNF292 | GGGCCTTTTGGGTTTAATGAATAGTTCACCTGTGTTAAGACTTACTACCAATAAG | SEQ ID NO: 1492 | Zinc finger protein 292. [Source:Uniprot/SWISSPROT;Acc:O60281] [ENST00000339907] |
| 625 | A_32_P114215 | COMMD6 | AATTGCTATCATTGGGTTAAAGTGATGGACTTCAGTTTCGGCAAGCAAAACTAAATAAGGATGG | SEQ ID NO: 1493 | Homo sapiens COMM domain containing 6 (COMMD6), transcript variant 2, mRNA [NM_203495] |
| 626 | A_32_P1144 | AK091357 | GGGAGTTAATATTTAGATCTTACTACTAGGGATGTCATAGGTTTTAAGTGGTTTTAATGAGG | SEQ ID NO: 1494 | Homo sapiens cDNA FLJ34038 fis, clone FCBBF2005645. [AK091357] |
| 627 | A_32_P11451 | NMD3 | CAGTTTAGGGCAGTAGGTGCTTTTGTCATAAATATCTTCCTACGCAGATGAAAATGCTGC | SEQ ID NO: 1495 | Homo sapiens NMD3 homolog (S. cerevisiae) (NMD3), mRNA [NM_015938] |
| 628 | A_32_P115505 | ZNF294 | TGTGTGCAGAGGATTAATAGTTGAGAGTGAAGATGAAGTACTAGTGTGAGTTATAGATCTCTGGAA | SEQ ID NO: 1496 | Homo sapiens Zinc finger protein 294 (ZNF294), mRNA [NM_015565] |
| 629 | A_32_P11931 | LOC441073 | GTGTGATCCATGGGATCCGAAAGATGATGATGATGAAGTTCAGGTTGTACGTGGAGACTATAAA | SEQ ID NO: 1497 | PREDICTED: Homo sapiens similar to 60S ribosomal protein L26 (Silica-induced gene 20 protein) (SIG-20), (LOC441073), mRNA [XR_016376] |
| 630 | A_32_P12430 | SPG20 | TCAGGGTAAAGAATATGAAAACCTTAGACGTAATCCATGGTGGATAGGCATTATGGTTTC | SEQ ID NO: 1498 | Homo sapiens spastic paraplegia 20 spartin (Troyer syndrome) (SPG20), mRNA [NM_015087] |
| 631 | A_32_P124530 | THC2610143 | ATTAGGTGGGACTCAAAAGGGACATGTTTTGTTTTGTGAATTCACCTAAATGTCTCTCTA | SEQ ID NO: 1499 | AA490192 za43f10.r1 Soares_NhHMPu_S1 Homo sapiens cDNA clone IMAGE:823723 5', mRNA sequence [AA490192] |
| 632 | A_32_P125549 | RPL31P4 | TGTACAGACAGTCAATGTGGATGAGAGAACTAATCCGTGATCGTGAGATACATCAAATAAAG | SEQ ID NO: 1500 | PREDICTED: Homo sapiens ribosomal protein L31 pseudogene 4 (RPL31P4), mRNA [XR_018222] |
| 633 | A_32_P125917 | THC2753798 | GCTTATAAAGTGTAAGTGGAGAGACGCTAAATTGTGAGTACAAAGTTTCTTTTCACAACAG | SEQ ID NO: 1501 | BF233843 601904SSF1 NIH_MGC_54 Homo sapiens cDNA clone IMAGE:4132429 5', mRNA sequence [BF233843] |
| 634 | A_32_P128781 | A_32_P128781 | CATATATTGCATGGAGGGTACGGCGAATCTGAAGTCAGTAGAATGAACTAATCTACAAGAGTG | SEQ ID NO: 1502 | |
| 635 | A_32_P128930 | BC062780 | AGATGGGAAGAAGAGGAGTAGTGACAGGAGTAGTGACAGGAGTAAATGAAGACCTTTCATATCAT | SEQ ID NO: 1503 | Homo sapiens cDNA clone IMAGE:4700631, partial cds. [BC062780] |

Fig. 3-35

| No. | Probe ID No. | Symbols of genes | Sequence | SEQ ID NO: | Descriptions of genes (letters and numbers within [ ] indicates GenBank accession No.) |
|---|---|---|---|---|---|
| 636 | A_32_P135818 | RPS3A | CTTGCTTCATCGTTCTGTGTTGGTTTAATAAAAACGGAAGAATGAGATATGGAAGAC | SEQ ID NO: 1504 | Homo sapiens ribosomal protein S3A (RPS3A), mRNA [NM_001006] |
| 637 | A_32_P136319 | RPL36A | AAGTGATCAGTTCAAGTGTCATGTTTATCATGAAGAGAATAAAATCTTGAGTTTATG | SEQ ID NO: 1505 | Homo sapiens ribosomal protein L36a (RPL36A), mRNA [NM_021029] |
| 638 | A_32_P137266 | KIAA1799 | AAGTGGGACCCAAATCTACAATGTTTGTCAACATGTAATCCTTTGAATGAACGACAAG | SEQ ID NO: 1506 | Homo sapiens KIAA1799 protein (KIAA1799), mRNA [NM_032437] |
| 639 | A_32_P143323 | CR613267 | AGAGAAGCTCAAACAATGGGGTTTATGGAGTTACATACAAGGATCCTGCATATTTCAGGG | SEQ ID NO: 1507 | full-length cDNA clone CS0DL011YP14 of B cells (Ramos cell line) Cot 25-normalized of Homo sapiens (human) [CR613267] |
| 640 | A_32_P145153 | RPL31 | ATCGGTGTGCAGCGTCCAGAAAACGTAATGAGGATGAAGATCACCAAATAAGCCATAT | SEQ ID NO: 1508 | Homo sapiens ribosomal protein L31 (RPL31), mRNA [NM_000993] |
| 641 | A_32_P145159 | | CATACATGGGTGTACATAAAGGTTTGTGGAAAAGTTAGTTGTGTGATTATTCTCTTG | SEQ ID NO: 1509 | |
| 642 | A_32_P147747 | THC2575761 | TTGATACCTCTGCATTCTGCATGACAAACGCCCAATTTGGGCTTGTGCAGGTACATAGAAGTTG | SEQ ID NO: 1510 | HUMRPL7Y ribosomal protein L7 [Homo sapiens] (expr=-1; wgp=0; cg=0), partial (49%) [THC2575761] |
| 643 | A_32_P148524 | C1orf27 | GAAAAACAGATGTTATCTCAGGAGAGAAATTGAGTAAAGAGACTACAAAGGATGATGTC | SEQ ID NO: 1511 | Homo sapiens chromosome 1 open reading frame 27 (C1orf27), mRNA [NM_017847] |
| 644 | A_32_P1516 | AA714537 | CTGAGGATAAGAGGATCTTCGGTATCTGATTTTTGTGGTTTTTAGTAAAACCAAGAGAGAA | SEQ ID NO: 1512 | nw20g12.s1 NCI_CGAP_GC90 Homo sapiens cDNA clone IMAGE:1241062 3' similar to gb:M84711 40S RIBOSOMAL PROTEIN S3A (HUMAN), mRNA sequence [AA714537] |
| 645 | A_32_P153725 | KIAA1033 | TTTTGTAAAAGATAGCCAAGTTGTTACCTCCACTTGAGTGGGGTTTCCTTTTGGGCAAT | SEQ ID NO: 1513 | Homo sapiens KIAA1033 (KIAA1033), mRNA [NM_015275] |
| 646 | A_32_P155364 | RPL7 | TGAACAGGCTTATTAGAAAAATGAAAGCAAAGGTGTCACCAAGATTATTTCTAAGCTGG | SEQ ID NO: 1514 | Homo sapiens ribosomal protein L7 (RPL7), mRNA [NM_000971] |
| 647 | A_32_P155811 | CD2AP | AAAGCATGGTCTCTCTCAAAAGAAATTAAAGGATATTTATTGCCAGTCGTGTCAGTC | SEQ ID NO: 1515 | Homo sapiens CD2-associated protein (CD2AP), mRNA [NM_012120] |
| 648 | A_32_P158746 | RPL17 | TTTTGCTGAGATGGTAAAAAATGCAGAGAGTAATGGTGAAGTTAAAGGGTTAGATGTAG | SEQ ID NO: 1516 | Homo sapiens ribosomal protein L17 (RPL17), transcript variant 1, mRNA [NM_000985] |
| 649 | A_32_P159651 | PCAF | GAGTGTGTCTAGATTTCTAATGAAGAATCATGATACAGTTTGGATTAAGTATGTTTGGAC | SEQ ID NO: 1517 | Homo sapiens p300/CBP-associated factor (PCAF), mRNA [NM_003884] |
| 650 | A_32_P162150 | MAP3K7IP3 | AGGCATAGAAGAATTGTGCCTCTAAAAATATCAATGATGTATCCTGGAATGTGAAGATGTC | SEQ ID NO: 1518 | Homo sapiens mitogen-activated protein kinase kinase kinase 7 interacting protein 3 (MAP3K7IP3), mRNA [NM_152787] |
| 651 | A_32_P164203 | THC2683448 | TTGATGGTTCATTTCACGAGGCTATTGTATGGATTTACTGTGGAGTGCTGTTTACCACATGAT | SEQ ID NO: 1519 | Q7NZG3_PASP1 (Q7NZG3) Ferric uptake regulator, partial (8%) [THC2683448] |
| 652 | A_32_P167122 | RCOR3 | GTATCTGAGGGATGTCCTGTAATCTGATTTACATGCATTACAGCACACAGTAGAAAAGT | SEQ ID NO: 1520 | Homo sapiens REST corepressor 3 (RCOR3), mRNA [NM_018254] |
| 653 | A_32_P170444 | SUB1 | TAGGTATCTCTCGAAATTCTTTGCAGTTGATTGTTTTTATGGCAGTTAATCCAGTGAAAAC | SEQ ID NO: 1521 | Activated RNA polymerase II transcriptional coactivator p15 (SUB1 homolog) (Positive cofactor 4) (PC4) (p14). [Source:Uniprot/SWISSPROT;Acc:P53999] [ENST00000265073] |

Fig. 3-36

| No. | Probe ID No. | Symbols of genes | Sequence | SEQ ID NO: | Descriptions of genes (letters and numbers within [ ] indicates GenBank accession No.) |
|---|---|---|---|---|---|
| 654 | A_32_P170736 | AK098422 | ACGTCATAATTGTTGAGGGCAAGGTTCATTGTTGATAGTGCAAAGTGTCGCTGTTGTGAT | SEQ ID NO: 1522 | Homo sapiens cDNA FLJ25556 fis, clone JTH02629. [AK098422] |
| 655 | A_32_P172578 | THC2661509 | ACTTAATCAATGTGTCAAGCATTCTAGGCATTCTGCATCCATGGATTCCTTCTGTTCC | SEQ ID NO: 1523 | |
| 656 | A_32_P173385 | ENST00000334683 | AAATGCAAGCAGAGTGATGCTGAACTTAAGCGGTTCAGATGTAGATTCTCTGGTCATTGAAGCA | SEQ ID NO: 1524 | PREDICTED: Homo sapiens similar to 60S ribosomal protein L17 (L23) (LOC550848), mRNA [XR_019013] |
| 657 | A_32_P176819 | CMAH | GATTATATATGGTAGGTCTGATTCTGAAGATAGAAAGAATTCAATGGTGGAATTTGTCTGC | SEQ ID NO: 1525 | Homo sapiens cytidine monophosphate-N-acetylneuraminic acid hydroxylase (CMP-N-acetylneuraminate monooxygenase) (CMAH) on chromosome 6 [NR_002174] |
| 658 | A_32_P177040 | WBSCR19 | AACTTTGTATGTATTATTACACGTTGCTGAAGGGAGGCATGGTTTTTATCTGTATAC | SEQ ID NO: 1526 | Homo sapiens Williams Beuren syndrome chromosome region 19 (WBSCR19), mRNA [NM_175064] |
| 659 | A_32_P177953 | GCLM | ATTATTGTATGTGGCTAGCAGTTCATCGTTCTGAAAATATGCATTCAAGAGAAATGTG | SEQ ID NO: 1527 | Glutamate—cysteine ligase regulatory subunit (EC 6.3.2.2) (Gamma-glutamylcysteine synthetase) (Gamma-ECS) (GCS light chain) (Glutamate—cysteine ligase modifier subunit). [Source:Uniprot/SWISSPROT;Acc:P48507] [ENST00000370238] |
| 660 | A_32_P178966 | ENST00000379426 | GTAATATACAGGGTGAACTCTTACTGATACACAAGAGACAACTGTTAAAAAGTGAATCC | SEQ ID NO: 1528 | Novel protein. [Source:Uniprot/SPTREMBL;Acc:Q5T4T1] [ENST00000379426] |
| 661 | A_32_P180435 | WBSCR19 | GTTTCGAATCTTTGTATCTATTATTACACGTGCTGCTGAAGGGAAGCATGTTTTATGTATG | SEQ ID NO: 1529 | Homo sapiens Williams Beuren syndrome chromosome region 19 (WBSCR19), mRNA [NM_175064] |
| 662 | A_32_P186981 | RPL17 | CATTGAGATGATCCTTACGGAAAAGGAAGCAGATTGTTCCTAAACCAGAAGAGGAGGTTGC | SEQ ID NO: 1530 | Homo sapiens ribosomal protein L17 (RPL17), transcript variant 1, mRNA [NM_000985] |
| 663 | A_32_P190488 | hCG_26523 | CCCAGCAAGGTGGTTATCACTAGGCTAAAAGTGGACAAAGACCGCAAAAAATCCTGAA | SEQ ID NO: 1531 | PREDICTED: Homo sapiens similar to 60S ribosomal protein L26 (LOC646161), mRNA [XR_018048] |
| 664 | A_32_P193322 | RICTOR | ACCACATGAGTTTCTTCTTTATTTAGTAGTATATGTGTTCTGGGTGGTTATTTGGAGGTTCTGC | SEQ ID NO: 1532 | Homo sapiens rapamycin-insensitive companion of mTOR (RICTOR), mRNA [NM_152756] |
| 665 | A_32_P195387 | DKFZp779L1068 | ATATAAGCTTGGAATTCATTGTAATTATGTTGTAAGAAAGATTGTGTAGTATCAGTTCGC | SEQ ID NO: 1533 | Homo sapiens cDNA clone IMAGE:5555490. [BC110326] |
| 666 | A_32_P196483 | RPS3A | GGGCCAAGAAGAAAGTGGTTGATCCATTTTGTAAGAAAGATTGGTATGATGTGAAAGCA | SEQ ID NO: 1534 | Homo sapiens ribosomal protein S3A (RPS3A), mRNA [NM_001006] |
| 667 | A_32_P19752 | FAM76B | TTGTGCTTTAGCCTCTGTTTCCACTATTAATTAGCATTTACCAGCAGGGTCATTTTGAG | SEQ ID NO: 1535 | Homo sapiens family with sequence similarity 76, member B (FAM76B), mRNA [NM_144664] |
| 668 | A_32_P20240 | SP3 | GTTAGGGTCTTAATTGTAGTTAAATTCCAGTACTGCCACTGAGACCCAAAAGTTTTGT | SEQ ID NO: 1536 | Homo sapiens mRNA; cDNA DKFZp686N17231 (from clone DKFZp686N17231). [BX648857] |
| 669 | A_32_P202486 | RPL21 | AAGAGGAGAGGCAGGGGATATATGTTCTGTAGGGCTTTTAGAAAAGATTGGGAATGGGTAC | SEQ ID NO: 1537 | Homo sapiens ribosomal protein L21, clone IMAGE:6605632, complete cds. [BC104478] |
| 670 | A_32_P203320 | ROCK1 | AACCGCCATGAGTATCAAGATCAGCTCATGGAAGGAGTAAAGAAAATATCTCAAAATGAG | SEQ ID NO: 1538 | Homo sapiens Rho-associated, coiled-coil containing protein kinase 1, mRNA (cDNA clone MGC:5269902), complete cds. [BC041849] |

Fig. 3-37

| No. | Probe ID No. | Symbols of genes | Sequence | SEQ ID NO: | Descriptions of genes (letters and numbers within [ ] indicates GenBank accession No.) |
|---|---|---|---|---|---|
| 671 | A_32_P203367 | RPS7 | ATCCTTGAGGACCTTGGTCTTCAGAAGGAAAATTGTGGGCAAGAG AATCCGGGTGAAACTA | SEQ ID NO: 1539 | Homo sapiens ribosomal protein S7 (RPS7), mRNA [NM_001011] |
| 672 | A_32_P204330 | AK093982 | AAACCGTGAGCTTTTTCGTCTTGGTAGCAGATATGTGAAA AACCTACCCAGAATTG | SEQ ID NO: 1540 | Homo sapiens cDNA FLJ36663 fis, clone UTERU2002826. [AK093982] |
| 673 | A_32_P205550 | RPL26L1 | AGGTAGTTCGAGGAGACACTACAAAGGTCAGCAAATTGGCAAGGTA ATCCAGGGTGTACAGAA | SEQ ID NO: 1541 | Homo sapiens ribosomal protein L26-like 1 (RPL26L1), mRNA [NM_016093] |
| 674 | A_32_P205553 | RPL26L1 | TTCCGAATCTCTGGAACATTCATTCCTGTTTTGTTAGGTGTG GCTCTGTAAATCTACT | SEQ ID NO: 1542 | Homo sapiens ribosomal protein L26-like 1 (RPL26L1), mRNA [NM_016093] |
| 675 | A_32_P207231 | AI630435 | TTGCTTGGCTTTTTCTTAAGGGTTCTGGAAGGAGGAAGGCTC CTTCTTGTTCTTCT | SEQ ID NO: 1543 | AI630435 ad10b05.y1 Hembase: Erythroid Progenitor Cells (LCB:ad library) Homo sapiens cDNA clone ad10b05 random, mRNA sequence [AI630435] |
| 676 | A_32_P208178 | RPS3A | GGAAAAGACGTAGAAAAAGGGTGGCAAATCTATTTATCCTCTCCA TGATGTGTTGGTTAGA | SEQ ID NO: 1544 | Homo sapiens ribosomal protein S3A (RPS3A), mRNA [NM_001006] |
| 677 | A_32_P21384 | RPL17 | AGATGTCACTTTACAGAGAAAGAGAGTGTACCATTCCGACATTACA ACGGTGGAAGTTGGCAG | SEQ ID NO: 1545 | Homo sapiens ribosomal protein L17 (RPL17), transcript variant 1, mRNA [NM_000985] |
| 678 | A_32_P220127 | RPL34 | CAAAGCTAGGCTGTCTGAACCGCTGGTAATAGAATTGTTCACC TTTATACGAAGAAGGT | SEQ ID NO: 1546 | Homo sapiens ribosomal protein L34 (RPL34), transcript variant 2, mRNA [NM_033625] |
| 679 | A_32_P223319 | ESCO1 | ATGCGTCGATTACTGGACTTCATTTTGATACTTGTCTATGGTG ATAGTGCCCTCTACTT | SEQ ID NO: 1547 | Homo sapiens establishment of cohesion 1 homolog 1 (S. cerevisiae) (ESCO1), mRNA [NM_052911] |
| 680 | A_32_P224666 | CAPZA2 | AATGCTGTTTTGAGATTCGGAAATTAAATGAAAATAGTTATTTC AGAAATAGCATTTAATG | SEQ ID NO: 1548 | Homo sapiens capping protein (actin filament) muscle Z-line, alpha 2 (CAPZA2), mRNA [NM_006136] |
| 681 | A_32_P22539 | hCG_28523 | ACTAGGAAAGGTCAGCAAATTGGCAAAGTCGGTCCAGGGTTTAGAGG AAGAAATATGTTAATCT | SEQ ID NO: 1549 | PREDICTED: Homo sapiens similar to 60S ribosomal protein L26 (Silica-induced gene 20 protein) (SIG-20), (LOC400055), mRNA [XM_374987] |
| 682 | A_32_P226786 | BC045174 | TTATTGGTGCATGTAAGGCATTATCCTGTCTTAATGAAGGATT AATGCGTTGATTGTT | SEQ ID NO: 1550 | Homo sapiens cDNA clone IMAGE:5273245. [BC045174] |
| 683 | A_32_P2333 | SUB1 | AGGAAGAAAAGTAGATTTGTTTAAATCGAGAACAATGGAGCCAGC TGACAGAACAGAGATTC | SEQ ID NO: 1551 | Homo sapiens SUB1 homolog (S. cerevisiae) (SUB1), mRNA [NM_006713] |
| 684 | A_32_P233304 | LIN9 | AAAGGTTCCGTATTCTTTGTTGGTATTGTGCACTGCAGAACT TTAGTGGACAGAGTTTAT | SEQ ID NO: 1552 | Homo sapiens lin-9 homolog (C. elegans) (LIN9), mRNA [NM_173083] |
| 685 | A_32_P233314 | EXOC8 | AGGATTGGGAATTTGGGACATGACATGTACTATAAAAGTCAGTC TATGTACATACTGCT | SEQ ID NO: 1553 | Homo sapiens exocyst complex component 8 (EXOC8), mRNA [NM_175876] |
| 686 | A_32_P234736 | RPL21 | GTTGTAAAGAAAGAAAGTTAAGGGCAAGATTCTTGCAAGAGAAT TAAATGTGCGTATTCAG | SEQ ID NO: 1554 | Homo sapiens ribosomal protein L21 (RPL21), mRNA [NM_000982] |
| 687 | A_32_P226895 | KIAA1600 | AATTCTTGGTCCGCTCCGTGGAGAAAAGACTCTTCAGATGGTGATTGT GTACCTACTCTCTCTT | SEQ ID NO: 1555 | KIAA1600 (KIAA1600), mRNA [Source:RefSeq_dna;Acc:NM_020940] [ENST00000369243] |
| 688 | A_32_P230710 | RPL23 | ACGAAAGTCATACCGTAGAAAAGATGGCCGTGTTTTGTTATTTG AAGATAATGCAGGAGT | SEQ ID NO: 1556 | Homo sapiens ribosomal protein L23 (RPL23), mRNA [NM_000978] |
| 689 | A_32_P231182 | RPL7 | GTAGAAGACAAGAAGAAGGTTCCGCTGTGCCAGAAACCCTTAA GAAAAAGGGAAGGAAT | SEQ ID NO: 1557 | Homo sapiens ribosomal protein L7 (RPL7), mRNA [NM_000971] |

Fig. 3-38

| No. | Probe ID No | Symbols of genes | Sequence | SEQ ID NO: | Descriptions of genes (letters and numbers within [ ] indicates GenBank accession No.) |
|---|---|---|---|---|---|
| 690 | A_32_P3742 | RFX3 | CCTCTCAAAATTGGCAGGAGGTAAATAATAGTTTGTGGGCGATTTGTATTGTGTAGTGTA | SEQ ID NO: 1558 | transcription factor RFX3 [Source:Uniprot/SWISSPROT:Acc:P48380] [ENST00000382004] |
| 691 | A_32_P43217 | PSMA6 | TTGTTGTTAGTTTACCAGATCCGTGATGGGACTTACCTGTGTGTTTGGTAACAACAAAGA | SEQ ID NO: 1559 | Homo sapiens proteasome (prosome, macropain) subunit, alpha type, 6 (PSMA6), mRNA [NM_002791] |
| 692 | A_32_P4532 | LOC643932 | GATTCCAGACAGCAGCATTGGAAAAGAGACATAGAAAAGGCTTGGCAATCTATCGTGTGCATGAT | SEQ ID NO: 1560 | PREDICTED: Homo sapiens similar to 40S ribosomal protein S3a (V-fos transformation effector protein) (LOC643932), mRNA [XR_017289] |
| 693 | A_32_P46765 | C12orf29 | TTAGAATAGGCAGTGATGATCACTAGGTAATTCTCATATCCATGCCTTTTTCTCCTGTTTAC | SEQ ID NO: 1561 | Homo sapiens chromosome 12 open reading frame 29 (C12orf29), mRNA [NM_001099894] |
| 694 | A_32_P49164 | AV714556 | AAATGAGAGCTTTGTTATTTGCCAAAGAAGAATTCATCATGTTCCTTCCTTTTTTCC | SEQ ID NO: 1562 | AV714556 AV714556 DCB Homo sapiens cDNA clone DCBAD806 5', mRNA sequence [AV714556] |
| 695 | A_32_P49392 | A_32_P49392 | AATTTTGGGAAATCTGGAAGAAGATGATGGAAATCATGAGGCAAGAGGTGCAGACAAATG | SEQ ID NO: 1563 | |
| 696 | A_32_P50417 | LOC649314 | AATCAGCCTGAATTTCTAAATGGAACTTCATCATTGTGGAAATCAGCAAGACTGCACTTC | SEQ ID NO: 1564 | Homo sapiens cDNA FLJ35212 fis, clone PROST1000136, [AK092531] |
| 697 | A_32_P54305 | LOC401397 | AGATATCTTAGGAAATCAGCAGTGTTCGGTTCTATAATCAGTGCCTCCTGAATGTTGAGGAG | SEQ ID NO: 1565 | Homo sapiens hypothetical LOC401397, mRNA (cDNA clone IMAGE:4244115), complete cds, [BC107860] |
| 698 | A_32_P58074 | RPS3A | GTTGCTTTACTAAAAAACCAGAAATCAGATACGGAAGACCTCTTATGCTCAGCAGCAA | SEQ ID NO: 1566 | Homo sapiens ribosomal protein S3A (RPS3A), mRNA [NM_001006] |
| 699 | A_32_P61857 | KIAA1468 | TCAGTGTACAGTTCCACTGGAATTTGACAGTGTCTCTACAGTCATGCAACTCGAAGTAG | SEQ ID NO: 1567 | Homo sapiens KIAA1468 (KIAA1468), mRNA [NM_020854] |
| 700 | A_32_P62342 | GLT8D3 | TGTGATGTAACTGATGTAACGATTGACAATCTATGTGTGCGTTTATACATTCATCTCTG | SEQ ID NO: 1568 | Homo sapiens glycosyltransferase 8 domain containing 3, mRNA (cDNA clone MGC:21651 IMAGE:4506300), complete cds, [BC039145] |
| 701 | A_32_P68566 | ARL1 | TTGGGTTACCTGCCTTGAAGGACCGAAAATGCAGATATGGGAGATATGAAAACGTCAGCAACCAAAG | SEQ ID NO: 1569 | Homo sapiens ADP-ribosylation factor-like 1 (ARL1), mRNA [NM_001177] |
| 702 | A_32_P7118 | PSMC6 | AGCAGACTGAGAAATGTTTGTACTGAAGCAGGTACGTTCGCAATTCGCCTCCTGATCATGA | SEQ ID NO: 1570 | Homo sapiens proteasome (prosome, macropain) 26S subunit, ATPase, 6 (PSMC6), mRNA [NM_002806] |
| 703 | A_32_P77571 | AK024584 | GTCATGCTGTTAATGAAGCATTATGCAGGTGTTAAAGATGATAGATGTAAGGTTATGAG | SEQ ID NO: 1571 | Homo sapiens cDNA: FLJ20931 fis, clone ADSE01282 [AK024584] |
| 704 | A_32_P81768 | TMEM167 | CCTCAGTAGTACTGTGACTACAATATTCATTCTGGAAATGTTATTCTGTTGTATCAGATACG | SEQ ID NO: 1572 | Homo sapiens transmembrane protein 167 (TMEM167), mRNA [NM_174909] |
| 705 | A_32_P83784 | CENTD1 | ACAGAGCCCATACTTCAGTCAGTAATCAGTCGAATCATAGTAGCATGATGTGGGGTAAGATGCTATGA | SEQ ID NO: 1573 | Homo sapiens centaurin, delta 1 (CENTD1), transcript variant 1, mRNA [NM_015230] |
| 706 | A_32_P86400 | LYSMD3 | AAAATGTTGCTCAGGTAATCAGTATTTTCTTCCACGTATGTGCATATTGCACTGTTAGATC | SEQ ID NO: 1574 | Homo sapiens LysM, putative peptidoglycan-binding domain containing 3 (LYSMD3), mRNA [NM_198273] |
| 707 | A_32_P86494 | A_32_P86494 | TGAGCCTTGCGTGCCACATTGAGAATGATGGTTACTGAAAAGGAACAGATTGTTCCTAAAC | SEQ ID NO: 1575 | |
| 708 | A_32_P8857 | A_32_P8857 | TAATGTCGGAATGGTACAGACTGTTTCTGTAAAGTGAGATGTTTCAGATAGTTGGTGGCT | SEQ ID NO: 1576 | |

Fig. 3-39

| No. | Probe ID No. | Symbols of genes | Sequence | SEQ ID NO: | Descriptions of genes (letters and numbers within [ ] indicate GenBank accession No.) |
|---|---|---|---|---|---|
| 709 | A_32_P89679 | THC2643265 | TTATAGGTCAGAAAAATGAGGTCGCACACTAATTTTGCCTCTTCC ACAGGGAGATAGATTC | SEQ ID NO: 1577 | ALU1_HUMAN (P39188) Alu subfamily J sequence contamination warning entry, partial (5%) [TH:2643265] |
| 710 | A_32_P93782 | RPL26 | AGGTTGTACATGGACACTATAAAGGTCAGCAAATTGGCAAAGTA GTGCAGGTTTAGAGGA | SEQ ID NO: 1578 | Homo sapiens ribosomal protein L26 (RPL26), mRNA [NM_000987] |
| 711 | A_32_P9382 | RP11-11C5.2 | AACAAAGCAGGAAATATATTGAGAAGGATGGTGTTTACAGAG GACTTCTTTAAAGTGT | SEQ ID NO: 1579 | Homo sapiens similar to RIKEN cDNA 2410129H14 (LOC440145), mRNA [XM_001071775] |
| 712 | A_32_P96213 | TPT1 | GAAAGCAGAGTAATCACTGGTGTGATGTTGTCATGAACCATCA CCTGCAGGAAAGAAGT | SEQ ID NO: 1580 | Homo sapiens tumor protein, translationally-controlled 1 (TPT1), mRNA [NM_003295] |
| 713 | A_32_P98313 | NDUFA4 | AGCCGTGGAACAAAGTGGGTCCCAATGATCAATAGAAGTTCTGC TCAGTGAATGTGGATT | SEQ ID NO: 1581 | Homo sapiens NADH dehydrogenase (ubiquinone) 1 alpha subcomplex, 4, 9kDa (NDUFA4), nuclear gene encoding mitochondrial protein, mRNA [NM_002489] |

Fig. 4-1

| No. | Probe ID No. | Symbols of genes | Sequence | SEQ ID NO: | Descriptions of genes (letters and numbers within; [ ] indicates GenBank accession No.) |
|---|---|---|---|---|---|
| 1 | A_32_P184330 | AK130741 | TGTGACCGTTTGTGACGAGTTATCTCAGTGCTCACATGAGTTGTTACATGAGTCCCTCTA | SEQ ID NO: 923 | Homo sapiens cDNA FLJ27231 fis, clone SYN06240 [AK130741] |
| 2 | A_32_P209582 | THC2663187 | CAATGTAAAGCCAGAATATCAAGCGTCCTTTTGTCAAGATTTCAAACCTATTTGGCTGAT | SEQ ID NO: 927 | ALU1_HUMAN (P39188) Alu subfamily J sequence contamination warning entry, partial (5%) [THC2663187] |
| 3 | A_32_P213509 | THC2663555 | GATTGTTTGGAGTGTTGGAGCCCTTTTTAATGAAAATTCTGAAGACCTACACTGGAAAAA | SEQ ID NO: 929 | |
| 4 | A_32_P227110 | THC2512146 | TAAAACAAATCGTTTTGATTCAAGCGAGTGTGTATTGATAATGGGTTATTTATTACAATCA | SEQ ID NO: 932 | |
| 5 | A_32_P71171 | A_32_P71171 | TCTAGATAGTAATAGGAAAACAAGAATCCAAGCCTGGTGATGGCTGGAGGGAGTGATTGAA | SEQ ID NO: 946 | |
| 6 | A_32_P98940 | THC2745859 | AAGAGTATTCCCAAGATAAGGAAAAGGTGTGTTGTTTTTAGGAGGTGTATTTCAAGGTAGTTA | SEQ ID NO: 952 | |
| 7 | A_23_P128930 | PSMC6 | GAACAAGCAAGATTAGAGACATAGTGAAAATCCATGCAGGTCGGATTACAAAGCATGGTGAA | SEQ ID NO: 986 | Homo sapiens proteasome (prosome, macropain) 26S subunit, ATPase, 6 (PSMC6), mRNA [NM_002806] |
| 8 | A_23_P143958 | RPL22L1 | ATTGGCTTCCAGTGGTTGCATGTGACAAGGAGACCTAGGAACTTCGTTACTTCCAGATTA | SEQ ID NO: 998 | Homo sapiens ribosomal protein L22-like 1, mRNA (cDNA clone IMAGE:4865966), [BC049823] |
| 9 | A_23_P144497 | RPS3A | GCAAATCCGGAAGAAGAATGATGGAAATCATGACCGGAGAGGTGCAGACAAATGAGTTGAA | SEQ ID NO: 1000 | Homo sapiens ribosomal protein S3A (RPS3A), mRNA [NM_001006] |
| 10 | A_23_P14708 | SUHW4 | TCTTGTAGCTCCATACAAGTGTTAGCTGCCACGCGTGTAAGGCTTAGGTTAATTAAACTT | SEQ ID NO: 1006 | Homo sapiens suppressor of hairy wing homolog 4 (Drosophila) (SUHW4), transcript variant 1, mRNA [NM_017661] |
| 11 | A_23_P14734 | RPS27L | TAGAAGATCACCACGGTTTTCAGCCATGCTCAGACAGTGGTTCTTTGTGTAGGTTGTTCA | SEQ ID NO: 1007 | Homo sapiens ribosomal protein S27-like (RPS27L), mRNA [NM_015920] |
| 12 | A_23_P152002 | BCL2A1 | TGTAACCATATTTGGATTTGAAGGTATTCTCATCGAAGAAACTTCACGACGAAATTGG | SEQ ID NO: 1013 | Homo sapiens BCL2-related protein A1 (BCL2A1), mRNA [NM_004049] |
| 13 | A_23_P156842 | EEF1E1 | AAGAAAAAGGAATCGTTCAGCACGTGGTTAGAATACAGGGCTACTCAAGTAGATGGGCACT | SEQ ID NO: 1019 | Homo sapiens eukaryotic translation elongation factor 1 epsilon 1 (EEF1E1), mRNA [NM_004280] |
| 14 | A_23_P157449 | POLR2K | GGTCTCTCTTGCTTCAAAATATCTCTTGTACAAGTACTCACCATTTTAGATGTGGTTGAC | SEQ ID NO: 1020 | Homo sapiens polymerase (RNA) II (DNA directed) polypeptide K, 7.0kDa (POLR2K), mRNA [NM_005034] |
| 15 | A_23_P158650 | COX7B | CAAAATACGGTAATGCTGTATTAGCTAGTGGAGCCACTTTCTGTATTGTTACATGGACATA | SEQ ID NO: 1022 | Homo sapiens cytochrome c oxidase subunit VIIb (COX7B), nuclear gene encoding mitochondrial protein, mRNA [NM_001866] |
| 16 | A_23_P162596 | ACTR6 | TTAAGCGGCTTCACTGGACGAGTTTCGTTAGAAGGTAGTTTTGTGACTGTGACTAAACT | SEQ ID NO: 1027 | Homo sapiens ARP6 actin-related protein 6 homolog (yeast) (ACTR6), mRNA [NM_022496] |
| 17 | A_23_P18325 | PDCD10 | CCAACGGAGTAATTCATCAAACCAAGTTAATACTTCAGACGTTCAAAACTGTGGCCTGAA | SEQ ID NO: 1039 | Homo sapiens programmed cell death 10 (PDCD10), transcript variant 1, mRNA [NM_007217] |
| 18 | A_23_P200955 | A_23_P200955 | AGAGCATGATTGAACCTCACATTGATGTGAAGACTACCGGATGGTTATTTGTTTCATCTAG | SEQ ID NO: 1046 | |

Fig. 4-2

| No | Probe ID No. | Symbols of genes | Sequence | SEQ ID NO: | (descriptions of genes (letters and numbers within [ ] indicates GenBank accession No.) |
|---|---|---|---|---|---|
| 19 | A_23_P215751 | NDUFA5 | TAAAAGTGGAGTCACTAAATAGTTTGGAGTACGTTTCTAATATAAGTGTAGGTGGGTATC | SEQ ID NO: 1073 | Homo sapiens NADH dehydrogenase (ubiquinone) 1 alpha subcomplex, 5, 13kDa (NDUFA5), nuclear gene encoding mitochondrial protein, mRNA [NM_005000] |
| 20 | A_23_P252201 | EAF2 | CAGGATTCGTTGATATAGATGCCAGTCATAATAGATTTGAGAGCAACAGTGGCCTTCTCGAT | SEQ ID NO: 1099 | Homo sapiens ELL associated factor 2 (EAF2), mRNA [NM_018456] |
| 21 | A_23_P26021 | COPS2 | TGGTTTTTGATCAACTGGTTTGTGTTTGCTGCTGGATTATCCCAAGAAAACAGCTT | SEQ ID NO: 1107 | Homo sapiens COP9 constitutive photomorphogenic homolog subunit 2 (Arabidopsis) (COPS2), mRNA [NM_004236] |
| 22 | A_23_P2705 | P2RY5 | TCTGTATTGCTGTTTCCAACTGTTGTTTGACCGTATAGTTTACTACTTTAGATCGGACA | SEQ ID NO: 1108 | Homo sapiens purinergic receptor P2Y, G-protein coupled, 5 (P2RY5), mRNA [NM_005767] |
| 23 | A_23_P307940 | CAPZA2 | CTACAAGATTGGACAAAGAGATGCAGAAATGCATAAGATGAACATTGATGACCGGATCATT | SEQ ID NO: 1117 | Homo sapiens capping protein (actin filament) muscle Z-line, alpha 2 (CAPZA2), mRNA [NM_006136] |
| 24 | A_23_P312246 | CCDC82 | GGCTTATAACGAGATGAGTGTCAAGTGAATGAGCGTGTTGATATCCTGTCAGTTTAGTCAA | SEQ ID NO: 1121 | Homo sapiens coiled-coil domain containing 82 (CCDC82), mRNA [NM_024725] |
| 25 | A_23_P33045 | RPL26 | TACAAAGGTGGACAAATTGGCAAAGTAGTCAGAGGTTACAGGAAAGAAATATGTTATCTAC | SEQ ID NO: 1132 | Homo sapiens ribosomal protein L26 (RPL26), mRNA [NM_000987] |
| 26 | A_23_P339480 | HAT1 | AACATGAACAGCTGGAAGAGAGCTTTTCAGGACCAGTAGTGGAAGATTACGGGTGTTATTG | SEQ ID NO: 1134 | Homo sapiens histone acetyltransferase 1 (HAT1), transcript variant 1, mRNA [NM_003642] |
| 27 | A_23_P38275 | THC2504576 | TCTGGCCAAAATGAAGTTTAATCCCTTTGTGACTTCGACCGAAGGAAGAATACGGAAAAG | SEQ ID NO: 1154 | RL26_BOVIN (P61257) 60S ribosomal protein L26, complete [THC2504576] |
| 28 | A_23_P405873 | C9orf72 | GAGAATGGAGAATGCAGGGTCAGAGTATTATTCCAATGGCTACTGGAGAAGTGATTCCTGT | SEQ ID NO: 1162 | Homo sapiens chromosome 9 open reading frame 72 (C9orf72), transcript variant 2, mRNA [NM_145005] |
| 29 | A_23_P44257 | COMMD8 | AACATTTACTTCTGCGCTTCTATGTTTGGGAAACATTGCTGTGATAAAATAGCTGTC | SEQ ID NO: 1179 | Homo sapiens COMM domain containing 8 (COMMD8), mRNA [NM_017845] |
| 30 | A_23_P46396 | PTBP2 | AACCAAGGTGGGACCGAAAGTTTATGTGCCTTTAGTCTTAATTTAGCTTGCATTGTAATATT | SEQ ID NO: 1183 | Homo sapiens polypyrimidine tract binding protein 2 (PTBP2), mRNA [NM_021190] |
| 31 | A_23_P50907 | ITGAV | AAAGAGTGATTAAGTGAGGTTATTTACGGCGTAAATGGTCCATTCTGCATTGTATTTTCAGG | SEQ ID NO: 1191 | Homo sapiens integrin, alpha V (vitronectin receptor, alpha polypeptide, antigen CD51) (ITGAV), mRNA [NM_002210] |
| 32 | A_23_P59921 | SUB1 | CAGATTTGGGAAATGAGGTAGTGTTCGCGATTTTAAAGGCAAAGTGCTAATTGAT | SEQ ID NO: 1205 | Homo sapiens SUB1 homolog (S. cerevisiae) (SUB1), mRNA [NM_006713] |
| 33 | A_23_P61674 | CLK4 | GAAAGGATGCAGTTTGTCCATTGTGACAGTTGTTTAATAAAACCACATACACACTTTA | SEQ ID NO: 1207 | Homo sapiens CDC-like kinase 4 (CLK4), mRNA [NM_020666] |
| 34 | A_23_P63343 | UTS2 | AGAATCTGGAAACGCATACAAGAAAACGTGAGACTCCTGATTGGTCTGGAAATACTGTGTC | SEQ ID NO: 1211 | Homo sapiens urotensin 2 (UTS2), transcript variant 1, mRNA [NM_021995] |
| 35 | A_23_P65768 | C15orf15 | TCCTGGATTGGCATTGCATGCTACATAATATCAGATATTACGGATGTTAGATTGCATCTCAGTGTT | SEQ ID NO: 1216 | Homo sapiens chromosome 15 open reading frame 15 (C15orf15), mRNA [NM_016304] |
| 36 | A_23_P66260 | ZNF267 | TGTGATTGGTAGTGTGGTAAAGCCTTCAGGTATGTCAGGATGCATACCTCACTACACATGGGAGAGT | SEQ ID NO: 1217 | Homo sapiens zinc finger protein 267 (ZNF267), transcript variant 498723, mRNA [NM_003414] |
| 37 | A_23_P70328 | CENPQ | CAATGGCTTACAGTTTGTGTGGTCATCTGGAACTTGAAAATGGTGAAATGCCTTCAC | SEQ ID NO: 1224 | Homo sapiens centromere protein Q (CENPQ), mRNA [NM_018132] |

Fig. 4-3

| No. | Probe ID No. | Symbols of genes | Sequence | SEQ ID NO: | Descriptions of genes letters and numbers within [ ] indicates GenBank accession No.) |
|---|---|---|---|---|---|
| 38 | A_23_P76480 | BF213738 | AAATCGAACGAGGACAATGGGTAGATGGAGCTACATTTACGAAATG GTTTCGGCATGCAGAGG | SEQ ID NO: 1239 | BF213738 601847628F1 NIH_MGC_55 Homo sapiens cDNA clone IMAGE 4078519 5'. mRNA sequence [BF213738] |
| 39 | A_23_P78092 | EVI2A | GGTGAATGACAGAGCTTGGAAAAGAACAAAACAGGTCAGGAGAGCG AACCTAGTGATGCAA | SEQ ID NO: 1244 | Homo sapiens ecotropic viral integration site 2A (EVI2A), transcript variant 1, mRNA [NM_001039927] |
| 40 | A_23_P63278 | CHMP5 | CATTGCTCTTTTATTTTTCGATTAAGGACTCATTGCTTGGGAA ATGCTTTCTTCGTAC | SEQ ID NO: 1251 | Homo sapiens chromatin modifying protein 5 (CHMP5), mRNA [NM_016410] |
| 41 | A_23_P87769 | C12orf48 | GTAAGAAATATGCTCAGTCGTCGTCCTAATGCATATTGTGACTGTTTG CATATACTTCTGTT | SEQ ID NO: 1254 | Homo sapiens chromosome 12 open reading frame 48 (C12orf48), mRNA [NM_017915] |
| 42 | A_23_P87879 | CD69 | TGTGCAATATGTGATGTGGCAAATGTCTATTAGGAAATATTCTGT AATCTTCGAGCCTAG | SEQ ID NO: 1255 | Homo sapiens CD69 molecule (CD69), mRNA [NM_001781] |
| 43 | A_24_P11045 | THC2785765 | CGACCAGAAACGTACACGTGATTTTGATGAGAAATACGGTAGCAA CACAAGTGGGAATAG | SEQ ID NO: 1283 | COX7B_HUMAN (P24311) Cytochrome c oxidase polypeptide VIIb, mitochondrial precursor, partial (78%) [THC2785765] |
| 44 | A_24_P115774 | BIRC2 | GATAGGCATTTGGTTAAAGGAAATGCTGCGGCCAACATGTTCAAA AACTGTCTAAAAGAA | SEQ ID NO: 1285 | Homo sapiens baculoviral IAP repeat-containing 2 (BIRC2), mRNA [NM_001166] |
| 45 | A_24_P144666 | LOC401975 | TGTCGAATGTCAAGACTAATGATGGCTACTTCTTTAATCTGTTCTG TGTTGGTTTTACTGA | SEQ ID NO: 1301 | PREDICTED: Homo sapiens similar to ribosomal protein S3a (LOC401975), mRNA [XR_017247] |
| 46 | A_24_P153324 | LOC390413 | GAAGCTTAACAAGGTTCAATTCAACATGCTGGGGATTGTAGAACC ATATATTGCAGGGTA | SEQ ID NO: 1304 | PREDICTED: Homo sapiens similar to 60S ribosomal protein L7 (LOC390413), mRNA [XR_018341] |
| 47 | A_24_P175187 | SAMD9 | CAAGGAGGGATAGTAACTAGTCATCAAAATGTAATTTTCCCTAATAAAAT TATGGATAATGGGCAG | SEQ ID NO: 1316 | Homo sapiens sterile alpha motif domain containing 9 (SAMD9), mRNA [NM_017654] |
| 48 | A_24_P175188 | SAMD9 | TGCCAATGTACTGCAGATAATTAACACATAACAACCTATGTTTTTGAACAA AAAGAACCACCGATA | SEQ ID NO: 1317 | Homo sapiens sterile alpha motif domain containing 9 (SAMD9), mRNA [NM_017654] |
| 49 | A_24_P201702 | CLEC2B | ATTGGAATTACAAGTAAATACAAACTGTTCCACTCAACATGCGGACC TAACTATAATTGACA | SEQ ID NO: 1327 | Homo sapiens C-type lectin domain family 2, member B (CLEC2B), mRNA [NM_005127] |
| 50 | A_24_P203909 | RPL34 | GAGGGAGCTTCGTGCGTAGTGTTAAGACTAAAGTTCTTATGAAATTGCA AAACAAACAACATG | SEQ ID NO: 1328 | Homo sapiens ribosomal protein L34 (RPL34), transcript variant 2, mRNA [NM_033625] |
| 51 | A_24_P212664 | LOC646161 | ACAGAACATAGAACGTGGGATCGCATGATACCCATCCGAAAGAATGATGAAGT TAGGCTTGTTACCAGG | SEQ ID NO: 1331 | PREDICTED: Homo sapiens similar to 60S ribosomal protein L26 (LOC646161), mRNA [XR_018048] |
| 52 | A_24_P221375 | A_24_P221375 | TACTTTGGTTACCCATGTACCTACCCACTTTCAAAAATCTACAGAG AGTCAATGTCGAGGA | SEQ ID NO: 1332 | |
| 53 | A_24_P243749 | PDK4 | ATTTGACATTGTGTGTAATTTCATGGTGGCCTAGTGTTGTTGGTG CTTCTGGTAATTGGTA | SEQ ID NO: 1345 | Homo sapiens pyruvate dehydrogenase kinase, isozyme 4 (PDK4), mRNA [NM_002612] |
| 54 | A_24_P286054 | ZFYVE16 | GTGTATGTATTCTGCCATGTAAGTAATTGAAGAGTGTTAAAATAA CCAAATGGTAGAGGG | SEQ ID NO: 1359 | Zinc finger FYVE domain-containing protein 16 (Endofin) (Endosome-associated FYVE domain protein). [Source:Uniprot/SWISSPROT;Acc:Q7Z3T8] [ENST00000380248] |
| 55 | A_24_P298604 | LOC731599 | GATGGAAATCATGACCAGAAGGTCCGGCAAATGCTGAAAGAATT GGTCAATAAAATGAT | SEQ ID NO: 1365 | PREDICTED: Homo sapiens hypothetical protein LOC731599 (LOC731599), mRNA [XR_015536] |
| 56 | A_24_P306527 | ENST00000308989 | ACCGCATCCGTGCGTGGTTATCCAGAAAAATGTAGAGGATGAAG ATTCACCAAATAAGT | SEQ ID NO: 1366 | PREDICTED: Homo sapiens similar to ribosomal protein L31 (LOC729905), mRNA [XM_001133428] |

Fig. 4-4

| No | Probe ID No. | Symbols of genes | Sequence | SEQ ID NO: | Descriptions of genes (letters and numbers within [ ] indicates GenBank accession No.) |
|---|---|---|---|---|---|
| 57 | A_24_P316074 | LOC730902 | TATCAATGGTGTGAGGGCAAAGGTCAAAGGTGTTGCAGCTTCTTCCCTTCGTCAAATCTT | SEQ ID NO: 1372 | PREDICTED: Homo sapiens similar to 60S ribosomal protein L7 (LOC730902), mRNA [XR_015600] |
| 58 | A_24_P320323 | SUB1 | CAGAAAAACCTGTAAAGAAACAAAAGACAAGGTGAGACTTGAGAGCCCTGTCATCTTCTA | SEQ ID NO: 1373 | Homo sapiens SUB1 homolog (S. cerevisiae) (SUB1), mRNA [NM_006713] |
| 59 | A_24_P324224 | A_24_P324224 | AAAGRTGTCTGGGGCAAAGGAATAAGGAATTCCTATAGGCATGTGCGGTTGTCCAGAAAA | SEQ ID NO: 1375 |  |
| 60 | A_24_P324224 | A_24_P33213 | GACCATATATTACATGGGGGTACCCAAATCTGAAGTCAGTAAATGAACTTATCTAGAAGG | SEQ ID NO: 1379 |  |
| 61 | A_24_P33213 | A_24_P333112 | GGTCATCAGAATCAGAGGTATCAATGTGTGAGCCCACAAGGACCAAAAGGTATTGCAACTT | SEQ ID NO: 1380 |  |
| 62 | A_24_P33607 | LOC652558 | TAAGAAAATAATTGCTTTGACAGAGCAAAGGGTTTGATTGGCTCGAATCTCTTGGTAAATATATGG | SEQ ID NO: 1382 | PREDICTED: Homo sapiens similar to 60S ribosomal protein L7 (LOC652558), mRNA [XR_019386] |
| 63 | A_24_P349636 | LOC388401 | AGTTGCTTCGACAGATAAGACTTTGATTGGTGAGCTCTTGGTAAATAGCATCAACTG | SEQ ID NO: 1383 | PREDICTED: Homo sapiens similar to 60S ribosomal protein L7 (LOC388401), mRNA [XR_016679] |
| 64 | A_24_P366165 | LOC391126 | ACTTCGAACCAAATCAAAAATAGCAAAAGGGATTCAATGCAACCTTCCCAGAATTCACAGG | SEQ ID NO: 1393 | PREDICTED: Homo sapiens similar to 60S ribosomal protein L26 (Silica-induced gene 20 protein) (SIG-20) (LOC391126), mRNA [XR_019504] |
| 65 | A_24_P366646 | RPL31P10 | CGGCTGTCCAGAAAAGGTAATGAGGATGAAGATTCAAATAAGCTCTATACTTTGGTTACC | SEQ ID NO: 1394 | PREDICTED: Homo sapiens similar to ribosomal protein L31 (LOC390283), mRNA [XR_018695] |
| 66 | A_24_P367191 | LOC652890 | AGTTAAGCATGCTGAGGAGTGTAGAGCCATATATTGCGTGTGGGTACCCAAAATCTGAAGTC | SEQ ID NO: 1396 | PREDICTED: Homo sapiens similar to 60S ribosomal protein L7 (LOC652890), mRNA [XR_019544] |
| 67 | A_24_P367199 | A_24_P367199 | TCTTATGCTCAGCACCAACAGTCTGCCAAATCGCAGAAGATCGAGAAGGTGTAATCATGACCTGAGA | SEQ ID NO: 1397 |  |
| 68 | A_24_P381625 | PSMC6 | ATGAAGCAGTCAGAAAAGTGGGCTGATTCTAAGGAAGCTGGAGTCTAAATTGGACTACAAA | SEQ ID NO: 1404 | Homo sapiens proteasome (prosome, macropain) 26S subunit, ATPase, 6 (PSMC6), mRNA [NM_002806] |
| 69 | A_24_P383899 | RPS3A | TGGTTTTACTAAAAAAGGCAACAATCAGATACAGAAGACCTCTTATGCCCAGCACCAACGG | SEQ ID NO: 1405 | Homo sapiens ribosomal protein S3A (RPS3A), mRNA [NM_001006] |
| 70 | A_24_P384411 | A_24_P384411 | ATGGGCAAAATCAATAAGAGTGAAGCTTTGACAGATAATGCTTTGACAGGTCGATCTCTTG | SEQ ID NO: 1406 |  |
| 71 | A_24_P384539 | LOC730452 | CAAGAAAAGCTGGCAACTTCTATGTACGCAGAAAACGGAAATTGGCATTTCATCAGGA | SEQ ID NO: 1407 | PREDICTED: Homo sapiens similar to 60S ribosomal protein L7 (LOC730452), mRNA [XR_001125895] |
| 72 | A_24_P414656 | TTC33 | TACTCAACATTTGGTATATTGTTTGAGTAATGAGATGTTTGTTTTTGTGTAATTTGTGA | SEQ ID NO: 1421 | Homo sapiens tetratricopeptide repeat domain 33 (TTC33), mRNA [NM_012382] |
| 73 | A_24_P41551 | LOC641790 | AAGGAGAATGGGAACTCCTGATGTGCGCATTGATATGAGGCACAACAAAGTAGCTCGGAAA | SEQ ID NO: 1423 | PREDICTED: Homo sapiens similar to 60S ribosomal protein L31 (LOC641790), mRNA [XR_018025] |
| 74 | A_24_P418712 | A_24_P418712 | TGCGTCAACAAAGCTGTCTCTGGGCCAAAGAAATAAGGAATATCGATACCATATCTGTGTTA | SEQ ID NO: 1426 |  |
| 75 | A_24_P50437 | BC065737 | TGCAGAATGATGAAGTTGGATTCATTAGAAATTCCTGATTACTGAAGATGTTCAGGGCAAAA | SEQ ID NO: 1430 | Homo sapiens cDNA clone IMAGE:30404477, partial cds [BC065737] |
| 76 | A_24_P57837 | THC2567891 | AGAAATCCGGAAGACCTCTTATGCCAGTACCAGCCAAATCCGGAAGAAGATGATGGAAA | SEQ ID NO: 1440 | Q6NXR8_HUMAN (Q6NXR8) Ribosomal protein S3a, partial (91%) [THC2567891] |

Fig. 4-5

| No. | Probe ID No. | Symbols of genes | Sequence | SEQ ID NO. | Descriptions of genes (letters and numbers within [ ] indicates GenBank accession No.) |
|---|---|---|---|---|---|
| 77 | A_24_P587938 | A_24_P587938 | CTTCAAAGAGCAAAAGGTGGAGATGGTGGCAACAGAGGAGGACCAGATTAACAAGTCTTAT | SEQ ID NO: 1441 | |
| 78 | A_24_P606663 | LOC392030 | TGTGCGGTTGCCCAGAAACGTAATGCGGGTGAAGATTCAGGAAATAAGGTCGATACTT | SEQ ID NO: 1442 | PREDICTED: Homo sapiens hypothetical LOC392030 (LOC392030), mRNA [XR_018063] |
| 79 | A_24_P685729 | A_24_P685729 | TTGAAGGTTATGTTGGATTGCAAGACTATCAGTGATTATTGCTTGTGTTTTGTGTGG | SEQ ID NO: 1448 | |
| 80 | A_24_P6975 | LOC342994 | GGAAGACTTCGAGGGGTTCGTGCTGTAAGAGCGTAAAGTGTTATGAAATTGTCAAAAACA | SEQ ID NO: 1450 | PREDICTED: Homo sapiens similar to ribosomal protein L34 (LOC342994), mRNA [XM_938494] |
| 81 | A_24_P75158 | FTAR1 | GGATTAGATTTGTTGTTATGTGACCATGTAGCAAGCCAGGTATAAAGTATTGTATTTCTG | SEQ ID NO: 1454 | Homo sapiens mRNA; cDNA DKFZp313P0917 (from clone DKFZp313P0917). [AL832663] |
| 82 | A_24_P755505 | A_24_P755505 | ATACAGAAGAAGCGTTATGGTCAGGACGACAAGAGAAAAGTAAAAATGCTGAAGAAGCCAA | SEQ ID NO: 1455 | |
| 83 | A_24_P76358 | LOC643981 | TTACTGAAGATGTTCAGGGCAAAAACTGCCTAACTCCGGCATGGATCTTATTCGTGACA | SEQ ID NO: 1456 | PREDICTED: Homo sapiens similar to 40S ribosomal protein S3a (V-fos transformation effector protein) (LOC643981), mRNA [XR_018444] |
| 84 | A_24_P792734 | PSMC6 | AGAAACGTTAAGGAGTTACTGAATCAAATGAGGATTTGATACTCTGCATAGAGTTAAA | SEQ ID NO: 1459 | Homo sapiens proteasome (prosome, macropain) 26S subunit, ATPase, 6 (PSMC6), mRNA [NM_002806] |
| 85 | A_24_P64808 | LOC729449 | GAATTGGTTTGAACAGATAACGGTTTGGAATCTCTTGGAAAATATGGGATCATCTGTATCG | SEQ ID NO: 1466 | PREDICTED: Homo sapiens similar to 60S ribosomal protein L7 (LOC729449), mRNA [XR_015548] |
| 86 | A_24_P850167 | A_24_P850167 | TAAATGAACTAATCTCAGAAGCGTGCTTATGGGAAAAATCAATTGACTTGCAGTTTCCTAC | SEQ ID NO: 1467 | |
| 87 | A_24_P113154 | LOC730861 | ACCACAGTCCAAGAATCTGTTAAAGTTCAGACTTAAAACAGTACCAAATAAAAAGTCC | SEQ ID NO: 1491 | PREDICTED: Homo sapiens similar to 40S ribosomal protein S3a (V-fos transformation effector protein) (LOC730861), mRNA [XR_015591] |
| 88 | A_24_P11931 | LOC441073 | GTGTGATCGATGCCCATCCGAGAAAGGATGATGAAGTTCAGGTTGTACGTGGACACTATAAA | SEQ ID NO: 1497 | PREDICTED: Homo sapiens similar to 60S ribosomal protein L26 (Silica-induced gene 20 protein) (SIG-20) (LOC441073), mRNA [XR_016376] |
| 89 | A_24_P125549 | RPL31P4 | TCTACAAGAGTCAATGTGGATGGAAGTAATCCTGAAGTCAGTAAATGAAC ATACATCAAATAAAG | SEQ ID NO: 1500 | PREDICTED: Homo sapiens ribosomal protein L31 pseudogene 4 (RPL31P4), mRNA [XR_018222] |
| 90 | A_32_P128781 | A_32_P128781 | GATATATTGGATGGGGTACCCAATCTGAAGTCAGTAAATGAACTAATCTACAAGAGTG | SEQ ID NO: 1502 | |
| 91 | A_32_P135818 | RPS3A | CTTCTTCATCTCTGTCTCTGTGTTTGGTTTAATAAAAAACGCAACAATCAGATATGGAAGAC | SEQ ID NO: 1504 | Homo sapiens ribosomal protein S3A (RPS3A), mRNA [NM_001006] |
| 92 | A_32_P145153 | RPL31 | ATCCGTGTGGCAGCTGTCCAGAAAACGTAATGAGGATGAAGATTCAGCAAATAAGGCCATAT | SEQ ID NO: 1508 | Homo sapiens ribosomal protein L31 (RPL31), mRNA [NM_000993] |
| 93 | A_32_P153725 | KIAA1033 | TTTGTAAAAGATGGCAAGTTTGTTACCTCAGTTGAGTGGGGTTTGCTTTTGGGGAAT | SEQ ID NO: 1513 | Homo sapiens KIAA1033 (KIAA1033), mRNA [NM_015275] |
| 94 | A_32_P155364 | RPL7 | TCAACAGGCTATTAGAAAAATGACCAAGGTGTCTACCATGATTATTTTGTAAAGTGG | SEQ ID NO: 1514 | Homo sapiens ribosomal protein L7 (RPL7), mRNA [NM_000971] |
| 95 | A_32_P164203 | THC2683448 | TTGATGGTCATTGTACGAGGTATTGTATGGATTACTGTGGAGTGCTGTTTACCAGATGAT | SEQ ID NO: 1519 | Q7NZG3_PASPI (Q7NZG3) Ferric uptake regulator, partial (8%) [THC2683448] |

Fig. 4-6

| No. | Probe ID No. | Symbols of genes | Sequence | SEQ ID NO: | Descriptions of genes (letters and numbers written [ ] indicates GenBank accession No.) |
|---|---|---|---|---|---|
| 96 | A_32_P190488 | hCG_26523 | CCGAAGGAAGGTGGTTATCACTAGGCTAAAAGTGGACAAAGACGGCAAAAGATCCTTGAA | SEQ ID NO: 1531 | PREDICTED: Homo sapiens similar to 60S ribosomal protein L26 (LOC646161), mRNA [XR_018048] |
| 97 | A_32_P196483 | RPS3A | GGGGCCAAGAAGAAAGTGGTTGATCCATTTTCTAAGAAAGAATTGGTATGATGTGAAAGCA | SEQ ID NO: 1534 | Homo sapiens ribosomal protein S3A (RPS3A), mRNA [NM_001006] |
| 98 | A_32_P208178 | RPS3A | GGAAAAGACGTAGAAAAGGGTTGCCAATCTATTTATCCTGCATGATGTGTTCGTTAGA | SEQ ID NO: 1544 | Homo sapiens ribosomal protein S3A (RPS3A), mRNA [NM_001006] |
| 99 | A_32_P226127 | RPL34 | CAAAACTAGGCTGTGGTGGTGAACGCGCTGGTAATAGAATTGTTGTTGTT | SEQ ID NO: 1546 | Homo sapiens ribosomal protein L34 (RPL34), transcript variant 2, mRNA [NM_033625] |
| 100 | A_32_P22539 | hCG_26523 | ACTACGAAGGTCAGCAAATTGGCAAAGTGGTCCAAGGTTTACAGGAAGAAATATGTTATCT | SEQ ID NO: 1549 | PREDICTED: Homo sapiens similar to 60S ribosomal protein L26 (Silica-induced gene 20 protein) (SIG-20) (LOC430055), mRNA [XM_374987] |
| 101 | A_32_P2353 | SUB1 | AGGGAAAAGATATTTCTTTAAATCCAGAACAATGGAGCCAGGTGACGAACAGATTTC | SEQ ID NO: 1551 | Homo sapiens SUB1 homolog (S. cerevisiae) (SUB1), mRNA [NM_006713] |
| 102 | A_32_P4532 | LOC643932 | GATCCAGACAGGACATTGGAAAAAGACATAGAAAAAGGGCTTGGCAATCTATGCTGTCGATGAT | SEQ ID NO: 1560 | PREDICTED: Homo sapiens similar to 40S ribosomal protein S3a (V-fos transformation effector protein) (LOC643932), mRNA [XR_017289] |
| 103 | A_32_P49392 | A_32_P49392 | AATTCTGCCAAATCTGGAAGAAGATGATGGAAATCATGACCAAGAGGTGCACACAAATG | SEQ ID NO: 1563 | |
| 104 | A_32_P58074 | RPS3A | GTTGGTTTTACTAAAAACGGCAAAAATCAGATACGGAAGAACCTCTTATGCTCAGCACGAA | SEQ ID NO: 1566 | Homo sapiens ribosomal protein S3A (RPS3A), mRNA [NM_001006] |
| 105 | A_32_P7118 | PSMC6 | AGCAGACGTGAGAAATGTTTGTAGTGAAGCAGGTATGTTGGCAATTCGTCTGATCATGA | SEQ ID NO: 1570 | Homo sapiens proteasome (prosome, macropain) 26S subunit, ATPase, 6 (PSMC6), mRNA [NM_002806] |
| 106 | A_32_P77571 | AK024584 | GTGATCCTCTTAATGAAGCATTATGCAGGTGTTAAAGATGATAGATGTAAAGGTTATGAG | SEQ ID NO: 1571 | Homo sapiens cDNA: FLJ20931 fis, clone ADSE01282, [AK024584] |
| 107 | A_32_P93782 | RPL26 | AGGTTGTACATGGACACTATAAAGGTCAGCAAATTGGCAAGTAGTCCAAGGTTTACAGGA | SEQ ID NO: 1578 | Homo sapiens ribosomal protein L26 (RPL26), mRNA [NM_000987] |

Fig. 5-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P141415 | MYCBPAP | TCTGCAGGTGACTCTCCGGGCCCAAGCAACCTTCTGGAAAACGGGG TTAATAAATAAATCAA | SEQ ID NO: 1582 | Homo sapiens MYCBP associated protein (MYCBPAP), mRNA [NM_032133] |
| 2 | A_23_P143247 | TSHZ2 | CCCAAGAGCGTATGCAAATCTCTAAGTTTACGGAGACTCTCAA TGACCACTATCAGTCA | SEQ ID NO: 1583 | Homo sapiens teashirt zinc finger family member 2 (TSHZ2), mRNA [NM_173485] |
| 3 | A_23_P146325 | DDEF1IT1 | TGGAAAGTGAAGTGAAGAGATTTTTGTCATACAGCCAGTAAGTGC CAGAACTCACTCGAAC | SEQ ID NO: 1584 | Homo sapiens DDEF1 intronic transcript 1 (DDEF1IT1) on chromosome 8 [NR_027765] |
| 4 | A_23_P151426 | FOXO1 | GAGGGTTAGTGAGCAAGGTTAGACTTAAAAGTACTTCAGATTGTC TGACACGAGGAACTGA | SEQ ID NO: 1585 | Homo sapiens forkhead box O1A (FOXO1), mRNA [NM_002015] |
| 5 | A_23_P151805 | FBLN5 | GGGAACCCGTGGAGTGAGTAGTAGTTGCTTTTTGCGTACACAGAGA AGGCTATGTAAACAAA | SEQ ID NO: 1586 | Homo sapiens fibulin 5 (FBLN5), mRNA [NM_006329] |
| 6 | A_23_P153616 | MADCAM1 | GTTTCTGGACGGAAGCAGCAGGTACTTTTTACATACATTGATTCATG TCTCACGTCTCCCTAA | SEQ ID NO: 1587 | Homo sapiens mucosal vascular addressin cell adhesion molecule 1 (MADCAM1), transcript variant 1, mRNA [NM_130760] |
| 7 | A_23_P154627 | TSHZ2 | GTATTGGGGTTCTTGTAGCTTGTTAAAAATTGTCTGCTCGAATC GAGGGTTATTAGGCGA | SEQ ID NO: 1588 | Teashirt homolog 2 (Zinc finger protein 218) (Ovarian cancer-related protein 10-2) (OVC10-2). [Source:Uniprot/SWISSPROT;Acc:Q9NRE2] [ENST00000371497] |
| 8 | A_23_P157299 | AEBP1 | ACAGTAGAGACCTACACAGTGAAGTTTGGGGACTCTGAGATCA GCCTCCTACCAAGACC | SEQ ID NO: 1589 | Homo sapiens AE binding protein 1 (AEBP1), mRNA [NM_001129] |
| 9 | A_23_P157333 | EPHA1 | TATGGGAGGATGAGCAATCAGGAGGTTATGAAGAGGATTGAGGA TGGGTACCGGTTGCCC | SEQ ID NO: 1590 | Homo sapiens EPH receptor A1 (EPHA1), mRNA [NM_005232] |
| 10 | A_23_P163492 | BAIAP3 | GACGCATTTTGTAATCACAGCGTGGGAGTGAAAGGGTGCCA CTGGCACGACTGGGTG | SEQ ID NO: 1591 | Homo sapiens BAI1-associated protein 3 (BAIAP3), mRNA [NM_003933] |
| 11 | A_23_P16496 | A_23_P16496 | GGGAATCTGGGCGCTGGGAAGAGAATGTAAAGCAACCTAAACAGT AATTTAAGAATGGAGA | SEQ ID NO: 1592 | |
| 12 | A_23_P202520 | ABLIM1 | TCACTGCACTCCTTTGTCATATACTCTGCATCACTGTCATAGTC ACAACTTGGTGAATAA | SEQ ID NO: 1593 | Homo sapiens actin binding LIM protein 1 (ABLIM1), transcript variant 3, mRNA [NM_001003407] |
| 13 | A_23_P209055 | CD22 | GCCTCAGGCCACAAGAAAATGTGGACTATGTGATCGTCAAACATT GAGAGTGGAATGGGCTG | SEQ ID NO: 1594 | Homo sapiens CD22 molecule (CD22), mRNA [NM_001771] |
| 14 | A_23_P214821 | EDN1 | AGCGGCCTGGCACTTCAGGGAGAAAGTGCAAAGTGCCACACA AGATTTTCTAAGGAAT | SEQ ID NO: 1595 | Homo sapiens endothelin 1 (EDN1), mRNA [NM_001955] |
| 15 | A_23_P250212 | DKFZp761P0423 | GAAGTGAATGACGCTGGACACTGGGCTCAATACCCTTGTTAGG ATTTGTTCACGCTTTT | SEQ ID NO: 1596 | tyrosine-protein kinase SgK223 (EC 2.7.10.2) (Sugen kinase 223). [Source:Uniprot/SWISSPROT;Acc:Q86Y45] [ENST00000330777] |
| 16 | A_23_P255896 | ENST00000333459 | GCAAGGGGCTCTACGCAGAGTACGTCTTCAATGTATTGCCGGA AACTGGGAGCGCAAGA | SEQ ID NO: 1597 | Homo sapiens hypothetical protein LOC129293, mRNA (cDNA clone IMAGE:5762496), partial cds. [BC051789] |
| 17 | A_23_P315378 | ATG16L1 | CTGTGTTTCCACTTTATACTCTTTGTCCAAAACTGAGTTTCAAA ATATTGCAATGGGAC | SEQ ID NO: 1598 | Homo sapiens cDNA FLJ10035 fis, clone HEMBA1000919. [AK000897] |
| 18 | A_23_P315386 | RHPN1 | CGGCTGGCCTGAAGGAGGGGAGCTAGCATTGTGTCAGTGAATGGG CAGCCATGCCAGGTGGT | SEQ ID NO: 1599 | Homo sapiens rhophilin, Rho GTPase binding protein 1 (RHPN1), mRNA [NM_052924] |

Fig. 5-2

| No. | Probe ID No. | Symbols of genes | Sequence | SEQ ID NO: | Descriptions of genes (letters and numbers within [ ] indicates GenBank accession No.) |
|---|---|---|---|---|---|
| 19 | A_23_P338919 | SPEG | GCAGGGGGCACTGTAGTGAGGGTGGAGTGGAGAAATTTGGAAACAGCT ATTCTTAACTCAAAT | SEQ ID NO: 1600 | Homo sapiens cDNA FLJ30825 fis, clone FEBRA2001706, highly similar to Human APEG-1 mRNA. [AK055357] |
| 20 | A_23_P341938 | NOG | GCCAGGCGTGCGCGGTGGATTCCGAGTCCAGTACCCCATCCATTTCC GAGTGCAAGTGCTCGT | SEQ ID NO: 1601 | Homo sapiens noggin (NOG), mRNA [NM_005450] |
| 21 | A_23_P343398 | CCR7 | AAGAGAGCAACATTTACCGACCACACAGAGATAAAGTTTTCCGTTG AGGAAACAACAGGTTT | SEQ ID NO: 1602 | Homo sapiens chemokine (C-C motif) receptor 7 (CCR7), mRNA [NM_001838] |
| 22 | A_23_P344531 | SYNPO | TCCTGCTGCTGTGAAGATGAAGAAGGTGCTCTTAGTCAGTTAATG ATGAGTGACTATATTT | SEQ ID NO: 1603 | Synaptopodin. [Source:Uniprot/SWISSPROT;Acc:Q8N3V7] [ENST00000307662] |
| 23 | A_23_P357504 | AL834280 | CCCACAGCGGCAATCAACACGGTTCTGTGTGAATAAATAAAAGTTT ATCATTGGTACAAAG | SEQ ID NO: 1604 | |
| 24 | A_23_P359870 | C8orf16 | CTGAGGTTATAATTTCACTTAACATTGTCGAGTTGGCATTTTG GTTTTAGTCCAATGGT | SEQ ID NO: 1605 | Homo sapiens mRNA for hypothetical protein (C8ORF16). [AJ312026] |
| 25 | A_23_P361275 | DSCR1L2 | TAAATATGATTACTCTGTCGTGTTTCCAAATTGGGACCAGGA GAGAAATAGAAGTTG | SEQ ID NO: 1606 | Homo sapiens Down syndrome critical region gene 1-like 2 (DSCR1L2), mRNA [NM_013441] |
| 26 | A_23_P3921 | FLJ11710 | CCTGATTCATGATTGAAGTACCATTACCCATAAATGCTATACATC CATGCATTGGATGTTA | SEQ ID NO: 1607 | Homo sapiens cDNA FLJ11710 fis, clone HEMBA1005149. [AK021772] |
| 27 | A_23_P420873 | NR1D1 | CCCTTGACAGAATCGAAGCTGACGTTCTCTCGTTACGGAG ACGAAAAGGAAAAGCA | SEQ ID NO: 1608 | Homo sapiens nuclear receptor subfamily 1, group D, member 1 (NR1D1), mRNA [NM_021724] |
| 28 | A_23_P48585 | SALL2 | CTAGTAAATATTCAAGAACAAGAAAAGTTGGGGCCAGGCTAGGTTGTGTTTCC CCTATCATTAAAGGT | SEQ ID NO: 1609 | Homo sapiens sal-like 2 (Drosophila) (SALL2), mRNA [NM_005407] |
| 29 | A_23_P49638 | GRAP | GTCCAGAGCAGAAGAAGAAAAGTTGGGGCCAGAGCTAGGTTTTAAGAG ATCCTACAAGGATCCCA | SEQ ID NO: 1610 | Homo sapiens GRB2-related adaptor protein (GRAP), mRNA [NM_006613] |
| 30 | A_23_P500130 | ANKRD15 | TTAGGGTGTGACATTTAGTTTGGTCTCTATGTATTTAAATGT TTGAAGTGCCTTAGAC | SEQ ID NO: 1611 | Homo sapiens ankyrin repeat domain 15 (ANKRD15), transcript variant 2, mRNA [NM_153186] |
| 31 | A_23_P7582 | TCF7 | CCCAGAAAACCTCCAGTAGTGGACAACAGGTTTTCACCATAGCC TACGTTAAGCCATTTT | SEQ ID NO: 1612 | Homo sapiens transcription factor 7 (T-cell specific, HMG-box) (TCF7), transcript variant 1, mRNA [NM_003202] |
| 32 | A_23_P83388 | EPPK1 | GTTTTTGGTGTGTTTCTGGGGTCGTCTATGTGTCATATGGTTT TAGTTTTCTCGCGGAA | SEQ ID NO: 1613 | Homo sapiens epiplakin 1 (EPPK1), mRNA [NM_031308] |
| 33 | A_23_P84399 | CNTNAP2 | CCTTAAGCACATCCCTAAAATATCAGCACAAGTTGGGGAGGAGCAG GCAATGGAATATAATG | SEQ ID NO: 1614 | Homo sapiens contactin associated protein-like 2 (CNTNAP2), mRNA [NM_014141] |
| 34 | A_24_P128057 | MBNL1 | AGAATATTGGTGCAACACTATCTGTGATTGGTTATCTCTCTATC ATGCATTGGTTCAGAA | SEQ ID NO: 1615 | Homo sapiens muscleblind-like (Drosophila), mRNA (cDNA clone IMAGE:3936812), partial cds. [BC005296] |
| 35 | A_24_P252945 | BLR1 | TTTGTTTTAATAAAAAGGCACGTATAAAACAGGTCAATACAG TACAGGCAGGCAGACGAG | SEQ ID NO: 1616 | Homo sapiens Burkitt lymphoma receptor 1, GTP binding protein (chemokine (C-X-C motif) receptor 5) (BLR1), transcript variant 2, mRNA [NM_032966] |
| 36 | A_24_P280751 | DTX1 | TGGGAATTTTGAGAGGCAAAGGCTGGCGGCTTCGACTTCAGGAG CGAAAGGAGGAGGCCT | SEQ ID NO: 1617 | Homo sapiens deltex homolog 1 (Drosophila) (DTX1), mRNA [NM_004416] |
| 37 | A_24_P298360 | LTBP3 | CTGCTGTTGGGGAAGGACCCCGAAGAGATGAAGGACAGTTCAGGAGA GGATTCAGACGAGTGT | SEQ ID NO: 1618 | Homo sapiens latent transforming growth factor beta binding protein 3 (LTBP3), mRNA [NM_021070] |

Fig. 5-3

| No. | Probe ID No. | Symbols of genes | Sequence | SEQ ID NO: | Descriptions of genes (letters and numbers within ( ) indicates GenBank accession No.) |
|---|---|---|---|---|---|
| 38 | A_24_P312325 | C8orf15 | CTTGTTCAATGTGACTAGTTTAGTTGGGTGTCCAATATGAAGTAGAAAAGGAGATTCTG | SEQ ID NO: 1619 | Homo sapiens chromosome 8 open reading frame 15 (C8orf15), mRNA [NM_001033662] |
| 39 | A_24_P316414 | BC014346 | TAAGCTTGGGGTGTTGGGAGTAGAACTTTAGCTTTGAATATTTAAGGGCTTGGCCTGTA | SEQ ID NO: 1620 | Homo sapiens, clone IMAGE:4042968, mRNA, partial cds. [BC014346] |
| 40 | A_24_P340112 | THC2683124 | TCCAATTTGTAAGTGTTGAGTCCACGTGATGTAGAAGTTGTGACTTGTAAACCATTGATCC | SEQ ID NO: 1621 | |
| 41 | A_24_P360499 | DDEF1IT1 | TGTTCGTTTTAATGTAGCGGAGGTGCTATACTTCAGATTTAAGTTTGAAATGTAGCATAGG | SEQ ID NO: 1622 | Homo sapiens DDEF1 intronic transcript 1 (DDEF1IT1) on chromosome 8 [NR_002765] |
| 42 | A_24_P360722 | DIP2C | GGCTTAGGTTTGGCAAATAGGACTGTGTTTTCTTAGGTGCAAGAATTCATTGCACAATGTTT | SEQ ID NO: 1623 | Homo sapiens DIP2 disco-interacting protein 2 homolog C (Drosophila) (DIP2C), mRNA [NM_014974] |
| 43 | A_24_P37020 | THC2690931 | TGGTTCTACGGTCCAACTAAAGGGAAAAGAGGGTTGAAGGTCAGCCATGTAGGTATGAGA | SEQ ID NO: 1624 | AF235005 suppression of tumorigenicity 16 protein [Homo sapiens] (exp=-1; wgp=0; cg=0), partial (13%) [THC2690931] |
| 44 | A_24_P413126 | TMEPAI | AAGAAAGTGCTTGGTTGTATGAGTAAACATTAGTAGGCAATGATGACATTCTGAAAAGCT | SEQ ID NO: 1625 | Homo sapiens transmembrane, prostate androgen induced RNA (TMEPAI), transcript variant 1, mRNA [NM_020182] |
| 45 | A_24_P417352 | ENST00000390559 | TGAGCAGGTATGACAGGGTGAGCATCTCGTGGACCGGCCAGAATGGGGAAGGTGTGAAAA | SEQ ID NO: 1626 | immunoglobulin heavy chain C gene segment [Source:IMGT/GENE_DB;Acc:IGHM] [ENST00000390559] |
| 46 | A_24_P460763 | AK022443 | GTGAGTTAGCAGGGTACTTAAGATGCCTAGTGGGTGTAAATGTCAAATGCTATTCGGCAGAT | SEQ ID NO: 1627 | Homo sapiens cDNA FLJ12381 fis, clone MAMMA1002566. [AK022443] |
| 47 | A_24_P491923 | THC2491622 | CTTGTTGTTTCTCAATAAAGTAGAGAAGTCCATGTGATGGTGTTTAGTAGGGTATGA | SEQ ID NO: 1628 | |
| 48 | A_24_P548264 | AL512741 | AAGAATTGAGTTAGAACTGCCCATAATGTAATGCAGAATATTTCCCAATATGCCTAGG | SEQ ID NO: 1629 | Homo sapiens mRNA; cDNA DKFZp667N064 (from clone DKFZp667N064) [AL512741] |
| 49 | A_24_P542771 | AK024956 | ATTCTCCATATATTTTAGTGTTCTATTGGCTAGAAGACAAACAAGGGAATCTGG | SEQ ID NO: 1630 | Homo sapiens cDNA: FLJ21303 fis, clone COL02107. [AK024956] |
| 50 | A_24_P662177 | THC2666469 | GGGGAAGGTAGGATTTCAATGGCATGTTACATAAGGATCCTCTAAAGGGACAGAATGTACA | SEQ ID NO: 1631 | |
| 51 | A_24_P713312 | THC2639056 | TTTATATGGTCGGATGGTCCATGTTAGGATTAAGGGGTAATTAATAGTAATGTATGTGGA | SEQ ID NO: 1632 | ALU8_HUMAN (P39195) Alu subfamily SX sequence contamination warning entry, partial (10%) [THC2639056] |
| 52 | A_24_P728115 | AK024937 | ACTGCATAGTCACTAGCTTTAGTGAGTTTGAAATCTGTTTGGAGAGCTATGTAAGTACCA | SEQ ID NO: 1633 | Homo sapiens cDNA: FLJ21284 fis, clone COL01911. [AK024937] |
| 53 | A_24_P792389 | THC2671169 | ATGCTAGCTGGAGAGCTAAGGACATACAAGTATGACTAGAAATTGCCAGCTACACATTAGA | SEQ ID NO: 1634 | |
| 54 | A_24_P7974 | SLC26A6 | GTTGCTTTATGTAGCAAATTCTCCGGTTTGGAGGTTTTAAAATAGGATTATTTGCCAGAAC | SEQ ID NO: 1635 | Homo sapiens HSPC106 mRNA, partial cds. [AF161369] |
| 55 | A_24_P79855 | ENST00000390643 | AAAACGATTGGTCGCCTTTACCCAGGGAAGGAGTCAAGAAGCCGAACGGTGATAGGAGATGG | SEQ ID NO: 1636 | Homo sapiens hypothetical protein DKFZp566R0824, mRNA (cDNA clone MGC:129790 IMAGE:40021976), complete cds. [BC104430] |
| 56 | A_24_P910490 | BX099367 | AGGCCGAGAGTTGCAGAGCACGTTGGGGTACACAGTGAGAGGCTGTCTGTACAAAACTA | SEQ ID NO: 1637 | BX099367 Soares_fetal_liver_spleen_1NFLS_S1 Homo sapiens cDNA clone IMAGp998D05977, mRNA sequence [BX099367] |

Fig. 5-4

| No. | Probe ID No. | Symbols of genes | Sequence | SEQ ID NO: | Descriptions of genes (letters and numbers within [ ] indicates GenBank accession No.) |
|---|---|---|---|---|---|
| 57 | A_24_P914102 | A_24_P914102 | TTAGTAGACGGGTAGATTTTGTGTAGAAATGTAAAATGTTATTT TACTGTTGAAAATCAG | SEQ ID NO: 1638 | |
| 58 | A_24_P915361 | AF086536 | AGTGACTGCAGAAGGTGAGAGGTCTGGAACTGAGGGCCTGCGGAG CTCTGTTACGAAGGAA | SEQ ID NO: 1639 | Homo sapiens full length insert cDNA clone ZE08A03. [AF086536] |
| 59 | A_24_P926025 | DKFZp547E087 | TGTTATGAACATAGTTCATGTTAAGCTCCATTTAAATACAACG TGAAATACCAAGTTA | SEQ ID NO: 1640 | Homo sapiens cDNA FLJ30147 fis, clone BRACE2000266. [AK054709] |
| 60 | A_24_P927090 | AF116678 | TGTCGTTTCTGTTAACAGATTCAGGGCTCATGCTTGACTCG GAACCAGGAAGGAATT | SEQ ID NO: 1641 | Homo sapiens PR01995 mRNA, complete cds. [AF116678] |
| 61 | A_24_P930337 | THC2503773 | AGGAAGTGGACGCGACCCAAAATATGAGTTGAAGAATGTAAT TTAAAATGTAGGATAG | SEQ ID NO: 1642 | |
| 62 | A_24_P930391 | AK022351 | AAGTTGGGTTTAATTTCCTTTCATGAAAGGAAAAGATTAGGTTTC ATCCAAAACACTTGGTC | SEQ ID NO: 1643 | Homo sapiens cDNA FLJ12239 fis, clone MAMMA1001788. [AK022351] |
| 63 | A_24_P930963 | LOC650392 | GCACGATTTCGAGTATATAACCAGGAGGAGGGAAAAATGGTGCTTGAAAT AAGCATGCCAGAAAGG | SEQ ID NO: 1644 | Homo sapiens cDNA clone IMAGE:5264670. [BC036550] |
| 64 | A_24_P933548 | A_24_P933548 | CACGTGCACGTTTACTACTTCTTTATACGTGCAGAAGTATAA CCTAAGGAAAGGAATG | SEQ ID NO: 1645 | |
| 65 | A_24_P934861 | A_24_P934861 | GGAGGTATCAAGGAGGAAAATCCAGTTCTGGAAATAGTGGAG CAGATCGTCTCCATGG | SEQ ID NO: 1646 | |
| 66 | A_24_P935682 | AY358248 | AGTCAGTTAATGACAGATTCAATGATAGGTCTAACGATGC TTGACAGTTATGCAAC | SEQ ID NO: 1647 | Homo sapiens clone DNA166629 MRSS6228 (UNQ6228) mRNA, complete cds. [AY358248] |
| 67 | A_24_P945096 | CACNA1I | CTTAGAAGGTGCTCTTTAGGGAGGAGAACACATACTCTTTTTGT GTTTGTTGGAATAATCA | SEQ ID NO: 1648 | Homo sapiens calcium channel, voltage-dependent, T type, alpha 1I subunit (CACNA1I), transcript variant 1, mRNA [NM_021096] |
| 68 | A_32_P101002 | CA433167 | CTGTGAACTGTCAAACATGATGGACTGAAGTATTTTAAATTCT ACTCAGGAGAGATTG | SEQ ID NO: 1649 | Homo sapiens cDNA clone UI-H-CQ0-ark-e-04-0-UI.s1 NCI_CGAP_Sub9 Homo sapiens cDNA clone UI-H-CQ0-ark-e-04-0-UI 3', mRNA sequence [CA433167] |
| 69 | A_32_P105940 | A_32_P105940 | GTGCCAAGGTAAGCTACGACTTTGGTTTTATTTCAAGCACAA GATGAAATAAGGATTC | SEQ ID NO: 1650 | |
| 70 | A_32_P111394 | THC2643957 | GAATACAGTGTTCGTTTTCATGGGATATTTGACTGAACCTAAGG CAGATGCAATTATAAGG | SEQ ID NO: 1651 | |
| 71 | A_32_P112546 | LOC649344 | AGGGAGGAGGTCAGTATGCAGTATGCGAGCACTGGGAACACTGGGAACAGGAAGGAGCCCAC CTGAGGGCTCAGCCCTA | SEQ ID NO: 1652 | PREDICTED: Homo sapiens similar to Keratin, type II cytoskeletal 8 (Cytokeratin-8) (CK-8) (Keratin-8) (K8) (LOC649344), mRNA [XR_018597] |
| 72 | A_32_P116997 | THC2719256 | AAACATTAGGTAGCAGCTTGTAGAGGATATATTTAGGGTGCATGA TGTCCTTCTTGTTGGC | SEQ ID NO: 1653 | BE147120 PM2-HT0224-221099-001-b10 HT0224 Homo sapiens cDNA, mRNA sequence [BE147120] |
| 73 | A_32_P121978 | A_32_P121978 | CAGATTAGAGCAGCTGCACCTCATAATGAGTTCTTGATTGGCACTGCAGAT TGTCTTCATGGGGCAC | SEQ ID NO: 1654 | |
| 74 | A_32_P125589 | THC2649341 | CGCTCATCCGTTTGCTTTAGGCTTTGAATGAAAGTGAGATGTC TCATCAGGTCAGATAG | SEQ ID NO: 1655 | |
| 75 | A_32_P12703 | THC2697162 | TTGAAAGGGAAAAGAGTATAAGGGGGGGAAGTGCCAGAGCTAAAACGAAT GCTAAGTAAGGATAGGGT | SEQ ID NO: 1656 | |
| 76 | A_32_P131294 | BM854107 | AGTAGGGAAAAAGGTTTGTTCGTTAATTAGAGAGGTAGTGTGGAA ATGGTAAGAGTTGTGC | SEQ ID NO: 1657 | K-EST0136406 S22SNU16n1 Homo sapiens cDNA clone S22SNU16n1-145-F11 5', mRNA sequence [BM854107] |

Fig. 5-5

| No. | Probe ID No. | Symbols of genes | Sequence | SEQ ID NO: | Descriptions of genes (letters and numbers within [ ] indicates GenBank accession No.) |
|---|---|---|---|---|---|
| 77 | A_32_P132936 | THC2673888 | AAATGAAGTATTGACCAGATTAAACAGTGGTTAAGTGATGGGCATGAATGAATTACCA | SEQ ID NO: 1658 | Q65S49_9ALPH (Q65S49) Glycoprotein G, partial (4%) [THC2673888] |
| 78 | A_32_P136033 | AK090477 | AGGCTCAGTCTAGAGTCTCATGTCCTTCTGTGTCAGTGGTTGA CTTGAATATTGATCAA | SEQ ID NO: 1659 | Homo sapiens mRNA for FLJ00399 protein. [AK090477] |
| 79 | A_32_P136597 | THC2714184 | CCGCAGTGTTTTGGCCCAGAGAAATACATAGTGAAGATTGTTGC CATATTCTTCCTACTA | SEQ ID NO: 1660 | |
| 80 | A_32_P146826 | THC2652700 | ACCTCTAGGAGGAGTTTGGAAAGTTGTCAAGTTTTCAATTGT CTGGAGGATGTGGTTC | SEQ ID NO: 1661 | |
| 81 | A_32_P146844 | THC2639689 | CGTGTGGGGTGATTCCAGACTGAGAGTTGAAGTTTGTGTGCAT CATCATGCCATAA | SEQ ID NO: 1662 | |
| 82 | A_32_P147969 | AL080232 | TAATCAGGTCTTTTCGGCATCAAGGCAAGGAACTGTCCAGAGA GCTCTGGAGAATTCTT | SEQ ID NO: 1663 | Homo sapiens mRNA; cDNA DKFZp586A061 (from clone DKFZp586A061). [AL080232] |
| 83 | A_32_P155841 | AL079294 | CCTTCCTGTTATAACCTGGAGTTAGCATGTTCTTGTTAAGGAA GAATGGCAAATGGCAAA | SEQ ID NO: 1664 | Homo sapiens mRNA full length insert cDNA clone EUROIMAGE 362780. [AL079294] |
| 84 | A_32_P156062 | THC2681718 | GTGGAGGTTGGCATTGGTTTCAGTGTCTCAGGGAGGTCAGGG CTCAAGTGCGTTC | SEQ ID NO: 1665 | |
| 85 | A_32_P164573 | THC2611661 | AGCTGTGTTTCTATTAACACTGAAGTCTGAGAGCTTGGAAAT TTTCAAGTGGAAAATC | SEQ ID NO: 1666 | RR12_SPIMX (P42344) Chloroplast 30S ribosomal protein S12, partial (11%) [THC2611661] |
| 86 | A_32_P165407 | AK024926 | AAAGGAGGAGGATCCGTGGAGTTAGCATGTTTCACAGGAACCAAA CATGATTCAATGAAAAA | SEQ ID NO: 1667 | Homo sapiens cDNA: FLJ21273 fis, clone COL01778. [AK024926] |
| 87 | A_32_P171253 | THC2674305 | GGCTCAGACCTTAAGAAACTGATGGTCTTTTGTTTTACTTCTACA CAAAAGTCTAAGCAGT | SEQ ID NO: 1668 | Q9F8W7_CARHY (Q9F8W7) DTDP-glucose 4,6-dehydratase (Fragment), partial (11%) [AK024926] |
| 88 | A_32_P179526 | ZBTB20 | TTTGAAGTTGGAAATCAAGGGGAATCTAAAACCGACCAGATGTT TCTCCTGCTGGAAAGG | SEQ ID NO: 1669 | Homo sapiens zinc finger and BTB domain containing 20, mRNA (cDNA clone IMAGE:4291354), partial cds. [BC010934] |
| 89 | A_32_P179998 | DMRTC1 | ATATGCCAGAGTTTTATTCGTCTTCTGATTCTGACATACCCTG TGCACTCATGTGTATA | SEQ ID NO: 1670 | Homo sapiens DMRT-like family C1 (DMRTC1), mRNA [NM_033531] |
| 90 | A_32_P182458 | A_32_P182458 | ACCTAGCACAGTGGAGTGAAACACTTAAATAGGACTTGCTCCT TGAGTATATATGGAAA | SEQ ID NO: 1671 | |
| 91 | A_32_P185398 | THC2750143 | AAATATCCTGATACTTTAGGCATATCTGGAATTATAAGAATTAAA TATCAAATTATAGGAT | SEQ ID NO: 1672 | ALU1_HUMAN (P39188) Alu subfamily J sequence contamination warning entry, partial (11%) [THC2750143] |
| 92 | A_32_P194372 | AK129647 | AGACCAGAGAAAGATAGAGCCCATGACCTAAGCCTTGGACCAAGCATAGG TTAAAACTAGGGGAGG | SEQ ID NO: 1673 | Homo sapiens cDNA FLJ26036 fis, clone PRS00145. [AK129647] |
| 93 | A_32_P196287 | THC2652466 | GCCTTTGCAGAAAGACTGTAAGCCTTACCCAAGGCATTAATTTTGGT GCATAGGCGGCCTGTT | SEQ ID NO: 1674 | Q9BHW3_PARTE (Q9BHW3) Cyclophilin-RNA interacting protein, partial (4%) [THC2652466] |
| 94 | A_32_P208039 | AL049390 | GTTGCATGTTTGAGGATTCAGATTGGGCTTATTCTGAAGGGAT GTGGCAAACCTCACAA | SEQ ID NO: 1675 | Homo sapiens mRNA; cDNA DKFZp586Q1318 (from clone DKFZp586Q1318). [AL049390] |
| 95 | A_32_P208200 | THC2659414 | GAGATTAAATGAGTGGAGAAGAAAACCTGAAAGCGGGAGAGA ATAAGACTAAATTTC | SEQ ID NO: 1676 | |
| 96 | A_32_P20912 | AK025669 | ACAACTAGGTGTAGGTGGGGAGAACATGTTCACATGCCCATAA AGTCCATTTTGGCAAA | SEQ ID NO: 1677 | Homo sapiens cDNA: FLJ22016 fis, clone HEP07422. [AK025669] |

Fig. 5-6

| No. | Probe ID No. | Symbols of genes | Sequence | SEQ ID NO: | Descriptions of genes, letters and numbers within [ ] indicates GenBank accession No. |
|---|---|---|---|---|---|
| 97 | A_32_P209562 | THC2663167 | CAATGTAAAGCAGAATATCAACGTCCTTTGTCAAGATTTCAAACCTATTTGGCTGAT | SEQ ID NO: 1678 | ALU1_HUMAN (P39188) Alu subfamily J sequence contamination warning entry, partial (5%) [THC2663167] |
| 98 | A_32_P211048 | A_32_P211048 | GTTCACAAAACACCTAGTAGGTATTCAGTTCATATTGGAATGAATGAGAAATGAGCAG | SEQ ID NO: 1679 | |
| 99 | A_32_P213509 | THC2863555 | GATTTGTTGGAGTGTTGGAGCGCCTTTTTAATGAAAATTCAACACCTACACTGGAAAAA | SEQ ID NO: 1680 | |
| 100 | A_32_P214054 | THC2755661 | GGGTTATCTGTCTTTGTTTTAACAGATGGGGTTTGGCTTCCATAGCAATGATTTGCAAAT | SEQ ID NO: 1681 | |
| 101 | A_32_P216122 | AK130891 | TTCTTCCTGTATATGTTTGGGAGGGCATTCATGAGGAATTGAGTACACATATATGGGTC | SEQ ID NO: 1682 | Homo sapiens cDNA FLJ27391 fis, clone UBA07680. [AK130891] |
| 102 | A_32_P225301 | THC2727302 | GGCTCAATGAGTTTGATTGGAATGGCCAACAAATTACCTAAGCATTTTGCTAACGTGAAGAA | SEQ ID NO: 1683 | ALU6_HUMAN (P39193) Alu subfamily SP sequence contamination warning entry, partial (9%) [THC2727302] |
| 103 | A_32_P227110 | THC2512148 | TAAAACAAATCGTTTGATTCAGGCCACTGTGTATTGATAATGGCTTAATTATTACAATCA | SEQ ID NO: 1684 | |
| 104 | A_32_P232851 | THC2845586 | CTTTGAAAAGGATATCCTTCACATTGGTTTCCAGAAAATTGAAGGTCAGCTGAGTGATTTC | SEQ ID NO: 1685 | Q9P3E1_NEUCR (Q9P3E1) Related to rna-binding protein fus/tls, partial (5%) [THC2645586] |
| 105 | AL833696 | AL833696 | CTGGCCAGAGTCAACTGCCAACCGTTGGGAGTGGGAGATGGAGGGTCGTTTGGTGTAGGGGTGTTGTTTTGAGTGT | SEQ ID NO: 1686 | Homo sapiens mRNA; cDNA DKFZp667D139 (from clone DKFZp667D139). [AL833696] |
| 106 | A_32_P40673 | CATCACACTTGATATTAGGACACGTAGGTGTTGTTTGAGTGTCACAGAGGTGATATGTA | SEQ ID NO: 1687 | |
| 107 | A_32_P41089 | THC2658419 | AGGGGCAGAAAATTTGGGTTCCTCGGGTTTATTAGTAAAGTGTCTTTGGACTATTGTCTC | SEQ ID NO: 1688 | |
| 108 | A_32_P42976 | THC2713078 | GTTATCGTTTGCTTTTGTTGTGTCAAGCTGGCCAACATTGTGGCTCATTCTTTCTGCTA | SEQ ID NO: 1689 | |
| 109 | A_32_P43878 | DB111455 | ATGTGAGAAAGGTTTCTTTTAAGGTTTAATGACCAGTTCCATGTGAGCTCTTACTTGGGA | SEQ ID NO: 1690 | DB111455 THYMU2 Homo sapiens cDNA clone THYMU20150235', mRNA sequence. [DB111455] |
| 110 | A_32_P46404 | AK092468 | CTCTATGGGAAGCTCTTTTTGGCATAAAATACTTATGATTCAGCGAAGAGGAAAGGACT | SEQ ID NO: 1691 | Homo sapiens cDNA FLJ35149 fis, clone PLACE6010485. [AK092468] |
| 111 | A_32_P5542 | AF131762 | GAAGCCTCTAGAATCTAAGCTCACTAACGTAACGAAAACTGGGAGGAAATGTCTTATAAATAACAGGA | SEQ ID NO: 1692 | Homo sapiens clone 24941 mRNA sequence. [AF131762] |
| 112 | A_32_P55427 | THC2701763 | CACTTTATCCCTATCGTAAAACAAACGGCGGTAAATTGAGAGAGTAGATTGATAGGTTGG | SEQ ID NO: 1693 | Q9F8M7_CARHY (Q9F8M7) DTDP-glucose 4,6-dehydratase (Fragment), partial (11%) |
| 113 | A_32_P55438 | GTTCCCTCGTCAAACCTGGTGAGGTTTTGTATGTTTAGTCTCACTACAGCAGCAG | SEQ ID NO: 1694 | |
| 114 | A_32_P61706 | AGGAGGCAAGTAGTTGTCTCTACACCAGAAATGGTGTGTTCTCACTGCTTCCAAGGAGACCAT | SEQ ID NO: 1695 | |
| 115 | ANKRD15 | ANKRD15 | GGAAGGTTCTGTTGACTCCCACACAAAGTGGTGTGGTTCTCACTGAGACGTTTAAGATTT | SEQ ID NO: 1696 | Homo sapiens ankyrin repeat domain 15 (ANKRD15), transcript variant 2, mRNA [NM_153186]. |
| 116 | A_32_P65067 | THC2618974 | GGCGGAAAGTGAATTTTAAACTTGAGTTATTTATGCCGTTCTCATAGCAACAGGAAAACT | SEQ ID NO: 1697 | |

Fig. 5-7

| No. | Probe ID No. | Symbols of genes | Sequence | SEQ ID NO: | Descriptors of genes (letters and numbers within [ ] indicates GenBank accession No.) |
|---|---|---|---|---|---|
| 117 | A_32_P67209 | BU726029 | CTCGAGTTATATTTATCTGCACCTACCTGCAGGTGACACTCTGGTATTGTTCAGAGAAG | SEQ ID NO: 1698 | UI-E-C10-aao-g-02-0-UI.s1 UI-E-C10 Homo sapiens cDNA clone UI-E-C10-aao-g-02-0-UI 3', mRNA sequence [BU726029] |
| 118 | A_32_P70875 | CD239706 | CTTGTTCTGAGAAGTTCCTAATGGAGTGAGTAGGAGAACAAAGTGACAGTTTGTTATTACTG | SEQ ID NO: 1699 | FNPBXF03 FMP Homo sapiens cDNA, mRNA sequence [CD239706] |
| 119 | A_32_P71171 | A_32_P71171 | TCTAGATAGTAATAGGAAAACCAAGAATCCAGCCTGGTGATGGCTGGAGGGAGTGATTGAA | SEQ ID NO: 1700 | |
| 120 | A_32_P79103 | BM932034 | GTGCTACAGAATGAAAATAGCATTTAGGAAGGTTGAGTCAGAGGTCGGAGTGGGGCATA | SEQ ID NO: 1701 | UI-E-EJ1-aji-k-24-0-UI.r1 UI-E-EJ1 Homo sapiens cDNA clone UI-E-EJ1-aji-k-24-0-UI 5', mRNA sequence [BM932034] |
| 121 | A_32_P88967 | AK022346 | ATGGGAAGTTACTACCCAGGCTTACCAAAAGGTCAGGTTTATATAAAGTCGCGTTCCTTT | SEQ ID NO: 1702 | Homo sapiens cDNA FLJ12284 fis, clone MAMMA1001757 [AK022346] |
| 122 | A_32_P89087 | AL134462 | TTCATGGAGGTTCTAGTCAAGCGAGAACGACTAAAGAGTAAAGGGACAAATAGGATTAGT | SEQ ID NO: 1703 | DKFZp547J085_r1 547 (synonym: hlbr) Homo sapiens cDNA clone DKFZp547J085 5', mRNA sequence [AL134462] |
| 123 | A_32_P91328 | THC2641595 | GTTAGGCGAATAATGTCATTGAAGTCTTTAACTCTAGGGTGACTCTAAGGCGAGGGTTCA | SEQ ID NO: 1704 | |
| 124 | A_32_P97305 | THC2681839 | AATATGCACACACAAAAGTAAAGAAAAGGATGTGACTGACCACACAGCTTCCTGCCCCT | SEQ ID NO: 1705 | |
| 125 | A_32_P98940 | THC2745859 | AAGAGTATTGCCAAGATAGGAAAAGGTGTGTTTTGTTTTTTTAGGCAGGTGTATTTCAGCTAGTTA | SEQ ID NO: 1706 | |
| 126 | A_23_P102235 | SNRPG | ACAACAGAGAATATTGGAATGGTGGTAATACCAGGAGAAATAGTACATCATGTTAGAAGC | SEQ ID NO: 1707 | Homo sapiens small nuclear ribonucleoprotein polypeptide G (SNRPG), mRNA [NM_003096] |
| 127 | A_23_P104054 | C1orf9 | TAAATTTCTTTGGTCTGTGACAATTAGCATTCAGAGCAAGAGGCCTGATTTTATAGA | SEQ ID NO: 1708 | Homo sapiens chromosome 1 open reading frame 9 (C1orf9), transcript variant 2, mRNA [NM_016227] |
| 128 | A_23_P106131 | KTN1 | ATGTTTTCACCCGTTCTACTTTGTCTCAGAAGTTGAATCACTGAACAGAGTTTTGCTTTTCTAATGG | SEQ ID NO: 1709 | Homo sapiens kinectin 1 (kinesin receptor) (KTN1), transcript variant 1, mRNA [NM_182926] |
| 129 | A_23_P108751 | FHL2 | TTACAGGTGTGTAAACTCGGGTTCGGTCAAGTCTAAAGGAAGATTATGTGACTTGCAAT | SEQ ID NO: 1710 | Homo sapiens four and a half LIM domains 2 (FHL2), transcript variant 2, mRNA [NM_201555] |
| 130 | A_23_P110362 | MAP2K1IP1 | AGTGAGCAAGTTGTGGAAGTTTCTTAATCTGACAGTGGTTTGAGTGTGTAGGTATGTT | SEQ ID NO: 1711 | Homo sapiens mitogen-activated protein kinase kinase 1 interacting protein 1 (MAP2K1IP1), mRNA [NM_021970] |
| 131 | A_23_P110611 | ZH2C2 | GTCTTGAAAAGGAGAGTTTCAGTCTGTTGGAGTCTTCGAAACCAGGTTCGTTGAATACTTAA | SEQ ID NO: 1712 | Homo sapiens zinc finger, H2C2 domain containing (ZH2C2), mRNA [NM_017676] |
| 132 | A_23_P113811 | COX7C | AGCCTGTGGAAGTGGATCAAAGTAGAACTCATATGGCATACTAGATATGTTGTCAATAA | SEQ ID NO: 1713 | Homo sapiens cytochrome c oxidase subunit VIIc (COX7C), nuclear gene encoding mitochondrial protein, mRNA [NM_001867] |
| 133 | A_23_P111583 | CD36 | CTTTGGTTAATGAGACTGGGACCATTGTGATGATGAGAAAGGCAAACATGTTCAGAAGTCAA | SEQ ID NO: 1714 | Homo sapiens CD36 molecule (thrombospondin receptor) (CD36), transcript variant 2, mRNA [NM_001001547] |
| 134 | A_23_P114662 | CRYZ | AACATGCTAGTTCAAAATAAGAAGTCTGGTTTCAGTTTCCAAGGGTTTTCAAGCCTACTTACCTT | SEQ ID NO: 1715 | Homo sapiens crystallin, zeta (quinone reductase) (CRYZ), mRNA [NM_001889] |

Fig. 5-8

| No. | Probe ID No. | Symbols of genes | Sequence | SEQ ID NO: | Descriptions of genes (letters and numbers within [ ] indicates GenBank accession No.) |
|---|---|---|---|---|---|
| 135 | A_23_P11652 | USP1 | TTGGGCATGGACTAATTTGTATCTGTTTAAGTGATATTGTGGAC GATCTGTATATAGTAG | SEQ ID NO: 1716 | Homo sapiens ubiquitin specific peptidase 1 (USP1), transcript variant 1, mRNA [NM_003368] |
| 136 | A_23_P11665 | PLA2G4A | GAAATGGCAGCAGTTCTGATGCTGAGGCAGTTTGGAATGGGAT GACAACTGGATTTAAA | SEQ ID NO: 1717 | Homo sapiens phospholipase A2, group IVA (cytosolic, calcium-dependent) (PLA2G4A), mRNA [NM_024420] |
| 137 | A_23_P117721 | RPS17 | AATTATGTTCCTGAGGTCTCAGCCTTGGATGGAGGAGATTATGA AGTAGATCGTGAGCAT | SEQ ID NO: 1718 | Homo sapiens ribosomal protein S17 (RPS17), mRNA [NM_001021] |
| 138 | A_23_P117852 | KIAA0101 | TAGTGGTGGCATTTTATTGGTGTTTGATTATGGAATGGTGCC ATATGTCACTCCTTC | SEQ ID NO: 1719 | Homo sapiens KIAA0101 (KIAA0101), transcript variant 1, mRNA [NM_014736] |
| 139 | A_23_P118516 | FAM18B | TATTCTGTAGATTGTTTTCAGGAGAAAAGTTTTGCTTGTCTATGT AAGAGTGAGCAGTTTG | SEQ ID NO: 1720 | Homo sapiens family with sequence similarity 18, member B (FAM18B), mRNA [NM_016078] |
| 140 | A_23_P120348 | BAZ2B | TATTTTCGTCTGAAGGTAAATGATAAGGTACAGTCTGTACAGTA ATTACCTGTACCAAC | SEQ ID NO: 1721 | Homo sapiens bromodomain adjacent to zinc finger domain, 2B (BAZ2B), mRNA [NM_013450] |
| 141 | A_23_P120316 | MTHFD2 | AGGATTATTGCTTGCTATTAGTAGCTACTGATTTATGTATGTTAGCC TTCAGTTAAGTTCTCCG | SEQ ID NO: 1722 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 142 | A_23_P1206 | RPS24 | TTTGGATTCAGAAGTCCATTTTGGTGGTGGCAAGACAACTGGCTT TGGCATGATTTATGAT | SEQ ID NO: 1723 | Homo sapiens ribosomal protein S24 (RPS24), transcript variant 2, mRNA [NM_001026] |
| 143 | A_23_P120902 | LGALS2 | GTAGGTACCTGAGCGTAAGGGCGGGTTCAAGATGTCGTCTTT CAAGTTAAAGAATAA | SEQ ID NO: 1724 | Homo sapiens lectin, galactoside-binding, soluble, 2 (LGALS2), mRNA [NM_006498] |
| 144 | A_23_P121386 | IFT57 | TGGAACACAACACTACTCCAATCAAAGCTGAAGCAGAAGAGTCCAAC ATGACTAGGAACATGC | SEQ ID NO: 1725 | Homo sapiens intraflagellar transport 57 homolog (Chlamydomonas) (IFT57), mRNA [NM_018010] |
| 145 | A_23_P121622 | SULT1B1 | GAAATAGAGATGTCTGTAGTTGATTGAATGAAACGAGGGGCAGTTATG AATTGATTTGGGCAAT | SEQ ID NO: 1726 | Homo sapiens mRNA for ST1B2, complete cds. [D89479] |
| 146 | A_23_P121825 | FLJ13611 | CATGTGTTACTGTTACAAAACTTTCTCTCCCATGTAATCACAC TTAGTTATGAGCAAAG | SEQ ID NO: 1727 | Homo sapiens hypothetical protein FLJ13611 (FLJ13611), mRNA [NM_024941] |
| 147 | A_23_P122174 | XRCC4 | AAACCAAACTGATGTCTCTGGTTGGCTTCAGCTGCTGTAAGTA AAGATGATTCCATTAT | SEQ ID NO: 1728 | Homo sapiens X-ray repair complementing defective repair in Chinese hamster cells 4 (XRCC4), transcript variant 3, mRNA [NM_022550] |
| 148 | A_23_P123315 | BC067244 | CTTCAAATGATCAGTGTCTGGTTTGGGAGGGGGTGGATACATCGTCATTT TCTGTACATGATGCAT | SEQ ID NO: 1729 | Homo sapiens cDNA clone IMAGE:4807381, partial cds. [BC067244] |
| 149 | A_23_P123343 | NUDCD1 | TTGGGCTCTTTTGTAGTGGAAAAGTATTCAGTGGTACCTGGAGGT CTGGACAGTTTACTG | SEQ ID NO: 1730 | Homo sapiens NudC domain containing 1 (NUDCD1), mRNA [NM_032869] |
| 150 | A_23_P123608 | JAK2 | GGATAACATGGCTGGATGAAGAAGAAAGTGACGTTCATTCTGAGACC AAAGTAGATTTACAGA | SEQ ID NO: 1731 | Homo sapiens Janus kinase 2 (a protein tyrosine kinase) (JAK2), mRNA [NM_004972] |
| 151 | A_23_P127279 | FAM35A | TGCTACATTCCAGGCATTGTACTAAGTATGGGGAAGCAGACGAGA AGAGATTCGGTCAGAA | SEQ ID NO: 1732 | Homo sapiens family with sequence similarity 35, member A (FAM35A), mRNA [NM_019054] |
| 152 | A_23_P127579 | PTS | GTGTTTATAAAGGAGAATAGCTATGCGGTACAAAGTGGTACAGACCAAGTATGCGAA AGCCCAGTTTCTTTCT | SEQ ID NO: 1733 | Homo sapiens 6-pyruvoyltetrahydropterin synthase (PTS), mRNA [NM_000317] |
| 153 | A_23_P128192 | PFDN5 | CAGGTCCATTGGTCAGCTCAAAGTGGTACAGACCAAGTATGTGG AAGCAAGGACTGTCT | SEQ ID NO: 1734 | Homo sapiens prefoldin subunit 5 (PFDN5), transcript variant 1, mRNA [NM_002624] |

Fig. 5-9

| No. | Probe ID No. | Symbols of genes | Sequence | SEQ ID NO: | Descriptions of genes (letters and numbers within [ ] indicates GenBank accession No.) |
|---|---|---|---|---|---|
| 154 | A_23_P128384 | VPS29 | CAGGTAATTGGAGGATGATGAAAGTAGAAGGAATCGAATAGAA AAAAGGTTAAATAGGAAG | SEQ ID NO: 1735 | Homo sapiens vacuolar protein sorting 29 homolog (S. cerevisiae) (VPS29), transcript variant 2, mRNA [NM_057180] |
| 155 | A_23_P128470 | CLEC12A | CCACCAAATTATGTCGTGAGGTATATAGGAAAGAACAAGAGCAC AAATGTAAGCGTTGTC | SEQ ID NO: 1736 | Homo sapiens C-type lectin domain family 12, member A (CLEC12A), transcript variant 1, mRNA [NM_138337] |
| 156 | A_23_P128930 | PSMC6 | GAACAAGCAAGATTAGACATAGTGAAAATGGATGCAGGTCCAT TACAAAGGATGGTCAA | SEQ ID NO: 1737 | Homo sapiens proteasome (prosome, macropain) 26S subunit, ATPase, 6 (PSMC6), mRNA [NM_002806] |
| 157 | A_23_P130444 | ZNF701 | CTCCTTGCAGAATATCATAAGGTTCATTTTGAGGTAATAGTTA GAAATGCGGTGAGGAC | SEQ ID NO: 1738 | Homo sapiens zinc finger protein 701 (ZNF701), mRNA [NM_018260] |
| 158 | A_23_P132363 | ENST00000306024 | AGGTAAATGGTATTTTGATTTTTCTCAAGGTGTCCAATAAATAT GACCACGAAGATGCAG | SEQ ID NO: 1739 | U6 snRNA-associated Sm-like protein LSm3. [Source:Uniprot/SWISSPROT;Acc:P62310] [ENST00000306024] |
| 159 | A_23_P132936 | SPCS3 | GAATGTCACTTGACCGTGTCTTGGAAGGTCGTACCAAATGCTG GAATTCTACCTCTTGT | SEQ ID NO: 1740 | Homo sapiens signal peptidase complex subunit 3 homolog (S. cerevisiae) (SPCS3), mRNA [NM_021928] |
| 160 | A_23_P133293 | MCTP1 | AGGAAGCCAGTAAGTACAGTTATCAAAAATACTAGGAAAGTATA TCCATATCGCTTTTGG | SEQ ID NO: 1741 | Homo sapiens cDNA: FLJ22334 fis, clone HRC06080. [AK025997] |
| 161 | A_23_P133445 | GZMA | GAATGAATATGGTTTGTGGAAGCCTCCGAGGTGGAAAAAAGT TCGTGAAATAGAGATT | SEQ ID NO: 1742 | Homo sapiens granzyme A (granzyme 1, cytotoxic T-lymphocyte-associated serine esterase 3) (GZMA), mRNA [NM_006144] |
| 162 | A_23_P133646 | FAM8A1 | ACTTCGCCGAATTACAAAATGAGTGTTTTTAGATTCAAGTGAC GGTAAAAGGATTGTT | SEQ ID NO: 1743 | Homo sapiens family with sequence similarity 8, member A1 (FAM8A1), mRNA [NM_016255] |
| 163 | A_23_P134714 | HRSP12 | TAAATTAGACCCTGTGTGCACCTGATTACTGAATATAGGAAGA GATACCCATTAGATAG | SEQ ID NO: 1744 | Homo sapiens heat-responsive protein 12 (HRSP12), mRNA [NM_005836] |
| 164 | A_23_P134786 | PHF20L1 | AGTTGTATGTGCCCCGAGTGCTACATACGCAGGGTATGCGTAAGT GTGTATGGTTGTTTA | SEQ ID NO: 1745 | Homo sapiens PHD finger protein 20-like 1 (PHF20L1), transcript variant 1, mRNA [NM_016018] |
| 165 | A_23_P134925 | BNIP3L | ATTTGGGGACAAAAAGGCACGGCGTTCATTTTCATATGTTTGATG AAAACTGGCTCAAGAT | SEQ ID NO: 1746 | Homo sapiens BCL2/adenovirus E1B 19kDa interacting protein 3-like (BNIP3L), mRNA [NM_004331] |
| 166 | A_23_P135123 | BG216229 | CTGGTGTGAAGGGTCACGGGGTGTTCACCTGTGTTCTTACTC ATAATTGATTATTCAA | SEQ ID NO: 1747 | BG216229 RST35803 Athersys RAGE Library Homo sapiens cDNA. mRNA sequence. [BG216229] |
| 167 | A_23_P135494 | CLIC4 | CTCCTCAAGCCGATAATGTTGAACAGAAATTGGAGTATTTCTTTA TAATTCGTGAAACAGG | SEQ ID NO: 1748 | Homo sapiens chloride intracellular channel 4 (CLIC4), mRNA [NM_013943] |
| 168 | A_23_P135498 | CLIC4 | CTTCGGTTTTTACTGATGTAGATGCAGATATATGTATACAGTTCTGT TGTCTTTACTAAGGAA | SEQ ID NO: 1749 | Homo sapiens chloride intracellular channel 4 (CLIC4), mRNA [NM_013943] |
| 169 | A_23_P137366 | C1QB | GACCGGACAAGAACATCACTACTGCTGGGCATGAGGCTGCCAACAGGA TCTTTCCGGGGTCCT | SEQ ID NO: 1750 | Homo sapiens complement component 1, q subcomponent, B chain (C1QB), mRNA [NM_000491] |
| 170 | A_23_P137434 | RNF11 | TGTAGTATCCATATGTTGCTTAAATTTCCTATGAGCCCCATGA TGGAAAGACTTAAAGA | SEQ ID NO: 1751 | Homo sapiens ring finger protein 11 (RNF11), mRNA [NM_014372] |
| 171 | A_23_P138306 | CD58 | AACCTGTATCCCAAGCAGGAGGTGATTCAAGACACAGATATGCAC TTATACGGATACCATT | SEQ ID NO: 1752 | Homo sapiens CD58 molecule (CD58), mRNA [NM_001779] |
| 172 | A_23_P138541 | AKR1C3 | TTTTGAGTTCCAGTTGACTCCAGAGGACGATGAAAAGGCCATAGATG GCCTAGACAGAAATCT | SEQ ID NO: 1753 | Homo sapiens aldo-keto reductase family 1, member C3 (3-alpha hydroxysteroid dehydrogenase, type II) (AKR1C3), mRNA [NM_003739] |

Fig. 5-10

| No. | Probe ID No. | Symbols of genes | Sequence | SEQ ID NO. | Descriptions of genes (refers and numbers within [ ] indicates GenBank accession No.) |
|---|---|---|---|---|---|
| 173 | A_23_P140301 | PSMA3 | TGAACTAGAACTCAAGCTGGGTTGGTGAATTAACTAATGGAAGAC ATGAAATTGTTCCAAA | SEQ ID NO: 1754 | Homo sapiens proteasome (prosome, macropain) subunit, alpha type, 3 (PSMA3), transcript variant 1, mRNA [NM_002788] |
| 174 | A_23_P141549 | RPS7 | GTCAAACTAGATGGCAAGGCGGGGTCATAAACGGTTGATTTGGACAA AGGCAAGCAGAACAAT | SEQ ID NO: 1755 | Homo sapiens ribosomal protein S7 (RPS7), mRNA [NM_001011] |
| 175 | A_23_P142560 | ZEB2 | CTTTTAATCGTGTTTTGTGCAAGTGCCATCCTTGTACAAGTGTTA AGAGGGTAACATGGGT | SEQ ID NO: 1756 | Homo sapiens zinc finger E-box binding homeobox 2 (ZEB2), mRNA [NM_014795] |
| 176 | A_23_P143958 | RPL22L1 | ATTGGGTTGAGTGGTTCCATCTGACAAGGAGAGCCTACGAACTT CGTACTTCCAGATTA | SEQ ID NO: 1757 | Homo sapiens ribosomal protein L22-like 1, mRNA [cDNA clone IMAGE:4865966], [BC049823] |
| 177 | A_23_P144145 | DCUN1D1 | TCTTTAGTAGAATATCATCTGGATATCTCTCTGTAAGTTCAATGTG TTTGTACAGTCCGTG | SEQ ID NO: 1758 | Homo sapiens RP42 protein mRNA, complete cds. [AF291200] |
| 178 | A_23_P144151 | DCUN1D1 | TATGCTCTGTTTCTTTAAAAGTCATATGGGTTGGTGGCCTAAT GCCTTGGATTTTACAT | SEQ ID NO: 1759 | Homo sapiens RP42 protein mRNA, complete cds. [AF291200] |
| 179 | A_23_P144497 | RPS3A | CCAAATCGGAAGAAGATGATGGAAATGATGACCCGAGAGGTGC AGACAAATGAGTTGAA | SEQ ID NO: 1760 | Homo sapiens ribosomal protein S3A (RPS3A), mRNA [NM_001006] |
| 180 | A_23_P145114 | GCLC | AGAATGCGTGGTTTTCGTTTGCAATTTGCTTGTGTGAAATCAGGT TGTCAAAAGGCAGATA | SEQ ID NO: 1761 | Homo sapiens glutamate-cysteine ligase, catalytic subunit (GCLC), mRNA [NM_001498] |
| 181 | A_23_P145397 | CCNG | TAGTGGACCACTTGGACATAAACCATTGCACAGATTTCAGTAAT GTCTCAGTGGAACAC | SEQ ID NO: 1762 | Homo sapiens cyclin G (CCNG), transcript variant 1, mRNA [NM_005190] |
| 182 | A_23_P14664 | GPR65 | AACAAGTTTAAATTGTTGGTCATCCAATTCTGTAGTGTTTTG TAACCGAAACAGGAAG | SEQ ID NO: 1763 | Homo sapiens G protein-coupled receptor 65 (GPR65), mRNA [NM_003608] |
| 183 | A_23_P145777 | NDUFA4 | AGGCTGCTTTAGAATGAAGGTCTTCCAGAAGCCACATCCCACA ATTTCCACTTAAGGA | SEQ ID NO: 1764 | Homo sapiens NADH dehydrogenase (ubiquinone) 1 alpha subcomplex, 4, 9kDa (NDUFA4), nuclear gene encoding mitochondrial protein, mRNA [NM_002489] |
| 184 | A_23_P14708 | SUHW4 | TGTTTGTACCTCCATACAAGTGTTAGGCTGCCAAGGCTGTAAGGT TACGTAATTAAAGTT | SEQ ID NO: 1765 | Homo sapiens suppressor of hairy wing homolog 4 (Drosophila) (SUHW4), transcript variant 1, mRNA [NM_017661] |
| 185 | A_23_P14734 | RPS27L | TACAAGATCAGCACGGTTTCAGGCGATGCTCAGACAGTGGTTCT TTGTGTAGGTGTTCA | SEQ ID NO: 1766 | Homo sapiens ribosomal protein S27-like (RPS27L), mRNA [NM_015920] |
| 186 | A_23_P147404 | A_23_P147404 | TGGGTCCCTCTCATGTG GGGTCCCTCTCATGTG | SEQ ID NO: 1767 | |
| 187 | A_23_P148969 | LRRC40 | GCATGTATATCAATTTATATAGGTAGATAGGTTTTGGATG ATTGAGGCATGGTTAT | SEQ ID NO: 1768 | Homo sapiens leucine rich repeat containing 40 (LRRC40), mRNA [NM_017768] |
| 188 | A_23_P149775 | ARHGAP12 | TGTATAATAAAACACAGGGTTTGGAAGGTTTTGTTACAGGGAGC ATGGTCTGTTGAAGAT | SEQ ID NO: 1769 | Homo sapiens Rho GTPase activating protein 12 (ARHGAP12), mRNA [NM_018287] |
| 189 | A_23_P149892 | GALNACT-2 | CATGGTGGTTCAGAATAGATGAGGAATAGCATGGTTTTGTTGTT TTTGCTTCAATTTC | SEQ ID NO: 1770 | Homo sapiens chondroitin sulfate GalNAcT-2 (GALNACT-2), mRNA [NM_018590] |
| 190 | A_23_P151018 | LEMD3 | CCCCATCTTGTAAGCTGTTGCAAAGAGTGAATGTAAAAAATAGTT GTGGGATTTTAAAGG | SEQ ID NO: 1771 | Homo sapiens LEM domain containing 3 (LEMD3), mRNA [NM_014319] |
| 191 | A_23_P151637 | RNASE2 | GTGTTAACCCAAATATGAGCTGTCGTAGTAACAAAAGTCGCAAA AATTGTCACCACAGTG | SEQ ID NO: 1772 | Homo sapiens ribonuclease, RNase A family, 2 (liver, eosinophil-derived neurotoxin) (RNASE2), mRNA [NM_002934] |

Fig. 5-11

| No. | Probe ID No. | Symbols of genes | Sequence | SEQ ID NO. | Descriptions of genes (letters and numbers within [ ] indicates GenBank accession No.) |
|---|---|---|---|---|---|
| 192 | A_23_P152002 | BCL2A1 | TGTAACCATATTTGCATTTGAAGGTATTTCTCATCAAGAAAGTTCTACGACAGCAAATTGC | SEQ ID NO: 1773 | Homo sapiens BCL2-related protein A1 (BCL2A1), mRNA [NM_004049] |
| 193 | A_23_P154330 | TXNDC9 | GTCAGTTGTTAAATTATCTGGGAAGGGTCTGGATTCTGTATTTTGAGATTGACTTTATG | SEQ ID NO: 1774 | Homo sapiens thioredoxin domain containing 9 (TXNDC9), mRNA [NM_005783] |
| 194 | A_23_P155765 | HMGB2 | TAAAAATGCAGGTTGTAGGTTTTGATGGGCTAGTACATAGAGTAGATTTTACAGGTTC | SEQ ID NO: 1775 | Homo sapiens high-mobility group box 2 (HMGB2), mRNA [NM_002129] |
| 195 | A_23_P155815 | NCAPG | AAGTTAGGAAAGACGATGGAGGTGGAATCCTTAAGATTATGTCGAGTTATTTGCTTTAA | SEQ ID NO: 1776 | Homo sapiens non-SMC condensin I complex, subunit G (NCAPG), mRNA [NM_022346] |
| 196 | A_23_P156355 | TMEM161B | AGGTTTTGGACCTGGCATATTTGTTTATTCTGTGATGCTAAGTAGTTCCTTTTAATAGG | SEQ ID NO: 1777 | Homo sapiens transmembrane protein 161B (TMEM161B), mRNA [NM_153354] |
| 197 | A_23_P156842 | EEF1E1 | AAGAAAAGCCAATCGTTCAGCAGTTGGTTAGAATACAGGGTACATCAAGTAGAATGGGCACT | SEQ ID NO: 1778 | Homo sapiens eukaryotic translation elongation factor 1 epsilon 1 (EEF1E1), mRNA [NM_004280] |
| 198 | A_23_P157449 | POLR2K | GGTCTCTCTTGCTTCAAATATCTCTTGTATAGAGTAGTCACCATTTAGATGTGGTTGAC | SEQ ID NO: 1779 | Homo sapiens polymerase (RNA) II (DNA directed) polypeptide K, 7.0kDa (POLR2K), mRNA [NM_005034] |
| 199 | A_23_P157452 | POLR2K | GGAATGTTCAGTTATAGTTGGATTTGCTCTCTTCCGATTTGGATTGTGTTATAAGCTT | SEQ ID NO: 1780 | Homo sapiens polymerase (RNA) II (DNA directed) polypeptide K, 7.0kDa (POLR2K), mRNA [NM_005034] |
| 200 | A_23_P157795 | CTNNAL1 | GGATAGTAAAAGTTGAGAAGGTCAGATCTGTGAAGATCATGTGATGAAGCT | SEQ ID NO: 1781 | Homo sapiens catenin (cadherin-associated protein), alpha-like 1 (CTNNAL1), mRNA |
| 201 | A_23_P159650 | COX7B | CAAATACGGTTAATGCTGTATTAGCTAGGTAGGCGAGCCACTTTGTATTGTTACATGGACATA | SEQ ID NO: 1782 | Homo sapiens cytochrome c oxidase subunit VIIb (COX7B), nuclear gene encoding mitochondrial protein, mRNA [NM_001866] |
| 202 | A_23_P159839 | C1GALT1C1 | TCCAAATCAGATGGATGCGTATATTAGCTAGTGATGGGTATACGGCGTTAGGGCATTTGGGCATAT | SEQ ID NO: 1783 | Homo sapiens C1GALT1-specific chaperone 1 (C1GALT1C1), transcript variant 1, mRNA [NM_152692] |
| 203 | A_23_P160406 | KCTD3 | TTGTAGGAGTGGAGTTGCAGTTCTGAATTTGGGTTAAAGGTTTTGGGTGCTGTAAGAATGTGAAT | SEQ ID NO: 1784 | Homo sapiens potassium channel tetramerisation domain containing 3 (KCTD3), mRNA [NM_016121] |
| 204 | A_23_P160466 | SLC19A2 | CTTGGTATGTGGGCATATTATAGAATGCTGAACTCAATGTGGAAGTTGTACTGTATGCA | SEQ ID NO: 1785 | Homo sapiens solute carrier family 19 (thiamine transporter), member 2 (SLC19A2), mRNA [NM_006996] |
| 205 | A_23_P161091 | ZMYM1 | GAAGGTATTTTCCTAAGTGGTATTGTAGGGTGTATACTGTGTCTTCAGCTTGTGTTGTGTG | SEQ ID NO: 1786 | Homo sapiens zinc finger, MYM-type 1 (ZMYM1), mRNA [NM_024772] |
| 206 | A_23_P162596 | ACTR6 | TTAACGGCTTCACTGACGACAGTTTCCTTAGAAGGTAGTTTTGTCTGACTGTGACTAAAGT | SEQ ID NO: 1787 | Homo sapiens ARP6 actin-related protein 6 homolog (yeast) (ACTR6), mRNA [NM_022496] |
| 207 | A_23_P163113 | PRPF39 | TAGTAATAGGGGAGGAAAATGTCAATTAGGTTAGCCACAGATACTGTTTCCTACCATTTA | SEQ ID NO: 1788 | Homo sapiens PRPF39 pre-mRNA processing factor 39 homolog (S. cerevisiae) (PRPF39), mRNA |
| 208 | A_23_P167828 | RWDD1 | GAGGATGCTGGAACAACGTGTAGGGTGAGATGATGAGCTGTTTTGTTGGAAGAAATGGAGTTG | SEQ ID NO: 1789 | Homo sapiens RWD domain containing 1 (RWDD1), transcript variant 2, mRNA [NM_016104] |
| 209 | A_23_P16817 | CLK1 | ATGAAAAGGATTCTTGGACCTCTAGGAACCTCTAGGAAAACATATGAAACAGAGAAACCAGGAAAAGGTAAA | SEQ ID NO: 1790 | Homo sapiens CDC-like kinase 1 (CLK1), transcript variant 1, mRNA [NM_004071] |
| 210 | A_23_P168656 | GTPBP10 | AATTTGTTGGATTTCTGATACAATGTCTTGTACTGAGCCACGATCAAAGGCATGCTGTTACT | SEQ ID NO: 1791 | Homo sapiens GTP-binding protein 10 (putative) (GTPBP10), transcript variant 2, mRNA [NM_033107] |
| 211 | A_23_P169050 | MRPS28 | GAAGGAACAACAGATACAACTGTACTAGAGGCTAATGCAGTTCTCTTGGGAATCCAGGAGA | SEQ ID NO: 1792 | Homo sapiens mitochondrial ribosomal protein S28 (MRPS28), nuclear gene encoding mitochondrial protein, mRNA [NM_014018] |

Fig. 5-12

| No. | Probe ID No. | Symbols of genes | Sequence | SEQ ID NO: | Descriptions of genes (letters and numbers within [ ] indicates GenBank accession No.) |
|---|---|---|---|---|---|
| 212 | A_23_P17021 | SCRN3 | GTGAAAGTTAGTTCTTAGTGATCATATGGTCAGGTAATATTAGT TCTTAGTGATCAGTGG | SEQ ID NO: 1793 | Homo sapiens secernin 3 (SCRN3), mRNA [NM_024583] |
| 213 | A_23_P170233 | CSTA | AACTGGCTACTGAGTCATGATCCTTGCTGATAAATATAACCATG AATAAAGAAGGATTCT | SEQ ID NO: 1794 | Homo sapiens cystatin A (stefin A) (CSTA), mRNA [NM_005213] |
| 214 | A_23_P18325 | PDCD10 | CGAACCGACTAATTCATCGAAACGAACGTTAATAGTTCGAGACGTTC AAAAGTGTGGCCTGAA | SEQ ID NO: 1795 | Homo sapiens programmed cell death 10 (PDCD10), transcript variant 1, mRNA [NM_007217] |
| 215 | A_23_P18422 | MRPL3 | CAGTAGAAAACAATATGGAGACTATAGTGCAACGTATTTGGGTA AAGAAACCATTTGCTA | SEQ ID NO: 1796 | Homo sapiens mitochondrial ribosomal protein L3 (MRPL3), nuclear gene encoding mitochondrial protein, mRNA [NM_007208] |
| 216 | A_23_P18596 | PI4K2B | AGGCTTAAAACCAATGTCACGACTTGGGGTTAACTGGGTAATTT GTGGTGTAGGCCTTTT | SEQ ID NO: 1797 | Homo sapiens phosphatidylinositol 4-kinase type 2 beta (PI4K2B), mRNA [NM_018323] |
| 217 | A_23_P19291 | TUBB2A | ACTTGTCAGATCAATGATCGTGCATCCTTAGTGAACTTCTGTTGTCC TGAAGCATGGCTTTC | SEQ ID NO: 1798 | Homo sapiens tubulin, beta 2A (TUBB2A), mRNA [NM_001069] |
| 218 | A_23_P200030 | FPGT | TAAAATTGGTAAACTAGAAGTAAGTTGTCGACAACGTCAGTT ATGATAGTTATGTGGG | SEQ ID NO: 1799 | Homo sapiens fucose-1-phosphate guanylyltransferase (FPGT), mRNA [NM_003838] |
| 219 | A_23_P200298 | AGL | TAGATTTTTAACAGGTCTGATTTGACTAAAGTTTCGGTAGAAT GGTTCATAGTTGAGTC | SEQ ID NO: 1800 | Homo sapiens amylo-1, 6-glucosidase, 4-alpha-glucanotransferase (glycogen debranching enzyme, glycogen storage disease type III) (AGL), transcript variant 4, mRNA [NM_000028] |
| 220 | A_23_P202567 | CHN4 | GGTTGAAGTCAGGGTACACTACAGTGCACAGTTGAAGAGCCAG AGACTTCTTAAATGAT | SEQ ID NO: 1801 | Homo sapiens carmichon homolog 4 (Drosophila) (CNIH4), mRNA [NM_014184] |
| 221 | A_23_P200955 | A_23_P200955 | AGACATGATTGAACCTAGATTGATGTGAAGACTAGGGATGGT TATTTGTTTCATCTAG | SEQ ID NO: 1802 | |
| 222 | A_23_P201619 | NEK7 | TGAAGGCCAAGAAGGAAGTCACTGTTAAAGGACTGTGTGGCCATGT TACAACCTTGGATGAA | SEQ ID NO: 1803 | Serine/threonine-protein kinase Nek7 (EC 2.7.11.1) (NimA-related protein kinase 7). [Source:Uniprot/SWISSPROT;Acc:Q8TDX7] [ENST00000367385] |
| 223 | A_23_P201918 | ABCB10 | CATGGATAGGCCTAAGACCCTAAGAAGTAATTAAGTCAATGTAAA TCAAATGGAAGTTTTC | SEQ ID NO: 1804 | Homo sapiens ATP-binding cassette, sub-family B (MDR/TAP), member 10 (ABCB10), nuclear gene encoding mitochondrial protein, mRNA [NM_012089] |
| 224 | A_23_P202587 | KIAA1598 | GTAATAATTGCAGTGTTGATTGTATTGTATTTTGGACGGTTGT GGTAAGCATAGGGTTG | SEQ ID NO: 1805 | Homo sapiens KIAA1598 (KIAA1598), mRNA [NM_018330] |
| 225 | A_23_P203376 | MS4A6A | ACGGGGGTGTAAATTAGCATTAGTAGATTAGGGAAATAGTGTG AATTTCCAGAAAACAA | SEQ ID NO: 1806 | Homo sapiens membrane-spanning 4-domains, subfamily A, member 6A (MS4A6A), transcript variant 1, mRNA [NM_152852] |
| 226 | A_23_P203498 | TRIM22 | GTACATAAGAATCTATCACTAAGTAATGTATCCTTGAGAATGTG TTGGTTTACCAGTGAC | SEQ ID NO: 1807 | Homo sapiens tripartite motif-containing 22 (TRIM22), mRNA [NM_006074] |
| 227 | A_23_P203645 | CREB2F | TCTGTTGGAGTATTTCTTTGGTCAACATAGTTTCCTGCAT TATTCAAATTGTGGG | SEQ ID NO: 1808 | Homo sapiens CREB/ATF bZIP transcription factor (CREB2F), mRNA [NM_001039618] |
| 228 | A_23_P204187 | FLJ22028 | GTATAAGGTTGTACTGCTGGGAAAAATACAATGACAGGGGTTAG GTTGAGATCATGAATT | SEQ ID NO: 1809 | Homo sapiens hypothetical protein FLJ22028 (FLJ22028), mRNA [NM_024854] |
| 229 | A_23_P204269 | USP15 | GACCAGGATAAATGAGGTATGTTGATCATGGCTTGCTTTATAT CTTGATATTTAAAGCTG | SEQ ID NO: 1810 | Homo sapiens ubiquitin specific peptidase 15 (USP15), mRNA [NM_006313] |

Fig. 5-13

| No. | Probe ID No. | Symbols of genes | Sequence | SEQ ID NO: | Descriptions of genes (letters and numbers within [ ] indicates GenBank accession No.) |
|---|---|---|---|---|---|
| 230 | A_23_P205027 | ABHD13 | ATTTGTCAGAATGATAAAGAATGTTCCTTTAGAAGTGTGTTATGTCTGTACCTGTCTG | SEQ ID NO: 1811 | Homo sapiens abhydrolase domain containing 13 (ABHD13), mRNA [NM_032859] |
| 231 | A_23_P205336 | C14orf129 | CAATTCATTGCCAGACTTCATTGGAATGGTTCGTTGTTTGATGATGTATGTTCATTCTCAGGT | SEQ ID NO: 1812 | Homo sapiens chromosome 14 open reading frame 129 (C14orf129), mRNA [NM_016472] |
| 232 | A_23_P205646 | MAP4K5 | CTAATGTAGGAGGGGGAAGTATTTAATTGGCATGATATGTATTTTAGTTATACTATGCC | SEQ ID NO: 1813 | Homo sapiens mitogen-activated protein kinase kinase kinase kinase 5 (MAP4K5), transcript variant 2, mRNA [NM_198794] |
| 233 | A_23_P20606 | NIPSNAP3A | GTAAGTACCACTTCAAAAAATAGTTCTGTTTAGTTTCTGCATGGTATTTCAGTGTGTGTC | SEQ ID NO: 1814 | Homo sapiens nipsnap homolog 3A (C. elegans) (NIPSNAP3A), mRNA [NM_015469] |
| 234 | A_23_P206228 | VPS13C | GGGATCATTATCAGTAATTTGATAGGCAACTGTTCTAGTGTTTTGTGTTTTTAAAACAGAA | SEQ ID NO: 1815 | Homo sapiens vacuolar protein sorting 13 homolog C (S. cerevisiae) (VPS13C), transcript variant 1A, mRNA [NM_017684] |
| 235 | A_23_P207299 | LOC51136 | CCAAAACAGCAATTTGAAATTAGAACTAGTGGTTTTAGAAGAAGTCAGGTATTCTTTCCTG | SEQ ID NO: 1816 | Homo sapiens PTD016 protein (LOC51136), mRNA [NM_016125] |
| 236 | A_23_P209032 | ZNF302 | TCAGAAAATGTATAGTTGGGGAAAAGTTGTATGAAGGTGGTGAACATGGGAGACTTTTAG | SEQ ID NO: 1817 | Homo sapiens zinc finger protein 302 (ZNF302), transcript variant 1, mRNA [NM_018443] |
| 237 | A_23_P209232 | CLIP4 | GCTTATGAAATGTCATTAAAGTTCAGTTGTTGAGCATCAATAAAAAGGGAAGCTGTGTG | SEQ ID NO: 1818 | Homo sapiens CAP-GLY domain containing linker protein family, member 4 (CLIP4), mRNA [NM_034466] |
| 238 | A_23_P209625 | CYP1B1 | CTGTTTATATGGAAGAAAGTAAGGTGCTTGGAGTTTACCTGGCTTATTTAATATGCTT | SEQ ID NO: 1819 | Homo sapiens cytochrome P450, family 1, subfamily B, polypeptide 1 (CYP1B1), mRNA [NM_000104] |
| 239 | A_23_P210001 | PAX8 | CAAGTTCCTTCCTAACGCCCAGACTTGGCCTGTGAGTGAAATGTCTGTTTGGG | SEQ ID NO: 1820 | Homo sapiens paired box gene 8 (PAX8), transcript variant PAX8A, mRNA [NM_003466] |
| 240 | A_23_P210274 | PREI3 | GGATGAGTATGCGTAGGAATTTACAGAATATTTACAGAATATAATACACTACTTCTTTCATCATCGGCAG | SEQ ID NO: 1821 | Homo sapiens preimplantation protein 3 (PREI3), transcript variant 1, mRNA [NM_015337] |
| 241 | A_23_P210829 | PCMTD2 | TCCTGGGAGCTTACCAGAATTCAGTATAATACACTACTTTCTGTTTCAAACAGATA | SEQ ID NO: 1822 | Homo sapiens protein-L-isoaspartate (D-aspartate) O-methyltransferase domain containing 2 (PCMTD2), mRNA [NM_018257] |
| 242 | A_23_P211640 | UBE1C | GGCAGGGTAGAGGGAAAAAATAGAACAGTTAGTTACAGAGTCGGTAAGCTCTATTGAAGAA | SEQ ID NO: 1823 | Homo sapiens ubiquitin-activating enzyme E1C (UBA3 homolog, yeast) (UBE1C), transcript variant 1, mRNA [NM_003969] |
| 243 | A_23_P212383 | SACM1L | GCCTCTGAGAGGGTCTGTTCTAGATTTCATATTGCACTTGGAGGGTAACAGCTCGTTTT | SEQ ID NO: 1824 | Homo sapiens SAC1 suppressor of actin mutations 1-like (yeast) (SACM1L), mRNA [NM_014016] |
| 244 | A_23_P2129 | TMEM126B | CATATGCATGATTGGCACACTTCCATTTTGTCTACGTGTGTTACTGAGAAGCTTTTTG | SEQ ID NO: 1825 | Homo sapiens transmembrane protein 126B (TMEM126B), mRNA [NM_018480] |
| 245 | A_23_P213638 | PANK3 | TGTATATAGCCATGCTTAAATCCTTAAATGCAATACAGGGTCTGATTATTGAAGCTGCTC | SEQ ID NO: 1826 | Homo sapiens pantothenate kinase 3 (PANK3), mRNA [NM_024594] |
| 246 | A_23_P213661 | HISPPD1 | GTATGTAAGTTTTCTGTTTGTGAAAATGTAGTTAATGTAGTCACTGTGGAGGTCATAAGG | SEQ ID NO: 1827 | Homo sapiens histidine acid phosphatase domain containing 1 (HISPPD1), mRNA [NM_015216] |
| 247 | A_23_P213718 | UQCRQ | TTCCTGTCCTGTCTGAAAGAGCTTTCTGGAAGGAGGAGTCTGCATTGTAGTGTCTGAAAGA | SEQ ID NO: 1828 | Homo sapiens ubiquinol-cytochrome c reductase, complex III subunit VII, 9.5kDa (UQCRQ), nuclear gene encoding mitochondrial protein, mRNA [NM_014402] |

Fig. 5-14

| No. | Probe ID No. | Symbols of genes | Sequence | SEQ ID NO: | Descriptions of genes (letters and numbers within [ ] indicates GenBank accession No.) |
|---|---|---|---|---|---|
| 248 | A_23_P214108 | TPMT | GGTTGATGCTTTTGAAGAACGACATAAAAGTTGGGAATTCACTGTCTTTTGAAAAGTT | SEQ ID NO: 1829 | Homo sapiens thiopurine S-methyltransferase (TPMT), mRNA [NM_000367] |
| 249 | A_23_P215051 | ECHDC1 | TTTTTGCAGAGGTAAAGTCTAGATTACTGTGTCAAGCCAATACTATTGGCCATAGATGT | SEQ ID NO: 1830 | Homo sapiens enoyl Coenzyme A hydratase domain containing 1 (ECHDC1), mRNA [NM_018479] |
| 250 | A_23_P215751 | NDUFA5 | TAAAAGTGGAGTCAGTAAATAGTTTGCAGTACGTTCTAATATAAGTGTAGGTGGGTATC | SEQ ID NO: 1831 | Homo sapiens NADH dehydrogenase (ubiquinone) 1 alpha subcomplex, 5, 13kDa (NDUFA5), nuclear gene encoding mitochondrial protein, mRNA [NM_005000] |
| 251 | A_23_P216708 | RFK | AGTCAGAAAAACATCAAAGCTGTTTGGAGAAGAGGACTCATATAAATAGTTGGATTGCG | SEQ ID NO: 1832 | Homo sapiens riboflavin kinase (RFK), mRNA [NM_018339] |
| 252 | A_23_P21734 | TAF9 | CATGGTTGTGATTTCTTCCCTGAACGCTGGTTTGATATAGTTTTGTGCCTGAGAACAGAT | SEQ ID NO: 1833 | Homo sapiens TAF9 RNA polymerase II, TATA box binding protein (TBP)-associated factor, 32kDa (TAF9), transcript variant 3, mRNA [NM_001015891] |
| 253 | A_23_P217384 | AP1S2 | AAACGTGTTGCTGTCTTGAGATATTATGTAAAGTCATTGTTTAAAGCAGGAAATGTTC | SEQ ID NO: 1834 | Homo sapiens adaptor-related protein complex 1, sigma 2 subunit (AP1S2), mRNA [NM_003916] |
| 254 | A_23_P217564 | ACSL4 | GTTATAGGTCCTTTAGAAACACATAATTAACAGTTAAGGTTGGGTGCTGCTAATTCTTTG | SEQ ID NO: 1835 | Homo sapiens acyl-CoA synthetase long-chain family member 4 (ACSL4), transcript variant 1, mRNA [NM_004458] |
| 255 | A_23_P217797 | DDX3Y | CACTGATAGGAAGGTCCACATCGACAAAGTTTCTCTTGAGTTTTGTTATGTGTTTTCCTG | SEQ ID NO: 1836 | Homo sapiens DEAD (Asp-Glu-Ala-Asp) box polypeptide 3, Y-linked (DDX3Y), mRNA [NM_004660] |
| 256 | A_23_P218928 | C4orf18 | CAGATGAGTTCATTTGTTCTGTAGATGTGTTTCAGAGCTAGGTACAAGAGGAATGTTTC | SEQ ID NO: 1837 | Homo sapiens chromosome 4 open reading frame 18 (C4orf18), transcript variant 2, mRNA [NM_016613] |
| 257 | A_23_P219072 | SAMD9 | AACCTACCTCCAGATTAGTAAAGCCAGTTGAAAACTAAAAGATCAGGTTCAGAAGCT | SEQ ID NO: 1838 | Homo sapiens sterile alpha motif domain containing 9 (SAMD9), mRNA [NM_017654] |
| 258 | A_23_P219161 | OLFM1 | GGGCTAAGTTAAAAGAGTTTTTCAATGCTGCAGTGAGTGAAGAAACAGTGACTCCCAT | SEQ ID NO: 1839 | Homo sapiens olfactomedin 1 (OLFM1), transcript variant 2, mRNA [NM_006334] |
| 259 | A_23_P22433 | RP2 | TTATTCTCTTGGCATTAATAGTAGTGCTGTGTTTTGTTTGGTTGTTTATATTATGTCTA | SEQ ID NO: 1840 | Homo sapiens retinitis pigmentosa 2 (X-linked recessive) (RP2), mRNA [NM_006915] |
| 260 | A_23_P2262 | SURB7 | ATGTGGCTGAGAAAAGAAGAACTGTTTGAGTGCATTAAGAATTCTGCATCAGACTAGATAC | SEQ ID NO: 1841 | Homo sapiens SRB7 suppressor of RNA polymerase B homolog (yeast) (SURB7), mRNA [NM_004264] |
| 261 | A_23_P22671 | SYBL1 | CAAACGGAATACCGGTCACGAGGTCAAGTCACAGGGTTTGGGCTTGATTCCTGTTGAATAATA | SEQ ID NO: 1842 | Homo sapiens synaptobrevin-like 1 (SYBL1), mRNA [NM_005638] |
| 262 | A_23_P2366 | NUDT4 | CATCAGTCTGTGGTTTATTGTCATCAGATTACTGTGGGTATAGGTAGCCCAAAATTG | SEQ ID NO: 1843 | Homo sapiens nudix (nucleoside diphosphate linked moiety X)-type motif 4 (NUDT4), transcript variant 2, mRNA [NM_199040] |
| 263 | A_23_P23765 | ITGB3BP | AGTATACAGGCTTTGGAGGGCAGTAGAGAGCCTGAAAATGTCATTGAATGCTGGTGTGCA | SEQ ID NO: 1844 | Homo sapiens integrin beta 3 binding protein (beta3-endonexin) (ITGB3BP), mRNA [NM_014288] |
| 264 | A_23_P23960 | BLOC1S2 | GAGTAAACTGGAGGACTGGCGTATTCCTGAACCTCTTGAGACAGAATCCCTCAGAAT | SEQ ID NO: 1845 | Homo sapiens biogenesis of lysosome-related organelles complex-1, subunit 2 (BLOC1S2), transcript variant 2, mRNA [NM_001001342] |
| 265 | A_23_P24385 | ANKRD49 | GGGCACTGGTTGTATAGTCTCTCAAGTTCACAGGAAAATGTTGATTTTGTAAGGTCCTCAT | SEQ ID NO: 1846 | Homo sapiens ankyrin repeat domain 49 (ANKRD49), mRNA [NM_017704] |

Fig. 5-15

| No. | Probe ID No. | Symbols of genes | Sequence | SEQ ID NO: | Descriptions of genes (tables and numbers within [ ] indicates GenBank accession No.) |
|---|---|---|---|---|---|
| 266 | A_23_P250062 | HACE1 | TAAGGAGTCAT TGTGTTTGGGAGTAATGTTTGAGAGACATGTAAGTTGAAAAGTTTTGCTA | SEQ ID NO: 1847 | Homo sapiens HECT domain and ankyrin repeat containing, E3 ubiquitin protein ligase 1 (HACE1), mRNA [NM_020771] |
| 267 | A_23_P250800 | ST3GAL6 | ATGTCACGAAGTTCACCTAGGTGGTTTAAATACAACTTTCTGACCTGAAGAGTCCTTT | SEQ ID NO: 1848 | Homo sapiens ST3 beta-galactoside alpha-2,3-sialyltransferase 6 (ST3GAL6), mRNA [NM_006100] |
| 268 | A_23_P250930 | CRBN | TGATGTATGGAGAATTCAGCTCCTTAAAATTGGCAGTGCTATCCAGGGACTTCGGTGTGA | SEQ ID NO: 1849 | Homo sapiens cereblon (CRBN), mRNA [NM_016302] |
| 269 | A_23_P250984 | ANAPC10 | GATTCATGTTCCCTTAACTGACAATCATAAGAAGGCAAACTGCTACATTCATGATACAGAT | SEQ ID NO: 1850 | Homo sapiens anaphase promoting complex subunit 10 (ANAPC10), mRNA [NM_014885] |
| 270 | A_23_P251937 | CPEB4 | GTATGTCAGTTAATTGTACTACTTGGGTGAATTTCCATATAGTTTTTACTGTGTATGGGG | SEQ ID NO: 1851 | Homo sapiens cytoplasmic polyadenylation element binding protein 4 (CPEB4), mRNA [NM_030627] |
| 271 | A_23_P252145 | C1GALT1 | ATATGTCTATATATATGAGGAAGTTGTGTTTTTTTAAATGGTGCCCAGGTAGGAAGTAG | SEQ ID NO: 1852 | Homo sapiens core 1 synthase, glycoprotein-N-acetylgalactosamine 3-beta-galactosyltransferase, 1 (C1GALT1), mRNA [NM_020156] |
| 272 | A_23_P252291 | EAF2 | CAGGATTCGTGATATAGATGGCAGTCATAATGGAGATATTGGAGACAACAGTGGGCTTCTGAT | SEQ ID NO: 1853 | Homo sapiens ELL associated factor 2 (EAF2), mRNA [NM_018456] |
| 273 | A_23_P252235 | CLEC4D | GATTTAACCCACCAGAGGAGAATGGCATTCTGGGATAAGAATGAAGGCGAGACAGTGCCTTCTGAT | SEQ ID NO: 1854 | Homo sapiens C-type lectin domain family 4, member D (CLEC4D), mRNA [NM_080387] |
| 274 | A_23_P252371 | RBBP8 | GGGAAGGAGGAGGAGCAGTATGAGCAGTTTGAAACAGAGAAACAGAAGAAGGATGAAGGCACAGTTTTT | SEQ ID NO: 1855 | Homo sapiens retinoblastoma binding protein 8 (RBBP8), transcript variant 1, mRNA [NM_002894] |
| 275 | A_23_P252493 | COMMD10 | GCGTCGATGGATACAAGATAAGATGTGTACGTTAGTAGAATACAGAGGTTTGGTAATTAC | SEQ ID NO: 1856 | Homo sapiens COMM domain containing 10 (COMMD10), mRNA [NM_016144] |
| 276 | A_23_P253412 | MRPL50 | GAAAAGTTTTGAGAGGGGACTGTGAAGTTGGGTTAAGAGAGGAGGACATTGCAAGTTCA | SEQ ID NO: 1857 | Homo sapiens mitochondrial ribosomal protein L50 (MRPL50), nuclear gene encoding mitochondrial protein, mRNA [NM_019051] |
| 277 | A_23_P254472 | C6orf211 | TTGATTCAATAGGTTCGTTTCATTTGGCACGGCCTTTGTATTTTGATTGACCTGTAGAATGG | SEQ ID NO: 1858 | Homo sapiens chromosome 6 open reading frame 211 (C6orf211), mRNA [NM_024573] |
| 278 | A_23_P254792 | DEK | TTTTTATTACTGCTTTTGCCCATATAAGATGGTGATATTTACTGAAAAGCTAGCCAGC | SEQ ID NO: 1859 | Homo sapiens DEK oncogene (DNA binding) (DEK), mRNA [NM_003472] |
| 279 | A_23_P25503 | FNDC3A | ATACTTGGCATTTGAGGCCTCACTGGAAAATTAGTGCAGAGGAGAAAAGAATTTTTAATGT | SEQ ID NO: 1860 | Homo sapiens fibronectin type III domain containing 3A (FNDC3A), transcript variant 2, mRNA [NM_014923] |
| 280 | A_23_P255663 | MANEA | AAAGAGTCTGTAGATCTCAGAGTTTGCAGTCGGCAATTTGTTGGCCATGGATGTAGAACC | SEQ ID NO: 1861 | Homo sapiens mannosidase, endo-alpha (MANEA), mRNA [NM_024641] |
| 281 | A_23_P255827 | FKSG2 | ACTACGGTAGGATGGTCAGTATGAGACCCCATATATGATTTTTAAGGAAATGGTTTAGAAA | SEQ ID NO: 1862 | Homo sapiens apoptosis inhibitor (FKSG2), mRNA [NM_021631] |
| 282 | A_23_P25638 | C13orf7 | CTTGCATTCCAGGAGGGAGTTTCTTTGAGTAGTAGTATGTTTGTTTTGGCATGTTCCTGTTC | SEQ ID NO: 1863 | Homo sapiens chromosome 13 open reading frame 7 (C13orf7), mRNA [NM_024546] |
| 283 | A_23_P25735 | PSMA6 | TAGGAGAGGAGACTAAGACATTGTCGTTAGTTTACCAGGATCCGTGATAGCACTTAGCTGT | SEQ ID NO: 1864 | Homo sapiens proteasome (prosome, macropain) subunit, alpha type, 6 (PSMA6), mRNA [NM_002791] |
| 284 | A_23_P257911 | USP16 | GTAGTTTGTGTTTAATATATGGGTGATGGATGCACAAGACAGACATCAATAAACTGACTTACC | SEQ ID NO: 1865 | Homo sapiens ubiquitin specific peptidase 16 (USP16), transcript variant 1, mRNA [NM_006447] |

Fig. 5-16

| No. | Probe ID No. | Symbols of genes | Sequence | SEQ ID NO: | Descriptions of genes (letters and numbers within [ ] indicates GenBank accession No.) |
|---|---|---|---|---|---|
| 285 | A_23_P258108 | LOC731224 | GTAAGCCAGGTGTTGGTGTTGAATATCCAAGCCCAAGAAAGATGAAGTTGATAGTTAAA | SEQ ID NO: 1866 | PREDICTED: Homo sapiens similar to 60S ribosomal protein L9 (LOC731224), mRNA [XR_015767] |
| 286 | A_23_P253582 | GK5 | ATGTCCATTTTGGAGAGAGAATATGATAGAACGTAGAAATTAAGTTGCATTTCTGCAAGTGC | SEQ ID NO: 1867 | Homo sapiens glycerol kinase 5 (putative) (GK5), mRNA [NM_001039547] |
| 287 | A_23_P259054 | SNX14 | CATCAGACTTCTGTTTGATGGTTACAGGAACCAGTAGTCAACAAGCAGTCACTTATGT | SEQ ID NO: 1868 | Homo sapiens sorting nexin 14 (SNX14), transcript variant 1, mRNA [NM_153816] |
| 288 | A_23_P26021 | COPS2 | TGGTTTTTGATCAACATGGTTCTGTTGTTTTTGGTGCTGCATTATGCCAAGAAAAACAGGTT | SEQ ID NO: 1869 | Homo sapiens COP9 constitutive photomorphogenic homolog subunit 2 (Arabidopsis) (COPS2), mRNA [NM_004236] |
| 289 | A_23_P26713 | RPL23 | TGGCGCGGGAATTGATCCAATGCTCGGCAGCATTGGATGATTGTCCAGTATATTCTAAAA | SEQ ID NO: 1870 | Homo sapiens ribosomal protein L23 (RPL23), mRNA [NM_000978] |
| 290 | A_23_P2705 | P2RY5 | TCTGTATTGCTGTTTCCAACTCTTGTTTGACGGTATAGTTTACTTTACATCGGACA | SEQ ID NO: 1871 | Homo sapiens purinergic receptor P2Y, G-protein coupled, 5 (P2RY5), mRNA [NM_005767] |
| 291 | A_23_P29005 | SAMSN1 | CTCTGGTTGCTATATCTGATCAATGAAGAATTGCATCATGGCAAAGAGGATGGAGTCTGA | SEQ ID NO: 1872 | Homo sapiens SAM domain, SH3 domain and nuclear localization signals 1 (SAMSN1), mRNA [NM_022136] |
| 292 | A_23_P302550 | RGS18 | GAGGCTAAGCGCGTAGGGATTGGGCATCGTCCCACATTGGTTGATATTCAGAAAGTGTTA | SEQ ID NO: 1873 | Homo sapiens regulator of G-protein signaling 18 (RGS18), mRNA [NM_130782] |
| 293 | A_23_P30307 | CRSP9 | GAATTGACTCTGGACAGAATGAACATCAAAGAGAAAATTCAGGTCATAGGAGAGATCAGAT | SEQ ID NO: 1874 | Homo sapiens cofactor required for Sp1 transcriptional activation, subunit 9, 33kDa (CRSP9), mRNA [NM_004270] |
| 294 | A_23_P305140 | C10orf32 | AAATGGGACTCTATATTGTTCAGGTCTTCATTGACTAAGAGATTGAGAGAAATC | SEQ ID NO: 1875 | Homo sapiens chromosome 10 open reading frame 32 (C10orf32), mRNA [NM_144591] |
| 295 | A_23_P307940 | CAPZA2 | CTACAAGATTGGCAAAGAGATGCCAATGAAGATGAAGTGCATAAGATGAAGATTGCAATGACCGGATCATT | SEQ ID NO: 1876 | Homo sapiens capping protein (actin filament) muscle Z-line, alpha 2 (CAPZA2), mRNA [NM_006136] |
| 296 | A_23_P308800 | GLS | CGGAAGAAGACATAAGATACTGCAAAATGGTCTTTGTTGCCACAGTAAGAAAGAAAAACTTTGC | SEQ ID NO: 1877 | Homo sapiens glutaminase 6, complete cds [AF158555] |
| 297 | A_23_P308956 | KIAA0776 | TTTTTTCAATTCTGTCAAAATGGTCTGGGGTTGTTCTGCTGCTGCACGTTTATGCT | SEQ ID NO: 1878 | Homo sapiens KIAA0776 (KIAA0776), mRNA [NM_015323] |
| 298 | A_23_P31097 | OSTM1 | GCTGAAAATGGCTGGGGTTGTTCTGCTGCACGTTTATGCTGCTGAAACTTAGGAGT | SEQ ID NO: 1879 | Homo sapiens osteopetrosis associated transmembrane protein 1 (OSTM1), mRNA [NM_014028] |
| 299 | A_23_P312246 | CCDC82 | GGGTTTATAACAGATGACTGTCAACTGAAGTCATAGAGGTCGTTGATATCCTGTCAGTTTAGTCAA | SEQ ID NO: 1880 | Homo sapiens coiled-coil domain containing 82 (CCDC82), mRNA [NM_024725] |
| 300 | A_23_P314191 | ZDHHC17 | TCGATACTTTTAGGAAATAGGAAGCTTAATTCTGAGCACTGAACATGAAATTAGTTCCTTGG | SEQ ID NO: 1881 | Homo sapiens zinc finger, DHHC-type containing 17 (ZDHHC17), mRNA [NM_015336] |
| 301 | A_23_P314591 | NFYB | GGAAGGCATTTACTAAGCAGTTACGAGGCTGGCTTAATAACCACAGACGGTCAAGACAAACAAA | SEQ ID NO: 1882 | Homo sapiens nuclear transcription factor Y, beta (NFYB), mRNA [NM_006166] |
| 302 | A_23_P31671 | UQCRB | AAGCCATAAGAAGACTTCCTGAGAACCTTTATAATGACAGGATGTTCGGATTAAGAGGG | SEQ ID NO: 1883 | Homo sapiens ubiquinol-cytochrome c reductase binding protein (UQCRB), mRNA [NM_006294] |
| 303 | A_23_P31702 | PXMP3 | CTTGTGTGGGATGTTTTGCTCAATTTCTGATTTTCTTCTTACCACTTATCAATGTCCAG | SEQ ID NO: 1884 | Homo sapiens peroxisomal membrane protein 3, 35kDa (Zellweger syndrome) (PXMP3), transcript variant 1, mRNA [NM_000318] |
| 304 | A_23_P317347 | ESCO1 | GCTAATTTTAAAAGGGCTGAACTACTTTGAAGAAAACCCGTATAGAAAGGAAGCTC | SEQ ID NO: 1885 | Homo sapiens establishment of cohesion 1 homolog 1 (S. cerevisiae) (ESCO1), mRNA [NM_052911] |

Fig. 5-17

| No. | Probe ID No. | Symbols of genes | Sequence | SEQ ID NO: | Description of genes (letters and numbers within [ ] indicates GenBank accession No.) |
|---|---|---|---|---|---|
| 305 | A_23_P319133 | DNAJC10 | TCTAGGAAAGGGATCTTCTAGTTTCTGTGTTGTTTAGAGTCAAAGAATCACAAATTTGTC | SEQ ID NO: 1886 | Homo sapiens DnaJ (Hsp40) homolog, subfamily C, member 10 (DNAJC10), mRNA [NM_018981] |
| 306 | A_23_P3204 | MAPK6 | AACGTGCTCACTGTGTATAGGAATTTGTATTTTGGAGGTGCTTGATCTATCTACAAAGAA | SEQ ID NO: 1887 | Homo sapiens mitogen-activated protein kinase 6 (MAPK6), mRNA [NM_002748] |
| 307 | A_23_P324633 | C9orf72 | TTTGTGGATTAGTCCCTGGGATTCAGTGTGTAGAAATGTCTAATAGTCTCTATAGTCC | SEQ ID NO: 1888 | Homo sapiens chromosome 9 open reading frame 72 (C9orf72), transcript variant 1, mRNA [NM_018325] |
| 308 | A_23_P327022 | MDFIC | TTATGATTTCTAATGGAAAATGTTTGTTGAAGTATATGGCTATCGACTAAGTGCTA | SEQ ID NO: 1889 | Homo sapiens MyoD family inhibitor domain containing (MDFIC), mRNA [NM_199072] |
| 309 | A_23_P33045 | RPL26 | TACAAAGGTCAGGAAATTGGCAAAATGGCAAAGTAGTCCAGGTTTACAGGAGAAATATGTTATCTAC | SEQ ID NO: 1890 | Homo sapiens ribosomal protein L26 (RPL26), mRNA [NM_000987] |
| 310 | A_23_P332439 | NUPL1 | ATTGAAATCTTGAATGTATTGAATCTCTCAAGGTACACAGACGGTGCCTTTGTAAATGTTG | SEQ ID NO: 1891 | Homo sapiens KIAA0410 mRNA, partial cds [AB007870] |
| 311 | A_23_P339480 | HAT1 | AACATGAACAGTGGAAGAGAGTTTCAGGAACTAGTGGAAGATTACCGGCGTGTTATG | SEQ ID NO: 1892 | Homo sapiens histone acetyltransferase 1 (HAT1), transcript variant 1, mRNA [NM_003642] |
| 312 | A_23_P341418 | ZDHHC20 | TGTGACTTAAATGTTGATGCTTTGCTTTGTCTTTTGGGCTGGCCTAACCTAGAATTGACATGT | SEQ ID NO: 1893 | Homo sapiens cDNA FLJ25952 fis, clone SYN00911. [AK098818] |
| 313 | A_23_P34307 | PIGK | ATTCATTTCACAGTCTTCTATTGTTGGACCACTACAATTGTACCAAATGTTTCGTTTGG | SEQ ID NO: 1894 | Homo sapiens phosphatidylinositol glycan anchor biosynthesis, class K (PIGK), mRNA [NM_005482] |
| 314 | A_23_P345591 | PSMA2 | GCCTGGAAAAGTCACAGCAATGGGAAAAGAACTATGTGAAATGGGAAGACTTTCCTTGAGAAA | SEQ ID NO: 1895 | Homo sapiens proteasome (prosome, macropain) subunit, alpha type, 2 (PSMA2), mRNA [NM_002787] |
| 315 | A_23_P347059 | MOBKL1A | CTAGAAGGGGAAAAATCATCTAAGTTATGAAATCCAACATAGGGGCTATATTACAAACTG | SEQ ID NO: 1896 | Homo sapiens MOB1, Mps One Binder kinase activator-like 1A (yeast) (MOBKL1A), mRNA [NM_173468] |
| 316 | A_23_P347198 | SP3 | GACCAGGTCAAATTTAAAGGCTACGTTTATTTGTACGTTTAAGTGTATTATAACAGTGGG | SEQ ID NO: 1897 | Homo sapiens Sp3 transcription factor (SP3), transcript variant 1, mRNA [NM_003111] |
| 317 | A_23_P349083 | FCHO2 | GTGAAATGGTTAAACTTTCGCAGCTTCCTTAGTAGTTACCACACACACATCCAAGTATTGGG | SEQ ID NO: 1898 | Homo sapiens FCH domain only 2 (FCHO2), mRNA [NM_138782] |
| 318 | A_23_P351467 | CMAH | GCTTACATTTGTTGGGTATATTTTGGAAGGTGCCAGAATTGGTTACGTTGTTCCATCCAC | SEQ ID NO: 1899 | Homo sapiens cytidine monophosphate-N-acetylneuraminic acid hydroxylase (CMP-N-acetylneuraminate monooxygenase) (CMAH) on chromosome 6 [NR_002174] |
| 319 | A_23_P351903 | TMEM167 | AAACTGGATTGTTGGGGTATATTTGGGATGTGCCAGAATTGGTGAACGGGAACAGTCGTT | SEQ ID NO: 1900 | Homo sapiens transmembrane protein 167 (TMEM167), mRNA [NM_174909] |
| 320 | A_23_P353704 | RP5-1022P6.2 | TGTTCTGTCACTACGTATTACAGACAGTGCGTTGCTTTGTGGGTTTGTTTGTATGTGGTGTGT | SEQ ID NO: 1901 | Homo sapiens hypothetical protein KIAA1434 (KIAA1434), mRNA [NM_019593] |
| 321 | A_23_P354694 | ZNF567 | ACGTAAGAGTTACCACTGTAGGGTAGCGTATAGACATCAAAAGGTAGTTTTGATGTTTTGA | SEQ ID NO: 1902 | Homo sapiens zinc finger protein 567 (ZNF567), mRNA [NM_152603] |
| 322 | A_23_P355067 | TMCO1 | AACTCAAGAAGACTGTTATTTCTACATTCTTCTAGACACACAGACATCAGACTGGCAA | SEQ ID NO: 1903 | Homo sapiens transmembrane and coiled-coil domains 1 (TMCO1), mRNA [NM_019026] |
| 323 | A_23_P355244 | SAMD9 | TCACTGGAGGAAGATTTTCGCTTGCTTGTGCATAAAATTTAAGTCCAATAACTTATAAGC | SEQ ID NO: 1904 | Homo sapiens sterile alpha motif domain containing 9 (SAMD9), mRNA [NM_017654] |
| 324 | A_23_P356122 | ZNF451 | TTTTACCTGCTTAGACTTTTATGTGACTTGTATGGTCTGCTGGTTAAAGGGAATGGTGTC | SEQ ID NO: 1905 | Homo sapiens zinc finger protein 451 (ZNF451), transcript variant 2, mRNA [NM_015555] |

Fig. 5-18

| No. | Probe ID No | Symbols of genes | Sequence | SEQ ID NO | Descriptions of genes (letters and numbers within [ ] indicates GenBank accession No) |
|---|---|---|---|---|---|
| 325 | A_23_P358470 | CCDC111 | ATGACCCTGATGTAAAGGAGAAAACTGAAATCTGACTGTTTCGCATTAGTGCTGAAAG | SEQ ID NO: 1906 | Homo sapiens coiled-coil domain containing 111 (CCDC111), mRNA [NM_152683] |
| 326 | A_23_P358828 | DPY19L1 | ATATAAATTAGCTTTCCAGAAGGATGCTTTGTTTGTAAGCAGTGTTATGAATGTAAGCCCC | SEQ ID NO: 1907 | Homo sapiens DPY-19-like protein 1 (DPY19L1) mRNA, complete cds. [DQ287932] |
| 327 | A_23_P361446 | SESN3 | AAGGACACAGTGTTTGATTTTCAGCTGGAGTACATGTTCATTCATTTCGTCAT | SEQ ID NO: 1908 | Homo sapiens sestrin 3 (SESN3), mRNA [NM_144665] |
| 328 | A_23_P364107 | C14orf106 | AGCAGACAGTGTTGTATTTGACGTGGAGTACATGTATTTCTTTGTAAAGTAGGTTCC | SEQ ID NO: 1909 | Homo sapiens chromosome 14 open reading frame 106 (C14orf106), mRNA [NM_018353] |
| 329 | A_23_P36776 | PUS7L | GGGCTTCAGTTCAACATCTGTAAAATGGGCATGTTAAGCATTGCCTACCTCATAGGATTA | SEQ ID NO: 1910 | Homo sapiens pseudouridylate synthase 7 homolog (S. cerevisiae)-like (PUS7L), mRNA [NM_031292] |
| 330 | A_23_P3681 | NETO2 | AGACTTGGAAATGCTGGACATAAGCTGTTCTTCCTTTTGTAACTGTATTTAGTTGTG | SEQ ID NO: 1911 | Homo sapiens neuropilin (NRP) and tolloid (TLL)-like 2 (NETO2), mRNA [NM_018092] |
| 331 | A_23_P368681 | GIMAP2 | ATGGCAAGTGAAGGAAGTAATGGACTGTATTGGAGGATCGTGTGATGGAGAAAATGGTG | SEQ ID NO: 1912 | Homo sapiens GTPase, IMAP family member 2 (GIMAP2), mRNA [NM_015660] |
| 332 | A_23_P371266 | DNM3 | ACTGTCTTCTTGGCACTTCAGGATTTCTTAATGCTGATATATGGACTGTTAGAATGGAA | SEQ ID NO: 1913 | Homo sapiens dynamin 3 (DNM3), mRNA [NM_015569] |
| 333 | A_23_P37275 | CGRRF1 | GAGCAAGATAAAGACAAGACCGAAGACTCTTGAAGAACATGCTAACACTGAAAAGTACACT | SEQ ID NO: 1914 | Homo sapiens cell growth regulator with ring finger domain 1 (CGRRF1), mRNA [NM_006568] |
| 334 | A_23_P37441 | B2M | TTGTCTTCAGCAAGGACTGGTCTTGTATCTCTTGTAGTACAGTGAATTCACCCCCAGT | SEQ ID NO: 1915 | Homo sapiens beta-2-microglobulin (B2M), mRNA [NM_004048] |
| 335 | A_23_P37836 | FAM96A | CTTGAAGCTGACTGATAGCTGTGTTTAAGAGCCACTGGCCTGTAATTGTTTGATATATTTG | SEQ ID NO: 1916 | Homo sapiens family with sequence similarity 96, member A (FAM96A), transcript variant 1, mRNA [NM_032231] |
| 336 | A_23_P380648 | TXNL5 | CTGGTGGAAATGTTGTTCTCTGAAGATTAAGATTTGACTCGGACGGAAATCATGCTGAATGT | SEQ ID NO: 1917 | Homo sapiens thioredoxin-like 5 (TXNL5), mRNA [NM_032731] |
| 337 | A_23_P384576 | THC2504576 | TCTGGCCAAAATGAAGTTTAATCCCTTTGTGACTTCGGACCGAAGCAAGAATGGCAAAAG | SEQ ID NO: 1918 | RL26_BOVIN (P61257) 60S ribosomal protein L26, complete [THC2504576] |
| 338 | A_23_P384056 | CCDC14 | TAGGTCAGTAATCATCTCCCTTCATGTAAGCAGGACGTTTAAGTCTTAGGAAGCTGAATG | SEQ ID NO: 1919 | Homo sapiens coiled-coil domain containing 14 (CCDC14), mRNA [NM_022757] |
| 339 | A_23_P390734 | FGFR1OP2 | CGAGGAGATAGAACAAATGTGGTTTAACATGCATGAAAGGTAATTTTGTATGTGTCG | SEQ ID NO: 1920 | Homo sapiens FGFR1 oncogene partner 2 (FGFR1OP2), mRNA [NM_015633] |
| 340 | A_23_P394276 | RWDD4A | TGTTCAGGGTTATTATGGCTCATCAAAGATGCATAACAGCTATTATATCTAGAGTACATGCGAATGA | SEQ ID NO: 1921 | Homo sapiens RWD domain containing 4A (RWDD4A), mRNA [NM_152622] |
| 341 | A_23_P394605 | SEC24A | GATTATTGTTCTAATGCATAAGAATGCATAACAGCTATTATATCTAGGGAGAGGAAATGTG | SEQ ID NO: 1922 | Homo sapiens SEC24 related gene family, member A (S. cerevisiae) (SEC24A), mRNA [NM_021982] |
| 342 | A_23_P397999 | FZD5 | GGGGCTTACAATGCTAAGGTTGGGGTTGTAATGAAGTTGCAGTTGGTTGGGTTTGTTT | SEQ ID NO: 1923 | Homo sapiens frizzled homolog 5 (Drosophila) (FZD5), mRNA [NM_003468] |
| 343 | A_23_P410017 | TBCEL | ATACAGTTGCATGTAAAGGAGCTTGTCATTTAATTCAGGGGATGTGGGTATTTTTAGGG | SEQ ID NO: 1924 | Homo sapiens leucine rich repeat containing 35, mRNA (cDNA clone IMAGE:3913004), [BC020501] |
| 344 | A_23_P41114 | CSTA | AAACAAATGAGACTATGGAAAATTGGAGTCGTGCAGTATAAAACTGAAGTGTTGCTG | SEQ ID NO: 1925 | Homo sapiens cystatin A (stefin A) (CSTA), mRNA [NM_005213] |
| 345 | A_23_P413796 | CCDC5 | GCATGGATGGTTCTCTGTGTCATCAGTCGTAGTAGGACTATCAGAGAAACTGGCAAGAT | SEQ ID NO: 1926 | Homo sapiens coiled-coil domain containing 5 (spindle associated) (CCDC5), mRNA [NM_138443] |

Fig. 5-19

| No. | Probe ID No | Symbols of genes | Sequence | SEQ ID NO: | Descriptions of genes (letters and numbers within [ ] indicates GenBank accession No) |
|---|---|---|---|---|---|
| 346 | A_23_P41512 | C4orf15 | TAAGGCTGTTAGTCTTGAAGATTGAAAATTACTGAAAACTGAAT CTTTATTACGTGTCCT | SEQ ID NO: 1927 | Homo sapiens chromosome 4 open reading frame 15 (C4orf15), mRNA [NM_024511] |
| 347 | A_23_P41645 | ELL2 | TGTCTTTCAAAGTGGTGGCAGTTGAAAAGGGAAGGATTATGT TACAAATCTGTTTTGA | SEQ ID NO: 1928 | Homo sapiens elongation factor, RNA polymerase II, 2 (ELL2), mRNA [NM_012081] |
| 348 | A_23_P41664 | ENST00000334994 | TGGGTTGGAGGCAGATTCGAGTTCATAAAGAAATTGTTCGTGAAA ATGAGGCACAGGTCAT | SEQ ID NO: 1929 | Synleurin (CGI_01891). [Source:Uniprot/SPTREMBL;Acc:Q7Z2O7] [ENST00000334994] |
| 349 | A_23_P421563 | LSM3 | CATAAGAGAAACCTGCATAGATTTTGATATTAAGAAAATAATTCC GGGGATTCTTCGACTC | SEQ ID NO: 1930 | Homo sapiens LSM3 homolog, U6 small nuclear RNA associated (S. cerevisiae) (LSM3), mRNA [NM_014463] |
| 350 | A_23_P422794 | NSMCE2 | CATTGTTCGCATGATTGAGTGGAGGCAAAACGGAAGAAAAAGG CCTATTGCCCTCAAAT | SEQ ID NO: 1931 | Homo sapiens non-SMC element 2, MMS21 homolog (S. cerevisiae) (NSMCE2), mRNA [NM_173685] |
| 351 | A_23_P42718 | NFE2L3 | CAGCCATCCTTTTAAGAGTAAGTTGGTTAGTTCAAAAGAGA AACACGTGGGATCAAA | SEQ ID NO: 1932 | Homo sapiens nuclear factor (erythroid-derived 2)-like 3 (NFE2L3), mRNA [NM_004289] |
| 352 | A_23_P428468 | ENST00000369577 | AAAACTACCGTCAGTCTGAAAAACTTGAAGTACATTCAAATGA TCCAAGATATGTCTGTT | SEQ ID NO: 1933 | Zinc finger protein 292. [Source:Uniprot/SWISSPROT;Acc:O60281] [ENST00000369577] |
| 353 | A_23_P429491 | FLJ25416 | GCTTAGTCACCTGAATGTTTTCATAAAAGTCAGTGAACCTGA ATTCCTGAACTTTTAA | SEQ ID NO: 1934 | Homo sapiens hypothetical protein FLJ25416 (FLJ25416), mRNA [NM_145018] |
| 354 | A_23_P42975 | PRKAR2B | GCCACATTTTTAGAACACGTGTTAACATTTTTGCAAAACCTTCT TGTAGGAAAAGAGAGC | SEQ ID NO: 1935 | Homo sapiens protein kinase, cAMP-dependent, regulatory, type II, beta (PRKAR2B), mRNA [NM_002736] |
| 355 | A_23_P43049 | DCTN6 | AAATACATTTGAAGTCATCCGTCGAGAATACGGTGATCTATGGTG CAGAGTGCCTTCGTCG | SEQ ID NO: 1936 | Homo sapiens dynactin 6 (DCTN6), mRNA [NM_006571] |
| 356 | A_23_P43150 | ZHX1 | TTTTAAAGACTGGTGCTGGTCATTCATATTGGGAAGACCCTTT CTTTGTGACCATAGG | SEQ ID NO: 1937 | Homo sapiens zinc fingers and homeoboxes 1 (ZHX1), transcript variant 1, mRNA [NM_001017926] |
| 357 | A_23_P43157 | MYBL1 | ATACATATTTGGGTTGGTAGTGGTTGAATCCTTGAGTTAACTGC TTTGTTGCTTTTT66CA | SEQ ID NO: 1938 | Homo sapiens v-myb myeloblastosis viral oncogene homolog (avian)-like 1 (MYBL1), mRNA [NM_001080416] |
| 358 | A_23_P43175 | SEPT10 | AAATGGACATAATTCATATTGAGGTGGTATTTGGATTCAGTGC CTTACGTGGTATTCTCA | SEQ ID NO: 1939 | Homo sapiens septin 10 (SEPT10), transcript variant 1, mRNA [NM_144710] |
| 359 | A_23_P43311 | C5orf35 | GTTCCAATGACAGAGAGGAGGTAATGTGTTGTTATCAGGAATTGAT GTGGGTGCAGTTTTCC | SEQ ID NO: 1940 | Homo sapiens chromosome 5 open reading frame 35 (C5orf35), mRNA [NM_153706] |
| 360 | A_23_P434809 | S100A8 | AAAGGCATGAAGAAACCAGAAGAGAGTAGCTGAGTTACTGGGGC CAGAGGCTGGGGCCT | SEQ ID NO: 1941 | Homo sapiens S100 calcium binding protein A8 (S100A8), mRNA [NM_002964] |
| 361 | A_23_P44257 | COMMD8 | AACATTTTACTTCTGCGGCTTCTATGTTTGGGAAACATTGCTGTG ATAAAAATATGCTGTC | SEQ ID NO: 1942 | Homo sapiens COMM domain containing 8 (COMMD8), mRNA [NM_017845] |
| 362 | A_23_P44974 | MRPL13 | ATGGAGTAAAACAACTGCTACAGTTCAGGATCAAGGACCTGTTTATGTGC CGAATGACTGTGGGGA | SEQ ID NO: 1943 | Homo sapiens mitochondrial ribosomal protein L13 (MRPL13), nuclear gene encoding mitochondrial protein, mRNA [NM_014078] |
| 363 | A_23_P45180 | GYPA | ACGTGCCTAAGTTGTACAATTTCAGAATGGAATTTTCATTATAA TGAGTTCCAGTAGTC | SEQ ID NO: 1944 | Homo sapiens glycophorin A (MNS blood group) (GYPA), mRNA [NM_002099] |

Fig. 5-20

| No. | Probe ID No. | Symbols of genes | Sequence | SEQ ID NO: | Descriptions of genes (letters and numbers within [ ] indicates GeneBank accession No.) |
|---|---|---|---|---|---|
| 364 | A_23_P45246 | SH2D1A | TTCTAAAGGCATTGTAGTCCTGTAATGGAAGGCATGTAAGGCATGTC GTCAAAGGTGAAATGG | SEQ ID NO: 1945 | Homo sapiens SH2 domain protein 1A (Duncan's disease (lymphoproliferative syndrome) (SH2D1A), mRNA [NM_002351] |
| 365 | A_23_P45934 | SRP9 | TATAGGCATTCTGATGGGAACTTGTGTGTTAAAGTAACAGATGA TTTAGTTGTTGGTG | SEQ ID NO: 1946 | Homo sapiens signal recognition particle 9kDa (SRP9), mRNA [NM_003133] |
| 366 | A_23_P46396 | PTBP2 | AACGAGGTGGGACCAAAGTTTATGTGGCTTTAGTGTTGTTAATTTAC CTTGCATTGTAATATT | SEQ ID NO: 1947 | Homo sapiens polypyrimidine tract binding protein 2 (PTBP2), mRNA [NM_021190] |
| 367 | A_23_P48166 | TWF1 | TGGAGCAGAACCAAGGTGAAGGCTGTTATTTTCAGTCAGGAAGAAC TACCTGCATGAAGGT | SEQ ID NO: 1948 | Homo sapiens twinfilin, actin-binding protein, homolog 1 (Drosophila) (TWF1), mRNA [NM_002822] |
| 368 | A_23_P501080 | ZNF92 | GAATATTAAGTGCTACTTGAGGTACATGTTCGAGACTAAGAATTCT TGCAGTATAGTGAG | SEQ ID NO: 1949 | Homo sapiens zinc finger protein 92 (ZNF92), transcript variant 1, mRNA [NM_007139] |
| 369 | A_23_P501276 | TUBB2A | GTGGACGAGCAGATGCTCAACGTCCAAGAACAAGAAGCAGGATC CTTCGTTGGAGTGGATC | SEQ ID NO: 1950 | Homo sapiens tubulin, beta 2A (TUBB2A), mRNA [NM_001069] |
| 370 | A_23_P502425 | MRPL47 | GTTCCAGATCTTGGTGGAAGCCGAAAAAGTGAAGTCTGTGTAAG ATGTCTGAACTATTAA | SEQ ID NO: 1951 | Homo sapiens mitochondrial ribosomal protein L47 (MRPL47), nuclear gene encoding mitochondrial protein, transcript variant 1, mRNA [NM_020409] |
| 371 | A_23_P502797 | WDFY1 | GTAACAGTTTAGTGGTTGTTCCATTCGTGAATATGCAGGGTAAT TTGTACAGATAGGGAT | SEQ ID NO: 1952 | Homo sapiens WD repeat and FYVE domain containing 1 (WDFY1), mRNA [NM_020830] |
| 372 | A_23_P50907 | ITGAV | AAAGAGTGATAAGTGAGGTTATTACCCTAAATGGTGGCATC TGCATTGTATTTCAGG | SEQ ID NO: 1953 | Homo sapiens integrin, alpha V (vitronectin receptor, alpha polypeptide, antigen CD51) (ITGAV), mRNA [NM_002210] |
| 373 | A_23_P51009 | NDUFB3 | CCCGAATGAAGCTTGGAGATACATGGGTGGCTTTGCAAAAGAGTG TTTGCTTTTCTGATGT | SEQ ID NO: 1954 | Homo sapiens NADH dehydrogenase (ubiquinone) 1 beta subcomplex, 3, 12kDa (NDUFB3), mRNA [NM_002491] |
| 374 | A_23_P51317 | CCDC76 | CGCTTTGTTATAAGCTTTATGTCAAGTAAGGTAGTTTGTTTAAGT TAGTTACCCATGTCCC | SEQ ID NO: 1955 | Homo sapiens coiled-coil domain containing 76 (CCDC76), mRNA [NM_019083] |
| 375 | A_23_P51487 | GBP3 | AATCCTAAAGCATAAGTTAGTGTCTTCCTGATTCTTAAAGGTCA TACTTGAAATCCTGCC | SEQ ID NO: 1956 | Homo sapiens guanylate binding protein 3 (GBP3), mRNA [NM_018284] |
| 376 | A_23_P53368 | NFYB | TGGGCTCATATTCTGTGCATAGCATTTGTAACCTGGTTTTTTGAC TTAACATATATTGGG | SEQ ID NO: 1957 | Homo sapiens nuclear transcription factor Y, beta (NFYB), mRNA [NM_006166] |
| 377 | A_23_P53957 | C14orf112 | TTATAGCTTCCAGCTATTCCATGTCGTGTCGATGAAAGTAAGAATGT TGGCCAGGTATATTT | SEQ ID NO: 1958 | Homo sapiens chromosome 14 open reading frame 112 (C14orf112), mRNA [NM_016468] |
| 378 | A_23_P56550 | TNNT1 | TCCGAGGGTAAGAAGCCTGTGGACATTGAGTACATGGGAGGAGGA AGAGCTCCGGGAGAAA | SEQ ID NO: 1959 | Homo sapiens troponin T type 1 (skeletal, slow), mRNA (cDNA clone MGC:104241 IMAGE:42473799), complete cds. [BC107798] |
| 379 | A_23_P5611 | RIF1 | ATGTATTCTTGACTGCTATGCGTGGGTTTTCAGGAAATTTAATT ATCTTACTGAGATGTG | SEQ ID NO: 1960 | Homo sapiens RAP1 interacting factor homolog (yeast) (RIF1), mRNA [NM_018151] |
| 380 | A_23_P56386 | ZC3H15 | GTCCACGGAAGTAAGAAGTGTATGTGCCTTCCATCTTTTGGTT TTGATTGGGCATGTG | SEQ ID NO: 1961 | Homo sapiens zinc finger CCCH-type containing 15 (ZC3H15), mRNA [NM_018471] |
| 381 | A_23_P56734 | HNMT | CGTTTTGTTGCAGCATGGATATATCTGACTGCTTATTGATGGTA ATGAAAATGGAGACCT | SEQ ID NO: 1962 | Homo sapiens histamine N-methyltransferase (HNMT), transcript variant 1, mRNA [NM_006895] |
| 382 | A_23_P56759 | KRCC1 | GATATCGGTTCATACCACTTTTCTTATGTGAATAGGTTGTCTTT AACTCTGTAACAAAGGG | SEQ ID NO: 1963 | Homo sapiens lysine-rich coiled-coil 1 (KRCC1), mRNA [NM_016618] |

Fig. 5-21

| No. | Probe ID No. | Symbols of genes | Sequence | SEQ ID NO: | Descriptions of genes (letters and numbers within [ ] indicates GenBank accession No.) |
|---|---|---|---|---|---|
| 383 | A_23_P57277 | C21orf7 | CCAGGTTCTAGCTTGAGAGAAAGGGATATTTAAATGAGATCATTAAGGTGAAACTATTAC | SEQ ID NO: 1964 | Homo sapiens chromosome 21 open reading frame 7 (C21orf7), mRNA [NM_020152] |
| 384 | A_23_P58390 | C4orf32 | TAATACTAACTATTTAGTATACTGTCAGTACTGTAGATGTGCACACTGGTGTTAATAGGG | SEQ ID NO: 1965 | Homo sapiens chromosome 4 open reading frame 32 (C4orf32), mRNA [NM_152400] |
| 385 | A_23_P58396 | PDGFC | CATGGAATATTTTTATGTACAGAAGTATGTCTGTTAACCAGTCACTTATTGTACTGTGGG | SEQ ID NO: 1966 | Homo sapiens platelet derived growth factor C (PDGFC), mRNA [NM_016205] |
| 386 | A_23_P58877 | GOPC | AAGGTTCATGTGATTCATGTGTAAGATGACAGTATTGACATCCTGATTATGTAATGG | SEQ ID NO: 1967 | Homo sapiens golgi associated PDZ and coiled-coil motif containing (GOPC), transcript variant 1, mRNA [NM_020399] |
| 387 | A_23_P58912 | SLC35A1 | ATGATCAGTGCGGTTATGTGGAAAGAACAACAACAAACAAACGAAGGTATCTGAGTGAAGTGG | SEQ ID NO: 1968 | Homo sapiens solute carrier family 35 (CMP-sialic acid transporter), member A1 (SLC35A1), mRNA [NM_006416] |
| 388 | A_23_P58837 | DOCK4 | TTTGGGAGTGAGCAGTTGAATTTAGTTGAATTTACATGTGTGTGATTTCTGAAGCAG | SEQ ID NO: 1969 | Homo sapiens dedicator of cytokinesis 4 (DOCK4), mRNA [NM_014705] |
| 389 | A_23_P59921 | SUB1 | CAGATTGGGAAAATGAGGTAGGTTAGTGTTGGGATTTAAAGGCAAAGTGTTAATTGAT | SEQ ID NO: 1970 | Homo sapiens SUB1 homolog (S. cerevisiae) (SUB1), mRNA [NM_006713] |
| 390 | A_23_P60246 | TXN | GGACAAAAGGTGGGTGAATTTTGGGAGCCAATAAGGAAAAGCTTGAAGCACCATTAAT | SEQ ID NO: 1971 | Homo sapiens thioredoxin (TXN), mRNA [NM_003329] |
| 391 | A_23_P61674 | CLK4 | GAAAAGGCATGCAGTTTGTCCATTGTGACAGTTTGTTAATAAACCACATACACAGTTTA | SEQ ID NO: 1972 | Homo sapiens CDC-like kinase 4 (CLK4), mRNA [NM_020666] |
| 392 | A_23_P63655 | ATP5C1 | AGAGAGCTGAAACCAGGTGAAATATGGATTCAGATCTTTAGGTCTGTATGAAAAAGCT | SEQ ID NO: 1973 | Homo sapiens ATP synthase, H+ transporting, mitochondrial F1 complex, gamma polypeptide 1 (ATP5C1), nuclear gene encoding mitochondrial protein, transcript variant 2, mRNA [NM_051174] |
| 393 | A_23_P63668 | IFIT5 | AAGATAGAATCCAGAGAAAATGAGAATTCCTGACTGCTGTGTGTGAGGCTCCGACTTTCCATT | SEQ ID NO: 1974 | Homo sapiens interferon-induced protein with tetratricopeptide repeats 5 (IFIT5), mRNA [NM_012420] |
| 394 | A_23_P63896 | FAS | ATGTCTATCCACAGAGGGTAACCCCACTCTATGAATCAATAAGAAGCTATGACCTTTGC | SEQ ID NO: 1975 | Homo sapiens Fas (TNF receptor superfamily, member 6) (FAS), transcript variant 1, mRNA [NM_000043] |
| 395 | A_23_P65230 | TMTC4 | AGAGGGCAACACATGTGTGTGAAGCTGCTTTTTAGTGTGTTATCTGAAGGCGGTTTCCA | SEQ ID NO: 1976 | Homo sapiens transmembrane and tetratricopeptide repeat containing 4 (TMTC4), transcript variant 1, mRNA [NM_032813] |
| 396 | A_23_P65768 | C15orf15 | TGGTGGATTGCCATCTACATAATATCAGATATTACGGATGTTAGATTGCATCTCAGTGTT | SEQ ID NO: 1977 | Homo sapiens chromosome 15 open reading frame 15 (C15orf15), mRNA [NM_016304] |
| 397 | A_23_P66260 | ZNF267 | GTGATGAATGTGGTAAAGGCTTGAGTATAGGTCATACCTCACTACACATCGGAGAAGT | SEQ ID NO: 1978 | Homo sapiens zinc finger protein 267 (ZNF267), transcript variant 498723, mRNA [NM_003414] |
| 398 | A_23_P68472 | DPM1 | CTATTGGCGAGGTTCGAATATGCATTGTGGATGGTGTTTATGGTGAATGGAAGTTGGGAG | SEQ ID NO: 1979 | Homo sapiens dolichyl-phosphate mannosyltransferase polypeptide 1, catalytic subunit (DPM1), mRNA [NM_003859] |
| 399 | A_23_P69109 | PLSCR1 | GTTTAGCTCTACACTCTATCCTTCCTAGAAAAATGGTAATTGAGATTGAGATATTAA | SEQ ID NO: 1980 | Homo sapiens phospholipid scramblase 1 (PLSCR1), mRNA [NM_021105] |
| 400 | A_23_P69695 | ZCD2 | ATTTGTGTCTTAGTAAAGCAGGTTATTGTAGGTGTTGGCGTTCTAAAAGGTTTCCTGCCT | SEQ ID NO: 1981 | Homo sapiens zinc finger, CDGSH-type domain 2 (ZCD2), mRNA [NM_001008388] |

Fig. 5-22

| No. | Probe ID No. | Symbols of genes | Sequence | SEQ ID NO: | Descriptions of genes (letters and numbers within [ ] indicates GenBank accession No.) |
|---|---|---|---|---|---|
| 401 | A_23_P68908 | GLRX | CTGATAAAACTTACAGCCCCCTACAGGAAGAGTGTATCTGTGAAAGAGCTCCTACACTT | SEQ ID NO: 1982 | Homo sapiens glutaredoxin (thioltransferase) (GLRX), mRNA [NM_002064] |
| 402 | A_23_P70290 | TMEM30A | ATCTCTCGCTCAAGCTGTAAACCACGTAAGTAAGTGCTTAATGGAGACTGTTTTCATTCTTG | SEQ ID NO: 1983 | Homo sapiens transmembrane protein 30A (TMEM30A), mRNA [NM_018247] |
| 403 | A_23_P70318 | ENPP4 | TGTTTTTTGGGTGTCTGCTTCTTGTGCCCATATCTGATAAAGTTTATGGATTATTGCATTT | SEQ ID NO: 1984 | Homo sapiens ectonucleotide pyrophosphatase/phosphodiesterase 4 (putative function) (ENPP4), mRNA [NM_014936] |
| 404 | A_23_P70328 | CENPQ | CAATGGCTTACAGTTTCTGTGTGGTCATCTGGAAGCTTGAAAAATCCTCAAATGCTTCAC | SEQ ID NO: 1985 | Homo sapiens centromere protein Q (CENPQ), mRNA [NM_018132] |
| 405 | A_23_P7066 | RPL9 | GGTCTCTTGTTGAAATCCGAAATTTCTTGGGTGAAAAATATATCCGCAGGTTCGGATGA | SEQ ID NO: 1986 | Homo sapiens ribosomal protein L9 (RPL9), transcript variant 1, mRNA [NM_000661] |
| 406 | A_23_P70938 | STARD3NL | GGATTATGTGTATGGCCTGAAGTGTTGGACTTGGAAAAGGGGAAGAAAAGGAATTGGGAAT | SEQ ID NO: 1987 | Homo sapiens STARD3 N-terminal like (STARD3NL), mRNA [NM_032016] |
| 407 | A_23_P71433 | UBE2W | CATGAGGGCTACTGCCTAAAGACGTATTTCATTTATGTTTGGAAACGCGTAAACAT | SEQ ID NO: 1988 | Homo sapiens ubiquitin-conjugating enzyme E2W (putative) (UBE2W), transcript variant 1, mRNA [NM_001014431] |
| 408 | A_23_P72117 | SMPDL3A | TTTGTGGGAATTTACATAAATCTTTGTTAATTAGTGAGTGGGCAAGTAGACTTCCTGTC | SEQ ID NO: 1989 | Homo sapiens sphingomyelin phosphodiesterase, acid-like 3A (SMPDL3A), mRNA [NM_006714] |
| 409 | A_23_P7221 | RPL34 | CGAGGAGCAGAAATGTTGTGAAAGTGTTGAAGGAGAAGCACAGAGTCAGAAAGCTAA | SEQ ID NO: 1990 | Homo sapiens ribosomal protein L34 (RPL34), transcript variant 2, mRNA [NM_033625] |
| 410 | A_23_P7229 | RPL34 | CGAACCCTGTATAGAATTGTTTACCTTTATACCAAGAAGTTGGGAAAGCAGGAAAA | SEQ ID NO: 1991 | Homo sapiens ribosomal protein L34 (RPL34), transcript variant 2, mRNA [NM_033625] |
| 411 | A_23_P72568 | SNX4 | AAGCTCAGTAATAGAGCCTAAATTTAGTCTGGTTGGCTCTCACACATGGCATTTCAGGGT | SEQ ID NO: 1992 | Homo sapiens sorting nexin 4 (SNX4), mRNA [NM_003794] |
| 412 | A_23_P7262 | MARCH1 | GATTATTGTGTTCTTTGATATTCATGTAAAAGTACCAGTTGAATTGACAGTGAGC | SEQ ID NO: 1993 | Homo sapiens cDNA FLJ20668 fis, clone KAIA5565. [AK000675] |
| 413 | A_23_P7282 | ELMOD2 | TTCAAGTAGCTTTCTGTGGGGGGAAAAAGTACCAGTTGGACACTTAAAGGAATTGGGATTT | SEQ ID NO: 1994 | ELMO domain-containing protein 2. [Source:Uniprot/SWISSPROT:Acc:Q8IZ81] [ENST00000323579] |
| 414 | A_23_P73577 | DYNLT3 | TGTTTCTTTATGCTGTAGGCTTTTGTGCCGTGAAGATCATAATAGTGACCAAAATATAC | SEQ ID NO: 1995 | Dynein light chain Tctex-type 3 (T-complex-associated testis-expressed 1-like) (Protein 91/23). [Source:Uniprot/SWISSPROT:Acc:P51808] [ENST00000376578] |
| 415 | A_23_P74001 | S100A12 | TGAAGGCTTTTTACCCAGCAATGTCCTCAATGAGGGTCTTTCTTTGGGTCACGAAAACC | SEQ ID NO: 1996 | Homo sapiens S100 calcium binding protein A12 (S100A12), mRNA [NM_005621] |
| 416 | A_23_P74799 | SLC25A24 | GATTGTGTATCTTTTCGAAAAAAGCCGAGAGAGTTGAAGATAGTATATTTCTGGTAGTACTG | SEQ ID NO: 1997 | Homo sapiens solute carrier family 25 (mitochondrial carrier; phosphate carrier), member 24 (SLC25A24), transcript variant 2, mRNA [NM_213651] |
| 417 | A_23_P75028 | REEP3 | AGAAAGAGGACAAGTGTATTTTAGTGATGATCAGACGTCAAATACCCAGCAGAGATAT | SEQ ID NO: 1998 | Homo sapiens receptor accessory protein 3 (REEP3), mRNA [NM_001001330] |
| 418 | A_23_P7543 | ZFYVE16 | TCTGCCTCAGCATTATCTAAATGATCTTGATAGTGGTCTCGATACCTGTGATCCATGGTGG | SEQ ID NO: 1999 | Homo sapiens zinc finger, FYVE domain containing 16 (ZFYVE16), mRNA [NM_014733] |

Fig. 5-23

| No. | Probe ID No. | Symbols of genes | Sequence | SEQ ID NO: | Descriptions of genes (letters and numbers within [ ] indicates GenBank accession No.) |
|---|---|---|---|---|---|
| 419 | A_23_P75769 | MS4A4A | CAGGAAAAGATCAACAGACACAAATGCTCGAGAAATGTATGCTGAACTGTGACGACAAGAGGCT | SEQ ID NO: 2000 | Homo sapiens membrane-spanning 4-domains, subfamily A, member 4 (MS4A4A), transcript variant 1, mRNA [NM_024021] |
| 420 | A_23_P76159 | EEA1 | TATTGTGTTTACTTCTGTGATGAATGTAGTTGTGGCTTACTTGTCAGAAAGGTTAGGTG | SEQ ID NO: 2001 | Homo sapiens early endosome antigen 1 (EEA1), mRNA [NM_003566] |
| 421 | A_23_P76480 | BF213738 | AAATCGAACAGGACAATGGGTAGATGAGATGAAGGTAGATTTACCAAATCGTTTGGGATGACAGG | SEQ ID NO: 2002 | BF213738 601847628F1 NIH_MGC_55 Homo sapiens cDNA clone IMAGE:4078519 5', mRNA sequence [BF213738] |
| 422 | A_23_P76951 | TXNDC1 | ATTTCTGTAATGTCCCCTTCCTTCTGTAGGCTGTGTTGCTGTGTGTGAATCGATTAGATTTACA | SEQ ID NO: 2003 | Homo sapiens thioredoxin domain containing 1 (TXNDC1), mRNA [NM_030755] |
| 423 | A_23_P78092 | EVI2A | GCTGAATGAGACAGTTGAAAAGAACAAAACAGGCTCACGAGAGCCAAGCTAGTGATGCAA | SEQ ID NO: 2004 | Homo sapiens ecotropic viral integration site 2A (EVI2A), transcript variant 1, mRNA [NM_014210] |
| 424 | A_23_P79199 | DBI | TGCTCACGATACGGCTCTAACAGATTAGGGGCTAAAACGATTACTGAGTTTCCTTGAGTA | SEQ ID NO: 2005 | Homo sapiens diazepam binding inhibitor (GABA receptor modulator, acyl-Coenzyme A binding protein) (DBI), transcript variant 1, mRNA [NM_020548] |
| 425 | A_23_P84212 | MRPS18C | ATGGGGTTTATGCCAGTACATACGAAGGATGGTGGATATGTCAAGGAACCCTAAAGTTTGT | SEQ ID NO: 2006 | Homo sapiens mitochondrial ribosomal protein S18C (MRPS18C), nuclear gene encoding mitochondrial protein, mRNA [NM_016067] |
| 426 | A_23_P83278 | CHMP5 | CATTGTCTCTTTATTTTTTCCATTAAGAGAGTGATTGCTGGTGGGAAATGCTTTGTTGGTAG | SEQ ID NO: 2007 | Homo sapiens chromatin modifying protein 5 (CHMP5), mRNA [NM_016410] |
| 427 | A_23_P84070 | LARP7 | AATTGCTAGAAGGGACAACTGCCGTATGATGATGTAAAAACGTTCCCATCTCCTGAGGATGGTGA | SEQ ID NO: 2008 | Homo sapiens La ribonucleoprotein domain family, member 7 (LARP7), transcript variant 1, mRNA [NM_016648] |
| 428 | A_23_P8640 | GPR30 | AACAGCTGGGACAACTGCGGTATGATGTAAAAAACGTTCCCAAAATGTAAGAAAAGC | SEQ ID NO: 2009 | Homo sapiens G protein-coupled receptor 30 (GPR30), transcript variant 2, mRNA [NM_001505] |
| 429 | A_23_P86653 | SRGN | AGGACTTGGGTCAACATGGAATTAGAAGAGGATTTATGTTATAAAAGAGGATTTCCCAC | SEQ ID NO: 2010 | Homo sapiens serglycin (SRGN), mRNA [NM_002727] |
| 430 | A_23_P87879 | CD69 | TGTGCAATATGTGATGTGGAAATCTGTATTAGGGAAATATTCTGTAATCTTCAGACCTAG | SEQ ID NO: 2011 | Homo sapiens CD69 molecule (CD69), mRNA [NM_001781] |
| 431 | A_23_P89145 | ZNF83 | GTATAATGAATGTAGGAGAGCCTTTAGTTTTTGTTGTTCAAGGGTTAATAACCGTTAGGTAGA | SEQ ID NO: 2012 | Homo sapiens zinc finger protein 83 (ZNF83), mRNA [NM_018300] |
| 432 | A_23_P9056 | RB1CC1 | TTCATTTTCTCAAAGGGCATACCTTGTGGATTGGCTTATGATGAGCCATATTAATTGC | SEQ ID NO: 2013 | Homo sapiens RB1-inducible coiled-coil 1 (RB1CC1), mRNA [NM_014781] |
| 433 | A_23_P91346 | BC038667 | GGGCTTAGGAGTGAGATTTCTGGTCTACAGAAATGATCATGCTCATGAATTTTGACATTT | SEQ ID NO: 2014 | Homo sapiens cDNA clone MGC:17708 IMAGE:3868595, complete cds. [BC038667] |
| 434 | A_23_P92410 | CASP3 | TCCACCAAGCTCACTGGCTGTCAGTATGACATTTCACGGGAGATTTCGTGTTGCTCAAA | SEQ ID NO: 2015 | Homo sapiens caspase 3, apoptosis-related cysteine peptidase (CASP3), transcript variant alpha, mRNA [NM_004346] |
| 435 | A_23_P92842 | SAR1B | TAATCTGACATCACCCCAGCGCCATTGTAAAGAGCAAGTTTCCAGCAGTACATTTGAAAG | SEQ ID NO: 2016 | Homo sapiens SAR1 gene homolog B (S. cerevisiae) (SAR1B), transcript variant 2, mRNA [NM_016103] |
| 436 | A_23_P933 | RWDD3 | GGAATCTTTTAGTAAAATAGCAGTGTTTTTCTTGTTTTGGATTCGATTTGGGAGTGG | SEQ ID NO: 2017 | Homo sapiens RWD domain containing 3 (RWDD3), mRNA [NM_015485] |

Fig. 5-24

| No. | Probe ID No. | Symbols of genes | Sequence | SEQ ID NO: | Descriptions of genes (letters and numbers within [ ] indicates GenBank accession No.) |
|---|---|---|---|---|---|
| 437 | A_23_P94230 | LY96 | TGAAGGCTATTCTGGGACCCAGAGAGAAATGCTCTTTTGCTTGG AGTTTGTCATCCTACA | SEQ ID NO: 2018 | Homo sapiens lymphocyte antigen 96 (LY96), mRNA [NM_015364] |
| 438 | A_23_P94301 | ANXA1 | GGCTGTCTTTGTGGAGGAAACTAAACATTCCCTCGATGGTCTCAAG CTATGACAGAAGACT | SEQ ID NO: 2019 | Homo sapiens annexin A1 (ANXA1), mRNA [NM_000700] |
| 439 | A_23_P94533 | CTSL1 | AAGACAATGGATCATGGTCTGCTGGTCTGGCTAGGATTTGAA AGCACAGAATCAGATA | SEQ ID NO: 2020 | Homo sapiens cathepsin L1 (CTSL1), transcript variant 1, mRNA [NM_001912] |
| 440 | A_23_P95594 | NAT1 | TGCTTGCAGAGAAAGCTTGTGCCCAAACATGGTTGATAGATTTTT TACTATTTAGAAATAAG | SEQ ID NO: 2021 | Homo sapiens N-acetyltransferase 1 (arylamine N-acetyltransferase) (NAT1), mRNA [NM_000662] |
| 441 | A_23_P9574 | ECT2 | TAATAGTTAAGTGACTATAGATTGTTTTCTATGCCATGTATGTG CCACTTCGGAGAGTAG | SEQ ID NO: 2022 | Homo sapiens epithelial cell transforming sequence 2 oncogene (ECT2), mRNA [NM_018098] |
| 442 | A_23_P96658 | C7orf15B | ATGCCGTAAAGTTAATACCAGAGGAGTCATATTTTATCAGATGTAA ATCTGGATGTAAGCTC | SEQ ID NO: 2023 | lipopolysaccharide-specific response 5-like protein [Source:RefSeq_peptide;Acc:NP_115965] [ENSG00000332832] |
| 443 | A_23_P98382 | TIMM8B | TTGTTACTAAGCAGATTTAATAACGGAAGGTCAGTGGGGAAGGTATCAA GCCATTGTGAGATCAG | SEQ ID NO: 2024 | Homo sapiens translocase of inner mitochondrial membrane 8 homolog B (yeast) (TIMM8B), mRNA [NM_012459] |
| 444 | A_23_P98446 | SC5DL | TGTGAACAGCAGGAGTTTAATCTTATGCTTAAAATGGCAGATGT TGTTCGGGGACAACT | SEQ ID NO: 2025 | Homo sapiens sterol-C5-desaturase (ERG3 delta-5-desaturase homolog, S. cerevisiae)-like (SC5DL), transcript variant 2, mRNA [NM_001024956] |
| 445 | A_23_P99980 | HMGB1 | GGATTCTTTCCATTTGCATTTTATTGTAATTTTGAGGAGGAAT ACTGAAGATGGAGTC | SEQ ID NO: 2026 | Homo sapiens high-mobility group box 1 (HMGB1), mRNA [NM_002128] |
| 446 | A_23_P99985 | HMGB1 | TGGGCCAGCTTTCAAACAAAGATGGGAGATTCAAAATAGGGTA TATTTTGGTATATAC | SEQ ID NO: 2027 | Homo sapiens high-mobility group box 1 (HMGB1), mRNA [NM_002128] |
| 447 | A_23_P105648 | BX111927 | TTATAGAATGCTTCAGTTCAAATAACAGTGCAGTAATTCACCTA TATCTAAAAGAACTGCC | SEQ ID NO: 2028 | BX111927 Soares_multiple_sclerosis_2NbHMSP Homo sapiens cDNA clone IMAGp998G05519, mRNA sequence [BX111927] |
| 448 | A_24_P105794 | RPL31 | CAGAGCCGTGTACAAAAGGTTTTAGAGTTGAAATATGAAAATGT GATGTGGGTATGGAAA | SEQ ID NO: 2029 | Homo sapiens ribosomal protein L31, mRNA (cDNA clone MGC:88191 IMAGE:4714258), complete cds. [BC070210] |
| 449 | A_24_P105913 | THC2606573 | CTGTGCTCTAGGAAATGCACGAATACGAAAGGTCAATGTGGAAA TATGGGCATGTTTGCC | SEQ ID NO: 2030 | AY151386 NAP1 [Homo sapiens] (exp=0; wgp=0; cg=0), partial (35%) [THC2606573] |
| 450 | A_24_P107257 | LIN7C | TATTAGTGTGGGACGTGTGACTGAGGTCTTAAAGAGTGAAAGAGT TGGGGTTCATTTTCTG | SEQ ID NO: 2031 | Homo sapiens lin-7 homolog C (C. elegans) (LIN7C), mRNA [NM_018362] |
| 451 | A_24_P110045 | THC2785765 | CCACCAGAAACGGTACACGTGATTTTCATGACAAATACGGTAGCA ACACAAGTCGGAATAG | SEQ ID NO: 2032 | COX7B_HUMAN (P24311) Cytochrome c oxidase polypeptide VIIb, mitochondrial precursor, partial (78%) [THC2785765] |
| 452 | A_24_P114249 | GALNT3 | ATTTCAAATGCAGAATACTTGACTCATTAAAGGTAAATTTGT TACTGATTCAATTATA | SEQ ID NO: 2033 | Homo sapiens UDP-N-acetyl-alpha-D-galactosamine:polypeptide N-acetylgalactosaminyltransferase 3 (GalNAc-T3) (GALNT3), mRNA [NM_004482] |
| 453 | A_24_P115774 | BIRC2 | GATACATTTTGGTTAAAGGAAATGCTGCGGCCAACATCTTCAA AAACTGTCTAAAGAA | SEQ ID NO: 2034 | Homo sapiens baculoviral IAP repeat-containing 2 (BIRC2), mRNA [NM_001166] |

Fig. 5-25

| No. | Probe ID No | Symbols of genes | Sequence | SEQ ID NO: | Descriptions of genes, letters and numbers within [ ] indicates GenBank accession No.) |
|---|---|---|---|---|---|
| 454 | A_24_P116766 | ZNF207 | TTTCTGAGAGCACGTATACCAGTGAAAATTAGCTTGTGAGTAAATTTGTAATTTATGCCC | SEQ ID NO: 2035 | Homo sapiens mRNA; cDNA DKFZp761N202 (from clone DKFZp761N202), [AL834501] |
| 455 | A_24_P118855 | ENST00000329784 | GCTATGGTGGGCAGAGTAAGCCGATTTTGTGAGAAAAAGGCTAAAACTACAAAAGAATACTG | SEQ ID NO: 2036 | PREDICTED: Homo sapiens similar to large subunit ribosomal protein L36a (LOC284230), mRNA [XM_208185] |
| 456 | A_24_P124992 | PSMA4 | AAAGGTCCCTTTGGTGTTTGCATTGCTGTGATTGGCTGGGATAAGCACTATGGGTTTCAG | SEQ ID NO: 2037 | Homo sapiens proteasome (prosome, macropain) subunit, alpha type, 4 (PSMA4), mRNA [NM_002789] |
| 457 | A_24_P126741 | ENST00000309178 | AGCCTGGAAGCACACTAAGAAGATTAAGAGATTACTTGGAAGCAGCTGACAGGAGCGAGAAT | SEQ ID NO: 2038 | |
| 458 | A_24_P126390 | RPL9 | GGTGTTGCTTGTTCAGTATGTCAAACCCGAGAAAGCATGAATTAATCCTTGAAGGAGAAATGAC | SEQ ID NO: 2039 | Homo sapiens ribosomal protein L9 (RPL9), transcript variant 1, mRNA [NM_000661] |
| 459 | A_24_P127181 | LOC442237 | AACTGAAATCTTTCCAGAAAATCCAAGTCCAGCTAGTAGAATTGGAGAAAAGTTGAGTG | SEQ ID NO: 2040 | PREDICTED: Homo sapiens similar to 40S ribosomal protein S7 (S8) (LOC442237), mRNA [XR_019963] |
| 460 | A_24_P127621 | A_24_P127621 | TCGAAGGAAGTACCACAAAGAGGATTCAATTCAGTTCAGCTTTCGCACATTTCTCAGAAATATTAG | SEQ ID NO: 2041 | |
| 461 | A_24_P132787 | RAB18 | TAAAAACCTCAGATTGACTTGATTTGAATTTAGCATTCGTAGTCTACATTACATGTGTTGAAGG | SEQ ID NO: 2042 | Homo sapiens RAB18, member RAS oncogene family (RAB18), mRNA [NM_021252] |
| 462 | A_24_P133991 | ANKRD12 | TTTGGAATGGAGTATATGCCTGAAAAGGTTTTGGATTCAGAAAAGAAAAGGATTGGTTAGT | SEQ ID NO: 2043 | Homo sapiens ankyrin repeat domain 12 (ANKRD12), mRNA [NM_015208] |
| 463 | A_24_P134392 | STCH | TGAGTAACTTATTTTGTATCAGGAAATGTTTTGGACTGTAGTGTGTTTTCACTCAAACCACTGAC | SEQ ID NO: 2044 | Homo sapiens stress 70 protein chaperone, microsome-associated, 60kDa (STCH), mRNA [NM_006948] |
| 464 | A_24_P135242 | A_24_P135242 | GATGGCAAGAAAAAGCTGGCAAGCTACTTTGTACCTGGAGAACCCAAAGTGGGATTTGTCAT | SEQ ID NO: 2045 | |
| 465 | A_24_P135551 | LOC130865 | TAACAGGCATAGGTGTGCCTGTGGGCATTGAGCCCAAAGGTCGTTATCACTAGAGTAAAACT | SEQ ID NO: 2046 | PREDICTED: Homo sapiens similar to ribosomal protein L26 (Silica-induced gene 20 protein) (SIG-20) (LOC130865), mRNA [XR_019454] |
| 466 | A_24_P139208 | USP25 | CAATATACAGCAAGGTGATTATTTCAAGAGAATCCCAAAGTAGTTGAATAAGCGCTATTG | SEQ ID NO: 2047 | Homo sapiens ubiquitin specific peptidase 25 (USP25), mRNA [NM_013396] |
| 467 | A_24_P141214 | STOM | GGGTGACATTTGAACATTTGGTCTTTGAGACTGTAGTTCACCTAGAGAAGTCTAAGCA | SEQ ID NO: 2048 | Homo sapiens stomatin (STOM), transcript variant 2, mRNA [NM_198194] |
| 468 | A_24_P144383 | A_24_P144383 | GTGCGTTGAGGCTGACCAAAAGATCTAAGAGAATGCTGGGTAAAAGATGCAAGGCATTTGAACT | SEQ ID NO: 2049 | |
| 469 | A_24_P144866 | LOC401975 | TGTCGATGTCAAGACTATAATGGCTACTTCTTAATCTGTCTGTGTTGGTTTACTGA | SEQ ID NO: 2050 | PREDICTED: Homo sapiens similar to ribosomal protein S3a (LOC401975), mRNA [XR_017247] |
| 470 | A_24_P148151 | TSNAX | AAAGTTGAGTTATATACTTGAGATACATAGAAATGGTTTTAGTAGGATTATTTAGCA | SEQ ID NO: 2051 | Homo sapiens translin-associated factor X (TSNAX), mRNA [NM_005999] |
| 471 | A_24_P152753 | LOC285260 | TGTCTCATAGGGAATCCGTGTGGGATTATCGAAGAAGAGTGAAGATTCACGAAATAAGCT | SEQ ID NO: 2052 | PREDICTED: Homo sapiens similar to ribosomal protein L31 (LOC285260), mRNA [XR_019376] |
| 472 | A_24_P152775 | LOC442195 | ACACAAAGAAGGTGTGTGAGGAGGATCCCCATTATCGTCAGGCAAGAAGCTCCACAACAAGA | SEQ ID NO: 2053 | PREDICTED: Homo sapiens hypothetical LOC442195 (LOC442195), mRNA [XR_019264] |
| 473 | A_24_P153324 | LOC390413 | GAAGGTTAACAAGGTTCAATAAGCATGGTGGGGATTGTAGAACCATATATTGCAGGGTA | SEQ ID NO: 2054 | PREDICTED: Homo sapiens similar to 60S ribosomal protein L7 (LOC390413), mRNA [XR_018341] |

Fig. 5-26

| No. | Probe ID No. | Symbols of genes | Sequence | SEQ ID NO: | Descriptions of genes (letters and numbers within [ ] indicates GenBank accession No.) |
|---|---|---|---|---|---|
| 474 | A_24_P153511 | OSBPL8 | CCTTGTGCATATACACACAAAATTTTGTGGAAGGGAAGTTTTAA GTTTCTGAAGAATATC | SEQ ID NO: 2055 | Homo sapiens oxysterol binding protein-like 8 (OSBPL8), transcript variant 1, mRNA [NM_020841] |
| 475 | A_24_P15765 | AK098605 | TCCAAGTCTGGCTAGTACGTGAATTGGAGAAAAAAGTTGGAGAAG CATGTTGTTTATTG | SEQ ID NO: 2056 | Homo sapiens cDNA FLJ25739 fis, clone TST05834. [AK098605] |
| 476 | A_24_P161914 | LOC130728 | CTATATGTCTGGAAAACACTTCAAAGAGAAAATAAGTTGGTGGGGC CATTCAAATTATGTTC | SEQ ID NO: 2057 | PREDICTED: Homo sapiens similar to 60S ribosomal protein L7 (LOC130728), mRNA [XR_019248] |
| 477 | A_24_P165595 | ARL5A | GAAGTAACTTGACCCAAAACACCTTTTATGTTTGGTTAGGGTAT ATTTTTCAGTGTGTG | SEQ ID NO: 2058 | Homo sapiens ADP-ribosylation factor-like 5A (ARL5A), transcript variant 1, mRNA [NM_012097] |
| 478 | A_24_P166864 | P2RY14 | TTTTTCTGGAAAACAGACGGATTTTACTTCTGGAGACATGGCAT ACGGTTACTGACTTAT | SEQ ID NO: 2059 | Homo sapiens purinergic receptor P2Y, G-protein coupled, 14 (P2RY14), transcript variant 2, mRNA [NM_014879] |
| 479 | A_24_P167063 | ZNF518 | AAAGAAAGGCATAGATAGAATGGTTCAAGCTATCTTGCTATGCA CATTATCTTGCTACTG | SEQ ID NO: 2060 | Homo sapiens zinc finger protein 518 (ZNF518), mRNA [NM_014803] |
| 480 | A_24_P169378 | RPS7 | AACTGAAATGTTTGGAGAAAATGAAATCGAAATCGCGCTAGTAAGTGAA TGGAGAAAAAGTTCA | SEQ ID NO: 2061 | Homo sapiens ribosomal protein S7 (RPS7), mRNA [NM_001011] |
| 481 | A_24_P171873 | FBXO4 | GATTGCACAGATATGAAAAAGTGTGAAGTTGTAGATGGGTTCA TCTATGTGCAAATGC | SEQ ID NO: 2062 | Homo sapiens F-box protein 4 (FBXO4), transcript variant 1, mRNA [NM_012176] |
| 482 | A_24_P172481 | TRIM22 | TGCCCTTAAAGATTGAAGAAAGAGAAACTTGTCAACTCAATCATAT CCACGTTATCTAGCAA | SEQ ID NO: 2063 | Homo sapiens tripartite motif-containing 22 (TRIM22), mRNA [NM_006074] |
| 483 | A_24_P175059 | ATG5 | GACAAGAGGGCTGGTGTGAATATGATTGTTCACATTAAGCAGT GTTATTGCTGGGTTC | SEQ ID NO: 2064 | Homo sapiens ATG5 autophagy related 5 homolog (S. cerevisiae) (ATG5), mRNA [NM_004849] |
| 484 | A_24_P175176 | PHTF2 | AGATTGAACTTCAAAACAGACTTGGGAGTTGATTATTAAGTACA GTATACCTCCAACAG | SEQ ID NO: 2065 | Homo sapiens putative homeodomain transcription factor 2 (PHTF2), mRNA [NM_020432] |
| 485 | A_24_P175187 | SAMD9 | CAACCAGGGATACGGTAATCAAAATGTAAATTTTCCCTAAATAAAA TTATGGATATGGGCAG | SEQ ID NO: 2066 | Homo sapiens sterile alpha motif domain containing 9 (SAMD9), mRNA [NM_017654] |
| 486 | A_24_P175188 | SAMD9 | TGCAATGTAGTTGGGACAGGATTAACATACAACCTACTGTTTTGAACA AAAACAACCAGCGATA | SEQ ID NO: 2067 | Homo sapiens sterile alpha motif domain containing 9 (SAMD9), mRNA [NM_017654] |
| 487 | A_24_P175519 | TXN | AAGTAGATGTGGATGACTGTGAGGATGTTGCTTCAGAGTGTGAA GTCAAATGCACGCCAA | SEQ ID NO: 2068 | Homo sapiens thioredoxin (TXN), mRNA [NM_003329] |
| 488 | A_24_P175989 | VPS29 | GAGAGAGAGACTTCGATGAGAATGTGAATTATCCAGAACAACAGAAAG TTGTGACTGTTGGACA | SEQ ID NO: 2069 | Homo sapiens vacuolar protein sorting 29 homolog (S. cerevisiae) (VPS29), transcript variant 2, mRNA [NM_057180] |
| 489 | A_24_P178602 | ZNF600 | ATAAGATAATTCACACCGGAGAGAGAAACCATACAAATGTAAGGTT TGTGACAAGGGTTTTG | SEQ ID NO: 2070 | Homo sapiens zinc finger protein 600 (ZNF600), mRNA [NM_198457] |
| 490 | A_24_P179351 | TPT1 | GAACAGAGCACAGAAGAGTAAAGCTTATATGAGAGGGGGTGC AGAAGAAATCAAGCAC | SEQ ID NO: 2071 | Homo sapiens tumor protein, translationally-controlled 1 (TPT1), mRNA [NM_003295] |
| 491 | A_24_P180424 | TMEM30A | CAATGTGTTATGGCACATTCTCTTAGTTAAGGCACCAATTGTTT GGTTGGTTTTCGTAAG | SEQ ID NO: 2072 | Homo sapiens transmembrane protein 30A (TMEM30A), mRNA [NM_018247] |
| 492 | A_24_P181120 | PFDN5 | CACCGACTGAAACAGGCCGTCATGGAAAATGAGAGTGAGAAGAT TCAGCAGGTCAGAGGC | SEQ ID NO: 2073 | Homo sapiens prefoldin subunit 5 (PFDN5), transcript variant 1, mRNA [NM_002624] |
| 493 | A_24_P183864 | IMPA1 | TCAGCCTTATCCCTTGGCACGTAAACAGAACTAGTAGAGTTATTG TAGGTTGTTTGAGCT | SEQ ID NO: 2074 | Homo sapiens inositol(myo)-1(or 4)-monophosphatase 1 (IMPA1), mRNA [NM_005536] |

Fig. 5-27

| No | Probe ID No. | Symbols of genes | Sequence | SEQ ID NO: | Descriptions of genes (letters and numbers within [ ] indicates GenBank accession No.) |
|---|---|---|---|---|---|
| 494 | A_24_P186944 | LOC389404 | AGGAAGCGTGCGGAGGAGAGTTCAATCACATGGTAGAAGTCAGTCTTGTTGGAAAGAAAAA | SEQ ID NO: 2075 | PREDICTED: Homo sapiens similar to 60S ribosomal protein L9 (LOC389404), mRNA [XR_018133] |
| 495 | A_24_P188600 | MARCH1 | GTCACGCAAAAGATTTTCAGAAAATGTTCGGAATAATTAGGTCTGTTAAATAGCCACAG | SEQ ID NO: 2076 | Homo sapiens membrane-associated ring finger (C3HC4) 1 (MARCH1), mRNA [NM_017923] |
| 496 | A_24_P188878 | RPL34 | TGTTTAGGTTTATACCAAGAAGAGTTGGAAAGAGCAAAATCTGCATGTGGTGTGTGCCC | SEQ ID NO: 2077 | Homo sapiens ribosomal protein L34 (RPL34), transcript variant 2, mRNA [NM_033625] |
| 497 | A_24_P190804 | AP1S2 | GGTGGAAGTAAGGTAAGGAGTCTTCATGTACTTGATTAAAAATAA CATGGATTCCATACTG | SEQ ID NO: 2078 | Homo sapiens adaptor-related protein complex 1, sigma 2 subunit (AP1S2), mRNA [NM_003916] |
| 498 | A_24_P191417 | NAB1 | AAGTTCCTTAAGTATCTTATGTTTCTAGTCTTTCAAGGCTTAGTGATAAGGTGGAAGCAC | SEQ ID NO: 2079 | Homo sapiens NGFI-A binding protein 1 (EGR1 binding protein 1) (NAB1), mRNA [NM_005966] |
| 499 | A_24_P191833 | SFRS12 | AAGGAGTTAGGAGTATATGGAGGGTTATTGGTTTTATGTTTAAG GATACGTTTAGTTGAG | SEQ ID NO: 2080 | Homo sapiens splicing factor, arginine/serine-rich 12 (SFRS12), transcript variant 2, mRNA [NM_139168] |
| 500 | A_24_P194313 | C21orf66 | ATTTAAATTAACCCTCTCAGTTAATGTGCCCTGTAAACGATGTGTGAGTGTAAATTGT | SEQ ID NO: 2081 | Homo sapiens chromosome 21 open reading frame 66 (C21orf66), transcript variant 1, mRNA |
| 501 | A_24_P199500 | RNF2 | AAAGTGCTTAGATTTTGTTGATGACATTAGATAGTAGTGCATTAAATAACTAAATTCC | SEQ ID NO: 2082 | Homo sapiens ring finger protein 2 (RNF2), mRNA [NM_007212] |
| 502 | A_24_P20120 | KIAA1212 | TTGAGAATGAAAATGGGTTAAAGGAATGATATGGATAAAGT TGCACTTATAACACCC | SEQ ID NO: 2083 | Homo sapiens KIAA1212 (KIAA1212), mRNA [NM_018084] |
| 503 | A_24_P201353 | C10orf32 | TCCAATCTTTTTAAATGACATTAGCACTGAGTCTGTGTCAAACGT AAATATCTTGTTGA | SEQ ID NO: 2084 | Homo sapiens chromosome 10 open reading frame 32 (C10orf32), mRNA [NM_144591] |
| 504 | A_24_P201702 | CLEC2B | ATTGGAATTCAAGTAAATAGAACTGTTCCAGTGAACATGCCAG CTAACTATAATTGACA | SEQ ID NO: 2085 | Homo sapiens C-type lectin domain family 2, member B (CLEC2B), mRNA [NM_005127] |
| 505 | A_24_P203103 | SH2D1A | AAAGGGTAAGGTTCACTGTAAAATAACTGGGAATTCTGCATTGTGTATGGGTGTTGGT | SEQ ID NO: 2086 | Homo sapiens SH2 domain protein 1A, Duncan's disease (lymphoproliferative syndrome) (SH2D1A), mRNA [NM_002351] |
| 506 | A_24_P203827 | LOC730647 | CTTGGTTTCCATGACAGTTGCCCTCAAGCAGCAAACGTTTTCTGTTGATATCGGAAAAAA | SEQ ID NO: 2087 | PREDICTED: Homo sapiens similar to Histidine triad nucleotide-binding protein 1 (Adenosine 5-monophosphoramidase) (Protein kinase C inhibitor 1) (Protein kinase C-interacting protein 1) (PKC1-1), (LOC730647), mRNA [XM_001126674] |
| 507 | A_24_P203909 | RPL34 | GAAGGGTTGCTCTGTAAGAGCTTAAAGTTCTATGAAATTGTCC AAAACAAGAAACATG | SEQ ID NO: 2088 | Homo sapiens ribosomal protein L34 (RPL34), transcript variant 2, mRNA [NM_033625] |
| 508 | A_24_P208045 | EDEM3 | TTTAGAGGGGGTAGAATTTAGTAGATAATTCAGACGGGTCGTTT TATGCAAAGGCTTCA | SEQ ID NO: 2089 | Homo sapiens ER degradation enhancer, mannosidase alpha-like 3 (EDEM3), mRNA [NM_025191] |
| 509 | A_24_P20996 | BC043173 | CTGAAAATGTTCATATATGTATATGAAGTCTCTTTATGCT GAAGGCGTCTGATTGG | SEQ ID NO: 2090 | Homo sapiens cDNA clone IMAGE:5287121. [BC043173] |
| 510 | A_24_P212864 | LOC646161 | ACAGAAGTACAACGTGGGATCCATGATCCGGAAAGAATGATGAAGTTAGGCTTGTACCAGG | SEQ ID NO: 2091 | PREDICTED: Homo sapiens similar to 60S ribosomal protein L26 (LOC646161), mRNA [XR_018048] |
| 511 | A_24_P213354 | LOC731048 | CACGTGCTTAAAAACACAGAGAATGTGAACTTAAGGGTGATTGTGTGGCATTCAG | SEQ ID NO: 2092 | PREDICTED: Homo sapiens similar to 60S ribosomal protein L17 (L23) (LOC731048), mRNA [XR_015710] |
| 512 | A_24_P213375 | A_24_P213375 | AAATGTTCCATGATCAAAAAATGGCAGACAAAGATTCTTCATCTGTTCTGTTGGTT | SEQ ID NO: 2093 | |

Fig. 5-28

| No. | Probe ID No. | Symbols of genes | Sequence | SEQ ID NO: | Descriptions of genes (letters and numbers within [ ] indicates GenBank accession No.) |
|---|---|---|---|---|---|
| 513 | A_24_P213783 | RPL31 | GTTTGGTTACCTATGTAGCTGTTGACCACTTTGAAAAATCTACAGACAGTCAATGGATG | SEQ ID NO: 2094 | Homo sapiens ribosomal protein L31 (RPL31), mRNA [NM_000993] |
| 514 | A_24_P221375 | A_24_P221375 | TACTTTGGTTACCCATGTACCTAGCACGTTTCAAAAATCTACAGAGAGTCAATGTGGAGGA | SEQ ID NO: 2095 | |
| 515 | A_24_P222655 | C1QA | GGGTGACCCAGGTCTGGGTTGAAAAGAGCCCGAAAAAGGGTCACATTTACCAGGGGTCTGA | SEQ ID NO: 2096 | Homo sapiens complement component 1, q subcomponent, A chain (C1QA), mRNA [NM_015991] |
| 516 | A_24_P222911 | SFRS7 | GAGAAATGTCAATGAGAGTAAGTGGTTTGTAAATCTAGCTATATTTAGCAACACTCC | SEQ ID NO: 2097 | Homo sapiens splicing factor, arginine/serine-rich 7, 35kDa (SFRS7), mRNA [NM_010316884] |
| 517 | A_24_P225308 | ARID4B | GTTGAAAATGGTTTCAAGTATTGCAAATTGTACAGGAGTGTAAAGATTGTTGACAGCA | SEQ ID NO: 2098 | Homo sapiens AT rich interactive domain 4B (RBP1-like) (ARID4B), transcript variant 1, mRNA [NM_016374] |
| 518 | A_24_P225468 | ANP32E | TCATCTTAGTGTGCAAATCAAAATTAGAGTACTTTGTTTGAAAAACAAGACTTAGAGCCTG | SEQ ID NO: 2099 | Homo sapiens acidic (leucine-rich) nuclear phosphoprotein 32 family, member E (ANP32E), mRNA [NM_030920] |
| 519 | A_24_P225719 | PREI3 | GACTATTTTGTTAGTGAATATTTATACTAAGGTAGTGAGTGAAGATTTGGTATGGTGGCTG | SEQ ID NO: 2100 | Homo sapiens preimplantation protein 3 (PREI3), transcript variant 1, mRNA [NM_015387] |
| 520 | A_24_P229066 | ENST00000078131 | AAGAAGCTCCAACAAGAAGACAGGAGGTTATGTGACCATCTGATGAAGCAGATTGAGAGA | SEQ ID NO: 2101 | OTTHUMP00000016594. [Source:Uniprot/SPTREMBL;Acc:Q9NU96] [ENST00000078131] |
| 521 | A_24_P232856 | RPL9 | GAAGCCTGGCGGAGGAGGGATGTCAATCACGTAGAAGCTCAGCGTCTGGAAGAGAAAA | SEQ ID NO: 2102 | Homo sapiens ribosomal protein L9 (RPL9), transcript variant 1, mRNA [NM_020661] |
| 522 | A_24_P233429 | ABCA1 | CCAAAGAGGGATGTGTCATCTAATAGTGAACCACTTTGAATGTGTACAGATATTGAGAGA | SEQ ID NO: 2103 | Homo sapiens ATP-binding cassette, sub-family A (ABC1), member 1 (ABCA1), mRNA [NM_005502] |
| 523 | A_24_P236008 | SCYL2 | CCAAAGAGGGATGTACTACTGTCTGGTTTTTGTTTGTTATTTTGGAATGCTTAAAGCTCC | SEQ ID NO: 2104 | Homo sapiens mRNA for KIAA1360 protein, partial cds. [AB037781] |
| 524 | A_24_P237511 | EIF1AY | GTTTCAGTTACTTAGATGGTCTCATAAGGTTTCTGATACAATTGAAGACAGAAATCTGG | SEQ ID NO: 2105 | Homo sapiens eukaryotic translation initiation factor 1A, Y-linked (EIF1AY), mRNA [NM_004681] |
| 525 | A_24_P242299 | ZRANB2 | GACTTTTGAAAGTCTACCTTCTAAATTGGCCCGACGATGTAGATTGTACATGTTACCAT | SEQ ID NO: 2106 | Homo sapiens zinc finger, RAN-binding domain containing 2 (ZRANB2), transcript variant 2, mRNA [NM_005455] |
| 526 | A_24_P25326 | ZMYM6 | AGGACTATTTAAATCAGTGTCTGTAACTCAGTTTGGATAAATGCAAAGACAAGTTACCC | SEQ ID NO: 2107 | Homo sapiens zinc finger, MYM-type 6 (ZMYM6), mRNA [NM_007167] |
| 527 | A_24_P255252 | A_24_P255252 | GGACTACTGGAAGGATGTGTGACTCGATGTGATATTTCTTGAGGATGATTTAGAAA | SEQ ID NO: 2108 | |
| 528 | A_24_P263524 | TXNDC9 | TGACTTGAGCAGCAGAAAACTTTAGAATGGGGGCTCAGTTGTTCTGAGATTCTTAATTACAG | SEQ ID NO: 2109 | Homo sapiens thioredoxin domain containing 9 (TXNDC9), mRNA [NM_005783] |
| 529 | A_24_P264549 | A_24_P264549 | ATTCATAGTAGGATACAGAACATGATCAAAAGGTGTTACAGTGGACTCCATTAGAATATG | SEQ ID NO: 2110 | |
| 530 | A_24_P265856 | SENP7 | TTGTGTGTTGGGGGATACTTTAAAGGTGACTATTGTTTGTACATCTAATTTGGGA | SEQ ID NO: 2111 | Homo sapiens SUMO1/sentrin specific peptidase 7 (SENP7), transcript variant 1, mRNA [NM_020654] |
| 531 | A_24_P268786 | MYNN | TGGAGGATCATACTTTGAGTGAACAGGATTCCATACAAAAAGTGGTTTTATCAGAAAC | SEQ ID NO: 2112 | Homo sapiens myoneurin (MYNN), mRNA [NM_018657] |

Fig. 5-29

| No. | Probe ID No. | Symbols of genes | Sequence | SEQ ID NO: | Descriptions of genes (letters and numbers within [ ] indicates GenBank accession No.) |
|---|---|---|---|---|---|
| 532 | A_24_P268917 | RAB33B | CCCAGAATCTAATGTAGTTCGCTATTAATAACAATGCATTATTG AAAGTATATTGCAAAT | SEQ ID NO: 2113 | Homo sapiens RAB33B, member RAS oncogene family (RAB33B), mRNA [NM_031296] |
| 533 | A_24_P276583 | TMCO1 | CGTTCATTTGCTGCTATATTCTGTGTACTACTGATTGGAGAG AACATCAGAAGATTC | SEQ ID NO: 2114 | Homo sapiens transmembrane and coiled-coil domains 1 (TMCO1), mRNA [NM_019026] |
| 534 | A_24_P278908 | DCTN6 | CTATGAAAGGAAGGTCAAGTCCAGTAAGAGTAAAGAACAGTGT ATAACATGAAGATAAC | SEQ ID NO: 2115 | Homo sapiens dynactin 6 (DCTN6), mRNA [NM_006571] |
| 535 | A_24_P278460 | MLSTD2 | ACCCATGGAAGAATATGCTTAGGATTACAGGAGGAGTAGTCCTTAC TTACACTTCTGTCTCG | SEQ ID NO: 2116 | Homo sapiens male sterility domain containing 2 (MLSTD2), mRNA [NM_032228] |
| 536 | A_24_P280897 | LOC388532 | AGCACTCTGAGAGCTGGGATAGCTTCGTGAAATACATGAAGGAA AATGATCAGAAAAGA | SEQ ID NO: 2117 | PREDICTED: Homo sapiens similar to ribosomal protein L21 (LOC388532), mRNA [XM_001127035] |
| 537 | A_24_P281304 | A_24_P281304 | GAGGAGAGGCACCCGATATATGTCTGTAAGGGTTTAGAAAAC AAGTTTTCCTTGGC | SEQ ID NO: 2118 | |
| 538 | A_24_P285179 | THC2649313 | AGTGGGAATTTTGAAATGCCATGTCCTATATATCTGTGGCATATT TGTTGGCACATTGCA | SEQ ID NO: 2119 | |
| 539 | A_24_P286054 | ZFYVE16 | GTGTATGTATTCTGGCATGTAAGTAATTGAAGACAGTGTTAAAATA AGCAAATGGTAGAGGG | SEQ ID NO: 2120 | Zinc finger FYVE domain-containing protein 16 (Endofin). [Endosome-associated FYVE domain protein]. [Source:Uniprot/SWISSPROT:Acc:Q7Z3T8] [ENST00000380248] |
| 540 | A_24_P287756 | NUDT21 | CCCAATACTTAGCTGAGTGTTATACATCACGTATATTTGGGTT AAAGTGACTCATTTC | SEQ ID NO: 2121 | Homo sapiens nudix (nucleoside diphosphate linked moiety X)-type motif 21 (NUDT21), mRNA |
| 541 | A_24_P290031 | LSM3 | CCCTCCACTGAGTGTTTGGCTGAAACAAAGAATTTGTCCTGTATG GAAAAGAGGAGACTTT | SEQ ID NO: 2122 | Homo sapiens LSM3 homolog, U6 small nuclear RNA associated (S. cerevisiae) (LSM3), mRNA [NM_014463] |
| 542 | A_24_P290257 | A_24_P290257 | CCAATTCATTCAACATAGAACAAGCAGCCAATTATACCATGCAGTCA TTGAAGGACAGGAAGA | SEQ ID NO: 2123 | |
| 543 | A_24_P295543 | BLOC1S2 | GTTTATTTTCTATGTGAGTCAGATTCAGATGCCAGATCAGTTTGGG AAATGTGATGAAAAGA | SEQ ID NO: 2124 | Homo sapiens biogenesis of lysosome-related organelles complex-1, subunit 2 (BLOC1S2), transcript variant 2, mRNA [NM_001001342] |
| 544 | A_24_P298238 | A_24_P298238 | ATGCTTGAAGGAAAATGAGATTGAGGTTGTTCAATTCAGCAAGC CACAACAGTTAAAAC | SEQ ID NO: 2125 | |
| 545 | A_24_P298604 | LOC731599 | GATGGAAATCATGACCAGAGGTGCGGGCAAATGACTTGAAGAAT TGGTCAATAAAATGAT | SEQ ID NO: 2126 | PREDICTED: Homo sapiens hypothetical protein LOC731599 (LOC731599), mRNA [XR_015536] |
| 546 | A_24_P301194 | IFIT5 | AAATGTGGCTTCTGTAATGTAGTTTCTTTGATTAGGAGTACACA ATTATGTACCATCACA | SEQ ID NO: 2127 | Homo sapiens interferon-induced protein with tetratricopeptide repeats 5 (IFIT5), mRNA [NM_012420] |
| 547 | A_24_P303118 | RPL34 | AGGAGGCCAGAAAATCGTTGTGTGAAAGTGTTGAAGGCACAAGCAC AGAGTCAGAAGCTAA | SEQ ID NO: 2128 | Homo sapiens ribosomal protein L34 (RPL34), transcript variant 2, mRNA [NM_033625] |
| 548 | A_24_P303127 | C5orf29 | CCCAATGCCTAGAACATGACATAAGGCACTAAATGCCTCATCGT TTTACTGACGGGAATT | SEQ ID NO: 2129 | Homo sapiens chromosome 5 open reading frame 29 (C5orf29), mRNA [NM_152687] |
| 549 | A_24_P305570 | RIN2 | TATGCAGTGAGGTTTGGACAAAATGTATTCCCAAAATGTGTGATTTGCT TGTAGAAACAATTTTG | SEQ ID NO: 2130 | Homo sapiens Ras and Rab interactor 2 (RIN2), mRNA [NM_018993] |
| 550 | A_24_P306469 | LOC257039 | AGAGAAAAACAGAGACAATGTATTCCCGAGATGTGAGTCGGA TGAGGACACGTTGAA | SEQ ID NO: 2131 | PREDICTED: Homo sapiens similar to 40S ribosomal protein S17 (LOC257039), mRNA [XM_172230] |

Fig. 5-30

| No | Probe ID No | Symbols of genes | Sequence | SEQ ID NO: | Descriptions of genes (before and numbers within [ ] indicates GenBank accession No.) |
|---|---|---|---|---|---|
| 551 | A_24_P306527 | ENST00000308889 | ACCGCATCCGTGCGTGGTTATCCAGAAAATGTAATGAGGATGAA GATTCACCAAATAAGT | SEQ ID NO: 2132 | PREDICTED: Homo sapiens similar to ribosomal protein L31 (LOC729605), mRNA [XM_001133428] |
| 552 | A_24_P306726 | TPT1 | GACCAGAAACAGTAAAACCTTTTATGACAGGAGGCTGCAAAACAA ATCAAGGACATCCTTG | SEQ ID NO: 2133 | Homo sapiens tumor protein, translationally-controlled 1 (TPT1), mRNA [NM_003295] |
| 553 | A_24_P310894 | CAPZA1 | TGTATTATTTGTCCTTCATACTATCATCCATCATACCACACTATCT TCTATATCAGGTAGTC | SEQ ID NO: 2134 | Homo sapiens capping protein (actin filament) muscle Z-line, alpha 1 (CAPZA1), mRNA [NM_006135] |
| 554 | A_24_P312417 | ZBTB26 | AGAGGGAAGAATTTTTAAAGCTTTATCATTCAGCATTGTAT TTTATGGATCCCCAGG | SEQ ID NO: 2135 | Zinc finger and BTB domain-containing protein 26 (Zinc finger protein 481) (Zinc finger protein Biore). [Source:Uniprot/SWISSPROT:Acc:Q9HCK0] [ENST00000373656] |
| 555 | A_24_P315326 | LOC341412 | AAGCCTATACTTTGGTTACGGACGTAGCCGGTTAGCGGCTTTTCAA AAATCTACAGGGAATG | SEQ ID NO: 2136 | AGENCOURT_10640955 NIH_MGC_126 Homo sapiens cDNA clone IMAGE:6723558 5', mRNA sequence [CA456253] |
| 556 | A_24_P316074 | LOC730902 | TATGAATGGTGTGAGGGCAAAGGTCAAAGGTGTTGCAGGCTGTT CCCTTCGTCGAAATCTT | SEQ ID NO: 2137 | PREDICTED: Homo sapiens similar to 60S ribosomal protein L7 (LOC730902), mRNA [XR_015600] |
| 557 | A_24_P320328 | SUB1 | CAGAAATCCTGTAAAGAACAAAAGACAAGGTGAGAGTTGAGA GGCCCGTCATCTCTA | SEQ ID NO: 2138 | Homo sapiens SUB1 homolog (S. cerevisiae) (SUB1), mRNA [NM_006713] |
| 558 | A_24_P321511 | GOLT1B | TTAAGAGCAAGAATAGTATCTGCTAATGTAAGGACATCTGTATT TAAGTCCTTTGTAGAAC | SEQ ID NO: 2139 | Homo sapiens golgi transport 1 homolog B (S. cerevisiae) (GOLT1B), mRNA [NM_016072] |
| 559 | A_24_P324224 | A_24_P324224 | AAAGTTCTGTCTGGCCAAAGAGGAATAAAGGAATTCCTATAAGGCATGT TGTGACATGCGTGT | SEQ ID NO: 2140 | |
| 560 | A_24_P324506 | A_24_P324506 | GCAATATAAGGCAGTAATTGCAAATACAACAAGTATGGGCTATTTCC TAACCATCAGCTGTG | SEQ ID NO: 2141 | |
| 561 | A_24_P32790 | YOD1 | CTAGGACTATAATTAAGGACAATAAAGTACAATCTTGAGGTAC TAAGCAGCTACAAAG | SEQ ID NO: 2142 | Homo sapiens YOD1 OTU deubiquinating enzyme 1 homolog (S. cerevisiae) (YOD1), mRNA [NM_018566] |
| 562 | A_24_P33213 | A_24_P33213 | GACCATATTTACATGGGGTAGGGTATCAATGTCTGAGCCGGCAGGACCA GAACTTATCAAGA | SEQ ID NO: 2143 | |
| 563 | A_24_P333112 | A_24_P333112 | GGTCAATCAGAATGAAGGTATCAATGTGTGAGCCCAGCAGGACCA AAAGGTATTGCAAGTT | SEQ ID NO: 2144 | |
| 564 | A_24_P33607 | LOC652558 | TAAGAAAATAATTGGTTTGACAGACAGAACAAAGGTTTGATTGCTCCAT CTCTTGTAAATATGG | SEQ ID NO: 2145 | PREDICTED: Homo sapiens similar to 60S ribosomal protein L7 (LOC652558), mRNA [XR_019386] |
| 565 | A_24_P339869 | ZNF295 | TCATATGCTTAGCAGAGTAAGTCATTCATTTTTGGATTTAGTAGG AATAAGCTTTTTTCGAA | SEQ ID NO: 2146 | Homo sapiens zinc finger protein 295 (ZNF295), mRNA [NM_020727] |
| 566 | A_24_P349636 | LOC388401 | AGTTGTGAGAGAATAACAGTTGATTGGTGGATGTCGTTGGTA AATATAAGCATCAACTG | SEQ ID NO: 2147 | PREDICTED: Homo sapiens similar to 60S ribosomal protein L7 (LOC388401), mRNA [XR_016879] |
| 567 | A_24_P351435 | CRBN | GAAAGTGAAAGCAATTGAACAAGACAAAGGTTCAAAGTGCTTGAGG TAAGAACAGAGTCAGA | SEQ ID NO: 2148 | Homo sapiens cereblon (CRBN), mRNA [NM_016302] |
| 568 | A_24_P352445 | MRPL42 | TTTTTTAGTGCATCACAATGACGAAAGGGAGTTGGTTTTGTTGAGC CAAGAATGTGCTTTCC | SEQ ID NO: 2149 | Homo sapiens mitochondrial ribosomal protein L42 (MRPL42), nuclear gene encoding mitochondrial protein, transcript variant 3, mRNA [NM_172178] |
| 569 | A_24_P354412 | AK091335 | TGTAGAGTGAAGGAGTGCTTTGAAACACAGGGCGAGCATTAAATGTG ACTCTGCGCTGCTCT | SEQ ID NO: 2150 | Homo sapiens cDNA FLJ34016 fis, clone FCBBF2002541 [AK091335] |
| 570 | A_24_P354954 | CCDC126 | ACTGGAACTCTTGAGGACTTTAGCAGAGGTGTATATAATAAAGGT ACTTTTGTGCTGCATT | SEQ ID NO: 2151 | Homo sapiens coiled-coil domain containing 126 (CCDC126), mRNA [NM_138771] |

Fig. 5-31

| No. | Probe ID No. | Symbols of genes | Sequence | SEQ ID NO: | Descriptions of genes (letters and numbers within [ ] indicates GenBank accession No.) |
|---|---|---|---|---|---|
| 571 | A_24_P357518 | RPL21 | GGCCACATATATGGTAATCTATAAGAAAGGTGATATTGCAGACATCAAGGGAAGGGGGTAC | SEQ ID NO: 2152 | Homo sapiens ribosomal protein L21 (RPL21), mRNA [NM_000982] |
| 572 | A_24_P358205 | | TGTTCAAAAAGATGCCCCAAGTGTTACGATGGCTAAATGGAAGAGTGTGCAGTGTTGG | SEQ ID NO: 2153 | |
| 573 | A_24_P362646 | TXNDC9 | CTCCAGATTCAGGTGTAAATACTAGACAGAGACATGGCAATATGTCCAAGAAGACACCT | SEQ ID NO: 2154 | Homo sapiens thioredoxin domain containing 9 (TXNDC9), mRNA [NM_005783] |
| 574 | A_24_P364025 | UBE2D1 | ATGTAATGGGTATAGTCATTAGGAAAGCATTTAAATACAGTTGAGTATTTGTCATGGTTG | SEQ ID NO: 2155 | Homo sapiens ubiquitin-conjugating enzyme E2D 1 (UBC4/5 homolog, yeast) (UBE2D1), mRNA [NM_003338] |
| 575 | A_24_P364807 | AYTL1 | TGTAACTCTGTTGTCTGTAAGTAATGGTTCTCTCGAACAAACTTCTCAAGCGTCTGTGTAA | SEQ ID NO: 2156 | Homo sapiens mRNA; cDNA DKFZp686H22112 (from clone DKFZp686H22112). [BX641069] |
| 576 | A_24_P366165 | LOC91126 | ACTTCCAAGCGAAATCAAAATAGCAAAAGGAGTTCAATGAGCTTCCCAGATTCACAGG | SEQ ID NO: 2157 | PREDICTED: Homo sapiens similar to 60S ribosomal protein L26 (Silica-induced gene 20 protein) (SIG-20) (LOC91126), mRNA [XR_019504] |
| 577 | A_24_P366546 | RPL31P10 | CGGCTGTGCAGAAAACGTAATGAGGATGAAGATTCAAATAAGCTGTATACTTTTGGTTACC | SEQ ID NO: 2158 | PREDICTED: Homo sapiens similar to 60S ribosomal protein L31 (LOC390283), mRNA [XR_018065] |
| 578 | A_24_P367139 | | AGACCATGAAACTGCTCAGTGTCAGGGCCATGCAAGGGTATACATAAAAGCCAAGAATATCTGTAAAG | SEQ ID NO: 2159 | |
| 579 | A_24_P367191 | LOC652890 | AGTTAAGATGCTGAAGACTGTAGAAGCATATATTGCGTGTGGGTAGCCAAATCTGAAGTC | SEQ ID NO: 2160 | PREDICTED: Homo sapiens similar to 60S ribosomal protein L7 (LOC652890), mRNA [XR_019544] |
| 580 | A_24_P367199 | | TCTTATGCTGAGCACCAACAGTCTGCGAAATCCAGAAGAAGGTCTAATCATGAGCTGAGA | SEQ ID NO: 2161 | |
| 581 | A_24_P367369 | | ATTTAAAGTTTCTACATGTAGATTCTGTCGTCGTCAGGATATCGAAGTGAACAAAGCATCTAA | SEQ ID NO: 2162 | |
| 582 | A_24_P368575 | SLC4A7 | TTTTTAATGAGATTTTGGACAACTGATTAGTTTTGTGTCGGTTTGTTGTTTAT | SEQ ID NO: 2163 | Homo sapiens solute carrier family 4, sodium bicarbonate cotransporter, member 7 (SLC4A7), mRNA [NM_003615] |
| 583 | A_24_P370096 | ZNF230 | GAAAGCTTATATTTGTGAGAAATGTGGACAGGGGGTTCATTCAGGATTTAAAGGTTCAGAA | SEQ ID NO: 2164 | Homo sapiens zinc finger protein 230 (ZNF230), mRNA [NM_006300] |
| 584 | A_24_P371053 | ORMDL1 | GAATGAAAAGAGTTACAGAGAGCAAGCTAAAACATCAATTGGTGTCAGTAAAGTGACTTTTGG | SEQ ID NO: 2165 | Homo sapiens ORM1-like 1 (S. cerevisiae) (ORMDL1), mRNA [NM_016467] |
| 585 | A_24_P371363 | C3orf63 | GTCAGTCTCAAGAAAATGAGAATTACTTCTTATCTGCTTATACTGAAAGCTTGGATAGAC | SEQ ID NO: 2166 | Homo sapiens chromosome 3 open reading frame 63 (C3orf63), mRNA [NM_015224] |
| 586 | A_24_P371399 | C3orf58 | TAAAATAGTTGCATTCGGTTAATTTTTAGACATAGTGCATTGCGTATATCAACTGGCCC | SEQ ID NO: 2167 | Homo sapiens chromosome 3 open reading frame 58 (C3orf58), mRNA [NM_173552] |
| 587 | A_24_P374319 | RAP2C | ATTGTGTGAGTGTTCAAATAAAGTGGTATCTACATTCAGAATGGGTCGATTTATGGCAGGATG | SEQ ID NO: 2168 | Homo sapiens RAP2C, member of RAS oncogene family (RAP2C), mRNA [NM_021183] |
| 588 | A_24_P375599 | LOC731681 | TGTATGCTCAGTTCCCCATCCAAGTCGTTATCCAGAATGGGTCTCGTTGTTGAAATCGAA | SEQ ID NO: 2169 | PREDICTED: Homo sapiens similar to 60S ribosomal protein L9 (LOC731681), mRNA [XR_015944] |
| 589 | A_24_P375849 | ENST00000359659 | AAGAAGCTCTCGAACAAGAATAGGACCATGGTCACGACATCTGATGAAGCCGGATTCAGAGA | SEQ ID NO: 2170 | Q8BT90_MOUSE (Q8BT90) 10, 11 days embryo whole body cDNA RIKEN full-length enriched library, clone:2810021H19 product:ribosomal protein S17, full insert sequence. (Fragment), partial (98%) [THC2555910] |

Fig. 5-32

| No. | Probe ID No. | Symbols of genes | Sequence | SEQ ID NO: | Descriptions of genes (letters and numbers within [ ] indicates GenBank accession No.) |
|---|---|---|---|---|---|
| 590 | A_24_P375932 | A_24_P375932 | ATGGTTAAAAATGGAGAGAGCAATGCAGAGACTTAAGGGTTTAGATGTAGATTGCTGGTC | SEQ ID NO: 2171 | |
| 591 | A_24_P379379 | CAPZA1 | ACCAGTTTCAGCCTAAAAACTTCTGGAATGGTCGTTGGAGAATCACAGTGGAAGTTCAGGA | SEQ ID NO: 2172 | Homo sapiens capping protein (actin filament) muscle Z-line, alpha 1 (CAPZA1), mRNA [NM_006135] |
| 592 | A_24_P381625 | PSMC6 | ATGAAAAGGAGTCAGAAAAGTGGCTGATTCTAAGAAGCGTGGAGTCTAAATTGGAGTACAAA | SEQ ID NO: 2173 | Homo sapiens proteasome (prosome, macropain) 26S subunit, ATPase, 6 (PSMC6), mRNA [NM_002806] |
| 593 | A_24_P383569 | LOC391130 | ATGCTACGTGGTGAAGTGGATTCAGAGGGGGTAAGATAGCAGTAAGAGGTATCTCCATCAAG | SEQ ID NO: 2174 | PREDICTED: Homo sapiens similar to 40S ribosomal protein S17 (LOC391130), mRNA [XR_019503] |
| 594 | A_24_P383939 | RPS3A | TGGTTTACTTAAAAAACGCAAGAATCAGATAGAAGAAGACCTCTTATGCCCAGGAGCAAGG | SEQ ID NO: 2175 | Homo sapiens ribosomal protein S3A (RPS3A), mRNA [NM_001006] |
| 595 | A_24_P384411 | A_24_P384411 | CAAGACAAATCAATAAGGAGTGAAGGTTTGAAGATAATGCTTGACAGGTCGAATCTCTTG | SEQ ID NO: 2176 | |
| 596 | A_24_P384539 | LOC730452 | CAAGAAAAGGCTGGGAACGTTCTATGTACCCACAAGACCCAAATTGGCATTTGTCATCAGGA | SEQ ID NO: 2177 | PREDICTED: Homo sapiens similar to 60S ribosomal protein L7 (LOC730452), mRNA [XM_001125895] |
| 597 | A_24_P387869 | PKN2 | TTGTCCAGAGATCATTTATATTACCTTCCAAATTGTTTATACCCAAGATCCTTGGGAG | SEQ ID NO: 2178 | Homo sapiens protein kinase N2 (PKN2), mRNA [NM_006256] |
| 598 | A_24_P392231 | LOC641784 | CCATCAATATTCACAAGTGGATCATGGAGTGGGCAAGAAGGGTGCCGGTCGGGAACTGA | SEQ ID NO: 2179 | xr55h07.x1 NCI_CGAP_Ov26 Homo sapiens cDNA clone IMAGE:2764093 3' similar to gb:X69181 60S RIBOSOMAL PROTEIN L31 (HUMAN)., mRNA sequence [AW302767] |
| 599 | A_24_P392900 | A_24_P392900 | GTCGTTGTTGTTGGTTTCCGTAAAAACAATGTAACAATGGGAAAACCTTTATGCTC | SEQ ID NO: 2180 | |
| 600 | A_24_P398378 | CCPG1 | TACTTTTGTCGCTGGAACGTTGATCAGTTCATCAATAAGTTTTTGTAAACGGTGT | SEQ ID NO: 2181 | Homo sapiens cell cycle progression 1 (CCPG1), transcript variant 1, mRNA [NM_004748] |
| 601 | A_24_P393811 | TMCO1 | ATGAGACGACCAGAGTGTTGGTTCATTTTGGTGTATATTCGGTACTATGGGATTCG | SEQ ID NO: 2182 | Homo sapiens transmembrane and coiled-coil domains 1 (TMCO1), mRNA [NM_019026] |
| 602 | A_24_P399942 | ATP1IC | TGAGGATGTTACGTACTAAACTGAAAACATTCATTGAGATATGTACTGAGACATACGACAAG | SEQ ID NO: 2183 | Homo sapiens ATPase, Class VI, type IIC (ATP1IC), transcript variant 1, mRNA [NM_173694] |
| 603 | A_24_P40417 | FMR1 | TTGTCAGTTTGTTCTTGAATTTTCATTTACAGTTACTTTCCTTGCATACAAACAAG | SEQ ID NO: 2184 | Homo sapiens fragile X mental retardation 1 (FMR1), mRNA [NM_002024] |
| 604 | A_24_P405022 | PDIK1L | TGGTGGTAAGGATACATTTTGTCATTATGATGAAGTAAGTGTTAAGTGTCAGATAAATAGC | SEQ ID NO: 2185 | Homo sapiens PDLIM1 interacting kinase 1 like (PDIK1L), mRNA [NM_152835] |
| 605 | A_24_P405288 | PPP1CB | GTATTAGGTAAGTCACAAAGGTTTATCTGAGGTGATTTAAATAACTTCCTGATTGGAC | SEQ ID NO: 2186 | Homo sapiens protein phosphatase 1, catalytic subunit, beta isoform (PPP1CB), transcript variant 1, mRNA [NM_002709] |
| 606 | A_24_P405430 | TIA1 | GGATTTCTCTGTGTTAAATCAGAAAAATGATAGTGCCCAATCGTTCTTTATAGGAGG | SEQ ID NO: 2187 | Homo sapiens cDNA FLJ36425 fis, clone THYMU2011482. [AK093744] |
| 607 | A_24_P406034 | SLC35A1 | ATGTAGAGTATTTTGTCCTAGGAGGCATAAGAGCATAAGCCTAGGTCTTTCTTACAGAAGAGCAGAA | SEQ ID NO: 2188 | Homo sapiens solute carrier family 35 (CMP-sialic acid transporter), member A1 (SLC35A1), mRNA [NM_006416] |
| 608 | A_24_P409681 | A_24_P409681 | ACATGAGGCTGTCCTCCCGGCATTGAGATGTTGTTGAAAAGGAACAGATTGTTGATAAAC | SEQ ID NO: 2189 | |

Fig. 5-33

| No. | Probe ID No. | Symbols of genes | Sequence | SEQ ID NO: | Descriptions of genes (letters and numbers within [ ] indicates GenBank accession No.) |
|---|---|---|---|---|---|
| 609 | A_24_P414256 | CCDC72 | TCTTTGGTCGTTGTTCTACCCTAAACTTTGTATCCACCTGAAATTAAGGAACTCATTTGA | SEQ ID NO: 2190 | Homo sapiens HSPC330 mRNA, partial cds. [AF161448] |
| 610 | A_24_P414556 | TTC33 | TACTCAAGATTTGGTATATTGTTGAGTAATGTATGTGTTTTTGTGTAATTTGTGA | SEQ ID NO: 2191 | Homo sapiens tetratricopeptide repeat domain 33 (TTC33), mRNA [NM_012382] |
| 611 | A_24_P414952 | TMEM168 | TTTTGTACTGAGGTCAGAGGATAGGAAAGAAGTATTTGTGTTCTGGTATACATGTAATG | SEQ ID NO: 2192 | Homo sapiens transmembrane protein 168 (TMEM168), mRNA [NM_022484] |
| 612 | A_24_P41551 | LOC641790 | AAGGAGATGGGAAACTCCTGATGTGCGGCATTGATATGAGGCACAACAAAGTAGTGTGGAAA | SEQ ID NO: 2193 | PREDICTED: Homo sapiens similar to ribosomal protein L31 (LOC641790), mRNA [XR_018025] |
| 613 | A_24_P417281 | TXNDC10 | ATGATGAGTGATTCTTGGGAAGATAAATGTTAATGTTCGGAATAGTCAAGCTTGTTTTGC | SEQ ID NO: 2194 | Homo sapiens thioredoxin domain containing 10 (TXNDC10), mRNA [NM_019022] |
| 614 | A_24_P418418 | RPS17 | GATGAACTTGAAAATGCCTGGGGAGACCTGTTTGAATTTTCTGCAGTGCTGTATTATTT | SEQ ID NO: 2195 | Homo sapiens ribosomal protein S17 (RPS17), mRNA [NM_001021] |
| 615 | A_24_P418712 | A_24_P418712 | AGGCTGAACAAAGCTGTGTGGGGCCAAAGAAATAAGGAATATGGATACCATATCTGTGTTA | SEQ ID NO: 2196 | |
| 616 | A_24_P487736 | CXorf23 | TGCATACCTAGTATGTGTGTAAGAGGCAAATGCATGGAATTTTTAAATGAAATTTTAGGCCC | SEQ ID NO: 2197 | Homo sapiens chromosome X open reading frame 23 (CXorf23), mRNA [NM_195279] |
| 617 | A_24_P50437 | BC065737 | TGCAGAATGATGAAGTTGCATTTAGAAAATTCCTGATTAGTGAAGATGTTCAGGGCAAAA | SEQ ID NO: 2198 | Homo sapiens cDNA clone IMAGE:30404477, partial cds. [BC065737] |
| 618 | A_24_P50472 | LOC649839 | TAAAAGTACAAGAAGAGATTGTGCTGGGCTTGAGTGCATTCAGCCCAAGTGCAGATCCAA | SEQ ID NO: 2199 | PREDICTED: Homo sapiens similar to large subunit ribosomal protein L36a (LOC649839), mRNA [XM_001129410] |
| 619 | A_24_P50554 | LOC391855 | TCAAGGTTTAGATGTAGATTTCTCTGGTCATTGAGTATAACCGAGTAAGAAAAGAGGTA | SEQ ID NO: 2200 | PREDICTED: Homo sapiens similar to 60S ribosomal protein L17 (L23) (LOC391855), mRNA [XR_018405] |
| 620 | A_24_P50567 | A_24_P50567 | CCTTGGTAATTTCAAAAGTACCAGAAGCTGAATCCAGATGGCATGGTTGCTCTGGAGCTA | SEQ ID NO: 2201 | |
| 621 | A_24_P538403 | ROCK1 | TTAGAGGTTTGGTTGGACTTTGATAAATTGAGTACAAATCTTTGGACAAAGTACCTGCTAC | SEQ ID NO: 2202 | Homo sapiens Rho-associated, coiled-coil containing protein kinase 1 (ROCK1), mRNA [NM_005406] |
| 622 | A_24_P54178 | TMED5 | GCTCTGATATGCATTGGATGATTGATTAATGTTATGCTGTTCTTTCATGTGAATGTCAAGACA | SEQ ID NO: 2203 | Homo sapiens transmembrane emp24 protein transport domain containing 5 (TMED5), mRNA |
| 623 | A_24_P561223 | THC2697551 | TTATGCCAGTTACATACAAGGATCCTGGCATATTTCAGGGACCCTAAAGTTTATAACAT | SEQ ID NO: 2204 | ALU1_HUMAN (P39188) Alu subfamily J sequence contamination warning sequence, partial (8%) [THC2697551] |
| 624 | A_24_P56240 | CPNE8 | GTATCTAAAACATGAACAGCTACTGTGTGTATATTGATTTTATTGGAGTTGACTGAG | SEQ ID NO: 2205 | Homo sapiens copine VIII (CPNE8), mRNA [NM_153634] |
| 625 | A_24_P56252 | AF086032 | TAGTATTGAGGAGACC | SEQ ID NO: 2206 | Homo sapiens full length insert cDNA clone YW25G09. [AF086032] |
| 626 | A_24_P57837 | THC2567891 | AGAAATCCGGAAGAGCCTGTTATGCTCAGTACCAGCCAAATGCGGAAGAAGATGATGGAAA | SEQ ID NO: 2207 | Q6NXR8_HUMAN (Q6NXR8) Ribosomal protein S3a, partial (91%) [THC2567891] |
| 627 | A_24_P587938 | A_24_P587938 | GTTCAAAGAAGCAAAAGGTAATGGAGATGGCGCAACAGGAGGAGGAATGATTGCTTTAGATTAACGATCTTAT | SEQ ID NO: 2208 | |
| 628 | A_24_P606663 | LOC392030 | TGTGGGGTTGCCCAGAAACCTAATGCGGGTGAAGATTGAGGAAATAAGGTCCATAGTTT | SEQ ID NO: 2209 | PREDICTED: Homo sapiens hypothetical LOC392030 (LOC392030), mRNA [XR_018063] |

Fig. 5-34

| No | Probe ID No. | Symbols of genes | Sequence | SEQ ID NO. | Descriptions of genes (letters and numbers shown [] indicates GenBank accession No.) |
|---|---|---|---|---|---|
| 629 | A_24_P62530 | RHOU | GGCTGAAGTACAAGTGTAGGCCAGGATTATTATAAATAGA GGATACTCAAAACTG | SEQ ID NO: 2210 | Homo sapiens ras homolog gene family, member U (RHOU), mRNA [NM_021205] |
| 630 | A_24_P62860 | STAM2 | GTCTATATGGTAGTTGATGTACATTTAAGTGGAAAAATTAGCAG TATTGAAAGGTCAGT | SEQ ID NO: 2211 | Homo sapiens signal transducing adaptor molecule (SH3 domain and ITAM motif) 2 (STAM2), mRNA [NM_005843] |
| 631 | A_24_P630039 | AL049321 | AAGACATGAGACAATACAAAATTACATTTTTGGAGGATATAAAAC TGCAAGAAGAGAGGG | SEQ ID NO: 2212 | Homo sapiens mRNA; cDNA DKFZp564D156 (from clone DKFZp564D156). [AL049321] |
| 632 | A_24_P63347 | PF4V1 | CTAGATATTTACGTTGAAGTTAGAATTAGAGTTGGAATAAATA TAGTAGGCTTAAGC | SEQ ID NO: 2213 | Homo sapiens platelet factor 4 variant 1 (PF4V1), mRNA [NM_002620] |
| 633 | A_24_P652786 | THC2533996 | TGCTTGTTCGTATGTCAGCCCGAAGATGATATCGTTGAGGAAT GACATTGAGGTTGTTT | SEQ ID NO: 2214 | HSU09954 ribosomal protein L9 [Homo sapiens] (exp=-1; wgp=0; cg=0) partial (42%) [THC2533996] |
| 634 | A_24_P67100 | LOC646949 | AGTCATACCGCAGAAAAGATGGCGTGTTTCTTATTTGAAGAT AATGCAGAGGGTCAGAG | SEQ ID NO: 2215 | PREDICTED: Homo sapiens similar to ribosomal protein L23 (LOC646949), mRNA [XR_017294] |
| 635 | A_24_P675947 | ENST00000389400 | GTTCATGCGAAGGTAGGAGTTCTGGAAAAAGGTAGTGGAGAAGA GACAGGTTCTAAAGTT | SEQ ID NO: 2216 | similar to 40S ribosomal protein S3a (V-fos transformation effector protein) (LOC391706), mRNA [Source:RefSeq_dna;Acc:XR_017186] [ENST00000389400] |
| 636 | A_24_P685729 | A_24_P685729 | TTGAAGGCTATGTATGTGAAGACTATCAGTCGATTATTTGCTT TGTCTGTTTGTGTGG | SEQ ID NO: 2217 | |
| 637 | A_24_P6975 | LOC342894 | GGAAGACTTCGGAGGGGTTCGTGCTGGTGTAAGACCTAAAGTTGTTAT GAAATGTCAAAAAGA | SEQ ID NO: 2218 | PREDICTED: Homo sapiens similar to ribosomal protein L34 (LOC342894), mRNA [XM_933484] |
| 638 | A_24_P703614 | A_24_P703614 | AAAGAACATTACCCGAATTAACTCACAGGTGTGCACTGTAAGTCATCAGTAG CAGCTTTGTGTGTGTG | SEQ ID NO: 2219 | |
| 639 | A_24_P7181 | A_24_P7181 | TCATGGTGGGATTAACTCACAGGTGATCTCTCCTGGCACATGA AAATGATCTTTAGTGA | SEQ ID NO: 2220 | |
| 640 | A_24_P71936 | SMAD1 | TGTATTCAGTTATGCTCTCGTACATTGAGTACTTTATTGAAA ACTAGTGGGTTTTCTC | SEQ ID NO: 2221 | Homo sapiens SMAD family member 1 (SMAD1), transcript variant 1, mRNA [NM_005900] |
| 641 | A_24_P75156 | PTAR1 | GGATTAGATTTGTTCTTATGTGACCATGTAGGAGCCAGCTATA AAGTATTGATTTCTG | SEQ ID NO: 2222 | Homo sapiens mRNA; cDNA DKFZp313P0917 (from clone DKFZp313P0917). [AL832683] |
| 642 | A_24_P755505 | A_24_P755505 | ATACAAGAAGGCTCTTATGCTCAGGACGACAACAAGAAAAGTAAAAA TGGTGAAGAAGGCCCAA | SEQ ID NO: 2223 | |
| 643 | A_24_P76169 | ENST00000331366 | TTCCTAAAATTCAGTGGACTTTCTGTAAGAAGTGTGGCAAGCAT CAAGCCCGACAAAGTGA | SEQ ID NO: 2224 | PREDICTED: Homo sapiens similar to large subunit ribosomal protein L36a (LOC728202), mRNA [XM_001129191] |
| 644 | A_24_P76356 | LOC643981 | TTAGTGAAGATGTCAGGGAGAAAAACTGGCAACTTCGGGCATG GATCTTATTCGTGACA | SEQ ID NO: 2225 | PREDICTED: Homo sapiens similar to 40S ribosomal protein S3a (V-fos transformation effector protein) (LOC643981), mRNA [XR_018444] |
| 645 | A_24_P77681 | PAIP1 | AGCTGATCCAGATTACCAAGAAGAAATACCAAGAATTACTTGAAA GAGAGGAGTTTTTCC | SEQ ID NO: 2226 | Homo sapiens poly(A) binding protein interacting protein 1 (PAIP1), transcript variant 1, mRNA [NM_006451] |
| 646 | A_24_P792734 | PSMC6 | AGAAAGGTTAACGGAGTTAGTGAATCAAATGGATTTGATAC TCTGGATAGAGTTAAA | SEQ ID NO: 2227 | Homo sapiens proteasome (prosome, macropain) 26S subunit, ATPase, 6 (PSMC6), mRNA [NM_002806] |

Fig. 5-35

| No. | Probe ID No. | Symbols of genes | Sequence | SEQ ID NO. | Descriptions of genes (letters and numbers within [ ] indicates GenBank accession No.) |
|---|---|---|---|---|---|
| 647 | A_24_P813147 | TUBB8 | TAGCTAAGCGGTGGCTGCCATTTCAGGGGGTCGGCATGCCCATGAGGGAGGTGGGATGAACAA | SEQ ID NO: 2228 | Homo sapiens tubulin, beta 8 (TUBB8), mRNA [NM_177987] |
| 648 | A_24_P81965 | RAP2A | TTCTTTGATGTTGGAACTTTGGGTCTTTAAACTGTGATAGTGATGGTAAGTGATGC | SEQ ID NO: 2229 | Homo sapiens RAP2A, member of RAS oncogene family (RAP2A), mRNA [NM_021033] |
| 649 | A_24_P830667 | RPL21 | CTGTTCGTTTGGGCACGTATATGGGAATCTATAAGAAAGGTGATATTGTAGACATCAAGG | SEQ ID NO: 2230 | Homo sapiens ribosomal protein L21 (RPL21), mRNA [NM_000982] |
| 650 | A_24_P83968 | LOC730887 | AGAAAGCCCAGCAGAAACAACGTGGAACACAGAGAAGAAAGTTTTTCTGGTCTCTCTAAGAAGC | SEQ ID NO: 2231 | PREDICTED: Homo sapiens similar to 40S ribosomal protein S7 (S8) (LOC730887), mRNA [XR_015607] |
| 651 | A_24_P84408 | A_24_P84408 | AAGCTAGATGAGGCAGTGGTCATTGACAAGTGATACCAGAGAAAAGATGGCGTGTTCTT | SEQ ID NO: 2232 |  |
| 652 | A_24_P84808 | LOC729449 | GAATTGCTTGAGAGATAAGGCTTTGGGATCTCTTGGAAAATATGGCATGCATCTGTATGG | SEQ ID NO: 2233 | PREDICTED: Homo sapiens similar to 60S ribosomal protein L7 (LOC729449), mRNA [XR_015548] |
| 653 | A_24_P867291 | AK022997 | CTGACAGTGTGATAAATATTTCAGTGACTTTCAGATTTATTCTGTTAGCCGCGTGTGTC | SEQ ID NO: 2234 | Homo sapiens cDNA FLJ12935 fis, clone NT2RP2004982. [AK022997] |
| 654 | A_24_P879895 | BC043357 | AGATACCTTCAGCTGCAGAAGTCAGTTTATGACACGTTGAATAAAAACAAAAGTGGAG | SEQ ID NO: 2235 | Homo sapiens, clone IMAGE:3833659, mRNA [BC043357] |
| 655 | A_24_P886040 | DCP2 | CATTTGGAACAGGTTTCATTCTGTTTGTAGATTTATGTGTGTAGTTGAACAGGCAAGTG | SEQ ID NO: 2236 | PREDICTED: Homo sapiens DCP2 decapping enzyme homolog (S. cerevisiae) (DCP2), mRNA [NM_152624] |
| 656 | A_24_P886536 | CR627148 | AATTGGCTTCTTGTAACGCTAAGTATGGTGAAGGAGAATACCAGAATTGGCTCTCAAAAGTCTTC | SEQ ID NO: 2237 | Homo sapiens mRNA; cDNA DKFZp779F2127 (from clone DKFZp779F2127). [CR627148] |
| 657 | A_24_P915806 | HNMT | GGACAAGAAGGCTGGCAGGCATAATAACAAGAAGATACCAGAATTGGCTGTTAACAAATAAATA | SEQ ID NO: 2238 | Homo sapiens histamine N-methyltransferase (HNMT), transcript variant 2, mRNA [NM_001024074] |
| 658 | A_24_P91952 | DYNLT3 | ATACATATAGAGAGCGGAAGCATAACTCATTGAATTTTGGAGAGGAATAAGCTTAGCGTT | SEQ ID NO: 2239 | Homo sapiens dynein, light chain, Tctex-type 3 (DYNLT3), mRNA [NM_006520] |
| 659 | A_24_P91916 | NXT2 | AAGCTAGTGCTTCTTGTGTAGTACTGATTGAAAGTTAGACGTTTTATTCTACTCATAGTGAGC | SEQ ID NO: 2240 | Homo sapiens nuclear transport factor 2-like export factor 2 (NXT2), mRNA [NM_018698] |
| 660 | A_24_P925505 | CD36 | CGTACGCGTTACTACGACAGAGTTGGTCTGTTTATCCTGTAAGTACCAAAATATGAATGCC | SEQ ID NO: 2241 | CD36-collagen type I/thrombospondin receptor (gene exon) [human; Partial, 369 nt], [S67044] |
| 661 | A_24_P931282 | THC2726401 | GGGAAATATTTCTCGTCTAAATGCATGAAATCATGTTAAGGTAATCTACTGGAGATTACAC | SEQ ID NO: 2242 | Q26195_PLAVI (Q26195) Pval protein, partial (14%) [THC2726401] |
| 662 | A_24_P935986 | BCAT1 | ATGCTCTGAAGTTTGAAGAAGCACAATTAAACATCAAAATGGGTTTGTTAGAGGAGA | SEQ ID NO: 2243 | Homo sapiens branched chain aminotransferase 1, cytosolic (BCAT1), mRNA [NM_005504] |
| 663 | A_24_P937095 | SLC30A1 | TTTGATGTAGCTCACCGATACTATGTGGTAATGCTATTTGTTTACTAACAAGGTCTG | SEQ ID NO: 2244 | Zinc transporter 1 (Znt-1) (Solute carrier family 30 member 1). [Source:Uniprot/SWISSPROT;Acc:Q9Y6M5] [ENST00000367000] |
| 664 | A_24_P940426 | QKI | AAGCTGTTGAATGAGTCTTAAAAATTATAGTACTACTGTTAAGTGGACCAAGTTGGTGAAGC | SEQ ID NO: 2245 | Homo sapiens quaking homolog, KH domain RNA binding (mouse) (QKI), transcript variant 4, mRNA [NM_206855] |
| 665 | A_24_P940776 | BDP1 | TCGGAGCGGAAAATGTCTATAAGGTAGGCATTTATTCATGATTGATATGTCAGAGAAATC | SEQ ID NO: 2246 | Homo sapiens B double prime 1, subunit of RNA polymerase III transcription initiation factor IIIB (BDP1), mRNA [NM_018429] |

Fig. 5-36

| No | Probe ID No | Symbols of genes | Sequence | SEQ ID NO. | Descriptions of genes (letters and numbers within [ ] indicates GenBank accession No.) |
|---|---|---|---|---|---|
| 666 | A_24_P941643 | PLCB1 | ATGATGTGCAGTTTGTGCCTTTATGTATTGCCTTGTTGTTTG TGGAATGTGTGAAATT | SEQ ID NO: 2247 | Homo sapiens phospholipase C, beta 1 (phosphoinositide-specific) (PLCB1), transcript variant 2, mRNA [NM_182734] |
| 667 | A_24_P941699 | PCGF5 | TGGTATATTCAACTACAGAGTTTCTAAGGATAGGAGTACTTTCAT GTGTAGTAATACACTG | SEQ ID NO: 2248 | Homo sapiens polycomb group ring finger 5 (PCGF5), mRNA [NM_032373] |
| 668 | A_24_P98210 | TFEC | ACATGGGCTTACAAGTGCTTCTGTCCAAGTAGTCTACGAATG AAAAGAGAAATAGAG | SEQ ID NO: 2249 | Homo sapiens transcription factor EC (TFEC), transcript variant 1, mRNA [NM_012252] |
| 669 | A_24_P99046 | STK38L | GCTATCTGTCTTTTGCTGATCTACAAATAAATGAATTGAGAATT TAGTCCATAGAAGTCGC | SEQ ID NO: 2250 | Homo sapiens serine/threonine kinase 38 like (STK38L), mRNA [NM_015000] |
| 670 | A_24_P10100 | A_32_P10100 | TATGAGGAAATAGTATCATCATGTTAGAAGGCTTGGAATGAGTA TAAATAATGGGTGGTC | SEQ ID NO: 2251 | |
| 671 | A_24_P105397 | THC2642694 | TAAAATGCTACTACAGTATTCTACGATGCAGGGTGAATGTATAT TACAAGTAATTGTGTGG | SEQ ID NO: 2252 | Q6IDT1_HUMAN (Q6IDT1) Protein transactivated by hepatitis B virus X antigen, partial (11%) [THC2642694] |
| 672 | A_32_P106732 | FANCM | AATCAAGCTGCTCAAGACATGGGGTTTTCAAAGACCTCTGACAATA TTAAATGGAGTTGAAT | SEQ ID NO: 2253 | Homo sapiens Fanconi anemia, complementation group M (FANCM), mRNA [NM_020937] |
| 673 | A_32_P107372 | GBP1 | GGTACTGAGACAGAGTCTTAGGTAAAAGTCTGGAAATATTTGG GCATTGGTGTGGGAA | SEQ ID NO: 2254 | Homo sapiens guanylate binding protein 1, interferon-inducible, 67kDa (GBP1), mRNA [NM_002053] |
| 674 | A_32_P107717 | BX100535 | TCTTGTGGACCCAAGAGTCTGCTCTCTGTTGTAAAATCCTGTTCAG ACCTGGTCTAATTGGT | SEQ ID NO: 2255 | BX100535 Soares_testis_NHT Homo sapiens cDNA clone IMAGp998I094457, mRNA sequence [BX100535] |
| 675 | A_32_P109495 | THC2618720 | AAAGATATATCAGGCAACCACTGCGAAGTGGTCACCATGAATTTT GGTTGTTGATAAGAA | SEQ ID NO: 2256 | |
| 676 | A_32_P109653 | THC2660092 | TTGGTTTGGTATTCCAAGTGGGGTCTTTTGAGAATGTGTGGA GTAGGTGAAGAATGGAA | SEQ ID NO: 2257 | |
| 677 | A_32_P113154 | LOC730861 | ACCACCAGTCCAAGAATCTGTTTAAAGTTCAGAGCTTAAAAGAGT AAGAAAATAAAAAGTCG | SEQ ID NO: 2259 | PREDICTED: Homo sapiens similar to 40S ribosomal protein S3a (V-fos transformation effector protein) (LOC730861), mRNA [XR_015591] |
| 678 | A_32_P113584 | ZNF292 | GGGGCTTTTGGGTTTTATTGAATAGTTCATTCACCTGTTTAAG ACTTACACAAATAAG | SEQ ID NO: 2259 | Zinc finger protein 292. [Source:Uniprot/SWISSPROT;Acc:060281] [ENST00000339907] |
| 679 | A_32_P113742 | RPL21 | ATGTTGTCTAGGCGTTTGTTTTAGAAAACATGGAGGAATGGGTACTGT TCAAAAAGGAATGCCC | SEQ ID NO: 2260 | Homo sapiens ribosomal protein L21, mRNA (cDNA clone IMAGE:6605832), complete cds. [BC104473] |
| 680 | A_32_P114215 | COMMD6 | AATTGGTATGATTCATTGTAAGTCATGGACTTCAGCTTTGGGCAACAA AAGTAAATAAGGATGG | SEQ ID NO: 2261 | Homo sapiens COMM domain containing 6 (COMMD6), transcript variant 2, mRNA [NM_203495] |
| 681 | A_32_P1144 | AK091357 | GGACTTTAATATTTTACATCTTACTGGCCATGCATAGGTTTTA AGTGCTTTTAATGGGG | SEQ ID NO: 2262 | Homo sapiens cDNA FLJ34038 fis, clone FCBBF2005645. [AK091357] |
| 682 | A_32_P11451 | NMD3 | CAGTTTAGGGCAGTAGCCTGCTTTTGTCATAAATGTTGGTAGC AGATAAAAATGTGC | SEQ ID NO: 2263 | Homo sapiens NMD3 homolog (S. cerevisiae) (NMD3), mRNA [NM_015938] |
| 683 | A_32_P115505 | ZNF294 | TGGTGCAGAGGATTATAGTTGAGAGTGAAGTAGTATGTGTGAG TTATAGATGTGTCGAA | SEQ ID NO: 2264 | Homo sapiens zinc finger protein 294 (ZNF294), mRNA [NM_015565] |

Fig. 5-37

| No. | Probe ID No. | Symbols of genes | Sequence | SEQ ID NO: | Descriptions of genes (letters and numbers within [ ] indicates GenBank accession No.) |
|---|---|---|---|---|---|
| 684 | A_32_P11931 | LOC441073 | GTGTGATCCATGGCATCCGAAAGGATGATGAAGTTCAGGTTGTAGGTGGAACACTATAAA | SEQ ID NO: 2265 | PREDICTED: Homo sapiens similar to 60S ribosomal protein L26 (Silica-induced gene 20 protein) (SIG-20) (LOC441073), mRNA [XR_016376] |
| 685 | A_32_P125549 | RPL31P4 | TCTAGAGACAGTCAATGGATGGAGAGAACTAATCCCTGATCGTCAGATACATCAAATAAAG | SEQ ID NO: 2266 | PREDICTED: Homo sapiens ribosomal protein L31 pseudogene 4 (RPL31P4), mRNA [XR_018222] |
| 686 | A_32_P125917 | THC2753798 | GCTTATAAAGTGTAAGTGGAGACGCTAAATTGTGAGTACAAAGTTTCTTTTCACAACAG | SEQ ID NO: 2267 | BF233843 601904455F1 NIH_MGC_54 Homo sapiens cDNA clone IMAGE:4132429 5', mRNA sequence [BF238843] |
| 687 | A_32_P128781 | A_32_P128781 | CATATATTGCATGGGGGTACCCGAATCTGAAGTCAGTAAATGAACTAATCTACAAGAGTG | SEQ ID NO: 2268 | |
| 688 | A_32_P135818 | RPS3A | GTTGGTTGATCTGTTCTGTGTTGGTTTTAATAAAAAAGGCAAACAATCAGATATGGAAGAC | SEQ ID NO: 2269 | Homo sapiens ribosomal protein S3A (RPS3A), mRNA [NM_001006] |
| 689 | A_32_P136319 | RPL36A | AAGTGATCCAGTTCTAAGTGTCATCTTTTATCATGAAGACAATAAAATCTTGAGTTTATG | SEQ ID NO: 2270 | Homo sapiens ribosomal protein L36a (RPL36A), mRNA [NM_021029] |
| 690 | A_32_P137266 | KIAA1799 | AAGTGGGACCGAAATCTACAATGGTTGTGAAGATGTAATGCCTTTGAATGAACGACAAG | SEQ ID NO: 2271 | Homo sapiens KIAA1799 protein (KIAA1799), mRNA [NM_032437] |
| 691 | A_32_P143323 | CR613287 | AGAGAGGCTCAAACAACAATGGGGTTTATGCCAGTTACATAGAAGGATCCTGGCATATTTCAGGG | SEQ ID NO: 2272 | full-length cDNA clone CS0DL011YP14 of B cells (Ramos cell line) Cot 25-normalized of Homo sapiens (human) [CR613287] |
| 692 | A_32_P145153 | RPL31 | ATCCGGTGTGCAGCTGTACATAGAAGGTGTAATGAGGATGAAGAATTCACCAAATAAGCCATAT | SEQ ID NO: 2273 | Homo sapiens ribosomal protein L31 (RPL31), mRNA [NM_000993] |
| 693 | A_32_P145159 | A_32_P145159 | CATACATTGGGCGTGTACATAAATTGTGGAAAACTTAGTTGTGTGATTATTCTCTTTG | SEQ ID NO: 2274 | |
| 694 | A_32_P145477 | BX350256 | TGGCAACCATCCTAAGAAGAACGGAAAACCCAAGGAACAGATGTCTACATAGGAGTGTA | SEQ ID NO: 2275 | BX350256 BX350256 Homo sapiens PLACENTA COT 25-NORMALIZED Homo sapiens cDNA clone CS0DI081YM18 3-PRIME mRNA sequence [BX350256] |
| 695 | A_32_P147747 | THC2575761 | TTGATACGTCTGATTCTGATGAGAACGGCAAATTGGGTTCTGCAGGTACATAGAAGTTG | SEQ ID NO: 2276 | HUMRPL7Y ribosomal protein L7 [Homo sapiens] (exp=-1; wgp=0; cg=0), partial (40%) [THC2575761] |
| 696 | A_32_P148824 | C1orf27 | GAAAAACAGATGTTATCCTGAGGACAAATTCAGTAAAGAGACTACAAAGGATGATGTTC | SEQ ID NO: 2277 | Homo sapiens chromosome 1 open reading frame 27 (C1orf27), mRNA [NM_017847] |
| 697 | A_32_P1516 | AA714537 | CTGAGCATAAGAGGTCTTCCGTATCTGATTTTTCGGTTTTTTAGTAAAACGAACACAGAA | SEQ ID NO: 2278 | nw20g12.s1 NCI_CGAP_GC80 Homo sapiens cDNA clone IMAGE:1241062 3' similar to gb:M84711 40S RIBOSOMAL PROTEIN S3A (HUMAN);, mRNA sequence [AA714537] |
| 698 | A_32_P153725 | KIAA1033 | TTTTGTAAAAGATGGGAAGTTGTTACCTGACTGAGTGGGGTTTTCCTTTTCCCCAAT | SEQ ID NO: 2279 | Homo sapiens KIAA1033 (KIAA1033), mRNA [NM_015275] |
| 699 | A_32_P153364 | RPL7 | TCAACAGGCTTATAGAAAATGAACCAAGGTGTCACTGATGATTATTTCTAAGGTGG | SEQ ID NO: 2280 | Homo sapiens ribosomal protein L7 (RPL7), mRNA [NM_000971] |
| 700 | A_32_P155811 | CD2AP | AAAGGATGGTTGCTGCTGTCAAAAAGAAAATTAAAGGATTTTATTGCCAGTCGTGTCAGTG | SEQ ID NO: 2281 | Homo sapiens CD2-associated protein (CD2AP), mRNA [NM_012120] |
| 701 | A_32_P158746 | RPL17 | TTTTGCTGCAGATGCTAAAAATGCAGAGAGTAAGGTGAAGTTAAGGGTTTAGATGTAG | SEQ ID NO: 2282 | Homo sapiens ribosomal protein L17 (RPL17), transcript variant 1, mRNA [NM_000985] |
| 702 | A_32_P158966 | KLRF1 | TAGGTGATAGTATAAAACCAATGTGACTTGATCATGTGATCATATCCAGGATTTTATTCGTCG | SEQ ID NO: 2283 | Homo sapiens killer cell lectin-like receptor subfamily F, member 1 (KLRF1), mRNA [NM_016523] |

Fig. 5-38

| No | Probe ID No. | Symbols of genes | Sequence | SEQ ID NO. | Descriptions of genes (letters and numbers within [ ] indicates GenBank accession No.) |
|---|---|---|---|---|---|
| 703 | A_32_P158651 | PCAF | GAGTGGTGTCTAGATTTCTATGAAGAATGATACAGTTTGGATTAAGTATCTTGAAC | SEQ ID NO: 2284 | Homo sapiens p300/CBP-associated factor (PCAF), mRNA [NM_003884] |
| 704 | A_32_P162250 | ARHGAP18 | AAGTCCTGAATAAGTCACTGGAGAATTATTCTTCTGGGTGAAAAAGCTTTTGTTGTG | SEQ ID NO: 2285 | Homo sapiens Rho GTPase activating protein 18 (ARHGAP18), mRNA [NM_033515] |
| 705 | A_32_P164203 | THC2683446 | TTGATGGTCATTGTAGGAGGTATTGTATGGATTAGTGTGGAGTGCTGTTTACCACATCAT | SEQ ID NO: 2286 | Q7WZG3_PASPI (Q7WZG3) Ferric uptake regulator, partial (8%) [THC2683446] |
| 706 | A_32_P165340 | SRP9 | ACATTGAAATATGTTTTGTATAAATTTGTCATGTTGAACAAGAATTAGCATGGTAAGTT | SEQ ID NO: 2287 | Homo sapiens signal recognition particle 9kDa (SRP9), mRNA [NM_003133] |
| 707 | A_32_P167122 | RCOR3 | GTATCTGAGGGATGCTGCTGTAATCTGATTTACAATGGATTAGAGCACACAGTAGAAAAAGT | SEQ ID NO: 2288 | Homo sapiens REST corepressor 3 (RCOR3), mRNA [NM_018254] |
| 708 | A_32_P170444 | SUB1 | TAGGTATGCTGCCTGAAATTCTTGCAGTTCATTTTTATGGGAGTTAATCGAGTGAAAAG | SEQ ID NO: 2289 | Activated RNA polymerase II transcriptional coactivator p15 (SUB1 homolog) (Positive cofactor 4) (PC4) (p14). [Source:Uniprot/SWISSPROT;Acc:P53999] [ENST00000265073] |
| 709 | A_32_P170736 | AK098422 | ACGTCATAATTGTTGAGGGCAAGGTTCATTGTTGATAGTGCAAAGTGTCGCTGTTGTGCAT | SEQ ID NO: 2290 | Homo sapiens cDNA FLJ25556 fis, clone JTH02629. [AK098422] |
| 710 | A_32_P171163 | ENST00000366149 | TCCTTAGTGAGTTTTAAATCTCAGGCTAGATTTATTTGTTTTCTGTGTGTGTATCAG | SEQ ID NO: 2291 | Rho GTPase-activating protein 18 (MacGAP) [Source:Uniprot/SWISSPROT;Acc:Q8N392] [ENST00000361149] |
| 711 | A_32_P173385 | ENST00000334683 | AAATGCAGAGAGTGATGCTGAACTTAAGGGTTCAGATAGATTCTCTGGTCATTGACCA | SEQ ID NO: 2292 | PREDICTED: Homo sapiens similar to 60S ribosomal protein L17 (L23) (LOC650848), mRNA [XR_019013] |
| 712 | A_32_P17504 | THC2696682 | ATGCTATGCGTTTCACTATGCTGAAATATTCCAGGCTTTTCCCCTTGATGCCAAA | SEQ ID NO: 2293 | |
| 713 | A_32_P178819 | CMAH | GATTATATAGTAGGTCGATTCTGAAGATACAACAGAATTGAATGGTGGAATTTGTCTCC | SEQ ID NO: 2294 | Homo sapiens cytidine monophosphate-N-acetylneuraminic acid hydroxylase (CMP-N-acetylneuraminate monooxygenase) (CMAH) on chromosome 6 [NR_002174] |
| 714 | A_32_P177685 | THC2632286 | TTTGACTGAGATTTGTAGAGTCTTAATGACTGAAATGAATTTGGAGGCACTGACAAAG | SEQ ID NO: 2295 | AA665072 nu76b01.s1 NCI_CGAP_Alv1 Homo sapiens cDNA clone IMAGE:1216585, mRNA sequence [THC2632286] |
| 715 | A_32_P178945 | YOD1 | TTGCCAGGATTTTTGAAGTAATAGACTGCTGTACCTGGAAGATGTCTAACTTCATTTT | SEQ ID NO: 2296 | Homo sapiens YOD1 OTU deubiquinating enzyme 1 homolog (S. cerevisiae) (YOD1), mRNA [NM_018566] |
| 716 | A_32_P178966 | ENST00000379426 | GTAATATACAAGGGTGAACTCTTTACTGATACACAAGAGAAGTGTTAAAAAGTGAATCC | SEQ ID NO: 2297 | Novel protein. [Source:Uniprot/SPTREMBL;Acc:Q5T4T1] [ENST00000379426] |
| 717 | A_32_P180435 | WBSCR19 | CTTTCAACTGTTGTATGTATTATTACACGTGCTGCTGAAGGGAGCATGTTTTATCTATG | SEQ ID NO: 2298 | Homo sapiens Williams Beuren syndrome chromosome region 19 (WBSCR19), mRNA [NM_175064] |
| 718 | A_32_P186961 | RPL17 | CATTGAGATGATGCTTACGGGAAAAGGAACAGATTGTTGAAACCAGAAGAAGGAAGGTTGC | SEQ ID NO: 2299 | Homo sapiens ribosomal protein L17 (RPL17), transcript variant 1, mRNA [NM_000985] |
| 719 | A_32_P190468 | hCG_26523 | CCCAGACAAGGTGCTTATCACTAGGGTAAAAGTGGACAAGACCGCAAAAAGATGGTGAA | SEQ ID NO: 2300 | PREDICTED: Homo sapiens similar to 60S ribosomal protein L26 (LOC646161), mRNA [XR_018048] |

Fig. 5-39

| No. | Probe ID No. | Symbols of genes | Sequence | SEQ ID NO: | Descriptions of genes (letters and numbers within [ ] indicates GenBank accession No.) |
|---|---|---|---|---|---|
| 720 | A_32_P192480 | ENST00000370857 | TAGTCCTGTGTAGTGCTTGTTGTTTATGTTTAAAAGTGGACATTATGCAGCTCATTTTAGTAGTGC | SEQ ID NO: 2301 | Muscleblind-like X-linked protein (Muscleblind-like protein 3) (Cys3His CCG1-required protein) (Protein HCHCR). [Source:Uniprot/SWISSPROT;Acc:Q9NUK0] [ENST00000370857] |
| 721 | A_32_P193322 | RICTOR | ACCACATGAGTTGTTCTTCTTTTTTATTTAGTAATACGGTGCTACAATATTTGGAGGTTCTGG | SEQ ID NO: 2302 | Homo sapiens rapamycin-insensitive companion of mTOR (RICTOR), mRNA [NM_152756] |
| 722 | A_32_P194821 | RPL21 | GAAGACAAAGAAGAAAAGAAGAGGGAGAGCCGGATATATGTCTTTAGGCCTTTTAGAAAACA | SEQ ID NO: 2303 | Homo sapiens ribosomal protein L21 (RPL21), mRNA [NM_000982] |
| 723 | A_32_P195387 | DKFZP779L1068 | ATATAACGTTGGAATTCTATTCTAATTATGTTGTTCTGGCTGCTTGTAGTATCAGTTCGC | SEQ ID NO: 2304 | Homo sapiens cDNA clone IMAGE:5555490. [BC110326] |
| 724 | A_32_P196047 | DPY19L4 | ATATTAAGATAGTTGCAGGCAGTGTACCTCAGGTTGACTGTGTACATCTGAATAGTGAGT | SEQ ID NO: 2305 | Homo sapiens dpy-19-like 4 (C. elegans) (DPY19L4), mRNA [NM_181787] |
| 725 | A_32_P196463 | RPS3A | GGGGCCAAGAAGAAAGTGGTTGATCCATTTTCTAAGAAAGATTGGTATGATGTGAAAGCA | SEQ ID NO: 2306 | Homo sapiens ribosomal protein S3A (RPS3A), mRNA [NM_001006] |
| 726 | A_32_P19752 | FAM76B | TTGTGCTTTTAGCATGTGTTTTCCAGCATTAATTAGCATTTGTGCAGGTGTGAAAGCA | SEQ ID NO: 2307 | Homo sapiens family with sequence similarity 76, member B (FAM76B), mRNA [NM_144664] |
| 727 | A_32_P20240 | SP3 | CTTAGGCTCTTAATTGTAGTTTAAATTCGACTAGTAGTGCGTAGTCAGAACCAAAGTTTTGT | SEQ ID NO: 2308 | Homo sapiens mRNA; cDNA DKFZp686N17231 (from clone DKFZp686N17231). [BX648857] |
| 728 | A_32_P202488 | RPL21 | AAGAGGAGAGGCACCGAGTATATGTTGTAGGCCTTTTAGAAAACATGGAATGGGTAC | SEQ ID NO: 2309 | Homo sapiens ribosomal protein L21, mRNA (cDNA clone IMAGE:5269982), complete cds. [BC041849] |
| 729 | A_32_P203154 | RPL21 | CTTTGGCCAGGTGTATGTGAATCTATAAGAAAGGTGATATTGTAGAGATCAAGGGAATGG | SEQ ID NO: 2310 | Homo sapiens ribosomal protein L21 (RPL21), mRNA [NM_000982] |
| 730 | A_32_P203320 | ROCK1 | AAAGGCATCACTACTGAAGATCAGATCAGCTCATGGAAGGAGTAAAGAAAATATCTGAAAATGAG | SEQ ID NO: 2311 | Homo sapiens Rho-associated, coiled-coil containing protein kinase 1, mRNA (cDNA clone IMAGE:5269982), complete cds. [BC041849] |
| 731 | A_32_P20367 | RPS7 | ATCCTTCGAGGGCTGGTCTTCAGAAGGAAAATTGTGGGCAAGAGAATCCGGCGTGAAAGTA | SEQ ID NO: 2312 | Homo sapiens ribosomal protein S7 (RPS7), mRNA [NM_001011] |
| 732 | A_32_P204330 | AK093982 | AAACCCTGAGGTTTTTGGTCGTCGTAGAAGGTCAGCAAATTGGCAAGGTAAACCTACGGCAGAATTG | SEQ ID NO: 2313 | Homo sapiens cDNA FLJ36663 fis, clone UTERU2002826. [AK093982] |
| 733 | A_32_P205550 | RPL26L1 | AGGTAGTTCGAGGACGACTACAAAGGTCAGACAATTGGCAAGGTAATCCAGGTGTACAGAA | SEQ ID NO: 2314 | Homo sapiens ribosomal protein L26-like 1 (RPL26L1), mRNA [NM_016093] |
| 734 | A_32_P205553 | RPL26L1 | TTCGGAATGTCGGAACATTCATTCCTGTTGTTGTTACCTGTGGCTCTGTAAATCTAGT | SEQ ID NO: 2315 | Homo sapiens ribosomal protein L26-like 1 (RPL26L1), mRNA [NM_016093] |
| 735 | A_32_P207231 | AI630435 | TTCGTTCGCTTTTTCTTAAGGGTTCTTGAAACAGGACGGAACCTCCTTCTCTCTCTCT | SEQ ID NO: 2316 | AI630435_ad10b05.y1 Hambase: Erythroid Progenitor Cells (LCB-ad library) Homo sapiens cDNA clone ad10b05 random, mRNA sequence [AI630435] |
| 736 | A_32_P208178 | RPS3A | GGAAAAGACGTAGAAAAAGCTTGCAATCTATTTATCCTCTCGATGATGCTCTGTTTAGA | SEQ ID NO: 2317 | Homo sapiens ribosomal protein S3A (RPS3A), mRNA [NM_001006] |
| 737 | A_32_P21384 | RPL17 | AGATGTCACTTTAGGAGAAAGCAGAGTGTGATACCATTCCGACATTAGAACGGTGGAATGGCAG | SEQ ID NO: 2318 | Homo sapiens ribosomal protein L17 transcript variant 1, mRNA [NM_000985] |
| 738 | A_32_P219031 | RPL21 | AGAAGCACCGGATATATGTTCTCTAGGCCTTTTAGAAAACATGGGAACCGGGTACTGTTCA | SEQ ID NO: 2319 | Homo sapiens ribosomal protein L21, mRNA (cDNA clone IMAGE:6605832), complete cds. [BC104478] |

Fig. 5-40

| No. | Probe ID No | Symbols of genes | Sequence | SEQ ID NO. | Descriptions of genes (notes and numbers within [ ] indicates GenBank accession No.); |
|---|---|---|---|---|---|
| 739 | A_32_P220127 | RPL34 | CAAAACTAGGCTGTCGGTGAACCCGTGGTAATAAGAATGTTCACCTTTATACCAAGAAGGT | SEQ ID NO: 2320 | Homo sapiens ribosomal protein L34 (RPL34), transcript variant 2, mRNA [NM_033625] |
| 740 | A_32_P223319 | ESCO1 | ATGGGCTCATTACGTGGACTTCATTTTGATACTGTTGTCTATCCTTCATAGGTGCCCTCAGTT | SEQ ID NO: 2321 | Homo sapiens establishment of cohesion 1 homolog 1 (S. cerevisiae) (ESCO1), mRNA [NM_052911] |
| 741 | A_32_P224866 | CAPZA2 | AATTGTGTTTTGACATTCTGAGAATTAAATGAAAATACTTATTTCAGAAATGCATTTAATG | SEQ ID NO: 2322 | Homo sapiens capping protein (actin filament) muscle Z-line, alpha 2 (CAPZA2), mRNA [NM_006136] |
| 742 | A_32_P22539 | hCG_26523 | AGTACGAAGGTCAGCAAATTGGCAAAGTGGTCTGCCAGGTTTAACAGGAAGAAATATGTTATCT | SEQ ID NO: 2323 | PREDICTED: Homo sapiens similar to 60S ribosomal protein L26 (Silica-induced gene 20 protein) (SIG-20) (LOC400055), mRNA [XM_374987] |
| 743 | A_32_P226786 | BC045174 | TTATTGGTGCATGTAAGGCATTTATCCTGTCTTTAATGAACGGATTAATGTGTTGTTGATTGTT | SEQ ID NO: 2324 | Homo sapiens cDNA clone IMAGE:5273245 [BC045174] |
| 744 | A_32_P2330 | SUB1 | AGGAAGAAAAGGTATTTGTTTAAATCCAGAACAATCGAGCCAGGTGACAACAACAGATTTG | SEQ ID NO: 2325 | Homo sapiens SUB1 homolog (S. cerevisiae) (SUB1), mRNA [NM_006713] |
| 745 | A_32_P26895 | KIAA1600 | AATTGTTGCCCTCGTCCGTGGAGAAACTCTCAGATGGTCATTGTGTACCTACTCTCTGTT | SEQ ID NO: 2326 | KIAA1600 (KIAA1600), mRNA [Source:RefSeq_dna;Acc:NM_020940] [ENST00000369248] |
| 746 | A_32_P30710 | RPL23 | AGGAAAGTCATACCGTAGAAAGGTTCGTGGTGTGCCAGAAACCCTTAAAAGATAATGCAGGAGT | SEQ ID NO: 2327 | Homo sapiens ribosomal protein L23 (RPL23), mRNA [NM_000978] |
| 747 | A_32_P31182 | RPL7 | GTAGAACAAGAAGGAAGGTTCGTGGTGTGCCAGAAACCCTTAAAGAAAAACGAAGGAAT | SEQ ID NO: 2328 | Homo sapiens ribosomal protein L7 (RPL7), mRNA [NM_000971] |
| 748 | A_32_P336445 | HINT1 | TGATGATGAAAGTCTT...AACCCAAGAAGATATATCCAGATTTCTGGGAGAAGA | SEQ ID NO: 2329 | Homo sapiens histidine triad nucleotide binding protein 1 (HINT1), mRNA [NM_005340] |
| 749 | A_32_P36101 | ARL1 | CTATTCAAACACAGATCGAGCATCATTTATGTAGTAGACAGTGTGACCGAGACCGAATTGG | SEQ ID NO: 2330 | Homo sapiens ADP-ribosylation factor-like 1 (ARL1), mRNA [NM_001177] |
| 750 | A_32_P43217 | PSMA6 | TTGTTGTTAGTTTACCAGATCGGTGATGCCACGTACCTGTGTGTTGGTAACACCAAAGA | SEQ ID NO: 2331 | Homo sapiens proteasome (prosome, macropain) subunit, alpha type, 6 (PSMA6), mRNA [NM_002791] |
| 751 | A_32_P4532 | LOC643932 | GATTCCACGACAGCATTGTTATTTGCCAAAGAAGAATTCATCATGTTCCGTATCCTCTCATGAT | SEQ ID NO: 2332 | PREDICTED: Homo sapiens similar to 40S ribosomal protein S3a (v-fos transformation effector protein) (LOC643932), mRNA [XR_012289] |
| 752 | A_32_P49164 | AV714556 | AAATGCAGACTTTGTTATTTGCCAAAGAAGAATGATGGAAATGATGACGAATGACGCAATGCCTTTCTTTTTCCC | SEQ ID NO: 2333 | AV714556 AV714556 DCB Homo sapiens cDNA clone DCBADG06 5', mRNA sequence [AV714556] |
| 753 | A_32_P49392 | A_32_P49392 | AATTCTGCCAAATGTGAAAAGAAATCACCACTGTTGGGTTATATCACTGCCTGGAGGTGCAGCAGAAATG | SEQ ID NO: 2334 | |
| 754 | A_32_P54305 | LOC401397 | AGAATCTTTAGGAAATTACCACTGTTGGGTTATATCACTGCCTGCTGAATCGTTGAGGAG | SEQ ID NO: 2335 | Homo sapiens hypothetical LOC401397, mRNA (cDNA clone IMAGE:4244115), complete cds. [BC107860] |
| 755 | A_32_P58074 | RPS3A | TGGGTTTTACTAAAAAACAGGAAAATCAGATACGGAGCAGTCTTATGCTCAGGACCAA | SEQ ID NO: 2336 | Homo sapiens ribosomal protein S3A (RPS3A), mRNA [NM_001006] |
| 756 | A_32_P61857 | KIAA1468 | TCAGTGTCACAGTTCGAGTGGAATTTGACAGTTGTGTGTACAGTCATGAAGTCGAAGTAG | SEQ ID NO: 2337 | Homo sapiens KIAA1468 (KIAA1468), mRNA [NM_020854] |
| 757 | A_32_P68566 | ARL1 | TCGGTTACCTGCCTTGAAGGACGGAAAATGCCAGATATTGAAAACGTCAGCAACCAAAG | SEQ ID NO: 2338 | Homo sapiens ADP-ribosylation factor-like 1 (ARL1), mRNA [NM_001177] |
| 758 | A_32_P7118 | PSMC6 | AGCAGAGTGTAGAAACAGTTTGTTACTGAAGGAGGTATGTTCGGAATTTCGTCGCTGATCATGA | SEQ ID NO: 2339 | Homo sapiens proteasome (prosome, macropain) 26S subunit, ATPase, 6 (PSMC6), mRNA [NM_002806] |

Fig. 5-41

| No. | Probe ID No. | Symbols of genes | Sequence | SEQ ID NO. | Descriptions of genes [factors and numbers within [ ] indicate GenBank accession No.] |
|---|---|---|---|---|---|
| 759 | A_32_P73222 | AA631847 | TTTGTTTGTTTTTGGACAAATCTCATAAGAAGTTTAGGTCTTACAG CACGAACCCGTCGAAGG | SEQ ID NO: 2340 | mp61b02.s1 NCI_CGAP_Br2 Homo sapiens cDNA clone IMAGE:1130763 3' similar to TR:G971836 G971836 60S RIBOSOMAL PROTEIN L34. mRNA sequence |
| 760 | A_32_P77102 | BC042469 | AAATGTGAAGTCTGGCGTTTGAAGAGGTGTATAACACACATAAT TTACTGTGCATCAGTC | SEQ ID NO: 2341 | Homo sapiens, clone IMAGE:5198554, mRNA. [BC042469] |
| 761 | A_32_P81768 | TMEM167 | CCTCAGTACTGTGAGTACAAATATTACATTCTGCAAATGTTATTC TGTTGTATCAGATACG | SEQ ID NO: 2342 | Homo sapiens transmembrane protein 167 (TMEM167), mRNA [NM_174909] |
| 762 | A_32_P83784 | CENTD1 | ACAGGCCCATACTTGTCAGTCAGTCCAATCATAGTACAGTGATGTG GTGGTAGATGCTATGA | SEQ ID NO: 2343 | Homo sapiens centaurin, delta 1 (CENTD1), transcript variant 1, mRNA [NM_015230] |
| 763 | A_32_P86400 | LYSMD3 | AAATGTTGTCTCAGGTAATCACTATTTCTTCCACGTATGTGGAT ATTGCACTGTTAGATC | SEQ ID NO: 2344 | Homo sapiens LysM, putative peptidoglycan-binding, domain containing 3 (LYSMD3), mRNA |
| 764 | A_32_P86494 | A_32_P86494 | TGAGCCTTCCCTGCCACATTGAGATGATCGTTACTGAAAAGGAA CAGATTGTTCCTAAAG | SEQ ID NO: 2345 | |
| 765 | A_32_P8857 | A_32_P8857 | TAATGTCCGGAATGGTACACTGTTTCGTAAAGTGACATCTTT CAGATACTTCGTGTGGCT | SEQ ID NO: 2346 | |
| 766 | A_32_P93782 | RPL26 | AGGTTGTACATCGGACACTATAAAGGTCAGCAAATTGGCAAAGTA GTCCAGGTTTACAGGA | SEQ ID NO: 2347 | Homo sapiens ribosomal protein L26 (RPL26), mRNA [NM_000987] |
| 767 | A_32_P9382 | RP11-11C5.2 | AAGAAAGCAGGAAAATATATTGAGAAGGGATCGTGTTACAGAG GACTTCTTTAAAGTGT | SEQ ID NO: 2348 | Homo sapiens similar to RIKEN cDNA 2410129H14 (LOC440145), mRNA [XM_001071775] |
| 768 | A_32_P86134 | DPY19L1 | ATAACTGGTTCATTTGCTGGGAACCATTACAAGTAGTATAAATT AGCTTTTCCAGAAGG | SEQ ID NO: 2349 | Homo sapiens DPY-19-like protein 1 (DPY19L1) mRNA, complete cds. [DQ287932] |
| 769 | A_32_P86213 | TPT1 | GAAAGCAGAGTAATCACTGGTGTCGTGATGTTGTCATGAACCATCA CCTGCAGGAAACAAGT | SEQ ID NO: 2350 | Homo sapiens tumor protein, translationally-controlled 1 (TPT1), mRNA [NM_003295] |
| 770 | A_32_P96933 | AL571926 | GAGCCTGACAAATGTTCTGGATGTAACAGTATGAACACGCTATGA GGTGGGACTACTTCTG | SEQ ID NO: 2351 | AL571926 Homo sapiens PLACENTA_COT 25-NORMALIZED Homo sapiens cDNA clone CS0D1029YJ06 3-PRIME, mRNA sequence [AL571926] |
| 771 | A_32_P98313 | NDUFA4 | AGCCCTGGAAGAAACTGGGGTCCCAATCATCAATCAATACAAGTTCTGC TCAGTGAATGTGGATT | SEQ ID NO: 2352 | Homo sapiens NADH dehydrogenase (ubiquinone) 1 alpha subcomplex, 4, 9kDa (NDUFA4), nuclear gene encoding mitochondrial protein, mRNA [NM_002489] |

Fig. 6-1

| No. | Probe ID No. | Symbols of genes | Sequence | SEQ ID NO: | Descriptions of genes (tables and numbers within [ ] indicates GenBank accession No.) |
|---|---|---|---|---|---|
| 1 | A_23_P143247 | TSHZ2 | CCCAAGAAGGGTATAGGAAATCTCTAAGTTTACGGGAGTCTCGAATGACCGACTATCAGTCA | SEQ ID NO: 1583 | Homo sapiens teashirt family zinc finger 2 (TSHZ2), mRNA [NM_173485] |
| 2 | A_23_P341938 | NOG | GCCAGGGCTGCGGCTGGATTCCGATCCAGTAGCCATGATTTGCGAGTGCAAGTGCTCGT | SEQ ID NO: 1601 | Homo sapiens noggin (NOG), mRNA [NM_005450] |
| 3 | A_23_P500130 | ANKRD15 | TTTACCGTGTCAGATTTACTTTGGTCCTCTATGTATTTAAATGTTTGAAGTGCGTTAGAC | SEQ ID NO: 1611 | Homo sapiens ankyrin repeat domain 15 (ANKRD15), transcript variant 2, mRNA [NM_153186] |
| 4 | A_23_P84399 | CNTNAP2 | CTTGAGGAGATCCTTAAAATATCAGGAGAAGTTGGGGGAGGGCAGGGAATGGAATATAATG | SEQ ID NO: 1614 | Homo sapiens contactin associated protein-like 2 (CNTNAP2), mRNA [NM_014141] |
| 5 | A_24_P930963 | LOC650392 | GCCGCATTCAAGTATAACCAGGAGGAAAATGGTGCTTGAAATAAGCATGCACAAAGG | SEQ ID NO: 1644 | Homo sapiens cDNA clone IMAGE:5264670 [BC036550] |
| 6 | A_32_P111394 | THC2643957 | GAATACAAGTGTCGTTTCATCCGATATTTGACTGAAGCTAAGACAGATCAATTATAAGG | SEQ ID NO: 1651 | |
| 7 | A_32_P209582 | THC2663167 | CAATGTAAAGCCAGAGATATCAACGTCCTTTTGTCAAGATTTCAAACCTATTTGGCTGAT | SEQ ID NO: 1678 | ALU1_HUMAN (P39188) Alu subfamily J sequence contamination warning entry, partial (5%) [THC2663167] |
| 8 | A_32_P213509 | THC2663555 | GATTTGTTGCAGTGTTGGAGCCCGGTTTTAATGAAAATTCAACACCTACACTGGAAAAA | SEQ ID NO: 1680 | |
| 9 | A_32_P227110 | THC2512148 | TAAAACAAATCGTTTTGATTGAGCCACTGTGTATTGATAATGGCTTATTATTATAGAATCA | SEQ ID NO: 1684 | |
| 10 | A_23_P128930 | PSMC6 | GAACAAGCAAGATTAGAATACGTCGAAAATCGATGCAGATGCCATTACAAAGGCATGGTGAA | SEQ ID NO: 1737 | Homo sapiens proteasome (prosome, macropain) 26S subunit, ATPase, 6 (PSMC6), mRNA [NM_002806] |
| 11 | A_23_P134925 | BNIP3L | ATTTGGGGACAAAAAGGCAGGGTTCATTTTCATATGTTTGATGAAAAGTGGGCTCAAGAT | SEQ ID NO: 1746 | Homo sapiens BCL2/adenovirus E1B 19kDa interacting protein 3-like (BNIP3L), mRNA [NM_004331] |
| 12 | A_23_P137366 | C1QB | CACCGACAAGAAGTCACTACTGGGCATGAGGGGTGCCAACAGGATCTTTTCCGGGTTCCT | SEQ ID NO: 1750 | Homo sapiens complement component 1, q subcomponent, B chain (C1QB), mRNA [NM_000491] |
| 13 | A_23_P137434 | RNF11 | TGTAGTATCCATATGTTGGTTAAATTTGGTTATGACGCCGATGATGGAAGACTTAAAGA | SEQ ID NO: 1751 | Homo sapiens ring finger protein 11 (RNF11), mRNA [NM_014372] |
| 14 | A_23_P143958 | RPL22L1 | ATTGGCTTGGAGTGGTTGCATGTCGACAAGGAGAGGTACGAACTTCGTTACCTTCGAAGTTA | SEQ ID NO: 1757 | Homo sapiens ribosomal protein L22-like 1, mRNA (cDNA clone IMAGE:4865966), [BC049823] |
| 15 | A_23_P144497 | RPS3A | CCAAATCGGGAAGAAGATAATGAAAATGACGCGGAGAGGTGCAGACAAATGAGTTGAA | SEQ ID NO: 1560 | Homo sapiens ribosomal protein S3A (RPS3A), mRNA [NM_001006] |
| 16 | A_23_P14708 | SUHW4 | TCTTTGTACCTCCATACAGAGTGTTAGGCTGCCAGGCTGTAAGCTTAGCTTAATTAAACTT | SEQ ID NO: 1765 | Homo sapiens suppressor of hairy wing homolog 4 (Drosophila) (SUHW4), transcript variant 1, mRNA [NM_017661] |
| 17 | A_23_P14734 | RPS27L | TACAAGATACAGCACGGTTTTCAGCCATGCTCAGACAGTGGTTCTTTGTGTAGGTTGTTCA | SEQ ID NO: 1766 | Homo sapiens ribosomal protein S27-like (RPS27L), mRNA [NM_015920] |
| 18 | A_23_P152002 | BCL2A1 | TGTAACCATATTTGCATTTGAAGGTATCTCATCAAGAAACTTCTACGACAGGCAAATTGC | SEQ ID NO: 1773 | Homo sapiens BCL2-related protein A1 (BCL2A1), mRNA [NM_004049] |
| 19 | A_23_P156842 | EEF1E1 | AAGAAAAAGCAACATGTTCAGCAGGTTCAGTCGGTTAGAATACAGCGGTGACTCAAGTAGAATGGGGAGT | SEQ ID NO: 1778 | Homo sapiens eukaryotic translation elongation factor 1 epsilon 1 (EEF1E1), mRNA [NM_004280] |

Fig. 6-2

| No. | Probe ID No. | Symbols of genes | Sequence | SEQ ID NO. | Descriptions of genes (letters and numbers within [ ] indicates GenBank accession No.) |
|---|---|---|---|---|---|
| 20 | A_23_P157449 | POLR2K | GGTCTCTCTTGGTTCAAAATATCTTCTTGTACAGTACTCACCAT TTTAGATGTCTTGAC | SEQ ID NO: 1779 | Homo sapiens polymerase (RNA) II (DNA directed) polypeptide K, 7.0kDa (POLR2K), mRNA [NM_005034] |
| 21 | A_23_P157452 | POLR2K | GGAATGTCTCAGTTGTATAAGTTGGATTTGCTCTCTCCCATTCT GATTGTTGTATAGCTT | SEQ ID NO: 1780 | Homo sapiens polymerase (RNA) II (DNA directed) polypeptide K, 7.0kDa (POLR2K), mRNA [NM_005034] |
| 22 | A_23_P159650 | COX7B | CAAATACGGTAATGCTGTATTAGCTAGTGGAGGCAGCTTCTGTA TTGTTACATGGACATA | SEQ ID NO: 1782 | Homo sapiens cytochrome c oxidase subunit VIIb (COX7B), nuclear gene encoding mitochondrial protein, mRNA [NM_001866] |
| 23 | A_23_P162586 | ACTR6 | TTAACGGCTCACTGGACAGTTTTCTTAGAAGGTAGTTTTTGTG TGACTGTGACTAAAACT | SEQ ID NO: 1787 | Homo sapiens ARP6 actin-related protein 6 homolog (yeast) (ACTR6), mRNA [NM_022496] |
| 24 | A_23_P170233 | CSTA | AAGTGGGTACTGAGTCATGATCCTTGCTGATAAATATAACCATC AATAAACAAGCCATTCT | SEQ ID NO: 1794 | Homo sapiens cystatin A (stefin A) (CSTA), mRNA [NM_005213] |
| 25 | A_23_P18325 | PDCD10 | CCAACCGAGCTAATTCATCAAACCAACTTAATACTTCAGACCTTC AAAACTGTGGCCTGAA | SEQ ID NO: 1795 | Homo sapiens programmed cell death 10 (PDCD10), transcript variant 1, mRNA [NM_007217] |
| 26 | A_23_P19291 | TUBB2A | ACTTCTCAAGATGAATGGTGGATCGCTTAGTGAACTCTGTGTGCC TCAAGCATGGTCTTC | SEQ ID NO: 1798 | Homo sapiens tubulin, beta 2A (TUBB2A), mRNA [NM_001069] |
| 27 | A_23_P200955 | A_23_P200955 | AGACCTGATTGAAGCTCAGATTGAATGTCAAGAACTACGATGGT TATTGTTTCATCTAC | SEQ ID NO: 1802 | |
| 28 | A_23_P215751 | NDUFA5 | TAAAAGTGGAGTCACTAAATAGTTTGCAGTACGTTCTCTTGAGTTTT AGTGTAGGTGGGTATG | SEQ ID NO: 1831 | Homo sapiens NADH dehydrogenase (ubiquinone) 1 alpha subcomplex, 5, 13kDa (NDUFA5), nuclear gene encoding mitochondrial protein, mRNA [NM_005000] |
| 29 | A_23_P217797 | DDX3Y | CAGTGATAGGAAGGTCGAGCATCCAGAAAGTTTCTCTTGAGTTTT GTTATGTGTTTTGCTG | SEQ ID NO: 1836 | Homo sapiens DEAD (Asp-Glu-Ala-Asp) box polypeptide 3, Y-linked (DDX3Y), mRNA [NM_004660] |
| 30 | A_23_P218928 | C4orf18 | CAGATGAGTTCATTTGGTCTGTAGATGTGTTTTCAGAGGACTAGG TACGAGGAATGTTTG | SEQ ID NO: 1837 | Homo sapiens chromosome 4 open reading frame 18 (C4orf18), transcript variant 2, mRNA [NM_016613] |
| 31 | A_23_P252261 | EAF2 | CAGGATTTCGTGATATAATGACCAGTGCATAATAAGATTTCGGAGACA ACAGTGCCCTTCTGAT | SEQ ID NO: 1853 | Homo sapiens ELL associated factor 2 (EAF2), mRNA [NM_018456] |
| 32 | A_23_P25235 | CLEC4D | CATTTAAGCACGCAGCAGTATTCTGGCATAAGAATGAACCCGAC AAGTCTCAGGGAGAAA | SEQ ID NO: 1854 | Homo sapiens C-type lectin domain family 4, member D (CLEC4D), mRNA [NM_080387] |
| 33 | A_23_P26021 | COPS2 | TGGTTTTTATCAACTGGTTTGTTTGGTGTGGTGGAATGAATTATC CCAAGAAAAGAGGTT | SEQ ID NO: 1869 | Homo sapiens COP9 constitutive photomorphogenic homolog subunit 2 (Arabidopsis) (COPS2), mRNA [NM_004236] |
| 34 | A_23_P2705 | P2RY5 | TCTGTATTGCTGTTCAAGCTGTTGTTTGACCCTAGTTAC TACTTTACATCGGACA | SEQ ID NO: 1871 | Homo sapiens purinergic receptor P2Y, G-protein coupled, 5 (P2RY5), mRNA [NM_005767] |
| 35 | A_23_P302550 | RGS18 | GAGTCTAAGGCGCTAGGAGATTGGGCATGCTGCCACATTGGTTA TATTCAGAAAGTGTTA | SEQ ID NO: 1873 | Homo sapiens regulator of G-protein signalling 18 (RGS18), mRNA [NM_130782] |
| 36 | A_23_P307940 | CAPZA2 | CTACAAGATTGTGATAAGAGATGAGTGCAGAATGCAGATAAGATGAACATT GCATGACCGGATCAT | SEQ ID NO: 1876 | Homo sapiens capping protein (actin filament) muscle Z-line, alpha 2 (CAPZA2), mRNA [NM_006136] |
| 37 | A_23_P312246 | CCDC82 | GGGTTTATAAGCAGAGATGACTGTGAAGTGAATGAGGTGTTGATATC CTGTCAGTTTAGTCAA | SEQ ID NO: 1880 | Homo sapiens coiled-coil domain containing 82 (CCDC82), mRNA [NM_024725] |
| 38 | A_23_P33045 | RPL26 | TACAAAAGGTCAGACAAATTGGCAAAGTAGTCCAGGTTACAGGAA GAAATATGTTATGTAC | SEQ ID NO: 1890 | Homo sapiens ribosomal protein L26 (RPL26), mRNA [NM_000987] |

Fig. 6-3

| No | Probe ID No. | Symbols of genes | Sequence | SEQ ID NO: | Descriptions of genes (letters and numbers within [ ] indicates GenBank accession No.) |
|---|---|---|---|---|---|
| 39 | A_23_P339480 | HAT1 | AACATGAACAGCTGGAAGAGAGTTTCAGGAAGCTAGTGGAAGATTACCCGGCTGTTATTG | SEQ ID NO: 1892 | Homo sapiens histone acetyltransferase 1 (HAT1), transcript variant 1, mRNA [NM_003642] |
| 40 | A_23_P347059 | MOBKL1A | CTAGAAGGGGAAAATCATCTAAGTTATGAAATGGAAGATAGGCGCTATATTAGAAAGTG | SEQ ID NO: 1896 | Homo sapiens MOB1, Mps One Binder kinase activator-like 1A (yeast) (MOBKL1A), mRNA [NM_173468] |
| 41 | A_23_P41114 | CSTA | AAACAAATGAGACTTATGGAAAATTGGAAGCTGTGCAGTATAAAACTCAAGTTGTTGGTG | SEQ ID NO: 1925 | Homo sapiens cystatin A (stefin A) (CSTA), mRNA [NM_005213] |
| 42 | A_23_P44257 | COMMD8 | AAGATTTACTTCTGGGCTTCTATGTTTGGGAAAGCATTGTCTGATAAAAAATAGGCTGTC | SEQ ID NO: 1942 | Homo sapiens COMM domain containing 8 (COMMD8), mRNA [NM_017845] |
| 43 | A_23_P501276 | TUBB2A | GTGGACGGAGCAGATGCTCAACGTGCAGAAGAAGAACAGCAGAGCTACTTCGTGGAGTGGATC | SEQ ID NO: 1950 | Homo sapiens tubulin, beta 2A (TUBB2A), mRNA [NM_001069] |
| 44 | A_23_P50907 | ITGAV | AAAGAGTGATTAAGTGAGGTTATTTACCCGCTAAATGGTGCATTCTGCATTGTATTTCAGG | SEQ ID NO: 1953 | Homo sapiens integrin, alpha V (vitronectin receptor, alpha polypeptide, antigen CD51) (ITGAV), mRNA [NM_002210] |
| 45 | A_23_P56734 | HNMT | CCTTTTGTCCACCATGGATATATATCGAGTGGTTTATTGATGGTAATGAAAATGGAGAAGT | SEQ ID NO: 1962 | Homo sapiens histamine N-methyltransferase (HNMT), transcript variant 1, mRNA [NM_006895] |
| 46 | A_23_P59921 | SUB1 | GAGATTGGAAAATGAGGTACGTTAGTGTTCGGGATTTTAAAGGCAAAGTGGCTAATTGAT | SEQ ID NO: 1970 | Homo sapiens SUB1 homolog (S. cerevisiae) (SUB1), mRNA [NM_006713] |
| 47 | A_23_P65768 | C15orf15 | TCCTGCATTGCCATCCTACATAATATCAGATATTACGGATGGTTAGATTGCATCTCAGTGTT | SEQ ID NO: 1977 | Homo sapiens chromosome 15 open reading frame 15 (C15orf15), mRNA [NM_016304] |
| 48 | A_23_P66260 | ZNF267 | TGTGATGAAATGTGGTAAAGCCTTCAGGTATAGGTCATACGTCACTACACATCGGAAGT | SEQ ID NO: 1978 | Homo sapiens zinc finger protein 267 (ZNF267), transcript variant 498723, mRNA [NM_003414] |
| 49 | A_23_P70328 | CENPQ | CAATGGCTTACAGTTTCTGTCTGGTCATCTGGAACTTGAAAAATGGTCAAATGCCTTCAC | SEQ ID NO: 1985 | Homo sapiens centromere protein Q (CENPQ), mRNA [NM_018132] |
| 50 | A_23_P7221 | RPL34 | AGGAGCAGAGAAAATGGTTGTGGAAAGTGTTGAAGGCACACAAGGACAGAGTCAGAAAGGCTAA | SEQ ID NO: 1990 | Homo sapiens ribosomal protein L34 (RPL34), transcript variant 2, mRNA [NM_033625] |
| 51 | A_23_P7229 | RPL34 | CGAACCCTGGTAATAGAATTGTTTACGTTTATACCAAGAAGGTTGGGAAAAGGAGCGAAAA | SEQ ID NO: 1991 | Homo sapiens ribosomal protein L34 (RPL34), transcript variant 2, mRNA [NM_033625] |
| 52 | A_23_P75769 | MS4A4A | CACCAAAAGATCAACAGACAGTTGGAAAAAGAACAAAACAGCTCACACGGACCTGTGACGAAGAAGAGCCT | SEQ ID NO: 2000 | Homo sapiens membrane-spanning 4-domains, subfamily A, member 4 (MS4A4A), transcript variant 1, mRNA [NM_024021] |
| 53 | A_23_P78092 | EVI2A | GCTGAATCAGACGATGTGGAAAAAAGGAACAAAAGCAGCTCACACGACCGAACCTAGTGATGCAA | SEQ ID NO: 2004 | Homo sapiens ecotropic viral integration site 2A (EVI2A), transcript variant 1, mRNA [NM_001003927] |
| 54 | A_23_P83278 | CHMP5 | CATTGCTCTTTTATTTTTCGATTAAGAGACATCATTGCTTGGGAAATGCTTTCTCGTAC | SEQ ID NO: 2007 | Homo sapiens chromatin modifying protein 5 (CHMP5), mRNA [NM_016410] |
| 55 | A_23_P87879 | CD69 | TGAAGCTATATGTGATGTGGCAAATGTCTATTAGGAAAATATTCTGTAATCTTCAGAAGCTAG | SEQ ID NO: 2011 | Homo sapiens CD69 molecule (CD69), mRNA [NM_001781] |
| 56 | A_23_P94230 | LY96 | TGAAGCTATTTCTGGGAGCCCCAGAAGAAGAAATGGTGTTTTGTTGGAGTTTGTCATGGTACA | SEQ ID NO: 2018 | Homo sapiens lymphocyte antigen 96 (LY96), mRNA [NM_015364] |
| 57 | A_23_P94501 | ANXA1 | GGCTCTTTGTGGAGGAAAACTAAACATTGCTTGATGGTGTCAAGCTATGATGCAGAAGAGT | SEQ ID NO: 2019 | Homo sapiens annexin A1 (ANXA1), mRNA [NM_000700] |

Fig. 6-4

| No. | Probe ID No. | Symbols of genes | Sequence | SEQ ID NO: | Description of genes (letters and numbers within [ ] indicates GenBank accession No.) |
|---|---|---|---|---|---|
| 58 | A_23_P96658 | C7orf15B | ATGCCCTAAAGTTAATACCAGGCAGTCATATTTTATCAGATGTAA ATCTGGATGTAAGCTC | SEQ ID NO: 2023 | lipopolysaccharide-specific response 5-like protein [Source:RefSeq peptide;Acc:NP_115965] [ENST00000382832] |
| 59 | A_24_P110045 | THC2785765 | CCACCAGAAACGTACAACCTGATTTTCATGACAAATACGGTAGCA ACACAAGTCGGAATAG | SEQ ID NO: 2032 | COX7B_HUMAN (P24311) Cytochrome c oxidase polypeptide VIIb, mitochondrial precursor, partial (78%) [THC2785765] |
| 60 | A_24_P135551 | LOC130865 | TAACAGCATAGCTGTCCCTGTGGGCATTCACCCAAAGTGGTTA TCACTAGACTAAAAGT | SEQ ID NO: 2046 | PREDICTED: Homo sapiens similar to 60S ribosomal protein L26 (Silica-induced gene 20 protein) (SIG-20) (LOC130865), mRNA [XR_019454] |
| 61 | A_24_P144866 | LOC401975 | TGTCGATGTCAAGAGTAATGATGGCTACTTCTTTAATCTGTCT GTGTCGTTTTCTGA | SEQ ID NO: 2050 | PREDICTED: Homo sapiens similar to ribosomal protein S3a (LOC401975), mRNA [XR_017247] |
| 62 | A_24_P153324 | LOC390413 | GAAGGTTAAGACAGAGGTTTCAATTAAGATGCTGGGGATTGTAGAAAC CATATATTGCAGGGTA | SEQ ID NO: 2054 | PREDICTED: Homo sapiens similar to 60S ribosomal protein L7 (LOC390413), mRNA [XR_018341] |
| 63 | A_24_P188873 | RPL34 | TGTTTACGTTTATACGCAAGAAGGTTGGGAAAGCACCAAAATCTG CATGTGTGTGTGCCC | SEQ ID NO: 2077 | Homo sapiens ribosomal protein L34 (RPL34), transcript variant 2, mRNA [NM_033625] |
| 64 | A_24_P201702 | CLEC2B | ATTGGAATTCAAGTAAATACAACGTTTCCACTCAAGATGCCGAC CTAACTATAATTGACA | SEQ ID NO: 2085 | Homo sapiens C-type lectin domain family 2, member B (CLEC2B), mRNA [NM_005127] |
| 65 | A_24_P203909 | RPL34 | GAAGGGGTTCGTGCTGTAAGGTTCTTATGAAATTGTCC AAAACAAACAAACATG | SEQ ID NO: 2088 | Homo sapiens ribosomal protein L34 (RPL34), transcript variant 2, mRNA [NM_033625] |
| 66 | A_24_P221375 | A_24_P221375 | TACTTTGGTTACCCATGTAGCTACGTACCTACGACTTCAAAAATCTACAGA GAGTCAATGTGGAGGA | SEQ ID NO: 2095 | |
| 67 | A_24_P237511 | EIF1AY | GTTTCAGTTACTTACATGGTCTCATAAGGTTTCTGATACAATTT GAAGACAGAAATGTGC | SEQ ID NO: 2105 | Homo sapiens eukaryotic translation initiation factor 1A, Y-linked (EIF1AY), mRNA [NM_004681] |
| 68 | A_24_P298604 | LOC731599 | GATGGAAATCATGACCAGAGGTGCGGCAAATGACTTGAAAGAAT TGGTCAATAAAATGAT | SEQ ID NO: 2126 | PREDICTED: Homo sapiens hypothetical protein LOC731599 (LOC731599), mRNA [XR_015536] |
| 69 | A_24_P303118 | RPL34 | CGAAGGAGCAGAAAATCGTTCTGAAAGTGTTGAAGGCACAAGSAC AGAGTCAAAAGGTAA | SEQ ID NO: 2128 | Homo sapiens ribosomal protein L34 (RPL34), transcript variant 2, mRNA [NM_033625] |
| 70 | A_24_P306527 | ENST00000308989 | ACCGCATCCGTGCGTGGTTATCCAGAAAATGTAATGAGGATGAA GATTCACCAAATAAGT | SEQ ID NO: 2132 | PREDICTED: Homo sapiens similar to ribosomal protein L31 (LOC729605), mRNA [NM_001133428] |
| 71 | A_24_P320328 | SUB1 | CAGAAAACCTGTAAAGAAACAAAAGACAGGTGAGACTTCGAGA GCGGTTGTCATCTTGTA | SEQ ID NO: 2138 | Homo sapiens SUB1 homolog (S. cerevisiae) (SUB1), mRNA [NR_006713] |
| 72 | A_24_P324224 | A_24_P324224 | AAAGTGTCTGGGCCAAAGGAATAAGGAATTCCTATAGGCATGT GCGGTTGTCAGAAAAA | SEQ ID NO: 2140 | |
| 73 | A_24_P33213 | A_24_P33213 | GAGCATATATTACATGGGGCATGAGGGTACCCAAATCTGAAGTCAGTAAAT GAAGTTATCTAGAAGG | SEQ ID NO: 2143 | |
| 74 | A_24_P333112 | A_24_P333112 | GGTGATCGAGATCAGAGGTATCAATGTGTGAGGCCACAGGACCA AAAGGTATTGCAACTT | SEQ ID NO: 2144 | |
| 75 | A_24_P33607 | LOC652558 | TAAGAAATAATTGCTTTGACAGAGAACGCTTTGATTGCTCGAT CTCTTGGTAAATATGG | SEQ ID NO: 2145 | PREDICTED: Homo sapiens similar to 60S ribosomal protein L7 (LOC652558), mRNA [XR_019336] |
| 76 | A_24_P349636 | LOC388401 | AGTTGCTTCGACAGATAACAGTTTGATTGGTCTGATCTCTTGGTA AATATAGGCATCAACTG | SEQ ID NO: 2147 | PREDICTED: Homo sapiens similar to 60S ribosomal protein L7 (LOC388401), mRNA [XR_018791] |

Fig. 6-5

| No. | Probe ID No. | Symbols of genes | Sequence | SEQ ID NO: | Descriptions of genes (letters and numbers within [ ] indicates GenBank accession No.) |
|---|---|---|---|---|---|
| 77 | A_24_P366546 | RPL31P10 | CGGCTGTCCAGAAAACGTAATGAGGATGAAGATTCAAATAAGCTCTATACTTTGGTTACC | SEQ ID NO: 2158 | PREDICTED: Homo sapiens similar to ribosomal protein L31 (LOC390283), mRNA [XR_018695] |
| 78 | A_24_P367191 | LOC652890 | AGTTAACATGCTGAGGAGCTGTAGAGGCCATATATTGCCTGTCGGGTACCCAAATCTGAAGTC | SEQ ID NO: 2160 | PREDICTED: Homo sapiens similar to 60S ribosomal protein L7 (LOC652890), mRNA [XR_019544] |
| 79 | A_24_P367199 | A_24_P367199 | TCTTATGTCAGCAGCACCAACAGTCTGCCAAATCAGAAGAAGAGGTGTAATCATGACCTGAGA | SEQ ID NO: 2161 | |
| 80 | A_24_P381625 | PSMC6 | ATGAAAGCAGTCAGAAAAGTGGCTGATTCTAAGAAGCTGGAGTCTAAATTGGACTACAAA | SEQ ID NO: 2173 | Homo sapiens proteasome (prosome, macropain) 26S subunit, ATPase, 6 (PSMC6), mRNA [NM_002806] |
| 81 | A_24_P383999 | RPS3A | TGGTTTTACTAAAAAAGGGAACAACATCAGATACAGAAGACCTCTTATGCCCAGCACCACG | SEQ ID NO: 2175 | Homo sapiens ribosomal protein S3A (RPS3A), mRNA [NM_001006] |
| 82 | A_24_P384411 | A_24_P384411 | ATGGCAAAATCAATAAGAGTGAAGCTTTGACAGATAATGCTTTGACAGCTCGATGCTCTTG | SEQ ID NO: 2176 | |
| 83 | A_24_P392900 | A_24_P392900 | GTCTGTCTGTGTTGGTTTTCCTAAAAACAATGTAACAATCCGAAAAACCTTTATGCTC | SEQ ID NO: 2180 | |
| 84 | A_24_P414556 | TTC33 | TACTCAACATTTGGTATATTGTTTTGAGTAATGGATGTGTTTGTTTTTGTGTAATTTGTGA | SEQ ID NO: 2191 | Homo sapiens tetratricopeptide repeat domain 33 (TTC33), mRNA [NM_012382] |
| 85 | A_24_P41551 | LOC641790 | AAGGAAGAATGGGAAGTCCCTGATGGTGCCGCATTGATGATGAGGCACACACAAATCTGAAA | SEQ ID NO: 2193 | PREDICTED: Homo sapiens similar to ribosomal protein L31 (LOC641790), mRNA [XR_018025] |
| 86 | A_24_P50437 | BC065737 | TGCAGAATGATGAAGTTGGATTGAAATTGGAAAATTGGTGATTAGTGAAGATGTTCAGGGCAAAA | SEQ ID NO: 2198 | Homo sapiens cDNA clone IMAGE:30404477, partial cds. [BC065737] |
| 87 | A_24_P57837 | THC2567891 | AGAAATCCGAAGACCTCTTATGCTCAGTAGGAGGCAAATCCGGAAGAAGATGATGGAAA | SEQ ID NO: 2207 | Q6NXR9_HUMAN (Q6NXR9) Ribosomal protein S3a, partial (91%) [THC2567891] |
| 88 | A_24_P606663 | LOC392030 | TGTGCCGGTTGCCCAGAAAAAGGTAATGCGGGGTGAAGATTCAGGAAATAAGCTCCATACTTT | SEQ ID NO: 2209 | PREDICTED: Homo sapiens hypothetical LOC392030 (LOC392030), mRNA [XM_018063] |
| 89 | A_24_P63347 | PF4V1 | CTACATATTTACCTTGAAGTGTTAGAATTAGGTTGCAATAAATATTAGTAGCTCTTAAGC | SEQ ID NO: 2213 | Homo sapiens platelet factor 4 variant 1 (PF4V1), mRNA [NM_002620] |
| 90 | A_24_P685729 | A_24_P685729 | TGAAGCTTATGTTGATGTGAAGAGTATCAGTGATTATTGCTTTGTGTGTTTTGTGG | SEQ ID NO: 2217 | |
| 91 | A_24_P6975 | LOC3429994 | GGAAGACTTCGAGGGTTGGTGCTGTAAGAGGTAAAGTTCTTATGAAATTGTCAAAAAGA | SEQ ID NO: 2219 | PREDICTED: Homo sapiens similar to ribosomal protein L34 (LOC3429994), mRNA [XM_933464] |
| 92 | A_24_P7555505 | A_24_P7555505 | ATACAGAAGAGACCTCTTATGCTCAGCACCAACAGAAAAGTAAAATGCTGAAGAAGCCCAA | SEQ ID NO: 2223 | |
| 93 | A_24_P792734 | PSMC6 | AGAACGTTCAAGCGAGTACTAGTGAAATGGATGGATTTGATACTCTGCATAGAGTTAAA | SEQ ID NO: 2227 | Homo sapiens proteasome (prosome, macropain) 26S subunit, ATPase, 6 (PSMC6), mRNA [NM_002806] |
| 94 | A_24_P84608 | LOC729449 | GAATTGCTTTGACAGATAACGGCTTTGGGATCTCTTGGAAAATATGGCATCATCTGTATGG | SEQ ID NO: 2233 | PREDICTED: Homo sapiens similar to 60S ribosomal protein L7 (LOC729449), mRNA [XR_015548] |
| 95 | A_24_P941643 | PLCB1 | ATGATGTGCAGTTTTGTGGCTTTATGTTATTGGGTTGTCTCTTGTCGAATGTGTGAAATT | SEQ ID NO: 2247 | Homo sapiens phospholipase C, beta 1 (phosphoinositide-specific) (PLCB1), transcript variant 2, mRNA [NM_182734] |
| 96 | A_32_P107717 | BX100535 | TCTTGTGCACCGAAGATCGTGGTCTGTGTTGTAAATCGTGTTCAGAGCTTGGTCTAATTGGT | SEQ ID NO: 2255 | BX100535 Soares_testis_NHT Homo sapiens cDNA clone IMAGp998l094457, mRNA sequence [BX100535] |

Fig. 6-6

| No. | Probe ID No. | Symbols of genes | Sequence | SEQ ID NO: | Descriptions of genes (letters and numbers within [ ] indicates GenBank accession No.) |
|---|---|---|---|---|---|
| 97 | A_32_P109653 | THC2669092 | TGTGGTTTGGTATTCGAAGTGGGGTGTTTTTGAGAATGTGTGCACTAGTGTGAGATGCAA | SEQ ID NO: 2257 | |
| 98 | A_32_P113154 | LOC730861 | AGGAGGAGTCCAAGAATCTGTTTAAAGTTCAGACTTAAAACAGTACCAAATAAAAAGTCC | SEQ ID NO: 2258 | PREDICTED: Homo sapiens similar to 40S ribosomal protein S3a (V-fos transformation effector protein) (LOC730861), mRNA [XR_015591] |
| 99 | A_32_P114215 | COMMD6 | AATTGCTATCCATTCTAAAGTCATGGAGTTCACTTTCGGCAACGAAAACTAAATAAGGATGG | SEQ ID NO: 2261 | Homo sapiens COMM domain containing 6 (COMMD6), transcript variant 2, mRNA [NM_203495] |
| 100 | A_32_P125549 | RPL31P4 | TCTACAGACAGTCAATGTGGATGGAGAACTAATCCCTGATCGTCAGATACATCAAATAAAG | SEQ ID NO: 2266 | PREDICTED: Homo sapiens ribosomal protein L31 pseudogene 4 (RPL31P4), mRNA [XR_018222] |
| 101 | A_32_P128781 | A_32_P128781 | CATATATTGCATGGGGGTACCCCAATCTGAAGTCAGTAAATGAACTAATCTAGAAGAGTG | SEQ ID NO: 2268 | |
| 102 | A_32_P135818 | RPS3A | CTTGCTTCATGCTGTCTGTGTTGGTTTAATAAAAACGCAACAATCAGATATGGAAGAC | SEQ ID NO: 2269 | Homo sapiens ribosomal protein S3A (RPS3A), mRNA [NM_001006] |
| 103 | A_32_P145153 | RPL31 | ATCCGTGTGCAGCTGTCCAGAAAAACGTAATAATGAGGATGAAGATTCAGAAATAAGCCATAT | SEQ ID NO: 2273 | Homo sapiens ribosomal protein L31 (RPL31), mRNA [NM_000993] |
| 104 | A_32_P155364 | RPL7 | TCAACAGGCTTATTAGAAAAAAATGAAGCAAGGTGTGTACATGATGATTATTTTTCTAAGTCTGG | SEQ ID NO: 2280 | Homo sapiens ribosomal protein L7 (RPL7), mRNA [NM_000971] |
| 105 | A_32_P164203 | THC2683448 | TTGATGGTCATTGTACGAGCTATTGTATGATTAGTGTGGAGTGCTGTTTTACGACACGTGG | SEQ ID NO: 2286 | Q7WZG3_PASPI (Q7WZG3) Ferric uptake regulator, partial (8%) [THC2683448] |
| 106 | A_32_P178945 | YOD1 | TTGCCAGGAGCTGTCCTGAAGTAATACACTGCTGCTACCTGGAAGAGTCTAACTTCATTT | SEQ ID NO: 2296 | Homo sapiens YOD1 OTU deubiquinating enzyme 1 homolog (S. cerevisiae) (YOD1), mRNA [NM_018566] |
| 107 | A_32_P198483 | RPS3A | GGGGCCAAGAAGAAAGTTGATGATGCATTTTCTAAGAAAGATTCGTATGATGTGAAGTGCA | SEQ ID NO: 2306 | Homo sapiens ribosomal protein S3A (RPS3A), mRNA [NM_001006] |
| 108 | A_32_P208178 | RPS3A | GGAAAAGAGGTAGAAAAGGGCTTGCGAATCTATTATCCTCCAGATGTGCTTCGTTAGA | SEQ ID NO: 2317 | Homo sapiens ribosomal protein S3A (RPS3A), mRNA [NM_001006] |
| 109 | A_32_P220127 | RPL34 | CAAAAGTAGGCTGTCCTGAACCCTGGTAATAGAAATTGTTCACCTTTATACCAAGAGGT | SEQ ID NO: 2320 | Homo sapiens ribosomal protein L34 (RPL34), mRNA [NM_033625] |
| 110 | A_32_P224666 | CAPZA2 | AATTCTGTTTTGAGATTCTGAAATTAAATCGAAATTAACTTAATTCAGAATGCATTTAATG | SEQ ID NO: 2322 | Homo sapiens capping protein (actin filament) muscle Z-line, alpha 2 (CAPZA2), mRNA [NM_006136] |
| 111 | A_32_P2333 | SUB1 | AGGAAGAAAGGTATAGAAAAAGGCAAAAATCAGAACACATGAGAGGCAGCTGACAGAACAGATTTC | SEQ ID NO: 2325 | Homo sapiens SUB1 homolog (S. cerevisiae) (SUB1), mRNA [NM_006713] |
| 112 | A_32_P4532 | LOC643932 | GATTCCAGACAGCATTGGAAAAAGACATAGAAGAAAGGCTTGCCAATCTATGCTGTCATGAT | SEQ ID NO: 2332 | PREDICTED: Homo sapiens similar to 40S ribosomal protein S3a (V-fos transformation effector protein) (LOC643932), mRNA [XR_017289] |
| 113 | A_32_P49392 | A_32_P49392 | AATTCTGCCAAATCTGGAAGAAGATGAAATCATGACGCAAGAGGTGCAGACAAATG | SEQ ID NO: 2334 | |
| 114 | A_32_P58074 | RPS3A | GTTGGTTTTATAAAAAACGCAAAAATCAGATACGGAAGAGGTCTTATGCTCAGGACCAA | SEQ ID NO: 2336 | Homo sapiens ribosomal protein S3A (RPS3A), mRNA [NM_001006] |
| 115 | A_32_P7118 | PSMC6 | AGCAGACCTGAGAAATGTTTACTGAAGCAGGTATGTTCGGAAAGCGGTGGTGATGATGA | SEQ ID NO: 2339 | Homo sapiens proteasome (prosome, macropain) 26S subunit, ATPase, 6 (PSMC6), mRNA [NM_002806] |

Fig. 6-7

| No. | Probe ID No. | Symbols of genes | Sequence | SEQ ID NO. | Descriptions of genes (letters and numbers within [ ] indicates GenBank accession No.) |
|---|---|---|---|---|---|
| 116 | A_32_P73222 | AA631847 | TTTGTTTGTTTGGACAATCTGATAAGAACTTAGGTCTTACAAG CACGAACCCCTCGAAG | SEQ ID NO: 2346 | np61b02.s1 NCI_CGAP_Br2 Homo sapiens cDNA clone IMAGE:1130763 3' similar to TR:G971838 G971838 60S RIBOSOMAL PROTEIN L34 ;., mRNA sequence [AA631847] |

Fig. 7-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P105803 | FGF9 | CAAAAGGAGTGCGGGCGTGATGCATGCTGGAAAAGAGACGGTTTTCATTGTGATCAGTT | SEQ ID NO: 2353 | Homo sapiens fibroblast growth factor 9 (glia-activating factor) (FGF9), mRNA [NM_002010] |
| 2 | A_23_P123172 | OR2A9P | CAGGCTCAGTTGTCAGGTGGACTCTTGATGCCAATTATTGGCTCAATCGAGAAAAGTTT | SEQ ID NO: 2354 | Homo sapiens olfactory receptor, family 2, subfamily A, member 9 pseudogene (OR2A9P) on chromosome 7 [NR_002157] |
| 3 | A_23_P153676 | TLE2 | CGTGCTCAGTCGTCGTGAGTGTGACATCTCCAGAAATAACAAATACATTGTGACAGGTCGGA | SEQ ID NO: 2355 | Homo sapiens transducin-like enhancer of split 2 (E(sp1) homolog, Drosophila) (TLE2), mRNA [NM_003260] |
| 4 | A_23_P157299 | AEBP1 | ACAGTAGGACCTACAGAGTGAAGTTGAACTTCTGGGGACTTCTGAGATCAGCGTGGTACGAAGACC | SEQ ID NO: 2356 | Homo sapiens AE binding protein 1 (AEBP1), mRNA [NM_001129] |
| 5 | A_23_P159907 | MAGED4 | GGGAGGCGTGGATGATGGTTCAAGACAATGGATGTGGATATGGCCGAAGGAACATGCCAG | SEQ ID NO: 2357 | Homo sapiens melanoma antigen family D, 4 (MAGED4), transcript variant 1, mRNA [NM_030801] |
| 6 | A_23_P166280 | THC2614148 | CTCAGGGAGTTCTCAGCTTGGACCGTTATCTCGGCAGAAGATCGTGGAACCTGCTCCTTGT | SEQ ID NO: 2358 | Q59G86_HUMAN (Q59G86) Androgen-regulated short-chain dehydrogenase/reductase 1 variant (Fragment), partial (7%) [THC2614148] |
| 7 | A_23_P166371 | VPREB3 | TGCCGCTCGATATCTCGTCACTACGGCTCGGAGGAGGATCACCACCGGAGCCTGCTGACAT | SEQ ID NO: 2359 | Homo sapiens pre-B lymphocyte gene 3 (VPREB3), mRNA [NM_013378] |
| 8 | A_23_P200015 | AK5 | AATGCAGAGGAACACCAGGACGTTTTGTTCAACTCTGCACAGGTATTGACTCTATT | SEQ ID NO: 2360 | Homo sapiens adenylate kinase 5 (AK5), transcript variant 1, mRNA [NM_174858] |
| 9 | A_23_P202520 | ABLIM1 | TCAGTGGAGTCGTTTGCATATACTCTGCATCACTGTCATACTCACAACGTCGTGAATAA | SEQ ID NO: 2361 | Homo sapiens actin binding LIM protein 1 (ABLIM1), transcript variant 3, mRNA [NM_001003408] |
| 10 | A_23_P202881 | FEZ1 | TGGTGAGAAACATCCTTCTTGCCATGAAGGAGGATAATGAAGGTGCCTAGTTTGCTAA | SEQ ID NO: 2362 | Homo sapiens fasciculation and elongation protein zeta 1 (zygin I) (FEZ1), transcript variant 1, mRNA [NM_005103] |
| 11 | A_23_P209055 | CD22 | GGGTCAGGCACAAGAAATGTGGACTATGTGATCGTGAAGCATGACACGTGGATGGGCTG | SEQ ID NO: 2363 | Homo sapiens CD22 molecule (CD22), mRNA [NM_001771] |
| 12 | A_23_P21495 | FCGBP | TCAGTCATCACGAAGGAAGCAGTAGGGAAGAGATTTCCTGAAGAGACGGTGGTCCCTGTGGAGGTTGCG | SEQ ID NO: 2364 | Homo sapiens Fc fragment of IgG binding protein (FCGBP), mRNA [NM_003890] |
| 13 | A_23_P250212 | DKFZp761P0423 | GAACTGAATGCAGGCGTGGAGACGGTGGCTCAATACGTTGTTAGGATTCTGACGCGTTTT | SEQ ID NO: 2365 | tyrosine-protein kinase SgK223 (EC 2.7.10.2) (Sugen kinase 223). [Source:Uniprot/SWISSPROT;Acc:Q86YV5][ENSG00000330777] |
| 14 | A_23_P25060 | FLJ13769 | CAGAGTTCTTGGAGGATTCTGAGGTAGGAGTAGGAGATAAATCATTTGTGTTTTATTGT | SEQ ID NO: 2366 | Homo sapiens cDNA FLJ13769 fis, clone PLACE4000222 [AK023631] |
| 15 | A_23_P255896 | ENST00000335459 | GCAAGGGGCTCTACGGAGAGTACGCTCTTCAATGCTATTGGGGGAAACTGGGAGCGAAGA | SEQ ID NO: 2367 | Homo sapiens hypothetical protein LOC129293, mRNA (cDNA clone IMAGE:5762496), partial cds. [BC051789] |
| 16 | A_23_P30634 | BACH2 | GCCTCTGTACCTCTCAACTGGTCAAGGACTGTAAGCAGGGTTACATCAGGTGTTTTCTA | SEQ ID NO: 2368 | Homo sapiens BTB and CNC homology 1, basic leucine zipper transcription factor 2 (BACH2), mRNA [NM_021813] |
| 17 | A_23_P315376 | ATG16L1 | CTGTGTTTCCACTTTATACTCTTTGTCCAAAACTCAGTTTCAAAATATTGGAATGGAC | SEQ ID NO: 2369 | Homo sapiens cDNA FLJ10035 fis, clone HEMBA1000919 [AK000697] |

Fig. 7-2

| No. | Probe ID No. | Symbols of genes | Sequence | SEQ ID NO: | Descriptions of genes (letters and numbers within [ ] indicates GenBank accession No.) |
|---|---|---|---|---|---|
| 18 | A_23_P316472 | DNHD1 | TAAGCTGCAGAAGGAGGAAACATGGTGATGCCATGCGTTTACCCAC CAAGCTCACCCGCAA | SEQ ID NO: 2370 | Homo sapiens dynein heavy chain domain 1 (DNHD1), mRNA [NM_144666] |
| 19 | A_23_P329212 | ETS1 | GTCAACCCAGCCTATCCAGAATCCGGCTATACCTCGGATTACTTC ATTAGCTATGGTATT | SEQ ID NO: 2371 | Homo sapiens v-ets erythroblastosis virus E26 oncogene homolog 1 (avian) (ETS1), mRNA [NM_005238] |
| 20 | A_23_P329375 | POU6F1 | GTTGCTTTGCGGGGAGAAATTGCACTAAAACAGAAGCTTTTCTTAA TCGATGTTGGAAGGA | SEQ ID NO: 2372 | Homo sapiens POU domain, class 6, transcription factor 1 (POU6F1), mRNA [NM_002702] |
| 21 | A_23_P341938 | NOG | GCCAGCGCTGCGGCTGGATTCGCATCGCACACAGAGTACCCATCATTCGG AGTGGAAGTGCTCGT | SEQ ID NO: 2373 | Homo sapiens noggin (NOG), mRNA [NM_005450] |
| 22 | A_23_P343398 | CCR7 | AAGAGAGGCAAACATTTTACCCACACACAGATAAAGTTTTGCGTTGA GGAAACAACAGGCTTT | SEQ ID NO: 2374 | Homo sapiens chemokine (C-C motif) receptor 7 (CCR7), mRNA [NM_001838] |
| 23 | A_23_P344531 | SYNPO | TCCTGCTGCTGTGAAGATGTAGGCTGTCTTACTCAGTTAATGA TGAGTGACTATATT | SEQ ID NO: 2375 | Synaptopodin. [Source:Uniprot/SWISSPROT;Acc:Q8N3V7] [ENST00000307662] |
| 24 | A_23_P344884 | KIAA1394 | ACCGAAATTCTAGGATAGGTCTGAAGGCTGGTGGAAAGCTTGGTGG CATCCAACCTGCCTC | SEQ ID NO: 2376 | Homo sapiens KIAA1394 protein, mRNA (cDNA clone IMAGE:4310128), complete cds. [BC036557] |
| 25 | A_23_P356681 | ROBO3 | GGGCGTAGGTGAAGCCCATTGGGTTCCGACGATTCCAATGGCTGAGG AAGGCAGAAGGCTAG | SEQ ID NO: 2377 | Homo sapiens roundabout, axon guidance receptor, homolog 3 (Drosophila) (ROBO3), mRNA [NM_022370] |
| 26 | A_23_P357104 | ANXA6 | CTGTCAACATCCGGAGGGAATTCATTGAGAAATATGACAAGTCT CTCACCAAGCCATT | SEQ ID NO: 2378 | Homo sapiens annexin A6 (ANXA6), transcript variant 1, mRNA [NM_001155] |
| 27 | A_23_P357717 | TCL1A | TTTCCGCCCGTTTATAGATGGTCACGCACCTGGGTGTTACAAAGTT GTATGTGGGATGAAT | SEQ ID NO: 2379 | Homo sapiens T-cell leukemia/lymphoma 1A (TCL1A), mRNA [NM_021966] |
| 28 | A_23_P359870 | C8orf16 | CTGAAGTTATAATTTTCACTTAACATTGTCGGATTGTGGCATTTTGG TTTTTAGTCGAATGGT | SEQ ID NO: 2380 | Homo sapiens mRNA for hypothetical protein (C8ORF16). [AJ312026] |
| 29 | A_23_P368996 | LRRC56 | CAAACCAACATTTCCAGCTCTCAGGTGTACAGAAATGCGGGTTTAC TTTGTAGGGCAGGTT | SEQ ID NO: 2381 | Homo sapiens leucine rich repeat containing 56 (LRRC56), mRNA [NM_198075] |
| 30 | A_23_P39067 | SPIB | CCTGTCCAAGGTTCCGTCTTGTGCAGATCTGAGATTCCTAGGTTAT GTGTCGGGGCCTCTG | SEQ ID NO: 2382 | Homo sapiens Spi-B transcription factor (Spi-1/PU.1 related) (SPIB), mRNA [NM_003121] |
| 31 | A_23_P38356 | FFAR1 | GACCGGTTACTTGGGAAGGGGTGCTGGCTGAAGACAGTGTGTGC GGCAAGAAGGCAAGG | SEQ ID NO: 2383 | Homo sapiens free fatty acid receptor 1 (FFAR1), mRNA [NM_005303] |
| 32 | A_23_P398294 | HIP1R | GTTAGCATTTCCTCCTGAAGTGTCTGTTGGCAATAAAATGCACT TTGACTGTTGTTGT | SEQ ID NO: 2384 | Homo sapiens huntingtin interacting protein 1 related (HIP1R), mRNA [NM_003959] |
| 33 | A_23_P407601 | C8orf6 | GTCTCCTAGGTAGTGTAGGAGAGATTCTATTCTCAGATATAAGACT TCCATGTCCAGGTGAA | SEQ ID NO: 2385 | Homo sapiens mRNA for hypothetical protein (C8orf6 gene). [AJ307469] |
| 34 | A_23_P40989 | USP13 | TGGAGTAGAGAATAAATGCCAATGGAAACATTATTTCTGAGGCAA GCCGCAAGGACCTAG | SEQ ID NO: 2386 | Homo sapiens ubiquitin specific peptidase 13 (isopeptidase T-3) (USP13), mRNA [NM_003940] |
| 35 | A_23_P420873 | NR1D1 | CCCTTGTACAGAATGGAAGTCTGCACTTCTCTCTCCTTTACGAGA CGAAAGGAAAAGGCA | SEQ ID NO: 2387 | Homo sapiens nuclear receptor subfamily 1, group D, member 1 (NR1D1), mRNA [NM_021724] |
| 36 | A_23_P48585 | SALL2 | CTATAAATGTCAAGAAGCAAGAACAGAGGGAGATATTAGTGTCTTCCC TCTATCATTAAAGGT | SEQ ID NO: 2388 | Homo sapiens sal-like 2 (Drosophila) (SALL2), mRNA [NM_005407] |
| 37 | A_23_P49643 | GRAP | CATCTGCCAGGAAGGTTGAGGACTCCAGGTTCACCCACTGGAG GCTCAACCTAAGGAA | SEQ ID NO: 2389 | Homo sapiens GRB2-related adaptor protein (GRAP), mRNA [NM_006613] |

Fig. 7-3

| No. | Probe ID No. | Symbols of genes | Sequence | SEQ ID NO: | Descriptions of genes (letters and numbers within [ ] indicates GenBank accession No.) |
|---|---|---|---|---|---|
| 38 | A_23_P57236 | GGTL3 | GGAAGGACCAACCTTCATCATCGCTGTTAAGGACCCCTGGGAGCCCAGATGCAGCTGGA | SEQ ID NO: 2390 | Homo sapiens gamma-glutamyltransferase-like 3 (GGTL3), mRNA [NM_178026] |
| 39 | A_23_P83388 | EPPK1 | GTTTTTGGTCTGTGTTTTCTGGGTCGTCTATGTGTCATATGGTTTTACTTTCTCCCGGAA | SEQ ID NO: 2391 | Homo sapiens epiplakin 1 (EPPK1), mRNA [NM_031308] |
| 40 | A_23_P85269 | TTN | CTGACAACGCTGATCATCATGGACGTGAGGAAGAAGAGGATTCCAACATGGTGGACTTTATCACCCTGAGT | SEQ ID NO: 2392 | Homo sapiens titin (TTN), transcript variant N2-A, mRNA [NM_133378] |
| 41 | A_23_P88222 | PLD4 | TGAAAGTGTTCATGGTCGGTGCCGGTGGGAAGGATACAAATCCAACATCGGATTCAGGAGGGTGAACC | SEQ ID NO: 2393 | Homo sapiens phospholipase D family, member 4 (PLD4), mRNA [NM_138790] |
| 42 | A_24_P102512 | CABIN1 | GTCCGTGGGTGATATTTCTGGGGAGGAATAAATCCAAGAAAAGGGGTAAAACCGAGAAGAA | SEQ ID NO: 2394 | Homo sapiens calcineurin binding protein 1 (CABIN1), mRNA [NM_012295] |
| 43 | A_24_P134816 | BCL9L | TGCTTCCTACCCAGGAGGAGCTCCGTATCCGGCCTTGGTCAGAGGCTGAAGCCATATACGACT | SEQ ID NO: 2395 | Homo sapiens B-cell CLL/lymphoma 9-like (BCL9L), mRNA [NM_182557] |
| 44 | A_24_P229184 | HIP1R | CCTGAGGCTGAAGCTCTTCAGAAAATAGTGTTTTAATATTCCTGTTCAGAAATAGTGTT | SEQ ID NO: 2396 | Homo sapiens huntingtin interacting protein 1 related (HIP1R), mRNA [NM_003959] |
| 45 | A_24_P298360 | LTBP3 | CTGCTGTTTGGGAAGGCCCCAAGAGAGCAAGTGAGAGAGTTGAGAGAGGATTCAGACGAGTGT | SEQ ID NO: 2397 | Homo sapiens latent transforming growth factor beta binding protein 3 (LTBP3), mRNA [NM_021070] |
| 46 | A_24_P302506 | AMIGO1 | AATTGGAGAATTGAATAATCAGACATATGTAAGCGGCAGAGAACCCTGTGTCAGACGAGTGC | SEQ ID NO: 2398 | Amphoterin-induced protein 1 precursor (AMIGO-1) (Alivin-2). [Source:Uniprot/SWISSPROT:Acc:Q86WK6] [ENST00000369364] |
| 47 | A_24_P312325 | C8orf15 | GTTGTTCAATGTGACTAGTTCAGTTGCCGTCCAATATGAAGTAGAAAAGCAGATTTCTG | SEQ ID NO: 2399 | Homo sapiens chromosome 8 open reading frame 15 (C8orf15), mRNA [NM_001036621] |
| 48 | A_24_P324838 | IGHD | AGATGGTGCAGTGGTTAGAGGCTGAGGCTTATCCACAGAGAACCCTGGCCGCTTGGTCAA | SEQ ID NO: 2400 | Homo sapiens mRNA for FLJ00382 protein. [AK090461] |
| 49 | A_24_P354715 | NT5E | TCTGGGTCGAAATCTGAACAGTCACTGTAAATCATGTTAAGGCCCAGATAGAGAACTTG | SEQ ID NO: 2401 | Homo sapiens 5'-nucleotidase, ecto (CD73) (NT5E), mRNA [NM_002526] |
| 50 | A_24_P37020 | THC2690931 | TGCTTCTACGGTCCAACTAAAAGGGCAAAAGAGGGTTGAAGGTGAGCCATGTTAGTTATGAGA | SEQ ID NO: 2402 | AF235005 suppression of tumorigenicity 16 protein [Homo sapiens] (exp=-1; wgp=0; cg=0), partial (13%) [THC2690931] |
| 51 | A_24_P383012 | BC030084 | TCCCCCTCATCTGTTGGGTGAAATAGTGTTTATCCTTTAGTAGTAAAAATTCTGAAAAGGT | SEQ ID NO: 2403 | Homo sapiens cDNA clone IMAGE:4791887. [BC030084] |
| 52 | A_24_P413126 | TMEPAI | AAGAAACTGCTTGTTGTGTATCAGTAATCATTAGTGGCAATGATGACATTCTGAAAAGGT | SEQ ID NO: 2404 | Homo sapiens transmembrane, prostate androgen induced RNA (TMEPAI), transcript variant 1, mRNA [NM_020182] |
| 53 | A_24_P419028 | MGP-1 | ACCCGGGTGACTTTTCAGAGAGGTATAGTTGTCCTTTTGATTCTCCAGTTAAAGCTAGAA | SEQ ID NO: 2405 | Homo sapiens mRNA for MGP-1, complete cds. [AB014771] |
| 54 | A_24_P525144 | A_24_P525144 | GGTGATGACAAGCTCTATTGGGGATTGGGACCTTCTCAAGCTTCCTATGAAATATTCTT | SEQ ID NO: 2406 | |
| 55 | A_24_P62505 | GLT25D2 | AGCATTTAGACTAGGACGTGTTCTACTGTGAAGAAAGTTCTGTGTCCTTTAGCCCGGTTT | SEQ ID NO: 2407 | Homo sapiens glycosyltransferase 25 domain containing 2 (GLT25D2), mRNA [NM_015101] |
| 56 | A_24_P662177 | THC2666469 | GGGCAGGTAGGATTTCAATGGGCATGTTACATAACCATGGTGTAAAGGGACAGAATGTAGA | SEQ ID NO: 2408 | |
| 57 | A_24_P8257 | BC039036 | GTCCGTACATGAAAGTAAGCCTGAAGACTGCAGGTCTCGTCGTCTCATTTTGTGAAGATTT | SEQ ID NO: 2409 | Homo sapiens cDNA clone IMAGE:4155841, partial cds. [BC039036] |

Fig. 7-4

| No. | Probe ID No. | Symbols of genes | Sequence | SEQ ID NO: | Descriptions of genes (letters and numbers within [ ] indicates GenBank accession no.) |
|---|---|---|---|---|---|
| 58 | A_24_P910490 | BX099367 | AGGGCGAGAGTTGGAGACCCACTTGGGCTACACAGAGTGACAGCCTG TCTGTACAAAAGTA | SEQ ID NO: 2410 | BX099367 Soares_fetal_liver_spleen_1NFLS_S1 Homo sapiens cDNA clone IMAGp998C05977, mRNA sequence [BX099367] |
| 59 | A_24_P923809 | AF272377 | AAGAAAAAGCAGGCTTCCACGCACCAGAATCAGGTCTAGAGCGGAAG CTGGAGTGGTTGGCT | SEQ ID NO: 2411 | Homo sapiens clone 1370-48 MLL protein mRNA, partial cds. [AF272377] |
| 60 | A_24_P924462 | PRKCZ | GCATGAGATGAAAAGATACATATTTTAATTCTATCATTGAGGCATAG TGTTTGAACACACC | SEQ ID NO: 2412 | Homo sapiens mRNA, chromosome 1 specific transcript KIAA0505. [AB029074] |
| 61 | A_24_P930963 | LOC650392 | GCCCATTTCAAGTATAACGAGGAGGAAAATGGTGGTTGAAATA AGCATGCCAGAAAGG | SEQ ID NO: 2413 | Homo sapiens cDNA clone IMAGE:5264670. [BC036550] |
| 62 | A_24_P933492 | ZDHHC21 | GGGAAGGAGGCGGCAGGACCAATGAAGAAGTTTTCAGTTACTGCAGG AATTCAGCTTCAGG | SEQ ID NO: 2414 | Homo sapiens zinc finger, DHHC-type containing 21 (ZDHHC21), mRNA [NM_178566] |
| 63 | A_24_P940346 | FAM129C | AGACAAGCTTTTACGGAGTTCCTCTGCTTGCCAGGAGAAGTCATCT GGTAAGTGGATATTG | SEQ ID NO: 2415 | Homo sapiens family with sequence similarity 129, member C (FAM129C), mRNA [NM_173544] |
| 64 | A_24_P943283 | RASA4 | TCCTGCATAGTCTATGTTTGTGTATATCTTGAACTTTTGAAGAATA AAAAGGTTAAAAAG | SEQ ID NO: 2416 | Homo sapiens RAS p21 protein activator 4 (RASA4), transcript variant 1, mRNA [NM_006989] |
| 65 | A_24_P945396 | SF3B3 | ATCCAGTTTTGTGATCCAATTGAGAAAACATTTCATGAACAACT ACTTGTGGCATGCAT | SEQ ID NO: 2417 | Homo sapiens KIAA0017 mRNA, complete cds. [D13642] |
| 66 | A_32_P111394 | THC2643957 | GAATAGAGTGTTCCTTTCATCGCATATTTGACTGAACCTAAGAC ACATCAATATAAGG | SEQ ID NO: 2418 | |
| 67 | A_32_P125589 | THC2649341 | CGGTCATCCGTTGGTTTAGCCTTTGGTTCCTTAATTAGAGGTAGTGTGTCGAGATAG CATGAGTCGAGATAG | SEQ ID NO: 2419 | |
| 68 | A_32_P131294 | BM854107 | AGTAGGGAAAAAGGTTTGTTCCTTAATTAGAGGTAGTCTGGGAAA TGCTAGCAGTTGTGG | SEQ ID NO: 2420 | K-EST0136406 S22SNU16n1 Homo sapiens cDNA clone S22SNU16n1-145-F11 5', mRNA sequence [BM854107] |
| 69 | A_32_P133767 | C12orf42 | AAGGGGTGAGAGTACTGGTTTCGACAAGAACGAATTGTTAGGCTT TTGTGAAGCATTTT | SEQ ID NO: 2421 | Homo sapiens chromosome 12 open reading frame 42 (C12orf42), mRNA [NM_195521] |
| 70 | A_32_P145764 | BC043547 | GGTCGGGGTGCCTCTCTGTAAGCAATAAGGAATGCCATATAAATG GAAAAGTATAAAGAA | SEQ ID NO: 2422 | Homo sapiens, clone IMAGE:5171873, mRNA. [BC043547] |
| 71 | A_32_P146659 | LOC401431 | AGTTCTGCATGCAGTAGCTTTTACTATTGGTGGAAAGTGATGTTTT TTGGTTGAAAGTCTA | SEQ ID NO: 2423 | Homo sapiens hypothetical gene LOC401431 (LOC401431), mRNA [NM_001008745] |
| 72 | A_32_P148844 | THC2639689 | CCTGTGGGCCTGATTGAAGACTGAGAGTTCCACCTCTGAGAGTGAAGTCCAGAG ATCATGTCCATTAA | SEQ ID NO: 2424 | |
| 73 | A_32_P15829 | AW389914 | TGATGTCGAAGGTTCGACCTCTGAGAGTGAAGTCCAGAG AGCCACACCACTAGA | SEQ ID NO: 2425 | AW389914 RC4-ST0173-191099-032-f06 ST0173 Homo sapiens cDNA mRNA sequence [AW389914] |
| 74 | A_32_P2703271 | THC2703271 | GAAAGAACAATGAAAAGCATTCGAATCAAGAAAAGCCACCTGGTTT TAGAGTTTAATTTG | SEQ ID NO: 2426 | |
| 75 | A_32_P164378 | THC2611661 | AGCGTTTTCTATTAACAGTGAAGTACTCTGAGAGCTTGGAAATT TTGAAGTGCAAAATC | SEQ ID NO: 2427 | RR12 SPIMX (P42344) Chloroplast 30S ribosomal protein S12, partial (11%) [THC2611661] |
| 76 | A_32_P164573 | THC2673977 | GATAGGGTCTGAGGGAGGAGAAAAAGGAGGATAGTCCAATTAGTT TCTCAAAACACATAG | SEQ ID NO: 2428 | ALU1_HUMAN (P39188) Alu subfamily J sequence contamination warning entry, partial (14%) [THC2673977] |
| 77 | A_32_P170397 | ENST00000309874 | CTGTTTGGCCAGGACGATTGCAGGGCCTGGTGAAATGAGAACCC TGTGGGTCGGAACAA | SEQ ID NO: 2429 | Homo sapiens cDNA FLJ33063 fis, clone TRACH2000047. [AK057625] |

Fig. 7-5

| No. | Probe ID No. | Symbols of genes | Sequence | SEQ ID NO: | Descriptions of genes (letters and numbers within [ ] indicates GenBank accession No.) |
|---|---|---|---|---|---|
| 78 | A_32_P179998 | DMRTC1 | ATATGCAAGAAGTTTTTATTCGTCTTGTGATTGCTGAGAATAGCTGTGGAGTCATGTGTATA | SEQ ID NO: 2430 | Homo sapiens DMRT1-like family C1 (DMRTC1), mRNA [NM_033053] |
| 79 | A_32_P184039 | A_32_P184039 | ATCATTGTTAGTCTTGGCCCAAAAATAGTTGTTATTGTATGATGCGTAATAAGTGAGCAGC | SEQ ID NO: 2431 | |
| 80 | A_32_P190682 | THC2739159 | TGAATAAGGTTTTATTTGGTGTCCAGGTTACCTAGAATGAAAAATTGAGACCCAGAATGCATGC | SEQ ID NO: 2432 | ALU8_HUMAN (P39195) Alu subfamily SX sequence contamination warning entry, partial (8%) [THC2739159] |
| 81 | A_32_P195287 | THC2652466 | GCTTTCAACAAGACTGTAAGCCTTACCCAAGGATCCTTTTGTGCATAAGGCGGCCTGTT | SEQ ID NO: 2433 | Q96BM3_PARTE (Q96BM3) Cyclophilin-RNA interacting protein, partial (4%) [THC2652466] |
| 82 | A_32_P209582 | THC2663167 | CAATGTAAAGCCAGAATATCAACGTCCTTTTGTCAAGATTTTCAAAGGTATTTGGCTGAT | SEQ ID NO: 2434 | ALUJ_HUMAN (P39188) Alu subfamily J sequence contamination warning entry, partial (5%) [THC2663167] |
| 83 | A_32_P32254 | COL6A1 | ATGTAATGTGTTCGACGTTTTATCAAAGGCCCCCTTGTATGTTCATGTTAGTTTTGGT | SEQ ID NO: 2435 | Homo sapiens collagen, type VI, alpha 1 (COL6A1), mRNA [NM_001848] |
| 84 | A_32_P3342 | THC2676548 | TATAGCATTTTCTGAAGATCATGTTCTAGTGTTCTTTTCGTCTAGATGATTGGTGAACAG | SEQ ID NO: 2436 | ALU7_HUMAN (P39194) Alu subfamily SQ sequence contamination warning entry, partial (19%) [THC2676548] |
| 85 | A_32_P356316 | HLA-DOA | TGGAAAAGGTGTTTTCTCATCTCGTCCTAAGGCTTGATAAAGTCAATAAATTGTGTC | SEQ ID NO: 2437 | Homo sapiens major histocompatibility complex, class II, DO alpha (HLA-DOA), mRNA [NM_002119] |
| 86 | A_32_P40673 | A_32_P40673 | CATCACAGTTGATATTAGGAGAGGGTACCTAGCTGTGTTGAGTGTCACAGCCTGATATGTA | SEQ ID NO: 2438 | |
| 87 | A_32_P62371 | THC2674900 | GTCTTGCCTGAAAGTATTTTCTCAGTCTTTGAGAAAACAGTGGAACTGACTCATGTGGTC | SEQ ID NO: 2439 | |
| 88 | A_32_P71171 | A_32_P71171 | TCTAGATAGTAATAGCAAGAAATCCAGGGTCGTGATGGCTGGAGGGAGTGATTGAA | SEQ ID NO: 2440 | |
| 89 | A_32_P79103 | BM932034 | GTGCTACAGAATGAAGAATAGGCATTTTAGGAAGGTTGAGTCAGAGGATGGAAGTTGGGGCATA | SEQ ID NO: 2441 | U1-E-EJ1-aj1-k-24-0-UI.r1 U1-E-EJ1 Homo sapiens cDNA clone U1-E-EJ1-aj1-k-24-0-UI 5', mRNA sequence [BM932034] |
| 90 | A_32_P82111 | LRFN2 | ATGCCGGACTGAGCCCTGAGTGTTTGGAAAAGGCGAGACTGCGGCCTTGTAATCACAAATG | SEQ ID NO: 2442 | Homo sapiens leucine rich repeat and fibronectin type III domain containing 2 (LRFN2), mRNA [NM_020737] |
| 91 | A_32_P88987 | AK022346 | ATGGGAAGTTACTACCCAGGGTTACGAGAAAAAGGTCACGTTTATATAAAGTGGCGTTCCTTT | SEQ ID NO: 2443 | Homo sapiens cDNA FLJ12284 fis, clone MAMMA1001757 [AK022346] |
| 92 | A_32_P88229 | THC2682291 | AGAGGGATTAGATGCGGAGCGACATTACGGATATATGCAGAATGGTGTCAGGAAGA | SEQ ID NO: 2444 | |
| 93 | A_32_P90468 | A_32_P90468 | AAGCCAGGAATAATTTTCTATGCATGCTACCTAACTGGTGGAAGTTATCATGAGAACCCT | SEQ ID NO: 2445 | |
| 94 | A_32_P91328 | THC2641595 | GTTAGCGCAATAATGTCATTGAAGTCTTAAGTCTAGCGTGACTCTAAGGCCAGGGTTCA | SEQ ID NO: 2446 | |
| 95 | A_32_P91743 | THC2724906 | TTCAAAGGATTCTCCAAGGGGTCAGTGATTCTCAAAGATTAAGAGGCAGTAATTTAAGCC | SEQ ID NO: 2447 | Q96HL9_HUMAN (Q96HL9) CHP protein, partial (39%) [THC2724906] |
| 96 | A_32_P98940 | THC2745859 | AAGAGTAATGCCAAGATAGCAAAGGTGTGTGTTTTTAAGCAAGGTGTATTCAGGTAGTTA | SEQ ID NO: 2448 | |

Fig. 7-6

| No. | Probe ID No. | Symbols of genes | Sequence | SEQ ID NO: | Descriptions of genes (letters and numbers within [ ] indicates GenBank accession No.) |
|---|---|---|---|---|---|
| 97 | A_23_P102360 | SSFA2 | GTATGATCGAAATAATGGGCGGTATGACTTGAATGAATAGAAATGAATAAGCTGGTGTTT | SEQ ID NO: 2449 | Homo sapiens sperm specific antigen 2 (SSFA2), mRNA [NM_006751] |
| 98 | A_23_P102160 | FAM82A | GGGTATTGTGGTTAGATTTGAAGGTAAAGCCATGTTTGTGGAGAATGGATTCCACTAGTA | SEQ ID NO: 2450 | Homo sapiens unknown mRNA. [AF435956] |
| 99 | A_23_P102235 | SNRPG | ACAACAGACACATATTGGAATGGTGGTAATACAGGAAAATAGTATCATCAGTTAGAAGG | SEQ ID NO: 2451 | Homo sapiens small nuclear ribonucleoprotein polypeptide G (SNRPG), mRNA [NM_003096] |
| 100 | A_23_P102391 | SLC40A1 | CTCATGTTATCATCATTAGTGATCTGTGTTGTAGAAACATGAAGGGTGTAAGCCTTCAGCGT | SEQ ID NO: 2452 | Homo sapiens solute carrier family 40 (iron-regulated transporter), member 1 (SLC40A1), mRNA [NM_014585] |
| 101 | A_23_P104054 | C1orf9 | TAAATTCTTTCCTGTCTGCACAATTAGGTATTCAGAGACAAGAGGGCCTGATTTTATAGA | SEQ ID NO: 2453 | Homo sapiens chromosome 1 open reading frame 9 (C1orf9), transcript variant 2, mRNA [NM_016227] |
| 102 | A_23_P104471 | DUSP13 | GAATTGCTGACCCAATTCAGAGATTGTTTATGCAAAAGTGAGTTCAGTCCATCGTATA | SEQ ID NO: 2454 | Homo sapiens dual specificity phosphatase 13 (DUSP13), transcript variant 1, mRNA [NM_001007271] |
| 103 | A_23_P107847 | LILRA5 | CCAGTGAGCTGCTGGAGATTGCGGCTCAGGAGGCAGCTGATAAGCCTCAGTCCGTCAGAAA | SEQ ID NO: 2455 | Homo sapiens leukocyte immunoglobulin-like receptor, subfamily A (with TM domain), member 5 (LILRA5), transcript variant 2, mRNA [NM_181985] |
| 104 | A_23_P108394 | THC2783023 | ATTCAGAAACGTTGCTGTGTGATACATAGTAAGTCTGCTTCATTTATTACTGCTTGTGTG | SEQ ID NO: 2456 | Q8IUM9_HUMAN (Q8IUM9) ACSL3 protein, complete [THC2467888] |
| 105 | A_23_P110362 | MAP2K1IP1 | ACTGAGACAAGTGTGGAAGTTGTTAATCTGACAGTGGTTTCAGTGTTACTTGTT | SEQ ID NO: 2457 | Homo sapiens mitogen-activated protein kinase kinase 1 interacting protein 1 (MAP2K1IP1), mRNA [NM_021970] |
| 106 | A_23_P110611 | ZH2C2 | GTGTTGAAAAGCAGACTTCAGTCTGTTGGACTGTTCAAACCAGGTTCTTGAATAGTTAA | SEQ ID NO: 2458 | Homo sapiens zinc finger, H2C2 domain containing (ZH2C2), mRNA [NM_017676] |
| 107 | A_23_P111321 | ARG1 | TGGAATCAGGAGGACAAAGCTACCACATGTGGAAAGTACTACATGTGTCCATGTCATTCAAA | SEQ ID NO: 2459 | Homo sapiens arginase, liver (ARG1), mRNA [NM_000045] |
| 108 | A_23_P111583 | CD36 | CTTTGGCTTAATGAGACTGGGACCTTCAGGTGATGAGAAGGCAAACATGTTCAGAAGTCAA | SEQ ID NO: 2460 | Homo sapiens CD36 molecule (thrombospondin receptor) (CD36), transcript variant 2, mRNA [NM_001001547] |
| 109 | A_23_P11201 | GPR34 | AGTAGGAGTGAAAGCAGCTTCAGAATTTAAAGCAGGATAGTCCCTGCATGATACATCTGTG | SEQ ID NO: 2461 | Homo sapiens G protein-coupled receptor 34 (GPR34), transcript variant 1, mRNA [NM_005300] |
| 110 | A_23_P112251 | LOC552891 | AGAATTCTTAAGTTCACAAGTGTTTTACTTCACCGATGTGGGTTTGATTAATTTGGGAC | SEQ ID NO: 2462 | Homo sapiens hypothetical protein LOC552891 (LOC552891), mRNA [NM_04125] |
| 111 | A_23_P113972 | EXOC1 | CGGTGCAGACAGGGCATAAGGAGGAGGAAGTAAGTTACCAACTTGCATTTAACAAGAAGA | SEQ ID NO: 2463 | Homo sapiens exocyst complex component 1 (EXOC1), transcript variant 1, mRNA [NM_018261] |
| 112 | A_23_P114947 | RGS2 | TAGATGTGGGATTATGTGCCCTTAGGTAGGTTGGTTGTACATCTTTCCCTAAATCGATCGA | SEQ ID NO: 2464 | Homo sapiens regulator of G-protein signaling 2, 24kDa (RGS2), mRNA [NM_002923] |
| 113 | A_23_P11685 | PLA2G4A | GAAATGGCAGGCAGTTCTCGATGGTGAGGGAAGTTGCAATCCCATGACAACTGGATTTAAA | SEQ ID NO: 2465 | Homo sapiens phospholipase A2, group IVA (cytosolic, calcium-dependent) (PLA2G4A), mRNA [NM_024420] |
| 114 | A_23_P118361 | CKLF | GGAGAAGCCCGTGAACCATATATTGTTATGACTGGATTTGAAGTCACCGTTATGTTATTT | SEQ ID NO: 2466 | Homo sapiens chemokine-like factor (CKLF), transcript variant 4, mRNA [NM_181641] |

Fig. 7-7

| No. | Probe ID No. | Symbols of genes | Sequence | SEQ ID NO: | Descriptions of genes (letters and numbers within [ ] indicates GenBank accession No.) |
|---|---|---|---|---|---|
| 115 | A_23_P118245 | GINS2 | TGTGTGATGGTGCAAGGAATGGATTCAGGATGTTGTTGGAGAAAC AAGTTGTGATTAGT | SEQ ID NO: 2467 | Homo sapiens GINS complex subunit 2 (Psf2 homolog) (GINS2), mRNA [NM_016095] |
| 116 | A_23_P118516 | FAM18B | TATTTGTAGATTGTTTTCAGGAGAAAGTTTCGTCTCTATGGTA ACAGTGAGCACTTTG | SEQ ID NO: 2468 | Homo sapiens family with sequence similarity 18, member B (FAM18B), mRNA [NM_016076] |
| 117 | A_23_P119222 | RETN | CAATAAGCAGGCATTGGCCTGGAGTGCCAGAGGCGTCACCTCCACGG GGGACCTGGCTACTT | SEQ ID NO: 2469 | Homo sapiens resistin (RETN), mRNA [NM_020415] |
| 118 | A_23_P120046 | BAZ2B | TATTTTGTCTCGAAGGTAATGATAGCTATACAGTCTGTACAGTAA TTATGTCTCTACCAAC | SEQ ID NO: 2470 | Homo sapiens bromodomain adjacent to zinc finger domain, 2B (BAZ2B), mRNA [NM_013450] |
| 119 | A_23_P120316 | MTHFD2 | AGGATTATTCCTTGCTATTAGTAGTCATTTTATGTATGTTACCCT TCAGTAAGTTCTGCC | SEQ ID NO: 2471 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 120 | A_23_P120345 | PELI1 | CTTCCACACGCTTTTTTCAAAGGCACGAAAGTATAGAGACAGTTGGA GTAGATCAAATCTTT | SEQ ID NO: 2472 | Homo sapiens pellino homolog 1 (Drosophila) (PELI1), mRNA [NM_020651] |
| 121 | A_23_P121253 | TNFSF10 | GGAAGAATCCATCTCTGAAGTAGTGTATCAGAGTAGTAGGCCTCGA GGTTCGTTAAGGGA | SEQ ID NO: 2473 | Homo sapiens tumor necrosis factor (ligand) superfamily, member 10 (TNFSF10), mRNA [NM_003810] |
| 122 | A_23_P121622 | SULT1B1 | GAAATAGAGATTGTCGTAGTTGAATGAAACCAGGCAGTTATGCA ATTGATTTGGGCAAT | SEQ ID NO: 2474 | Homo sapiens mRNA for ST1B2, complete cds. [D89479] |
| 123 | A_23_P121716 | ANXA3 | TGGACATTCGAACAGAGTTCAAGAAGGATTATGGGTATTCGGTAT ATTCAGGAATTAAAT | SEQ ID NO: 2475 | Homo sapiens annexin A3 (ANXA3), mRNA [NM_005139] |
| 124 | A_23_P121825 | FLJ13611 | CATGTTACTGTTAGAAAGTTTGTCGTCGATGTAATCACACT TAGTTATGAGCAAAG | SEQ ID NO: 2476 | Homo sapiens hypothetical protein FLJ13611 (FLJ13611), mRNA [NM_024941] |
| 125 | A_23_P122007 | C5orf30 | ATCAGATTTCGTCCGTTGGGCTGGAAATGTTTGGGCTGTTGTATATT TAAAGTAAATTGCAC | SEQ ID NO: 2477 | Homo sapiens chromosome 5 open reading frame 30 (C5orf30), mRNA [NM_033211] |
| 126 | A_23_P122174 | XRCC4 | AAACCAAACTGATCTCTCTGGGTTGGGTTGAGCTGCTGTAAGTAA AGATGATTCCATTAT | SEQ ID NO: 2478 | Homo sapiens X-ray repair complementing defective repair in Chinese hamster cells 4 (XRCC4), transcript variant 3, mRNA [NM_022550] |
| 127 | A_23_P122724 | VNN2 | AAAGAGCCTGGGTGTTGGGTCAGATAAATAAAGATGAAAGTCGA GCTCGAAGCTCATTT | SEQ ID NO: 2479 | Homo sapiens vanin 2 (VNN2), transcript variant 1, mRNA [NM_004665] |
| 128 | A_23_P123608 | JAK2 | GGATAACATGCTGGCTGGATGAAAAGAAATGAGGTTCATTCTGAGACCA AAGTAGATTTACAGA | SEQ ID NO: 2480 | Homo sapiens Janus kinase 2 (a protein tyrosine kinase) (JAK2), mRNA [NM_004972] |
| 129 | A_23_P123727 | ZCCHC6 | TTGAGAGGGGAAATTATACTTTACTTGTTACTGAATCCTGGT GTGAAAAGCATATCAG | SEQ ID NO: 2481 | Homo sapiens zinc finger, CCHC domain containing 6 (ZCCHC6), mRNA [NM_024617] |
| 130 | A_23_P128364 | VPS29 | CAGCTAATTTGAGATGATGTGAAAGTAGAGAACGGAATCGAATACAAAA AAACGTTAAAGCCAG | SEQ ID NO: 2482 | Homo sapiens vacuolar protein sorting 29 homolog (S. cerevisiae) (VPS29), transcript variant 2, mRNA [NM_057180] |
| 131 | A_23_P128447 | LRRK2 | GCAGAAAGAGATAGAAATCTTGCTTGACGGTTTGGGAGATCAATGT TCGACATGAAGTGCA | SEQ ID NO: 2483 | Homo sapiens leucine-rich repeat kinase 2 (LRRK2), mRNA [NM_198578] |
| 132 | A_23_P128930 | PSMC6 | GAACAAGCAAGATTAGAACATACTGAAAATCCATGCAGGTCCATT ACAAAGCATGGTGAA | SEQ ID NO: 2484 | Homo sapiens proteasome (prosome, macropain) 26S subunit, ATPase, 6 (PSMC6), mRNA [NM_002806] |

Fig. 7-8

| No. | Probe ID No. | Symbols of genes | Sequence | SEQ ID NO: | Descriptions of genes (letters and numbers within [ ] indicates GenBank accession No.) |
|---|---|---|---|---|---|
| 133 | A_23_P128940 | C14orf138 | TTGGTATTGAGCGCGAGGCTGAAATCTGCGAAAATCAGCCAACATGATTTGAGTGCACGTT | SEQ ID NO: 2485 | Homo sapiens chromosome 14 open reading frame 138 (C14orf138), transcript variant 1, mRNA [NM_024553] |
| 134 | A_23_P129935 | TMEM49 | CACAGGGAGAAAACTGGTTGTCGTGGATTGTCTTGAAAAGTTGGTCCTTGTGATGGTGTGTT | SEQ ID NO: 2486 | Homo sapiens transmembrane protein 49 (TMEM49), mRNA [NM_030938] |
| 135 | A_23_P132910 | FLJ20273 | CACGGGATTTTGTTGATGGTGAATTCTTGTGGATTCATAAGAGGATCATGCCGTTAGC | SEQ ID NO: 2487 | Homo sapiens RNA-binding protein (FLJ20273), mRNA [NM_019027] |
| 136 | A_23_P133470 | PJA2 | GTTGTTTCCTTTTAAGTACTGTTGATCAGTGTGTAGAGTACTGGTTAAACTTACGTTG | SEQ ID NO: 2488 | Homo sapiens praja 2, RING-H2 motif containing (PJA2), mRNA [NM_014819] |
| 137 | A_23_P133648 | FAM8A1 | ACTTCGCCGCAATTACAAAATGAGTGTGTTTTAGATTCAAGTGACGGTAAAAGGATTTGTT | SEQ ID NO: 2489 | Homo sapiens family with sequence similarity 8, member A1 (FAM8A1), mRNA [NM_016255] |
| 138 | A_23_P133691 | RRAGD | CTGCTGTGATATGATAGATGTGGTTATTGACATCGTCTTGTATTATGGTCTGAAAGAAGA | SEQ ID NO: 2490 | Homo sapiens Ras-related GTP binding D (RRAGD), mRNA [NM_021244] |
| 139 | A_23_P134786 | PHF20L1 | AGTTGTATGTGCCCCGAGTGCTGTACAATACGCAGGTATGCGTAAGTCTGATGGTTGTTTTA | SEQ ID NO: 2491 | Homo sapiens PHD finger protein 20-like 1 (PHF20L1), transcript variant 1, mRNA [NM_016018] |
| 140 | A_23_P134910 | GGH | GGAGGTCAATTGCACAGGAGGAATGTTCGAGAATTGGAGTATTTTTCCTACTGAGTTGTTGCTGTCATTA | SEQ ID NO: 2492 | Homo sapiens gamma-glutamyl hydrolase (conjugase, folylpolygammaglutamyl hydrolase) (GGH), mRNA [NM_003878] |
| 141 | A_23_P135494 | CLIC4 | CTCCTCAAGCCGTAATGTTGAAGAGAATTGTTCTTGAACAGG | SEQ ID NO: 2493 | Homo sapiens chloride intracellular channel 4 (CLIC4), mRNA [NM_013943] |
| 142 | A_23_P135499 | CLIC4 | GTTCGCTTTTTGAGTGTAGATGGAGATATTCTATAGAGTCTGTTGTCTTTTACTAGGAC | SEQ ID NO: 2494 | Homo sapiens chloride intracellular channel 4 (CLIC4), mRNA [NM_013943] |
| 143 | A_23_P136964 | RPGR | GACGAGAACCATGAGTCAGAGATCATCAGAATATGCCACCAACAAATACAGAGAAGA | SEQ ID NO: 2495 | Homo sapiens retinitis pigmentosa GTPase regulator (RPGR), transcript variant A, mRNA [NM_000328] |
| 144 | A_23_P13701 | TMBIM4 | TGGACATGGAATGGCCTTTCTGAGAAAGTGTAGAGATTGTTCTCTGCAGGTTCTCT | SEQ ID NO: 2496 | Homo sapiens transmembrane BAX inhibitor motif containing 4 (TMBIM4), mRNA [NM_016056] |
| 145 | A_23_P137016 | SAT1 | GAAATAATAGAATGAGGACCATTCCAAGGTTTATTACGAGTGGCGTTGTTCATGTTT | SEQ ID NO: 2497 | Homo sapiens spermidine/spermine N1-acetyltransferase 1 (SAT1), mRNA [NM_002970] |
| 146 | A_23_P138262 | PADI4 | AAGAACATTCTGTCAAAGAAGAACATTGAGAGAACACATAATTCATTGTGGAGAGATGCATC | SEQ ID NO: 2498 | Homo sapiens peptidyl arginine deiminase, type IV (PADI4), mRNA [NM_012387] |
| 147 | A_23_P138308 | CD58 | AACCTGTATCCCAAGGAGGGGTGATTCAAGAACACAGATATGCAGTTATACGATACGATT | SEQ ID NO: 2499 | Homo sapiens CD58 molecule (CD58), mRNA [NM_001779] |
| 148 | A_23_P140069 | FBXL3 | TAACCCCAGTGGAATAGATTATTCTTAAAGCGGGCTCTTTCAGTAGTGTGACTTTTAGA | SEQ ID NO: 2500 | Homo sapiens F-box and leucine-rich repeat protein 3 (FBXL3), mRNA [NM_012158] |
| 149 | A_23_P14105 | RCBTB2 | TGACTTTCATGTCACTCAGTATAAAATAGGTCTCTTAACCTGGCACCAGTATAACTATAA | SEQ ID NO: 2501 | Homo sapiens regulator of chromosome condensation (RCC1) and BTB (POZ) domain containing protein 2 (RCBTB2), mRNA [NM_001268] |
| 150 | A_23_P143958 | RPL22L1 | ATTGCTTCGAGTGTTGGTTGCATCTGCATATCTCTGTAGAGGAGGCCTACGAAGTTCGTTACTTCCAGATTA | SEQ ID NO: 2502 | Homo sapiens ribosomal protein L22-like 1, mRNA (cDNA clone IMAGE:4865966), [BC049823] |
| 151 | A_23_P144145 | DCUN1D1 | TCTTTAGTGAATATCTGCATATCTCTGTAAGTTCGAATTGTGTTTCTTACAGTCCCTG | SEQ ID NO: 2503 | Homo sapiens RP42 protein mRNA, complete cds. [AF292100] |

Fig. 7-9

| No. | Probe ID No. | Symbols of genes | Sequence | SEQ ID NO: | Descriptions of genes (letters and numbers within [ ] indicates GenBank accession No.) |
|---|---|---|---|---|---|
| 152 | A_23_P144384 | GALNT7 | TACTGTAGGCTGGTTTGGAAATAATTCGGATATGCTTGCTTGTAAGTTGGTAATATCAC | SEQ ID NO: 2504 | Homo sapiens UDP-N-acetyl-alpha-D-galactosamine:polypeptide N-acetylgalactosaminyltransferase 7 (GalNAc-T7) (GALNT7), mRNA [NM_017423] |
| 153 | A_23_P144584 | ANKRD32 | AAACTTCTACAAAAGTCTAGTATGGGCTTCTGACTTTTTCCAGGGTGTAGAATTTGACTC | SEQ ID NO: 2505 | Homo sapiens ankyrin repeat domain 32 (ANKRD32), mRNA [NM_032290] |
| 154 | A_23_P14564 | GPR65 | AACAAGTTTAAATTCGTTGGTCATCCAATTCTGTACGTTTGTAACCGAAACAGGAAAG | SEQ ID NO: 2506 | Homo sapiens G protein-coupled receptor 65 (GPR65), mRNA [NM_003608] |
| 155 | A_23_P14708 | SUHW4 | TCTTGTACCTCCATACAAGTGTTAGCCTGCCAGGCTGTAAGGTTACCTTAATTAAAGTT | SEQ ID NO: 2507 | Homo sapiens suppressor of hairy wing homolog 4 (Drosophila) (SUHW4), transcript variant 1, mRNA [NM_017661] |
| 156 | A_23_P14734 | RPS27L | TACAAGATCACCACGACGTTTTCAGCACATGCTCAGACAAGTGGTTGTTTGTGTGTAGGTTGTTCA | SEQ ID NO: 2508 | Homo sapiens ribosomal protein S27-like (RPS27L), mRNA [NM_015920] |
| 157 | A_23_P148584 | DOCK11 | TTGCACCAGTGTGTTTGGTTTGTACTTTTTAGGTAAATCTATATGGTGAAAAGTAGAGC | SEQ ID NO: 2509 | Homo sapiens dedicator of cytokinesis 11 (DOCK11), mRNA [NM_144658] |
| 158 | A_23_P149775 | ARHGAP12 | TGTATAATAAACACACAGGTTTGTTAGAAGGTTTTGTTACAAGGGAAGCATGGCTGTTGAAGAT | SEQ ID NO: 2510 | Homo sapiens Rho GTPase activating protein 12 (ARHGAP12), mRNA [NM_018287] |
| 159 | A_23_P149892 | GALNACT-2 | CATGGTCGGTTCAGAATACTTCTTCCAAATGGTGCTGCATGTTTTTGCTTCAATTTTC | SEQ ID NO: 2511 | Homo sapiens chondroitin sulfate GalNAcT-2 (GALNACT-2), mRNA [NM_018590] |
| 160 | A_23_P150129 | SAPS3 | TTAACCTTGTTAACGAAGCATCACCAATGAAGATGGTTTCAGAGGCAATCGCATATTTTAACAGAC | SEQ ID NO: 2512 | Homo sapiens SAPS domain family, member 3 (SAPS3), mRNA [NM_018312] |
| 161 | A_23_P151018 | LEMD3 | CCGGATGTTGTAACCTGTTGCAAGAGGTGAATGTAAAAAATAGTTGTGGCATTTTAAAAGG | SEQ ID NO: 2513 | Homo sapiens LEM domain containing 3 (LEMD3), mRNA [NM_014319] |
| 162 | A_23_P151837 | RNASE2 | GTGGTAACCGAAATAGAGCTGTCCTAGTAACAAAGTCGCAAAAATTGTCAGGACAGTG | SEQ ID NO: 2514 | Homo sapiens ribonuclease, RNase A family, 2 (liver, eosinophil-derived neurotoxin) (RNASE2), mRNA [NM_002934] |
| 163 | A_23_P152002 | BCL2A1 | GTTACCATATTTGCATTTGAAGGTATTGTCATCAAGAAAACTTCACGAGCAAATTGC | SEQ ID NO: 2515 | Homo sapiens BCL2-related protein A1 (BCL2A1), mRNA [NM_004049] |
| 164 | A_23_P154235 | NMI | CCATGTTTGTGAATCTTCTTGTTCAAATGGTGCTGCATGTTTTCAAGTACAATAAGTC | SEQ ID NO: 2516 | Homo sapiens N-myc (and STAT) interactor (NMI), mRNA [NM_004688] |
| 165 | A_23_P154330 | TXNDC9 | GCTCAGTTCTTAAATTATGTGGGAAGGGTGTGGATTCGTCATTTTGAGATTGACTTTATC | SEQ ID NO: 2517 | Homo sapiens thioredoxin domain containing 9 (TXNDC9), mRNA [NM_005783] |
| 166 | A_23_P154367 | STK17B | TTTTCTTTGACTCAAATCCCATGCAACTTGTTTCAGATTTGCTCTGTTAGGCACTTTTTCTTTGACTCA | SEQ ID NO: 2518 | Homo sapiens serine/threonine kinase 17b (STK17B), mRNA [NM_004226] |
| 167 | A_23_P155765 | HMGB2 | TAAAAATGGAGGTTGTAGCTTTTGATGGGGTAGTCATACAGTACATTTAGAGCTTC | SEQ ID NO: 2519 | Homo sapiens high-mobility group box 2 (HMGB2), mRNA [NM_002129] |
| 168 | A_23_P155815 | NCAPG | CTGAGTTCTTAGGAAGACGATGGAGGTGGAATCCTTTAAGATATGTCCAGTTATTTGGTTTAA | SEQ ID NO: 2520 | Homo sapiens non-SMC condensin I complex, subunit G (NCAPG), mRNA [NM_022346] |
| 169 | A_23_P156609 | A_23_P156609 | TTCACGTGTTTAGTAGGTCCGGTTTCAAGTTAAATGGTGTTATTACGGGTTGGCTTCAT | SEQ ID NO: 2521 | |
| 170 | A_23_P156842 | EEF1E1 | AAGAAAAAGCAATGTTCAGCAGCAGTGGTTAGAATACAGAGGTCACTCAAGTAGAATGGGCACT | SEQ ID NO: 2522 | Homo sapiens eukaryotic translation elongation factor 1 epsilon 1 (EEF1E1), mRNA [NM_004280] |

Fig. 7-10

| No. | Probe ID No. | Symbols of genes | Sequence | SEQ ID NO: | Descriptions of genes (letters and numbers within [ ] indicates GenBank accession No.) |
|---|---|---|---|---|---|
| 171 | A_23_P157449 | POLR2K | GGTCTCTCGTTCTTCAAAATATCTTCTTGTGTACACATACTCAGGATTTTAGATGTGGTTGAC | SEQ ID NO: 2523 | Homo sapiens polymerase (RNA) II (DNA directed) polypeptide K, 7.0kDa (POLR2K), mRNA [NM_005034] |
| 172 | A_23_P157452 | POLR2K | GGAATGTCTTCACTTATAGTGGATTTGGTCTCTCCCATTGTGATGTTGTATAGGTT | SEQ ID NO: 2524 | Homo sapiens polymerase (RNA) II (DNA directed) polypeptide K, 7.0kDa (POLR2K), mRNA [NM_005034] |
| 173 | A_23_P159650 | COX7B | CAAATACGGTAATGCTGTATTAGCTAGTGGAGCCACTTCTGTATTGTTACATGGACATA | SEQ ID NO: 2525 | Homo sapiens cytochrome c oxidase subunit VIIb (COX7B), nuclear gene encoding mitochondrial protein, mRNA [NM_001866] |
| 174 | A_23_P159939 | C1GALT1C1 | TCCAAATCAGATGCGATGTGATGATGTATGGGGTATACCGCCTTAGGGCATTTGGGCATAT | SEQ ID NO: 2526 | Homo sapiens C1GALT1-specific chaperone 1 (C1GALT1C1), transcript variant 1, mRNA [NM_152692] |
| 175 | A_23_P160406 | KCTD3 | TTGTAGGACTGCAGTTGTGAATTTTGGGTTAAAGGTTTTGGGTGCTGTAAGAATGTGAAT | SEQ ID NO: 2527 | Homo sapiens potassium channel tetramerisation domain containing 3 (KCTD3), mRNA [NM_016121] |
| 176 | A_23_P160466 | SLC19A2 | CTTGGTATGTGGCCATATATTATAGAAATGCTGAACTCAATGTGTGAAGTTGTACTCTATGCA | SEQ ID NO: 2528 | Homo sapiens solute carrier family 19 (thiamine transporter), member 2 (SLC19A2), mRNA [NM_006996] |
| 177 | A_23_P162306 | IRAK3 | TTGTCTCATGACCAAATGCACGCTCAATTAGAGGCCATTCAAAATTCCTTAAGAGATCATGGG | SEQ ID NO: 2529 | Homo sapiens interleukin-1 receptor-associated kinase 3 (IRAK3), mRNA [NM_007199] |
| 178 | A_23_P162596 | ACTR6 | TTAAGGGTTCACTGGACAGATTTCCTTAGAGAAGGTAGTTTTGTGTGACTGACTAAAGT | SEQ ID NO: 2530 | Homo sapiens ARP6 actin-related protein 6 homolog (yeast) (ACTR6), mRNA [NM_022496] |
| 179 | A_23_P163216 | ATP8B4 | ATCAGTGTATTTTGATAAGTCATTCGGGGATATTTGTGTGAAAACGTTACGTTCTGTCA | SEQ ID NO: 2531 | Homo sapiens ATPase, Class I, type 8B, member 4 (ATP8B4), mRNA [NM_024837] |
| 180 | A_23_P165624 | TNFAIP6 | AAAGTAGTACGGAAGATAAGGAAATGTGCTACTGGCACATTAGAGCCAAGTATGTCAGCGG | SEQ ID NO: 2532 | Homo sapiens tumor necrosis factor, alpha-induced protein 6 (TNFAIP6), mRNA [NM_007115] |
| 181 | A_23_P167095 | GPR160 | AGGCACAGAATGCTTATTCTGTCAGTGCTTCGTTTCTATGTCAGGCATTCAGAGTTAGTACTGGG | SEQ ID NO: 2533 | Homo sapiens G protein-coupled receptor 160 (GPR160), mRNA [NM_014373] |
| 182 | A_23_P167963 | HIST1H2AC | GCATTATGCAAATGCATTCTTTGGACCTCTACCAAAAACATATGATACAGAAGAATAGTAGGCACTTGAGTT | SEQ ID NO: 2534 | Histone H2A type 1-C [Source:Uniprot/SWISSPROT:Acc:Q93077] [ENST00000314088] |
| 183 | A_23_P168617 | CLK1 | ATGGAAAGGAATTCTTGGACCTCTACCAAAAACATGATACAGAAGAAACCAGGAAACGTAAA | SEQ ID NO: 2535 | Homo sapiens CDC-like kinase 1 (CLK1), transcript variant 1, mRNA [NM_004071] |
| 184 | A_23_P168656 | GTPBP10 | AATTTGCAGCATTTGCTGATACAATGTGTCAGTGAAGGCACCATCAAAGCAICGTTACT | SEQ ID NO: 2536 | Homo sapiens GTP-binding protein 10 (putative) (GTPBP10), transcript variant 2, mRNA [NM_033107] |
| 185 | A_23_P168882 | TP53INP1 | GGGAAGGTTAGATCTGTGTTGTTTCAGGCTGGAGTGTATAAGATGGTTTGCTTCTGTATTTCCT | SEQ ID NO: 2537 | Homo sapiens tumor protein p53 inducible nuclear protein 1 (TP53INP1), mRNA [NM_033285] |
| 186 | A_23_P168974 | SDCBP | GGAAACGAACAAGTTCATGTCTGAGAATTATACAGACACTGGTGGAGAAGAAGCATGCTCAG | SEQ ID NO: 2538 | Homo sapiens cDNA FLJ46804 fis, clone TRACH3025270, highly similar to Homo sapiens syndecan binding protein (syntenin) (SDCBP). [AK128545] |
| 187 | A_23_P16915 | QPCT | CATATTGCATTTTTAAGAAGACGGTGTTCAGTTGTGCATCGATACCGTGTCTTGTTTGCCT | SEQ ID NO: 2539 | Homo sapiens glutaminyl-peptide cyclotransferase (glutaminyl cyclase) (QPCT), mRNA [NM_012413] |
| 188 | A_23_P169278 | AGTPBP1 | AAACCTGAGTATCATTGGATGAATGAATTTTTATCTCCCTATGGTTATATCCTGGATGAAGTGG | SEQ ID NO: 2540 | Homo sapiens ATP/GTP binding protein 1 (AGTPBP1), mRNA [NM_015239] |

Fig. 7-11

| No. | Probe ID No. | Symbols of genes | Sequence | SEQ ID NO: | Descriptions of genes (letters and numbers within [ ] indicate GenBank accession No.) |
|---|---|---|---|---|---|
| 189 | A_23_P169576 | EXOC6 | ATGGTGAATCTCCCTTTGCCTTTTCAGGATTTAGGCCTGTAAGAAACTATGCCTGATC | SEQ ID NO: 2541 | Homo sapiens exocyst complex component 6 (EXOC6), transcript variant 2, mRNA [NM_001013348] |
| 190 | A_23_P17021 | SCRN3 | GTCAAAGTTAGTTCTTAGTGATCATATGGTCAGGTAATATTAGTTCTTAGTGATCAGTGG | SEQ ID NO: 2542 | Homo sapiens secernin 3 (SCRN3), mRNA [NM_024583] |
| 191 | A_23_P170233 | CSTA | ATGGCTACTGAGTCCTGATCCTTGGCTGATAAATATAACGATGAATAAGAAGCATTC | SEQ ID NO: 2543 | Homo sapiens cystatin A (stefin A) (CSTA), mRNA [GG52131] |
| 192 | A_23_P18325 | PDCD10 | CCAAGGGACTAATTCATCAAAACGAACTAATAGTTGAGACCTTCAAAGTGTGGGGTGAA | SEQ ID NO: 2544 | Homo sapiens programmed cell death 10 (PDCD10), transcript variant 1, mRNA [NM_007217] |
| 193 | A_23_P18372 | B3GNT5 | AAATGTCAACAAAGGGAAAATAAACATCAGGTTGGATGGTCACTTGAATAGAAGATGGT | SEQ ID NO: 2545 | Homo sapiens UDP-GlcNAc:betaGal beta-1,3-N-acetylglucosaminyltransferase 5 (B3GNT5), mRNA [NM_032047] |
| 194 | A_23_P19543 | SRPK1 | CTGTCAAATTGGGAGGATCTCACTAAAGGATTTCTATTTGGTGTCAGTTAGTTAAAAATAAAGC | SEQ ID NO: 2546 | Homo sapiens SFRS protein kinase 1 (SRPK1), mRNA [NM_003137] |
| 195 | A_23_P200030 | FPGT | TAAAATTGGTAAAGTAAGTAAGTCACTAAGCCCTCAGTTATGATACTTATGTGCG | SEQ ID NO: 2547 | Homo sapiens fucose-1-phosphate guanylyltransferase (FPGT), mRNA [NM_003838] |
| 196 | A_23_P200493 | LBR | GAGCCCTTTATCAATACAGTGGTGCAATTCTGGATATCAGGTACAGTTGTTTTAAGT | SEQ ID NO: 2548 | Homo sapiens lamin B receptor (LBR), transcript variant 1, mRNA [NM_002296] |
| 197 | A_23_P200507 | CNIH4 | TGGTTGAAGTGAGGCTACACTACAGTGGACAGTTGAAGAGGGAGAGAGTTCTTAAATCAT | SEQ ID NO: 2549 | Homo sapiens cornichon homolog 4 (Drosophila) (CNIH4), mRNA [NM_014184] |
| 198 | A_23_P201619 | NEK7 | TGAAGGCCAAGAGGAAGTCACTGTTAAAGGAGTCTGTGGATGTTAGAACCTTGGATGAA | SEQ ID NO: 2550 | Serine/threonine-protein kinase Nek7 (EC 2.7.11.1) (NimA-related protein kinase 7). [Source:Uniprot/SWISSPROT;Acc:Q8TDX7] [ENST00000367385] |
| 199 | A_23_P201758 | CD46 | CTGATGAGTCGCAAGTGTGGCTTAGGTAATATTGCAATGTGGGGTGAATGTAGGTAGCATC | SEQ ID NO: 2551 | Homo sapiens CD46 molecule, complement regulatory protein (CD46), transcript variant a, mRNA [NM_023899] |
| 200 | A_23_P201951 | ARID4B | ATGTTACAGGTTTGAATTAGGCTAAAAGGTGTTGCAGTGGCTTTTCATGCCCGTTCAAA | SEQ ID NO: 2552 | Homo sapiens AT rich interactive domain 4B (RBP1-like) (ARID4B), transcript variant 1, mRNA [NM_016374] |
| 201 | A_23_P20225 | RRM2B | TGGTCGTTTGTAAAAAGTTAAAGATTTGAAAGAGAGATCTCATATTCCCGAGGCATTAGGA | SEQ ID NO: 2553 | Homo sapiens ribonucleotide reductase M2 B (TP53 inducible) (RRM2B), mRNA [NM_015713] |
| 202 | A_23_P202637 | SAPS3 | TGATTATTCCTAGAAGTGAAACAGTAGAGTATTTGGAGTGTATATGGGTTGTGTTTTGGG | SEQ ID NO: 2554 | Homo sapiens SAPS domain family, member 3 (SAPS3), mRNA [NM_018312] |
| 203 | A_23_P202978 | CASP1 | GTGTCCTGTGATGTGGAGGAAATTCGGCAAGGTTGATTTCATTTGAGCAGGCCAGA | SEQ ID NO: 2555 | Homo sapiens caspase 1, apoptosis-related cysteine peptidase (interleukin 1, beta, convertase) (CASP1), transcript variant alpha, mRNA [NM_033292] |
| 204 | A_23_P203376 | MS4A6A | ACGGGCTGTAAATTACCATTTAGTAGAATTAGGCAAATAGTGTGAATTTCGAGAAAACAA | SEQ ID NO: 2556 | Homo sapiens membrane-spanning 4-domains, subfamily A, member 6A (MS4A6A), transcript variant 1, mRNA [NM_152852] |
| 205 | A_23_P203498 | TRIM22 | GTACATAAGAATGTAAATTCACTAGATTAATGTATCCTTCAAATAGTGTGTGGTTTACCAGTGAC | SEQ ID NO: 2557 | Homo sapiens tripartite motif-containing 22 (TRIM22), mRNA [NM_006074] |

Fig. 7-12

| No. | Probe ID No. | Symbols of genes | Sequence | SEQ ID NO. | Descriptions of genes (letters and numbers within [ ] indicates GenBank accession No.) |
|---|---|---|---|---|---|
| 206 | A_23_P204269 | USP15 | GACCAGGATAAATCAGGTATGTTGATCATGGCTTTGCTTATATG TTGATATTAAAGGTG | SEQ ID NO: 2558 | Homo sapiens ubiquitin specific peptidase 15 (USP15), mRNA [NM_006313] |
| 207 | A_23_P204564 | PPP1R12A | GTATAAGATGTTAGATTCTGTAATCTCAGATTCATTTAGAAGG TACTAGTGATGGTG | SEQ ID NO: 2559 | Homo sapiens protein phosphatase 1, regulatory (inhibitor) subunit 12A (PPP1R12A), mRNA [NM_002480] |
| 208 | A_23_P205027 | ABHD13 | ATTTGTGCAGAATGATAAAGAAGTTCGTTTCGTTTAGAAGTGTGTTAT GTCTGTACCTGTCTG | SEQ ID NO: 2560 | Homo sapiens abhydrolase domain containing 13 (ABHD13), mRNA [NM_032859] |
| 209 | A_23_P205336 | C14orf129 | CAATTCATTGGCAGAGTTCATTGGAATGGCTTTGTTGTTGATGTA TGTTCATCTCACCT | SEQ ID NO: 2561 | Homo sapiens chromosome 14 open reading frame 129 (C14orf129), mRNA [NM_016472] |
| 210 | A_23_P20606 | NIPSNAP3A | GTAAGTACGACGTTGAAAAATAGTTCTGTTTACTTTCTCGATGGT ATTCAGTCTCTGTC | SEQ ID NO: 2562 | Homo sapiens nipsnap homolog 3A (C. elegans) (NIPSNAP3A), mRNA [NM_015469] |
| 211 | A_23_P206396 | CKLF | ATTATCAAGTCAGTTGGTAACAACAAGTATTCATGCTCATGTATCT GTGTTGGCACTGATA | SEQ ID NO: 2563 | Homo sapiens chemokine-like factor (CKLF), transcript variant 1, mRNA [NM_016951] |
| 212 | A_23_P207299 | LOC51136 | CCAAAACAGGCAATTTGAAATTAAGACTAGTGGTGTTTAGAGAACTC AGGTATCTTCCTG | SEQ ID NO: 2564 | Homo sapiens PTD016 protein (LOC51136), mRNA [NM_016125] |
| 213 | A_23_P207666 | USP6 | TCCATTGGCTTTCTTGGTCATAGGTAGTAATTACCAATGAATGAAC AAGCATTGTGTTCT | SEQ ID NO: 2565 | Homo sapiens ubiquitin specific peptidase 6 (Tre-2 oncogene) (USP6), mRNA [NM_004505] |
| 214 | A_23_P207999 | PMAIP1 | TTAGAGAATCGGTCTGTAGTGTTTTGGCGAAGATTACCGCTGGCCT ACTGTGAAGGGAGAT | SEQ ID NO: 2566 | Homo sapiens phorbol-12-myristate-13-acetate-induced protein 1 (PMAIP1), mRNA [NM_021127] |
| 215 | A_23_P208119 | PSTPIP2 | AATTAGGTTTCAACATGGGAAGGATGAAATGCCACTTCTCGGATTT GGAGCATCCACTCA | SEQ ID NO: 2567 | Homo sapiens proline-serine-threonine phosphatase interacting protein 2 (PSTPIP2), mRNA [NM_024430] |
| 216 | A_23_P209116 | CYP4F3 | GTTGAAATTTGGGTGGATAAATAAATTTCTGGATTTATCTATCCA TGTTGGACCAATACC | SEQ ID NO: 2568 | Homo sapiens mRNA for leukotriene B4 omega-hydroxylase, complete cds. [AB024454] |
| 217 | A_23_P209625 | CYP1B1 | CTGTTTTATATGCAAGAAGAAGTAAGGTCGTTGGAGTTTACCTGGC TTATTTAATATGCTT | SEQ ID NO: 2569 | Homo sapiens cytochrome P450, family 1, subfamily B, polypeptide 1 (CYP1B1), mRNA [NM_000104] |
| 218 | A_23_P210274 | PREI3 | GGATCAGTATGCCGTAGGATTACAGAATATTTCACATGCTTAT TTTCATCATCGGCAG | SEQ ID NO: 2570 | Homo sapiens preimplantation protein 3 (PREI3), transcript variant 1, mRNA [NM_015387] |
| 219 | A_23_P211047 | BACH1 | ATGTTAGATGCAGTAGAACGATAGAGGTTGCATGTGGACACTCAGT CACATTAACAACTTG | SEQ ID NO: 2571 | Homo sapiens BTB and CNC homology 1, basic leucine zipper transcription factor 1 (BACH1), mRNA [NM_206866] |
| 220 | A_23_P211840 | UBE1C | GCCACCCTAGACGGCAAAAAATAGAACACTTTACTTACAGTGGTA ACCTGTTGAAGAA | SEQ ID NO: 2572 | Homo sapiens ubiquitin-activating enzyme E1C (UBA3 homolog, yeast) (UBE1C), transcript variant 1, mRNA [NM_003968] |
| 221 | A_23_P211899 | THC2522889 | AAACAAAGCATTTCGTTAAAATGTTGGTAGGTAAGCTGTCGTG TTCTACTGATGGTTG | SEQ ID NO: 2573 | GPR27_HUMAN (Q9NS67) Probable G-protein coupled receptor 27 (Super conserved receptor expressed in brain 1), complete [THC2522889] |
| 222 | A_23_P212061 | MME | TTTATTACTCCCAGAACAACAACTATCCTGACTTCTAATATCATT CACTAGTTTTGCCTG | SEQ ID NO: 2574 | Homo sapiens membrane metallo-endopeptidase (MME), transcript variant 2b, mRNA [NM_007289] |
| 223 | A_23_P212726 | TBC1D23 | TGTACCCTGTTAACAGGCCAGTCATTTTGATTTACTTATGAAAATG AAGTGAATAAAAGGG | SEQ ID NO: 2575 | Homo sapiens TBC1 domain family, member 23, mRNA (cDNA clone MGC:8800 IMAGE:3847561), complete cds. [BC029551] |

Fig. 7-13

| No. | Probe ID No. | Symbols of genes | Sequence | SEQ ID NO: | Descriptions of genes (titles and numbers within [ ] indicate GenBank accession No.) |
|---|---|---|---|---|---|
| 224 | A_23_P213247 | FBXL5 | ATGGAGGTGATGGTTGTCTTTACACAGTTAACACTGTACCAAGCTTTGCAGATGTTTTCC | SEQ ID NO: 2576 | Homo sapiens F-box and leucine-rich repeat protein 5 (FBXL5), transcript variant 2, mRNA [NM_035355] |
| 225 | A_23_P213661 | HISPPD1 | GTATGTAAGTTTCTGTTTGTGAAAGTAGTTAATGTACTGACTGTGGAGGTCATAAGG | SEQ ID NO: 2577 | Homo sapiens histidine acid phosphatase domain containing 1 (HISPPD1), mRNA [NM_015216] |
| 226 | A_23_P215751 | NDUFA5 | TAAAAGTGGAGTGACTAAATAGTTTGCAGTAGGTTCTAATATAAGTGTAGGTGGGTATC | SEQ ID NO: 2578 | Homo sapiens NADH dehydrogenase (ubiquinone) 1 alpha subcomplex, 5, 13kDa (NDUFA5), nuclear gene encoding mitochondrial protein, mRNA [NM_005000] |
| 227 | A_23_P216325 | ASAH1 | ATGAAGTCGATGCTAAGCAGGGTAGATGGTATGTGTACAAAGAAATTATGACGGTTGGA | SEQ ID NO: 2579 | Homo sapiens N-acylsphingosine amidohydrolase (acid ceramidase) 1 (ASAH1), transcript variant 2, mRNA [NM_004315] |
| 228 | A_23_P217384 | AP1S2 | AAACGTGTTGCTCTCTTCACAGTATTATGTGTAAAGTCATTGTTTAAAGGACGAATGTC | SEQ ID NO: 2580 | Homo sapiens adaptor-related protein complex 1, sigma 2 subunit (AP1S2), mRNA [NM_003916] |
| 229 | A_23_P217564 | ACSL4 | GTTATAGGTGGTTTAGAAACAGATAATTAAGACAGTTAAGGTTGGGTGCTGCTAATTCTTTG | SEQ ID NO: 2581 | Homo sapiens acyl-CoA synthetase long-chain family member 4 (ACSL4), transcript variant 1, mRNA [NM_004458] |
| 230 | A_23_P217737 | ENST00000341514 | CACAACGATGAGTTCTGTTCTTCAGTTAAAAGAGGTTCTTTGACAGTGTTGATTAACAAA | SEQ ID NO: 2582 | Copper-transporting ATPase 1 (EC 3.6.3.4). (Copper pump 1) (Menkes disease-associated protein). [Source:Uniprot/SWISSPROT;Acc:Q04656] [ENST00000341514] |
| 231 | A_23_P218928 | C4orf18 | CAGAATGAGTCATTCATTTGGTTCTGTAGATGTGTTTCAGAGGTAGGTACAGAGGAATGTTTG | SEQ ID NO: 2583 | Homo sapiens chromosome 4 open reading frame 18 (C4orf18), transcript variant 2, mRNA [NM_016613] |
| 232 | A_23_P219072 | SAMD9 | AAGCTACCTCGAGACTCAGTAAAAGCCAGTTGAAAAGTAAAAGATCAGCTTGGAGAAGTC | SEQ ID NO: 2584 | Homo sapiens sterile alpha motif domain containing 9 (SAMD9), mRNA [NM_017654] |
| 233 | A_23_P22433 | RP2 | TTATTGTCTTGCATTAATAGTACGTGGTGTTTTGTTTTGTTGTTCTTTATATTTATGTCTA | SEQ ID NO: 2585 | Homo sapiens retinitis pigmentosa 2 (X-linked recessive) (RP2), mRNA [NM_006915] |
| 234 | A_23_P23048 | S100A9 | AAGAATGGTGGAAAAGAGATCTGGAAAATTTTCGAAGAAGGAGAATAAGAATGAAAAGGTC | SEQ ID NO: 2586 | Homo sapiens S100 calcium binding protein A9 (S100A9), mRNA [NM_002965] |
| 235 | A_23_P23705 | SPATA6 | GATCTTTGCTAAGTGTCTGATTATCTTCTATCCCCTAGGAGGAAAGAGTGGTCCATGTG | SEQ ID NO: 2587 | Spermatogenesis-associated protein 6 precursor. [Source:Uniprot/SWISSPROT;Acc:Q9NWH7] [ENST00000371847] |
| 236 | A_23_P23960 | BLOC1S2 | GAGTAAATGGAGGAGCTGTGGCTATTGGTGGAACCTTGTTTGAGACAGAAATCCGTCAGAAT | SEQ ID NO: 2588 | Homo sapiens biogenesis of lysosome-related organelles complex-1, subunit 2 (BLOC1S2), transcript variant 2, mRNA [NM_001001342] |
| 237 | A_23_P24404 | IFIT2 | AGGTGACGGAGCATCAGGCGACACTGTGGGTTGGAAAATGTTTGCCTGTTGGAATTAATT | SEQ ID NO: 2589 | Homo sapiens interferon-induced protein with tetratricopeptide repeats 2 (IFIT2), mRNA [NM_001547] |
| 238 | A_23_P24260 | ENST00000371207 | AAGCGACCATCTTATTTTTCCAAGGTTTAATTTAGTGAGAGGGCAGCATTAGTGTGGAGTG | SEQ ID NO: 2590 | Ectonucleoside triphosphate diphosphohydrolase 1 (EC 3.6.1.5) (NTPDase 1) (Ecto-ATP diphosphohydrolase) (ATPDase) (Lymphoid cell activation antigen) (Ecto-apyrase) (CD39 antigen). [Source:Uniprot/SWISSPROT;Acc:P49961] [ENST00000371207] |

Fig. 7-14

| No. | Probe ID No. | Symbols of genes | Sequence | SEQ ID NO: | Descriptions of genes (letters and numbers within [ ] indicates GenBank accession No.) |
|---|---|---|---|---|---|
| 239 | A_23_P24365 | ANKRD49 | GGGCAGTGGTTGTATAGTCGCAAGTTGACAAGGAAAATGTTGATT TTCTAAGGTCCTCAT | SEQ ID NO: 2591 | Homo sapiens ankyrin repeat domain 49 (ANKRD49), mRNA [NM_017704] |
| 240 | A_23_P250002 | HACE1 | TAAGGAGTCATTGTGTTTGGGCAGTAATGTTTGAGACAGATGTAAG TTGAAAGTTTTGGTA | SEQ ID NO: 2592 | Homo sapiens HECT domain and ankyrin repeat containing, E3 ubiquitin protein ligase 1 (HACE1), mRNA [NM_020771] |
| 241 | A_23_P250600 | ST3GAL6 | ATGTCAGGAAGTTCAGGTAGGTGGTTTAAATACAAGTTTGTGA CCTGAAGAGTCCTTT | SEQ ID NO: 2593 | Homo sapiens ST3 beta-galactoside alpha-2,3-sialyltransferase 6 (ST3GAL6), mRNA [NM_006100] |
| 242 | A_23_P251002 | A_23_P251002 | CCTGAAGATCTGAGAAGATGGACGGTGGAGGATGAAGATGTGT GATTAGTTTTGACTG | SEQ ID NO: 2594 | |
| 243 | A_23_P251480 | NBN | TTGGGAAGAAGCTGAACTGAAGAAGACTCACTATGGTCAGGTA AAGAAATATCTAACA | SEQ ID NO: 2595 | Homo sapiens nibrin (NBN), transcript variant 1, mRNA [NM_002485] |
| 244 | A_23_P251825 | IFRD1 | CTATGACACAGCTTTAAGGAGGTTGTTGGATCAGGAATGCAGTAGCC AGTGGAGTGCAAAT | SEQ ID NO: 2596 | Homo sapiens interferon-related developmental regulator 1 (IFRD1), transcript variant 2, mRNA [NM_001007245] |
| 245 | A_23_P251937 | CPEB4 | GTATGTCAGTTAATTGTAGTAGTGGGTGAATTTGGATATAGTTT TTACTGTGTATGGGG | SEQ ID NO: 2597 | Homo sapiens cytoplasmic polyadenylation element binding protein 4 (CPEB4), mRNA [NM_030627] |
| 246 | A_23_P252145 | C1GALT1 | ATATGTCTATATATATGAGGAAGTTGTGTTTTTTAAATGGTGGGC AGGTAGAGGAACTAG | SEQ ID NO: 2598 | Homo sapiens core 1 synthase, glycoprotein-N-acetylgalactosamine 3-beta-galactosyltransferase, 1 (C1GALT1), mRNA [NM_020156] |
| 247 | A_23_P252201 | EAF2 | CAGGATTCCTGATATAGATGCCAGTCATAATAGATTTCAGACAA CAGTGCCTTCTGAT | SEQ ID NO: 2599 | Homo sapiens ELL associated factor 2 (EAF2), mRNA [NM_018456] |
| 248 | A_23_P25235 | CLEC4D | CATTTAACCCAGGCAGGATATTCTGGCATAAGGACTGAACCCGACA AGTGTCAGGAGAAA | SEQ ID NO: 2600 | Homo sapiens C-type lectin domain family 4, member D (CLEC4D), mRNA [NM_080387] |
| 249 | A_23_P252371 | RBBP8 | GGCAAGGAGCAGAAGACATAGACGTTGAAACAAGAAGAAGGAT GAAGGACAGTTTTTT | SEQ ID NO: 2601 | Homo sapiens retinoblastoma binding protein 8 (RBBP8), transcript variant 1, mRNA [NM_002894] |
| 250 | A_23_P253012 | GRAMD1C | GAATTCCACGGAAGGACATAGGTAAGGGGTAACAGTGAAGCTAGGTGG GTTTGTTTTGTTTTG | SEQ ID NO: 2602 | Homo sapiens GRAM domain containing 1C (GRAMD1C), mRNA [NM_017577] |
| 251 | A_23_P253802 | BMX | TTATGGTCCTGATATAACAAGTTGGAGGCGTATAGGAAGGAA CATTTCAGACTGCA | SEQ ID NO: 2603 | Homo sapiens BMX non-receptor tyrosine kinase (BMX), mRNA [NM_001721] |
| 252 | A_23_P254472 | C6orf211 | TTCATTTCAATAGGTGTTTCATTTGGCAGGGGTTTGTATTTGAT TGAGCTGTAGAAATGG | SEQ ID NO: 2604 | Homo sapiens chromosome 6 open reading frame 211 (C6orf211), mRNA [NM_024573] |
| 253 | A_23_P254702 | DEK | TTTTTTATTAACTGCTTTTGCCCATATAACATGCTCATATTTACT GGAAACGTAGCCGAGC | SEQ ID NO: 2605 | Homo sapiens DEK oncogene (DNA binding) (DEK), mRNA [NM_003472] |
| 254 | A_23_P255503 | FNDC3A | ATACTTGCCATTTGAGGCTCACTGCAAAATTAGTGCAGAGGAGAA AACAATTTTAATGT | SEQ ID NO: 2606 | Homo sapiens fibronectin type III domain containing 3A (FNDC3A), transcript variant 2, mRNA [NM_014923] |
| 255 | A_23_P255444 | DAPP1 | AGAAGAATGAGATAGTAGTTGATGTGCAGAGTTGATTGGCAGAAATGTAA CCCTTCGTATCT | SEQ ID NO: 2607 | Homo sapiens dual adaptor of phosphotyrosine and 3-phosphoinositides (DAPP1), mRNA [NM_014395] |
| 256 | A_23_P256231 | FBXO30 | GCCTTTTAAAGTTTGGTGAAGAATGTGTCTGTGGTTAGGATAGC ACAAGGATTAACTTC | SEQ ID NO: 2608 | Homo sapiens F-box protein 30 (FBXO30), mRNA [NM_032145] |
| 257 | A_23_P256342 | SNX13 | ATTAGGCAGGTGAATGAATGCTTGAAACATCTCTTCAGGTGTGA GAAAGAGAGAATG | SEQ ID NO: 2609 | Homo sapiens sorting nexin 13 (SNX13), mRNA [NM_015132] |

Fig. 7-15

| No. | Probe ID No. | Symbols of genes | Sequence | SEQ ID NO: | Descriptions of genes (letters and numbers within ( ) indicates GenBank accession No.) |
|---|---|---|---|---|---|
| 258 | A_23_P256432 | PPP2R5A | TTGGTCAAGTATTTCTCAGATGTTTGTTATCAGAGTAGCATTGCAATCTTAAGTTGC | SEQ ID NO: 2610 | Homo sapiens protein phosphatase 2, regulatory subunit B', alpha isoform (PPP2R5A), mRNA [NM_006243] |
| 259 | A_23_P25735 | PSMA6 | TAGGCAGAGAGAGACTAAACATTGTGGTTAGTTAGTTACCAGATGCGTGATGCCAGTTACCTGT | SEQ ID NO: 2611 | Homo sapiens proteasome (prosome, macropain) subunit, alpha type, 6 (PSMA6), mRNA [NM_002791] |
| 260 | A_23_P259054 | SNX14 | CATGAGACTTCTGTTTGATGGGTTACAGGCAACCAGTAGTCAACAAGCAGCTGACTTATGT | SEQ ID NO: 2612 | Homo sapiens sorting nexin 14 (SNX14), transcript variant 1, mRNA [NM_153816] |
| 261 | A_23_P26021 | COPS2 | TGCTTTTTGATCAAGTGGTTTGTGTTTGCTGGTGCATTTATCCAAGAAAACAGCTT | SEQ ID NO: 2613 | Homo sapiens COP9 constitutive photomorphogenic homolog, subunit 2 (Arabidopsis) (COPS2), mRNA [NM_004236] |
| 262 | A_23_P2765 | P2RY5 | TCTGTATTGCTGTTTCCAACTGTTGTTTGACGGTATAGTTTAGTAGTTTACATCGGACA | SEQ ID NO: 2614 | Homo sapiens purinergic receptor P2Y, G-protein coupled, 5 (P2RY5), mRNA [NM_005767] |
| 263 | A_23_P28169 | ARL6IP6 | GGAAAGCAAAAATGCCTACTACTGCGGACTTTATAGAAGGTAACTTTAAATGAGAATAT | SEQ ID NO: 2615 | Homo sapiens ADP-ribosylation-like factor 6 interacting protein 6 (ARL6IP6), mRNA [NM_152522] |
| 264 | A_23_P28485 | GCA | TGGTGGTGTTTCAGGGTTGGCTAGAAGATGAAAATGAAGGCTGGCATTTTGTGCCATGTTTGTAATA | SEQ ID NO: 2616 | Homo sapiens grancalcin, EF-hand calcium binding protein (GCA), mRNA [NM_012198] |
| 265 | A_23_P29005 | SAMSN1 | CTCTGGTTGCTATATCTCATCAGGAGAATTCAGATAATGGCAAAGAGGATCGGAGCTGA | SEQ ID NO: 2617 | Homo sapiens SH3 domain and nuclear localization signals 1 (SAMSN1), mRNA [NM_022136] |
| 266 | A_23_P29069 | FLJ13033 | AGATTTGTTAAGTGCGCTACACAGTTCTATTCTAAATGATCAAGAGTACAGTTCCTGG | SEQ ID NO: 2618 | Homo sapiens cDNA FLJ13681 fis, clone PLACE2000014, weakly similar to HYPOTHETICAL HELICASE C28H8.3 IN CHROMOSOME III [AK023743] |
| 267 | A_23_P30175 | ERBB2IP | TAGTTGAGGCAGTCTGGAAGCTGTCTTCATTAGAGCAATATTTGGTTATTGCACTTCATTTT | SEQ ID NO: 2619 | Homo sapiens erbb2 interacting protein (ERBB2IP), transcript variant 2, mRNA [NM_018695] |
| 268 | A_23_P302470 | SULT1B1 | TGTCTAAGTGACAAATCTGAAGAAATAAGACATTGTGTCGTAGTTGATGAAACGAGGCA | SEQ ID NO: 2620 | Homo sapiens sulfotransferase family, cytosolic, 1B, member 1 (SULT1B1), mRNA [NM_014465] |
| 269 | A_23_P302550 | RGS18 | GAGTGTAAGGCTAGGCCATTGGGACATTGGGCACATTGGTTCATATTCAGAAGTGTTA | SEQ ID NO: 2621 | Homo sapiens regulator of G-protein signalling 18 (RGS18), mRNA [NM_130782] |
| 270 | A_23_P30307 | CRSP9 | GAATTGTACTGGACAGAATGAAGCATCAAAAGAGAAATTGCAGGTCATAGGAGAGATCAGAT | SEQ ID NO: 2622 | Homo sapiens cofactor required for Sp1 transcriptional activation, subunit 9, 33kDa (CRSP9), mRNA [NM_004270] |
| 271 | A_23_P303210 | IKIP | TTTTAGGTCCAACTGTGTTTAGAGATGAGTTTGCTAGATCGATGGTCGTCTAGATGGTTTAC | SEQ ID NO: 2623 | Homo sapiens IKK interacting protein (IKIP), mRNA [NM_153687] |
| 272 | A_23_P303260 | STX7 | GTCTGATGTTTACGGGGGAGAGTGTAGTTACTAAAAATGTTTAACATAATTTGGAAGAAG | SEQ ID NO: 2624 | Homo sapiens syntaxin 7 (STX7), mRNA [NM_003569] |
| 273 | A_23_P305060 | PBEF1 | TGCCTGGGTCTAATATGCAGGTCAAGATTTAAGGAGATAATGTTTTTTAGAGAGAAT | SEQ ID NO: 2625 | Homo sapiens pre-B-cell colony enhancing factor 1 (PBEF1), mRNA [NM_005746] |
| 274 | A_23_P305723 | MIER1 | TGATGTATTTCAAATAGAGTTCAGGATGTGGAATTCAGTTCAAGACAAGTTTGTTGAGG | SEQ ID NO: 2626 | Homo sapiens mesoderm induction early response 1 homolog (Xenopus laevis) (MIER1), transcript variant 1, mRNA [NM_020948] |
| 275 | A_23_P305759 | ABHD3 | AGTGCTAGAGTGAAGTCAGTAGGAGGTATTCCAGTATTGTGTAAATTCTGTCGAGTCATGTT | SEQ ID NO: 2627 | Homo sapiens abhydrolase domain containing 3 (ABHD3), mRNA [NM_138340] |
| 276 | A_23_P307940 | CAPZA2 | CTACAGATTGGCAAAGAGATGCAGAATGCAGAATGGAACATTGCATGACCGGATCATT | SEQ ID NO: 2628 | Homo sapiens capping protein (actin filament) muscle Z-line, alpha 2 (CAPZA2), mRNA [NM_006136] |

Fig. 7-16

| No. | Probe ID No. | Symbols of genes | Sequence | SEQ ID NO: | Descriptions of genes (letters and numbers within [ ] indicates GenBank accession No.) |
|---|---|---|---|---|---|
| 277 | A_23_P308800 | GLS | GGGAAGAAGAGATAAGATACTGCGAATAGGCCCTCAAACTTAAAAAAGAAAAACTTTGC | SEQ ID NO: 2629 | Homo sapiens glutaminase C mRNA, complete cds. [AF158555] |
| 278 | A_23_P30995 | CYB5R4 | TGGATTTGTGGACCAGTGCCATTTACAGAACAAGGAGTAAGGTTGCTGCATGATGTCAAC | SEQ ID NO: 2630 | Homo sapiens cytochrome b5 reductase 4 (CYB5R4), mRNA [NM_016230] |
| 279 | A_23_P31097 | OSTM1 | AGTGAAAATGTGGTGGGGTTTGTTCTCTGCTGTCAGTGTTTATGCTGCTGGAACTTAGCACT | SEQ ID NO: 2631 | Homo sapiens osteopetrosis associated transmembrane protein 1 (OSTM1), mRNA [NM_014028] |
| 280 | A_23_P312246 | CCDC82 | GGCTTTATAAGAGATGACTGTCAAGTGAATGAGCTGTTGATATGCTGTCAGTTAGTCAA | SEQ ID NO: 2632 | Homo sapiens coiled-coil domain containing 82 (CCDC82), mRNA [NM_024725] |
| 281 | A_23_P312932 | KRTAP8-1 | GGGTATGGCTTCGGCTACAACGGCTGTGGGGCTTTCGGCTACAGGAGATACTGG | SEQ ID NO: 2633 | Homo sapiens keratin associated protein 8-1 (KRTAP8-1), mRNA [NM_175857] |
| 282 | A_23_P314191 | ZDHHC17 | TGATAGTTTAGGAAATAGGAACTTAATTCTCAGCACTGAACATGAATTACTTCCTTGG | SEQ ID NO: 2634 | Homo sapiens zinc finger, DHHC-type containing 17 (ZDHHC17), mRNA [NM_015336] |
| 283 | A_23_P314591 | NFYB | GGAGGCATTTAGTAACCAGTTACCAGTCGGCTTAATAACCACAGACCGTCAACAACAAAA | SEQ ID NO: 2635 | Homo sapiens nuclear transcription factor Y, beta (NFYB), mRNA [NM_006166] |
| 284 | A_23_P317001 | BNIP2 | TTGAACGGGTAGTTTGTTTGACCTAGTTAGATTGTGTGTTTATTCAAGTTTGAAATCA | SEQ ID NO: 2636 | Homo sapiens BCL2/adenovirus E1B 19kDa interacting protein 2 (BNIP2), mRNA [NM_004330] |
| 285 | A_23_P317347 | ESCO1 | GGTAATTTTAAAAGGCCTGAACTATACTTTGAAGAAAACCCGTATAGAAAAGGAAAGCTC | SEQ ID NO: 2637 | Homo sapiens establishment of cohesion 1 homolog 1 (S. cerevisiae) (ESCO1), mRNA [NM_052911] |
| 286 | A_23_P317465 | RAB8B | CCTTGGATAATAGAGGGACCTAGACGAGGAGTTTTTAATCTCTTGGGGCTCGTAATAATTTCAAGATCAGCAG | SEQ ID NO: 2638 | Homo sapiens RAB8B, member RAS oncogene family (RAB8B), mRNA [NM_016530] |
| 287 | A_23_P321354 | TMEM71 | AACCACGTTGTACATGGAACCAAGTTTTATATCTCTTGGGGCTCGTAATTACCTTCAGTTAA | SEQ ID NO: 2639 | Homo sapiens transmembrane protein 71 (TMEM71), mRNA [NM_144649] |
| 288 | A_23_P324633 | C9orf72 | TTTGTGGATTTAGTCCGTGGGATTCAGTCGTCAGAAATGTGTAATAGTCTCTATAGTCC | SEQ ID NO: 2640 | Homo sapiens chromosome 9 open reading frame 72 (C9orf72), transcript variant 1, mRNA [NM_018325] |
| 289 | A_23_P325501 | MORC3 | GATGCCATAAAATACTATGCTTATTGGTCCCATGTTTTTGTGCAATTTTAAAGAGATGGC | SEQ ID NO: 2641 | Homo sapiens MORC family CW-type zinc finger 3 (MORC3), mRNA [NM_015358] |
| 290 | A_23_P329196 | OBFC2A | ACATGTCATAAGTGGTACCCACTTCCCGTTTTTAGTGTAGGGTGGATAAGTGTTAGGATT | SEQ ID NO: 2642 | Homo sapiens oligonucleotide/oligosaccharide-binding fold containing 2A (OBFC2A), mRNA [NM_001017161] |
| 291 | A_23_P330561 | C19orf59 | CTGTCTCCCTGTTGTGTAAACATACTGTGCGGGGTGTTTTCGTGTCTACCCA | SEQ ID NO: 2643 | Homo sapiens chromosome 19 open reading frame 59 (C19orf59), mRNA [NM_174918] |
| 292 | A_23_P332439 | NUPL1 | ATTGAATCGTGAATGTATTGAATCGTCAAGGTACACAGGGGTCCCTTGTAAATGTC | SEQ ID NO: 2644 | Homo sapiens KIAA0410 mRNA, partial cds. [AB007870] |
| 293 | A_23_P339480 | HAT1 | AACAATGAACAGCTGAAGAGAGTTTTCAGGAACTAGTGGTGTTCTTGAATATTTCAACCGACGGTATTTG | SEQ ID NO: 2645 | Homo sapiens histone acetyltransferase 1 (HAT1), transcript variant 1, mRNA [NM_003642] |
| 294 | A_23_P339554 | MLSTD2 | CAATACCTCGTCTTCACAAAGCTATGGCTGTTCTTGAATATTTCATCAAGTAATTGTTGGG | SEQ ID NO: 2646 | Homo sapiens male sterility domain containing 2 (MLSTD2), mRNA [NM_032228] |
| 295 | A_23_P34307 | PIGK | ATTCATTTCACATGTCTTCTATTGTTGGACCACTTACATTGTACCAAATGTTCTTGG | SEQ ID NO: 2647 | Homo sapiens phosphatidylinositol glycan anchor biosynthesis, class K (PIGK), mRNA [NM_005482] |
| 296 | A_23_P346006 | CCPG1 | TATGGTGGACTAATGGAAGACAAAATGGCAAATCTTGAAATAGAATTGGGGCAATTACCT | SEQ ID NO: 2648 | Homo sapiens cell cycle progression 1 (CCPG1), transcript variant 2, mRNA [NM_020739] |

Fig. 7-17

| No. | Probe ID No. | Symbols of genes | Sequence | SEQ ID NO: | Descriptions of genes (letters and numbers within [ ] indicates GenBank accession No.) |
|---|---|---|---|---|---|
| 297 | A_23_P347059 | MOBKL1A | CTAGAAGGGAAAAATCATCTAAGTTATGAAATCCAACATACGCCCTATATTACAAACTG | SEQ ID NO: 2649 | Homo sapiens MOB1, Mps One Binder kinase activator-like 1A (yeast) (MOBKL1A), mRNA [NM_173468] |
| 298 | A_23_P34710 | EGLN1 | TGATTGTCAAAATGTACAGCCAGCGCTTTAATTGGGAGCCCCTGTGTGTCATTCAAAT | SEQ ID NO: 2650 | Egl nine homolog 1 (EC 1.14.11.-) (Hypoxia-inducible factor prolyl hydroxylase 2) (HIF-prolyl hydroxylase 2) (HIF-PH2) (HPH-2) (Prolyl hydroxylase domain-containing protein 2) (PHD2) (SM-20). [Source:Uniprot/SWISSPROT:Acc:Q9GZT9] [ENST00000357180] |
| 299 | A_23_P347198 | SP3 | GAGGACCTCAAATTTAAAGGCTACCTTATTGTACCTTTAAAGTGTATTATAACAGTGTGG | SEQ ID NO: 2651 | Homo sapiens Sp3 transcription factor (SP3), transcript variant 1, mRNA [NM_003111] |
| 300 | A_23_P349983 | FCHO2 | GTGAAATGTTAAACTCTCTGCACTTTCTTAGTTACCACCAGTCTCATACCAAGTATTGGG | SEQ ID NO: 2652 | Homo sapiens FCH domain only 2 (FCHO2), mRNA [NM_138782] |
| 301 | A_23_P350187 | ENST00000265149 | TTGGTAATATAGGAATATCAGGTTGACTATATAGCCATACTACTTGAAAATGTCTGAGTGG | SEQ ID NO: 2653 | Homo sapiens mRNA for KIAA1546 protein, partial cds. [AB046766] |
| 302 | A_23_P353704 | RP5-1022P6.2 | TGTCTCAGTACTACCTATTACACACTGTGTCTTGTGGGTTTGTTTGTATGTGGGTGTGT | SEQ ID NO: 2654 | Homo sapiens hypothetical protein KIAA1434 (KIAA1434), mRNA [NM_019593] |
| 303 | A_23_P354074 | LYST | GTGGCATGTTGTAGGCAAACATTTGTAAATTATACAAGCTCGTTACCTTTATATACGC | SEQ ID NO: 2655 | Homo sapiens lysosomal trafficking regulator (LYST), transcript variant 1, mRNA [NM_000081] |
| 304 | A_23_P355067 | TMCO1 | AACTCAAGAACTCTTTATTTTCTATCATTCTTCTAGACACACACAGATCAGAGTGGCAA | SEQ ID NO: 2656 | Homo sapiens transmembrane and coiled-coil domains 1 (TMCO1), mRNA [NM_019026] |
| 305 | A_23_P355244 | SAMD9 | TGACTGGAGGAAGATTTTCCGTTGCTTGCTGTCGGATAAAATTTTAAGTCCAATACTTATAGC | SEQ ID NO: 2657 | Homo sapiens sterile alpha motif domain containing 9 (SAMD9), mRNA [NM_017654] |
| 306 | A_23_P356125 | KIAA1468 | GCACTGTCTTTAATTACTGCTGTATATTTTGATTTTGGAGTTACAACTGTGGTGATAG | SEQ ID NO: 2658 | Homo sapiens KIAA1468 (KIAA1468), mRNA [NM_020854] |
| 307 | A_23_P364107 | C14orf106 | AGCAGACAGTGTTTGTATTTTCAAGTGGAGTACAGTATGTATTTGTTTGTAAAGTAGCTTCC | SEQ ID NO: 2659 | Homo sapiens chromosome 14 open reading frame 106 (C14orf106), mRNA [NM_018353] |
| 308 | A_23_P371266 | DNM3 | ACTGTCTTCTTGGCAGTTTCAAGGATTTCTTAATGCTGAATATGGACTTAGAATGGAA | SEQ ID NO: 2660 | Homo sapiens dynamin 3 (DNM3), mRNA [NM_015569] |
| 309 | A_23_P37275 | CGRRF1 | GAGCAAGATAAAGACAAAGAACCGAAGACTCTTTGAAGACATCATCGGTAACACTGAAAAGTACAGT | SEQ ID NO: 2661 | Homo sapiens cell growth regulator with ring finger domain 1 (CGRRF1), mRNA [NM_006568] |
| 310 | A_23_P37441 | B2M | TTGTCCTTCAGCAGGAGGACTGGTCTTTCTATCTCTTGTACTACACTGAATTCACCCCCACT | SEQ ID NO: 2662 | Homo sapiens beta-2-microglobulin (B2M), mRNA [NM_004048] |
| 311 | A_23_P378722 | SAT1 | CCATGTACTATTTTACCTATGACCCGGTGGATTGGCAAGTTATTGTATCTTGAAGAGTTCT | SEQ ID NO: 2663 | Homo sapiens spermidine/spermine N1-acetyltransferase 1 (SAT1), mRNA [NM_002970] |
| 312 | A_23_P383764 | OR52K3P | TGCATCTCTGAGTTGTTGGAAAATTTGGTGAATTATGCACTGAGATTCCCGAGTTAGGAGCC | SEQ ID NO: 2664 | Homo sapiens clone IMAGE:110749 mRNA sequence. [AF143328] |
| 313 | A_23_P38723 | SMCHD1 | ACAAGTACCTGGGCATGAATGAATTTCCAATTCGATTCAGAGGGACTGGAAACAACCATTCAA | SEQ ID NO: 2665 | Homo sapiens cDNA FLJ44350 fis, clone TRACH3006228. [AK126324] |
| 314 | A_23_P38900 | SLC22A15 | AGGGCTAGGCTGGCCATCAGTTGCTTATTTCAGATGTCAGTGTCACTAAATTTTCCTTCTAGATG | SEQ ID NO: 2666 | Homo sapiens solute carrier family 22 (organic cation transporter), member 15 (SLC22A15), mRNA [NM_018420] |

Fig. 7-18

| No. | Probe ID No. | Symbols of genes | Sequence | SEQ ID NO: | Descriptions of genes (letters and numbers within [ ] indicates GenBank accession No.) |
|---|---|---|---|---|---|
| 315 | A_23_P390734 | FGFR1OP2 | CCACCAGATACAGAAAATGTGGTTTAAGATCAGTTGAAACCTAAAT TTCGTTATGTGTGG | SEQ ID NO: 2667 | Homo sapiens FGFR1 oncogene partner 2 (FGFR1OP2), mRNA [NM_015633] |
| 316 | A_23_P394545 | KIAA1033 | AGGATTTGAATACTATTTAATATTCGGCATATTGGTAATTCAATTC GAACACATGGCACGC | SEQ ID NO: 2668 | Homo sapiens KIAA1033 (KIAA1033), mRNA [NM_015275] |
| 317 | A_23_P394605 | SEC24A | GATTTATTTCTTGTAATCAAAGATGCATAACAGCTATTATGTGAGG GGAGCAGCCAAATGTG | SEQ ID NO: 2669 | Homo sapiens SEC24 related gene family, member A (S. cerevisiae) (SEC24A), mRNA [NM_021982] |
| 318 | A_23_P396353 | NIN | ATCTTGCAGGTCTAGTCATTTTAATAATGGACTATTACCCAGGGCA GATATTATGAAGAAAC | SEQ ID NO: 2670 | Homo sapiens ninein (GSK3B interacting protein) (NIN), transcript variant 2, mRNA [NM_020921] |
| 319 | A_23_P398073 | PPM1B | GGTTGAGTAACTTTTCATTTTATAACATGGGCACGGTACAGAGAGT GATTGTCACATAAGG | SEQ ID NO: 2671 | Homo sapiens protein phosphatase 1B (formerly 2C), magnesium-dependent, beta isoform (PPM1B), transcript variant 2, mRNA [NM_177968] |
| 320 | A_23_P398449 | VNN3 | ACATATCATTGTGACCGCAGAAGAATGGAATCTATGGTTGGATCTT CACCAGGGAAGAGCAT | SEQ ID NO: 2672 | Homo sapiens vanin 3 (VNN3), transcript variant 2, mRNA [NM_078625] |
| 321 | A_23_P40108 | COL9A3 | TCAAAAGGGCGTAGCCTAGCTAATAAACCTGTAAGCCGAAGCATTT GAAGAG AAGGTAGGGTGTGTA | SEQ ID NO: 2673 | Homo sapiens collagen, type IX, alpha 3 (COL9A3), mRNA [NM_001853] |
| 322 | A_23_P405873 | C9orf72 | GAGAATTGGAAGATGAAGGGTCAGAGTATTCCAATGGTTACTGTGG AGAAGTGATTGCTGT | SEQ ID NO: 2674 | Homo sapiens chromosome 9 open reading frame 72 (C9orf72), transcript variant 2, mRNA [NM_145005] |
| 323 | A_23_P406986 | MOSPD2 | TTACATTCGAAGGGTAGGTGTTGTGGTTTCATCTTCAAGAAG TTGATTCGAAAACTG | SEQ ID NO: 2675 | Homo sapiens motile sperm domain containing 2 (MOSPD2), mRNA [NM_152581] |
| 324 | A_23_P4096 | CA4 | TAATATGCCCAAACCTGAGATGAGCACTAGGATGGCAGGAGAGCAG CCTGTTGGACCTGCT | SEQ ID NO: 2676 | Homo sapiens carbonic anhydrase IV (CA4), mRNA [NM_000717] |
| 325 | A_23_P41114 | CSTA | AAACAAATGAGAGTTATGGAAAATTGGAAGCTGTGCAGTATAAAA CTCAAGTTGTTGGTA | SEQ ID NO: 2677 | Homo sapiens cystatin A (stefin A) (CSTA), mRNA [NM_005213] |
| 326 | A_23_P412980 | SNX13 | CCCGATCTGAAGCAAGAATGGCGTTGGTTTCTTCGATTTCAAACGT AATCAGGATTCTCCA | SEQ ID NO: 2678 | Homo sapiens sorting nexin 13 (SNX13), mRNA [NM_015132] |
| 327 | A_23_P41645 | ELL2 | TGTCTTTTCAAAGTGGTGCAGATTGAAGAGTTGAAAAGGAAGCATTATGTTT ACAAATCTGTTTTGA | SEQ ID NO: 2679 | Homo sapiens elongation factor, RNA polymerase II, 2 (ELL2), mRNA [NM_012081] |
| 328 | A_23_P41664 | ENST00000334994 | TGGCTGGAGCAGATTCGACTTCATAAACAAATTGTCCTGAAAA TGAGGCACAGGTCAT | SEQ ID NO: 2680 | Syntaurin (Q5LQI8891) [Source:Uniprot/SPTREMBL;Acc:Q72297] [ENST00000334994] |
| 329 | A_23_P420431 | XKR3 | CAGAGGTGGGCAGGTGGGCCATAGAATGGTACACTACAGCTTTCAGTTTTT AGAAAATGTGATAAT | SEQ ID NO: 2681 | Homo sapiens XK, Kell blood group complex subunit-related family, member 3 (XKR3), mRNA [NM_175878] |
| 330 | A_23_P422083 | TMEM55A | AAATTTATGGAATCAGCTGTCGGACGTGTCGCCATCTTTGCAGTTTG AAAAACAAATTGCTT | SEQ ID NO: 2682 | Homo sapiens transmembrane protein 55A (TMEM55A), mRNA [NM_018710] |
| 331 | A_23_P424080 | YIPF4 | AAAGCATTGTGTTTTAAGATGTGTCGATATTAACACAGGAACATGAG TGTGGCAAAAGGAGC | SEQ ID NO: 2683 | Homo sapiens Yip1 domain family, member 4 (YIPF4), mRNA [NM_032312] |
| 332 | A_23_P427217 | JMJD1C | TCCAGAACATCTGTAGAGTACATTTCATTTAACACAGGAACATGAA AGTTTTTGAAGGAAGA | SEQ ID NO: 2684 | Homo sapiens jumonji domain containing 1C (JMJD1C), transcript variant 2, mRNA [NM_004241] |
| 333 | A_23_P429431 | FLJ25416 | GCTTGGTCACCTGAATTGTTTGATAAAAGTCACCTGAAGCGAA TTCCTGAAGTTTAA | SEQ ID NO: 2685 | Homo sapiens hypothetical protein FLJ25416 (FLJ25416), mRNA [NM_145018] |
| 334 | A_23_P429689 | FAM44A | ACCAATACTCTTTGCATATTGTCTTTTGAGTGAAGAGAAATGCA TTCAAGAATTAGGTCC | SEQ ID NO: 2686 | Homo sapiens family with sequence similarity 44, member A (FAM44A), mRNA [NM_148894] |

Fig. 7-19

| No. | Probe ID No. | Symbols of genes | Sequence | SEQ ID NO: | Descriptors of genes (letters and numbers within [ ] indicates GenBank accession No.) |
|---|---|---|---|---|---|
| 335 | A_23_P42969 | FGL2 | TTGAGGTGGTTGGTTTGATGCATGTCTTTCTGCAAAGTTAAATGGCAAATATTATCACCA | SEQ ID NO: 2687 | Homo sapiens fibrinogen-like 2 (FGL2), mRNA [NM_006682] |
| 336 | A_23_P42975 | PRKAR2B | GCCACATTTTAGAACAGTGTTAACATTTTGGAAAACGTTCTTGTAGGAAAAGAGAGG | SEQ ID NO: 2688 | Homo sapiens protein kinase, cAMP-dependent, regulatory, type II, beta (PRKAR2B), mRNA [NM_002736] |
| 337 | A_23_P430161 | EXOC8 | AAGTACAGGATTTCTTGAGGTAAAATGTGTGTGTTCCAATTACAGTTGTAGGTGAAGGA | SEQ ID NO: 2689 | Homo sapiens exocyst complex component 8 (EXOC8), mRNA [NM_175876] |
| 338 | A_23_P431630 | USP32 | CCACTACCCTTCTTGTTCCTCATAGATAGTAGTAATGATAGGAATGTAACTAAGTATTGTGTGTG | SEQ ID NO: 2690 | Homo sapiens ubiquitin specific peptidase 32 (USP32), mRNA [NM_032582] |
| 339 | A_23_P434809 | S100A8 | AAAGGCCATGAAGAAGGCAGCAAAGAGTAGGTGAGTTAGTGGGAGCCAGAGGGTGGGCCCCT | SEQ ID NO: 2691 | Homo sapiens S100 calcium binding protein A8 (S100A8), mRNA [NM_002964] |
| 340 | A_23_P44257 | COMMD8 | AACATTTACTTCTGGGCTTCTATGTTTGGGAAAGATTGCTCTGATAAAAATAGGTGTC | SEQ ID NO: 2692 | Homo sapiens COMM domain containing 8 (COMMD8), mRNA [NM_017845] |
| 341 | A_23_P44768 | TBK1 | TGTACTGTGAGTGGGGTCAAATAAGTTATTTCTCTCACGGGTACTGGAAATATTTTA | SEQ ID NO: 2693 | Homo sapiens TANK-binding kinase 1 (TBK1), mRNA [NM_013254] |
| 342 | A_23_P46141 | CTSS | TGTGTTGGTGTAGATGCGGCGTGAGGCTCATGGTCTGCTTCTTCTTGCTCTCACGAAGAGTGTGTGCTAT | SEQ ID NO: 2694 | Homo sapiens cathepsin S (CTSS), mRNA [NM_004079] |
| 343 | A_23_P46396 | PTBP2 | AACCAGGTGGACCAAAGTTTATGTGCCGTTTAGTCTTAATTACCTTGCATGGTAATATT | SEQ ID NO: 2695 | Homo sapiens polypyrimidine tract binding protein 2 (PTBP2), mRNA [NM_021190] |
| 344 | A_23_P48186 | TWF1 | TGGAGCAGACCATAGGTGAAGCTGTTTATTTCAGTCAGGAAGAGTAACCTGCTGAAGGT | SEQ ID NO: 2696 | Homo sapiens twinfilin, actin-binding protein, homolog 1 (Drosophila) (TWF1), mRNA [NM_002822] |
| 345 | A_23_P48897 | CCPG1 | AAGTCAGAAGGCTCATATATATAATTGTAATGTCCCAGCTATGTCCATTCGATGTACCA | SEQ ID NO: 2697 | Homo sapiens cell cycle progression restoration protein (CPR8) mRNA, complete cds [AF011794] |
| 346 | A_23_P50108 | NDC80 | AAAGTTGGGAAATAAACTTGGAACGTCGTGTTAGAGATGGTTGGTAGACATGTTGGGTCTGTGTA | SEQ ID NO: 2698 | Homo sapiens NDC80 homolog, kinetochore complex component (S. cerevisiae) (NDC80), mRNA [NM_006101] |
| 347 | A_23_P502797 | WDFY1 | GTAAGAGTTACTGGTTGTTCCATTCCTGAATATGCAGGCTAATTTGTACAGATAGGGAT | SEQ ID NO: 2699 | Homo sapiens WD repeat and FYVE domain containing 1 (WDFY1), mRNA [NM_020830] |
| 348 | A_23_P50907 | ITGAV | AAAAGAGTGATTAAGTCAAGTCGAGGGTTATTTACGCGCTAAATGCTTCGATTCTGCCATTGTATTTCAGG | SEQ ID NO: 2700 | Homo sapiens integrin, alpha V (vitronectin receptor, alpha polypeptide, antigen CD51) (ITGAV), mRNA [NM_002210] |
| 349 | A_23_P50974 | HECW2 | GACAAAGATGAAGACCCATACAACATGATCAGCTCGACGGGTAATTTTTAGGGACTGAGGAGAATC | SEQ ID NO: 2701 | Homo sapiens HECT, C2 and WW domain containing E3 ubiquitin protein ligase 2 (HECW2), mRNA [NM_020760] |
| 350 | A_23_P51009 | NDUFB3 | GGGAAGTGAAGGTTGGAGATACATGGGTGGCTTGGAAAGAGTGTTCCTTTTCTGATGT | SEQ ID NO: 2702 | Homo sapiens NADH dehydrogenase (ubiquinone) 1 beta subcomplex, 3, 12kDa (NDUFB3), mRNA [NM_002491] |
| 351 | A_23_P51996 | STXBP3 | ATTTCAGTCGATTAATAGAATGGAGTGCATTTAACACTACAGAGTGTGTACTGTTTGGCACATAGTTC | SEQ ID NO: 2703 | Homo sapiens syntaxin binding protein 3 (STXBP3), mRNA [NM_007269] |
| 352 | A_23_P53467 | IKIP | GTTTAGAACCATTAGTAAATGAATTAACAACTACAGCATTGGGAGAATTGGTTAGGGAGTTAC | SEQ ID NO: 2704 | Homo sapiens IKK interacting protein (IKIP), transcript variant 2, mRNA [NM_201612] |
| 353 | A_23_P53663 | NFYB | TGGGCTGATATTGTGCAATACATTTGTAAGCTGGTGTTTTTTGACTTAAGCAATATATTTGGG | SEQ ID NO: 2705 | Homo sapiens nuclear transcription factor Y, beta (NFYB), mRNA [NM_006166] |

Fig. 7-20

| No. | Probe ID No. | Symbols of genes | Sequence | SEQ ID NO: | Descriptions of genes (letters and numbers within [ ] indicates GenBank accession No.) |
|---|---|---|---|---|---|
| 354 | A_23_P53891 | KLF5 | CGTTGAATTGATGATGGAGTTTCATATATCGAGATGTTCGCTCGTGCAGTCAGTCTTGGT | SEQ ID NO: 2706 | Homo sapiens Kruppel-like factor 5 (intestinal) (KLF5), mRNA [NM_001730] |
| 355 | A_23_P5611 | RIF1 | TGTATTCTTGGGTGCTATGGGTGGTTTTGAAGGAAATTTAATTATCTTACTCAGATGTG | SEQ ID NO: 2707 | Homo sapiens RAP1 interacting factor homolog (yeast) (RIF1), mRNA [NM_018151] |
| 356 | A_23_P56734 | HNMT | CCTTTGTCCACCATGGATATATCTGAGCTGGTTTATTGATGGTAATGAAAATGGAGACCT | SEQ ID NO: 2708 | Homo sapiens histamine N-methyltransferase (HNMT), transcript variant 1, mRNA [NM_006895] |
| 357 | A_23_P56759 | KRCC1 | GATATCCGTGTTGATACCACTTTCGTTATGTGAATAAGGTTCTTAACTTCTAACAAAGGC | SEQ ID NO: 2709 | Homo sapiens lysine-rich coiled-coil 1 (KRCC1), transcript variant 1, mRNA [NM_016618] |
| 358 | A_23_P57658 | HRASLS | GATGGAGAGGAAAAGAAAACCTGGGGTGAATACTATTTTCAGTGCATCATTACTGTTCG | SEQ ID NO: 2710 | Homo sapiens HRAS-like suppressor (HRASLS), mRNA [NM_020386] |
| 359 | A_23_P57856 | BCL6 | CTGGGTTAAAGGCTCGATTTGTATCTGCAGGCGAGACGGATCTGAGAATGTTTATTGA | SEQ ID NO: 2711 | Homo sapiens B-cell CLL/lymphoma 6 (zinc finger protein 51) (BCL6), transcript variant 2, mRNA [NM_138931] |
| 360 | A_23_P58390 | C4orf32 | TAATACTAAGCATTTTAGTATACGTCAGTACTGTAGATCTGCACAGTGGTGTTAATAGGG | SEQ ID NO: 2712 | Homo sapiens chromosome 4 open reading frame 32 (C4orf32), mRNA [NM_152400] |
| 361 | A_23_P58912 | SLC35A1 | ATGATGAGTGCGGTTATGTGGAAAACAACAAGAAACAAAACAGAAGCTATCTGAGTGAACTGC | SEQ ID NO: 2713 | Homo sapiens solute carrier family 35 (CMP-sialic acid transporter), member A1 (SLC35A1), mRNA [NM_006416] |
| 362 | A_23_P59637 | DOCK4 | TTTGGCAGTGAGCAGTTGAATTTATCTGAATTTATCATGTGTGTGTATTTCTGAAGCAG | SEQ ID NO: 2714 | Homo sapiens dedicator of cytokinesis 4 (DOCK4), mRNA [NM_014705] |
| 363 | A_23_P59921 | SUB1 | CAGATTCAGAAAATGAGGTACGTTAGTGTCGGATTTTAAAGGCAAAGTGCTAATTGAT | SEQ ID NO: 2715 | Homo sapiens SUB1 homolog (S. cerevisiae) (SUB1), mRNA [NM_006713] |
| 364 | A_23_P60565 | ZNF354A | AAACCAAAAGCTCATGCAGAAGAATACATGCTTGAGAGAGATGGTAATAAATGTAATGGATGTG | SEQ ID NO: 2716 | Homo sapiens zinc finger protein 354A (ZNF354A), mRNA [NM_005649] |
| 365 | A_23_P61674 | CLK4 | GAAAGGCATCGAGTTTGCCATTGTGACAGTTTGTTTAAAAAACCACATACAGAGTTTA | SEQ ID NO: 2717 | Homo sapiens CDC-like kinase 4 (CLK4), mRNA [NM_020666] |
| 366 | A_23_P62227 | CXorf21 | ACGAAGACTTTATCCATTTATTCTGAGAATGTGCAGGAGGGGTTAGTGAAGGGGGAATTAA | SEQ ID NO: 2718 | Homo sapiens chromosome X open reading frame 21 (CXorf21), mRNA [NM_025159] |
| 367 | A_23_P63343 | UTS2 | AGAATCTGGAAAGCCATACAAGAAAGTGAGACTGGTGATTGCTTCTGGAAATACTGTGTC | SEQ ID NO: 2719 | Homo sapiens urotensin 2 (UTS2), transcript variant 1, mRNA [NM_021995] |
| 368 | A_23_P63655 | ATP5C1 | AGAGAGGCTGAAACAGCCTCGAATATATGGATTTTAGGTCTGTATGAAAAGGT | SEQ ID NO: 2720 | Homo sapiens ATP synthase, H+ transporting, mitochondrial F1 complex, gamma polypeptide 1 (ATP5C1), nuclear gene encoding mitochondrial protein, transcript variant 2, mRNA [NM_005174] |
| 369 | A_23_P63396 | FAS | ATGTCATCCACAGGGTAACCGACTGTATGAATCAATAGAAGAAGCATCACGTTTGC | SEQ ID NO: 2721 | Homo sapiens Fas (TNF receptor superfamily, member 6) (FAS), transcript variant 1, mRNA [NM_000043] |
| 370 | A_23_P65262 | RP11-288P3.3 | AGCCAAGACTTAACAAGGACTGACTCTAAGCGGTACCGGTTCCCTTGAGCTACCA | SEQ ID NO: 2722 | Human BRCA2 region, mRNA sequence CG016. [U50529] |
| 371 | A_23_P65768 | C15orf15 | TCCTGCATTGGATCTACATAATATCAGATATTAGGATGTTAGATTGGAAATCGACGTGT | SEQ ID NO: 2723 | Homo sapiens chromosome 15 open reading frame 15 (C15orf15), mRNA [NM_016304] |
| 372 | A_23_P66260 | ZNF267 | TGTGATGAATGTGGTAAAGCGTTCAGGTATAAGGTACATACGTCAGTACACAGTCACTGTTGC | SEQ ID NO: 2724 | Homo sapiens zinc finger protein 267 (ZNF267), transcript variant 1, mRNA [NM_003414] |

Fig. 7-21

| No. | Probe ID No. | Symbols of genes | Sequence | SEQ ID NO: | Descriptions of genes (letters and numbers within [ ] indicates GenBank accession No.) |
|---|---|---|---|---|---|
| 373 | A_23_P68472 | DPM1 | CTATTGGCGAGGTTCCAATATCATTTGTGGATCGTGTTTATGGTGAATCCAAGTTGGGAG | SEQ ID NO: 2725 | Homo sapiens dolichyl-phosphate mannosyltransferase polypeptide 1, catalytic subunit (DPM1), mRNA [NM_003859] |
| 374 | A_23_P69109 | PLSCR1 | GTTAGGTCTTAGACGTCTATCGTTGCTAGAAATGGTAATTGAGATTACTCAGATATTAA | SEQ ID NO: 2726 | Homo sapiens phospholipid scramblase 1 (PLSCR1), mRNA [NM_021105] |
| 375 | A_23_P6914 | OSBPL11 | GGTGTTGGAATCAAGTGTGTGGTAACATACCTGTTGTTGTTTATCAGCCATTGTAGGTGGCTGTG | SEQ ID NO: 2727 | Homo sapiens oxysterol binding protein-like 11 (OSBPL11), mRNA [NM_022776] |
| 376 | A_23_P69808 | GLRX | CTGATAAAAGTTACAGCCCCCTACACCAAGAGTGTATCTGTGAAAGAGCTCCTACACTTT | SEQ ID NO: 2728 | Homo sapiens glutaredoxin (thioltransferase) (GLRX), mRNA [NM_002064] |
| 377 | A_23_P70290 | TMEM30A | ATGTTCTGCCTCAACTGTAAACGACAATGTAAGTGCTTAATGGAGACTGTTTTTCATTGTG | SEQ ID NO: 2729 | Homo sapiens transmembrane protein 30A (TMEM30A), mRNA [NM_018247] |
| 378 | A_23_P70297 | ANKRD6 | CCTTGTTGTGGAGTCAAGTGTTGATATACTTGAGGCATGTTATGTGTGTTGTAATTAAT | SEQ ID NO: 2730 | Homo sapiens mRNA for KIAA0957 protein, partial cds. [AB023174] |
| 379 | A_23_P70328 | CENPQ | CAATGGCTACAGTTTCTGTCTGGTCATGTGGAAACTTGAAAAATGCTCAAATGGCTTGAC | SEQ ID NO: 2731 | Homo sapiens centromere protein Q (CENPQ), mRNA [NM_018132] |
| 380 | A_23_P70936 | STARD3NL | GCATTAGTGTGATGGCCTGAAGTGTTGGACTTGCAAAGAGGGAAGAAAGGAATTGGGAAT | SEQ ID NO: 2732 | Homo sapiens STARD3 N-terminal like (STARD3NL), mRNA [NM_032016] |
| 381 | A_23_P71430 | UBE2W | AAATTGTGAAAGGTCCAGTCTCAGTACCATGTGAGTTAATGAATACTACAACTAAGTTC | SEQ ID NO: 2733 | Homo sapiens ubiquitin-conjugating enzyme E2W (putative) (UBE2W), transcript variant 1, mRNA [NM_001001481] |
| 382 | A_23_P71433 | UBE2W | CATGAGCCCTACTGCCTAAAACAGTCATTTGATTTATTTATGTTGGAAACGCGTAAGAT | SEQ ID NO: 2734 | Homo sapiens ubiquitin-conjugating enzyme E2W (putative) (UBE2W), transcript variant 1, mRNA [NM_001001481] |
| 383 | A_23_P72503 | KLHL2 | TTTTGATATTTAACAATGCTTAACAGTTTAAATGGGACTTGTGAGGAATGGAGCTGGTG | SEQ ID NO: 2735 | Homo sapiens kelch-like 2, Mayven (Drosophila) (KLHL2), mRNA [NM_007246] |
| 384 | A_23_P7282 | MARCH1 | GATTATTGTGTTCTTTGGATATTCATGTGAAAACTGATGTGTGAATGACATTGCAGTGAGC | SEQ ID NO: 2736 | Homo sapiens cDNA FLJ20668 fis, clone KAIA585. [AK006751] |
| 385 | A_23_P7282 | ELMOD2 | TTCAAGTAGCTTTCTCCTGGGGGAAAAAGTAGGACGTTGGACACTTAAAGGAATTGGGATTT | SEQ ID NO: 2737 | ELMO domain-containing protein 2 [Source:Uniprot/SWISSPROT;Acc:Q8IZ81] [ENST00000323570] |
| 386 | A_23_P74001 | S100A12 | GGAAGGCTTTTTACCCAGCGAATGCGGTGAATGAGGGTCTTTTCTTTCCGTGACAAAACC | SEQ ID NO: 2738 | Homo sapiens S100 calcium binding protein A12 (S100A12), mRNA [NM_005621] |
| 387 | A_23_P75028 | REEP3 | AGAAACGACCACACAAGTGTATTTTTAGTCATCTACAGGTGCACAAGCTCCAAATATCCCAAGACAGATTAT | SEQ ID NO: 2739 | Homo sapiens receptor accessory protein 3 (REEP3), mRNA [NM_001001330] |
| 388 | A_23_P7543 | ZFYVE16 | TCTGTGGGTGAGCATTATCCTAAAATGATCTTGATAGTGCTCTGATACCTGTGATCCATGCTGTCG | SEQ ID NO: 2740 | Homo sapiens zinc finger, FYVE domain containing 16 (ZFYVE16), mRNA [NM_014733] |
| 389 | A_23_P75769 | MS4A4A | GACGAAAAGATGACAAGAGACAATGGGGTAGAATGGAATGCTACATTCTATGCTGACTGTGACAAGAGCCT | SEQ ID NO: 2741 | Homo sapiens membrane-spanning 4-domains, subfamily A, member 4 (MS4A4A), transcript variant 1, mRNA [NM_024021] |
| 390 | A_23_P76480 | BF213738 | AAATGAAACAAGGACAATGGGTAGAATGGAATGCTACATTACCAAATCGTTGGCATGCACAGG | SEQ ID NO: 2742 | BF213738 601847628F1 NIH_MGC_55 Homo sapiens cDNA clone IMAGE:4075519 5', mRNA sequence [BF213738] |

Fig. 7-22

| No. | Probe ID No. | Symbols of genes | Sequence | SEQ ID NO: | Descriptions of genes (letters and numbers within) ; [ ] indicates GenBank accession No.) |
|---|---|---|---|---|---|
| 391 | A_23_P76799 | BAZ1A | TACAACATGAATGAATCGAATCTTATAACCTTGAAGTGCGTGTACCAGTGCTGGCTGCAGGT | SEQ ID NO: 2743 | Homo sapiens bromodomain adjacent to zinc finger domain, 1A (BAZ1A), transcript variant 1, mRNA [NM_013448] |
| 392 | A_23_P76951 | TXNDC1 | ATTTCTGTAATGTCCCGTTCTTTCTCAGGCTCTGTTGCTGTGTGAATGCATTAGATTTACA | SEQ ID NO: 2744 | Homo sapiens thioredoxin domain containing 1 (TXNDC1), mRNA [NM_030755] |
| 393 | A_23_P77286 | C15orf29 | TGGTTTACAGTTAATGCTGATCTGTATTTAAATTCAACACTTTGTGTCAGTACGTGG | SEQ ID NO: 2745 | Homo sapiens chromosome 15 open reading frame 29 (C15orf29), mRNA [NM_024713] |
| 394 | A_23_P78092 | EVI2A | GCTGAATCAGACAGTTGGAAAAAGAAGAAAAACAGCTCACAGGAGCCAAGCTAGTGATGCAA | SEQ ID NO: 2746 | Homo sapiens ecotropic viral integration site 2A (EVI2A), transcript variant 1, mRNA [NM_001003927] |
| 395 | A_23_P81248 | TAF7 | TGCTAGTTTGCATATGTTTCCTATGCAATAGTGTTGTTTCCCAGTTATTCAAAGGAGGTT | SEQ ID NO: 2747 | Homo sapiens TAF7 RNA polymerase II, TATA box binding protein (TBP)-associated factor, 55kDa (TAF7), mRNA [NM_005642] |
| 396 | A_23_P83047 | BU507302 | TCTGTTTCGTTAATGTCAGGCTGCCTGAACATTCAGCAGTTATAAATTGCTAATTTGTG | SEQ ID NO: 2748 | AGENCOURT_10306666 NIH_MGC_71 Homo sapiens cDNA clone IMAGE:6501220 5'. mRNA sequence [BU507302] |
| 397 | A_23_P8281 | IFNGR1 | CTTTAGATCCAGATAGGTTACCAGTGAACGGAACAGTATCAGTACTCCTGGTTCTAGGT | SEQ ID NO: 2749 | Homo sapiens interferon gamma receptor 1 (IFNGR1), mRNA [NM_000416] |
| 398 | A_23_P83073 | HIATL1 | AAACAACTCAAGCATTCTGGTGGCAACATAGAGATTGAGGCTGCTTCTAAGAAAGTTAT | SEQ ID NO: 2750 | Homo sapiens hippocampus abundant transcript-like 1 (HIATL1), mRNA [NM_032558] |
| 399 | A_23_P83094 | TLE4 | ACGTCCCTCTGAAAAACAAGAATGGACTCTCTCCTGGGATGAGGACTTGCTTGTTT | SEQ ID NO: 2751 | Homo sapiens transducin-like enhancer of split 4 (E(sp1) homolog, Drosophila) (TLE4), mRNA [NM_007005] |
| 400 | A_23_P83175 | PTPLAD2 | CATGCTTTTGTGTGATGACGAGTGAAGAGGAAGTCAAGAGAAATATGTCGTCGTCGT | SEQ ID NO: 2752 | Homo sapiens protein tyrosine phosphatase-like A domain containing 2 (PTPLAD2), mRNA [NM_001010915] |
| 401 | A_23_P83278 | CHMP5 | CATTGCTCTTTTATTTTTCCATTAAGAGACTCATTGCTGGGAAAATGGTTCTTCTAC | SEQ ID NO: 2753 | Homo sapiens chromatin modifying protein 5 (CHMP5), mRNA [NM_016410] |
| 402 | A_23_P84070 | LARP7 | TGATTTGCTAGAAGGGATACAGAGAATGCCATGCTAGATTTAAGACTCCTGAGGATGCTCA | SEQ ID NO: 2754 | Homo sapiens La ribonucleoprotein domain family, member 7 (LARP7), transcript variant 1, mRNA [NM_016648] |
| 403 | A_23_P8513 | SNX10 | TTTAAGAGGCATCCTCATCCGTTCAGCAATATGTATTTGAGTTGACACTATTTCTGTTT | SEQ ID NO: 2755 | Homo sapiens sorting nexin 10 (SNX10), mRNA [NM_013322] |
| 404 | A_23_P86653 | SRGN | AGGACTTGGGTCAACATGGATTAGAAGAGATTTATGTTATAAAGAGATTTTCGCAC | SEQ ID NO: 2756 | Homo sapiens serglycin (SRGN), mRNA [NM_002727] |
| 405 | A_23_P67879 | CD69 | TGTGCAATATGATGTGCAAAGATCTCATTAGGAAATATTCTGTAATCTTCAGACGTAG | SEQ ID NO: 2757 | Homo sapiens CD69 molecule (CD69), mRNA [NM_001781] |
| 406 | A_23_P89755 | RNF138 | TGTGACCGTGATATGTCAGAAAGATTCTACCAACCACTGTTCACTACTTTTAGTTAA | SEQ ID NO: 2758 | Homo sapiens ring finger protein 138 (RNF138), transcript variant 1, mRNA [NM_016271] |
| 407 | A_23_P9056 | RB1CC1 | TTCATTTCTCAAAGGGCATACCTTGTGCATTGTGGGTTATGATGAGGCATATTAATTGC | SEQ ID NO: 2759 | Homo sapiens RB1-inducible coiled-coil 1 (RB1CC1), mRNA [NM_014781] |
| 408 | A_23_P91346 | BC008667 | GGGCTTAGGAGTGAGATTTCTGGTCTACAGAAATGATGCTCATGAATTTTGACATTT | SEQ ID NO: 2760 | Homo sapiens cDNA clone MGC:17708 IMAGE:3868595, complete cds. [BC008667] |

Fig. 7-23

| No. | Probe ID No. | Symbols of genes | Sequence | SEQ ID NO: | Descriptions of genes (letters and numbers within [ ] indicates GenBank accession No.) |
|---|---|---|---|---|---|
| 409 | A_23_P92410 | CASP3 | TGCACCAAGTGTCACTGGCGTCAGTATGACATTTGACGGGAGAT TTCTGTTGCTCAAA | SEQ ID NO: 2761 | Homo sapiens caspase 3, apoptosis-related cysteine peptidase (CASP3), transcript variant alpha, mRNA [NM_004346] |
| 410 | A_23_P94216 | LONRF1 | GGGTCATTTATTGCCCAAGTTACAAGAGTAGGAGGATACAAGTTTT TGAAATTGAATTG | SEQ ID NO: 2762 | Homo sapiens LON peptidase N-terminal domain and ring finger 1 (LONRF1), mRNA [NM_152271] |
| 411 | A_23_P94230 | LY96 | TGAAGCTATTTCTGGGAGGCCAGAAGAAAACTAAACATTCCGTTGCTTGTCAAGC GTTTGTCATCCTAGA | SEQ ID NO: 2763 | Homo sapiens lymphocyte antigen 96 (LY96), mRNA [NM_015364] |
| 412 | A_23_P94501 | ANXA1 | GGCTGTTTGTGGAGGAAAACTAAACATTCCGTTGATGGTGTCAAGGC TATGATCAGAAGACT | SEQ ID NO: 2764 | Homo sapiens annexin A1 (ANXA1), mRNA [NM_000700] |
| 413 | A_23_P95130 | SLC37A3 | TTGAGGGATAGCTAATTTGCATTCCGGTTAGGGGATATTTTCAAG CTCTGCTTTATAGT | SEQ ID NO: 2765 | Homo sapiens solute carrier family 37 (glycerol-3-phosphate transporter), member 3 (SLC37A3), transcript variant 1, mRNA [NM_207113] |
| 414 | A_23_P95594 | NAT1 | TGCTTGCAGAGAAAGCTAATTGTGGCCAAACATGGTGATAGATTTTT ACTATTTAGAAATAAG | SEQ ID NO: 2766 | Homo sapiens N-acetyltransferase 1 (arylamine N-acetyltransferase) (NAT1), mRNA [NM_000662] |
| 415 | A_23_P9574 | ECT2 | TAATAGTTAAGTGACTATAGAATTGTTTCTATGCATGTATGTGC CACTCTGAGAGTAG | SEQ ID NO: 2767 | Homo sapiens epithelial cell transforming sequence 2 oncogene (ECT2), mRNA [NM_018098] |
| 416 | A_23_P98085 | PTEN | ACAGGACGAACATGACTTAACCATAAACATATAAATGTGGAGGCTATCAACAA AGAAATGGGCTTGAAA | SEQ ID NO: 2768 | Homo sapiens phosphatase and tensin homolog (mutated in multiple advanced cancers 1) (PTEN), mRNA [NM_000314] |
| 417 | A_23_P98382 | TIMM8B | TTGTTACTAAGGACAGATTTAAGGGTCAGTGGGGGAAGGCTATCAAG CCATTCTCAGATCAG | SEQ ID NO: 2769 | Homo sapiens translocase of inner mitochondrial membrane 8 homolog B (yeast) (TIMM8B), mRNA [NM_012459] |
| 418 | A_23_P98830 | C12orf35 | CCCATCTTGAGGGAGGAGACCGTTGCTCAGTTAAGGACTTGTTTATT TAAATGGGAGCTGTGTAA | SEQ ID NO: 2770 | Homo sapiens chromosome 12 open reading frame 35 (C12orf35), mRNA [NM_018169] |
| 419 | A_23_P99163 | DRAM | GCTCACGATGGAGTTTACAATGCTTCATTTCCACATCTGTCTGCACA ATTAGATTGGGAGCT | SEQ ID NO: 2771 | Homo sapiens damage-regulated autophagy modulator (DRAM), mRNA [NM_018370] |
| 420 | A_23_P99405 | ZMYM2 | GCTGGGTATTACCATGAAATAATCTGTGAGTGAAAGTTGCCATT ATTGTATATAGTGGT | SEQ ID NO: 2772 | Homo sapiens zinc finger, MYM-type 2 (ZMYM2), mRNA [NM_003453] |
| 421 | A_23_P99442 | FLT3 | GTTTTGTTACTGCTTGTTGAAGCCACTCATTGACATGTTGCAATAGG ATCATCCCTTGCACAA | SEQ ID NO: 2773 | Homo sapiens fms-related tyrosine kinase 3 (FLT3), mRNA [NM_004119] |
| 422 | A_23_P99853 | KIAA1370 | CTTTTGTTGCTAGTTGTGAAACCACTGATTGGACATGTGCAATAGG AAAAGGCCCAGTTAG | SEQ ID NO: 2774 | Homo sapiens KIAA1370 (KIAA1370), mRNA [NM_019600] |
| 423 | A_23_P99980 | HMGB1 | GGATTCTTCATTTGAATTTGTATTGTTTATGTAATTCAGGAGGAATA CTGAACATCTGAGTC | SEQ ID NO: 2775 | Homo sapiens high-mobility group box 1 (HMGB1), mRNA [NM_002128] |
| 424 | A_23_P99985 | HMGB1 | TGGGCCAGGTTTCAAACAAGATGGCACATTGAAAATAGGGTAT ATTTCCTATATTAG | SEQ ID NO: 2776 | Homo sapiens high-mobility group box 1 (HMGB1), mRNA [NM_002128] |
| 425 | A_24_P100387 | GK | TAAAAGTTCTGTTTGTTTGTTTGGGATCAAGATGGTAGCTTTATTGACT GGTGTAATTGTGCTG | SEQ ID NO: 2777 | Homo sapiens glycerol kinase (GK), transcript variant 1, mRNA [NM_203391] |
| 426 | A_24_P105648 | BX111927 | TTATGAGATGGTTCAGTTCAAATAAGAGTGCAGTAATTCACGTAT ATCTAAAAGACTGCC | SEQ ID NO: 2778 | BX111927 Soares_multiple_sclerosis_2NbHMSP Homo sapiens cDNA clone IMAGp998G05619, mRNA sequence [BX111927] |
| 427 | A_24_P105913 | THC2606573 | GTTGGCTGCAGGAAATGCAGCAATACCAAAGGTCAATGTCAATGTGGAAAT ATGGGCATGTTTGCG | SEQ ID NO: 2779 | AY151386 NAP1 [Homo sapiens] (exp=-1; wgp=0; cg=0), partial (35%) mRNA sequence [THC2606573] |

Fig. 7-24

| No. | Probe ID No. | Symbols of genes | Sequence | SEQ ID No. | Descriptions of genes (letters and numbers within [ ] indicates GenBank accession No.) |
|---|---|---|---|---|---|
| 428 | A_24_P107257 | LIN7C | TATTAGTGTGGGACTGTGACTGAGGTCTTAAAGACTGAAAGAGTTGGGGTTCATTTTCTG | SEQ ID NO: 2780 | Homo sapiens lin-7 homolog C (C. elegans) (LIN7C), mRNA [NM_018362] |
| 429 | A_24_P11045 | THC2785765 | GGAGCAGAAACGTACACCTGATTTCATGACAAATACAGTAGGAACACAAGTCGGAATAG | SEQ ID NO: 2781 | COX7B_HUMAN (P24311) Cytochrome c oxidase polypeptide VIIb, mitochondrial precursor, partial (78%) [THC2785765] |
| 430 | A_24_P114249 | GALNT3 | ATTTGAAATGGCAGAATACTTGACTCATTTAAAGGTAAATTTTGTTACTGATTGAATTATA | SEQ ID NO: 2782 | Homo sapiens UDP-N-acetyl-alpha-D-galactosamine:polypeptide N-acetylgalactosaminyltransferase 3 (GalNAc-T3) (GALNT3), mRNA [NM_004482] |
| 431 | A_24_P115774 | BIRC2 | GATACCATTTTGGTTAAAGGAAATGCTGGGGCCACATCTTGAAAAAGTGTCTAAAAGAA | SEQ ID NO: 2783 | Homo sapiens baculoviral IAP repeat-containing 2 (BIRC2), mRNA [NM_001166] |
| 432 | A_24_P118766 | ZNF207 | TTTCTGAGACCAGCTATACCAGTGAAAATTACCTTCTGAGTAAATTTGTAATTTATGCCC | SEQ ID NO: 2784 | Homo sapiens mRNA; cDNA DKFZp761N202 (from clone DKFZp761N202). [AL834501] |
| 433 | A_24_P123521 | CLK4 | CGCACAGTGAAAAAGACAGATATCAAAGTTGTTGACTTTGGAAGTGGAACGTATGATGAT | SEQ ID NO: 2785 | Homo sapiens CDC-like kinase 4 (CLK4), mRNA [NM_020666] |
| 434 | A_24_P124325 | IKZF5 | GCTACAAGTCTTGAACTTCAAGTTAAGGGCTAAGAATTTACTTTGAAAAAATTCCAGTGG | SEQ ID NO: 2786 | Homo sapiens mRNA; cDNA DKFZp781B0249 (from clone DKFZp781B0249). [CR749800] |
| 435 | A_24_P124992 | PSMA4 | AAACGTCCCTTTCTTGTTTCATTGGTGTAGATGGCTGGGATAAGCAGTATGGGTTTCAG | SEQ ID NO: 2787 | Homo sapiens proteasome (prosome, macropain) subunit, alpha type, 4 (PSMA4), mRNA [NM_002789] |
| 436 | A_24_P126060 | DDX3X | TGTTGAACGGCAGGTTGTCTAGGAAGGGATGGGACTAGAATTCTAAAATTTATTTGGACC | SEQ ID NO: 2788 | Homo sapiens DEAD (Asp-Glu-Ala-Asp) box polypeptide 3, X-linked (DDX3X), mRNA [NM_001356] |
| 437 | A_24_P126741 | ENST00000309178 | AGCCTCGAACCACACTAACAACAGATTCAAGATTAGTTGCAACAGCTCAGAGAGCGAGAAT | SEQ ID NO: 2789 | |
| 438 | A_24_P129232 | SERINC1 | CAGGGTCAGAAGAATGACTTAGTTGAAATGTTTTAGAATAAACTGCTTATTAGTATAGTACACAG | SEQ ID NO: 2790 | Homo sapiens serine incorporator 1 (SERINC1), mRNA [NM_020755] |
| 439 | A_24_P132787 | RAB18 | TAAAAGCTCACATTCTAGTTGATTTACAGTCCTAGTCTACATTAGATGGTTGAAGG | SEQ ID NO: 2791 | Homo sapiens RAB18, member RAS oncogene family (RAB18), mRNA [NM_021252] |
| 440 | A_24_P133991 | ANKRD12 | TTTGGAATGGAGTATATGCCTGAAAAGGTTTTGGATTCAGAAAGAAAACGATGGTTAGT | SEQ ID NO: 2792 | Homo sapiens ankyrin repeat domain 12 (ANKRD12), mRNA [NM_015208] |
| 441 | A_24_P137897 | IFRD1 | AACCAAAGTAGGAAGCAAATGTCGAGATAAGAGAGCAGAGTGTTGGAGAATTGTTCTAGAT | SEQ ID NO: 2793 | Homo sapiens interferon-related developmental regulator 1 (IFRD1), transcript variant 2, mRNA [NM_001007245] |
| 442 | A_24_P139208 | USP25 | CAATAAGAGCAAGGTGATTATTTCAAGCAGGAATCCAAAGTAGGTTGAATAAGGGCTATTG | SEQ ID NO: 2794 | Homo sapiens ubiquitin specific peptidase 25 (USP25), mRNA [NM_013396] |
| 443 | A_24_P148151 | TSNAX | AAAGTTGAGTTATATACTTGTACATACAATGGAAATGCTTTAAGAGTGATATTTAGCA | SEQ ID NO: 2795 | Homo sapiens translin-associated factor X (TSNAX), mRNA [NM_005999] |
| 444 | A_24_P150874 | BX647930 | GTATATTTGTAATAACCCGTAGATACGTACCTAACAAAACATCACTCGTATTAGCTC | SEQ ID NO: 2796 | Homo sapiens mRNA; cDNA DKFZp686I20201 (from clone DKFZp686I20201). [BX647930] |
| 445 | A_24_P153511 | OSBPL8 | CCTTGTGCCATATAACACAGCCTGTAAAGTTAGCACATATAAAATGGAAAGGAGTTTAAGTTTTCTGAAGAATATC | SEQ ID NO: 2797 | Homo sapiens oxysterol binding protein-like 8 (OSBPL8), transcript variant 1, mRNA [NM_020841] |
| 446 | A_24_P157415 | ATP11B | CGTGTACGTTAACACAGCCTGTAAAGTTAGCACATATAAAATGGAAGGGTATATCATATATAG | SEQ ID NO: 2798 | Homo sapiens ATPase, Class VI, type 11B (ATP11B), mRNA [NM_014616] |

Fig. 7-25

| No. | Probe ID No. | Symbols of genes | Sequence | SEQ ID NO: | Descriptions of genes (letters and numbers within [ ] indicates GenBank accession No.) |
|---|---|---|---|---|---|
| 447 | A_24_P165816 | AK023645 | AAGATTGAATGGCTAGGAGTAATTGTTCTGCTATAGGCAACTTAACTTCACTCTGTGAA | SEQ ID NO: 2799 | Homo sapiens cDNA FLJ13583 fis, clone PLACE1009050. [AK023645] |
| 448 | A_24_P166094 | ARFIP1 | TCATTGCTTCCTGTATATTTGTACTGAGAGAGGGCTATTTTATTCTTCCAGGAGAATTAC | SEQ ID NO: 2800 | Homo sapiens ADP-ribosylation factor interacting protein 1 (arfaptin 1) (ARFIP1), transcript variant 1, mRNA [NM_001025595] |
| 449 | A_24_P166794 | BC047111 | AGCTTACAGTGTTTCAGGTTGTGATTTATTTTGAAATGGAGTTGACTGTGAACATCACT | SEQ ID NO: 2801 | Homo sapiens cDNA clone IMAGE:5314178. [BC047111] |
| 450 | A_24_P167063 | ZNF518 | AAAGAAAGCGATAGATAGAATGCTTCAAGCTATCTTGGTATGCACATTATACTCTACTG | SEQ ID NO: 2802 | Homo sapiens zinc finger protein 518 (ZNF518), mRNA [NM_014803] |
| 451 | A_24_P172481 | TRIM22 | TGCCCTTAAAGATTGAAGAAGCAGAAAGCAAACTTGTCAACTCATATGCACGTTATCTAGCAG | SEQ ID NO: 2803 | Homo sapiens tripartite motif-containing 22 (TRIM22), mRNA [NM_006074] |
| 452 | A_24_P175059 | ATG5 | TTGCACAAGAGGCTGGTCGTCTGAATATGATTGTTCACATAAGAGTGTTTATTGTCGGTTC | SEQ ID NO: 2804 | Homo sapiens ATG5 autophagy related 5 homolog (S. cerevisiae) (ATG5), mRNA [NM_004849] |
| 453 | A_24_P175176 | PHTF2 | AGATTCAGGTTAACTTAGAAGTTGGAGGTTGATTTATTAAGTACACCACGTTATCTAGCGA | SEQ ID NO: 2805 | Homo sapiens putative homeodomain transcription factor 2 (PHTF2), mRNA [NM_020432] |
| 454 | A_24_P175187 | SAMD9 | CAACCAGCGATACGTAATGGATATGGGCAG | SEQ ID NO: 2806 | Homo sapiens sterile alpha motif domain containing 9 (SAMD9), mRNA [NM_017654] |
| 455 | A_24_P175188 | SAMD9 | TGCGAATGTACTGGCAGATTAACATACAACCTATGTTTTGAAGAAAAACAACCAGGGATA | SEQ ID NO: 2807 | Homo sapiens sterile alpha motif domain containing 9 (SAMD9), mRNA [NM_017654] |
| 456 | A_24_P186424 | TMEM30A | CAATGTGTATGGACAATTCTCTCTTAGTTAAGGACGAAGAATTGTTTGGTTGGTTTCCTAAG | SEQ ID NO: 2808 | Homo sapiens transmembrane protein 30A (TMEM30A), mRNA [NM_018247] |
| 457 | A_24_P18105 | ASPH | GCTCTGTTGAAAATAATGGTTTGTGAGACAGGTAAACAGAGAGTACTAGAGTATTGTGATGATTTTGAAAGG | SEQ ID NO: 2809 | Homo sapiens aspartate beta-hydroxylase (ASPH), transcript variant 3, mRNA [NM_032466] |
| 458 | A_24_P183684 | IMPA1 | CAGCCTTATCCTTGGCACGGTAAACAGAGACTACTAGAGTATTGTAGGTTCGTTTCGAGGT | SEQ ID NO: 2810 | Homo sapiens inositol(myo)-1(or 4)-monophosphatase 1 (IMPA1), mRNA [NM_005536] |
| 459 | A_24_P196804 | AP1S2 | GGTGGAAGACTCAAGGAGTCTCATGTACTCATTAAAAATAACATGGATTCGATACTG | SEQ ID NO: 2811 | Homo sapiens adaptor-related protein complex 1, sigma 2 subunit (AP1S2), mRNA [NM_003916] |
| 460 | A_24_P191417 | NAB1 | AAGTTTCGTTAACTATCATCTATGTCTCTAGTCGTTCAAGCTTAGTGATAGGTGGAAGCAC | SEQ ID NO: 2812 | Homo sapiens NGFI-A binding protein 1 (EGR1 binding protein 1) (NAB1), mRNA [NM_005966] |
| 461 | A_24_P196351 | PLXNC1 | AGTTCAAACAAACAAACAACAAATGGCTTAAAAGGAATGCATATGGATAAAGTTAGGTGAGAGGTCTGG | SEQ ID NO: 2813 | Homo sapiens mRNA for plexin C1 variant protein. [AB209934] |
| 462 | A_24_P20120 | KIAA1212 | ATTGGAATTCAAGTAAATAAAGAACTGTTCCACTCAACATGCCGACCTAAGTATAATTGACA | SEQ ID NO: 2814 | Homo sapiens KIAA1212 (KIAA1212), mRNA [NM_018041] |
| 463 | A_24_P201702 | CLEC2B | ATGCACAAGGCTTCA | SEQ ID NO: 2815 | Homo sapiens C-type lectin domain family 2, member B (CLEC2B), mRNA [NM_005127] |
| 464 | A_24_P208045 | EDEM3 | TTTAGGGGGGGTCTAGAATTAGTAAATAATAATAATAGGTATTCAAGAAAATGCACAAGGCTTCA | SEQ ID NO: 2816 | Homo sapiens ER degradation enhancer, mannosidase alpha-like 3 (EDEM3), mRNA [NM_025191] |
| 465 | A_24_P208567 | IL18R1 | GGGAAGGCTTGTTGATGTCAAAAGTAATAATATAGTATGAATGTGTCTTTATGCTGTCACCAAGTGACTGT | SEQ ID NO: 2817 | Homo sapiens interleukin 18 receptor 1 (IL18R1), mRNA [NM_003855] |
| 466 | A_24_P20996 | BC043173 | CTGGAAAATGTTCATATAATGTATGAATGTCTCTTTATGCTGAAGGGCTCGATTGG | SEQ ID NO: 2818 | Homo sapiens cDNA clone IMAGE:5287121. [BC043173] |

Fig. 7-26

| No. | Probe ID No. | Symbols of genes | Sequence | SEQ ID NO: | Descriptions of genes (letters and numbers without [ ] indicates GenBank accession No.) |
|---|---|---|---|---|---|
| 467 | A_24_P216654 | SOAT1 | CGGAGTAATGTTCTGCACAACAGTATTGTAATTGTAATGGAATGATAACCTGGTAACTAG | SEQ ID NO: 2819 | Homo sapiens sterol O-acyltransferase (acyl-Coenzyme A: cholesterol acyltransferase) 1 (SOAT1), transcript variant 688113, mRNA [NM_003101] |
| 468 | A_24_P223124 | FNDC3B | GTGACTGTTGGAGATACATTCGAAGGTTTCAAGTCTAGGAGAAAAAGAAAATCATGTTT | SEQ ID NO: 2820 | Homo sapiens fibronectin type III domain containing 3B (FNDC3B), mRNA [NM_022763] |
| 469 | A_24_P225308 | ARID4B | GTTGAAAATGGTTCAAGTTATTCAAATTTGTACAGGAGTGTAAAGATTTGTTGACAGCA | SEQ ID NO: 2821 | Homo sapiens AT rich interactive domain 4B (RBP1-like) (ARID4B), transcript variant 1, mRNA [NM_016374] |
| 470 | A_24_P225719 | PREI3 | GACTATTTTCTTAGTGAATATTTATACTAAGGTAGTGACTGAGATTTGGTGATCTGGCTG | SEQ ID NO: 2822 | Homo sapiens preimplantation protein 3 (PREI3), transcript variant 1, mRNA [NM_015387] |
| 471 | A_24_P235429 | ABCA1 | CCAAKAGAGCCATGTGTGATGTAATACTGAACCACTTGATATTGAGACATTAATTTGTAC | SEQ ID NO: 2823 | Homo sapiens ATP-binding cassette, sub-family A (ABC1), member 1 (ABCA1), mRNA [NM_005502] |
| 472 | A_24_P235988 | CLEC7A | TTTTTTCAGTAATTACCTGTAAAATGGTATTATTGGAATGAAAACTATATTTGCTCATGT | SEQ ID NO: 2824 | Homo sapiens C-type lectin domain family 7, member A (CLEC7A), transcript variant 1, mRNA [NM_197947] |
| 473 | A_24_P236008 | SCYL2 | ATAGCATGTACTTGTGTGGGTTTTTGTTGTTTTTATTTTGAAATGGTTATAAGGGTCC | SEQ ID NO: 2825 | Homo sapiens mRNA for KIAA1360 protein, partial cds. [AB037781] |
| 474 | A_24_P236799 | RAB31 | ATTAAAGAGCTCGAACTGTATCAGACGGGACTGGGTATCTAGCTTACTGTTTAACATC | SEQ ID NO: 2826 | Homo sapiens RAB31, member RAS oncogene family (RAB31), mRNA [NM_006868] |
| 475 | A_24_P242299 | ZRANB2 | GAGTTTTGAAAGTCTACCTTCTAAATTGCCGGAGGATCTAGATTGTACATGTTAGGAT | SEQ ID NO: 2827 | Homo sapiens zinc finger, RAN-binding domain containing 2 (ZRANB2), transcript variant 2, mRNA [NM_005455] |
| 476 | A_24_P248606 | ACSL3 | GTATTTGATGATAGGATCTGACTAAGAACATGAGAATTAACTTTATAACGGGTGAG | SEQ ID NO: 2828 | Homo sapiens acyl-CoA synthetase long-chain family member 3 (ACSL3), transcript variant 1, mRNA [NM_004457] |
| 477 | A_24_P250922 | PTGS2 | TGAGATATTTAAGGTTGAAATGTTTGTCCTTAGGATAGGGCTATGTGCTAGGGCAGCAAAGA | SEQ ID NO: 2829 | Homo sapiens prostaglandin-endoperoxide synthase 2 (prostaglandin G/H synthase and cyclooxygenase) (PTGS2), mRNA [NM_000963] |
| 478 | A_24_P251221 | PPP2R5A | TGAATTCTTCTTTGATTGTGTTGCACATAGAGATATAGTCTGCTGTGTATATTTTTCCC | SEQ ID NO: 2830 | Homo sapiens protein phosphatase 2, regulatory subunit B', alpha isoform (PPP2R5A), mRNA [NM_006243] |
| 479 | A_24_P25325 | ZMYM6 | AGGACTATTTAAATCAGTGTCTGTGTAAGTCAGTTTTTGGATAAATGCAAAGACAAGTTAGGCC | SEQ ID NO: 2831 | Homo sapiens zinc finger, MYM-type 6 (ZMYM6), mRNA [NM_007167] |
| 480 | A_24_P257151 | CLK1 | TATGCAAGTCTGTGAATTTTTGCACAGTAATAAGTTGACTGAGACAGATTTAAAGCCTG | SEQ ID NO: 2832 | Homo sapiens CDC-like kinase 1 (CLK1), transcript variant 1, mRNA [NM_004071] |
| 481 | A_24_P263144 | BMX | CAGCTCGGAGGAGGTGTTTCATTACTTCAAATACAGGCAGCAAGTCAGACGTATGGGCATTTG | SEQ ID NO: 2833 | Homo sapiens BMX non-receptor tyrosine kinase (BMX), mRNA [NM_001721] |
| 482 | A_24_P263524 | TXNDC9 | TGACTTCACCACAGAAACTTTAGAATGGGGGTCAGTTGTTGTGACATTCTTAATTACAG | SEQ ID NO: 2834 | Homo sapiens thioredoxin domain containing 9 (TXNDC9), mRNA [NM_005783] |
| 483 | A_24_P263655 | SENP7 | TTGTGTGTTTGGGGGGTACTTTTAAAGGTGACTATGTTTTGTACATGTAATTTTTGGGA | SEQ ID NO: 2835 | Homo sapiens SUMO1/sentrin specific peptidase 7 (SENP7), transcript variant 1, mRNA [NM_020654] |

Fig. 7-27

| No. | Probe ID No. | Symbols of genes | Sequence | SEQ ID NO: | Descriptions of genes [letters and numbers within ( ) indicates GenBank accession No.] |
|---|---|---|---|---|---|
| 484 | A_24_P268786 | MYNN | TGCAGAGGATCATACTTGAGTGAACAAGGATTGGATACAAAAAG TCCTTTATCAGAAAC | SEQ ID NO: 2836 | Homo sapiens myoneurin (MYNN), mRNA [NM_018657] |
| 485 | A_24_P268917 | RAB33B | CCCAGAATCTAATGTAGTTGGGTATTAATAAGAATGCATTATTGA AAGTATATTGCAAAT | SEQ ID NO: 2837 | Homo sapiens RAB33B, member RAS oncogene family (RAB33B), mRNA [NM_031296] |
| 486 | A_24_P274615 | ARRDC3 | AGCAAAACAAAGTGCAAATTAAATGTTTGCTTTATAGATTATAT TCTATGGCTGTTTGT | SEQ ID NO: 2838 | Homo sapiens arrestin domain containing 3 (ARRDC3), mRNA [NM_020801] |
| 487 | A_24_P276583 | TMCO1 | CCTTCATTTCCTGTATATTCTCGTACATGTCGATTCGACAGA ACATTCAGAAGATTC | SEQ ID NO: 2839 | Homo sapiens transmembrane and coiled-coil domains 1 (TMCO1), mRNA [NM_019026] |
| 488 | A_24_P278460 | MLSTD2 | ACCCATGGAAGAATAATGTTAGGAATTACAGGAGGAGTCGTTACT TACACTCTTGTCTG | SEQ ID NO: 2840 | Homo sapiens male sterility domain containing 2 (MLSTD2), mRNA [NM_032228] |
| 489 | A_24_P285501 | ZNF650 | CATGGTATAAATGTATTCAGAGCTTTGATTAGTACTACTTATTAAAATG GAATGTTTTATGTT | SEQ ID NO: 2841 | Homo sapiens zinc finger protein 650 (ZNF650), mRNA [NM_172070] |
| 490 | A_24_P286054 | ZFYVE16 | GTGTATGTATTCTGCATGTAGTAAGTAATTGAACAGTCTTAAAATAA CCAAATGTAGAGAGG | SEQ ID NO: 2842 | Zinc finger FYVE domain-containing protein 16 (Endofin) (Endosome- associated FYVE domain protein). [Source:Uniprot/SWISSPROT:Acc:Q7Z3T8] [ENST00000380248] |
| 491 | A_24_P28657 | AHCTF1 | AACACAGGCGTGTTCTCTACAGACAGAACTGTGTGGAATTAAGGA ATGGTACTTGATGTA | SEQ ID NO: 2843 | Homo sapiens AT hook containing transcription factor 1 (AHCTF1), mRNA [NM_015446] |
| 492 | A_24_P287756 | NUDT21 | CCCATACTACTTAGTTCAGTTCTGTTATACATCACTGATTATTGGGTTA AACTGGACTCATTTC | SEQ ID NO: 2844 | Homo sapiens nudix (nucleoside diphosphate linked moiety X)-type motif 21 (NUDT21), mRNA [NM_007006] |
| 493 | A_24_P290257 | A_24_P290257 | CCAATTCATTCAACATAGAACAACAGCCAATTATACCATCCAGTGAT TGAAGGACAGGAAGA | SEQ ID NO: 2845 | |
| 494 | A_24_P29277 | COL4A3BP | TTAAAGTACCTTGGGAGTGTAGAGTAACTTCTATAATAGCTTT ATGATCCTGATGATG | SEQ ID NO: 2846 | Goodpasture antigen-binding protein (EC 2.7.11.9) (GPBP) (Collagen type IV alpha-3-binding protein) (StAR-related lipid transfer protein 11) (StARD11) (START domain-containing protein 11). [Source:Uniprot/SWISSPROT:Acc:Q9Y5P4] [ENST00000380494] |
| 495 | A_24_P295543 | BLOC1S2 | GTTTATTTGTATGTGAGTGAGATCAAGATTGGACATCGATCAGTTGGGA AATCTGATGAAAACA | SEQ ID NO: 2847 | Homo sapiens biogenesis of lysosome-related organelles complex-1, subunit 2 (BLOC1S2), transcript variant 2, mRNA [NM_001001342] |
| 496 | A_24_P2995 | PUM2 | TTTTTGAATAGCCTACTCGCAAGTAAGAGCAAAATCTGTATGATAA CATTTTTCGCTCTGG | SEQ ID NO: 2848 | Homo sapiens pumilio homolog 2 (Drosophila) (PUM2), mRNA [NM_015317] |
| 497 | A_24_P30194 | IFIT5 | AATGTGGCTTCTCTAATGTAGTTCTTTGATTACCGACTAGAGAA TTATGTACCATCACA | SEQ ID NO: 2849 | Homo sapiens interferon-induced protein with tetratricopeptide repeats 5 (IFIT5), mRNA [NM_012420] |
| 498 | A_24_P303454 | TIAM2 | GCCAGAATTCAGTGTGCAGAGTTTAACATCTGTTCAGTGAGGA GTGTTTTATGAAAG | SEQ ID NO: 2850 | Homo sapiens T-cell lymphoma invasion and metastasis 2 (TIAM2), transcript variant 1, mRNA [NM_012454] |
| 499 | A_24_P303647 | FLJ31818 | ACTGTATGGGTACTCCTAAGAATTATTTCATTTTGGATATAAAGA AGTTATGAGGCCTCC | SEQ ID NO: 2851 | Homo sapiens hypothetical protein FLJ31818 (FLJ31818), mRNA [NM_152556] |

Fig. 7-28

| No. | Probe ID No. | Symbols of genes | Sequence | SEQ ID NO: | Descriptions of genes [letters and numbers within { } indicates GenBank accession No.] |
|---|---|---|---|---|---|
| 500 | A_24_P303852 | GNAQ | GCTTTTGGTAGACAGAAAAAACAGAAAGGTATTCGTTGGTAGAAGC ATTTTAAGTTCAGG | SEQ ID NO: 2852 | Guanine nucleotide-binding protein G(q) subunit alpha (Guanine nucleotide-binding protein alpha-q) [Source:Uniprot/SWISSPROT;Acc:P50148] [ENST00000376611] |
| 501 | A_24_P307395 | A_24_P307395 | CTCCTCTGTTTATGTGGACAGATCCAAGTCCAACTTAAATTGCA GGGCTGTGTTCCAT | SEQ ID NO: 2853 | |
| 502 | A_24_P310894 | CAPZA1 | TGTATTATTGTCCTTCATACTATCCATCCATCCATCAT ACCACACTATCTT CGTGATCAGGTAGTC | SEQ ID NO: 2854 | Homo sapiens capping protein (actin filament) muscle Z-line, alpha 1 (CAPZA1), mRNA [NM_006135] |
| 503 | A_24_P312417 | ZBTB25 | AGAGGAGGAAGAATTTTTAAAACCTTTATCATTCAGCATTGTATT TTATGAATCCCAAGG | SEQ ID NO: 2855 | Zinc finger and BTB domain-containing protein 25 (Zinc finger protein 481) (Zinc finger protein Bioref). [Source:Uniprot/SWISSPROT;Acc:Q9H8K0] [ENST00000373656] |
| 504 | A_24_P317604 | SLC37A3 | CCCGGTCTCTTTGTTGGCCTATTGAGGTTTAGCGTTTAAGGTTA ACTGTTGTTTGGAG | SEQ ID NO: 2856 | Homo sapiens solute carrier family 37 (glycerol-3-phosphate transporter), member 3 (SLC37A3), transcript variant 1, mRNA [NM_207113] |
| 505 | A_24_P320328 | SUB1 | CAGAAAAACCTGTAAAGAACAAAAGACAAGGTGAGAGTTCGAAGAG CCGTGTGATGTGTA | SEQ ID NO: 2857 | Homo sapiens SUB1 homolog (S. cerevisiae) (SUB1), mRNA [NM_006713] |
| 506 | A_24_P322353 | PSTPIP2 | AGAATCTTTCCCTTGCTAGACCCCAGAATTTTAAATGGATCGGTC TTACACTTTCACAAA | SEQ ID NO: 2858 | Homo sapiens proline-serine-threonine phosphatase interacting protein 2 (PSTPIP2), mRNA [NM_024430] |
| 507 | A_24_P324506 | A_24_P324506 | GCAATATAAGGCAGCTAATTGCAAATACAAGCATGGACATGTT GTGGACATGCTCTGT | SEQ ID NO: 2859 | |
| 508 | A_24_P324577 | KIAA1466 | AAGAATTTAAGTAGCCCCGTGAAGTTAGAGTTAAAGAAGGATAT TAACTGCCAGTCCCA | SEQ ID NO: 2860 | Homo sapiens mRNA for KIAA1466 protein, partial cds. [AB040899] |
| 509 | A_24_P324581 | KIAA1466 | ATAATAGTCAATAGAATGAATTGCTGTAGCAACCAAGCTAAAAA GAATTTAAGTAGCCC | SEQ ID NO: 2861 | Homo sapiens mRNA for KIAA1466 protein, partial cds. [AB040899] |
| 510 | A_24_P324886 | DOCK4 | ATTTCCCTTTTGTTCGGAAGCTCATTTAGTTTGAAAAATTGGGGTTTG TGTTTGGTAGC | SEQ ID NO: 2862 | Homo sapiens dedicator of cytokinesis 4 (DOCK4), mRNA [NM_014705] |
| 511 | A_24_P325176 | KIAA1109 | TTGATCCAGTAGGTGTTGATTATATCTTGAAAAATTGGGGTTTG ATGATGGTAGGAGTA | SEQ ID NO: 2863 | Homo sapiens KIAA1109, mRNA (cDNA clone IMAGE:3924668), complete cds. [BC108274] |
| 512 | A_24_P330397 | STRN3 | TTGGTAGGTAACTAAAGATTTGTTTGTGTAATGGATGATTAAGACA ATAAAGTATTTTTC | SEQ ID NO: 2864 | Homo sapiens striatin, calmodulin binding protein 3 (STRN3), mRNA [NM_014574] |
| 513 | A_24_P33213 | A_24_P33213 | GACCATATATTACATGGGGGTAGCCAAATGTGAAGTCAGTAAATG AACTATCTACAAGG | SEQ ID NO: 2865 | |
| 514 | A_24_P33112 | A_24_P33112 | GGTGATCAGAATTGAGAGGTATCAATGTGTGAGCCCACAGGACCAA AAGGTATTGCAACTT | SEQ ID NO: 2866 | |
| 515 | A_24_P336728 | LPGAT1 | AGAGCGAAAACTTTTTAAGTGTATTCTAGTTTGCAGAGTATGCACA CATATCTTGAATGGC | SEQ ID NO: 2867 | Homo sapiens lysophosphatidylglycerol acyltransferase 1 (LPGAT1), mRNA [NM_014873] |
| 516 | A_24_P351906 | STEAP4 | ATATCCCCTTGCATTTCACTTGCATTGTGCAATAAGCAAGAAGG GTGATAAAGTTCT | SEQ ID NO: 2868 | Homo sapiens STEAP family member 4 (STEAP4), mRNA [NM_024636] |
| 517 | A_24_P354412 | AK091335 | TGTAGACTGAGGAGTCTTTCAAAACACCCGAGCATTAAATCA CTCTGCGGTGGTTCT | SEQ ID NO: 2869 | Homo sapiens cDNA FLJ34016 fis, clone FCBBF2002541. [AK091335] |
| 518 | A_24_P354954 | CCDC126 | AATGGAAGCTCTTGAGGACTTTAGCGAGGTGTATATATAAAGGTA CTCTGTGGGTGGATT | SEQ ID NO: 2870 | Homo sapiens coiled-coil domain containing 126 (CCDC126), mRNA [NM_138771] |

Fig. 7-29

| No. | Probe ID No. | Symbols of genes | Sequence | SEQ ID NO: | Descriptions of genes (letters and numbers within [ ] indicates GenBank accession No.) |
|---|---|---|---|---|---|
| 519 | A_24_P355816 | DRAM | ATAATATAGAATGGATTAGTCTGGTTTAGGAGTTAGTTCATAATAAACAAATAGTCT | SEQ ID NO: 2871 | Homo sapiens damage-regulated autophagy modulator (DRAM), mRNA [NM_018370] |
| 520 | A_24_P357576 | KIAA1370 | TGCTGCATATGAACTGAAATGTTAGAGTGAATGACCAACAAACCCTCAGTTTTCAGCAAG | SEQ ID NO: 2872 | Homo sapiens KIAA1370 (KIAA1370), mRNA [NM_019600] |
| 521 | A_24_P362646 | TXNDC9 | CTCCACATTCAGGTGTAAAATACTAGAGAGAGATGGCAATATGTGAAGAAAGACCT | SEQ ID NO: 2873 | Homo sapiens thioredoxin domain containing 9 (TXNDC9), mRNA [NM_005783] |
| 522 | A_24_P364025 | UBE2D1 | ATGTCATGGGTGTAGTCATTAGGAAAGGATTTAAATCACTTGAGTATTTTGTCATGGTTC | SEQ ID NO: 2874 | Homo sapiens ubiquitin-conjugating enzyme E2D 1 (UBC4/5 homolog, yeast) (UBE2D1), mRNA [NM_003338] |
| 523 | A_24_P364066 | BC030112 | AATGTCATTAGGGTTTGCGATAGTATTTCTGTCTAGTTGTGAGTGATTTAAATGTGACC | SEQ ID NO: 2875 | Homo sapiens cDNA clone IMAGE:4799578. [BC030112] |
| 524 | A_24_P364807 | AYTL1 | TGTAAGTCTGTTTCTAGGTAATGCTTCTGTCTGTCAAGAAAGTTCTCAAGCGTCTGTGTAA | SEQ ID NO: 2876 | Homo sapiens mRNA; cDNA DKFZp686H22112 (from clone DKFZp686H22112). [BX641069] |
| 525 | A_24_P370096 | ZNF230 | GAAAGTTATATTTGTGAGAAATGTGGTCATCGTCATTCATGGAATTTAAAGCTCAGAA | SEQ ID NO: 2877 | Homo sapiens zinc finger protein 230 (ZNF230), mRNA [NM_006300] |
| 526 | A_24_P370172 | LILRA5 | AGCCACAGGATGGAATGCTCAGATGATGGTGATGGGCTGCAGGCATATCCTGCAGGTATGGTCA | SEQ ID NO: 2878 | Homo sapiens leukocyte immunoglobulin-like receptor, subfamily A (with TM domain), member 5 (LILRA5), transcript variant 3, mRNA [NM_181879] |
| 527 | A_24_P371053 | ORMDL1 | GAATGAAAAGAGTTACAGACCAACTTAAACATCAATTCGTCTCAGTAAACTGACTTTGG | SEQ ID NO: 2879 | Homo sapiens ORM1-like 1 (S. cerevisiae) (ORMDL1), mRNA [NM_016467] |
| 528 | A_24_P372625 | RNF141 | CTATAGTGAATTTAGAGGTTGAGAATAAAGTGGCTGATTCTAAGAAGCTGGAGTGTTCTAGTACGGACTG | SEQ ID NO: 2880 | Homo sapiens ring finger protein 141 (RNF141), mRNA [NM_016422] |
| 529 | A_24_P374319 | RAP2C | ATTGTGTGTGATGTTCAAATAAAGTGGTCATTCATGATGTTATGGGTCAGCATG | SEQ ID NO: 2881 | Homo sapiens RAP2C, member of RAS oncogene family (RAP2C), mRNA [NM_021183] |
| 530 | A_24_P379379 | CAPZA1 | ACCAGTTCAGCCTAAAACTTCTGGAATGGTCGTTGGAGATCAGAGTGCAAGGTTCACCA | SEQ ID NO: 2882 | Homo sapiens capping protein (actin filament) muscle Z-line, alpha 1 (CAPZA1), mRNA [NM_006135] |
| 531 | A_24_P380679 | FLJ39575 | GAAGCTGATTAGTTCCAGCAATGAAAGTAAGACACAGAGATATGACATAAGACACAGT | SEQ ID NO: 2883 | Homo sapiens hypothetical protein FLJ39575 (FLJ39575), mRNA [NM_182597] |
| 532 | A_24_P381625 | PSMC6 | ATGAAAGGAGTCAGAAAAGTTGGCTGATTCTAAGAAGCTGGAGTGTAAATTGCACTACAAA | SEQ ID NO: 2884 | Homo sapiens proteasome (prosome, macropain) 26S subunit, ATPase, 6 (PSMC6), mRNA [NM_002806] |
| 533 | A_24_P387859 | PKN2 | TTGTCAGAGATCATTTATATTACCTCCAAATTGTTTCATCAATAAGTTAAGTATCCTTTGGGAG | SEQ ID NO: 2885 | Homo sapiens protein kinase N2 (PKN2), mRNA [NM_006256] |
| 534 | A_24_P393378 | CCPG1 | TACTTTTTGTCGCTGGAACGAACTTGATCAGTTCATCAATAAGTTTTCCTAAACGGTGT | SEQ ID NO: 2886 | Homo sapiens cell cycle progression 1 (CCPG1), transcript variant 1, mRNA [NM_004748] |
| 535 | A_24_P393811 | TMCO1 | AGAATGACAGGACAGAGCTGTTCCTTCATTTCCTGTATATTCTGTGTACTATCGCATTCG | SEQ ID NO: 2887 | Homo sapiens transmembrane and coiled-coil domains 1 (TMCO1), mRNA [NM_019026] |
| 536 | A_24_P396231 | BC040653 | AGATGATGGATTTAGAGAACCAATTAATACCTGCAAAATAAAGGATACTGTAGTTC | SEQ ID NO: 2888 | Homo sapiens cDNA clone IMAGE:4797120. [BC040653] |
| 537 | A_24_P396702 | CD302 | GGATTCTTAGTGAGCAGTGATATGGTCTGTGTTTGAGAATTTAAAACTGATAACCAA | SEQ ID NO: 2889 | Homo sapiens CD302 molecule (CD302), mRNA [NM_014880] |
| 538 | A_24_P398940 | CASC4 | CAGTTGGTTGTATTGTAGGTATTACTATACAGCAACATTTCTTCAATTAGCAGTC | SEQ ID NO: 2890 | Homo sapiens cancer susceptibility candidate 4 (CASC4), transcript variant 1, mRNA [NM_139423] |

Fig. 7-30

| No. | Probe ID No. | Symbols of genes | Sequence | SEQ ID NO: | Descriptions of genes, letters and numbers within [ ] indicates GenBank accession No.: |
|---|---|---|---|---|---|
| 539 | A_24_P399942 | ATP11C | TGAGGATGTTAGGTACTAAACTGAAAAGATTCATTGCATATCTACTTACAGCATACACCAG | SEQ ID NO: 2891 | Homo sapiens ATPase, Class VI, type 11C (ATP11C), transcript variant 1, mRNA [NM_173694] |
| 540 | A_24_P40417 | FMR1 | TGTGAGTTTGTTTCTTTGAATTTCATTTTTAGAGTTACAGTTTTGCATACGAAACAAG | SEQ ID NO: 2892 | Homo sapiens fragile X mental retardation 1 (FMR1), mRNA [NM_002024] |
| 541 | A_24_P405298 | PPP1CB | GTATTAGGTTAGGTCACAAAAGGTTTTATCTGAGGTGATTTAAATAACTTCCTGATTGGAG | SEQ ID NO: 2893 | Homo sapiens protein phosphatase 1, catalytic subunit, beta isoform (PPP1CB), transcript variant 1, mRNA [NM_002709] |
| 542 | A_24_P405430 | TIA1 | GGATTTTCTCTGTTGTTAAATCACAAAAATGATAGTGCGAATCGTTCTTTATAGGAGG | SEQ ID NO: 2894 | Homo sapiens cDNA FLJ36425 fis, clone THYMU2011482 [AK093744] |
| 543 | A_24_P406034 | SLC35A1 | ATGTACAGTATTTGTCCTAGCAGCAGGCATAAAGACCTAGGTCTTTTCTTACAAGAGGGAGAA | SEQ ID NO: 2895 | Homo sapiens solute carrier family 35 (CMP-sialic acid transporter), member A1 (SLC35A1), mRNA [NM_006416] |
| 544 | A_24_P406060 | IBRDC2 | CTTATGGAGGTTTGACAAATGTACAGTATGCATTGAATGCATTGAAATGTAAATGACGATTTCTTGGAACC | SEQ ID NO: 2896 | Homo sapiens IBR domain containing 2 (IBRDC2), mRNA [NM_182757] |
| 545 | A_24_P407311 | ERO1L | AACATGTTGAAATGTCACATTAGTAGTAAAGTGGGGTTATTTATATAGTTGTTTAAGAA | SEQ ID NO: 2897 | Homo sapiens ERO1-like (S. cerevisiae) (ERO1L), mRNA [NM_014584] |
| 546 | A_24_P413669 | PFKFB2 | TCAAATGGTTCTTTATACTGTGGATGAGGACTCGTTACCTAAGATGTGATAAGC | SEQ ID NO: 2898 | Homo sapiens 6-phosphofructo-2-kinase/fructose-2,6-biphosphatase 2 (PFKFB2), transcript variant 2, mRNA [NM_001018053] |
| 547 | A_24_P414556 | TTC33 | ACTCAACATTTGGTATATTGTTTTGAGTAATGGATGTTTGTTTTTGTGTAATTTCTGA | SEQ ID NO: 2899 | Homo sapiens tetratricopeptide repeat domain 33 (TTC33), mRNA [NM_012382] |
| 548 | A_24_P417281 | TXNDC10 | ATGATGAGTGTTGTTCTTGGGAAGAATAAATGTTAATGTTCCAATAGTGCAGGTTGTTTGC | SEQ ID NO: 2900 | Homo sapiens thioredoxin domain containing 10 (TXNDC10), mRNA [NM_019022] |
| 549 | A_24_P419211 | MTMR6 | AGAAGAAAAACATAAAACCCAAAGTATCACTTGGAATTAGGAATATCACCCAACTGG | SEQ ID NO: 2901 | Homo sapiens myotubularin related protein 6 (MTMR6), mRNA [NM_004685] |
| 550 | A_24_P450172 | AK095151 | TATGCCACTGAATAAAGCTAGTAAACCAGAGTAATTTGGGATATTAATGGTAGGCTAC | SEQ ID NO: 2902 | Homo sapiens cDNA FLJ37832 fis, clone BRSSN2009630 [AK095151] |
| 551 | A_24_P45620 | UTS2 | AGAAAGTTTCAGGATTTCTGTGGACAAGAATGGATGGGATTTTTTAAATAGTCATCTTTTGGCC | SEQ ID NO: 2903 | Homo sapiens urotensin 2 (UTS2), transcript variant 1, mRNA [NM_021995] |
| 552 | A_24_P487796 | CXorf23 | TGCATAGGTAGTATGTGTCAGTTAAGGAAATGCTCATATTCTCGTCAATAAAGAGCAAACTCG | SEQ ID NO: 2904 | Homo sapiens chromosome X open reading frame 23 (CXorf23), mRNA [NM_198279] |
| 553 | A_24_P514678 | DB728175 | ATCACACAGTCTGTCACATTAAGGAATTGCTCATATTCCGTCAATAAGAGCAAACTCG | SEQ ID NO: 2905 | DB728175 RIKEN full-length enriched human cDNA library hypothalamus Homo sapiens cDNA clone H0336001B22 3', mRNA sequence [DB728175] |
| 554 | A_24_P532232 | CREB5 | TCGTGAAGACAGATTTATTGTTACCAATGGACAATGAGTTCATTAAGACTTGAGCTAGGT | SEQ ID NO: 2906 | Homo sapiens cAMP responsive element binding protein 5 (CREB5), transcript variant 1, mRNA [NM_182898] |
| 555 | A_24_P533403 | ROCK1 | TTAAGAGGTTTGTTTGGACTTCATAAATTGAGTACAAATCTTGGATCAAACTACCTGCTAC | SEQ ID NO: 2907 | Homo sapiens Rho-associated, coiled-coil containing protein kinase 1 (ROCK1), mRNA [NM_005406] |
| 556 | A_24_P54178 | TMED5 | GCTCTGATATGCATTTGGATGATTAATGTTATGCTGTCTTTCATGTGAATGTCAAGAGA | SEQ ID NO: 2908 | Homo sapiens transmembrane emp24 protein transport domain containing 5 (TMED5), mRNA [NM_016040] |

Fig. 7-31

| No | Probe ID No. | Symbols of genes | Sequence | SEQ ID NO: | Descriptions of genes (letters and numbers within [ ] indicates GenBank accession No.) |
|---|---|---|---|---|---|
| 557 | A_24_P551028 | LOC339745 | TCGAGTTGAACAAATATTGAGTGGCTATGATATGCAAGAGTAAC:GGTTACTAGGAATGA | SEQ ID NO: 2909 | Homo sapiens hypothetical protein LOC339745 (LOC339745), mRNA [NM_001001664] |
| 558 | A_24_P56240 | CPNE8 | TACAACTATGTGACTTAGTGCAGAACACATTGTGAAATAACCTA:CTCCTATATACTGAC | SEQ ID NO: 2910 | Homo sapiens copine VIII (CPNE8), mRNA [NM_153634] |
| 559 | A_24_P56252 | AF086032 | GTATCTAAAACTGAACAAGTACTGTGGTATATTGATTTTATTGG:AGTATTGAGAGAGCC | SEQ ID NO: 2911 | Homo sapiens full length insert cDNA clone YH25609. [AF086032] |
| 560 | A_24_P592591 | A_24_P592591 | GAATTTGTTACACTGGAAGAAAGGAGAGACCTTGAGGAAATATGG:CAGGATCTTCTGGAT | SEQ ID NO: 2912 | |
| 561 | A_24_P605190 | THC2615064 | CAGTGGTGTAACTGAATCAATGATGGTCATTTTATTCTCATATTTC:AGGTAAGTGAAAGGG | SEQ ID NO: 2913 | BX491310 DKFZp686K2197_r1 686 (synonym: hlcc3) Homo sapiens cDNA clone DKFZp686K2197 5', mRNA sequence [BX491310] |
| 562 | A_24_P62860 | STAM2 | GTGTATATGGTAGTTGAATCTACATTTAAGTGGAAAAATAGGAGT:ATTGAAAGGTCAGT | SEQ ID NO: 2914 | Homo sapiens signal transducing adaptor molecule (SH3 domain and ITAM motif) 2 (STAM2), mRNA [NM_005843] |
| 563 | A_24_P630039 | AL049321 | AACATGAGACAATAGAAAAGTTACATTTTTGGACCATATATAAAAC:GGAAGAAGACAGGGG | SEQ ID NO: 2915 | Homo sapiens mRNA; cDNA DKFZp564D156 (from clone DKFZp564D156). [AL049321] |
| 564 | A_24_P66027 | APOBEC3B | GCTGCGGGATCTATGATTAGGAGACCGCCTATATAAGGAGGCGGTG:CAAATGGTGCGGGAT | SEQ ID NO: 2916 | Homo sapiens apolipoprotein B mRNA editing enzyme, catalytic polypeptide-like 3B (APOBEC3B), mRNA [NM_004900] |
| 565 | A_24_P66125 | STAG2 | TAATCATTTCGAATGCCTTAATATGGTTGCAATAGAAGAAATATCTTC:AGATGGGTGAATACC | SEQ ID NO: 2917 | Homo sapiens stromal antigen 2 (STAG2), transcript variant 4, mRNA [NM_006603] |
| 566 | A_24_P675947 | ENST00000389400 | GTTCATGGCGAAGGTAGCAGTGTCGGAAAAAGCTACTGGAGAAGAG:ACAGGTTGTAAAGTT | SEQ ID NO: 2918 | similar to 40S ribosomal protein S3a (V-fos transformation effector protein) (LOC391706). mRNA [Source:RefSeq_dna Acc:XR_017186] [ENST00000389400] |
| 567 | A_24_P681266 | A_24_P681266 | TAAGCAGAAAAGGCACGATGAAAAATATCTTGTTTGTAGTTGATATCGCCCGA:TCAGGCTCGCTTTCC | SEQ ID NO: 2919 | |
| 568 | A_24_P688133 | AK124299 | TAGCCATATCTGCAGGAAGAATGATCATCCTATAGTTTGTATGATATCCGCCGA:ATAGTGATTGATTTC | SEQ ID NO: 2920 | Homo sapiens cDNA FLJ42306 fis, clone TRACH2001646. [AK124299] |
| 569 | A_24_P703614 | A_24_P703614 | AAGAACATTACCGGAATGGATCTGCACTGTAAGTACATCATCAGTAGC:AGCTTTGTGTGTG | SEQ ID NO: 2921 | |
| 570 | A_24_P71468 | QPCT | GTGTGGAAACATCTATAGATCATCCTATTCTTATGTGTGT:TTGGTTATCAGATCA | SEQ ID NO: 2922 | Homo sapiens glutaminyl-peptide cyclotransferase (glutaminyl cyclase) (QPCT), mRNA [NM_012413] |
| 571 | A_24_P71938 | SMAD1 | TGTATTCACTTATGCTGTCGATAGAATTGAGTACTTTATTCCAAAA:CTAGTGGGTTTTCTC | SEQ ID NO: 2923 | Homo sapiens SMAD family member 1 (SMAD1), transcript variant 1, mRNA [NM_005900] |
| 572 | A_24_P725998 | THC2706471 | GTCTGAAGCACATTAGTGAGTTGAACAAGGAGCATCATTGGTCT:TTGTCCAGAATTTGC | SEQ ID NO: 2924 | |
| 573 | A_24_P75158 | PTAR1 | CCATTAGATTTGTTCTTATGTGACCATGTACCAAGCCAGCTATAA:AGTATTGTATTTCTG | SEQ ID NO: 2925 | Homo sapiens mRNA; cDNA DKFZp313P0917 (from clone DKFZp313P0917). [AL832683] |
| 574 | A_24_P781846 | AK024092 | AGTTTTTATAGATACAAATGTATGTGGTAGTAGAAGGACTTT:GTTACTTTGGCGGTGC | SEQ ID NO: 2926 | Homo sapiens cDNA FLJ14030 fis, clone HEMBA1004086. [AK024092] |
| 575 | A_24_P791829 | THC2543120 | TTTTTGCTTTGCTAAATGGTTAGGTATTTGCTATAGGTGTTGT:GATGTCATGGAATTGT | SEQ ID NO: 2927 | |

Fig. 7-32

| No. | Probe ID No. | Symbols of genes | Sequence | SEQ ID NO: | Descriptions of genes (letters and numbers within [ ] indicates GenBank accession No.) |
|---|---|---|---|---|---|
| 576 | A_24_P792734 | PSMC6 | AGAACGTTAACGGAGTTAGTGAATGAAATGGATGGATTTGATACTCTGGATAGAGTTAAA | SEQ ID NO: 2928 | Homo sapiens proteasome (prosome, macropain) 26S subunit, ATPase, 6 (PSMC6), mRNA [NM_002806] |
| 577 | A_24_P80915 | BCLAF1 | AAGTTGTGAATGATGGTAATGGAGGAAAAGTGTACAGTTAATTAAGGTACCAGTTC | SEQ ID NO: 2929 | Homo sapiens BCL2-associated transcription factor 1 (BCLAF1), transcript variant 1, mRNA [NM_014739] |
| 578 | A_24_P82630 | SMCHD1 | TGTTAATATGTAACACGTAAGAACAATTGAAATTTCTTCTAAGATTTAATACTAGTCT | SEQ ID NO: 2930 | Homo sapiens mRNA for KIAA0650 protein, partial cds. [AB014550] |
| 579 | A_24_P858859 | THC2553238 | TTTAACCAGACGTCTGCACCCTTTTCCTGATATACTGAGGACACTCGGTCTCTAGGCAAT | SEQ ID NO: 2931 | 1305349A cystic fibrosis antigen. [Homo sapiens] (exp=-1; wgp=0; cg=0), partial (65%) [THC2553238] |
| 580 | A_24_P867201 | AK022997 | CTGACATGTGATAAATATTTCAGTGACTTTTCAGATTTATTTCTTGTTAGCCGCTGTGTG | SEQ ID NO: 2932 | Homo sapiens cDNA FLJ12935 fis, clone NT2RP2004982. [AK022997] |
| 581 | A_24_P886040 | DCP2 | CATTCGAACAGGTTCATTCTGTTTCTAGATTTATGTTGTGTATGTTGAACAGGCAAGTG | SEQ ID NO: 2933 | Homo sapiens DCP2 decapping enzyme homolog (S. cerevisiae) (DCP2), mRNA [NM_152624] |
| 582 | A_24_P890536 | CR627148 | AATTGCCTTCTTGTAACCCTAAGTATGGTGAAGGAGAATTGAATTCTACAAAAGTCTTTC | SEQ ID NO: 2934 | Homo sapiens mRNA; cDNA DKFZp779F2127 (from clone DKFZp779F2127). [CR627148] |
| 583 | A_24_P915269 | SRGN | GGCATCATATTCGGAAATATCTCCTAGGTTTATCTACCATTGAGTGTGTTTAGAGAC | SEQ ID NO: 2935 | Homo sapiens serglycin, mRNA (cDNA clone IMAGE:4688573), complete cds. [BC022313] |
| 584 | A_24_P91916 | NXT2 | AACCATGCTTTCTTCTAGTACTGATGAAACTTACACAGTTTTATTCTACTCATAGTGAGG | SEQ ID NO: 2936 | Homo sapiens nuclear transport factor 2-like export factor 2 (NXT2), mRNA [NM_018698] |
| 585 | A_24_P921366 | CALD1 | TTCCTTGTTTACTGGTTTCACTATAATTCTCTGTTATCTTATTCTTACGAGGTAAAACTGCAAGC | SEQ ID NO: 2937 | Homo sapiens caldesmon 1 (CALD1), transcript variant 1, mRNA [NM_033138] |
| 586 | A_24_P924697 | AK055915 | GGGCCAGGAATACCCAAAATTATTCACACGACGTTAACTTATTGGTACTGGGCTAAGCAATAC | SEQ ID NO: 2938 | Homo sapiens cDNA FLJ31353 fis, clone MESAN2000264. [AK055915] |
| 587 | A_24_P925505 | CD36 | CGTAGCCGTGTTACTACCAGTTGGTCTGTTTTATCGTGTAAGTACCAAATATGAATGGC | SEQ ID NO: 2939 | CD36-collagen type 1/thrombospondin receptor [one exon] [human, mRNA Partial 369 nt]. [S67044] |
| 588 | A_24_P935986 | BCAT1 | ATGCTCTGAAGGTTTTGTAGAAGCAGACAATAAAACATCTAAAATGGCTTTGTTACACCAGA | SEQ ID NO: 2940 | Homo sapiens branched chain aminotransferase 1, cytosolic (BCAT1), mRNA [NM_005504] |
| 589 | A_24_P936319 | BC030115 | GAAAGATAGATACCATTCTATGGTAACAACTACGTCTAAGTAACATCTGATGTTACATGCAC | SEQ ID NO: 2941 | Homo sapiens cDNA clone IMAGE:4801326. [BC030115] |
| 590 | A_24_P937095 | SLC30A1 | TTTGAGTGTAGGTCTACGGAATATGTGTGGTAATGCTATTTTGTTTACTAACAAGCTCTG | SEQ ID NO: 2942 | Zinc transporter 1 (Znt-1) (Solute carrier family 30 member 1). [Source:Uniprot/SWISSPROT;Acc:Q9Y6M5] [ENST00000367000] |
| 591 | A_24_P940426 | QKI | AAGGTGTTGAATGAGTCTTAAAAATTATACTACTGTTAAGTGGACCAAGTTTGGTGAAGC | SEQ ID NO: 2943 | Homo sapiens quaking homolog, KH domain RNA binding (mouse) (QKI), transcript variant 4, mRNA [NM_206855] |
| 592 | A_24_P940725 | C6orf111 | AATTATGATTAGTGAGTGGTCTAACAGTTTAAGGCATTGATAAGTTACAAGTAGAGTGGG | SEQ ID NO: 2944 | Splicing factor, arginine/serine-rich 130 (Serine-arginine-rich- splicing regulatory protein 130) (SRrp130) (SR-rich protein) [Source:Uniprot/SWISSPROT;Acc:Q8IF01] [ENST00000369239] |

Fig. 7-33

| No. | Probe ID No. | Symbols of genes | Sequence | SEQ ID NO. | Descriptions of genes (letters and numbers within [ ] indicates GenBank accession No.) |
|---|---|---|---|---|---|
| 593 | A_24_P941643 | PLCB1 | ATGAGTGCAGTTTGTGGGTTTATGTATTTGCTTGTCTTTGTCGAATGTGTGAAATT | SEQ ID NO: 2945 | Homo sapiens phospholipase C, beta 1 (phosphoinositide-specific) (PLCB1), transcript variant 2, mRNA [NM_182734] |
| 594 | A_24_P942002 | CENTB2 | TGGATTGTCATGGTCAGGATTTGTGAGATCTTAATCTAAGCTGCAAAGTTGTCTACTTTT | SEQ ID NO: 2946 | Homo sapiens centaurin, beta 2 (CENTB2), mRNA [NM_012287] |
| 595 | A_24_P942469 | SPAG9 | AAACAGAGTGTGATATAATTAACTGTGGTAAAGAACATGTGTCTTGCAAATGCCATGGA | SEQ ID NO: 2947 | Homo sapiens cDNA FLJ26141 fis, clone TST03911. [AK129652] |
| 596 | A_24_P942773 | SLMAP | AAAGTACAATAGAATTTCTGGAGTACAGATTAAGTATTTGGACTAACACACGTGAGGTG | SEQ ID NO: 2948 | Homo sapiens sarcolemma associated protein (SLMAP), mRNA [NM_007159] |
| 597 | A_24_P943957 | PIP5K3 | TTGGCTCTTATTAAGGTATTGGTAAATAGTAGGGTTATATCGATATCAGCTTTTGTGATGGC | SEQ ID NO: 2949 | Homo sapiens phosphatidylinositol-3-phosphate/phosphatidylinositol 5-kinase, type III (PIP5K3), transcript variant 2, mRNA [NM_015040] |
| 598 | A_24_P97526 | CMTM6 | GTGGATCTCTTAGTTGGTTCAGTTCAATCTTTCTTTTCAGAAAGATAGTATGTTCACTGG | SEQ ID NO: 2950 | Homo sapiens CKLF-like MARVEL transmembrane domain containing 6 (CMTM6), mRNA [NM_017801] |
| 599 | A_24_P98109 | SNX10 | AAGAGTGGCAGAGGGTAGTACAAAAAAGCAACGTTTCATTTTCAGTAAGAGTTTAAAAGC | SEQ ID NO: 2951 | Homo sapiens sorting nexin 10 (SNX10), mRNA [NM_013322] |
| 600 | A_24_P99046 | STK38L | GCTATCTGTCTTTTGCTGATCTACAAATAAATGAAGAATTGAGAATTAGTGCATAGAGGTCC | SEQ ID NO: 2952 | Homo sapiens serine/threonine kinase 38 like (STK38L), mRNA [NM_015000] |
| 601 | A_32_P100109 | REPS2 | GTGTGGAGATTGGATCAACTGAGTTGTGTTATTTTGTTTTAAGTCACGTTGTGCAGAGAA | SEQ ID NO: 2953 | Homo sapiens RALBP1 associated Eps domain containing 2 (REPS2), transcript variant 1, mRNA [NM_004726] |
| 602 | A_32_P101313 | PTPLAD2 | AAAGTGTGAATAACTGATAGTCATTGGTCGTATCATTGATGTATCACTCAATTTTTGGTAA | SEQ ID NO: 2954 | Homo sapiens protein tyrosine phosphatase-like A domain containing 2 (PTPLAD2), mRNA [NM_001010915] |
| 603 | A_32_P108254 | FAM20A | TCGTGGGTTGCCTTGCCTCCGTTTTCCAAAAAGCACTGGCTTCATGAAGGCCACCCACG | SEQ ID NO: 2955 | Homo sapiens family with sequence similarity 20, member A (FAM20A), mRNA [NM_017565] |
| 604 | A_32_P112452 | BI026064 | CGTGGGAGGTGTTGATGATGGTCTGTATGTTGCGTTCCAGCTGGGACATTTTGCAGTCA | SEQ ID NO: 2956 | BI026064 GMO-MT0374-060201-774-h11 MT0374 Homo sapiens cDNA, mRNA sequence [BI026064] |
| 605 | A_32_P113564 | ZNF292 | GGGGCTTTTAGGTTTTATTGAATAGTTCATTTCATTTCACCTGTTTAAGACTTACTACGAATAAG | SEQ ID NO: 2957 | Zinc finger protein 292. [Source:Uniprot/SWISSPROT;Acc:O60281] [ENST00000339907] |
| 606 | A_32_P11451 | NMD3 | CAGTTTAAGGGCAGTAGCTGGTTTTGTCATAAAATAGTTGGTACGACATCGAAAAATGGTGC | SEQ ID NO: 2958 | Homo sapiens NMD3 homolog (S. cerevisiae) (NMD3), mRNA [NM_015938] |
| 607 | A_32_P115220 | C9orf66 | TCCTCAAAAAATGTTTCGTCACAACGCTGGGGTAAGGTGAATGTTTTGTCGGAGAAACACTGA | SEQ ID NO: 2959 | Homo sapiens chromosome 9 open reading frame 66 (C9orf66), mRNA [NM_152569] |
| 608 | A_32_P115505 | ZNF294 | TGTGGTCAGAGGATTATAGTTGAGAGATGTTGAGAGTACTATGTCTGAGTATAGATGTCGGAA | SEQ ID NO: 2960 | Homo sapiens zinc finger protein 294 (ZNF294), mRNA [NM_015565] |
| 609 | A_32_P117313 | DKFZP779L1068 | ATGAGTGTAAGATCTTGAGAGATGTTCTTACTCATTCTGTAATTGCAGTAGTGTAGTC | SEQ ID NO: 2961 | Homo sapiens cDNA clone IMAGE:5555490. [BC110326] |
| 610 | A_32_P118325 | BU567832 | ATTAATTCTGACTAAATGGCATTAAAGGAGGTCTGAGGAATTGCATGTCACATTCTGGA | SEQ ID NO: 2962 | AGENCOURT_10399047 NIH_MGC_82 Homo sapiens cDNA clone IMAGE:6614537 5', mRNA sequence [BU567832] |

Fig. 7-34

| No. | Probe ID No. | Symbols of genes | Sequence | SEQ ID NO: | Descriptions of genes (letters and numbers within [ ] indicates GenBank accession No.) |
|---|---|---|---|---|---|
| 611 | A_32_P123204 | AI381562 | AACTGTACAAATGGTCTCCTTAAGCAGTGTCTGGTAATAATGT CATGAGTTTTCACTT | SEQ ID NO: 2963 | AI381562 te76g06.x1 Soares_NFL_T_GBC_S1 Homo sapiens cDNA clone IMAGE:2092666 3', mRNA sequence [AI381562] |
| 612 | A_32_P124580 | THC2610143 | ATTAGCTGGGACTAAAACGGACACATGTTTTGTTTGTGAATTGAC CTAAATGTCTCTA | SEQ ID NO: 2964 | AA490192 aa43f10.r1 Soares_NhHMPu_S1 Homo sapiens cDNA clone IMAGE:823723 5', mRNA sequence [AA490192] |
| 613 | A_32_P125917 | THC2753798 | GGTTATAAGTGTAAGTGGAGAGACGGCTAAATTGTGAGTACAAAGTT TCTTTTCACAACAG | SEQ ID NO: 2965 | BF238843 601904455F1 NIH_MGC_54 Homo sapiens cDNA clone IMAGE:4132429 5', mRNA sequence [BF238843] |
| 614 | A_32_P126023 | THC2559380 | AGTCTTCTAGATTTCTGCTAGCAAACTGATATGAGTAGAGTCCT GAAAGATCTTCAGC | SEQ ID NO: 2966 | ALU5_HUMAN (P39192) Alu subfamily SC sequence contamination warning entry, partial (9%) [THC2559380] |
| 615 | A_32_P126880 | BC062780 | AGATGGGAACACAGAGGAGTAGTGAGGAGTAGAGAAGCAGTGTAG ACCTTTCATATCAT | SEQ ID NO: 2967 | Homo sapiens cDNA clone IMAGE:4700531, partial cds. [BC062780] |
| 616 | A_32_P129694 | MEGF9 | TTTAGACAACATTTGTAGACACCTCAAATTTATGACTGTGTCT AGGGGAATATTCCC | SEQ ID NO: 2968 | Homo sapiens multiple EGF-like-domains 9 (MEGF9), mRNA [NM_001080497] |
| 617 | A_32_P131401 | AI276257 | TCAGAAAAAAAGAGAGTAAGGCACCAGTGTTGGGAAATTAAGGTAG CTTGGAGTAACAAGAT | SEQ ID NO: 2969 | AI276257 qi65f01.x1 Soares_NhHMPu_S1 Homo sapiens cDNA clone IMAGE:1877209 3', mRNA sequence [AI276257] |
| 618 | A_32_P148824 | C1orf27 | GAAAACAGATGTTATCCTCAGCACACAATTCAGTAAAGAGAGTAG AAAGGATGATCTTC | SEQ ID NO: 2970 | Homo sapiens chromosome 1 open reading frame 27 (C1orf27), mRNA [NM_017847] |
| 619 | A_32_P149404 | LOC728371 | GTAAAGTGTGGAATTCTGTTGATGATGGATGTGAGGATGGTGAA GCGGTGCGGGATGAT | SEQ ID NO: 2971 | PREDICTED: Homo sapiens similar to ankyrin repeat domain 20A (LOC728371), mRNA [XR_015273] |
| 620 | A_32_P153725 | KIAA1033 | TTTGTGAAAGATGGCAAGTTTGTTGGTCACTTGACTGAGTGGGTT TGCTTTTCCCCAAT | SEQ ID NO: 2972 | Homo sapiens KIAA1033 (KIAA1033), mRNA [NM_015275] |
| 621 | A_32_P162183 | C2 | GGTTGAGTTGACTCATCAGTCTTGTTCACTTCACATGGAATTCCC AGTTATGAAATTAAT | SEQ ID NO: 2973 | Homo sapiens complement component 2 (C2), mRNA [NM_000063] |
| 622 | A_32_P162250 | ARHGAP18 | AAGTGCTGAATAAGTCTACTGGGAAGAATATTCTTGTGGGTGAAA AAGGTTTGTTTGTG | SEQ ID NO: 2974 | Homo sapiens Rho GTPase activating protein 18 (ARHGAP18), mRNA [NM_033515] |
| 623 | A_32_P164203 | THC2683448 | TTGATGGTCATTGTACGGAGGCTATTGTATGGATTACTGTGGATGC TGTTAGGACACATGAT | SEQ ID NO: 2975 | G7WZG3_PASP1 (G7WZG3) Ferric uptake regulator, partial (8%) [THC2683448] |
| 624 | A_32_P166272 | THC2650457 | ATACATTTTAATTGCTCACGTTTTATATTGGAGAGTTCAGTACAG ACTGTGCATTAGTGC | SEQ ID NO: 2976 | ALU6_HUMAN (P39193) Alu subfamily SP sequence contamination warning entry, partial (12%) [THC2650457] |
| 625 | A_32_P167122 | RCOR3 | GTATGTGAGGGATGTGCTGTAATCTGATTACATGCATTAGAGCA CACAGTAGAAAAGT | SEQ ID NO: 2977 | Homo sapiens REST corepressor 3 (RCOR3), mRNA [NM_018254] |
| 626 | A_32_P170444 | SUB1 | TAGGTATGTCTCCTGAAATTCTTTGCAGTTCATTTTTATGGCAG TTAATCCAGTGAAAC | SEQ ID NO: 2978 | Activated RNA polymerase II transcriptional coactivator p15 (SUB1 homolog) (Positive cofactor 4) (PC4) (p14). [Source:Uniprot/SWISSPROT;Acc:P53999] [ENST00000265073] |
| 627 | A_32_P171313 | GNB4 | GATTTAAGTGTCTTAGATCTTCTTAGACACAGTGATTCATTGGTC TATTTGTGTACAGTGGC | SEQ ID NO: 2979 | Homo sapiens guanine nucleotide binding protein (G protein), beta polypeptide 4 (GNB4), mRNA [NM_021629] |

Fig. 7-35

| No. | Probe ID No. | Symbols of genes | Sequence | SEQ ID NO. | Descriptions of genes (letters and numbers within [ ] indicates GenBank accession No.) |
|---|---|---|---|---|---|
| 628 | A_32_P17163 | ENST00000368149 | TGGTTAGTAGTGAGTTTAAATGTCAGGCGTAGATTTTTATTGTTTTCTGTGTGTGTATGAG | SEQ ID NO: 2980 | Rho GTPase-activating protein 18 (MacGAP) [Source:Uniprot/SWISSPROT;Acc:Q8N392] [ENST00000368149] |
| 629 | A_32_P172578 | THC2661509 | AGTTAATCAATGTCTCAAACATTTCTAGGCATTCTGATCTCATGGCATTCCTCTGTTGG | SEQ ID NO: 2981 | |
| 630 | A_32_P17504 | THC2699682 | ATGTCTATGCTGTTTCACTATGCTGCAAATATTCCCAGCCTTTTGCCCTTGATGCCAAA | SEQ ID NO: 2982 | |
| 631 | A_32_P177040 | WBSCR19 | AATCTTGTATCTATTATTACACGTCGTTGCTGAAGGGAGGAATGGTTTTTATCTGTATG | SEQ ID NO: 2983 | Homo sapiens Williams Beuren syndrome chromosome region 19 (WBSCR19), mRNA [NM_175064] |
| 632 | A_32_P177685 | THC2632286 | TTTGAGTGAGTATTTGTTAGAATGGTTAATGACTGAAATGAATTTGGAGGCACTGATGAAAG | SEQ ID NO: 2984 | AA665072 nu76b01.s1 NCI_CGAP_Alv1 Homo sapiens cDNA clone IMAGE:1216585, mRNA sequence [AA665072] |
| 633 | A_32_P178866 | ENST00000379426 | GTAATATAGAGGGTGAACTGTTTACTGATACACACAAGAGAAACTGTTAAAGTGAATGG | SEQ ID NO: 2985 | Novel protein. [Source:Uniprot/SPTREMBL;Acc:Q5T4I1] [ENST00000379426] |
| 634 | A_32_P183435 | WBSCR19 | CTTTCAATGCTTTGTATCTATTATTACACGGTGCTGCTGAAAGGGAGGATGTTTTATCTCATG | SEQ ID NO: 2986 | Homo sapiens Williams Beuren syndrome chromosome region 19 (WBSCR19), mRNA [NM_175064] |
| 635 | A_32_P184417 | A_32_P184417 | AAGGCTCGTTGCTGTGGTAGGCATTCAGTTATTCCTAATAGTTTATTTAGGTACTATAC | SEQ ID NO: 2987 | |
| 636 | A_32_P184916 | GNB4 | CAAGTGCAACGCGTTACATTTGGACAGAAGAGTGTGAAAATCTAAGCAATCGCTAGCACATAT | SEQ ID NO: 2988 | Homo sapiens guanine nucleotide binding protein (G protein), beta polypeptide 4 (GNB4), mRNA [NM_021629] |
| 637 | A_32_P193322 | RICTOR | ACCAAGATGACGTTCTCTCTTTTATTTAGTAATACGGTGGTGGTACAATTTGGAGGTTGTGG | SEQ ID NO: 2989 | Homo sapiens rapamycin-insensitive companion of mTOR (RICTOR), mRNA [NM_152756] |
| 638 | A_32_P194032 | LONRF1 | GTTAGATCACCATGCCAACATGGTTTATATTCATGCTGCCCTAGAAGTTTTTGTAATT | SEQ ID NO: 2990 | Homo sapiens LON peptidase N-terminal domain and ring finger 1 (LONRF1), mRNA [NM_152271] |
| 639 | A_32_P195387 | DKFZP779L1068 | ATATAACCTTGGAATTCTGTATTCTAATTATAGTGTTGTTCTGGCTGTTGTAGTAGAATGCGC | SEQ ID NO: 2991 | Homo sapiens cDNA clone IMAGE:5555490. [BC110326] |
| 640 | A_32_P19752 | FAM76B | TGTGCTTTTAGCGTGCTACTATTAATTAGCAGTTATTGAC | SEQ ID NO: 2992 | Homo sapiens family with sequence similarity 76, member B (FAM76B), mRNA [NM_144664] |
| 641 | A_32_P20240 | SP3 | CTTAGGGTCTTAATTGTAGTTAAATTCCAGTACTGGCTACTCAGAAGGGTCATTTTGACACCGAAAAGTTTGT | SEQ ID NO: 2993 | Homo sapiens mRNA; cDNA DKFZp686N17231 (from clone DKFZp686N17231). [BX648657] |
| 642 | A_32_P203320 | ROCK1 | AAGGGCCATACTAGTATGAAGATCAGCTGATGGAAGGAGTAAAGAAAATATGTCAAATGAG | SEQ ID NO: 2994 | Homo sapiens Rho-associated, coiled-coil containing protein kinase 1, mRNA (cDNA clone IMAGE:5269382), complete cds. [BC041849] |
| 643 | A_32_P203749 | AF086547 | CAGGTGTCTATTTGGTAGACCATGCCTAGATTTGTTACATGGATTTTGCGGAGTT | SEQ ID NO: 2995 | Homo sapiens full length insert cDNA clone ZE12B03. [AF086547] |
| 644 | A_32_P205553 | RPL26L1 | TTGGAATGTCTGGAACATTTCATTTCGTGTTTGTTAGGTGTGGCTCTGTAAATCTAGT | SEQ ID NO: 2996 | Homo sapiens ribosomal protein L26-like 1 (RPL26L1), mRNA [NM_016093] |
| 645 | A_32_P207098 | BF513730 | AAACCACCTACCTAATCTGACTGGTAAATTCTAGCTTCTTGTTTTAAATATGCTCAAGG | SEQ ID NO: 2997 | BF513730 UI-H-BW1-any-e-05-0-UI.s1 NCI_CGAP_Sub7 Homo sapiens cDNA clone IMAGE:3071696 3', mRNA sequence [BF513730] |

Fig. 7-36

| No. | Probe ID No. | Symbols of genes | Sequence | SEQ ID NO: | Descriptions of genes (letters and numbers within [ ] indicates GenBank accession No.) |
|---|---|---|---|---|---|
| 646 | A_32_P221552 | BE173582 | ATTTAACTGAGGTAGACCAGATGTTCTAAATTCGGCGTTTCATA GAATGCCGTGAATCT | SEQ ID NO: 2998 | BE173582 RG2-HT0560-290200-014-F05 HT0560 Homo sapiens cDNA, mRNA sequence [BE173582] |
| 647 | A_32_P224666 | CAPZA2 | AATGTGTTTTGAGATTGTGAAATTAAATGAAATACTTATTCA GAAATGCATTTAATG | SEQ ID NO: 2999 | Homo sapiens capping protein (actin filament) muscle Z-line, alpha 2 (CAPZA2), mRNA [NM_006136] |
| 648 | A_32_P226678 | BX114764 | CCTCTACATCCTTACCTAGGATGGCATGCCAGCATGGCGAGTATTTG GAGGGGTCCAAATTA | SEQ ID NO: 3000 | BX114764 NCI_CGAP_GCB1 Homo sapiens cDNA clone IMAGp998M182012, mRNA sequence [BX114764] |
| 649 | A_32_P226786 | BC045174 | TTATTGGTGGATGTAAGCCATTATGCTGTCTTAATGAACCGATTA ATGCTGTTGATTCTT | SEQ ID NO: 3001 | Homo sapiens cDNA clone IMAGE:5273245 [BC045174] |
| 650 | A_32_P228438 | THC2637026 | GTGTCGTATTCCAGGCGTAGTGAAATAGATAATGCGTTGAACTATT CCTATCACGAGAGGT | SEQ ID NO: 3002 | Q8N4F7_HUMAN (Q8N4F7) Ring finger protein 175, partial (12%) [THC2637028] |
| 651 | A_32_P2333 | SUB1 | AGGAAGAAAAGGTATTTCTTAAATCCAGAACAATGGAGCGAGGCT GACAGAACAGATTTC | SEQ ID NO: 3003 | Homo sapiens SUB1 homolog (S. cerevisiae) (SUB1), mRNA [NM_006713] |
| 652 | A_32_P233314 | EXOC8 | AGGATTGGGAATTGGGACATGACATGTACTATAAAAGTCAGTGT ATGTACATACTGCTT | SEQ ID NO: 3004 | Homo sapiens exocyst complex component 8 (EXOC8), mRNA [NM_175876] |
| 653 | A_32_P26895 | KIAA1600 | AATTCTTGGTCCCTGGGTGGGTGCGTAGAGTTTCAGATGGTCATGTG TACCTACTGTCTT | SEQ ID NO: 3005 | KIAA1600 (KIAA1600), mRNA [Source:RefSeq_dna;Acc:NM_020940] |
| 654 | A_32_P31123 | THC2690780 | CATTAGGGAAGATACGATTCAGTGGGTGCATAGAGTTCGGATTCGGTCTTTGGAA AAAGGTCAGTCCTCA | SEQ ID NO: 3006 | [ENST00000369248] |
| 655 | A_32_P32315 | A_32_P32315 | CCTCTCAAAATTGGCAGGAGCTAAATAATAGTTGTGCGGGATTT GTATTGTGTACTGTA | SEQ ID NO: 3007 | transcription factor RFX3 [Source:Uniprot/SWISSPROT;Acc:P48380] [ENST00000382004] |
| 656 | A_32_P3742 | RFX3 | AAAGTGTGGTATTGAAAGTGTAGAACTGACTTGGAAAAAGGAAT TCCTCTCTAATTGGT | SEQ ID NO: 3008 | |
| 657 | A_32_P38745 | THC2656841 | TTGTTGTTAGTTAGGAGATCGGTGATGCCACTTAGTGTGTT TGGTAACACAGAAACA | SEQ ID NO: 3009 | |
| 658 | A_32_P43217 | PSMA6 | GAAGGAGATAAGGTTCGACTTACATTCTTCACACTGTCAAAAAT GGAGAAAAACTACAG | SEQ ID NO: 3010 | Homo sapiens proteasome (prosome, macropain) subunit, alpha type, 6 (PSMA6), mRNA [NM_002791] |
| 659 | A_32_P44394 | AIM2 | AAATGCAGACTTTGTTATTTGCCAAAGAAGATTCATCATGTTGCT TCCTTTGTTTTCGG | SEQ ID NO: 3011 | Homo sapiens absent in melanoma 2 (AIM2), mRNA [NM_004833] |
| 660 | A_32_P49164 | AV714556 | ATGTAATGAATCGTCAGAAAGCCTTGGTGATAGGTCAGGTCGCTAAA AGTACACTACACAG | SEQ ID NO: 3012 | AV714556 AV714556 DCB Homo sapiens cDNA clone DCBAD606 5, mRNA sequence [AV714556] |
| 661 | A_32_P6107 | A_32_P6107 | GATAGGATTCTTAACAGTAAGCTCTTTATAATTCAACAGATGAT GTTTACTCCTACCCC | SEQ ID NO: 3013 | |
| 662 | A_32_P61145 | AK096154 | TCAGTGTCAGAGTTCCACTGGAATTCGACAGTGTCTAGAGTGA TGCAACGCGGAAGTAG | SEQ ID NO: 3014 | Homo sapiens cDNA FLJ38835 fis, clone MESAN2002424 [AK096154] |
| 663 | A_32_P61857 | KIAA1468 | | SEQ ID NO: 3015 | Homo sapiens KIAA1468 (KIAA1468), mRNA [NM_020854] |
| 664 | A_32_P62342 | GLT8D3 | GTGATGTAACTGATGTAACCATTGACAATCTATGTGCCTTTA TACATTTCATCTCTG | SEQ ID NO: 3016 | Homo sapiens glycosyltransferase 8 domain containing 3, mRNA (cDNA clone MGC:21651 IMAGE:4508300), complete cds. [BC039145] |

Fig. 7-37

| No. | Probe ID No. | Symbols of genes | Sequence | SEQ ID NO. | Descriptions of genes (letters and numbers within [ ] indicates GenBank accession No.) |
|---|---|---|---|---|---|
| 665 | A_32_P63113 | THC2706386 | AGAAAAGAACAGAAGTCTGGGCTCCACACATACTATGTTCCAGATGACTGTATTTT | SEQ ID NO: 3017 | Q9TGMO_GLOFA (Q9TGMO) NADH-ubiquinone oxidoreductase subunit 1, partial (6%) [THC2706386] |
| 666 | A_32_P66881 | TLR4 | TTACTGAGTGTTTGAGAGTCTGTTGGTTTGAAGCAGGTGTAGGGTGATTGAACATCCCTG | SEQ ID NO: 3018 | Homo sapiens toll-like receptor 4 (TLR4), mRNA [NM_138554] |
| 667 | A_32_P7118 | PSMC6 | AGCAGACCTGAGAAATGTTTGTACTGAAGCAGGTATGTTGGCAATTCGTGCTGCTCATGA | SEQ ID NO: 3019 | Homo sapiens proteasome (prosome, macropain) 26S subunit, ATPase, 6 (PSMC6), mRNA [NM_002806] |
| 668 | A_32_P73222 | AA631847 | TTTGTTTGTTTTGGACAATCTCATAAGAAGTTTAGGTCTTACAGCACGAACCCCTCGAAG | SEQ ID NO: 3020 | np61b02.s1 NCI_CGAP_Br2 Homo sapiens cDNA clone IMAGE:1130763 3' similar to TR:G971838 G971838 60S RIBOSOMAL PROTEIN L34 ;, mRNA sequence [AA631847] |
| 669 | A_32_P75115 | BF373107 | AGAAGTCAAAAACTGAAGAATGTGGAGTGTTTACTGTCCCGTTACTCACAGAAGAGTGCT | SEQ ID NO: 3021 | BF373107 CM2-FT0123-260700-305-G12 FT0123 Homo sapiens cDNA, mRNA sequence [BF373107] |
| 670 | A_32_P79396 | PBEF1 | AGGGCCGATTATCTTTACATAGAGAGGGCGAGGAGGCGAATTTTGTTACACTGGAAGAAGGAA | SEQ ID NO: 3022 | Homo sapiens pre-B-cell colony enhancing factor 1 (PBEF1), mRNA [NM_005746] |
| 671 | A_32_P81768 | TMEM167 | CCTCAGTACTGCTCACTACAATATTAGATTCTGCAAATGTTATTCTGTTGTATCAGATACG | SEQ ID NO: 3023 | Homo sapiens transmembrane protein 167 (TMEM167), mRNA [NM_174909] |
| 672 | A_32_P83000 | FLJ31222 | AGCATCTGCTGGGACGGGGACACCCTCTGTTCTTGATCTCACTCCCAGAAAGACACTGAA | SEQ ID NO: 3024 | Homo sapiens cDNA FLJ31222 fis, clone KIDNE2004294. [AK055784] |
| 673 | A_32_P83266 | AK023663 | CAAATGTCCTTCAAAGCATCTTCAGAATCAAGATTGTCATGTAGATTGCACCCGAAGTT | SEQ ID NO: 3025 | Homo sapiens cDNA FLJ13601 fis, clone PLACE1010069. [AK023663] |
| 674 | A_32_P86400 | LYSMD3 | AAATGTTGTCAGTTGGTAATCAGTATTTCTTCGACGTATGTGGATATTGCACTGTTAGATC | SEQ ID NO: 3026 | Homo sapiens LysM, putative peptidoglycan-binding, domain containing 3 (LYSMD3), mRNA [NM_198273] |
| 675 | A_32_P877 | BM999343 | TAAAATGCTTGCACAACTCCACTGTCATTGTCAGAGATTTCCATTGGGAAGCCATGGCTA | SEQ ID NO: 3027 | BM999343 UI-H-DF0-avf-i-24-0-UI.s1 NCI_CGAP_Fs1 Homo sapiens cDNA clone IMAGE:5878751 3', mRNA sequence [BM999343] |
| 676 | A_32_P97046 | BU076193 | ATTTATATACAGACGAATGGGGCAGCCTAATGACGATATAAGATTAACTTTCCAAAGAAGT | SEQ ID NO: 3028 | tm55f06.x1 HR85 islet Homo sapiens cDNA clone IMAGE:6089339 3', mRNA sequence [BU076193] |
| 677 | A_32_P98435 | PCMTD1 | ACAGTTTGCCATGGTCAAAGAATGAAGGACAATATGGAAAAAGCCAATCTTCAAATATATC | SEQ ID NO: 3029 | Homo sapiens clone 122482 unknown mRNA. [AF293366] |

Fig. 8-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P341938 | NOG | GCCAGCGGTGCGGCCTGGATTCCGATCGGAGTAGCCGATCATTTCCGAGTGCAAGTGCTCGT | SEQ ID NO: 2373 | Homo sapiens noggin (NOG), mRNA [NM_005450] |
| 2 | A_24_P413126 | TMEPAI | AAGAAACTGCTTGTTGTGTATCAGTAATCATTAGTGGCAATGATGACATTCTGAAAAGCT | SEQ ID NO: 2404 | Homo sapiens transmembrane, prostate androgen induced RNA (TMEPAI), transcript variant 1, mRNA [NM_020182] |
| 3 | A_32_P11394 | THC2643957 | GAATACAGTGTTCCTTTTCATCCCATATTTGACTGAACGTAAGACACATCAATTATAAGG | SEQ ID NO: 2418 | |
| 4 | A_32_P125589 | THC2649341 | CGCTCTATCCCTTGTTTTAGGGTTTGAATGAAAGTGAGATGTCTCATCAGCTCAGATAG | SEQ ID NO: 2419 | |
| 5 | A_32_P164378 | THC2703271 | GAAAGAACATGAAAAGCATTGGAATCAAGGAAAGCCACCTGGTTTTAGACTTTAATTTTG | SEQ ID NO: 2426 | |
| 6 | A_32_P179998 | DMRTC1 | ATATGCCAGAGTTTTTATTCGTCTTGTGATTGGTGGTGACATACCTGTGCACTCATGTGTATA | SEQ ID NO: 2430 | Homo sapiens DMRT-like family C1 (DMRTC1), mRNA [NM_033053] |
| 7 | A_23_P11321 | ARG1 | TGGAATCAGGAGGAGACAAAAGCTACCACATGTGGAAAAGGTACTATGTGTCCATGTCAATTCAAA | SEQ ID NO: 2459 | Homo sapiens arginase, liver (ARG1), mRNA [NM_000045] |
| 8 | A_23_P11201 | GPR34 | AGTTAGGAGTGAAAGCACTTCAGAATTTAAACCAGGATAGTCCCTGCATGATACATGTGTG | SEQ ID NO: 2461 | Homo sapiens G protein-coupled receptor 34 (GPR34), transcript variant 1, mRNA [NM_005300] |
| 9 | A_23_P119222 | RETN | CAATAAGGACAGCATTGCCTGGAGTGCCAGAGGCTCAGGTCAGGTCGGGCACCTGGGTAGTT | SEQ ID NO: 2469 | Homo sapiens resistin (RETN), mRNA [NM_020415] |
| 10 | A_23_P124716 | ANXA3 | TGGACATTCGAACAGAGTTCAAGAAGCATTATGGCTATTCCGTATATTCAGCAATTAAAT | SEQ ID NO: 2475 | Homo sapiens annexin A3 (ANXA3), mRNA [NM_005139] |
| 11 | A_23_P14708 | SUHW4 | TCTTTGTACGTCCATACAAGTGTTAGCCTGCCAGGCTGTAAGGTTACCTTAATTAAAGTT | SEQ ID NO: 2507 | Homo sapiens suppressor of hairy wing homolog 4 (Drosophila) (SUHW4), transcript variant 1, mRNA [NM_017661] |
| 12 | A_23_P151637 | RNASE2 | GTGGTAAGCACAAATATGACCTCCTAGTAACAAAACTGCGAAAAATTGTCAGGCAGTG | SEQ ID NO: 2514 | Homo sapiens ribonuclease, RNase A family, 2 (liver, eosinophil-derived neurotoxin) (RNASE2), mRNA [NM_002934] |
| 13 | A_23_P152062 | BCL2A1 | TGTAACCATATTGCATTTCGAAGGTATTCTGATCAGAAAACTTCTACGACAGCAAATTGC | SEQ ID NO: 2515 | Homo sapiens BCL2-related protein A1 (BCL2A1), mRNA [NM_004049] |
| 14 | A_23_P158650 | COX7B | CAAATACGGTAATGCTGCTGTATTAGCTAGTGGAGCCACTTTGTTATTGTTACATGGAGATA | SEQ ID NO: 2525 | Homo sapiens cytochrome c oxidase subunit VIIb (COX7B), nuclear gene encoding mitochondrial protein, mRNA [NM_001866] |
| 15 | A_23_P170233 | CSTA | AACTGGCTACTGAGTCATCATGCTTGGTCGATAAATATAACCATCAATAAAGAAGGATTCT | SEQ ID NO: 2543 | Homo sapiens cystatin A (stefin A) (CSTA), mRNA [NM_005213] |
| 16 | A_23_P26235 | CLEC4D | CATTTAACCCAGCCAGCAGAGTATTCTGGCATAAGAATGAACGGGACAACTCTCAGGGAGAAA | SEQ ID NO: 2600 | Homo sapiens C-type lectin domain family 4, member D (CLEC4D), mRNA [NM_080387] |
| 17 | A_23_P253012 | GRAMD1C | GGATTCGAAGCATACCTAGGGGTAACAGTGAACCTACGTGGGTTTGTTTTGTTTG | SEQ ID NO: 2602 | Homo sapiens GRAM domain containing 1C (GRAMD1C), mRNA [NM_017577] |
| 18 | A_23_P302550 | RGS18 | GAGTCTAAGGCGCTAGGCATTGGGCATCGTGCCACATTGGTTCATATTCAGAAAGTGTTA | SEQ ID NO: 2621 | Homo sapiens regulator of G-protein signaling 18 (RGS18), mRNA [NM_130782] |

Fig. 8-2

| No. | Probe ID No. | Symbols of genes | Sequence | SEQ ID NO: | Descriptions of genes (letters and numbers within [ ] indicates GenBank accession No.) |
|---|---|---|---|---|---|
| 19 | A_23_P307940 | CAPZA2 | CTAGAAGATTGGGAAAGAGAATGCATAAGATGAACATTGCATGACCGGATCATT | SEQ ID NO: 2628 | Homo sapiens capping protein (actin filament) muscle Z-line, alpha 2 (CAPZA2), mRNA [NM_006136] |
| 20 | A_23_P314191 | ZDHHC17 | TGGATACTTTAGCAAATAGGAACGTTAATTGTCAGCACTGAACATGAATTACTTCCTTGG | SEQ ID NO: 2634 | Homo sapiens zinc finger, DHHC-type containing 17 (ZDHHC17), mRNA [NM_015336] |
| 21 | A_23_P324633 | C9orf72 | TTTGTGGATTAGTCCCTGGGATTCAGTCTGTAGAAATGTGTAATAGTTCTCTATAGTCC | SEQ ID NO: 2640 | Homo sapiens chromosome 9 open reading frame 72 (C9orf72), transcript variant 1, mRNA [NM_018325] |
| 22 | A_23_P347198 | SP3 | GACCAGGTCGAAATTTAAAGGCTACGTTATTGTAGGTTGTAAAGTGTATTATAACAGTGTGG | SEQ ID NO: 2651 | Homo sapiens Sp3 transcription factor (SP3), transcript variant 1, mRNA [NM_003111] |
| 23 | A_23_P349083 | FCHO2 | GTGAAATGGTTAAACTCTGCACTTCTTAGTTAGCACAGTGTTCATACCAAGTATTGGG | SEQ ID NO: 2652 | Homo sapiens FCH domain only 2 (FCHO2), mRNA [NM_138782] |
| 24 | A_23_P405873 | C9orf72 | GAGAATGGAAGATCAGGGTCAGAGTATTATTCCAATGTTAGTGGAGAAGTGATTCCTGT | SEQ ID NO: 2674 | Homo sapiens chromosome 9 open reading frame 72 (C9orf72), transcript variant 2, mRNA [NM_145005] |
| 25 | A_23_P41114 | CSTA | AAAGAAATGAGACTTATGGAAAATTGGAAGCTGTGCAGTATAAAACTCAAGTTGTTGCTG | SEQ ID NO: 2677 | Homo sapiens cystatin A (stefin A) (CSTA), mRNA [NM_005213] |
| 26 | A_23_P41664 | ENST00000334994 | TGGCTTGGAGCAGAGATTGGACTTGATAAACAAATTGTTCCTGAAAATGAGGCACAGGTCAT | SEQ ID NO: 2680 | Synleurin (CGLQ1891) [Source:Uniprot/SPTREMBL;Acc:Q7Z207] ENST00000334994] |
| 27 | A_23_P420431 | XKR3 | CAGAGGTAAGGCCATAGAATCCTACACTACAGGTTCAGTTTTTTAGAAATGTGATAAT | SEQ ID NO: 2681 | Homo sapiens XK, Kell blood group complex subunit-related family, member 3 (XKR3), mRNA [NM_175878] |
| 28 | A_23_P434809 | S100A8 | AAAGGCATGAATGAAGAAGCCACAAAGAGTAGTAGTTAGTGGCCCAGAGGGTGGGCCCT | SEQ ID NO: 2691 | Homo sapiens S100 calcium binding protein A8 (S100A8), mRNA [NM_002964] |
| 29 | A_23_P44257 | COMMD8 | AACATTTTAGTTCTGGGGCTTCTATGTTTGGGAAACATTGCTGTGATAAAAAATAGCTGTC | SEQ ID NO: 2692 | Homo sapiens COMM domain containing 8 (COMMD8), mRNA [NM_017845] |
| 30 | A_23_P50907 | ITGAV | AAAGAGTGATTAAGTGAGGTTATTTACGGCTAAATGGTCCATTCTGCATTGTATTTCAGG | SEQ ID NO: 2700 | Homo sapiens integrin, alpha V (vitronectin receptor, alpha polypeptide, antigen CD51) (ITGAV), mRNA [NM_002210] |
| 31 | A_23_P59637 | DOCK4 | TTTGGGAGTGAGGAGTGAAGTTGAATTTATCTTGAATTTATCATGTGTGTGTATTCGAAGCAG | SEQ ID NO: 2714 | Homo sapiens dedicator of cytokinesis 4 (DOCK4), mRNA [NM_014705] |
| 32 | A_23_P59921 | SUB1 | CAGATTGGGAAAATGAGGTACGTTAGTGTTCGGGGATTTTAAAGGCAAAGTGCTAATTGAT | SEQ ID NO: 2715 | Homo sapiens SUB1 homolog (S. cerevisiae) (SUB1), mRNA [NM_006713] |
| 33 | A_23_P63343 | UTS2 | AGAATCTGGAAAGCCATACAACAAGAAAACGTGAGACTTCCTGATTGCTTCTGGAAATAGTGTGTC | SEQ ID NO: 2719 | Homo sapiens urotensin 2 (UTS2), transcript variant 1, mRNA [NM_021995] |
| 34 | A_23_P65768 | C15orf15 | TCCTGCATTGGCATCGTCATCATAATATCAGATATTACGGATGATTAGATTGCATCTCAGTGTT | SEQ ID NO: 2723 | Homo sapiens chromosome 15 open reading frame 15 (C15orf15), mRNA [NM_016304] |
| 35 | A_23_P66260 | ZNF267 | TGTGATGAATTGGTAAAGCGCTTCAGCTTAAGCTGCTATAGGTGATACCTCAGTACACATGGGAGAAGT | SEQ ID NO: 2724 | Homo sapiens zinc finger protein 267 (ZNF267), transcript variant 498723, mRNA [NM_003414] |
| 36 | A_23_P74601 | S100A12 | TGAAGGCTTTTAGCCAGGAATGTCCTGAATGAGAGGGTCTTTCTTTCGCTCACCAAACC | SEQ ID NO: 2738 | Homo sapiens S100 calcium binding protein A12 (S100A12), mRNA [NM_005621] |
| 37 | A_23_P7543 | ZFYVE16 | TCGGCTGCAGCATTATCTAAATGATCTTGATAGTGCTGATACCTGTGATCTCATGGTGG | SEQ ID NO: 2740 | Homo sapiens zinc finger, FYVE domain containing 16 (ZFYVE16), mRNA [NM_014733] |
| 38 | A_23_P78092 | EVI2A | GGTGAATCAGAGACTTGGAAAAGAAGAAACAGAAAACACGCTCACAGAGACCCAAGTAGTGATGCAA | SEQ ID NO: 2746 | Homo sapiens ecotropic viral integration site 2A (EVI2A), transcript variant 1, mRNA [NM_001003927] |

Fig. 8-3

| No. | Probe ID No. | Symbols of genes | Sequence | SEQ ID NO: | Descriptions of genes (letters and numbers within [ ] indicates GenBank accession No.) |
|---|---|---|---|---|---|
| 39 | A_23_P82047 | BU507302 | TCTGTTTCGTTAATGTCAGGTGCCTGAACATTCAGCAAGTTTATAAATTGTTAATTTGTG | SEQ ID NO: 2748 | AGENCOURT_10309636 NIH_MGC_71 Homo sapiens cDNA clone IMAGE:6501220 5', mRNA sequence [BU507302] |
| 40 | A_23_P94230 | LY96 | TGAAGCTATTTCTGGGAGCCCAGAAGAAGAAATGGTGTTTTGCTTGGAGTTTGTCATGTAGA | SEQ ID NO: 2763 | Homo sapiens lymphocyte antigen 96 (LY96), mRNA [NM_015364] |
| 41 | A_23_P105648 | BX111927 | TTATGAGATGGTCAGTTCAAATAACAGTGCAGTAATTCACGTATATCTAAAGACTGCC | SEQ ID NO: 2778 | BX111927 Soares_multiple_sclerosis_2NbHMSP Homo sapiens cDNA clone IMAGp998G05619, mRNA sequence [BX111927] |
| 42 | A_24_P111045 | THC2785765 | CGACCAGAAACGTACACGTGATTTCATGAGACAAATACGGTAGCAACACAAGTCGGAATAG | SEQ ID NO: 2781 | COX7B_HUMAN (P24311) Cytochrome c oxidase polypeptide VIIb, mitochondrial precursor, partial (78%) [THC2785765] |
| 43 | A_24_P201702 | CLEC2B | AATTGGAATTCAAGTAAATACAGAACTGTTGGACTCAACATGCCGACCTAACTATAATTGACA | SEQ ID NO: 2815 | Homo sapiens C-type lectin domain family 2, member B (CLEC2B), mRNA [NM_005127] |
| 44 | A_24_P20996 | BC043173 | CTGGAAAATGTTCATATATATGTATATGAATGTCTGTTTATCTGAAGGGCTCTGATTGG | SEQ ID NO: 2818 | Homo sapiens cDNA clone IMAGE:5287121 [BC043173] |
| 45 | A_24_P235429 | ABCA1 | CAAAGAGACCATGTGTCATGTAATACGTGAACCAAGTTGATATTGAGACATTAATTTGTAC | SEQ ID NO: 2823 | Homo sapiens ATP-binding cassette, sub-family A (ABC1), member 1 (ABCA1), mRNA [NM_005502] |
| 46 | A_24_P286054 | ZFYVE16 | GTGTATGTATTCTGCCATGTAAGTAATGTAAGTCTTAAAATAACCAAATGGTAGAGGG | SEQ ID NO: 2842 | Zinc finger FYVE domain-containing protein 16 (Endofin) (Endosome-associated FYVE domain protein). [Source:Uniprot/SWISSPROT:Acc:Q7Z3T8] [ENST00000380248] |
| 47 | A_24_P320328 | SUB1 | CAGAAAAAGCTGTAAAGAAACAAAAGACACAGGTAGAGCTTCGAGAGGCCCTGTCATCTCTCTA | SEQ ID NO: 2857 | Homo sapiens SUB1 homolog (S. cerevisiae) (SUB1), mRNA [NM_006713] |
| 48 | A_24_P324581 | KIAA1466 | ATAATAGTCATAGAATGAATTGCTGTACCAACCAAGGCTAAAAAGAATTTAAGTAGCCC | SEQ ID NO: 2861 | Homo sapiens mRNA for KIAA1466 protein, partial cds. [AB040899] |
| 49 | A_24_P387869 | PKN2 | TTGTCCAGAGATGCATTTATATTTACCTTCCAAATTGTTATTACCGAAGATCCTTTGGAG | SEQ ID NO: 2885 | Homo sapiens protein kinase N2 (PKN2), mRNA [NM_006256] |
| 50 | A_24_P413669 | PFKFB2 | TCAAATGGTTGTTTTTATACTGTGGATGATACGAGACTGTGTTACCTAAGATGTGATAAGC | SEQ ID NO: 2898 | Homo sapiens 6-phosphofructo-2-kinase/fructose-2,6-biphosphatase 2 (PFKFB2), transcript variant 2, mRNA [NM_001018053] |
| 51 | A_24_P450172 | AK095151 | TATGCCACTCGAATAAAGGTACTTAAACAGAGAGTAATTTTGGGATATTAATCCTAGGGTAC | SEQ ID NO: 2902 | Homo sapiens cDNA FLJ37832 fis, clone BRSSN2009630. [AK095151] |
| 52 | A_24_P45620 | UTS2 | AGAAGATTTCAGGATTCCTGGAGAAGAATGGCAAGATTTACTGAGTCATCTTTTGGCC | SEQ ID NO: 2903 | Homo sapiens urotensin 2 (UTS2), transcript variant 1, mRNA [NM_021995] |
| 53 | A_24_P867201 | AK022997 | CTGACATGTGATAAATATTTCAGTGACTTTCAGATTTATTTCTTGTTAGCCAGCTGTGTG | SEQ ID NO: 2932 | Homo sapiens cDNA FLJ12935 fis, clone NT2RP2004982. [AK022997] |
| 54 | A_24_P890536 | CR627148 | AATTGCCTTCTTGTAACCCTAAGTATGGTGAAGCAGAATTGAATTCTACAAAAGTCTTTC | SEQ ID NO: 2934 | Homo sapiens mRNA; cDNA DKFZp779F2127 (from clone DKFZp779F2127). [CR627148] |
| 55 | A_32_P153725 | KIAA1033 | TTGGTAAAAGATGGCAAGTTTGTTACGCACTTGAGTGGGGTTTGCTTTTCCCCCAAT | SEQ ID NO: 2972 | Homo sapiens KIAA1033 (KIAA1033), mRNA [NM_015275] |
| 56 | A_32_P164203 | THC2683448 | TTGATGGTCATTGTACGAGCTATTGTATGGATTACTGTGGAGTGCTGTTTTACCACATGAT | SEQ ID NO: 2975 | Q7WZG3_PASP1 (Q7WZG3) Ferric uptake regulator, partial (8%) [THC2683448] |

Fig. 8-4

| No. | Probe ID No. | Symbols of genes | Sequence | SEQ ID NO: | Descriptions of genes (letters and numbers within [ ] indicates GenBank accession No.) |
|---|---|---|---|---|---|
| 57 | A_32_P17504 | THC2698682 | ATGTCTATGCTGTGTTCACTATGGTGCAAATATTCGCAGGCTTTT CCCCTTGATGCCGAAA | SEQ ID NO: 2982 | |
| 58 | A_32_P178966 | ENST00000379426 | GTAATATACAGGGTGAAGTCTTTACTGATACAGAAGACAAACT GTTAAAAAGTGAATCC | SEQ ID NO: 2985 | Novel protein. [Source:Uniprot/SPTREMBL;Acc:Q5T4T1] [ENST00000379426] |
| 59 | A_32_P224666 | CAPZA2 | AATGCTGTTTTGAGATTCTGAAATTAAATTAAATGAAAATAGTTATTTC AGAAATGCATTTAATG | SEQ ID NO: 2989 | Homo sapiens capping protein (actin filament) muscle Z-line, alpha 2 (CAPZA2), mRNA [NM_006136] |
| 60 | A_32_P226786 | BC045174 | TTATTGGTGCATGTAAGGCCATTATCCTGCTCTTAATGAACGGATT AATGCTGTTGATTGTT | SEQ ID NO: 3001 | Homo sapiens cDNA clone IMAGE:5273245. [BC045174] |
| 61 | A_32_P2333 | SUB1 | AGGAAGAAAAGGTATTTCTTTAAATGCAGAACAATGGAGGCAGC TGACAGAACAGAGATTTC | SEQ ID NO: 3003 | Homo sapiens SUB1 homolog (S. cerevisiae) (SUB1), mRNA [NM_006713] |

Fig. 21-1

| No. | Probe ID No. | Symbols of genes | Sequence | SEQ ID NO: | Descriptions of genes (letters and numbers within [ ] indicates GenBank accession No.) |
|---|---|---|---|---|---|
| 1 | A_23_P341938 | NOG | GGCAGGCGCTGGAGCTGGATTCCAATGGAGTAGCCCATCATTTGC GAGTGGAAGTCGTCGT | SEQ ID NO:3030 | Homo sapiens noggin (NOG), mRNA [NM_005450] |
| 2 | A_23_P359174 | BC069659 | CGAGGGGTGGATACTAGGGTAAAGAAAAATTTTGTAATAGCAAC AGTGGTTGGGCATTTT | SEQ ID NO:3031 | Homo sapiens cDNA clone IMAGE:7262526, with apparent retained intron. [BC069659] |
| 3 | A_24_P15797 | NUDT22 | CCCGGCCTCACATCTCATTGGGGTGGATGGCAAGAGCACGTCC ACCTGTCAGGAAAAAA | SEQ ID NO:3032 | Homo sapiens cDNA FLJ34477 fis, clone HLUNG2003833. [AK091796] |
| 4 | A_24_P930391 | AK022351 | AAGTGGGTTTAATTTCGTTTTCATGAAAGGAAAAGATTAGGTTTC ATGCAAACAGTTGGTC | SEQ ID NO:3033 | Homo sapiens cDNA FLJ12289 fis, clone MAMMA1001788. [AK022351] |
| 5 | A_24_P931364 | AK022662 | TCCCCATCTGGAGTATAGGTTGGAAGTCATTGCTTTGTAGTAAG GCATTATTTTCCTGGT | SEQ ID NO:3034 | Homo sapiens cDNA FLJ12000 fis, clone HEMBB1001531. [AK022062] |
| 6 | A_32_P111394 | THC2643957 | GAATACAGTGTTGCTTTTCATCCGATATTTGACTGAAGCTAAGA CAGATCAATTATAAGG | SEQ ID NO:3035 | |
| 7 | A_32_P125589 | THC2649341 | CGGCTCTATCCCTTGCTTTAGGCTTTTGAATGAAAGTGAGATGTC TCATCAGCTGAGATAG | SEQ ID NO:3036 | |
| 8 | A_32_P142802 | THC2699446 | CCGCGGCAACCACATCGGAAGAAAAGGGGTCAGGTATTGTAGGCG TACGGGGAGTGATAAA | SEQ ID NO:3037 | |
| 9 | A_32_P19561 | THC2728305 | AAGAAGGGACAGTTACAACAGTAATTGGAAAAACTTCTGCAAGGA CAGATGTGCATTTCTC | SEQ ID NO:3038 | |
| 10 | A_32_P209582 | THC2663167 | GAATGTAAAGCCAGAATATCAACGTCGTTTTGTCAAGATTTTCA AACCTATTGGCTGAT | SEQ ID NO:3039 | ALU1_HUMAN (P39188) Alu subfamily J sequence contamination warning entry, partial (5%) [THC2663167] |
| 11 | A_32_P226941 | THC2688491 | ACAGCTACTACAGCTGAGAAGTACTACATAGTTGAGTAACTTGGG AATGGAGTAGGCCCA | SEQ ID NO:3040 | |
| 12 | A_32_P33304 | ANK3 | TGTTGGAATACGGGGGGTGATCGTCGTCTTTTATAAACTCACGTGA TTTAAAGGAAAGATGA | SEQ ID NO:3041 | Homo sapiens cDNA FLJ44903 fis, clone BRAMY3005184, highly similar to Mus musculus ankyrin 3, epithelial (Ank3). [AK126851] |
| 13 | A_32_P71171 | A_32_P71171 | TCTAGATAGTAATAGGAAACGGAGAATCCAGGCTGGTGATGGCT GGAAGGGAGTGATTGAA | SEQ ID NO:3042 | |
| 14 | A_32_P98840 | THC2745859 | AAGAGTATTCCAAGATAGCAAGGGTGTGTTTGTTTTTAGGCAGGT GTATTTCAGCTAGTTA | SEQ ID NO:3043 | |
| 15 | A_23_P41664 | ENST00000334994 | TGGCTTGGAGGAGATTCGGACTTCATAAACAAATTGTTCCTGAAAA ATGAGGCACAGTCAT | SEQ ID NO:3044 | Synleurin (CGI_01891). [Source:Uniprot/SPTREMBL;Acc:Q77207] [ENST00000334994] |
| 16 | A_23_P65766 | C15orf15 | TCCTGCATTGCCATCTACATAATATCAGATATTAGGGATGTTAG ATTGCATCTCAGTGTT | SEQ ID NO:3045 | Homo sapiens chromosome 15 open reading frame 15 (C15orf15), mRNA [NM_016304] |
| 17 | A_23_P70007 | HMMR | ACTATTCTTGAGAGTTTGTCATATAGTGGTTGTCATCTGCATG TCTAGTCAGCATTTGA | SEQ ID NO:3046 | Homo sapiens hyaluronan-mediated motility receptor (RHAMM) (HMMR), transcript variant 1, mRNA [NM_012484] |
| 18 | A_23_P70328 | CENPQ | CAATGGCTTACAGTTCTGTCTGTCTGGTCATCTGGAACTTGAAAAAT GGTCAAATGCGTTCAG | SEQ ID NO:3047 | Homo sapiens centromere protein Q (CENPQ), mRNA [NM_018132] |

Fig. 21-2

| No. | Probe ID No. | Symbols of genes | Sequence | SEQ ID NO: | Descriptions of genes (letters and numbers within [ ] indicates GenBank accession No.) |
|---|---|---|---|---|---|
| 19 | A_23_P78092 | EVI2A | GCTGAATCAGAGACGTTGGAAAAGAACAAAACAGGTCACAGGACG CAAGCTAGTGATGGAA | SEQ ID NO: 3048 | Homo sapiens ecotropic viral integration site 2A (EVI2A), transcript variant 1, mRNA [NM_001003927] |
| 20 | A_24_P11045 | THC2785765 | CCACCAGAAACGTACAGGTGATTTTGATGACAAATACGGTAGCA ACACAAGTCGGAATAG | SEQ ID NO: 3049 | COX7B_HUMAN (P24311) Cytochrome c oxidase polypeptide VIIb, mitochondrial precursor, partial (78%) [THC2785765] |
| 21 | A_24_P126741 | ENST00000309178 | AGGGTGCAACCACCACGACTAAGAAGATTCAAGATTAGTTGCAACAGC TCACAGGAGCGAGAAT | SEQ ID NO: 3050 | |
| 22 | A_24_P169378 | RPS7 | AACTGAAATCTTCGAGAAAATGGAACTGGGCTAGTAAGTGAA TTGGAGAAAAAGTTCA | SEQ ID NO: 3051 | Homo sapiens ribosomal protein S7 (RPS7), mRNA [NM_001011] |
| 23 | A_24_P201702 | CLEC2B | ATTGGAATTCAAGTAAATACAACTGTTCCAGTCAACATGCCGAC CTAACTATAAATTGACA | SEQ ID NO: 3052 | Homo sapiens C-type lectin domain family 2, member B (CLEC2B), mRNA [NM_005127] |
| 24 | A_24_P276583 | TMCO1 | CCTTCATTTTCCTGTATATTCTCTGTACTATGTCGATTGGACAG AACATTCAGAAGAATTC | SEQ ID NO: 3053 | Homo sapiens transmembrane and coiled-coil domains 1 (TMCO1), mRNA [NM_019026] |
| 25 | A_24_P333112 | A_24_P333112 | GGTCATCAGAATCAGAGGTATCAATGTGTGAGCGCACAGGACCA AAAGGTATTGCAACTT | SEQ ID NO: 3054 | |

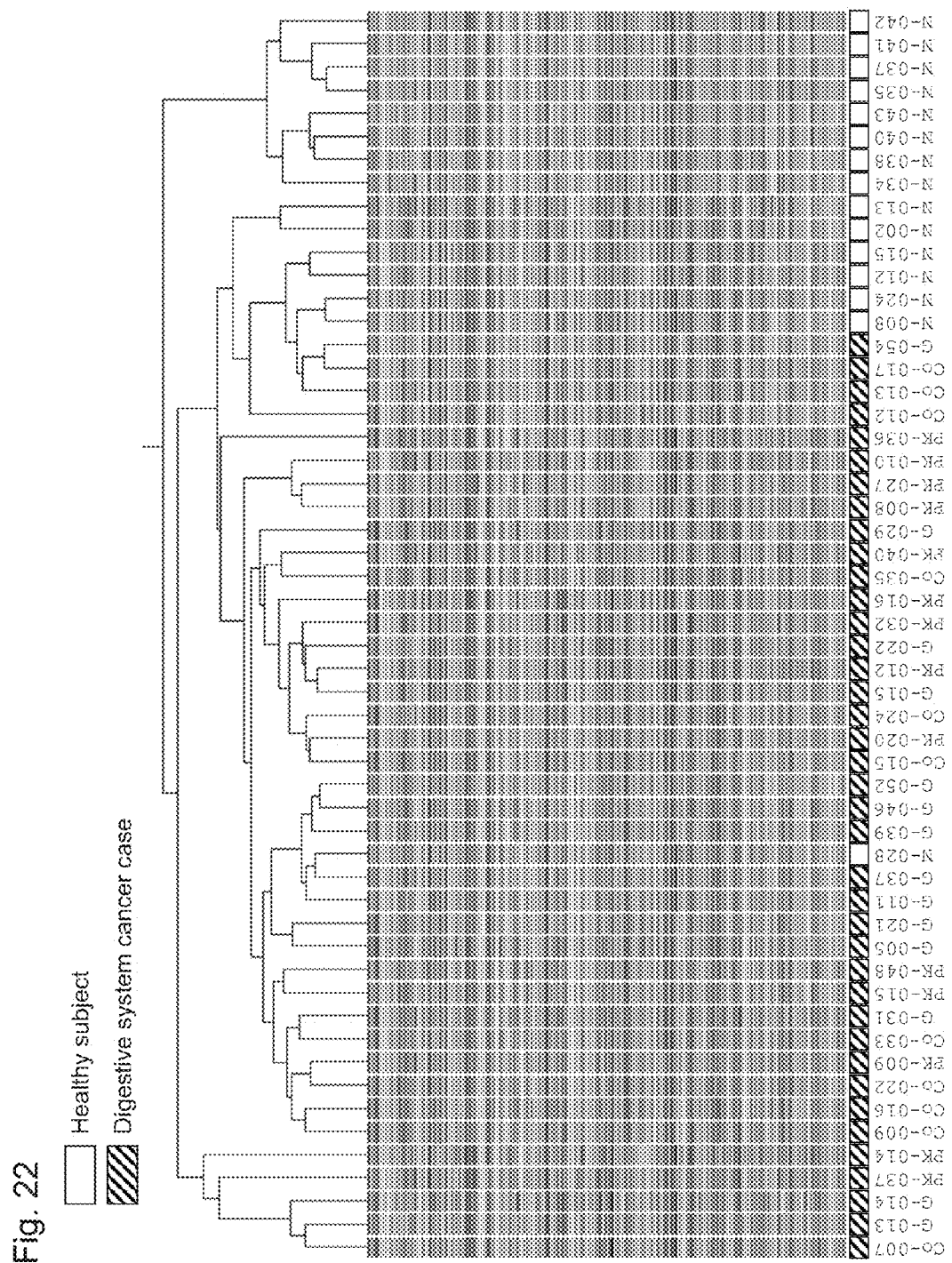

Fig. 24-1

| No. | Probe ID No. | Symbols of genes | Sequence | SEQ ID NO. | Descriptions of genes (letters and numbers within [ ] indicates GenBank accession No.) |
|---|---|---|---|---|---|
| 1 | A_23_P100263 | CMIP | GCGCGGCCGAATTCTTTAGCTTCGTAATTGGAACCTTTGACCTGATCTAAAGTGGACTT | SEQ ID NO: 3055 | Homo sapiens c-Maf-inducing protein (CMIP), transcript variant C-mip, mRNA [NM_198390] |
| 2 | A_23_P103561 | NAV1 | TCCTGCGCCAGAGATGTGGCTGGAAGCCGGAAGAAGGATGTGGTTTAAAAAATGTTT | SEQ ID NO: 3056 | Homo sapiens neuron navigator 1 (NAV1), mRNA [NM_020443] |
| 3 | A_23_P109122 | RP5-860F19.3 | CAAGCCGCCGCAGGTGGGCTCACATCTGCTCTGGTAAGTTTGGAGAAAAGAGAACAA | SEQ ID NO: 3057 | Homo sapiens KIAA1442 protein, mRNA (cDNA clone IMAGE:5502880), complete cds. [BC054347] |
| 4 | A_23_P115161 | DARC | TCCCGCTGAACTGAGAACTGAAGTCAGGTCGGACTTGGAAGATGTATGGAATCTTCGTAT | SEQ ID NO: 3058 | Homo sapiens Duffy blood group, chemokine receptor (DARC), mRNA [NM_002036] |
| 5 | A_23_P117694 | CORO2B | ATTAGCTAGGATGTACTAGATGCATTATACTCCATAGCTGCTTTCCATGGCGGCCTTA | SEQ ID NO: 3059 | Homo sapiens coronin, actin binding protein, 2B (CORO2B), mRNA [NM_006091] |
| 6 | A_23_P119143 | ICAM5 | GAGGCCCCCAGAGCTCAGACGGGGCTTATTATTGGTTTATTAATTAGTTATTCATTT | SEQ ID NO: 3060 | Homo sapiens intercellular adhesion molecule 5, telencephalin (ICAM5), mRNA [NM_003259] |
| 7 | A_23_P142187 | HIF3A | ACCCGGCCAGCTTTGTTTCTACAGATGGTGCTAGTCTGGCTCGGGCCGGTGTAACACAGGAAAAAGGCCTC | SEQ ID NO: 3061 | Homo sapiens hypoxia inducible factor 3, alpha subunit (HIF3A), mRNA [NM_022462] |
| 8 | A_23_P144796 | PDLIM4 | TGCTCCAGGCGTTGCTTGTTAAGGTCGGTGCTGGGCCGGTGTAAATATGTTCACCCTGT | SEQ ID NO: 3062 | Homo sapiens PDZ and LIM domain 4 (PDLIM4), mRNA [NM_003687] |
| 9 | A_23_P145881 | ACTL6B | CCCCGCAAACTGGAAGAAGAAGGCTACGCCAGGTGTCCAAGTCTGGCATAACTA | SEQ ID NO: 3063 | Homo sapiens actin-like 6B (ACTL6B), mRNA [NM_016188] |
| 10 | A_23_P150407 | CREB3L1 | TTGGCCCTCGGTTGTTTTATATTTTAGAAGTTAGTGCGGCCTTGCTGCTCCCTGGCC | SEQ ID NO: 3064 | Homo sapiens cAMP responsive element binding protein 3-like 1 (CREB3L1), mRNA [NM_052854] |
| 11 | A_23_P164258 | PIPOX | GAATGCGCCATAAAGACCAGATGATTGAGTGTGTACCTCGTTCCTTGGGCGGCTCCGTT | SEQ ID NO: 3065 | Homo sapiens pipecolic acid oxidase (PIPOX), mRNA [NM_016518] |
| 12 | A_23_P164927 | SYNGR4 | CAAAGTCCGCGGCCCTGGTATGATGCGGTGACAAGTAAATATCCTTATCCAAATGAATAA | SEQ ID NO: 3066 | Homo sapiens synaptogyrin 4 (SYNGR4), mRNA [NM_012451] |
| 13 | A_23_P18119 | IMPG2 | CGTGATCATAGGCACGCATTGCATCCGTCAGGGAGAGATGGTTGGACTTGTTGTCATGTTTCTGCTAT | SEQ ID NO: 3067 | Homo sapiens interphotoreceptor matrix proteoglycan 2 (IMPG2), mRNA [NM_016247] |
| 14 | A_23_P204144 | KRT85 | CTCCGTCGCCGTTTCATGCTAGGGAGGCATCCAGTTGTCGTCCTGGCAGCTGTTT | SEQ ID NO: 3068 | Homo sapiens keratin 85 (KRT85), mRNA [NM_002283] |
| 15 | A_23_P204998 | FARP1 | TCCTCCTGCAACTGTGTGGTTTGAAACTGGGCATTCTCAGTAGTATATGCTGCCTGTCT | SEQ ID NO: 3069 | Homo sapiens FERM, RhoGEF (ARHGEF) and pleckstrin domain protein 1 (chondrocyte-derived) (FARP1), transcript variant 1, mRNA [NM_005766] |
| 16 | A_23_P208482 | CLEC4M | CGACCCCAGACTCTTCTTGCTCCTATACAGTGCTTCGATTTGGCGTGTTTCTGAGTTGTA | SEQ ID NO: 3070 | Homo sapiens C-type lectin domain family 4, member M (CLEC4M), transcript variant 4, mRNA [NM_214677] |
| 17 | A_23_P203389 | CASP8 | GCCAGGCACCACAGCGTGGCTAATATTTTTAAAAATATTTTAGTAGAGACAGGGTTTCAGT | SEQ ID NO: 3071 | Homo sapiens caspase 8, apoptosis-related cysteine peptidase (CASP8), transcript variant C, mRNA [NM_033356] |
| 18 | A_23_P21495 | FCGBP | TCAGTCATGCAGCAGGAAGGAAGATTTGCTGAAGAAGACCTGCTGCCTGGAGGTTTGCG | SEQ ID NO: 3072 | Homo sapiens Fc fragment of IgG binding protein (FCGBP), mRNA [NM_003890] |
| 19 | A_23_P258381 | SPSB4 | CCAACGCAGCTCCCCGCCACCTTAATGTGAATTTGACTGATGAATGAAGAGGGTTTCTAATA | SEQ ID NO: 3073 | Homo sapiens spIA/ryanodine receptor domain and SOCS box containing 4 (SPSB4), mRNA [NM_080862] |

Fig. 24-2

| No. | Probe ID No. | Symbols of genes | Sequence | SEQ ID NO. | Descriptions of genes (letters and numbers within [ ] indicates GenBank accession No.) |
|---|---|---|---|---|---|
| 20 | A_23_P29079 | PFKL | CGAGCCGGCGCTACGTCTTCGAGGAGGACGGTTTCAACATGCACGGACTTAAAGTCAACGTGGA | SEQ ID NO: 3074 | Homo sapiens phosphofructokinase, liver (PFKL), transcript variant 1, mRNA [NM_001002021] |
| 21 | A_23_P329212 | ETS1 | GTGAAGCAGGAGCTATCCAGAATGGGCGTATAGCCTCGGGATTACTTCATTAGCTATGGTATT | SEQ ID NO: 3075 | Homo sapiens v-ets erythroblastosis virus E26 oncogene homolog 1 (avian) (ETS1), mRNA [NM_005238] |
| 22 | A_23_P341938 | NOG | GGGGAACGCGTGGGCTGGCTGGATTCCGATCCAGTAGGGCATCATTTCCGAGTGCAAGTGCTGT | SEQ ID NO: 3076 | Homo sapiens noggin (NOG), mRNA [NM_005450] |
| 23 | A_23_P44531 | SYNPO | TCTGCTGCTGTGTGAAGATGAGAAGGTGGTCTTACTCAGTTAATGATGAGTGACTATATTT | SEQ ID NO: 3077 | Synaptopodin [Source:Uniprot/SWISSPROT;Acc:Q8N3V7] [ENST00000307662] |
| 24 | A_23_P34554 | CACNA1E | CCCCCTCGATGCATGCTCCTTGTGTCACATGGAGAAAACGAAGACAGAATTGGGAAGCC | SEQ ID NO: 3078 | Homo sapiens calcium channel, voltage-dependent, R type, alpha 1E subunit (CACNA1E), mRNA [NM_000721] |
| 25 | A_23_P353370 | FOXE1 | CCCGGGTCATCGGAAATAGTTCCGTTGTTTGTCTAAAAGACTTGTAGGTGGGAAAA | SEQ ID NO: 3079 | H.sapiens HFKH4 mRNA for fork head like protein. [X94553] |
| 26 | A_23_P372144 | C19orf29 | CCCGGCGTACCGCAACGACGACAGGCGTTCACCGGGACGCCGTCGGCAA | SEQ ID NO: 3080 | Homo sapiens chromosome 19 open reading frame 29 (C19orf29), transcript variant 2, mRNA [NM_021231] |
| 27 | A_23_P39265 | LYPD3 | TCGGTACTCCTCCCCGATGTTTGGGGAATCGGTTTCCCACATATGTGTTTGCTTACTAGACTGT | SEQ ID NO: 3081 | Homo sapiens LY6/PLAUR domain containing 3 (LYPD3), mRNA [NM_014400] |
| 28 | A_23_P98774 | PLD1 | ACTGTTCCTGGGAATCAATCAATTTTTGATTCCGTGTTATTGATGTGATAAGAGTCTCCCCAA | SEQ ID NO: 3082 | Homo sapiens cDNA FLJ34578 fis, clone KIDNE2008404, highly similar to PHOSPHOLIPASE D1 (EC 3.1.4.4) [AK091897] |
| 29 | A_23_P40334 | NPBWR2 | GCTCCCACGATGGGTGCCAAGCGTCTCAGGAGGACATGGGACTTGCACAATGGCACGTT | SEQ ID NO: 3083 | Homo sapiens neuropeptides B/W receptor 2 (NPBWR2), mRNA [NM_005286] |
| 30 | A_23_P40760 | C8orf6 | GTGTCGTAGGTTAGTGTAGGAGATGTATTGTGAGATAAGACTTCGGTGTCGGGTGAA | SEQ ID NO: 3084 | Homo sapiens mRNA for hypothetical protein (C8orf6 gene). [AJ274691] |
| 31 | A_23_P49319 | ERN2 | CCCACCCCTCTTTTGAGGATTTGAGGAGGAGAAGCAACTCGAGTTGTTCCAGGAGGTCAGTGTGACT | SEQ ID NO: 3085 | Homo sapiens endoplasmic reticulum to nucleus signalling 2 (ERN2), mRNA [NM_033266] |
| 32 | A_23_P50348 | TRIP10 | CGGAGTTTGATGAGATTTGAGGAGGAATCCAGATCCAGTCCTTGTTCCAGGTCACTGTGTGGCCA | SEQ ID NO: 3086 | Homo sapiens thyroid hormone receptor interactor 10 (TRIP10), mRNA [NM_004240] |
| 33 | A_23_P74666 | C1orf158 | GGTAGCTGTCCCCCCTCAAAACGCACAGGTTCCTTGCTTTCCATCCAAGCAATTAAAGAT | SEQ ID NO: 3087 | Homo sapiens chromosome 1 open reading frame 158 (C1orf158), mRNA [NM_152290] |
| 34 | A_23_P75367 | OR10A4 | AGGTCTATGTATGTTACTTCTTCCTCAGAAAACTTCCTTCCTGGAGATAGGTTTCAACTTGGTC | SEQ ID NO: 3088 | Homo sapiens olfactory receptor, family 10, subfamily A, member 4 (OR10A4), mRNA [NM_207186] |
| 35 | A_23_P04398 | CNTNAP2 | CTTGAGCACATCCTTAAAATATCAGCACAAGTTGGGGGAGGCAGGCAATGGAATATAATG | SEQ ID NO: 3089 | Homo sapiens contactin associated protein-like 2 (CNTNAP2), mRNA [NM_014141] |
| 36 | A_23_P87310 | LMO1 | TCCTCGGGGGGCAGGGGGCGGGCGTGTAGACTGCTGTGTATATACTACGGGAACATTT | SEQ ID NO: 3090 | Homo sapiens LIM domain only 1 (rhombotin 1) (LMO1), mRNA [NM_002315] |
| 37 | A_24_P102885 | WDTC1 | CTTCGAGCCGTCTGTTGAGCTTGGTAATGAGGAAATGTGAAGGAGAGAAGAGCT | SEQ ID NO: 3091 | Homo sapiens WD and tetratricopeptide repeats 1 (WDTC1), mRNA [NM_015023] |
| 38 | A_24_P108517 | CRB3 | TGGGAAGCTGCGTCCGAAGCCATCACGTGCTATGATGGTGGTCTCTGGCTGTCTCGGCTGGCTGC | SEQ ID NO: 3092 | Homo sapiens crumbs homolog 3 (Drosophila) (CRB3), transcript variant 3, mRNA [NM_174881] |

Fig. 24-3

| No | Probe ID No. | Symbols of genes | Sequence | SEQ ID NO: | Descriptions of genes (letters and numbers within [ ] indicates GenBank accession No.) |
|---|---|---|---|---|---|
| 39 | A_24_P117368 | AK055306 | GTGCCTGGGTCCATTCAAAGTCGAGGAGCGGGGCTTGGATGAGGCAAGCTTTATTCCAAA | SEQ ID NO: 3093 | Homo sapiens cDNA FLJ30744 fis, clone FEBRA2003378. [AK055306] |
| 40 | A_24_P129107 | NKD2 | CCCCCACAGCGCACCGTACGGCCACAAGCCGGTACGGCCAAAAGGGCAGGGAGGGCACTGC | SEQ ID NO: 3094 | Homo sapiens naked cuticle homolog 2 (Drosophila) (NKD2), mRNA [NM_033120] |
| 41 | A_24_P150428 | FAM124A | CGTCCGTGGCGTCGTCAGGTGAACCACAGTGGTTTTGAACACAGAGGTGCCCCAGGGGCACA | SEQ ID NO: 3095 | Homo sapiens family with sequence similarity 124A (FAM124A), mRNA [NM_145019] |
| 42 | A_24_P15182 | LOC646960 | CCCAAGGAGGCCGTCGCGGAACCGGTGCGCCATGGCGGGCTGGGGGCCGTCGTTCGGAAGC | SEQ ID NO: 3096 | PREDICTED: Homo sapiens similar to transmembrane protease, serine 9 (LOC646960), mRNA [XM_929928] |
| 43 | A_24_P15797 | NUDT22 | CCCCGCCGTCACATTGTCTCATTGTGGGGTGCATGCCAAGAGCACGTCCACCTGTCAGGAAAAA | SEQ ID NO: 3097 | Homo sapiens cDNA FLJ34477 fis, clone HLNG2003833. [AK091796] |
| 44 | A_24_P161144 | MGC46336 | CGTCCGTCCAGAGAGACGCGGTCAGGAGGCTTTTCTGTATGGCAGATCTTTGTCAGAAG | SEQ ID NO: 3098 | Homo sapiens hypothetical protein MGC46336, mRNA (cDNA clone MGC:46336 IMAGE:5589928), complete cds. [BC036762] |
| 45 | A_24_P161581 | LOC729956 | TCTCGGATGGCCCCGTCGGAGGCTGGGGTGAAATCCGAGCTGAACGGCTACTGTT | SEQ ID NO: 3099 | PREDICTED: Homo sapiens hypothetical protein LOC729956 (LOC729956), mRNA [XM_001131873] |
| 46 | A_24_P166434 | PSORS1C2 | CCTACGGGCGGCCACGTCGTTCGGTGGAGAGACTGCCTGAAACTGGAGTGTGGCCGGCCCTGAA | SEQ ID NO: 3100 | Homo sapiens psoriasis susceptibility 1 candidate 2 (PSORS1C2), mRNA [NM_014069] |
| 47 | A_24_P178877 | LOC3398609 | TGGCCCAGGGCGCCAGCATGGCTTGGAAGACTGAAAGGCATAGAGGGATTCTTTTGCTGCA | SEQ ID NO: 3101 | Homo sapiens mRNA for KIAA2012 protein. [AB095932] |
| 48 | A_24_P20795 | IRX4 | CCCTTGGGCACTCTGCCGGCCGTAGAGCTTCTACCGCTTGGGCTATTCGGAGGTAAGCAGTCTCAGAA | SEQ ID NO: 3102 | Homo sapiens iroquois homeobox protein 4 (IRX4), mRNA [NM_016358] |
| 49 | A_24_P209389 | MLXIPL | CCACCGGCCTTGCCGATAGAGGTCTACCGGTTCGGCTATCGGAGCCTGCGTTTGGGCGTT | SEQ ID NO: 3103 | Homo sapiens MLX interacting protein-like (MLXIPL), transcript variant 4, mRNA [NM_032954] |
| 50 | A_24_P218074 | ZNF467 | GGATGCCCCGGCCGCCAAGCCCTGGGGTACCGTGGGCGCCGTGGCCTGGAAAAAATTGTCAGTGTGCGGGGGCCAGG | SEQ ID NO: 3104 | Homo sapiens zinc finger protein 467 (ZNF467), mRNA [NM_207336] |
| 51 | A_24_P252223 | C6orf85 | ACACAGCCCGGTTCGGGAGGCTACGCCTGTCAGCCTTTCAATAAAGTTATGGACAAATG | SEQ ID NO: 3105 | Homo sapiens chromosome 6 open reading frame 85 (C6orf85), mRNA [NM_021945] |
| 52 | A_24_P254133 | APC2 | TGTGCCCAGCCGCATCGTGGTTGGGCCAGGCAGCCAGCAGGCACCACGGACTCGGACGGCCGAGAGAAAAGGGCCGGC | SEQ ID NO: 3106 | Homo sapiens adenomatosis polyposis coli 2 (APC2), mRNA [NM_005883] |
| 53 | A_24_P272845 | DOCK3 | GCCGCCATTCATTCATCCTCTCTCGTCAGATGGGTCTAGTGAAGCAGAAACATGGTGA | SEQ ID NO: 3107 | Homo sapiens dedicator of cytokinesis 3 (DOCK3), mRNA [NM_004947] |
| 54 | A_24_P280497 | KIAA1545 | CATCCGGGCCCAGAGCAAGAGGGCCCCTGGAGACGTGAAGGTCAAGGAGAGCGCGGGAGG | SEQ ID NO: 3108 | Homo sapiens XTP9 (XTP9) mRNA, complete cds. [AF490258] |
| 55 | A_24_P306034 | ANKDD1A | CTCTCTCCGGTTGTTACTCATCAATTCTGCCAGTAAAATTGTCCTCTATGACGTGGAAA | SEQ ID NO: 3109 | Homo sapiens cDNA FLJ25870 fis, clone CBR02141. [AK098736] |
| 56 | A_24_P315066 | ZMIZ2 | CACCCAGCCTGCCTACGGAGCAACAATGACGAGCCTGCTTCTTCTGTTTGAGAACAACGTGAT | SEQ ID NO: 3110 | Homo sapiens zinc finger, MIZ-type containing 2 (ZMIZ2), transcript variant 1, mRNA [NM_031449] |
| 57 | A_24_P316454 | BC022826 | AGAACACAGAGGAGGGCCCCAGCCAATCAAGGTCATTGGTCTTCAAGATAAAGTGCGTA | SEQ ID NO: 3111 | Homo sapiens cDNA clone IMAGE:5441030, partial cds. [BC022826] |
| 58 | A_24_P331711 | THEM5 | TATCACCCTGCTCCCACAGCCACGCTGGCTTCCATCATGAGCGCAGTGTCATGTCAGCGG | SEQ ID NO: 3112 | Homo sapiens thioesterase superfamily member 5 (THEM5), mRNA [NM_182578] |
| 59 | A_24_P345837 | MSX1 | ACGGCCGCCGCAAGGAAGACAGGTACAAGAGGCAGAGAGGTGGAGAAGCTGAAAGATGGGCG | SEQ ID NO: 3113 | Homo sapiens msh homeobox 1 (MSX1), mRNA [NM_002448] |

Fig. 24-4

| No | Probe ID No. | Symbols of genes | Sequence | SEQ ID NO. | Descriptions of genes (letters and numbers added.[ ] indicates GenBank accession No.) |
|---|---|---|---|---|---|
| 60 | A_24_P348885 | CYB561D1 | GCTCCTCCTCTGAAAGTCTCCAGTGTGGTGTGAACTCAGAAGAAACGGTTACTGTGGGCT | SEQ ID NO:3114 | Homo sapiens cytochrome b-561 domain containing 1 (CYB561D1), mRNA [NM_182580] |
| 61 | A_24_P349274 | OR4X2 | GGAGGCTCATGCATTCCTTTGCACAAATGCTTCTCATCTTCCACCTGCTCTTGTGTGGC | SEQ ID NO:3115 | Homo sapiens olfactory receptor, family 4, subfamily X, member 2 (OR4X2), mRNA [NM_001004727] |
| 62 | A_24_P366122 | ACBD4 | TAGGGCCCCTCTCTATGAAGAGATGCTGGATGTTTCTACAGTTAGTACAGAAGCAGGACGATG | SEQ ID NO:3116 | Homo sapiens acyl-Coenzyme A binding domain containing 4 (ACBD4), mRNA [NM_024722] |
| 63 | A_24_P385012 | BC030084 | TCGGGCCTCATCTGTTGGGTGAAATACTGTTTATCCTTTAGTTACTAAATTTAAAAGTTAC | SEQ ID NO:3117 | Homo sapiens cDNA clone IMAGE:4791887. [BC030084] |
| 64 | A_24_P39484 | AK025430 | TCGAGCTCCGCAGCGGTCACGGACTCGGGGGGACCCACACCGGGAAATCCGCGC | SEQ ID NO:3118 | Homo sapiens cDNA: FLJ21777 fis, clone HEP00173. [AK025430] |
| 65 | A_24_P401270 | LOC649294 | TGCTCTCCTCCTCCAGCTCTCGGCATCATGAAATAATTGTGATAACGACACATGGAGTTTG | SEQ ID NO:3119 | Homo sapiens cDNA FLJ33940 fis, clone CTONG2018069. [AK091259] |
| 66 | A_24_P401294 | FLJ35934 | GCAGCCCCTTCTGCGGTCGGAACTGCCTTCACCTAGAAGCGCTGAGGGGTGCCGC | SEQ ID NO:3120 | Homo sapiens cDNA FLJ35934 fis, clone TESTI2011315. [AK093253] |
| 67 | A_24_P405982 | SYNPO | CTCGAGCCCCAAGGCAGCAGCTCCTTGGACGTGGGTGCCCAACCTGCCCAAGAGGGGCTCTCCC | SEQ ID NO:3121 | Homo sapiens synaptopodin (SYNPO), mRNA [NM_007286] |
| 68 | A_24_P418028 | MQP-1 | ACGGGCTCAGCTTTTCAGAGACCTATAGTTGTCTTTTTGATTCTCAGTTAAAACTACAA | SEQ ID NO:3122 | Homo sapiens mRNA for MQP-1, complete cds. [AB014771] |
| 69 | A_24_P478362 | NP511100 | ATGCCCCTGGCCGAAGAGAAGCACTGCGAGCGCCTCAAGGCCAGGCCGGCCAATCTACTAG | SEQ ID NO:3123 | GB|AB065467.1|BAC05726.1 seven transmembrane helix receptor [Homo sapiens] [NP511100] |
| 70 | A_24_P542291 | LOC339352 | CACTTCCGGCGGCTCGAGACTACTTCTCAGAGAGAGAGAGGCCCGGGACGTGCTCAAGCGC | SEQ ID NO:3124 | PREDICTED: Homo sapiens similar to ATP binding domain 3 (LOC339352), mRNA [XR_017668] |
| 71 | A_24_P662177 | THC2666469 | GGGAGGTGCGACCCAATGGAATGTACACAGAGCATGGTGAGTGAGGACATGAGA | SEQ ID NO:3125 | |
| 72 | A_24_P689119 | A_24_P689119 | CGGGGTGCCCAGACCACGAAAGACGAGAGAGCCAGCTGGTGAGTGCATCGGGACGCCCCTG | SEQ ID NO:3126 | |
| 73 | A_24_P752279 | A_24_P752279 | TCCAGCCCACCCTCTGAGACAGGCCACCAGGCTGTGGTGACCCGGCCTAGGCCGGCCAATCTCCT | SEQ ID NO:3127 | |
| 74 | A_24_P778928 | A_24_P778928 | TCCAGGCGGCGGCGGCAGGTGGATCCCCATTCAGGAAGAAGGGGCTCAGAGCAAACCGCTCTAG | SEQ ID NO:3128 | |
| 75 | A_24_P828125 | A_24_P828125 | CAGTGCGGCAGCGGCCACAGCAGCAGCAAAGTCAGCCCCAGGATTGAGACCCAGCAGTGGGGGCG | SEQ ID NO:3129 | |
| 76 | A_24_P848662 | CR594528 | CGCATGCCGGCGACGACGCATCCGAAAAATGAGGACTGAGCATGCCTGCCATCCGGCCAA | SEQ ID NO:3130 | full-length cDNA clone CS0DM002YG17 of Fetal liver of Homo sapiens (human) [CR594528] |
| 77 | A_24_P916317 | FOXC1 | CAGAACGCGCCCGACAAGAAGAICACGGTCAAGGGCATTTACCAGTCATCATGGAGACGG | SEQ ID NO:3131 | Homo sapiens FOXC4a mRNA, partial cds. [AF343007] |
| 78 | A_24_P928524 | THC2534212 | TCGTGGACCTATTATGCGTGGTGCTGATCTGTTCCTGGGAGCGGTCGAGCTTGGCTGGCTCTCA | SEQ ID NO:3132 | Q60448_HUMAN (Q60448) Neuronal thread protein AD7c-NTP, partial (15%) [THC2534212] |
| 79 | A_24_P939963 | LOC650392 | GCCCATTTGAAGTATAACGAGAGGGAAAATGGTCTTGAAATAAGGATGGCAGAAAGG | SEQ ID NO:3133 | Homo sapiens cDNA clone IMAGE:5264670 [BC036550] |
| 80 | A_32_P101073 | A_32_P101073 | GCCAGGCCCGACGTTGCGCGACCACCTGGTAGACAGGCGGAGCGTCACCGGAGCTGGAGGAGCGC | SEQ ID NO:3134 | |

Fig. 24-5

| No. | Probe ID No. | Symbols of genes | Sequence | SEQ ID NO: | Descriptions of genes (letters and numbers within [ ] indicates GenBank accession No.) |
|---|---|---|---|---|---|
| 81 | A_32_P125589 | THC2649341 | CGGTCTATCCGTTGCTTTAGCCTTTTGAATGAAAGTGAGATGTCTCATCCAGCTGAGATAG | SEQ ID NO: 3135 | |
| 82 | A_32_P132356 | THC2635710 | GTGTTTTTTGCGCGGCTCCAGAATCTAAGAGCCATAGCGTTCTCCAAATAAACGGCCAAT | SEQ ID NO: 3136 | |
| 83 | A_32_P136622 | BC020341 | CCGAGGCGGAAGAGCTGGTGGAGGTTGAGGTATAGTGGGGCAGGCGTCTGCAGGGTCCAAGCCG | SEQ ID NO: 3137 | Homo sapiens cDNA clone IMAGE:4177218. [BC020341] |
| 84 | A_32_P142202 | THC2699446 | CCGCGCAACGACATCGGAANGAAAAGGGGTGAGGTATTGTAGGCGTACGGGGACTGATAAA | SEQ ID NO: 3138 | |
| 85 | A_32_P145764 | BC043547 | GGTCCCGGTCCGTCGTGTAAGCAATAAGCAATGGCATATAAATGGAAAAGTATAAAGAA | SEQ ID NO: 3139 | Homo sapiens clone IMAGE:5171873, mRNA [BC043547] |
| 86 | A_32_P156776 | THC2603530 | CCCGCCCCTTTTTTTGGTTAAGGATAATTGTCTTAGGTTTGCGTAGTTTCATTTTAAGGA | SEQ ID NO: 3140 | AA360388 EST69518 T-cell lymphoma Homo sapiens cDNA 5' end similar to EST containing Alu repeat, mRNA sequence [AA360388] |
| 87 | A_32_P16662 | THC2567500 | TGGGTGGTGCTGGGCTAAATGATGATCAAGGTGAAACAGAAGCCAGGAAGGATCTGTGCTAATT | SEQ ID NO: 3141 | F10881 HSC3LQ012 normalized infant brain cDNA Homo sapiens cDNA clone c-31c01 3', mRNA sequence [F10881] |
| 88 | A_32_P172002 | A_32_P172002 | GGGACCCCAGGTCCTGTCCTCTCTCATTCATTCATTTATTCAAAACTATGCATCCAGGGC | SEQ ID NO: 3142 | |
| 89 | A_32_P199506 | BU191598 | GATCCTCTGAGGTTTCCAGGAAGAGACCCCCGCCCTAATCCTCTGAAGGTCGGAGGTCACAG | SEQ ID NO: 3143 | AGENCOURT_8099541 NIH_MGC_102 Homo sapiens cDNA clone IMAGE:6254414 5', mRNA sequence [BU191598] |
| 90 | A_32_P213509 | THC2663555 | GATTTGTTCCAGTGTTGGAGGCTAAATGAAATTCAACACCTACAGTGGAAAAA | SEQ ID NO: 3144 | |
| 91 | A_32_P29130 | BG058000 | CCCCCAAGCCGTTCGTTGAGGACTAAAGCATAAACTGGTGGGTGGTGAACAGGAAAGATTTCA | SEQ ID NO: 3145 | BG058000 7f7ad09 x1 Lupski dorsal_root_ganglion Homo sapiens cDNA clone IMAGE:3303708 3', mRNA sequence [BG058000] |
| 92 | A_32_P334325 | RIMBP2 | ACCGAGAGCCTGCACCCAATCAAAGCCATTAGCAAGTTCTGGAGTCGCCGGAAACACAAG | SEQ ID NO: 3146 | Homo sapiens RIMS binding protein 2 (RIMBP2), mRNA [NM_015347] |
| 93 | A_32_P37943 | A_32_P37943 | CCGGGGGCGGAGACCCCGTGTGGGAAAGCTCACACGTTGCATTAATAACATCGGTCTGGGAGCGGGGTC | SEQ ID NO: 3147 | |
| 94 | A_32_P4466 | FLJ32214 | AAGCCCCCGGCAGCCGGGAAAGCTCTACACGTTGCATTAATAACATGAACATACGGGAGAATG | SEQ ID NO: 3148 | Homo sapiens FLJ32214 protein, mRNA (cDNA clone IMAGE:40024597), complete cds. [BC104018] |
| 95 | A_32_P74615 | SP5 | CAGCCCGGCATCGGAGCTTTGGGGGTGAGGCGGCAGAGAGCACGTGCAGGCGGTCCTTCGG | SEQ ID NO: 3149 | Homo sapiens Sp5 transcription factor (SP5), mRNA [NM_001003845] |
| 96 | A_32_P76566 | THC2689192 | CTTCGCGTCGTCGGCGGGGGCGTGTGTGTTCAGATGGGCATCACCTTGCACACCCTGC | SEQ ID NO: 3150 | Q7XG69_ORYSA (Q7XG69) Expressed protein, partial (6%) [THC2689192] |
| 97 | A_32_P79103 | BM932034 | GTGCTACAGAATGAAAATAGGCATTTAGGAAGGTTGAGTCAGAGGTGCGAGTGGGGCATA | SEQ ID NO: 3151 | UI-E-EJ1-ajl-k-24-0-UI.r1 UI-E-EJ1 Homo sapiens cDNA clone UI-E-EJ1-ajl-k-24-0-UI 5', mRNA sequence [BM932034] |
| 98 | A_32_P82111 | LRFN2 | ATGCGGAGCTGAGCCTGAGTGTTTGGAAAGGCGGAGACTCCCCTTTCTAATCACAAATG | SEQ ID NO: 3152 | Homo sapiens leucine rich repeat and fibronectin type III domain containing 2 (LRFN2), mRNA [NM_020737] |

Fig. 24-6

| No. | Probe ID No. | Symbols of genes | Sequence | SEQ ID NO. | Descriptions of genes (letters and numbers within [ ] indicates GenBank accession No.) |
|---|---|---|---|---|---|
| 99 | A_23_P102235 | SNRPG | ACAACAGAACAATATTGGAATTGGTAATAATACGAGGAAATAGTATCATCATTAGAAGC | SEQ ID NO: 3153 | Homo sapiens small nuclear ribonucleoprotein polypeptide G (SNRPG), mRNA [NM_003096] |
| 100 | A_23_P106394 | THC2783023 | ATTCAGAAACCTGCTTGCTGTGTGATACATAGTAAGTGTCTTCATTTATTACTGCTTGTCTG | SEQ ID NO: 3154 | Q8IUM9_HUMAN (Q8IUM9) ACSL3 protein, complete [THC2467888] |
| 101 | A_23_P110362 | MAP2K11P1 | ACTGAGACAAGTGTGGAAGTTCTAATCTGAGAGTGGTTTGAGTGTGTACGTTATGTT | SEQ ID NO: 3155 | Homo sapiens mitogen-activated protein kinase kinase 1 interacting protein 1 (MAP2K11P1), mRNA [NM_021970] |
| 102 | A_23_P110611 | ZH2C2 | CTCTTGAAAACGAGAGCTTCAGTCTGTTGGACTCTTGAAACCAGGTTCTTGAATAGTTAA | SEQ ID NO: 3156 | Homo sapiens zinc finger, H2C2 domain containing (ZH2C2), mRNA [NM_017676] |
| 103 | A_23_P111321 | ARG1 | TGGAATCAGGAGGACAAAGGTACCACATGTGGAAAGGTAGTAGTGTCGCATGTGATTGAAA | SEQ ID NO: 3157 | Homo sapiens arginase, liver (ARG1), mRNA [NM_000045] |
| 104 | A_23_P111201 | GPR34 | AGTAGGAGTGAAAGCACTTCAGAATTTAAACCAAGAAGTAGTCGGTGGATAACATATCGTG | SEQ ID NO: 3158 | Homo sapiens G protein-coupled receptor 34 (GPR34), mRNA [NM_005300] |
| 105 | A_23_P112251 | LOC552891 | AGAATTCTTAACTTCACAAGGTTTTACTTGGAGATGTGGGTTTGATTTAATTTGGGAG | SEQ ID NO: 3159 | Homo sapiens hypothetical protein LOC552891 (LOC552891), mRNA [NM_001125] |
| 106 | A_23_P117852 | KIAA0101 | TACTGCTGCCATTTTATTGGTTGTTTGGATTATTGGAATGGTGGCATATTGTCACTCCTTC | SEQ ID NO: 3160 | Homo sapiens KIAA0101 (KIAA0101), transcript variant 1, mRNA [NM_014736] |
| 107 | A_23_P120046 | BAZ2B | TATTTCGTCTGAAGGTAATGATATAGACAGTGTGTACAGTAATTATGTCTACTACGAA | SEQ ID NO: 3161 | Homo sapiens bromodomain adjacent to zinc finger domain, 2B (BAZ2B), mRNA [NM_013450] |
| 108 | A_23_P120316 | MTHFD2 | AGGATTATTCCTGCTATTAGTACTCATTTTATGTATGTTAGGCTTGGTAAGTTGCGGG | SEQ ID NO: 3162 | Homo sapiens methylenetetrahydrofolate dehydrogenase (NADP+ dependent) 2, methenyltetrahydrofolate cyclohydrolase (MTHFD2), nuclear gene encoding mitochondrial protein, transcript variant 1, mRNA [NM_006636] |
| 109 | A_23_P121622 | SULT1B1 | GAAATAGAGATTGTGTAGTTGATTGAAACGAGGCAGTTATGAATTCATTCGGCAAT | SEQ ID NO: 3163 | Homo sapiens mRNA for ST1B2, complete cds [D89479] |
| 110 | A_23_P121716 | ANXA3 | TGGACATTCGAACAGAGTTCAAGAAGCATTATGGCATTCCCTATATTCAGCAATTAAAT | SEQ ID NO: 3164 | Homo sapiens annexin A3 (ANXA3), mRNA [NM_005139] |
| 111 | A_23_P128930 | PSMC6 | GAACAAGCAAGCTTAGACATTAGAGATAGTAGCATTAACCATGCAGGTCCCATTACAAAGCATGGTAG | SEQ ID NO: 3165 | Homo sapiens proteasome (prosome, macropain) 26S subunit, ATPase, 6 (PSMC6), mRNA [NM_002806] |
| 112 | A_23_P134714 | HRSP12 | TAAATTAGAGCTGTGTGGAGGTGTATTACTGAATATAGGAAAGAGATACCCATTACATAG | SEQ ID NO: 3166 | Homo sapiens heat-responsive protein 12 (HRSP12), mRNA [NM_005836] |
| 113 | A_23_P137366 | C1QB | CACCGACAAGAAGTCAGTAGTGGGCATGGAGGGTGCCAAACAGATCTTTTCCGGGGTTCCT | SEQ ID NO: 3167 | Homo sapiens complement component 1, q subcomponent, B chain (C1QB), mRNA [NM_000491] |
| 114 | A_23_P141549 | RPS7 | GTCAAAATGAATGGGAGGGGTCATAAAGGTTCATTTGGACAAAGCAGCAGAACAAT | SEQ ID NO: 3168 | Homo sapiens ribosomal protein S7 (RPS7), mRNA [NM_001011] |
| 115 | A_23_P143958 | RPL22L1 | ATTGGCTTGAATGGTGGATCGTGAGAGGAGACCTACGAACTTCGTTACTTCCAGATTA | SEQ ID NO: 3169 | Homo sapiens ribosomal protein L22-like 1, mRNA (cDNA clone IMAGE:4865966), [BC049823] |
| 116 | A_23_P144497 | RPS3A | GCAAATATCGGAAGAAGAGATGATGGAAATCATGAACCGACAGGTGCAGACAAATGACTTGAA | SEQ ID NO: 3170 | Homo sapiens ribosomal protein S3A (RPS3A), mRNA [NM_001006] |
| 117 | A_23_P14564 | GPR65 | AACAAGTTTAAATTGTTGGTGATGCCAATTCTGTACTGTTTGTAACCGAAACAGGAAG | SEQ ID NO: 3171 | Homo sapiens G protein-coupled receptor 65 (GPR65), mRNA [NM_003608] |

Fig. 24-7

| No. | Probe ID No. | Symbols of genes | Sequence | SEQ ID NO: | Descriptions of genes (letters and numbers within [ ] indicates GenBank accession No.) |
|---|---|---|---|---|---|
| 118 | A_23_P14708 | SUHW4 | TCTTTGTACCTCCATACAAGTGTTAAGCTGCCAGGCTGTAAGGTTACCTTAATTAAAGTT | SEQ ID NO: 3172 | Homo sapiens suppressor of hairy wing homolog 4 (Drosophila) (SUHW4), transcript variant 1, mRNA [NM_017661] |
| 119 | A_23_P14734 | RPS27L | TACAAGATCACCACGGTTTTGAGGGATGGTGCAGTGGTCAGACAGTGGTTGTTTGTGTAGGTTGTTCA | SEQ ID NO: 3173 | Homo sapiens ribosomal protein S27-like (RPS27L), mRNA [NM_015920] |
| 120 | A_23_P151637 | RNASE2 | GTGGTAAGCCAAATATGACCTGTCGTAGTAACAAAACTCGGAAAAATTGTCACCACAGTG | SEQ ID NO: 3174 | Homo sapiens ribonuclease, RNase A family, 2 (liver, eosinophil-derived neurotoxin) (RNASE2), mRNA [NM_002934] |
| 121 | A_23_P152002 | BCL2A1 | TGTAACCATATTTGGATTTGAAGTTGAAGGTATTCGATGAAGAAACTTCTACGACAGGAAAATGC | SEQ ID NO: 3175 | Homo sapiens BCL2-related protein A1 (BCL2A1), mRNA [NM_004049] |
| 122 | A_23_P153037 | ZNF624 | TGTGGTTAGATGACATGCAGATGGAGACAGGTATGGAAGAATATACACCAGGCTGTTAATATTGA | SEQ ID NO: 3176 | Homo sapiens zinc finger protein 624 (ZNF624), mRNA [NM_020787] |
| 123 | A_23_P155765 | HMGB2 | TAAAAAATGCAGGTTGTAAGCTTTTTGATGGGCTACTCATAGAGTTAGATTTTACAGCTTC | SEQ ID NO: 3177 | Homo sapiens high-mobility group box 2 (HMGB2), mRNA [NM_002129] |
| 124 | A_23_P155815 | NCAPG | AAGTTAGGAAGAAGGAATGGAGGTTGGAATCCTTAAGATTATGTCCAGTTATTTCTTAA | SEQ ID NO: 3178 | Homo sapiens non-SMC condensin I complex, subunit G (NCAPG), mRNA [NM_022346] |
| 125 | A_23_P156842 | EEF1E1 | AAGAAAAAGCCAATCGTTCAGCAGTGGTTAGAATACAGGGTCACTCAAGTAGATGGGCAGT | SEQ ID NO: 3179 | Homo sapiens eukaryotic translation elongation factor 1 epsilon 1 (EEF1E1), mRNA [NM_004280] |
| 126 | A_23_P157449 | POLR2K | GGTCTCTCTTGCTTCCAAATATCTTCTTGTACAGTACTGAGGATTTAGATGTGGTTGAC | SEQ ID NO: 3180 | Homo sapiens polymerase (RNA) II (DNA directed) polypeptide K, 7.0kDa (POLR2K), mRNA [NM_005034] |
| 127 | A_23_P159650 | COX7B | CAAATAGGGTAATGCTGTATTAGCTAGTGGAGGCACTTCTGTATTGTTAGATGGACATA | SEQ ID NO: 3181 | Homo sapiens cytochrome c oxidase subunit VIIb (COX7B), nuclear gene encoding mitochondrial protein, mRNA [NM_001866] |
| 128 | A_23_P160466 | SLC19A2 | CTTGGTATGTGGCCATATTTATAGAATGCTGAACTCAATGTGCAAGTGTAGTGTATGCA | SEQ ID NO: 3182 | Homo sapiens solute carrier family 19 (thiamine transporter), member 2 (SLC19A2), mRNA [NM_006996] |
| 129 | A_23_P162596 | ACTR6 | TTAACGGCTTCACTGGACAGTTTCCTTAGAACAAGGTAGTTTTGTGTGACTGTGACTAAACT | SEQ ID NO: 3183 | Homo sapiens ARP6 actin-related protein 6 homolog (yeast) (ACTR6), mRNA [NM_022496] |
| 130 | A_23_P163025 | RNASE3 | AGGCACACGCTCAGAGACTTCAGAGAACATGGTTGGGAAACATGGTTCGGAAAACTGTTCACTTCCGAAATTTGCT | SEQ ID NO: 3184 | Homo sapiens ribonuclease, RNase A family, 3 (eosinophil cationic protein) (RNASE3), mRNA [NM_002935] |
| 131 | A_23_P167163 | IGJ | TTGGGTGATGTAAAAGGAACTCCCTGCCACGAAAATATTAAAATAGTGAGATTGTTATC | SEQ ID NO: 3185 | Homo sapiens immunoglobulin J polypeptide, linker protein for immunoglobulin alpha and mu polypeptides (IGJ), mRNA [NM_144646] |
| 132 | A_23_P170233 | CSTA | AACTGGCTACTAGTGATCATGATGCTTGCTGATAATATAACCATCAATAAGAAGGATTGT | SEQ ID NO: 3186 | Homo sapiens cystatin A (stefin A) (CSTA), mRNA [NM_005213] |
| 133 | A_23_P18325 | PDCD10 | CCAAGCGAGTAATTCATCAAACGAAGTTAATACTTCAGAAGTTCAAAACGTGTCGGGCTGAA | SEQ ID NO: 3187 | Homo sapiens programmed cell death 10 (PDCD10), transcript variant 1, mRNA [NM_007217] |
| 134 | A_23_P18372 | B3GNT5 | AAATGTCAACAAAGGGAAAATAAAAGTATCAGGTTGGATGGTCACTTGAATAGAAGATGGT | SEQ ID NO: 3188 | Homo sapiens UDP-GlcNAc:betaGal beta-1,3-N-acetylglucosaminyltransferase 5 (B3GNT5), mRNA [NM_032047] |
| 135 | A_23_P19291 | TUBB2A | ACTTCTCAGATGAATGGCGTGCATCCTTAGTGAAGTTCTGTTTGTGTCCTCAAGGCATGGTCTTTC | SEQ ID NO: 3189 | Homo sapiens tubulin, beta 2A (TUBB2A), mRNA [NM_001069] |

Fig. 24-8

| No. | Probe ID No | Symbols of genes | Sequence | SEQ ID NO: | Descriptions of genes (letters and numbers within [ ] indicates GenBank accession No.) |
|---|---|---|---|---|---|
| 136 | A_23_P200030 | FPGT | TAAAAATTGGTAAACTAGAAGTAAGTGTCGACAACCCTCAGTTATGATACTTATGTGGG | SEQ ID NO: 3190 | Homo sapiens fucose-1-phosphate guanylyltransferase (FPGT), mRNA [NM_003838] |
| 137 | A_23_P200298 | AGL | TAGATTTTTAACAGGGTCGATTTGACTAAACGGTTCGGTAGAATGCTTCATAGTTGAGTG | SEQ ID NO: 3191 | Homo sapiens amylo-1, 6-glucosidase, 4-alpha-glucanotransferase (glycogen debranching enzyme, glycogen storage disease type III) (AGL), transcript variant 4, mRNA [NM_000028] |
| 138 | A_23_P200955 |  | AGACCTGATTGAACGTCACATTGATGTCAAGACTACCCATGGTTATTGTTCATGTAG | SEQ ID NO: 3192 |  |
| 139 | A_23_P20225 | RRM2B | TGCTCCTTTGTAAAAAGTTAAAGATTTGAAGAGGAATCTCATATTCCGAGGCATAGGA | SEQ ID NO: 3193 | Homo sapiens ribonucleotide reductase M2 B (TP53 inducible) (RRM2B), mRNA [NM_015713] |
| 140 | A_23_P204269 | USP15 | GACCAGGATAAATGAGGTGTATGTTGATCATGGCTTTGTTTGATGATGTGTGATAATTAAAGCTG | SEQ ID NO: 3194 | Homo sapiens ubiquitin specific peptidase 15 (USP15), mRNA [NM_006313] |
| 141 | A_23_P205336 | C14orf129 | CAATTCATTGGGAGAGTTCATTGGAATGCTTGTTGATGATGTATGTTCATTGTCAGGT | SEQ ID NO: 3195 | Homo sapiens chromosome 14 open reading frame 129 (C14orf129), mRNA [NM_016472] |
| 142 | A_23_P207299 | LOC51136 | GGAAAACAGCAATTGAAATAGAACTAGAGTGGTTTTAGAGAACTCAGGTATTCTTTGGTG | SEQ ID NO: 3196 | Homo sapiens PTD016 protein (LOC51136), mRNA [NM_016125] |
| 143 | A_23_P210274 | PREI3 | GGATCAGTATGCGTACGGATTTACACAGAATATTTCACATGCTTATTTCATGTCGGGCAC | SEQ ID NO: 3197 | Homo sapiens preimplantation protein 3 (PREI3), transcript variant 1, mRNA [NM_015387] |
| 144 | A_23_P2129 | TMEM126B | CATATGCATCATTTGGTACAGTTCCATTTTGTGACTGTTGTTGAGTGACAAGCTTTTG | SEQ ID NO: 3198 | Homo sapiens transmembrane protein 126B (TMEM126B), mRNA [NM_018480] |
| 145 | A_23_P213661 | HISPPD1 | GTAGTAAGTTTCTGTTTGTGAAATGTAGTAATGTACTGACTGTGGAGGTCATAAGG | SEQ ID NO: 3199 | Homo sapiens histidine acid phosphatase domain containing 1 (HISPPD1), mRNA [NM_015216] |
| 146 | A_23_P215751 | NDUFA5 | TAAAAGTGGAGTCACTGAACAAATAGTTCCAGTACGTTCTCTAATATAAGTCTAGTGGGTATC | SEQ ID NO: 3200 | Homo sapiens NADH dehydrogenase (ubiquinone) 1 alpha subcomplex, 5, 13kDa (NDUFA5), nuclear gene encoding mitochondrial protein, mRNA [NM_005000] |
| 147 | A_23_P217319 | FGF13 | TGATGGAAGAAAAGTTGGGTTCTGGGATAGAGTTTCAGAGCTAGGTGTAAGATTTTGTGCA | SEQ ID NO: 3201 | Homo sapiens fibroblast growth factor 13 (FGF13), transcript variant 1A, mRNA [NM_004114] |
| 148 | A_23_P218928 | C4orf18 | CAGATGAGTCATTTGCTTCTGTGAGATGTGTTTCAGAGCAGGAATGTTTG | SEQ ID NO: 3202 | Homo sapiens chromosome 4 open reading frame 18 (C4orf18), transcript variant 2, mRNA [NM_016613] |
| 149 | A_23_P250002 | HACE1 | TAAGGAGTGATTGTGTTGCCAGTAATGTTGAGAGAGACATGTAAGTTGAAAGTTTTGCTA | SEQ ID NO: 3203 | Homo sapiens HECT domain and ankyrin repeat containing, E3 ubiquitin protein ligase 1 (HACE1), mRNA [NM_020771] |
| 150 | A_23_P251937 | CPEB4 | GTATGCAGTTAATTACTGTACTAGGCTGAATTGCATATAGTTTTACTGTGTATGGGG | SEQ ID NO: 3204 | Homo sapiens cytoplasmic polyadenylation element binding protein 4 (CPEB4), mRNA [NM_030627] |
| 151 | A_23_P252201 | EAF2 | CAGGATTCGTGATATAGATGCCAGTACATAATAGATTTGGAGACAACAGTTGGCCGTTCTGAT | SEQ ID NO: 3205 | Homo sapiens ELL associated factor 2 (EAF2), mRNA [NM_018456] |
| 152 | A_23_P25235 | CLEC4D | GATTAACCCACGCACAGAGTATTGTGGGATAAGAATGAACCCGAGAACTCACGGGAAAA | SEQ ID NO: 3206 | Homo sapiens C-type lectin domain family 4, member D (CLEC4D), mRNA [NM_080387] |
| 153 | A_23_P252371 | RBBP8 | GGCAAGGAAGGAAGGAACATAGACGGTTGAAACAGAAAACAGAAGGATGAAGGACAGTTTTT | SEQ ID NO: 3207 | Homo sapiens retinoblastoma binding protein 8 (RBBP8), transcript variant 1, mRNA [NM_002894] |
| 154 | A_23_P26021 | COPS2 | TGCTTTTTGATCAACTGGTTGTGTTTTGCTGCTGCATTTATCGGAAGGACAGTTTTC | SEQ ID NO: 3208 | Homo sapiens COP9 constitutive photomorphogenic homolog subunit 2 (Arabidopsis) (COPS2), mRNA [NM_004236] |

Fig. 24-9

| No. | Probe ID No. | Symbols of genes | Sequence | SEQ ID NO: | Descriptions of genes (letters and numbers written in [ ] indicates GenBank accession No.) |
|---|---|---|---|---|---|
| 155 | A_23_P2705 | P2RY5 | TCTGTATTGCTTTCCAACTGTGTTTGACCCTATAGTTTAC TACTTTACATGGGACA | SEQ ID NO: 3209 | Homo sapiens purinergic receptor P2Y, G-protein coupled, 5 (P2RY5), mRNA [NM_005767] |
| 156 | A_23_P302470 | SULT1B1 | TGTCTCTAAGTGAGAAATCTGAAGAAATAAGAGATTGTGTAGTT GATTGAAACGGAGGGCA | SEQ ID NO: 3210 | Homo sapiens sulfotransferase family, cytosolic, 1B, member 1 (SULT1B1), mRNA [NM_014465] |
| 157 | A_23_P302550 | RGS18 | GAGTCTAAGGCCCTAGGCATTTGGGCATCTGCCAGATTGTTCA TATTCAGAAAGTGTTA | SEQ ID NO: 3211 | Homo sapiens regulator of G-protein signalling 18 (RGS18), mRNA [NM_130782] |
| 158 | A_23_P30307 | CRSP9 | CAATTGTACTGGACAGAATGAACATCAAGAGAGAAATTCAGGTC ATAGGAGAGATCAGAT | SEQ ID NO: 3212 | Homo sapiens cofactor required for Sp1 transcriptional activation, subunit 9, 33kDa (CRSP9), mRNA [NM_004270] |
| 159 | A_23_P305060 | PBEF1 | TGGCTGTGGCTCTAATATGCACCTCAAGATTTTAAGGAGATAAT GTTTTTAGAGAGAATT | SEQ ID NO: 3213 | Homo sapiens pre-B-cell colony enhancing factor 1 (PBEF1), mRNA [NM_005746] |
| 160 | A_23_P307940 | CAPZA2 | GTACAAGATTGGCAAAGACAGAGGAGAATGGATAAGATGAACATT GCATGACGGGATGATT | SEQ ID NO: 3214 | Homo sapiens capping protein (actin filament) muscle Z-line, alpha 2 (CAPZA2), mRNA [NM_006136] |
| 161 | A_23_P306800 | GLS | GGGAAGAAGAGATAAGATACTGCGAATACTGGAATAGGACCCTCAAAACTTAAA AAAGAAAAAACTTTGC | SEQ ID NO: 3215 | Homo sapiens glutaminase C mRNA, complete cds. [AF158555] |
| 162 | A_23_P30956 | KIAA0776 | TTTTTCATTTGTCAAAATGCTTCTTTTGTTGTTGCCAAGTAAGA ACAGTTTTATTGTTT | SEQ ID NO: 3216 | Homo sapiens KIAA0776 (KIAA0776), mRNA [NM_015323] |
| 163 | A_23_P312246 | CCDC82 | GGGTTTTATACAGAGATGACTGTCAAGTGAATGAGACTGTTGATATG CTGTCAGTTTAGTCAA | SEQ ID NO: 3217 | Homo sapiens coiled-coil domain containing 82 (CCDC82), mRNA [NM_024725] |
| 164 | A_23_P314491 | ZDHHC17 | TGGATACTTTTAGCAAATAAGGAAGTTAATTCTCAGCACTGAACA TGAATTAGTTGGTTGG | SEQ ID NO: 3218 | Homo sapiens zinc finger, DHHC-type containing 17 (ZDHHC17), mRNA [NM_015336] |
| 165 | A_23_P31671 | UQCRB | AAGCCATAAGAAGAGTTCCTGAGAAGCTTTATAATGAAGAGGATG TTTCCAATTAAGAGGG | SEQ ID NO: 3219 | Homo sapiens ubiquinol-cytochrome c reductase binding protein (UQCRB), mRNA [NM_006294] |
| 166 | A_23_P327022 | MDFIC | TTATGATTTGTTAATGTAAAATGTTTGTTGAAGTATATGGCTA TCATGACTAAGTGCTA | SEQ ID NO: 3220 | Homo sapiens MyoD family inhibitor domain containing (MDFIC), mRNA [NM_199072] |
| 167 | A_23_P33045 | RPL26 | TACAAAGGTCAGGAAATTGGCAAAGTAGTCCAAGTTTACAGGAA GAAATATGTTATCTAC | SEQ ID NO: 3221 | Homo sapiens ribosomal protein L26 (RPL26), mRNA [NM_000987] |
| 168 | A_23_P332439 | NUPL1 | ATTGAAATCTTGAATGTATTGAATGTGTCAAGGTAACGACGGGT GCCTTTGTAAATGTTC | SEQ ID NO: 3222 | Homo sapiens KIAA0410 mRNA, partial cds. [AB007870] |
| 169 | A_23_P339480 | HAT1 | AACATGAACAGCTGGAAGAGAGTTTCAGGAAGTAGTGGAAGAT TACGCGGCGTGTTATTG | SEQ ID NO: 3223 | Homo sapiens histone acetyltransferase 1 (HAT1), transcript variant 1, mRNA [NM_003642] |
| 170 | A_23_P347059 | MOBKL1A | GTAGAAGGGAAAAATCATCTAAGTTATGAAATGCAACATAGGC GCTATATTAGAAAGTG | SEQ ID NO: 3224 | Homo sapiens MOB1, Mps One Binder kinase activator-like 1A (yeast) (MOBKL1A), mRNA [NM_173468] |
| 171 | A_23_P348992 | MYSM1 | CATGTATTTTAAACCTATGAATTATAAAATAGTATTTAGATTCTA GCGTGAGTTAAATAGA | SEQ ID NO: 3225 | Homo sapiens mRNA for KIAA1915 protein, partial cds. [AB067502] |
| 172 | A_23_P349083 | FCHO2 | GTGAAATGGTTAAAGTCTGTGCACATTTCTTAGTTACAGAGTCTT CATACCAAGTATATGGG | SEQ ID NO: 3226 | Homo sapiens FCH domain only 2 (FCHO2), mRNA [NM_138782] |
| 173 | A_23_P353704 | RP5-1022P6.2 | TGTCTCTGAGTAGGTATTACACACTGTTCCTTTGTGGGTTTGTT TTGTATGTGGTGTGT | SEQ ID NO: 3227 | Homo sapiens hypothetical protein KIAA1434 (KIAA1434), mRNA [NM_019593] |
| 174 | A_23_P355067 | TMCO1 | AACTCAAGAACTGTTTATTTTGTATCATTCTTCTAGACACAGA CACATCAGACTGGCAA | SEQ ID NO: 3228 | Homo sapiens transmembrane and coiled-coil domains 1 (TMCO1), mRNA [NM_019026] |

Fig. 24-10

| No. | Probe ID No. | Symbols of genes | Sequence | SEQ ID NO: | Descriptions of genes (letters and numbers within [ ] indicates GenBank accession No.) |
|---|---|---|---|---|---|
| 175 | A_23_P37736 | TNFRSF17 | GATCTGTTAGGATGAGTGTATTTTCAGTGCCGATAAGCTTTTTGTCCGTCTAAGTGT | SEQ ID NO: 3229 | Homo sapiens tumor necrosis factor receptor superfamily, member 17 (TNFRSF17), mRNA [NM_001192] |
| 176 | A_23_P38275 | THC2504576 | TCTCGGCAAATGAAGTTTAATCCCTTGTGAGTTGGCACCGAAGCAAGAATCGCAAAAG | SEQ ID NO: 3230 | RL26 BOVIN (P61257) 60S ribosomal protein L26, complete [THC2504576] |
| 177 | A_23_P390734 | FGFR10P2 | CCACCAAGATACAGAAATGTGCTTAACATCAGTTGAAAGGTTAAATTTTCTTATGTTGTGG | SEQ ID NO: 3231 | Homo sapiens FGFR1 oncogene partner 2 (FGFR10P2), mRNA [NM_015633] |
| 178 | A_23_P405873 | C9orf72 | GAGAATGGAAGATCAGGGTCAGAGTATTATTCCAATGGTTAGTGGAGAAGTGATTCCTGT | SEQ ID NO: 3232 | Homo sapiens chromosome 9 open reading frame 72 (C9orf72), transcript variant 2, mRNA [NM_145005] |
| 179 | A_23_P41114 | CSTA | AAACAAATGAGACTTATGGAAAATTGGAAGCTGTGCAGTATAAAAGTCAAGTGTTGGTG | SEQ ID NO: 3233 | Homo sapiens cystatin A (stefin A) (CSTA), mRNA [NM_005213] |
| 180 | A_23_P41645 | ELL2 | TGTGTTTTCAAAGTGCTGCCAGTTGAAAGGGAAGCATTATGTTACAAATGTGTTTTGA | SEQ ID NO: 3234 | Homo sapiens elongation factor, RNA polymerase II, 2 (ELL2), mRNA [NM_012081] |
| 181 | A_23_P41664 | ENST00000334994 | TGGCTGGAGCAGAGAATGGACTTCATAAACAAATGTTCCTGAAAATGAGGCACAGGTCAT | SEQ ID NO: 3235 | Syntenurin (C9LG1891) [Source:Uniprot/SPTREMBL;Acc:Q72207] [ENST00000334994] |
| 182 | A_23_P421563 | LSM3 | CATAAGAGAAACCTGGACACATTTTGATATTAACAAATAATCCGGGGATTCTTCCAGTG | SEQ ID NO: 3236 | Homo sapiens LSM3 homolog, U6 small nuclear RNA associated (S. cerevisiae) (LSM3), mRNA [NM_014463] |
| 183 | A_23_P42975 | PRKAR2B | GGCACATTTTAGAAACACTGTTAACATTTGAAAAGCCTCTTGTAGGAAGAGAGG | SEQ ID NO: 3237 | Homo sapiens protein kinase, cAMP-dependent, regulatory, type II, beta (PRKAR2B), mRNA [NM_002736] |
| 184 | A_23_P434809 | S100A8 | AAAGCATGAAGAAAGGCCACAAAGAGTAGGTGAGTTACTGGGCCGAGAGGCTGGGGCCCT | SEQ ID NO: 3238 | Homo sapiens S100 calcium binding protein A8 (S100A8), mRNA [NM_002964] |
| 185 | A_23_P44257 | COMMD8 | AACATTTACTTCTGCGGCTTCATGTTTGGGAAACATTGCTGTGGATAAAAATAGCTGTG | SEQ ID NO: 3239 | Homo sapiens COMM domain containing 8 (COMMD8), mRNA [NM_017845] |
| 186 | A_23_P48166 | TWF1 | TGGAGCAGAGCCATAGGTGAAGCTGTTATTTCAGTCAGTGAGGAAGACTACGTGTCATGAAGGT | SEQ ID NO: 3240 | Homo sapiens twinfilin, actin-binding protein, homolog 1 (Drosophila) (TWF1), mRNA [NM_002822] |
| 187 | A_23_P48897 | CCPG1 | AAGTCAGAAGAGCCATCATATATAATTGTAATGTCGGCACGTATGTCCATTGGATGTACGGA | SEQ ID NO: 3241 | Homo sapiens cell cycle progression restoration 8 protein (CPR8), mRNA, complete cds. [AF011794] |
| 188 | A_23_P500956 | B3GNT2 | TGCTGGTGGTATGATAGTGTAATTTAGTATTTGAAAATCAGTGTGATTCCTTAATGGCC | SEQ ID NO: 3242 | Homo sapiens UDP-GlcNAc:betaGal beta-1,3-N-acetylglucosaminyltransferase 2 (B3GNT2), mRNA [NM_006577] |
| 189 | A_23_P501080 | ZNF92 | GAATATTAAGTGCTACTTGAGGTACATGTTCAGACTAACATTCTTTTGCAGGTAAGTGAG | SEQ ID NO: 3243 | Homo sapiens zinc finger protein 92 (ZNF92), transcript variant 1, mRNA [NM_007139] |
| 190 | A_23_P502425 | MRPL47 | GTTCCACATGTTGCTGAGGCGGCAAAAGTCAAGTCTTGTGTAAGATGTCGAACTATTAA | SEQ ID NO: 3244 | Homo sapiens mitochondrial ribosomal protein L47 (MRPL47), nuclear gene encoding mitochondrial protein, transcript variant 1, mRNA [NM_020409] |
| 191 | A_23_P50907 | ITGAV | AAAGAGTGATTAAGTGAGGTTATTTACCCGCTAAATGGTCCATTCTGCATTGTATTTCAGG | SEQ ID NO: 3245 | Homo sapiens integrin, alpha V (vitronectin receptor, alpha polypeptide, antigen CD51) (ITGAV), mRNA [NM_002210] |
| 192 | A_23_P51317 | CCDC76 | CCCTTGTTATAAGTTTTATGTCAAGTAAGGTAGTTTGTTTAAGTTAGTTACGGCATGTCCG | SEQ ID NO: 3246 | Homo sapiens coiled-coil domain containing 76 (CCDC76), mRNA [NM_019083] |

Fig. 24-11

| No. | Probe ID No. | Symbols of genes | Sequence | SEQ ID NO: | Descriptions of genes (letters and numbers within [ ] indicates GenBank accession No.) |
|---|---|---|---|---|---|
| 193 | A_23_P52846 | THC2694735 | TTTATGGGTTTTCAGTACAATAACAAGTAGAACAGTAGAACAGA TGATTAGTCACAGCAG | SEQ ID NO: 3247 | AB003177 proteasome subunit p27 [Homo sapiens] (exp=-1; wgp=0; cg=0), partial (9%) [THC2694735] |
| 194 | A_23_P53668 | NFYB | TGGGCTCATATTGTGCATACCACTGTTGTAAGCTGCTGTTTTTTCAG TTAACAATATATTGGG | SEQ ID NO: 3248 | Homo sapiens nuclear transcription factor Y, beta (NFYB), mRNA [NM_006166] |
| 195 | A_23_P56759 | KRCC1 | GATATCGGTGTTCATAGCACTTTTCTTATGTGAATAGGTTCTTT AACTTCTAACAAAGGC | SEQ ID NO: 3249 | Homo sapiens lysine-rich coiled-coil 1 (KRCC1), mRNA [NM_016618] |
| 196 | A_23_P58286 | S100P | GGAAAGTGTTTTGTTGGCAATATTGCCCTAGGCTGAGGCCTGGT CATGTAGCGTCGATTA | SEQ ID NO: 3250 | Homo sapiens S100 calcium binding protein P (S100P), mRNA [NM_005980] |
| 197 | A_23_P59637 | DOCK4 | TTTGGGAGTGAGCAGTTGAATTTATCTTGAATTTATGATGTGTC TGTATTTCTGAAGACAG | SEQ ID NO: 3251 | Homo sapiens dedicator of cytokinesis 4 (DOCK4), mRNA [NM_014705] |
| 198 | A_23_P59921 | SUB1 | GAGATTGGGAAATGAGGTAGGTTAGTGTTGTCGGGATTTTAAAGG CAAAGTGCTAATTGAT | SEQ ID NO: 3252 | Homo sapiens SUB1 homolog (S. cerevisiae) (SUB1), mRNA [NM_006713] |
| 199 | A_23_P60565 | ZNF354A | AAACCAAAGGCTCATGCAAGAAATACATGCTTGAGAGATGATAAT AAATGTAATGGATGTG | SEQ ID NO: 3253 | Homo sapiens zinc finger protein 354A (ZNF354A), mRNA [NM_005649] |
| 200 | A_23_P61674 | CLK4 | GAAAAGGCATGGAGTTTGTCCATTGTGACAGTTTGTTTAATAAAA CCAACATACACACTTTA | SEQ ID NO: 3254 | Homo sapiens CDC-like kinase 4 (CLK4), mRNA [NM_020666] |
| 201 | A_23_P63896 | FAS | ATGTCTATCCACAGGCTAACCCCACTGTCTATGAATCAATAGAAGA AGCTATGACGCTTTGC | SEQ ID NO: 3255 | Homo sapiens Fas (TNF receptor superfamily, member 6) (FAS), transcript variant 1, mRNA [NM_000043] |
| 202 | A_23_P65768 | C15orf15 | TCCTGGATTGCCATCTACATATATGAGATATTACGGATGGTTAG ATTGGATCTCAGTGTT | SEQ ID NO: 3256 | Homo sapiens chromosome 15 open reading frame 15 (C15orf15), mRNA [NM_016304] |
| 203 | A_23_P66280 | ZNF267 | TGTGATGAATGTGGTAAAGGCCTTGAGCTATAGGTCATACCTCAC TACACATGGAGAAGT | SEQ ID NO: 3257 | Homo sapiens zinc finger protein 267 (ZNF267), transcript variant 493723, mRNA [NM_003414] |
| 204 | A_23_P70007 | HMMR | ACTATTCTTCAGAGTTTGTGTATATAGTGCTGTCATGTGCATG TCTACTCAGCATTTGA | SEQ ID NO: 3258 | Homo sapiens hyaluronan-mediated motility receptor (RHAMM) (HMMR), transcript variant 1, mRNA [NM_012484] |
| 205 | A_23_P70328 | CENPQ | GAATGGCTTAGAGTTTCTCTGTCTGGTCATCTGGAACTTGAAAAAT CCTGAAATGGCTTCAG | SEQ ID NO: 3259 | Homo sapiens centromere protein Q (CENPQ), mRNA [NM_016321] |
| 206 | A_23_P71727 | CKS2 | GATAAAAGTTCTTGGAGTGAGTTTTTCTTAAGTGGCTGTTTG AGTTTACTGAAACAGT | SEQ ID NO: 3260 | Homo sapiens CDC28 protein kinase regulatory subunit 2 (CKS2), mRNA [NM_001827] |
| 207 | A_23_P7221 | RPL34 | CGAGGACCAGGAAATCGTTGTAGAAAGTGTTGAAAGGCACAAGCAG AGAGTCAGAAAAGCTAA | SEQ ID NO: 3261 | Homo sapiens ribosomal protein L34 (RPL34), transcript variant 2, mRNA [NM_033625] |
| 208 | A_23_P7229 | RPL34 | CGAACCCCTGGTAATAGAATTTGTTTACCTTTATACGAAGAAGGT TGGGAAAGGCACCAATG | SEQ ID NO: 3262 | Homo sapiens ribosomal protein L34 (RPL34), transcript variant 2, mRNA [NM_033625] |
| 209 | A_23_P72503 | KLHL2 | TTTTTGATATTTAACGAATGCTTAACACTTTAAATGCCACTTCTG AGGAATGGACCTGGTG | SEQ ID NO: 3263 | Homo sapiens kelch-like 2, Mayven (Drosophila) (KLHL2), mRNA [NM_007246] |
| 210 | A_23_P73114 | PROS1 | CCAGAACAAATTTAACAAAGGACAAGACAGAGGGATATAGT GAATATCTATGATTG | SEQ ID NO: 3264 | Homo sapiens protein S (alpha) (PROS1), mRNA [NM_000313] |
| 211 | A_23_P74031 | S100A12 | TGAAGGCTTTTACCCAGCAATGCTCAATGAGGGTCTTTTCT TCCGTGACAAGAACC | SEQ ID NO: 3265 | Homo sapiens S100 calcium binding protein A12 (S100A12), mRNA [NM_005621] |
| 212 | A_23_P75769 | MS4A4A | CACCAAAAGATCAACAGAGACAAATGCTCCAGAAATCTATGCTGAC TGTGACAAGAGCCT | SEQ ID NO: 3266 | Homo sapiens membrane-spanning 4-domains, subfamily A, member 4 (MS4A4A), transcript variant 1, mRNA [NM_024021] |

Fig. 24-12

| No. | Probe ID No. | Symbols of genes | Sequence | SEQ ID NO: | Descriptions of genes (letters and numbers within [ ] indicates GenBank accession No.) |
|---|---|---|---|---|---|
| 213 | A_23_P76460 | BF213738 | AAATCGAACAGGACAATGGGTAGATGGAGGTAGATTTAGGAAAT CGTTTGGCATGACAGG | SEQ ID NO: 3267 | BF213738 601847628F1 NIH_MGC_55 Homo sapiens cDNA clone IMAGE:4078519 5_, mRNA sequence [BF213738] |
| 214 | A_23_P78092 | EVI2A | GGTGAATCAGAACACTTGGAAAAGAGACAAAGAGGTAGAGGACC CAACCTAGTGATGGAA | SEQ ID NO: 3268 | Homo sapiens ecotropic viral integration site 2A (EVI2A), transcript variant 1, mRNA [NM_001003927] |
| 215 | A_23_P82047 | BU507302 | TGTGTTTGGTTAATGTCAGGTGGCTGAAGATTGAGCAGTTTATA AATTGCTTAATTTGTG | SEQ ID NO: 3269 | AGENCOURT_10309688 NIH_MGC_71 Homo sapiens cDNA clone IMAGE:6501220 5_, mRNA sequence [BU507302] |
| 216 | A_23_P83278 | CHMP5 | GATTGCTCTTTTATTTTTTTTTCCATTAAGAGAGTCATTGGTTGGGA AATGCTTTCTTCGTAC | SEQ ID NO: 3270 | Homo sapiens chromatin modifying protein 5 (CHMP5), mRNA [NM_016410] |
| 217 | A_23_P87769 | C12orf48 | GTAAGAAATATGGTCAGTCAGTCGGTCCTAATGATATTGTGACTGTTT GGATATACTCTGTT | SEQ ID NO: 3271 | Homo sapiens chromosome 12 open reading frame 48 (C12orf48), mRNA [NM_017915] |
| 218 | A_23_P87879 | CD69 | TGTCCAATATGATGTAGGGAGAAATCTCATTAGGAAATATTCTG TAATCTTCAGAACCTAG | SEQ ID NO: 3272 | Homo sapiens CD69 molecule (CD69), mRNA [NM_001781] |
| 219 | A_23_P94095 | ANKRD46 | GCTTCTTGGTATTTCTGTTCTGTATCTATGTATCTAGTATTGAGG CTTGCTCTTTCATGCTG | SEQ ID NO: 3273 | Homo sapiens ankyrin repeat domain 46 (ANKRD46), mRNA [NM_198401] |
| 220 | A_23_P94230 | LY96 | TGAAGGTATTTCTGGGAGCCCAGAAGAAATGGTGTTTTTGGTTGG AGTTTGTCATGGTACA | SEQ ID NO: 3274 | Homo sapiens lymphocyte antigen 96 (LY96), mRNA [NM_015364] |
| 221 | A_23_P94501 | ANXA1 | GGCTCTTTGTGGAGGAAAGCTTGTGCCCAAACATGGTGATAGATTTT CTATGATCAGAAGACT | SEQ ID NO: 3275 | Homo sapiens annexin A1 (ANXA1), mRNA [NM_000700] |
| 222 | A_23_P95594 | NAT1 | TCTTGGACAGAGAAGCCTTGTGCCCAAACATGGTGATAGATTTT TACTATTTAGAAATAAG | SEQ ID NO: 3276 | Homo sapiens N-acetyltransferase 1 (arylamine N-acetyltransferase) (NAT1), mRNA [NM_000662] |
| 223 | A_23_P99980 | HMGB1 | GGATTCTTTCCATTTGATTGTTTTATGTAATTCAGGAGGAAT ACTGAACATCGAGTC | SEQ ID NO: 3277 | Homo sapiens high-mobility group box 1 (HMGB1), mRNA [NM_002128] |
| 224 | A_24_P100387 | GK | TAAAAGGTTCTGTTTTGTTTGGAATCAATGGTAGCTTTATTGAC TGTTCTGATTGGCTG | SEQ ID NO: 3278 | Homo sapiens glycerol kinase (GK), transcript variant 1, mRNA [NM_203391] |
| 225 | A_24_P100630 | AMN1 | TCTTCAAAGAATTTAGGTATTTGTTTCAGCGAAATGAAGTGACT TATTAGGCCATTCAGCG | SEQ ID NO: 3279 | Homo sapiens antagonist of mitotic exit network homolog (S. cerevisiae) (AMN1), mRNA [NM_207371] |
| 226 | A_24_P105648 | BX111927 | TTATGAGATGCTCAGTTCAGTTCAAATAACAGTGCAGTAATTCACCTA TATCTAAAAGAGTGCG | SEQ ID NO: 3280 | BX111927 Soares multiple sclerosis 2NbHMSP Homo sapiens cDNA clone IMAGp998G05619, mRNA sequence [BX111927] |
| 227 | A_24_P106306 | RPL26L1 | TGGCAAGGTTAGTCAGGTCTAGAGAAAGAAAATATGTCATGTACA TCGAGCGGGTTGCAGCG | SEQ ID NO: 3281 | Homo sapiens ribosomal protein L26-like 1 (RPL26L1), mRNA [NM_016093] |
| 228 | A_24_P11045 | THC2785765 | CCACCAGAAACGTACACGTGATTTTCATGACAAATACGGTAGCA ACACAAGTGGGAATAG | SEQ ID NO: 3282 | COX7B_HUMAN (P24311) Cytochrome c oxidase polypeptide VIIb, mitochondrial precursor , partial (78%) [THC2785765] |
| 229 | A_24_P114249 | GALNT3 | ATTTCAAATGGAGAATAGTTGACTCATTTAAAGCTAAATTTTGT TACTGATTCAATTATA | SEQ ID NO: 3283 | Homo sapiens UDP-N-acetyl-alpha-D-galactosamine:polypeptide N-acetylgalactosaminyltransferase 3 (GalNAc-T3) (GALNT3), mRNA [NM_004482] |
| 230 | A_24_P118382 | A_24_P118382 | GATACCATGTCTGTCGTCGGTTGTCAGGAAATGAGGGTGAAGA TTCACCAAATAAGGTC | SEQ ID NO: 3284 | |
| 231 | A_24_P127621 | A_24_P127621 | TCGAAGCAAGTACCAGAAAAGGCATTTCAATGGCACTTCCCACA TTCTCAGAAATATTAG | SEQ ID NO: 3285 | |

Fig. 24-13

| No | Probe ID No. | Symbols of genes | Sequence | SEQ ID NO. | Descriptions of genes (letters and numbers within [ ] indicates GenBank accession No.) |
|---|---|---|---|---|---|
| 232 | A_24_P133991 | ANKRD12 | TTTGGAATGGAGTATATATGCTGAAAAGGTTTTGGATTCAGAAAG AAAAAGGATGGTTAGT | SEQ ID NO: 3286 | Homo sapiens ankyrin repeat domain 12 (ANKRD12), mRNA [NM_015208] |
| 233 | A_24_P134392 | STCH | TGAGTAAGTTATTTTGTATCAGGAAGTGTTTGGTACTGTGTTTT CACTCAAACGCACTGAG | SEQ ID NO: 3287 | Homo sapiens stress 70 protein chaperone, microsome-associated, 60kDa (STCH), mRNA [NM_006948] |
| 234 | A_24_P135242 | A_24_P135242 | GATGGCAAGAAAAGCTGGCAAGTACTTGTAGGTGCAGAACGGCA AACTGGCATTTGTCAT | SEQ ID NO: 3288 | |
| 235 | A_24_P135551 | LOC130865 | TAACAGGATAAGCTGTCTGCGGTGTGGGCATTCACCCAAAGGTGGTTA TCAGTAGACTAAAAC | SEQ ID NO: 3289 | PREDICTED: Homo sapiens similar to 60S ribosomal protein L26 (Silica-induced gene 20 protein) (SIG-20) (LOC130865), mRNA [XR_019454] |
| 236 | A_24_P144666 | LOC401975 | TGTCTGAGTGTCAAGACTAATGATGGGTACTTGTTTAATCTGTTCT GTGTTGGTTTTACTCGA | SEQ ID NO: 3290 | PREDICTED: Homo sapiens similar to ribosomal protein S3a (LOC401975), mRNA [XR_017247] |
| 237 | A_24_P152753 | LOC285260 | TGTCTGATACGGAATGCGGTGTGCGATTATCCAGAAAAGGATGAAG ATTGACCAAATAAGCT | SEQ ID NO: 3291 | PREDICTED: Homo sapiens similar to ribosomal protein L31 (LOC285260), mRNA [XR_019376] |
| 238 | A_24_P153324 | LOC390413 | GAAAGTTAACAAGGTTTCAATTAACATGCTGGGGATTGTAGAAC CATATATTGCAGGGTA | SEQ ID NO: 3292 | PREDICTED: Homo sapiens similar to 60S ribosomal protein L7 (LOC390413), mRNA [XR_018341] |
| 239 | A_24_P165864 | P2RY14 | TTTTGTGGAAAACAGAGACGGATTTACTTCTGGAGACATGGCAT ACGGTTACTGAGTTAT | SEQ ID NO: 3293 | Homo sapiens purinergic receptor P2Y, G-protein coupled, 14 (P2RY14), transcript variant 2, mRNA [NM_014879] |
| 240 | A_24_P175176 | PHTF2 | AGATTGAGGTTAACTTAGAGTTGGGAGTTGATTTATTAAGTACA GTATACGTCTCAACAG | SEQ ID NO: 3294 | Homo sapiens putative homeodomain transcription factor 2 (PHTF2), mRNA [NM_020432] |
| 241 | A_24_P188878 | RPL34 | TGTTTAGCTTTATACCAAGAAGGTTGGGAAAGCACCAAAATCTG CATGTCGTGTGCCC | SEQ ID NO: 3295 | Homo sapiens ribosomal protein L34 (RPL34), transcript variant 2, mRNA [NM_033625] |
| 242 | A_24_P201702 | CLEC2B | ATTGGAATTCAAGTAAATACAACTGTTCCAGTTGTTCAACATGCGAC CTAACTATAATTGACA | SEQ ID NO: 3296 | Homo sapiens C-type lectin domain family 2, member B (CLEC2B), mRNA [NM_005127] |
| 243 | A_24_P203909 | RPL34 | GAGGGGTTCGTGCTGTAAGACTTAAAGTTCTTATGAAGTGTCTTATGGT AAAACAAAACAAGATG | SEQ ID NO: 3297 | Homo sapiens ribosomal protein L34 (RPL34), transcript variant 2, mRNA [NM_033625] |
| 244 | A_24_P20996 | BC043173 | GAAGGGTCTGTATTGG | SEQ ID NO: 3298 | Homo sapiens cDNA clone IMAGE:5267121 [BC043173] |
| 245 | A_24_P213375 | A_24_P213375 | AAATGTGTTGATGATGCAAAAATGGCAGAAGAATGATTGTTCAT GTGTTCTGTGTTGGTT | SEQ ID NO: 3299 | |
| 246 | A_24_P213783 | RPL31 | CTTGGTTAGTATGTAGCTGTTACCAGTTGCAAAAATCTACAG ACAGTCAATGTGGATG | SEQ ID NO: 3300 | Homo sapiens ribosomal protein L31 (RPL31), mRNA [NM_000993] |
| 247 | A_24_P221375 | A_24_P221375 | TACTTTGGTTACCCATGTACCTACCACCAGTTCAAAAATCTACACAGA CAGTCAATCTGGAGGA | SEQ ID NO: 3301 | |
| 248 | A_24_P225308 | ARID4B | GTTGAAAATGGTTCAAGTTATTCAAATTTGTACAGGAGTGTGAA AGATTTGTTGACAGCA | SEQ ID NO: 3302 | Homo sapiens AT rich interactive domain 4B (RBP1-like) (ARID4B), transcript variant 1, mRNA [NM_016374] |
| 249 | A_24_P225719 | PREI3 | GACTATTTCTTAGTGTGAATATTCAAGGTAGTGACTGAGA TTTGGTGATCTGGGTG | SEQ ID NO: 3303 | Homo sapiens preimplantation protein 3 (PREI3), transcript variant 1, mRNA [NM_015387] |
| 250 | A_24_P235429 | ABCA1 | CCAAAGACAGCCATGTGTCATGTAATACTGAACCACTTTGATATTG AGACATAATTTGTAC | SEQ ID NO: 3304 | Homo sapiens ATP-binding cassette, sub-family A (ABC1), member 1 (ABCA1), mRNA [NM_005502] |

Fig. 24-14

| No. | Probe ID No. | Symbols of genes | Sequence | SEQ ID NO: | Descriptions of genes (letters and numbers within [ ] indicates GenBank accession No.) |
|---|---|---|---|---|---|
| 251 | A_24_P236608 | SCYL2 | ATAGAGTATGACTTGTCTGGGTTTTTGTTTGTTTTTATTTTGGAATGCTTATAAGGTCC | SEQ ID NO: 3305 | Homo sapiens mRNA for KIAA1360 protein, partial cds. [AB037781] |
| 252 | A_24_P243749 | PDK4 | ATTTGACATTTGTGTGTAATTTGAATGGTGGCCTAGTGTGTGGGTGCTTCTGTAATGGTA | SEQ ID NO: 3306 | Homo sapiens pyruvate dehydrogenase kinase, isozyme 4 (PDK4), mRNA [NM_002612] |
| 253 | A_24_P24890 | A_24_P24890 | ATGAAGCAGATTGGTCTTTGTATTCTTACGTTGGTGTAGTTGTAAGGTGGCCTGTACT | SEQ ID NO: 3307 | |
| 254 | A_24_P264549 | A_24_P264549 | ATTCATAGTAGCATACAGAACATGATCAAAGGTGTTACAGTGGACTTCCATTACAATATG | SEQ ID NO: 3308 | |
| 255 | A_24_P268917 | RAB33B | GGCAGAAATCTAATGTAGTCGGTATTAATAACAATGATTATTGAAAGTATTGGAAAT | SEQ ID NO: 3309 | Homo sapiens RAB33B, member RAS oncogene family (RAB33B), mRNA [NM_031296] |
| 256 | A_24_P276583 | TMCO1 | CCTTCATTTCCTGCTATATCTGTGTACTATGTCGATTCGAGAGAACATTCAGAAGATTC | SEQ ID NO: 3310 | Homo sapiens transmembrane and coiled-coil domains 1 (TMCO1), mRNA [NM_019026] |
| 257 | A_24_P278460 | MLSTD2 | AGCCATGGAACAATATGCTAGGATTACAGGAAGCAGCAGTGCATTACACTGTCTGTGCTG | SEQ ID NO: 3311 | Homo sapiens male sterility domain containing 2 (MLSTD2), mRNA [NM_052228] |
| 258 | A_24_P286054 | ZFYVE16 | GTGTATGTATTCTGCCATGTAAGTAATTGAACACTTAAAATAAGGAAATGGTAGAGGG | SEQ ID NO: 3312 | Zinc finger FYVE domain-containing protein 16 (Endofin) (Endosome-associated FYVE domain protein). [Source:Uniprot/SWISSPROT;Acc:Q7Z3T8] [ENST00000382248] |
| 259 | A_24_P298238 | A_24_P298238 | ATCCTTGAAGGAAATGACAATTGAGCTTGTTCAATTCAGGAAGCCAGAACAGTTAAAAAC | SEQ ID NO: 3313 | |
| 260 | A_24_P298804 | LOC731599 | GATGGAAATCATGACCAGAGGGTGGGGCAAATGAGTTGAAAGAATTGGTCAATAAAATGAT | SEQ ID NO: 3314 | PREDICTED: Homo sapiens hypothetical protein LOC731599 (LOC731599), mRNA [XR_015536] |
| 261 | A_24_P303118 | RPL34 | CGAGGAGGAGAAAATGTTGTGTAAAGTGTTGAAGGCACAAGGACAGAGTCAGAAGGTAA | SEQ ID NO: 3315 | Homo sapiens ribosomal protein L34 (RPL34), transcript variant 2, mRNA [NM_033625] |
| 262 | A_24_P306527 | ENST00000308999 | AGGGCATCCGTGGGTGGTTATCAGAAAATGTAATGAGGATGAAGATTCAGGAAATAAGT | SEQ ID NO: 3316 | PREDICTED: Homo sapiens similar to ribosomal protein L31 (LOC729035), mRNA [XM_001133428] |
| 263 | A_24_P315326 | LOC341412 | AAGCTGTATAGCTTGGTTGGTTAGGAAATGTACCGGGTTACCGCTTTCGAAAATCTACAGGGAATG | SEQ ID NO: 3317 | AGENCOURT_10640955 NIH_MGC_126 Homo sapiens cDNA clone IMAGE:6723568 5', mRNA sequence [CA455253] |
| 264 | A_24_P316374 | LOC730902 | TATCAATGGTGTGAGCCCAAAGGTCAAAGGTGTTGCAGCTCTTCCCTTGGTCAAATCTT | SEQ ID NO: 3318 | PREDICTED: Homo sapiens similar to 60S ribosomal protein L7 (LOC730902), mRNA [XR_015601] |
| 265 | A_24_P320328 | SUB1 | AAAGGTCTGTGTGGGCCAAAGGAACAAAGAACAGAGGTGAGAGTTGAGAGGGCTGTGTGTCATGTCTTCTA | SEQ ID NO: 3319 | Homo sapiens SUB1 homolog (S. cerevisiae) (SUB1), mRNA [NM_006713] |
| 266 | A_24_P324224 | A_24_P324224 | AAAGCTGTCTGGGCCAAAGGAATAATGGCTGTAGCAAGCAAGGCGTAAAAGCGCTTCGTCAGAGAA | SEQ ID NO: 3320 | |
| 267 | A_24_P324531 | KIAA1466 | ATAATAGCTCATAGAATGAATGGGGGTAGCCAAATCTGAAGTCAGTAGGCCAGAATTTAAGTAGGCC | SEQ ID NO: 3321 | Homo sapiens mRNA for KIAA1466 protein, partial cds. [AB040899] |
| 268 | A_24_P33213 | A_24_P33213 | GACCATTATATTACATGGGGGTAGCCAAATCTGAAGTGAGTAAAGAACTTATCTACAAGG | SEQ ID NO: 3322 | |
| 269 | A_24_P333052 | A_24_P333052 | TAGACATCAAGAAAATGGATACTGTTCAAAAATGCCCCACAAATGTTAACATGGGAAAA | SEQ ID NO: 3323 | |
| 270 | A_24_P333112 | A_24_P333112 | GGTCATCAGATCAGAGTCAGGTATCAATGTGTGAGGCCACAGGAGGAAAAGGTATTGCAACTT | SEQ ID NO: 3324 | |

Fig. 24-15

| No. | Probe ID No. | Symbols of genes | Sequence | SEQ ID NO. | Descriptions of genes (letters and numbers within [ ] indicates GenBank accession No.) |
|---|---|---|---|---|---|
| 271 | A_24_P33607 | LOC652558 | TAAGAAATAATTGCTTTGACAGAGAACGGCTTTGATTGCTCCAT CTCTTGGTAAATATGG | SEQ ID NO: 3325 | PREDICTED: Homo sapiens similar to 60S ribosomal protein L7 (LOC652558), mRNA [XR_019386] |
| 272 | A_24_P344537 | ZNF625 | TCGAGCGTTAAAATCGATGAAAGGAGTCACACTGGAGAAAAACC CGTAGCTCCAACACT | SEQ ID NO: 3326 | Homo sapiens zinc finger protein 625 (ZNF625), mRNA [NM_145233] |
| 273 | A_24_P349636 | LOC388401 | AGTTGCTTGCAGACGATAACACTTTGATTGGCTCGATCTCTTGGTA AATATAGCACAACTG | SEQ ID NO: 3327 | PREDICTED: Homo sapiens similar to 60S ribosomal protein L7 (LOC388401), mRNA [XR_016879] |
| 274 | A_24_P364025 | UBE2D1 | ATGTGATGGGTGTAGTGATTAGCAAAGGATTTAAATCACTGAAG TATTTGTCATGGTTC | SEQ ID NO: 3328 | Homo sapiens ubiquitin-conjugating enzyme E2D 1 (UBC4/5 homolog, yeast) (UBE2D1), mRNA [NM_003338] |
| 275 | A_24_P364807 | AYTL1 | TGTAACTCTGTTCTGTAGGTAATCGTTCTGTCTCAAGCAAAGTTC TCAAGGCGTCGTGTAA | SEQ ID NO: 3329 | Homo sapiens mRNA; cDNA DKFZp686H22112 (from clone DKFZp686H22112) [BX641069] |
| 276 | A_24_P366165 | LOC391126 | AGTTGGAAGGAAATGAAAAATAGAAAAATAGGAGATTCAATGCACC TTCCACATTCACAGG | SEQ ID NO: 3330 | PREDICTED: Homo sapiens similar to 60S ribosomal protein L26 (Silica-induced gene 20 protein) (SIG-20) (LOC391126), mRNA [XR_019504] |
| 277 | A_24_P366546 | RPL31P10 | CGGCTGTGGAGAAAAGGTAATGAGGATGAAGATTCAAATAAGCT CTATACTTGGTTACC | SEQ ID NO: 3331 | PREDICTED: Homo sapiens similar to ribosomal protein L31 (LOC390283), mRNA [XR_018695] |
| 278 | A_24_P367191 | LOC652890 | AGTTAAGATGGTGAAGGAGTGTAAGAGCAATATATTGCGTGTGGGT ACCAAATCGAAGTC | SEQ ID NO: 3332 | PREDICTED: Homo sapiens similar to 60S ribosomal protein L7 (LOC652890), mRNA [XR_019544] |
| 279 | A_24_P367199 | A_24_P367199 | TCTTATGCTCAGCACCAAATGCTGCCAAATCCAAGAAGGATG TAATCTGACCTGAGA | SEQ ID NO: 3333 | |
| 280 | A_24_P367369 | A_24_P367369 | ATTTAAAGGTTCGATGATAGTCTCTGGTCGGAGATATCGAAG TGAACAAAGATGTAA | SEQ ID NO: 3334 | |
| 281 | A_24_P375932 | A_24_P375932 | ATGGTTAAAATGCAGAGAGCAATGCGAGAACTTAAGGTTTAGA TGTAGATTCGTTGGTC | SEQ ID NO: 3335 | |
| 282 | A_24_P381625 | PSMC6 | ATGAAGCAGTCAGAAAAGTGGCTGATTCTAAGAAGCTGGAGTG TAAATTGGACTACAAA | SEQ ID NO: 3336 | Homo sapiens proteasome (prosome, macropain) 26S subunit, ATPase, 6 (PSMC6), mRNA [NM_002804] |
| 283 | A_24_P383999 | RPS3A | TGGTTTACTAAAAAACGCAACAATCAGATACAGAAGAGACCTCTT ATGCCAGGACACACG | SEQ ID NO: 3337 | Homo sapiens ribosomal protein S3A (RPS3A), mRNA [NM_001006] |
| 284 | A_24_P384411 | A_24_P384411 | ATGGCAAATCGAATAAGAGTGAAGCTTTGACAGATAATGCTTTG ACAGTTCGATCTCTTG | SEQ ID NO: 3338 | |
| 285 | A_24_P384539 | LOC730452 | CAAGAAAATGGGAAGTTTCTATGTACGGACACAAACCCAAATTG GCATTTGTCATCAGGA | SEQ ID NO: 3339 | PREDICTED: Homo sapiens similar to 60S ribosomal protein L7 (LOC730452), mRNA [XM_001258957] |
| 286 | A_24_P392622 | A_24_P392622 | CATGGAATTGTTGGTTTGGGCACAGTGATCTATAAGAAAGATGA AATGGAGACACCAA | SEQ ID NO: 3340 | |
| 287 | A_24_P39378 | CCPG1 | TACTTTTGTCGGCTGGAACGGAAACTTGAAGTTCATCAATAAGT TTTCGTAAGGGGTGT | SEQ ID NO: 3341 | Homo sapiens cell cycle progression 1 (CCPG1), transcript variant 1, mRNA [NM_004748] |
| 288 | A_24_P403303 | PHF20L1 | AAAGCCGAGTTATAAAGCTGTTAATTACATCGAATTGGTATGA GGAATAGAGGTAAAGG | SEQ ID NO: 3342 | Homo sapiens PHD finger protein 20-like 1 (PHF20L1), transcript variant 3, mRNA [NM_198513] |
| 289 | A_24_P414556 | TTC33 | TACTCAACATTTGGTATATTGTTTTGAGTAATCGATGATTGTTGTT TGTGTAATTGTGA | SEQ ID NO: 3343 | Homo sapiens tetratricopeptide repeat domain 33 (TTC33), mRNA [NM_012382] |
| 290 | A_24_P41551 | LOC641790 | AAGGAGATGGGAACTCCTGATGTGCGCATTGCATGATGAGGACACAA CAAAGGTAGTCTGGAAA | SEQ ID NO: 3344 | PREDICTED: Homo sapiens similar to 60S ribosomal protein L31 (LOC641790), mRNA [XR_018025] |

Fig. 24-16

| No. | Probe ID No. | Symbols of genes | Sequence | SEQ ID NO: | Descriptions of genes (letters and numbers within [ ] indicates GenBank accession No.) |
|---|---|---|---|---|---|
| 291 | A_24_P418712 | A_24_P418712 | AGGCTCAACAAAGCTGTCTGGGCGCAAAGAATAAGGAATATCGA TACGATATCTGTGTTA | SEQ ID NO: 3345 | |
| 292 | A_24_P4877 | ZCRB1 | GAAAAATTAATACATGATGTTAATACTATTGTCATCCGAA GAAAAAAGATATTTTA | SEQ ID NO: 3346 | Homo sapiens zinc finger CCHC-type and RNA binding motif 1 (ZCRB1), mRNA [NM_033114] |
| 293 | A_24_P50437 | BC065737 | TGCAGAATGATGAAGTTGCATTTAGAAAATTCCTGATTACTGAA GATGTTCAGGGCAAAA | SEQ ID NO: 3347 | Homo sapiens cDNA clone IMAGE:30404477, partial cds [BC065737] |
| 294 | A_24_P538403 | ROCK1 | TTAGAGGTTTGTTGGACTTTGATAAATTGAGTAGAATCTTTCA TCAAAGTACCTGGTAG | SEQ ID NO: 3348 | Homo sapiens Rho-associated, coiled-coil containing protein kinase 1 (ROCK1), mRNA [NM_005406] |
| 295 | A_24_P54178 | TMED5 | GCTCTGATATGCATTTGGATGATTAATGTTATGCTGTTCTTTCA TGTGAATGTCAAGACA | SEQ ID NO: 3349 | Homo sapiens transmembrane emp24 protein transport domain containing 5 (TMED5), mRNA [NM_016040] |
| 296 | A_24_P557232 | CB111670 | GTTTCTCTTCCTCAAAAACACACTCAAGTCGTCTCCAAGTTCGA AGCATTCAGCAAACAA | SEQ ID NO: 3350 | K-EST0153390 L5HLK1 Homo sapiens cDNA clone L5HLK1-3-D02 5', mRNA sequence [CB111670] |
| 297 | A_24_P56252 | AF086032 | GTATCTAAAACTGAACAGAGTCTGTGCTATATTGATTTTATTGG TAGTATTGACCAGAGG | SEQ ID NO: 3351 | Homo sapiens full length insert cDNA clone YM25G09 [AF086032] |
| 298 | A_24_P57837 | THC2567891 | AAGAATGCCGAAGAACCTCTTATGGTCAGTCAGGAGGGAAATCCGG AAGAAGATGATGGAAA | SEQ ID NO: 3352 | Q6NXR8_HUMAN (Q6NXR8) Ribosomal protein S3a, partial (91%) [THC2567891] |
| 299 | A_24_P587938 | A_24_P587938 | CTTGAAAGCAGAGAAAAGGTGGAGATGGTGCGGGTGAAGATTCACGAG AGATTAACAGTCTAT | SEQ ID NO: 3353 | |
| 300 | A_24_P606663 | LOC392030 | TGTGCGGTTGGCCAGAAAGAGTAATGCGGGTGAAGAATTCACCAA ATAAGCTCCATAGTTT | SEQ ID NO: 3354 | PREDICTED: Homo sapiens hypothetical LOC392030 (LOC392030), mRNA [XR_018063] |
| 301 | A_24_P62860 | STAM2 | GCTATATGGTACTTGATCTAGATTTAAGATTTTTGGACCATATTAAAAC TATTTGAAAGGTCAGT | SEQ ID NO: 3355 | Homo sapiens signal transducing adaptor molecule (SH3 domain and ITAM motif) 2 (STAM2), mRNA [NM_005843] |
| 302 | A_24_P630039 | AL049321 | AAGAGACAATAGAAAGATTACATTTTTGGACCATATTAAAAC TGCAAGAAGACAACGGGG | SEQ ID NO: 3356 | Homo sapiens mRNA; cDNA DKFZp564D156 (from clone DKFZp564D156) [AL049321] |
| 303 | A_24_P63347 | PF4V1 | CTACATATTTACCTTGAATGTTACAATTAGCTTGCCAATAAATA TTAGTAGCTCTTAAGG | SEQ ID NO: 3357 | Homo sapiens platelet factor 4 variant 1 (PF4V1), mRNA [NM_002620] |
| 304 | A_24_P652786 | THC2533996 | TGCTTGTTCGTATGTCAGCCGGAACGTGAGATGATTATCCTTGAGGAAT GACATTGAGCTTGTTT | SEQ ID NO: 3358 | HSU09954 ribosomal protein L9 [Homo sapiens] (exp=-1; wgp=0; cg=0), partial (42%) [THC2533996] |
| 305 | A_24_P685729 | A_24_P685729 | TTGAAGCTATGTTGATGTCAAGCTATCAGTGATTATTTGGTT TGTCTGTTGTGTGG | SEQ ID NO: 3359 | |
| 306 | A_24_P6975 | LOC342994 | GGAAGAGCTTCAGGGGGTTCGTGCTGCTGTAAGACCTAAGTTCTTAT GAAATTGTCAAAAGA | SEQ ID NO: 3360 | PREDICTED: Homo sapiens similar to ribosomal protein L34 (LOC342994), mRNA [XM_938434] |
| 307 | A_24_P75158 | PTAR1 | CGATTAGATTTGTTCGTTATGTGACCATGTAGCAAGCCCAGGCATA AAGTATTGTATTTCTG | SEQ ID NO: 3361 | Homo sapiens mRNA; cDNA DKFZp313P0917 (from clone DKFZp313P0917) [AL832263] |
| 308 | A_24_P755605 | A_24_P755605 | ATACAGAAGAAGCTCTTATGGTCAGCAGCAAGAAGAAAGTAAAAA TGGTGAAGAAGCCGAA | SEQ ID NO: 3362 | |
| 309 | A_24_P76358 | LOC643981 | TTACTGAAGATGTTCAGGGCAAAAACTGCCCTAAGTTCCGGGCATG GATCTTATTCGTGACA | SEQ ID NO: 3363 | PREDICTED: Homo sapiens similar to 40S ribosomal protein S3a (V-fos transformation effector protein) (LOC643981), mRNA [XR_018444] |

Fig. 24-17

| No. | Probe ID No. | Symbols of genes | Sequence | SEQ ID NO: | Descriptions of genes (letters and numbers within [ ] indicates GenBank accession No.) |
|---|---|---|---|---|---|
| 310 | A_24_P792734 | PSMC6 | AGAAGTTAAGCGAGTTACTGAATCAAATGGATGGATTTGATAC TCTGCATAGAGTTAAA | SEQ ID NO: 3364 | Homo sapiens proteasome (prosome, macropain) 26S subunit, ATPase, 6 (PSMC6), mRNA [NM_002806] |
| 311 | A_24_P82630 | SMCHD1 | TGTTTAATATGTAACACGTAAGAACAATTGAAATTTCTTCTAA GATTAATACTAGTCT | SEQ ID NO: 3365 | Homo sapiens mRNA for KIAA0650 protein, partial cds. [AB014560] |
| 312 | A_24_P63968 | LOC730887 | AGAAAGCCCAGGAGAGAACAACGTGGAACACAGAGAAAGTTTTCT GGTGTCTCTAAGAAGC | SEQ ID NO: 3366 | PREDICTED: Homo sapiens similar to 40S ribosomal protein S7 (S8) (LOC730887), mRNA [XR_015607] |
| 313 | A_24_P84608 | LOC729449 | GAATTGCTTTGACAGATAACGCTTTGGGATGTCTTGGAAAATAT GGGAATCTGTATGG | SEQ ID NO: 3367 | PREDICTED: Homo sapiens similar to 60S ribosomal protein L7 (LOC729449), mRNA [XR_015548] |
| 314 | A_24_P850187 | A_24_P850187 | TAAATGAAGTAATGTACAAGGGTGCTTATGGCAAAATCAATTTG ACTGCACTTGGTAC | SEQ ID NO: 3368 | |
| 315 | A_24_P967201 | AK022997 | CTGAGATGTGATAAATATTTCAGTGACTTTTCAGATTTATTTCT TGTTAGCGGTCTGTG | SEQ ID NO: 3369 | Homo sapiens cDNA FLJ12935 fis, clone NT2RP2004932. [AK022997] |
| 316 | A_24_P91852 | DYNLT3 | ATACATATAGAGAGCGGAAGCATAACTCATTGAATTTTTGGAGAG GAATAAGCTTAGGCGTT | SEQ ID NO: 3370 | Homo sapiens dynein, light chain, Tctex-type 3 (DYNLT3), mRNA [NM_006520] |
| 317 | A_24_P935986 | BCAT1 | ATGGCTCTGAAGGTTTTGTAGAAGCAGAATTAAACATGTAAATG GCTTGTTACCACAGA | SEQ ID NO: 3371 | Homo sapiens branched chain aminotransferase 1, cytosolic (BCAT1), mRNA [NM_005504] |
| 318 | A_24_P940426 | QKI | AAGCTGTTGAATGAGTCTTAAAAATTATACAGTGTTAAGTGGA CCAAGTTTGGTCAAGG | SEQ ID NO: 3372 | Homo sapiens quaking homolog, KH domain RNA binding (mouse) (QKI), transcript variant 4, mRNA [NM_206855] |
| 319 | A_24_P99046 | STK38L | GCTATCTGTCGTTTTGCTGATCTAGAAGATAAATGAATTGAGAATT TAGTCCATAGAGGTC | SEQ ID NO: 3373 | Homo sapiens serine/threonine kinase 38 like (STK38L), mRNA [NM_015000] |
| 320 | A_32_P10100 | A_32_P10100 | TATGAGGAAAATAGTATCATGCATGCTTAGAAGCCTTGGAATGAGTA TAAATAATGGCTGGTG | SEQ ID NO: 3374 | |
| 321 | A_32_P105397 | THC2642694 | TAAAATGCTACTACAGTATTCTACGGATGCAGGGTGAATGCATGTATAT TACAGTAATTCTCTGG | SEQ ID NO: 3375 | Q61DT1_HUMAN (Q61DT1) Protein transactivated by hepatitis B virus E antigen, partial (11%) [THC2642694] |
| 322 | A_32_P107935 | DB527271 | GTTTATGTGAAATAGAGTTTTCAGATTTATGTAGCATGGAAAAG TTTTAAATAGGTCAGAG | SEQ ID NO: 3376 | DB527271 RIKEN full-length enriched human cDNA library, testis Homo sapiens cDNA clone H013095F12 3', mRNA sequence [DB527271] |
| 323 | A_32_P108036 | ZNF493 | AAAGACGTCAATATGTGCTCACATCTTAGTAAACACCAGAGAGT TCATGCTTAATATAAAG | SEQ ID NO: 3377 | PREDICTED: Homo sapiens zinc finger protein 493 (ZNF493), transcript variant 1, mRNA [NM_175910] |
| 324 | A_32_P113154 | LOC730861 | ACCACAGTCAAGAATCGTGTTTAAAGTTCAGAGTTAAAACAGT ACGAAATAAAAAGTCC | SEQ ID NO: 3378 | PREDICTED: Homo sapiens similar to 40S ribosomal protein S3a (V-fos transformation effector protein) (LOC730861), mRNA [XR_015591] |
| 325 | A_32_P114215 | COMMD6 | AATTGCTATCATTCTAAAGTCATGAGAGTTCACTTTCGGCAACAA AACTAAATAAGGATGG | SEQ ID NO: 3379 | Homo sapiens COMM domain containing 6 (COMMD6), transcript variant 2, mRNA [NM_203495] |
| 326 | A_32_P11451 | NMD3 | CAGTTTAGGGCAGTTAGGGCAGTGCTTCTTGTCATAAATATCTTGTACC ACATAAAAATGCTGG | SEQ ID NO: 3380 | Homo sapiens NMD3 homolog (S. cerevisiae) (NMD3), mRNA [NM_015938] |
| 327 | A_32_P11931 | LOC441073 | GTGTGATCCATGCCCATCCGAAAGGATGATGAAGTTCAGGTTGT ACGTGGAAGCTATAAA | SEQ ID NO: 3381 | PREDICTED: Homo sapiens similar to 60S ribosomal protein L26 (Silica-induced gene 20 protein) (SIG-20) (LOC441073), mRNA [XR_016376] |
| 328 | A_32_P125549 | RPL31P4 | TCTACAGAGAGTCAATGTGGATGAGAACTAATCCTGATCGTCA GATACATGAAATAAAG | SEQ ID NO: 3382 | PREDICTED: Homo sapiens ribosomal protein L31 pseudogene 4 (RPL31P4), mRNA [XR_018222] |

Fig. 24-18

| No. | Probe ID No. | Symbols of genes | Sequence | SEQ ID NO: | Descriptions of genes (letters and numbers within [ ] indicates GenBank accession No.) |
|---|---|---|---|---|---|
| 329 | A_32_P125917 | THC2753798 | GCTTATAAAGTGTAAGTGGAGACGGTAAATTGTGAGTACAAAGTTTGTTTTTCACAACAG | SEQ ID NO: 3383 | BF238843 601904455F1 NIH_MGS_54 Homo sapiens cDNA clone IMAGE:4132429 5', mRNA sequence [BF238843] |
| 330 | A_32_P127454 | A_32_P127454 | GGACAGGTTCGATTCTATTCCGACTTGTGTTGGCTATGAGCCATGTAACAATACAAGAA | SEQ ID NO: 3384 | |
| 331 | A_32_P128781 | A_32_P128781 | CATATATTGCATGCGGGTAGCCCAATCTGAAGTGAGTAAATGAACTAATCTACAAGAGTG | SEQ ID NO: 3385 | |
| 332 | A_32_P135818 | RPS3A | CTTGCTTCATGTCTTCCTCTGTTCTTGGTTTTAATAAAAACGGACAGAATGAGATGGAAGAG | SEQ ID NO: 3386 | Homo sapiens ribosomal protein S3A (RPS3A), mRNA [NM_001006] |
| 333 | A_32_P137266 | KIAA1799 | AAGTGGGACCGAAATCTAGAAGTTTGTCAAGATGTAATGCCTTTGAATGAACGAAGAAG | SEQ ID NO: 3387 | Homo sapiens KIAA1799 protein (KIAA1799), mRNA [NM_032437] |
| 334 | A_32_P145153 | RPL31 | ATCCGTGTGCAGCTGTCCAGAAAAACGTAATGAGGATGAAGATTCAGAAATAAGCCATAT | SEQ ID NO: 3388 | Homo sapiens ribosomal protein L31 (RPL31), mRNA [NM_000993] |
| 335 | A_32_P153725 | KIAA1033 | TTCTTAAAAGATGGCAAGTTTGTTAGGTCACTTCAGTGAGGTTTTCCTTTTGGGCAAAT | SEQ ID NO: 3389 | Homo sapiens KIAA1033 (KIAA1033), mRNA [NM_015275] |
| 336 | A_32_P155364 | RPL7 | TGAACAGGGTTATTAGAAAATGAACCAAGGTGTCTACCATGATATTTTTTCTAAGCTGG | SEQ ID NO: 3390 | Homo sapiens ribosomal protein L7 (RPL7), mRNA [NM_000971] |
| 337 | A_32_P158745 | RPL17 | TTTGCTGGAGATGCTAAAAATGAGAAGATGAAGAGAGTAATGCTGAAGTTAAGGTTAGAATGTAG | SEQ ID NO: 3391 | Homo sapiens ribosomal protein L17 (RPL17), transcript variant 1, mRNA [NM_000985] |
| 338 | A_32_P164203 | THC2683448 | TTGATGGTCATCGAGGCTATTGTATGGCATTATTAAATTGTATAGTAGTGTGGAGTGCTGTTTAGGACGATGAT | SEQ ID NO: 3392 | Q7NZG3_PASPT (Q7NZG3) Ferric uptake regulator, partial (8%) [THC2683448] |
| 339 | A_32_P165340 | SRP9 | AGAATTGAAATATGTTTTGTATAAATTGTCATGTTGAACAACATTTTAGCATGGTAAGTT | SEQ ID NO: 3393 | Homo sapiens signal recognition particle 9kDa (SRP9), mRNA [NM_003133] |
| 340 | A_32_P170444 | SUB1 | TAGGTATGTCTCCTGAAATTGTTTGCAGTTGCATTTTTTTATGGCAGTTAATCGAGTCAAAGAAAC | SEQ ID NO: 3394 | Activated RNA polymerase II transcriptional coactivator p15 (SUB1 homolog) (Positive cofactor 4) (PC4) (p14) [Source:Uniprot/SWISSPROT:Acc:P53999] [ENST00000265973] |
| 341 | A_32_P1712 | RNASE2 | TCCAAGGTTGCCTTTAATGTACTGTAAGCTCACAAGTCCAAGTCCACAGAATATTTGAAACT | SEQ ID NO: 3395 | Homo sapiens ribonuclease, RNase A family, 2 (liver, eosinophil-derived neurotoxin) (RNASE2), mRNA [NM_002934] |
| 342 | A_32_P176819 | CMAH | GATTATATATGGGTAGGTCTCATTCTGAAGATACAGAGAATTGAATGGTGGAATTTGTGTCC | SEQ ID NO: 3396 | Homo sapiens cytidine monophosphate-N-acetylneuraminic acid hydroxylase (CMP-N-acetylneuraminate monooxygenase) (CMAH) on chromosome 6 [NR_021174] |
| 343 | A_32_P178366 | ENST00000379426 | GTAAATACAGGGTGAACGTGAACTCTTACTGATACAGACAACAAGAACTGTTAAAAGTGAATCC | SEQ ID NO: 3397 | Novel protein [Source:Uniprot/SPTREMBL:Acc:Q5T4T1] [ENST00000379426] |
| 344 | A_32_P184394 | TFEC | AGTTGCTTATGGCATACAAGGCTAAAATTAATTCAGGCTATTTAATCTTAATTAATTATTAT | SEQ ID NO: 3398 | Homo sapiens transcription factor EC (TFEC), transcript variant 1, mRNA [NM_012252] |
| 345 | A_32_P190488 | hCG_26523 | CCCAAGCAAGGTGCGTTATGCACTTAGGGTAAAGTGGAGAAAGACCCCAAAAAGATCGTTGAA | SEQ ID NO: 3399 | PREDICTED: Homo sapiens similar to 60S ribosomal protein L26 (LOC646161), mRNA [XR_018048] |
| 346 | A_32_P193322 | RICTOR | CACACATGAGTTGTTCTTTTTTATTTAGTAGTAATACCGCTGTAGATATTTGGAGGGTCTGG | SEQ ID NO: 3400 | Homo sapiens rapamycin-insensitive companion of mTOR (RICTOR), mRNA [NM_152756] |

Fig. 24-19

| No. | Probe ID No. | Symbols of genes | Sequence | SEQ ID NO. | Descriptions of genes (letters and numbers within [ ] indicates GenBank accession No.) |
|---|---|---|---|---|---|
| 347 | A_32_P196483 | RPS3A | GGGGCCAAGAAGAAGAAAGTGGTTGATCCATTTGTAAGAAAGATTC GTATGATGTGAAAGCA | SEQ ID NO: 3401 | Homo sapiens ribosomal protein S3A (RPS3A), mRNA [NM_001006] |
| 348 | A_32_P19752 | FAM76B | TTGTGTTTTAGGGTGTTTTCCACTATTAATTAGGATTTACCAG TAAGGTCATTTGAC | SEQ ID NO: 3402 | Homo sapiens family with sequence similarity 76, member B (FAM76B), mRNA [NM_144664] |
| 349 | A_32_P208178 | RPS3A | GGAAAAGACGTAGAAAAGGGTTGGAATGTATTATTATGTGTCGA TGATGTCGTTAGA | SEQ ID NO: 3403 | Homo sapiens ribosomal protein S3A (RPS3A), mRNA [NM_001006] |
| 350 | A_32_P224666 | CAPZA2 | AATGGTGTTTTGAGATTCTGAAATTAAATGAAATAGTTATTTC AGAAATGCATTTAATG | SEQ ID NO: 3404 | Homo sapiens capping protein (actin filament) muscle Z-line, alpha 2 (CAPZA2), mRNA [NM_006136] |
| 351 | A_32_P22539 | hCG_26523 | AGTACGAAGGTCAGCAAATTGGCAAAGTTGGTCCAGGTTTACAGG AAGAAATATGTTATCT | SEQ ID NO: 3405 | PREDICTED: Homo sapiens similar to 60S ribosomal protein L26 (Silica-induced gene 20 protein) (SIG-20) (LOC400055), mRNA [XM_374997] |
| 352 | A_32_P226786 | BC045174 | TTATTGGTGGATGTAAGCCATTTATCGTGTGTTAATGAACCGATT AATGCGTGTTGATTGTT | SEQ ID NO: 3406 | Homo sapiens cDNA clone IMAGE:5273245. [BC045174] |
| 353 | A_32_P2333 | SUB1 | AGGAGAAAAGGTATTCTTTAAATCAGAACAATGGAGCAGC TGACAGAACAGAATTC | SEQ ID NO: 3407 | Homo sapiens SUB1 homolog (S. cerevisiae) (SUB1), mRNA [NM_006713] |
| 354 | A_32_P4532 | LOC643932 | GATTCCAGACAGCATTGGAAAAAGACATAGAAAAAGGTTGCGAAT CTATGCTCTCCATGAT | SEQ ID NO: 3408 | PREDICTED: Homo sapiens similar to 40S ribosomal protein S3a (V-fos transformation effector protein) (LOC643932), mRNA [XR_017289] |
| 355 | A_32_P49164 | AV714556 | AAATGAGAGTTTGTTATTTGCCAAGAAGAATTGATCATGTTCC TTGCTTCTTTTGCC | SEQ ID NO: 3409 | AV714556 AV714556 DCB Homo sapiens cDNA clone DCBADG06 5', mRNA sequence [AV714556] |
| 356 | A_32_P49392 | A_32_P49392 | AATTGGTGCCAAATCTGAAGAAGATGATGGAAATCATGACCAA GAGGTGCAGACAAATG | SEQ ID NO: 3410 | |
| 357 | A_32_P58074 | RPS3A | GTTGGTTTTACTAAAAAGGGCAAAAATACAGATACGGAAGACCTC TTATGCTCAGGAGCAA | SEQ ID NO: 3411 | Homo sapiens ribosomal protein S3A (RPS3A), mRNA [NM_001006] |
| 358 | A_32_P66934 | BX641014 | AATGGCAGTTGCCAGCATTCTCGTAAAAATGCCAGTTGTGTCTGAG TTTATTCTTAGAAA | SEQ ID NO: 3412 | Homo sapiens mRNA; cDNA DKFZp686119109 (from clone DKFZp686119109) [BX641014] |
| 359 | A_32_P68586 | ARL1 | TGGGTTACCTGGCTTGAAGAGGCGGAAAATGGCAGATATTCAAA AGTCAGAGAAGCAAAG | SEQ ID NO: 3413 | Homo sapiens ADP-ribosylation factor-like 1 (ARL1), mRNA [NM_001177] |
| 360 | A_32_P7118 | PSMC6 | AGCAGACCTGAGAAATGTTTGTGTGAAGCAGGTATGCTTCGGAA TTCGTGCTGATCATGA | SEQ ID NO: 3414 | Homo sapiens proteasome (prosome, macropain) 26S subunit, ATPase, 6 (PSMC6), mRNA [NM_002806] |
| 361 | A_32_P73222 | AA631847 | TTTCTTTGTTTGGACAATGTCATAAGAACTTAGGTCTTACAGG CACGAACGCCGTCGAAG | SEQ ID NO: 3415 | np61b02.s1 NCI_CGAP_Br2 Homo sapiens cDNA clone IMAGE:1130763 3' similar to TR:G971633 G971633 60S RIBOSOMAL PROTEIN L34 ;, mRNA sequence [AA631847] |
| 362 | A_32_P93782 | RPL26 | AGGTTGTACATGGACACTATAAAGGTCAGGAAAATTGGGAAGTA GTCCAGGTTTACAGGA | SEQ ID NO: 3416 | Homo sapiens ribosomal protein L26 (RPL26), mRNA [NM_000987] |
| 363 | A_32_P9382 | RP11-11C5.2 | AACAAGGAGGAAAATATATTGAGAAGGATGGTGTTTACAGAG GAGTTCTTTAAAGTGT | SEQ ID NO: 3417 | Homo sapiens similar to RIKEN cDNA 2410129H14 (LOC440145), mRNA [NM_001071775] |

DETECTION OF DIGESTIVE ORGAN CANCER, GASTRIC CANCER, COLORECTAL CANCER, PANCREATIC CANCER, AND BILIARY TRACT CANCER BY GENE EXPRESSION PROFILING

CROSS-REFERENCE TO RELATED APPLICATIONS

This application is a divisional of U.S. patent application Ser. No. 13/391,858, filed Feb. 23, 2012, which in turn is a 371 of PCT/JP2010/063122, filed Aug. 3, 2010, which claims the benefit of Japanese Patent Application No. 2009-193702, filed Aug. 24, 2009, the contents of each of which are incorporated herein by reference.

FIELD OF THE INVENTION

The present invention relates to detection and diagnosis of digestive organ cancer, gastric cancer, colorectal cancer, pancreatic cancer, and biliary tract cancer via gene expression analysis using peripheral blood as a material.

BACKGROUND OF THE INVENTION

Digestive organ cancer is the most common form of malignant tumor among the Japanese. According to a survey by the Ministry of Health, Labour and Welfare, 177,000 patients die annually. Early detection and treatment can result in complete healing. The earlier the stage of the lesions, the fewer clinical symptoms are presented. Hence, some digestive organ cancer cases are detected in an advanced state, resulting in a poor prognostic outcome.

Gastric cancer is the most common form of digestive system malignant tumor among the Japanese. According to a survey by the Ministry of Health, Labour and Welfare, 50,000 patients die annually. Also, colorectal cancer is the form of digestive system malignant tumor that ranks $3^{rd}$ highest number in terms of deaths due to site-specific cancer (including both males and females) among the Japanese. According to a survey by the Ministry of Health, Labour and Welfare, 41,000 patients die annually. Both gastric cancer and colorectal cancer can be cured by early detection and treatment. The earlier the stage of the lesions, the fewer clinical symptoms are presented. Hence, some cases are detected in an advanced state, resulting in a poor prognostic outcome. Opportunities for early detection include many incidental detections by endoscopic examination and/or imaging studies upon examination and many detections during investigation of symptoms that are not directly associated with cancer. Currently, no hemodiagnosis marker useful for early detection of digestive organ cancer exists. It is extremely important to establish a system capable of diagnosing the presence of digestive organ cancer at as early a stage as possible.

In particular, pancreatic cancer is a form of digestive system malignant tumor that ranks the $5^{th}$ highest in terms of the number of deaths due to site-specific cancer (including both males and females) among the Japanese. According to a survey by the Ministry of Health, Labour and Welfare, 23,000 patients die annually. Cancer detection is very difficult and early cancer detection is rare. 75% of cases diagnosed with pancreatic cancer are already inoperable cases. Pancreatic cancer is a digestive organ cancer resulting in extremely poor prognosis such that the patients die within 1 to 2 years after detection (According a survey by the Center for Cancer Control and Information Services, National Cancer Center, http, colon, forward slash, forward slash, ganjoho, dot, jp, forward slash, public, forward slash, cancer, forward slash, data, forward slash, pancreas, dot, html). Although an advanced diagnostic technique for pancreatic cancer has long been desired, no useful early diagnosis method has been established.

Furthermore, biliary tract cancer is a form of malignant tumor that ranks $6^{th}$ highest in terms of the number of deaths due to site-specific cancer (including both males and females) among the Japanese. According to a survey by the Ministry of Health, Labour and Welfare, 15,000 patients die annually. In most cases, early detection is difficult because of the lack of subjective symptoms.

Recent development in DNA microarray techniques and human genome sequencing have enabled extensive gene expression analysis of all genes. Accordingly, new types of cancer diagnosis, prognostic prediction, prediction of recurrence rate after treatment, and the like have become possible. The present inventors have analyzed the pathological conditions of various diseases and developed for the purpose of developing a diagnostic tool through application of gene expression analysis such as analysis of gene expression profiles in chronic hepatitis patients (see non-patent documents 1 to 3) and gene expression analysis of liver tissue in diabetes mellitus patients. However, these forms of analysis are problematic in terms of their excessive invasiveness, and hospitalization and tissue (organ tissue such as liver tissue) sampling are required. Thereafter, a method requiring less invasiveness has been reported, wherein a gene group capable of distinguishing type C cirrhosis from type C liver cancer and peripheral blood mononuclear cells are used (see patent document 1 and non-patent document 4). This method is advantageous for patients because blood is used in this method and thus it offers a low degree of invasiveness for patients. However, the method is problematic in that collection of peripheral blood mononuclear cells requires several separation processes, the method is complicated as an actual test method, and the method requires much time for the test results to be obtained.

PRIOR ART DOCUMENTS

Patent Document

Patent document 1 JP Patent Publication (Kokai) No. 2008-126 A

Non-Patent Documents

Non-patent document 1 MASAO HONDA et al., GASTROENTEROLOGY 2001; 120:955-966

Non-patent document 2 MASAO HONDA et al., Am J Gastroenterol 2005; 100: 2019-2030

Non-patent document 3 YUKIHIRO SHIROTA et al., HEPATOLOGY Vol. 33, No. 4, 2001, 832-840

Non-patent document 4 YOSHIO SAKAI et al., Cancer Research; 68 (24) 2008. 10267-10279

SUMMARY OF THE INVENTION

Problem to be Solved by the Invention

An object of the present invention is to provide:

a method for detecting digestive organ cancer, gastric cancer, colorectal cancer, pancreatic cancer, and biliary tract cancer by analyzing genes with expression levels that vary in association with digestive organ cancer, gastric cancer, colorectal cancer, pancreatic cancer, and biliary tract cancer, whereby invasiveness to patients is low and genes can be easily extracted from patients; and an in vitro diagnostic.

Means for Solving the Problem

The present inventors have initiated clinical trials to verify if digestive organ cancer, gastric cancer, colorectal cancer, pancreatic cancer, and biliary tract cancer can be diagnosed by gene expression analysis using peripheral blood, and thus found that such diagnosis is possible.

Peripheral blood can be collected in a manner that requires a relatively low degree of invasiveness, and thus its practicality and usefulness in clinical examination are extremely high. Peripheral blood is composed of cell components including, in addition to erythrocytes and blood platelets, leukocytes containing lymphocytes, monocytes, and granulocytes. These cell components are thought to vary their phenotypes and functions depending on lesions in an in vivo environment.

The present inventors have conducted gene expression analysis of peripheral blood from 24 digestive organ cancer patients and 8 normal healthy subjects. Specifically, they have found that digestive organ cancer cases can be distinguished from normal healthy subjects by clustering analysis conducted using data from analysis with about 23,000 probes on DNA microarrays. Through comparison of the gene expression of a group of digestive organ cancer cases with that of a group of normal healthy subjects, 868 probes corresponding to genes with expression levels that differ significantly between the groups were found. With the use of the probe set, hierarchical clustering was performed for the above digestive organ cancer case group and the above normal healthy subject group, so that 2 clusters were formed. Thus the present inventors have found that the digestive organ cancer cases can be distinguished from the normal healthy subjects. Also, a prediction model was applied to 40 cancer cases and 13 normal healthy subject cases (differing from the cancer cases and the normal healthy subjects used for extraction of 868 probes), so that cancer cases and normal healthy subjects were determined. As a result, 39 out of 40 previously diagnosed cancer cases were determined to be actually cancer cases, and the probability that such cases had been properly diagnosed was 97.5%. Moreover, 9 out of 13 previously diagnosed normal healthy subject cases were determined to be normal healthy subject cases, and the probability that such cases had been properly diagnosed was 69.2%. The percentage of cases correctly determined was 90.6% (48/53).

Furthermore, the present inventors have conducted gene expression analysis of peripheral blood from 39 digestive organ cancer patients and peripheral blood from 15 normal healthy subjects. Specifically, they have found that digestive organ cancer cases can be distinguished from normal healthy subjects by clustering analysis conducted using data from analysis with about 23,000 probes on DNA microarrays. Through comparison of the gene expression of a group of digestive organ cancer cases with that of a group of normal healthy subjects, 25 probes corresponding to genes with expression levels that differ significantly between the groups were found. With the use of the probe set, hierarchical clustering was performed for the above digestive organ cancer case group and the above normal healthy subject group, so that 2 clusters were formed. Thus the present inventors have found that the digestive organ cancer cases can be distinguished from the normal healthy subjects.

As a result of the use of the above probes, the percentage of cases correctly determined was 92.3%.

Also, the present inventors have conducted gene expression analysis of peripheral blood from 8 gastric cancer patients and 8 normal healthy subjects. Specifically, they have found that gastric cancer cases can be distinguished from normal healthy subjects by clustering analysis conducted using data from analysis with about 22,000 probes on DNA microarrays. Through comparison of the gene expression of a group of gastric cancer cases with that of a group of normal healthy subjects, 713 probes corresponding to genes with expression levels that differ significantly between the groups were found. With the use of the probe set, hierarchical clustering was performed for the above gastric cancer case group and the above normal healthy subject group, so that 2 clusters were formed. Thus the present inventors have found that the gastric cancer cases can be distinguished from the normal healthy subjects. Also, a prediction model was applied to 10 cancer cases and 13 normal healthy subject cases (differing from the cancer cases and the normal healthy subjects used for extraction of 713 probes), so that cancer cases and normal healthy subjects were determined. As a result, 7 out of 10 previously diagnosed cancer cases were determined to be actually cancer cases, and the probability that such cases had been properly diagnosed was 70%. Moreover, 13 out of 13 previously diagnosed normal healthy subject cases were determined to be normal healthy subject cases, and the probability that such cases had been properly diagnosed was 100%. The percentage of cases correctly determined was 87.0% (20/23).

The present inventors have conducted gene expression analysis of peripheral blood from 8 colorectal cancer patients and 8 normal healthy subjects. Specifically, they have found that colorectal cancer cases can be distinguished from normal healthy subjects by clustering analysis conducted using data from analysis with about 22,000 probes on DNA microarrays. Through comparison of the gene expression of a group of colorectal cancer cases with that of a group of normal healthy subjects, 771 probes corresponding to genes with expression levels that differ significantly between the groups were found. With the use of the probe set, hierarchical clustering was performed for the above colorectal cancer case group and the above normal healthy subject group, so that 2 clusters were formed. Thus, colorectal cancer cases were distinguished from the normal healthy subjects. Also, a prediction model was applied to 10 cancer cases and 13 normal healthy subject cases (differing from the cancer cases and the normal healthy subjects used for extraction of 771 probes), so that cancer cases and normal healthy subjects are determined. As a result, 9 out of 10 previously diagnosed cancer cases were determined to be actually cancer cases, and the probability that such cases had been properly diagnosed was 90%. Moreover, 13 out of 13 previously diagnosed normal healthy subject cases were determined to be normal healthy subject cases, and the probability that such cases had been properly diagnosed was 100%. The percentage of cases correctly determined was 95.7% (22/23).

The present inventors have conducted gene expression analysis of peripheral blood from 8 pancreatic cancer patients and 8 normal healthy subjects. Specifically, they have found that pancreatic cancer cases can be distinguished from normal healthy subjects by clustering analysis conducted using data from analysis with about 22,000 probes on DNA microarrays. Through comparison of the gene expression of a group of pancreatic cancer cases with that of a group of normal healthy subjects, 677 probes corresponding to genes with expression levels that differ significantly between the groups were found. With the use of the probe set, hierarchical clustering was performed for the above pancreatic cancer case group and the above normal healthy subject group, so that 2 clusters were formed. Thus the present inventors have found that pancreatic cancer cases can be distinguished from the normal healthy subjects. Also, a prediction model was applied to 20 cancer cases and 13 normal healthy subject cases (differing from the cancer cases and the normal healthy subjects used for extraction of 677 probes), so that cancer cases and normal healthy subjects were determined. As a result, 15 out of 20 previously diagnosed cancer cases were determined to be actually cancer cases, and the probability that such cases had been properly diagnosed was 75%. Moreover, 13 out of 13 previously diagnosed normal healthy subject cases were determined to be normal healthy subject cases, and the probability that such cases had been properly diagnosed was 100%. The percentage of cases correctly determined was 84.8% (28/33).

The present inventors have conducted gene expression analysis of peripheral blood from 8 biliary tract cancer patients and 8 normal healthy subjects. Specifically, they have found that biliary tract cancer cases can be distinguished from normal healthy subjects by clustering analysis conducted (to form 3 clusters) using data from analysis with about 22,000 probes on DNA microarrays. Through comparison of the gene expression of a group of biliary tract cancer cases with that of a group of normal healthy subjects, 363 probes corresponding to genes with expression levels that differ significantly between the groups were found. With the use of the probe set, hierarchical clustering was performed for the above biliary tract cancer case group and the above normal healthy subject group, so that 2 clusters were formed. Thus the present inventors have found that the biliary tract cancer cases can be distinguished from the normal healthy subjects. Also, a prediction model was applied to 8 cancer cases and 13 normal healthy subject cases (differing from the cancer cases and the normal healthy subjects used for extraction of 363 probes), so that cancer cases and normal healthy subjects were determined. As a result, 8 out of 8 previously diagnosed cancer cases were determined to be actually cancer cases, and the probability that such cases had been properly diagnosed was 100%. Moreover, 13 out of 13 previously diagnosed normal healthy subject cases were determined to be normal healthy subject cases, and the probability that such cases had been properly diagnosed was 100%. The percentage of cases correctly determined was 100% (21/21).

Based on these results, it was found that examination of changes in expression of the gene set in peripheral blood enables diagnosis of digestive organ cancer, gastric cancer, colorectal cancer, pancreatic cancer, and biliary tract cancer. Thus, the present invention was completed. The method of the present invention enables preparation of a new practical diagnostic kit for diagnosis of digestive organ cancer by applying a DNA microarray developmental technique, a real-time PCR method, and an ELISA method.

Currently, general tumor markers covered by health insurance are not always useful for all digestive organ cancer patients. However, the detection sensitivity of the gene expression analysis of the present invention is 90.6%, allowing digestive organ cancer to be specified with very high detection sensitivity through convenient blood collection.

Specifically, the present invention is as follows.

[1] A reagent for detecting digestive organ cancer by measuring the expression of genes corresponding to probes consisting of nucleotide sequences shown in SEQ ID NO: 220, 506, 508, 523, 538, 554, 570, 589, 597, 602, 618, 654, 689, 701, 726, 744, 762, 763, 781, 795, and 849 in peripheral blood, wherein the reagent contains all probes consisting of the nucleotide sequences shown in SEQ ID NOs: 220, 506, 508, 523, 538, 554, 570, 589, 597, 602, 618, 654, 689, 701, 726, 744, 762, 763, 781, 795, and 849; or a reagent for detecting digestive organ cancer by measuring the expression of genes corresponding to probes consisting of the nucleotide sequences shown in SEQ ID NOs: 3030 to 3054 in peripheral blood, wherein the reagent contains all probes consisting of the nucleotide sequences shown in SEQ ID NOs: 3030 to 3054.

[2] The reagent for detecting digestive organ cancer according to [1], containing a DNA microarray in which the probes of [1] bind to a substrate.

[3] A method for detecting digestive organ cancer, comprising obtaining the gene expression profiles of all genes corresponding to probes consisting of the nucleotide sequences shown in SEQ ID NOs: 220, 506, 508, 523, 538, 554, 570, 589, 597, 602, 618, 654, 689, 701, 726, 744, 762, 763, 781, 795, and 849 in peripheral blood from a subject, or all genes corresponding to probes consisting of the nucleotide sequences shown in SEQ ID NOs: 3030 to 3054 in peripheral blood from a subject and then detecting digestive organ cancer based on the expression profiles.

[4] A reagent for detecting gastric cancer by measuring the expression of genes corresponding to probes consisting of the nucleotide sequences shown in SEQ ID NOs: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578 in peripheral blood, wherein the reagent contains all probes consisting of the nucleotide sequences shown in SEQ ID NO: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578.

[5] The reagent for detecting gastric cancer according to [4], containing a DNA microarray in which the probes of [4] bind to a substrate.

[6] A method for detecting gastric cancer, comprising obtaining the gene expression profiles of all genes corresponding to probes consisting of the nucleotide sequences shown in SEQ ID NOs: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578 in peripheral blood from a subject and then detecting gastric cancer based on the expression profiles.

[7] A reagent for detecting colorectal cancer by measuring the expression of genes corresponding to probes consisting of the nucleotide sequences shown in SEQ ID NOs: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340, wherein the reagent contains all probes consisting of the nucleotide sequences shown in SEQ ID NOs: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340.

[8] The reagent for detecting colorectal cancer according to [7], containing a DNA microarray in which the probes of [7] bind to a substrate.

[9] A method for detecting colorectal cancer, comprising obtaining the gene expression profiles of all genes corresponding to probes consisting of the nucleotide sequences shown in SEQ ID NOs: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340 in peripheral blood from a subject and then detecting colorectal cancer based on the gene expression profiles.

[10] A reagent for detecting pancreatic cancer by measuring the expression of genes corresponding to probes consisting of the nucleotide sequences shown in SEQ ID NOs: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003, wherein the reagent contains all probes consisting of the nucleotide sequences shown in SEQ ID NO: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003.

[11] The reagent for detecting pancreatic cancer according to [10], containing a DNA microarray in which the probes of [10] bind to a substrate.

[12] A method for detecting pancreatic cancer, comprising obtaining the gene expression profiles of all genes corresponding to probes consisting of the nucleotide sequences shown in SEQ ID NOs: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003 in peripheral blood from a subject and detecting pancreatic cancer based on the expression profiles.

[13] A reagent for detecting biliary tract cancer by measuring the expression of genes corresponding to probes consisting of the nucleotide sequences shown in SEQ ID NOs: 3055 to 3417, which contains all probes consisting of the nucleotide sequences shown in SEQ ID NOs: 3055 to 3417.

[14] The reagent for detecting biliary tract cancer according to [13], containing a DNA microarray in which the probes of [13] bind to a substrate.

[15] A method for detecting biliary tract cancer, comprising obtaining the gene expression profiles of all genes corresponding to probes consisting of the nucleotide sequences shown in SEQ ID NOs: 3055 to 3417 in peripheral blood from a subject, and then detecting biliary tract cancer based on the expression profiles.

This description includes the disclosure of the description and drawings of Japanese Patent Application No. 2009-193702, from which the present application claims priority.

Effects of the Invention

The expression levels of the genes corresponding to the probes of the present invention vary among digestive organ cancer, gastric cancer, colorectal cancer, pancreatic cancer, and biliary tract cancer. Through analysis of the expression profiles of these genes, digestive organ cancer, gastric cancer, colorectal cancer, pancreatic cancer, or biliary tract cancer can be detected. Furthermore, a risk of developing digestive organ cancer, gastric cancer, colorectal cancer, pancreatic cancer, or biliary tract cancer can be predicted, for example.

BRIEF DESCRIPTION OF THE DRAWINGS

FIG. 1-1 shows 868 probes of a 1$^{st}$ probe group that can be used for detection of digestive organ cancer.

FIG. 1-2 shows 868 probes that can be used for detection of digestive organ cancer (continuation).

FIG. 1-3 shows 868 probes that can be used for detection of digestive organ cancer (continuation).

FIG. 1-4 shows 868 probes that can be used for detection of digestive organ cancer (continuation).

FIG. 1-5 shows 868 probes that can be used for detection of digestive organ cancer (continuation).

FIG. 1-6 shows 868 probes that can be used for detection of digestive organ cancer (continuation).

FIG. 1-7 shows 868 probes that can be used for detection of digestive organ cancer (continuation).

FIG. 1-8 shows 868 probes that can be used for detection of digestive organ cancer (continuation).

FIG. 1-9 shows 868 probes that can be used for detection of digestive organ cancer (continuation).

FIG. 1-10 shows 868 probes that can be used for detection of digestive organ cancer (continuation).

FIG. 1-11 shows 868 probes that can be used for detection of digestive organ cancer (continuation).

FIG. 1-12 shows 868 probes that can be used for detection of digestive organ cancer (continuation).

FIG. 1-13 shows 868 probes that can be used for detection of digestive organ cancer (continuation).

FIG. 1-14 shows 868 probes that can be used for detection of digestive organ cancer (continuation).

FIG. 1-15 shows 868 probes that can be used for detection of digestive organ cancer (continuation).

FIG. 1-16 shows 868 probes that can be used for detection of digestive organ cancer (continuation).

FIG. 1-17 shows 868 probes that can be used for detection of digestive organ cancer (continuation).

FIG. 1-18 shows 868 probes that can be used for detection of digestive organ cancer (continuation).

FIG. 1-19 shows 868 probes that can be used for detection of digestive organ cancer (continuation).

FIG. 1-20 shows 868 probes that can be used for detection of digestive organ cancer (continuation).

FIG. 1-21 shows 868 probes that can be used for detection of digestive organ cancer (continuation).

FIG. 1-22 shows 868 probes that can be used for detection of digestive organ cancer (continuation).

FIG. 1-23 shows 868 probes that can be used for detection of digestive organ cancer (continuation).

FIG. 1-24 shows 868 probes that can be used for detection of digestive organ cancer (continuation).

FIG. 1-25 shows 868 probes that can be used for detection of digestive organ cancer (continuation).

FIG. 1-26 shows 868 probes that can be used for detection of digestive organ cancer (continuation).

FIG. 1-27 shows 868 probes that can be used for detection of digestive organ cancer (continuation).

FIG. 1-28 shows 868 probes that can be used for detection of digestive organ cancer (continuation).

FIG. 1-29 shows 868 probes that can be used for detection of digestive organ cancer (continuation).

FIG. 1-30 shows 868 probes that can be used for detection of digestive organ cancer (continuation).

FIG. 1-31 shows 868 probes that can be used for detection of digestive organ cancer (continuation).

FIG. 1-32 shows 868 probes that can be used for detection of digestive organ cancer (continuation).

FIG. 1-33 shows 868 probes that can be used for detection of digestive organ cancer (continuation).

FIG. 1-34 shows 868 probes that can be used for detection of digestive organ cancer (continuation).

FIG. 1-35 shows 868 probes that can be used for detection of digestive organ cancer (continuation).

FIG. 1-36 shows 868 probes that can be used for detection of digestive organ cancer (continuation).

FIG. 1-37 shows 868 probes that can be used for detection of digestive organ cancer (continuation).

FIG. 1-38 shows 868 probes that can be used for detection of digestive organ cancer (continuation).

FIG. 1-39 shows 868 probes that can be used for detection of digestive organ cancer (continuation).

FIG. 1-40 shows 868 probes that can be used for detection of digestive organ cancer (continuation).

FIG. 1-41 shows 868 probes that can be used for detection of digestive organ cancer (continuation).

FIG. 1-42 shows 868 probes that can be used for detection of digestive organ cancer (continuation).

FIG. 1-43 shows 868 probes that can be used for detection of digestive organ cancer (continuation).

FIG. 1-44 shows 868 probes that can be used for detection of digestive organ cancer (continuation).

FIG. 1-45 shows 868 probes that can be used for detection of digestive organ cancer (continuation).

FIG. 1-46 shows 868 probes that can be used for detection of digestive organ cancer (continuation).

FIG. 1-47 shows 868 probes that can be used for detection of digestive organ cancer (continuation).

FIG. 1-48 shows 868 probes that can be used for detection of digestive organ cancer (continuation).

FIG. 2 shows 21 probes with expression levels that differed significantly particularly between digestive organ cancer patients and normal healthy subjects, from among the 868 probes shown in FIG. 1.

FIG. 3-1 shows 713 probes that can be used for detection of gastric cancer.

FIG. 3-2 shows 713 probes that can be used for detection of gastric cancer (continuation).

FIG. 3-3 shows 713 probes that can be used for detection of gastric cancer (continuation).

FIG. 3-4 shows 713 probes that can be used for detection of gastric cancer (continuation).

FIG. 3-5 shows 713 probes that can be used for detection of gastric cancer (continuation).

FIG. 3-6 shows 713 probes that can be used for detection of gastric cancer (continuation).

FIG. 3-7 shows 713 probes that can be used for detection of gastric cancer (continuation).

FIG. 3-8 shows 713 probes that can be used for detection of gastric cancer (continuation).

FIG. 3-9 shows 713 probes that can be used for detection of gastric cancer (continuation).

FIG. 3-10 shows 713 probes that can be used for detection of gastric cancer (continuation).

FIG. 3-11 shows 713 probes that can be used for detection of gastric cancer (continuation).

FIG. 3-12 shows 713 probes that can be used for detection of gastric cancer (continuation).

FIG. 3-13 shows 713 probes that can be used for detection of gastric cancer (continuation).

FIG. 3-14 shows 713 probes that can be used for detection of gastric cancer (continuation).

FIG. 3-15 shows 713 probes that can be used for detection of gastric cancer (continuation).

FIG. 3-16 shows 713 probes that can be used for detection of gastric cancer (continuation).

FIG. 3-17 shows 713 probes that can be used for detection of gastric cancer (continuation).

FIG. 3-18 shows 713 probes that can be used for detection of gastric cancer (continuation).
FIG. 3-19 shows 713 probes that can be used for detection of gastric cancer (continuation).
FIG. 3-20 shows 713 probes that can be used for detection of gastric cancer (continuation).
FIG. 3-21 shows 713 probes that can be used for detection of gastric cancer (continuation).
FIG. 3-22 shows 713 probes that can be used for detection of gastric cancer (continuation).
FIG. 3-23 shows 713 probes that can be used for detection of gastric cancer (continuation).
FIG. 3-24 shows 713 probes that can be used for detection of gastric cancer (continuation).
FIG. 3-25 shows 713 probes that can be used for detection of gastric cancer (continuation).
FIG. 3-26 shows 713 probes that can be used for detection of gastric cancer (continuation).
FIG. 3-27 shows 713 probes that can be used for detection of gastric cancer (continuation).
FIG. 3-28 shows 713 probes that can be used for detection of gastric cancer (continuation).
FIG. 3-29 shows 713 probes that can be used for detection of gastric cancer (continuation).
FIG. 3-30 shows 713 probes that can be used for detection of gastric cancer (continuation).
FIG. 3-31 shows 713 probes that can be used for detection of gastric cancer (continuation).
FIG. 3-32 shows 713 probes that can be used for detection of gastric cancer (continuation).
FIG. 3-33 shows 713 probes that can be used for detection of gastric cancer (continuation).
FIG. 3-34 shows 713 probes that can be used for detection of gastric cancer (continuation).
FIG. 3-35 shows 713 probes that can be used for detection of gastric cancer (continuation).
FIG. 3-36 shows 713 probes that can be used for detection of gastric cancer (continuation).
FIG. 3-37 shows 713 probes that can be used for detection of gastric cancer (continuation).
FIG. 3-38 shows 713 probes that can be used for detection of gastric cancer (continuation).
FIG. 3-39 shows 713 probes that can be used for detection of gastric cancer (continuation).
FIG. 4-1 shows 107 probes with expression levels that differed significantly particularly between gastric cancer patients and normal healthy subjects, from among 713 probes shown in FIG. 3.
FIG. 4-2 shows 107 probes with expression levels that differed significantly particularly between gastric cancer patients and normal healthy subjects, from among the 713 probes shown in FIG. 3 (continuation).
FIG. 4-3 shows 107 probes with expression levels that differed significantly particularly between gastric cancer patients and normal healthy subjects, from among the 713 probes shown in FIG. 3 (continuation).
FIG. 4-4 shows 107 probes with expression levels that differed significantly particularly between gastric cancer patients and normal healthy subjects, from among the 713 probes shown in FIG. 3 (continuation).
FIG. 4-5 shows 107 probes with expression levels that differed significantly particularly between gastric cancer patients and normal healthy subjects, from among the 713 probes shown in FIG. 3 (continuation).
FIG. 4-6 shows 107 probes with expression levels that differed significantly particularly between gastric cancer patients and normal healthy subjects, from among the 713 probes shown in FIG. 3 (continuation).
FIG. 5-1 shows 771 probes that can be used for detection of colorectal cancer.
FIG. 5-2 shows 771 probes that can be used for detection of colorectal cancer (continuation).
FIG. 5-3 shows 771 probes that can be used for detection of colorectal cancer (continuation).
FIG. 5-4 shows 771 probes that can be used for detection of colorectal cancer (continuation).
FIG. 5-5 shows 771 probes that can be used for detection of colorectal cancer (continuation).
FIG. 5-6 shows 771 probes that can be used for detection of colorectal cancer (continuation).
FIG. 5-7 shows 771 probes that can be used for detection of colorectal cancer (continuation).
FIG. 5-8 shows 771 probes that can be used for detection of colorectal cancer (continuation).
FIG. 5-9 shows 771 probes that can be used for detection of colorectal cancer (continuation).
FIG. 5-10 shows 771 probes that can be used for detection of colorectal cancer (continuation).
FIG. 5-11 shows 771 probes that can be used for detection of colorectal cancer (continuation).
FIG. 5-12 shows 771 probes that can be used for detection of colorectal cancer (continuation).
FIG. 5-13 shows 771 probes that can be used for detection of colorectal cancer (continuation).
FIG. 5-14 shows 771 probes that can be used for detection of colorectal cancer (continuation).
FIG. 5-15 shows 771 probes that can be used for detection of colorectal cancer (continuation).
FIG. 5-16 shows 771 probes that can be used for detection of colorectal cancer (continuation).
FIG. 5-17 shows 771 probes that can be used for detection of colorectal cancer (continuation).
FIG. 5-18 shows 771 probes that can be used for detection of colorectal cancer (continuation).
FIG. 5-19 shows 771 probes that can be used for detection of colorectal cancer (continuation).
FIG. 5-20 shows 771 probes that can be used for detection of colorectal cancer (continuation).
FIG. 5-21 shows 771 probes that can be used for detection of colorectal cancer (continuation).
FIG. 5-22 shows 771 probes that can be used for detection of colorectal cancer (continuation).
FIG. 5-23 shows 771 probes that can be used for detection of colorectal cancer (continuation).
FIG. 5-24 shows 771 probes that can be used for detection of colorectal cancer (continuation).
FIG. 5-25 shows 771 probes that can be used for detection of colorectal cancer (continuation).
FIG. 5-26 shows 771 probes that can be used for detection of colorectal cancer (continuation).
FIG. 5-27 shows 771 probes that can be used for detection of colorectal cancer (continuation).
FIG. 5-28 shows 771 probes that can be used for detection of colorectal cancer (continuation).
FIG. 5-29 shows 771 probes that can be used for detection of colorectal cancer (continuation).
FIG. 5-30 shows 771 probes that can be used for detection of colorectal cancer (continuation).
FIG. 5-31 shows 771 probes that can be used for detection of colorectal cancer (continuation).
FIG. 5-32 shows 771 probes that can be used for detection of colorectal cancer (continuation).

FIG. 5-33 shows 771 probes that can be used for detection of colorectal cancer (continuation).

FIG. 5-34 shows 771 probes that can be used for detection of colorectal cancer (continuation).

FIG. 5-35 shows 771 probes that can be used for detection of colorectal cancer (continuation).

FIG. 5-36 shows 771 probes that can be used for detection of colorectal cancer (continuation).

FIG. 5-37 shows 771 probes that can be used for detection of colorectal cancer (continuation).

FIG. 5-38 shows 771 probes that can be used for detection of colorectal cancer (continuation).

FIG. 5-39 shows 771 probes that can be used for detection of colorectal cancer (continuation).

FIG. 5-40 shows 771 probes that can be used for detection of colorectal cancer (continuation).

FIG. 5-41 shows 771 probes that can be used for detection of colorectal cancer (continuation).

FIG. 6-1 shows 116 probes with expression levels that differed significantly particularly between colorectal cancer patients and normal healthy subjects, from among the 771 probes shown in FIG. 5.

FIG. 6-2 shows 116 probes with expression levels that differed significantly particularly between colorectal cancer patients and normal healthy subjects, from among the 771 probes shown in FIG. 5 (continuation).

FIG. 6-3 shows 116 probes with expression levels that differed significantly particularly between colorectal cancer patients and normal healthy subjects, from among the 771 probes shown in FIG. 5 (continuation).

FIG. 6-4 shows 116 probes with expression levels differed significantly particularly between colorectal cancer patients and normal healthy subjects, from among the 771 probes shown in FIG. 5 (continuation).

FIG. 6-5 shows 116 probes with expression levels differed significantly particularly between colorectal cancer patients and normal healthy subjects, from among the 771 probes shown in FIG. 5 (continuation).

FIG. 6-6 shows 116 probes with expression levels differed significantly particularly between colorectal cancer patients and normal healthy subjects, from among the 771 probes shown in FIG. 5 (continuation).

FIG. 6-7 shows 116 probes with expression levels differed significantly particularly between colorectal cancer patients and normal healthy subjects, from among the 771 probes shown in FIG. 5 (continuation).

FIG. 7-1 shows 677 probes that can be used for detection of pancreatic cancer.

FIG. 7-2 shows 677 probes that can be used for detection of pancreatic cancer (continuation).

FIG. 7-3 shows 677 probes that can be used for detection of pancreatic cancer (continuation).

FIG. 7-4 shows 677 probes that can be used for detection of pancreatic cancer (continuation).

FIG. 7-5 shows 677 probes that can be used for detection of pancreatic cancer (continuation).

FIG. 7-6 shows 677 probes that can be used for detection of pancreatic cancer (continuation).

FIG. 7-7 shows 677 probes that can be used for detection of pancreatic cancer (continuation).

FIG. 7-8 shows 677 probes that can be used for detection of pancreatic cancer (continuation).

FIG. 7-9 shows 677 probes that can be used for detection of pancreatic cancer (continuation).

FIG. 7-10 shows 677 probes that can be used for detection of pancreatic cancer (continuation).

FIG. 7-11 shows 677 probes that can be used for detection of pancreatic cancer (continuation).

FIG. 7-12 shows 677 probes that can be used for detection of pancreatic cancer (continuation).

FIG. 7-13 shows 677 probes that can be used for detection of pancreatic cancer (continuation).

FIG. 7-14 shows 677 probes that can be used for detection of pancreatic cancer (continuation).

FIG. 7-15 shows 677 probes that can be used for detection of pancreatic cancer (continuation).

FIG. 7-16 shows 677 probes that can be used for detection of pancreatic cancer (continuation).

FIG. 7-17 shows 677 probes that can be used for detection of pancreatic cancer (continuation).

FIG. 7-18 shows 677 probes that can be used for detection of pancreatic cancer (continuation).

FIG. 7-19 shows 677 probes that can be used for detection of pancreatic cancer (continuation).

FIG. 7-20 shows 677 probes that can be used for detection of pancreatic cancer (continuation).

FIG. 7-21 shows 677 probes that can be used for detection of pancreatic cancer (continuation).

FIG. 7-22 shows 677 probes that can be used for detection of pancreatic cancer (continuation).

FIG. 7-23 shows 677 probes that can be used for detection of pancreatic cancer (continuation).

FIG. 7-24 shows 677 probes that can be used for detection of pancreatic cancer (continuation).

FIG. 7-25 shows 677 probes that can be used for detection of pancreatic cancer (continuation).

FIG. 7-26 shows 677 probes that can be used for detection of pancreatic cancer (continuation).

FIG. 7-27 shows 677 probes that can be used for detection of pancreatic cancer (continuation).

FIG. 7-28 shows 677 probes that can be used for detection of pancreatic cancer (continuation).

FIG. 7-29 shows 677 probes that can be used for detection of pancreatic cancer (continuation).

FIG. 7-30 shows 677 probes that can be used for detection of pancreatic cancer (continuation).

FIG. 7-31 shows 677 probes that can be used for detection of pancreatic cancer (continuation).

FIG. 7-32 shows 677 probes that can be used for detection of pancreatic cancer (continuation).

FIG. 7-33 shows 677 probes that can be used for detection of pancreatic cancer (continuation).

FIG. 7-34 shows 677 probes that can be used for detection of pancreatic cancer (continuation).

FIG. 7-35 shows 677 probes that can be used for detection of pancreatic cancer (continuation).

FIG. 7-36 shows 677 probes that can be used for detection of pancreatic cancer (continuation).

FIG. 7-37 shows 677 probes that can be used for detection of pancreatic cancer (continuation).

FIG. 8-1 shows 61 probes with expression levels that differed significantly particularly between pancreatic cancer patients and normal healthy subjects, from among the 677 probes shown in FIG. 7.

FIG. 8-2 shows 61 probes with expression levels that differed significantly particularly between pancreatic cancer patients and normal healthy subjects, from among the 677 probes shown in FIG. 7 (continuation).

FIG. 8-3 shows 61 probes with expression levels that differed significantly particularly between pancreatic cancer patients and normal healthy subjects, from among the 677 probes shown in FIG. 7 (continuation).

FIG. 8-4 shows 61 probes with expression levels that differed significantly particularly between pancreatic cancer patients and normal healthy subjects, from among the 677 probes shown in FIG. 7 (continuation).

FIG. 9 shows the results of hierarchical clustering using 23352 probes for digestive organ cancer cases and normal healthy subjects.

FIG. 10 shows the results of hierarchical clustering using 868 probes corresponding to genes with expression levels that were observed to be attenuated or enhanced in digestive organ cancer cases compared with normal healthy subjects.

Figure 11:
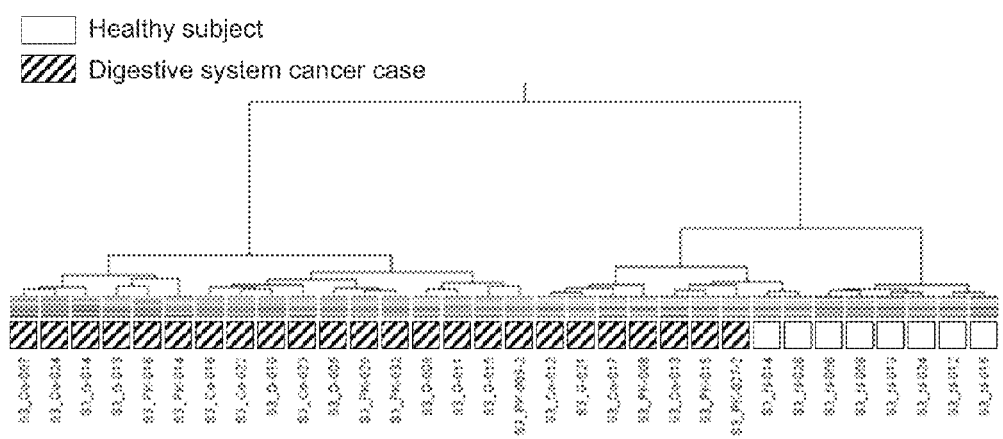

FIG. 11 shows the results of hierarchical clustering using 21 probes corresponding to genes with expression levels that were observed to be attenuated in digestive organ cancer cases at levels 0.4 times or less or enhanced in the same at levels 2.5 times or more than normal healthy subjects.

Figure 12:
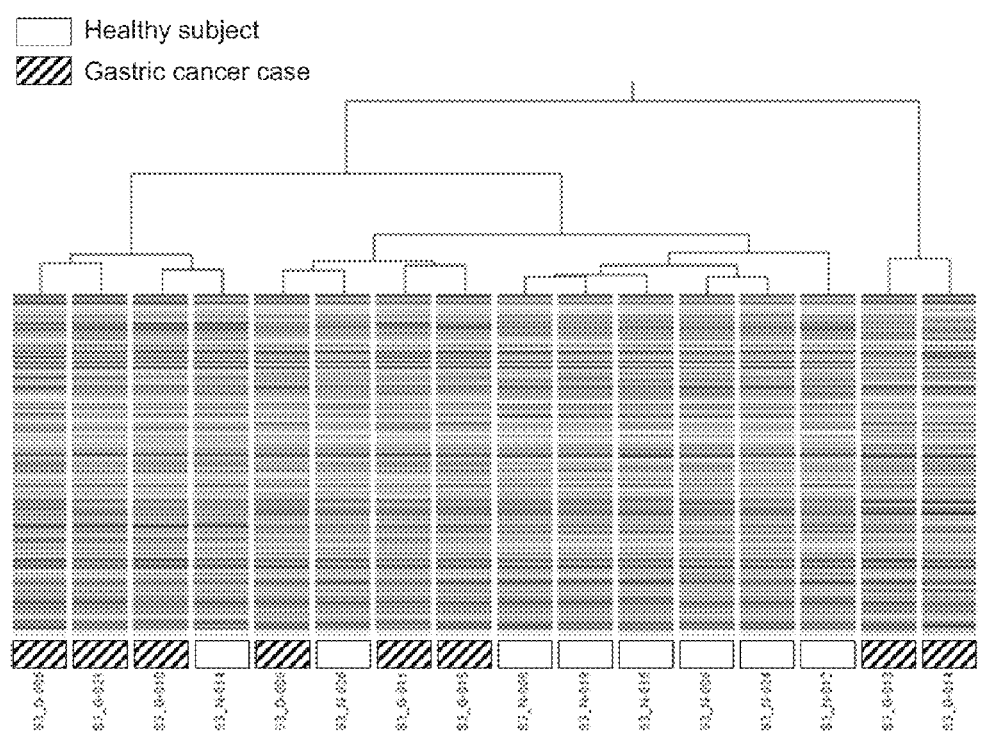

FIG. 12 shows the results of hierarchical clustering using 22155 probes for gastric cancer cases and normal healthy subjects.

Figure 13:
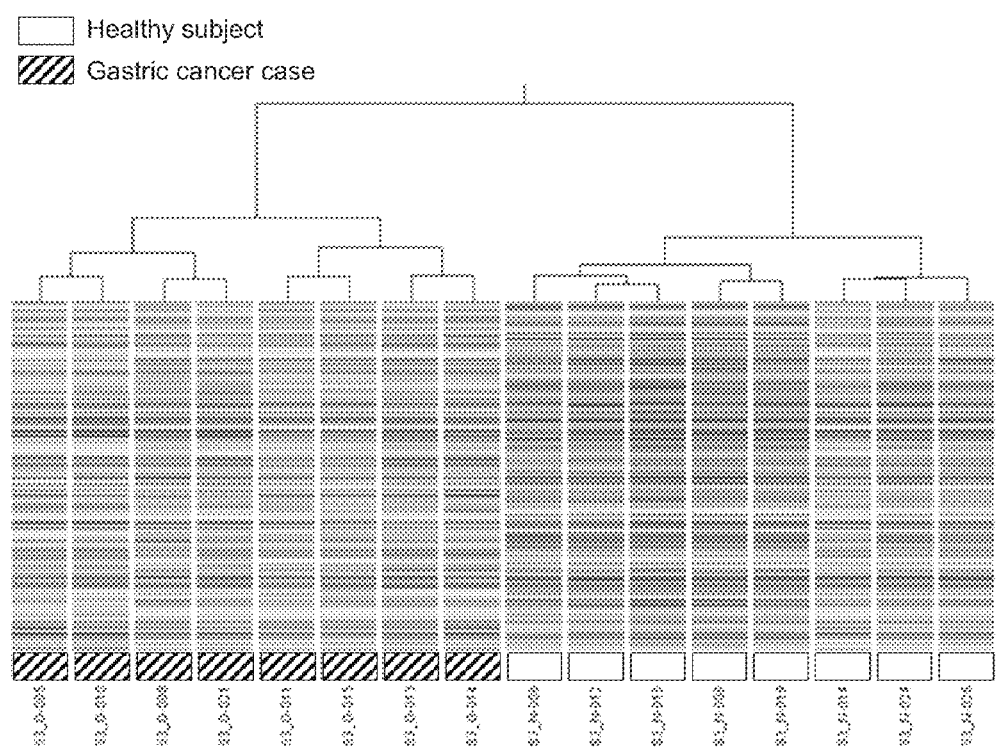

FIG. 13 shows the results of hierarchical clustering using 713 probes corresponding to genes with expression levels that were observed to be attenuated in gastric cancer cases at levels 0.5 times or less or enhanced in the same at levels 2.0 times or more than normal healthy subjects.

Figure 14:
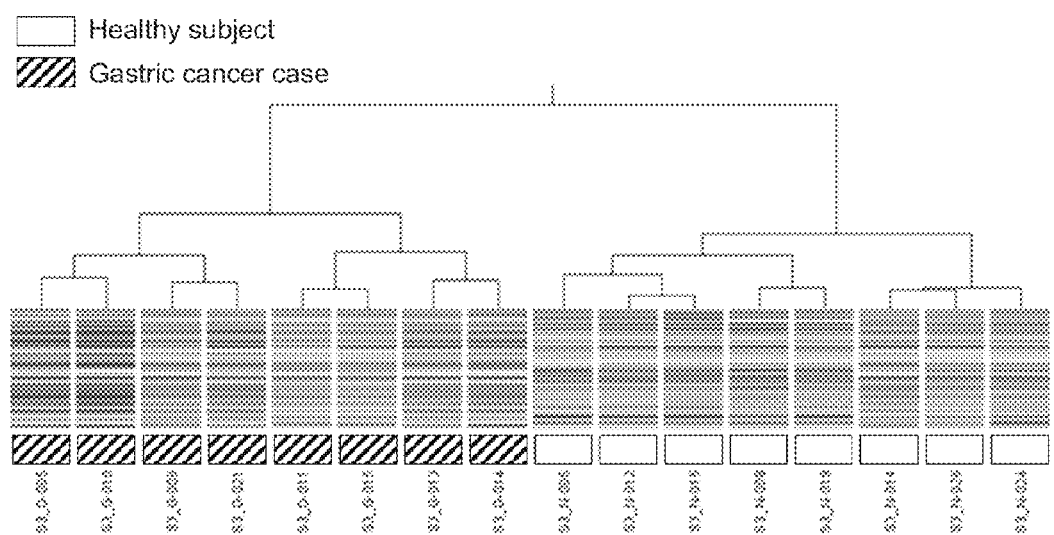

FIG. 14 shows the results of hierarchical clustering using 107 probes corresponding to genes with expression levels that were observed to be attenuated in gastric cancer cases at levels 0.33 times or less or enhanced in the same at levels 3 times or more than normal healthy subjects.

Figure 15:
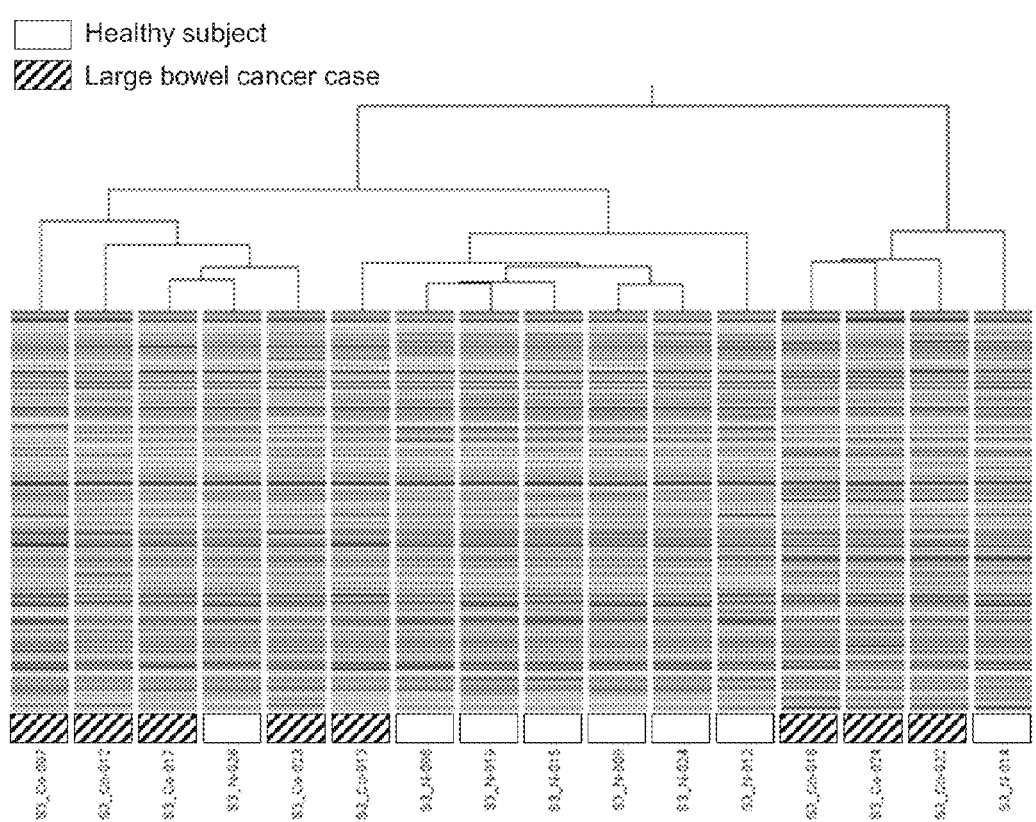

FIG. 15 shows the results of hierarchical clustering using 22181 probes for gastric cancer cases and normal healthy subjects.

Figure 16:
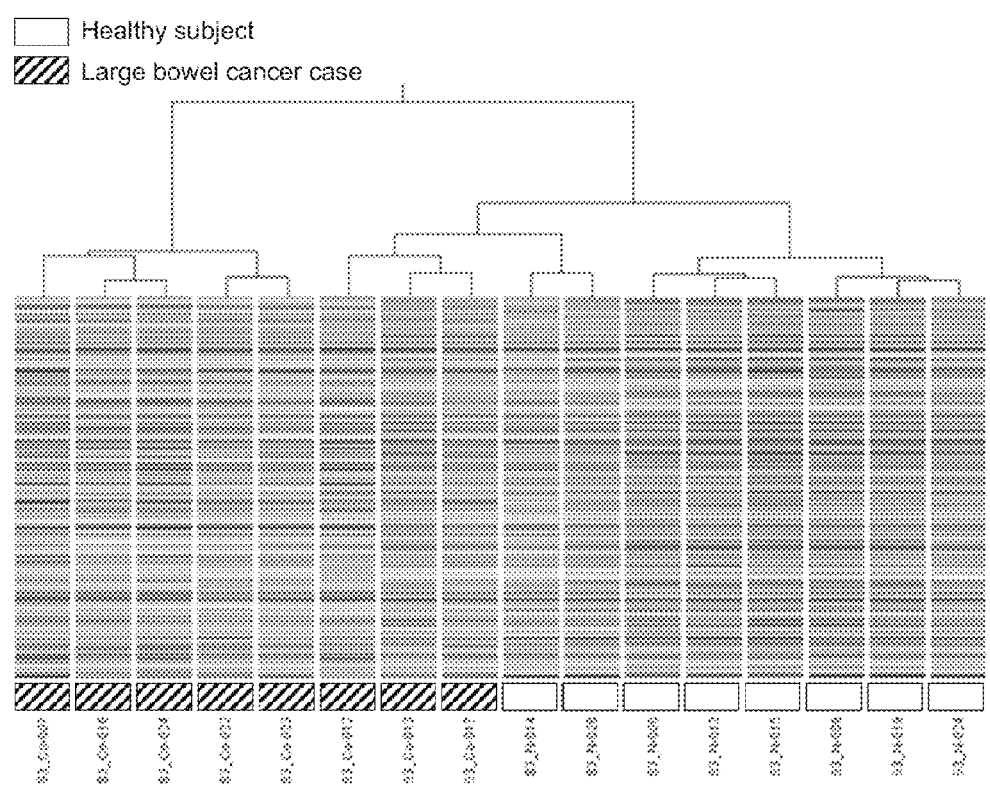

FIG. 16 shows the results of hierarchical clustering using 771 probes corresponding to genes with expression levels that were observed to be attenuated in colorectal cancer cases at levels 0.5 times or less or enhanced in the same at levels 2 times or more than normal healthy subjects.

Figure 17:
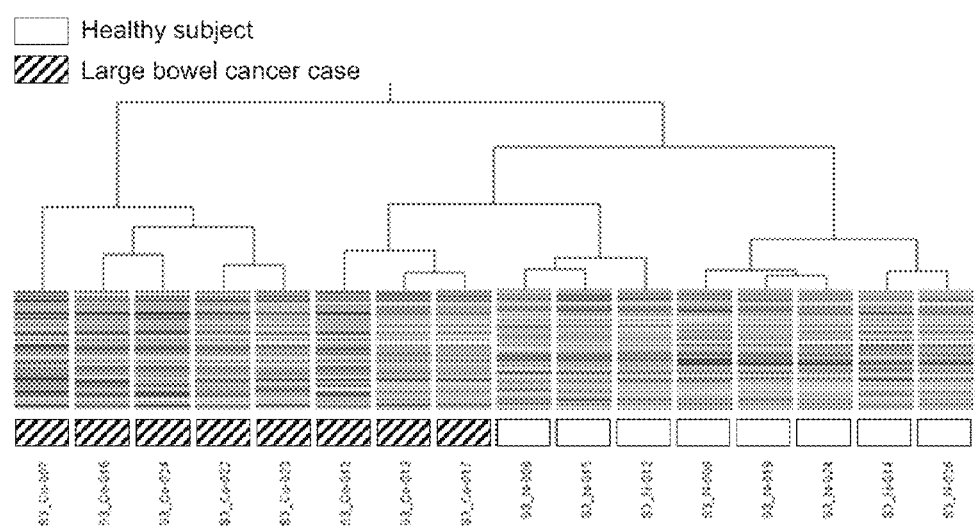

FIG. 17 shows the results of hierarchical clustering using 116 probes corresponding to genes with expression levels that were observed to be attenuated in colorectal cancer cases at levels 0.33 times or less or enhanced in the same at levels 3 times or more than normal healthy subjects.

Figure 18:
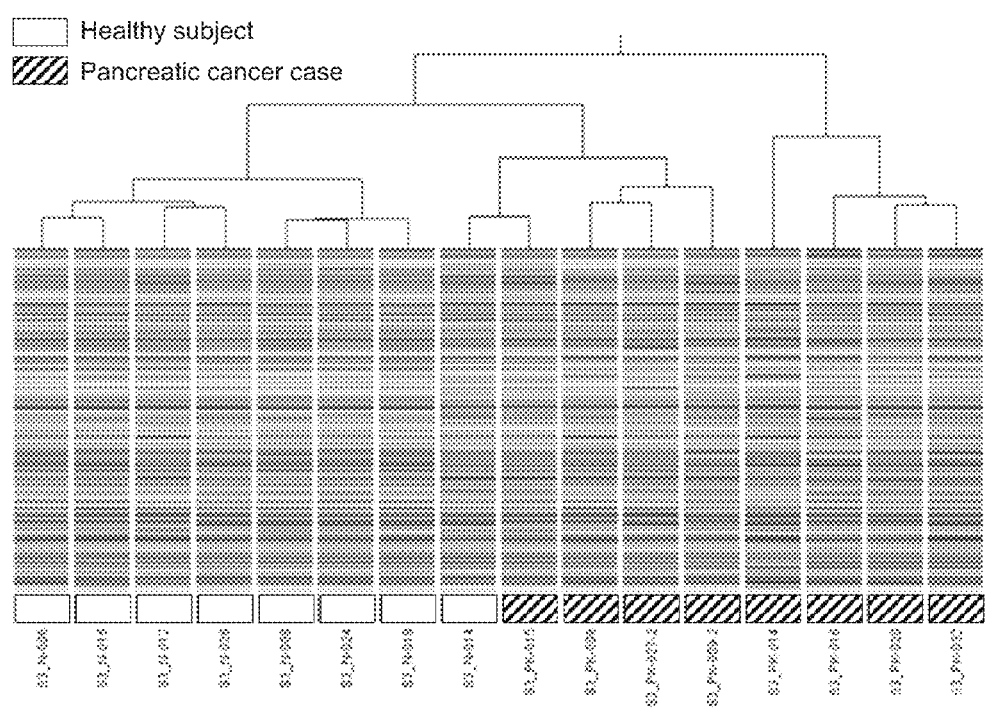

FIG. 18 shows the results of hierarchical clustering using 22149 probes for pancreatic cancer cases and normal healthy subjects.

Figure 19:
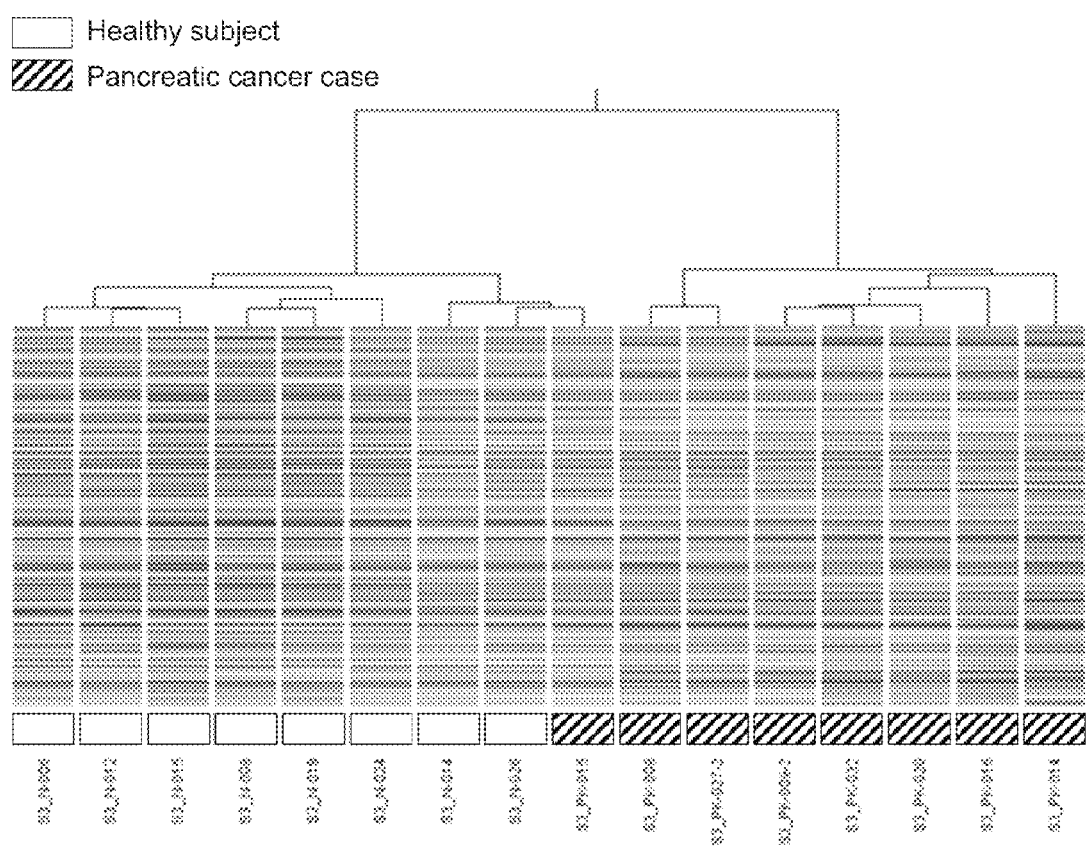

FIG. 19 shows the results of hierarchical clustering using 677 probes corresponding to genes with expression levels that were observed to be attenuated in pancreatic cancer cases at levels 0.5 times or less or enhanced in the same at levels 2 times or more than normal healthy subjects.

Figure 20:
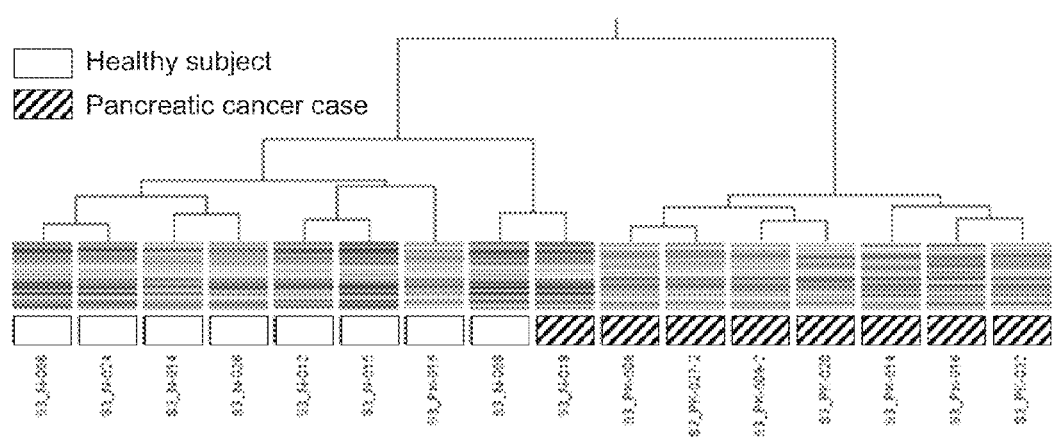

FIG. 20 shows the results of hierarchical clustering using 61 probes corresponding to genes with expression levels that were observed to be attenuated in pancreatic cancer cases at levels 0.33 times or less or enhanced in the same at levels 3 times or more than normal healthy subjects.

FIG. 21-1 shows 25 probes of a $2^{nd}$ probe group that can be used for detection of digestive organ cancer.

FIG. 21-2 shows 25 probes of a $2^{nd}$ probe group that can be used for detection of digestive organ cancer (continuation).

FIG. 22 shows the results of hierarchical clustering using 23278 probes for digestive organ cancer cases and normal healthy subjects.

Figure 23:
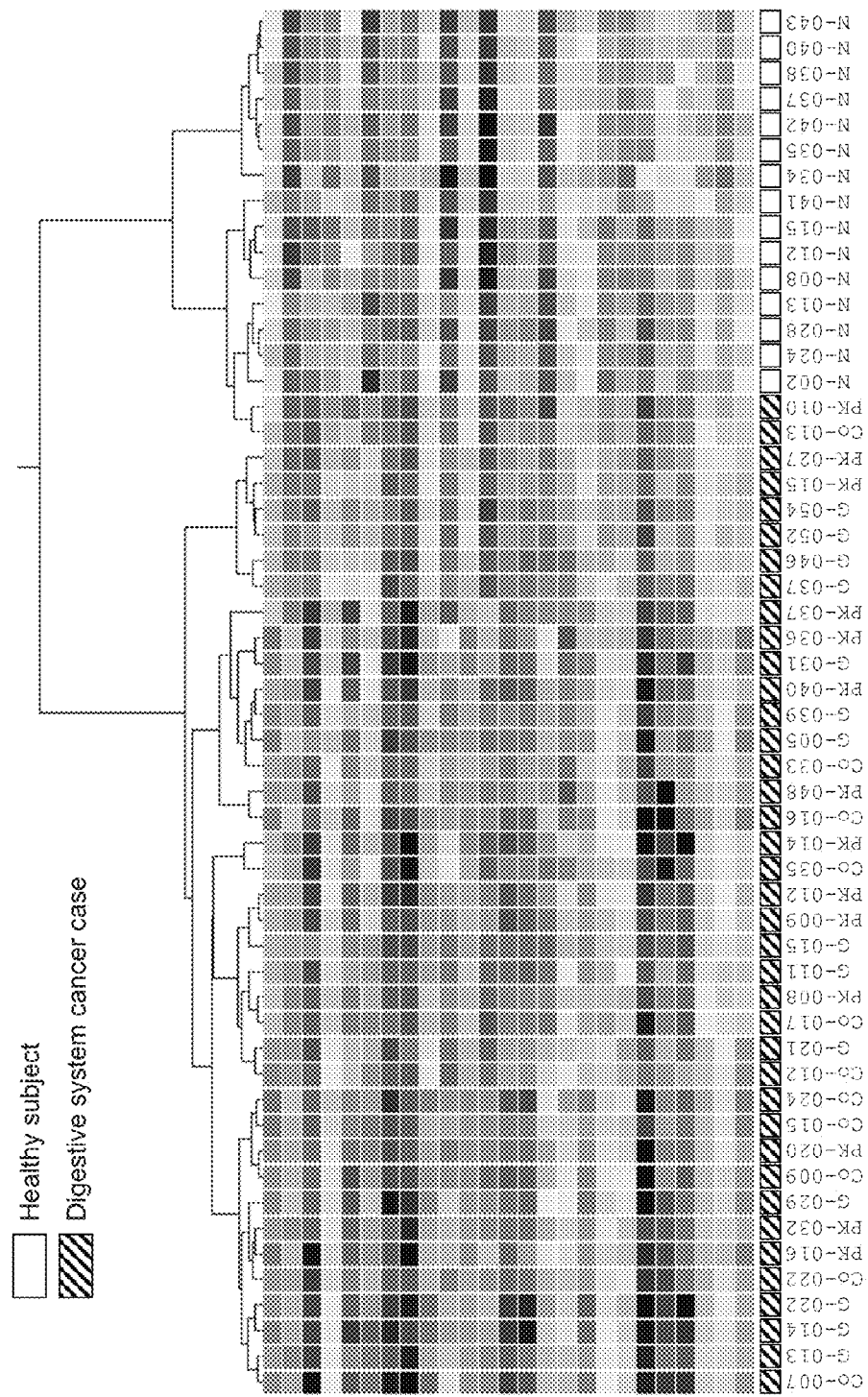

FIG. 23 shows the results of hierarchical clustering using 25 probes corresponding to genes with expression levels that were observed to be attenuated or enhanced in digestive organ cancer cases compared with normal healthy subjects.

FIG. 24-1 shows 363 probes that can be used for detection of biliary tract cancer.

FIG. 24-2 shows 363 probes that can be used for detection of biliary tract cancer (continuation).

FIG. 24-3 shows 363 probes that can be used for detection of biliary tract cancer (continuation).

FIG. 24-4 shows 363 probes that can be used for detection of biliary tract cancer (continuation).

FIG. 24-5 shows 363 probes that can be used for detection of biliary tract cancer (continuation).

FIG. 24-6 shows 363 probes that can be used for detection of biliary tract cancer (continuation).

FIG. 24-7 shows 363 probes that can be used for detection of biliary tract cancer (continuation).

FIG. 24-8 shows 363 probes that can be used for detection of biliary tract cancer (continuation).

Figure 9:
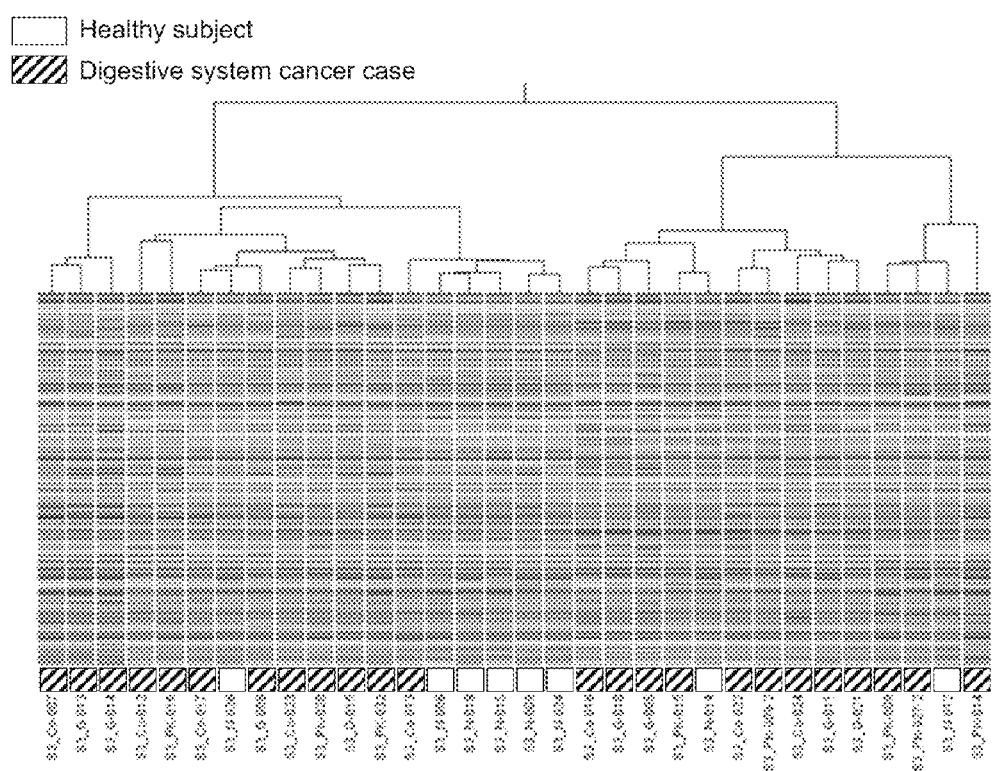

FIG. 24-9 shows 363 probes that can be used for detection of biliary tract cancer (continuation).

Figure 10:
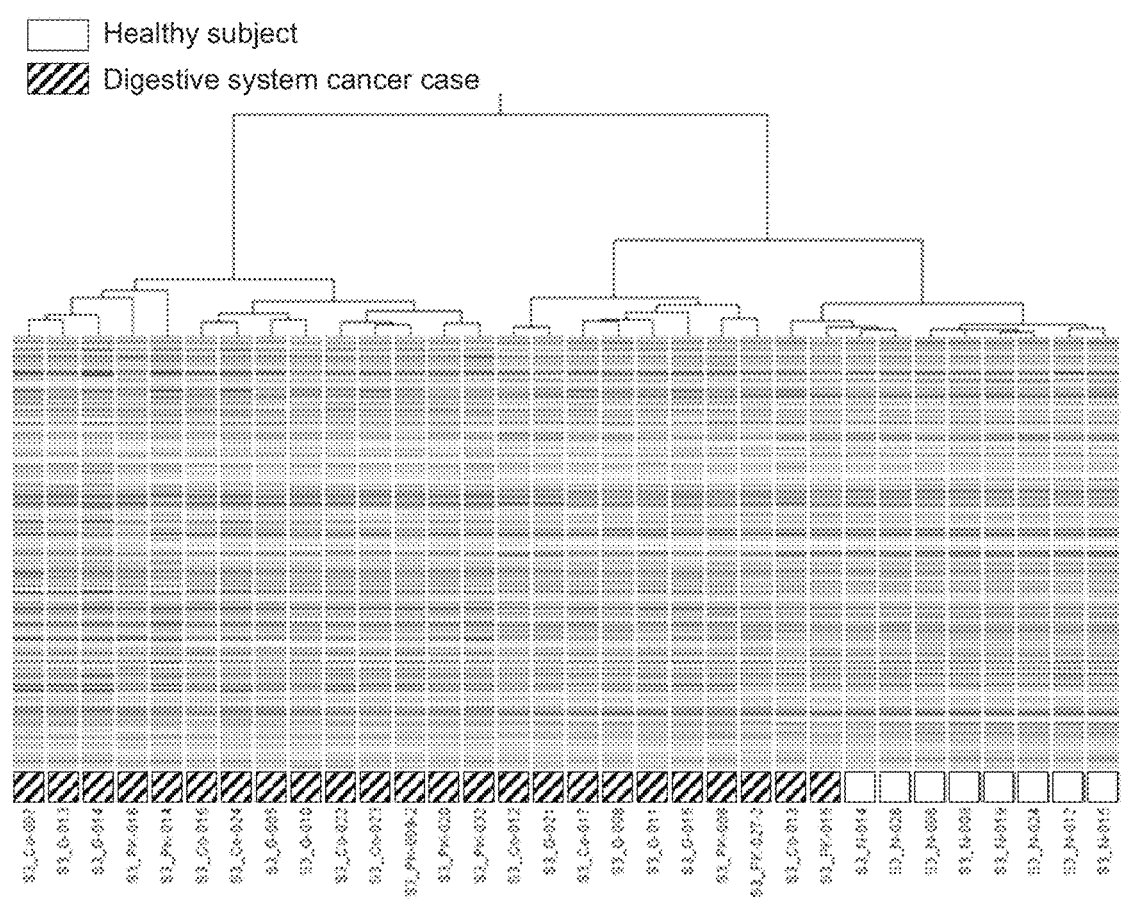

FIG. 24-10 shows 363 probes that can be used for detection of biliary tract cancer (continuation).

FIG. 24-11 shows 363 probes that can be used for detection of biliary tract cancer (continuation).

FIG. 24-12 shows 363 probes that can be used for detection of biliary tract cancer (continuation).

FIG. 24-13 shows 363 probes that can be used for detection of biliary tract cancer (continuation).

FIG. 24-14 shows 363 probes that can be used for detection of biliary tract cancer (continuation).

FIG. 24-15 shows 363 probes that can be used for detection of biliary tract cancer (continuation).

FIG. 24-16 shows 363 probes that can be used for detection of biliary tract cancer (continuation).

FIG. 24-17 shows 363 probes that can be used for detection of biliary tract cancer (continuation).

FIG. 24-18 shows 363 probes that can be used for detection of biliary tract cancer (continuation).

FIG. 24-19 shows 363 probes that can be used for detection of biliary tract cancer (continuation).

Figure 25:
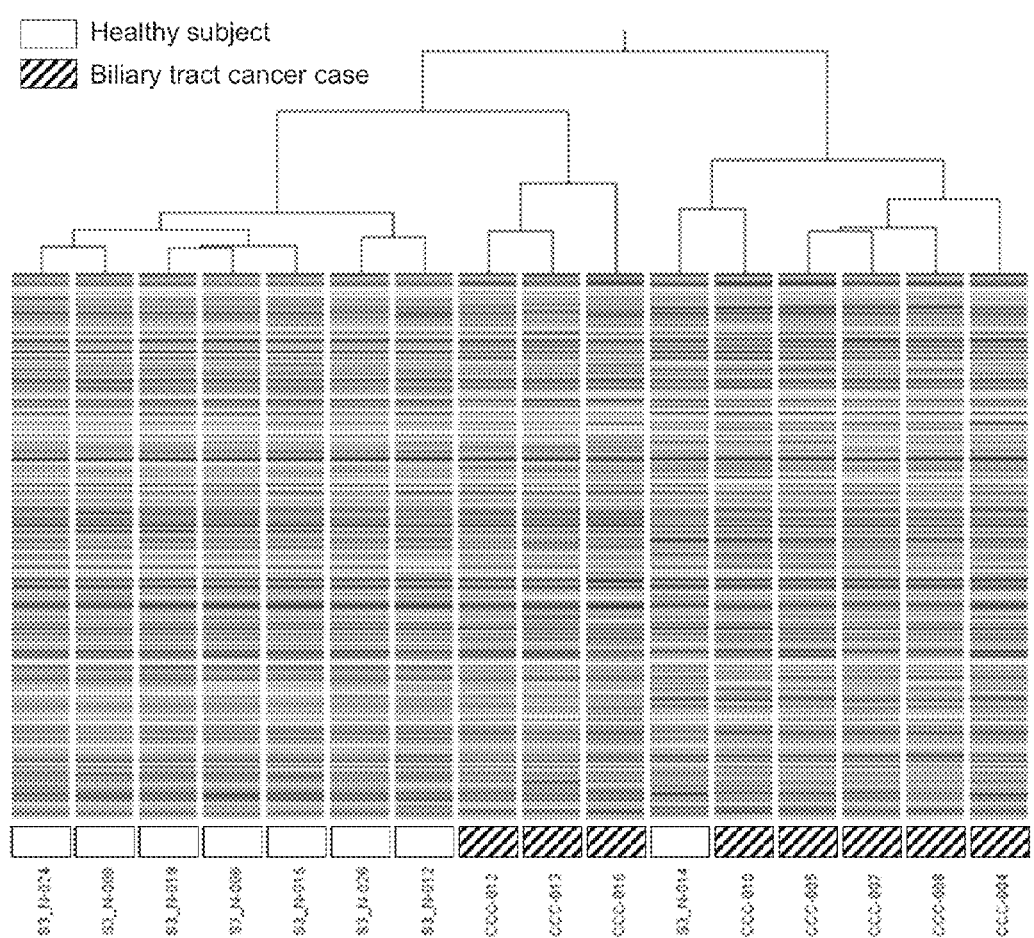

FIG. 25 shows the results of hierarchical clustering using 22066 probes for biliary tract cancer cases and normal healthy subjects.

Figure 26:
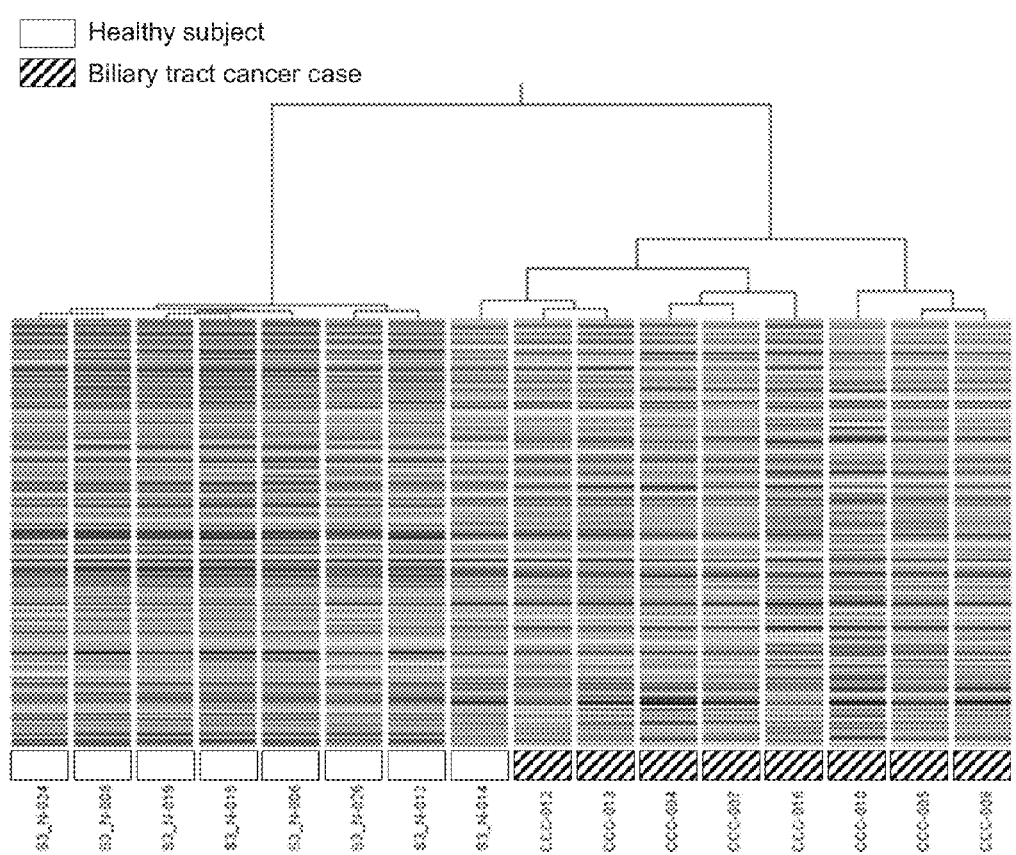

FIG. 26 shows the results of hierarchical clustering using 363 probes corresponding to genes with expression levels that were observed to be attenuated in biliary tract cancer cases at levels 0.33 times or less or enhanced in the same at levels 3 times or more than normal healthy subjects.

DETAILED DESCRIPTION OF THE INVENTION

In the present invention, examples of digestive organ cancer include gastric cancer, colorectal cancer, pancreatic cancer, and biliary tract cancer. All of these types of digestive organ cancer can be detected by the method for detecting digestive organ cancer of the present invention. Moreover, gastric cancer, colorectal cancer, pancreatic cancer, or biliary tract cancer can be specifically detected by the method for detecting gastric cancer, colorectal cancer, pancreatic cancer, or biliary tract cancer of the present invention.

The method of the present invention comprises measuring the expression in peripheral blood of:

a gene group with an expression level that varies in digestive organ cancer patients compared with normal healthy subjects;

a gene group with an expression level that varies in gastric cancer patients compared with normal healthy subjects;

a gene group with an expression level that varies in colorectal cancer patients compared with normal healthy subjects;

a gene group with an expression level that varies in pancreatic cancer patients compared with normal healthy subjects; or a gene group with an expression level that varies in biliary tract cancer patients compared with normal healthy subjects, so as to obtain the expression profile of each gene group, and then detecting digestive organ cancer, gastric cancer, colorectal cancer, pancreatic cancer, or biliary tract cancer. Here, examples of such variation in expression include attenuated expression and enhanced expression.

Gene expression in peripheral blood is measured by extracting and isolating mRNA from peripheral blood and then measuring mRNA. mRNA can be extracted and isolated from peripheral blood by a known method. Examples of mRNA that can be extracted and isolated from peripheral blood include mRNAs derived from, in addition to erythrocytes and blood platelets, leukocytes including lymphocytes, monocytes, and granulocytes in peripheral blood, for example.

In the method of the present invention, the expression levels of the above genes are measured.

In the present invention, the term "gene expression level" refers to a gene expression amount, expression intensity, or expression frequency. Such a gene expression level can be generally analyzed based on the production amount of a transcript corresponding to a gene, or the production amount of the translation product therefrom, activity, and the like. Also, the term "expression profiles" refers to information concerning the expression level of each gene. A gene expression level may be expressed with an absolute value or a relative value. In addition, expression profiles may also be referred to as expression patterns.

Expression levels may be measured by measuring gene transcripts (that is, mRNA) or measuring gene translation products (that is, proteins). Preferably, gene expression levels are measured by measuring gene transcripts. An example of a gene transcript is cDNA obtained from mRNA via reverse transcription.

A gene transcript can be measured by measuring the degree of gene expression using nucleotides containing full-length nucleotide sequences or partial nucleotide sequences of the above genes, or sequences complementary thereto, specifically, nucleotides consisting of the nucleotide sequences consisting of the nucleotide sequences of the genes or partial sequences of the genes, or sequences complementary thereto, as probes or primers. These nucleotides are nucleotides capable of hybridizing to the genes, nucleotides capable of binding to the genes, or nucleotides for detection, which can be used for detection of the genes. The degree of gene expression can be measured by a method using a microarray (microchip), a Northern blot method, or a quantitative PCR method using a gene to be quantitatively determined or a fragment thereof as a target, for example. Examples of a quantitative PCR method include an agarose gel electrophoresis method, a fluorescent probe method, an RT-PCR method, a real-time PCR method, an ATAC-PCR method (Kato, K. et al., Nucl. Acids Res., 25, 4694-4696, 1997), a Taqman PCR method (SYBR (trademark) Green method) (Schmittgen T D, Methods 25, 383-385, 2001), Body Map method (Gene, 174, 151-158 (1996)), a serial analysis of gene expression (SAGE) method (U.S. Pat. Nos. 527,154 and 544,861, EP Publication No. 0761822), and a MAGE method (Micro-analysis of Gene Expression) (JP Patent Publication (Kokai) No. 2000-232888 A). All methods listed herein can be performed by known techniques. The amount of messenger RNA (mRNA) transcribed from the full-length sequence or a partial sequence of the above gene may be measured using these methods. Specifically, the amount of mRNA can be measured using nucleotide probes or primers hybridizing to the mRNA. The base length of a probe or a primer to be used for measurement ranges from 10 bp to 100 bp, preferably ranges from 20 bp to 80 bp, and further preferably ranges from 50 bp to 70 bp.

A DNA microarray (DNA chip) can be prepared by immobilizing nucleotides consisting of the nucleotide sequences of the above genes or partial sequences thereof, or nucleotides containing complementary sequences thereof on an appropriate substrate.

Examples of a substrate for immobilization include glass plates, quartz plates, silicon wafers. Examples of the size of such a substrate include 3.5 mm×5.5 mm, 18 mm×18 mm, and 22 mm×75 mm. The size thereof can be set variously depending on the number of spots for probes or the size of the spots on a substrate. Polynucleotides or fragments thereof can be immobilized by the following methods. Polynucleotides or fragments thereof can be electrostatically bound to a solid-phase support surface-treated with a polycation such as polylysine, polyethylene imine, or polyalkylamine with the use of the electric charge of nucleotides. Alternatively, nucleotides, into which a functional group such as an amino group, an aldehyde group, an SH group, or biotin has been introduced, are covalently bound to the surface of a solid phase to which a functional group such as an amino group, an aldehyde group, or an epoxy group has been introduced. Immobilization may be performed using an array system. A DNA microarray is prepared by immobilizing at least one of genes corresponding to the above 868 probes or a fragment thereof to a substrate, the DNA microarray is brought into contact with subject-derived mRNA or cDNA labeled with a fluorescent substance for hybridization, and then fluorescence intensity on the DNA microarray is measured, so that the type and the amount of the mRNA can be determined. As a result, a gene(s) with expression levels that vary in a subject, can be detected, so that the gene expression profile can be obtained. A fluorescent substance for labeling subject-derived mRNA is not limited and any commercially available fluorescent substance can be used. For example, Cy3 and Cy5 may be used. mRNA can be labeled by a known method.

In the present invention, the term "probe" refers to the sequence of a nucleotide arranged on a DNA microarray. One nucleotide sequence is designated for one probe ID No. There is a single gene that corresponds to a plurality of probes comprising different nucleotide sequences. The expression "a probe(s) correspond(ing) to a gene(s)" means that the sequence of the probe is complementary to a partial nucleotide sequence of the gene or a sequence complementary thereto, so that the gene can hybridize to the probe. The nucleotide sequence of a gene corresponding to a probe contains the nucleotide sequence of the probe or a nucleotide sequence complementary thereto as a partial sequence.

Examples of nucleotides to be used as probes or primers in the present invention include nucleotides containing the sequences of the above genes, nucleotides consisting of the sequences of fragments thereof, and nucleotides consisting of sequences complementary to these sequences. Further examples of nucleotides to be used in the present invention include nucleotides hybridizing under stringent conditions to nucleotides having the above nucleotide sequences and nucleotides consisting of the sequences of the fragments thereof. Specific examples of such a nucleotide include a nucleotide and the like containing the nucleotide sequence having the degree of homology with the above nucleotide sequences, about 80% or more, preferably about 90% or more, and more preferably about 95% or more on an overall average. Hybridization can be performed according to a method known in the art or a method according thereto, such as the methods described in Current Protocols in Molecular Biology (Current protocols in molecular biology (edited by Frederick M. Ausubel et al., 1987)). Also, when a commercially available library is used, hybridization can be performed according to the methods described in the attached instructions. Here, the term "stringent conditions" refers to conditions of about "1×SSC, 0.1% SDS, 37° C.," more stringent conditions refer to conditions of about "0.5×SSC, 0.1% SDS, and 42° C.," and even more stringent conditions refer to conditions of about "0.2×SSC, 0.1% SDS, 65° C." As such, higher stringency of hybridization conditions enables isolation of a nucleotide having high homology with the probe sequence. Here, the above combinations of SSC, SDS, and temperature are merely examples. Persons skilled in the art can realize stringency similar to the above by appropriately combining the above or other factors (e.g., probe concentration, probe length, and reaction time for hybridization) for determination of stringency for hybridization. Moreover, these genes may have variants. Hence, examples of genes to be used in the present invention include variants of the above genes. The nucleotide sequences of variants can be obtained by accessing a gene database. Examples of the nucleotides of the present invention include nucleotides containing the nucleotide sequences of the variants or nucleotides consisting of the sequences of the fragments thereof.

Also, as a nucleotide to be used in the present invention, either a nucleotide consisting of a sense strand of the above gene or a nucleotide consisting of the antisense strand of the same can be used.

FIG. 1 (FIG. 1-1 to FIG. 1-48) shows 868 probes of the $1^{st}$ probe group that can be used for detection of digestive organ cancer. FIG. 1 shows probe ID numbers, symbols of genes corresponding to the probes, the nucleotide sequences (SEQ ID NOs: 1-868) of the probes, and descriptions of genes corresponding to the probes (gene names and GenBank accession numbers). The full-length sequences of these genes are known. Arbitrary partial sequences can be used as nucleotides for detection of the genes. FIG. 2 shows the nucleotide sequences (SEQ ID NOs: 220, 506, 508, 523, 538, 554, 570, 589, 597, 602, 618, 654, 689, 701, 726, 744, 762, 763, 781, 795, and 849) of 21 probes with expression levels that differ significantly particularly between digestive organ cancer patients and normal healthy subjects, from among the 868 probes shown in FIG. 1. In FIG. 1, genes corresponding to 555 probes (No. 1 to No. 555) (SEQ ID NOs: 1-555) exhibit attenuated expression in digestive organ cancer patients compared with normal healthy subjects. Genes corresponding to 313 probes (No. 556 to No. 868) (SEQ ID NOs: 556-868) exhibit enhanced expression in digestive organ cancer patients compared with normal healthy subjects. Also, in FIG. 2, genes corresponding to probes No. 1 to No. 6 (SEQ ID NOs: 220, 506, 508, 523, 538, and 554) exhibit attenuated expression in digestive organ cancer patients compared with normal healthy subjects. Genes corresponding to probes No. 7 to No. 21 (SEQ ID NOs: 570, 589, 597, 602, 618, 654, 689, 701, 726, 744, 762, 763, 781, 795, and 849) exhibit enhanced expression in digestive organ cancer patients compared with normal healthy subjects.

Furthermore, FIG. 21 (FIG. 21-1 and FIG. 21-2) shows 25 probes of the $2^{nd}$ probe group that can be used for detection of digestive organ cancer. FIG. 21 shows probe ID numbers, symbols of genes corresponding to the probes, the nucleotide sequences (SEQ ID NOs: 3030-3054) of the probes, and descriptions of genes corresponding to the probes (gene names and GenBank accession numbers). The full-length sequences of these genes are known. Arbitrary partial sequences can be used as nucleotides for detection of the genes.

FIG. 3 (FIG. 3-1 to FIG. 3-39) shows 713 probes that can be used for detection of gastric cancer. FIG. 3 shows probe ID numbers, symbols of genes corresponding to the probes, the nucleotide sequences (SEQ ID NOs: 869-1581) of the probes, and descriptions of genes corresponding to the probes (gene names and GenBank accession numbers). The full-length sequences of these genes are known. Arbitrary partial sequences can be used as nucleotides for detection of the genes. FIG. 4 (FIG. 4-1 to FIG. 4-6) shows the nucleotide sequences (SEQ ID NO: 923, 927, 929, 932, 946, 952, 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578) of 107 probes with expression levels that differ significantly particularly between gastric cancer patients and normal healthy subjects, from among the 713 probes shown in FIG. 3. In FIG. 3, genes corresponding to 84 probes (No. 1 to No. 84) (SEQ ID NOs: 869-952) exhibit attenuated expression in gastric cancer patients compared with normal healthy subjects. Genes corresponding to 629 probes (No. 85 to No. 713) (SEQ ID NOs: 953-1581) exhibit enhanced expression in gastric cancer patients compared with normal healthy subjects. Also, in FIG. 4, genes corresponding to probes No. 1 to No. 6 (SEQ ID NOs: 923, 927, 929, 932, 946, and 952) exhibit attenuated expression in gastric cancer patients compared with normal healthy subjects. Genes corresponding to probes No. 7 to No. 107 (SEQ ID NOs: 986, 998, 1000, 1006, 1007, 1013, 1019, 1020, 1022, 1027, 1039, 1046, 1073, 1090, 1107, 1108, 1117, 1121, 1132, 1134, 1154, 1162, 1179, 1183, 1191, 1205, 1207, 1211, 1216, 1217, 1224, 1239, 1244, 1251, 1254, 1255, 1283, 1285, 1301, 1304, 1316, 1317, 1327, 1328, 1331, 1332, 1345, 1359, 1365, 1366, 1372, 1373, 1375, 1379, 1380, 1382, 1383, 1393, 1394, 1396, 1397, 1404, 1405, 1406, 1407, 1421, 1423, 1426, 1430, 1440, 1441, 1442, 1448, 1450, 1454, 1455, 1456, 1459, 1466, 1467, 1491, 1497, 1500, 1502, 1504, 1508, 1513, 1514, 1519, 1531, 1534, 1544, 1546, 1549, 1551, 1560, 1563, 1566, 1570, 1571, and 1578) exhibit enhanced expression in gastric cancer patients compared with normal healthy subjects.

FIG. 5 (FIG. 5-1 to FIG. 5-41) shows 771 probes that can be used for detection of colorectal cancer. FIG. 5 shows probe ID numbers, symbols of genes corresponding to the probes, the nucleotide sequences (SEQ ID NOs: 1582-2352) of the probes, and descriptions of genes corresponding to the probes (gene names and GenBank accession numbers). The full-length sequences of these genes are known. Arbitrary partial sequences can be used as nucleotides for detection of the genes. FIG. 6 (FIG. 6-1 to FIG. 6-6) shows 116 probes (SEQ ID NO: 1583, 1601, 1611, 1614, 1644, 1651, 1678, 1680, 1684, 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340) with expression levels that differ significantly particularly between colorectal cancer patients and normal healthy subjects, from among 771 probes shown in FIG. 5. In FIG. 5, genes corresponding to 125 probes (No. 1 to No. 125) (SEQ ID NOs: 1582-1706) exhibit attenuated expression in colorectal cancer patients compared with normal healthy subjects. Genes corresponding to 646 probes (No. 126 to No. 771) (SEQ ID NOs: 1707-2352) exhibit enhanced expression in colorectal cancer patients compared with normal healthy subjects. Also, in FIG. 6, genes corresponding to probes No. 1 to No. 9 (SEQ ID NOs: 1583, 1601, 1611, 1614, 1644, 1651, 1678, 1680, and 1684) exhibit attenuated expression in colorectal cancer patients compared with normal healthy subjects. Genes corresponding to probes No. 10 to No. 116 (SEQ ID NOs: 1737, 1746, 1750, 1751, 1757, 1760, 1765, 1766, 1773, 1778, 1779, 1780, 1782, 1787, 1794, 1795, 1798, 1802, 1831, 1836, 1837, 1853, 1854, 1869, 1871, 1873, 1876, 1880, 1890, 1892, 1896, 1925, 1942, 1950, 1953, 1962, 1970, 1977, 1978, 1985, 1990, 1991, 2000, 2004, 2007, 2011, 2018, 2019, 2023, 2032, 2046, 2050, 2054, 2077, 2085, 2088, 2095, 2105, 2126, 2128, 2132, 2138, 2140, 2143, 2144, 2145, 2147, 2158, 2160, 2161, 2173, 2175, 2176, 2180, 2191, 2193, 2198, 2207, 2209, 2213, 2217, 2218, 2223, 2227, 2233, 2247, 2255, 2257, 2258, 2261, 2266, 2268, 2269, 2273, 2280, 2286, 2296, 2306, 2317, 2320, 2322, 2325, 2332, 2334, 2336, 2339, and 2340) exhibit enhanced expression in colorectal cancer patients compared with normal healthy subjects. FIG. 7 (FIG. 7-1 to FIG. 7-37) shows 677 probes that can be used for detection of pancreatic cancer.

FIG. 7 shows probe ID numbers, symbols of genes corresponding to the probes, the nucleotide sequences (SEQ ID NOs: 2353-3029) of the probes, and descriptions of genes corresponding to the probes (gene names and GenBank accession numbers). The full-length sequences of these genes are known. Arbitrary partial sequences can be used as nucleotides for detection of the genes. FIG. 8 (FIG. 8-1 to FIG. 8-3) shows 61 probes (SEQ ID NOs: 2373, 2404, 2418, 2419, 2426, 2430, 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003) with expression levels that differ significantly particularly between pancreatic cancer patients and normal healthy subjects, from among 677 probes. In FIG. 7, genes corresponding to 96 probes (No. 1 to No. 96) (SEQ ID NOs: 2353-2448) exhibit attenuated expression in pancreatic cancer patients compared with normal healthy subjects. Genes corresponding to 581 probes (No. 97 to No. 677) (SEQ ID NO: 2449 to 3029) exhibit enhanced expression in pancreatic cancer patients compared with normal healthy subjects. Also, in FIG. 8, genes corresponding to probes No. 1 to No. 6 (SEQ ID NOs: 2373, 2404, 2418, 2419, 2426, and 2430) exhibit attenuated expression in pancreatic cancer patients compared with normal healthy subjects. Genes corresponding to probes No. 7 to No. 61 (SEQ ID NOs: 2459, 2461, 2469, 2475, 2507, 2514, 2515, 2525, 2543, 2600, 2602, 2621, 2628, 2634, 2640, 2651, 2652, 2674, 2677, 2680, 2681, 2691, 2692, 2700, 2714, 2715, 2719, 2723, 2724, 2738, 2740, 2746, 2748, 2763, 2778, 2781, 2815, 2818, 2823, 2842, 2857, 2861, 2885, 2898, 2902, 2903, 2932, 2934, 2972, 2975, 2982, 2985, 2999, 3001, and 3003) exhibit enhanced expression in pancreatic cancer patients compared with normal healthy subjects.

FIG. 24 (FIG. 24-1 to FIG. 24-19) shows 363 probes that can be used for detection of biliary tract cancer. FIG. 24 shows probe ID numbers, symbols of genes corresponding to the probes, the nucleotide sequences (SEQ ID NOs: 3055-3417) of the probes, and descriptions of genes corresponding to the probes (gene names and GenBank accession numbers). The full-length sequences of these genes are known. Arbitrary partial sequences can be used as nucleotides for detection of the genes. In FIG. 24, genes corresponding to 98 probes (No. 1 to No. 98) (SEQ ID NOs: 3055-3152) exhibit attenuated expression in biliary tract cancer patients compared with normal healthy subjects. Genes corresponding to 265 probes (No. 99 to No. 363) (SEQ ID NOs: 3153-3417) exhibit enhanced expression in biliary tract cancer patients compared with normal healthy subjects.

The method for detecting digestive organ cancer of the present invention comprises measuring the expression levels of genes (described in the rightmost column in FIG. 1) in peripheral blood of a subject using at least one of 868 probes shown in FIG. 1, wherein the genes correspond to the 868 probes. At this time, with the use of at least 1 to 867 probes from among the 868 probes shown in FIG. 1, specifically at least 1, 2, 3, 4, 5, 6, 7, 8, 9, 10, 50, 100, 150, 200, 250, 300, 350, 400, 450, 500, 550, 600, 650, 700, 750, 800, 850, 867, or 868 probes, the expression levels of the genes corresponding thereto are measured. Also, with the use of at least one of probes corresponding to genes that exhibit attenuated expression in a group of digestive organ cancer patients, the expression level of the gene corresponding thereto may be measured. Also, with the use of at least one of probes corresponding to genes that exhibit enhanced expression in a group of digestive organ cancer patients, the expression level of the gene corresponding to the probe may be measured. Furthermore, with the use of a combination of at least one of probes corresponding to genes that exhibit attenuated expression in a group of digestive organ cancer patients and at least one of probes corresponding to genes that exhibit enhanced expression in the group of digestive organ cancer patients, the expression levels of the genes corresponding to the probes may be measured. Specifically, with the use of at least one of 555 probes (No. 1 to No. 555) (SEQ ID NOs: 1-555) shown in FIG. 1, the expression level of at least one of the genes corresponding to the probes may be measured. At this time, with the use of at least 1 to 554 probes from among the 555 probes, specifically at least 1, 2, 3, 4, 5, 6, 7, 8, 9, 10, 50, 100, 150, 200, 250, 300, 350, 400, 450, 500, 550, 554, or 555 probes, the expression levels of the genes corresponding thereto may be measured. Also, with the use of at least one of 313 probes (No. 556 to No. 868) (SEQ ID NOs: 556-868) shown in FIG. 1, the expression level of the gene corresponding thereto may be measured. At this time, with the use of at least 1 to 312 probes from among the 313 probes, specifically at least 1, 2, 3, 4, 5, 6, 7, 8, 9, 10, 50, 100, 150, 200, 250, 300, 312, or 313 probes, the expression levels of the genes corresponding thereto may be measured. Furthermore, with the use of a combination of at least one of the 555 probes (No. 1 to No. 555) (SEQ ID NOs: 1-555) shown in FIG. 1 and at least one of the 313 probes (No. 556 to No. 868) (SEQ ID NOs: 556-868) shown in FIG. 1, the expression levels of the genes corresponding thereto may be measured.

Furthermore, with the use of at least one of 21 probes shown in FIG. 2 corresponding particularly to genes with expression levels that vary significantly from among genes corresponding to the above 868 probes, the expression levels of the genes (described in the rightmost column in FIG. 2) corresponding to the probes may be measured. At this time, with the use of the 21 probes, specifically 1, 2, 3, 4, 5, 6, 7, 8, 9, 10, 11, 12, 13, 14, 15, 16, 17, 18, 19, 20, or 21 probes, the expression levels of the genes corresponding to the probes may be measured. Also, with the use of at least one of probes No. 1 to No. 6 (from among the 21 probes shown in FIG. 2) corresponding to genes that exhibit attenuated expression in digestive organ cancer patients compared with normal healthy subjects, the expression levels of the genes may be measured. With the use of, from among the 21 probes shown in FIG. 2, at least one of probes No. 7 to No. 21 corresponding to genes that exhibit enhanced expression in digestive organ cancer patients compared with normal healthy subjects, the expression levels of the genes may be measured. Furthermore, with the use of a combination of at least one of the probes No. 1 to No. 6 and at least one of the probes No. 7 to No. 21, the expression levels of the genes may be measured. At this time, 1, 2, 3, 4, 5, or 6 probes of the probes No. 1 to No. 6 may be used and 1, 2, 3, 4, 5, 6, 7, 8, 9, 10, 11, 12, 13, 14, or 15 probes of the probes No. 7 to No. 21 may be used.

The method for detecting digestive organ cancer of the present invention comprises measuring the expression levels of genes (described in the rightmost column in FIG. 1A) in peripheral blood of a subject using at least one of 25 probes shown in FIG. 21, wherein the genes correspond to the 25 probes. At this time, with the use 1, 2, 3, 4, 5, 6, 7, 8, 9, 10, 11, 12, 13, 14, 15, 16, 17, 18, 19, 20, 21, 22, 23, 24, or probes shown in FIG. 1A, the expression levels of the genes corresponding thereto may be measured. Also, with the use of at least one of probes corresponding to genes that exhibit attenuated expression in a group of digestive organ cancer patients, the expression level of the gene corresponding thereto may be measured. Also, with the use of at least one of probes corresponding to genes that exhibit enhanced expression in a group of digestive organ cancer patients, the expression level of the gene corresponding thereto may be measured. Furthermore, with the use of a combination of at least one of probes corresponding to genes that exhibit attenuated expression in a group of digestive organ cancer patients and at least one of probes corresponding to genes that exhibit enhanced expression in the group of digestive organ cancer patients, the expression levels of the genes corresponding to the probes may be measured. Specifically, with the use of at least one of 14 probes (No. 1 to No. 14) (SEQ ID NOs: 3030-3043) shown in FIG. 21, the expression level of at least one of the genes corresponding to the probes may be measured. At this time, with the use of 14 probes, specifically, 1, 2, 3, 4, 5, 6, 7, 8, 9, 10, 11, 12, 13, or 14 probes, the expression levels of the genes corresponding thereto may be measured. Also, with the use of at least one of 11 probes (No. 15 to No. 25) (SEQ ID NOs: 3044-3054) shown in FIG. 21, the expression level of the gene corresponding to the probe may be measured. At this time, with the use of 11 probes, specifically, 1, 2, 3, 4, 5, 6, 7, 8, 9, 10, or 11 probes, the expression levels of the genes corresponding thereto may be measured. Furthermore, with the use of a combination of at least one of 14 probes (No. 1 to No. 14) (SEQ ID NOs: 3030-3043) shown in FIG. 21 and at least one of 11 probes (No. 15 to No. 25) (SEQ ID NOs: 3044-3054) shown in FIG. 21, the expression levels of the genes corresponding thereto may be measured.

The method for detecting gastric cancer of the present invention comprises measuring the expression levels of genes in peripheral blood of a subject (described in the rightmost column in FIG. 3) using at least one of 713 probes shown in FIG. 3, wherein the genes correspond to the 713 probes. At this time, with the use of at least 1 to 712 probes from among the 713 probes shown in FIG. 3, specifically at least 1, 2, 3, 4, 5, 6, 7, 8, 9, 10, 50, 100, 150, 200, 250, 300, 350, 400, 450, 500, 550, 600, 650, 700, 712, or 713 probes, the expression levels of the genes corresponding thereto may be measured. Also, with the use of at least one of probes corresponding to genes that exhibit attenuated expression in a group of gastric cancer patients, the expression level of the gene corresponding thereto may be measured. Also, with the use of at least one of probes corresponding to genes that exhibit enhanced expression in a group of gastric cancer patients, the expression level of the gene corresponding to the probe may be measured. Furthermore, with the use of a combination of at least one of probes corresponding to genes that exhibit attenuated expression in a group of gastric cancer patients and at least one of probes corresponding to genes that exhibit enhanced expression in the group of gastric cancer patients, the expression levels of the genes corresponding to the probes may be measured. Specifically, with the use of at least one of 84 probes (No. 1 to No. 84) (SEQ ID NOs: 869-952) shown in FIG. 1, the expression level of at least one of the genes corresponding to the probes may be measured. At this time, with the use of at least 1 to 83 probes from among the 84 probes, specifically at least 1, 2, 3, 4, 5, 6, 7, 8, 9, 10, 20, 30, 40, 50, 60, 70, 80, 83, or 84 probes, the expression levels of the genes corresponding thereto may be measured. Also, with the use of at least one of 629 probes (No. 85 to No. 713) (SEQ ID NOs: 953-1581) shown in FIG. 3, the expression levels of the genes corresponding to the probes may be measured. At this time, with the use of at least 1 to 628 probes from among the 629 probes, specifically at least 1, 2, 3, 4, 5, 6, 7, 8, 9, 10, 50, 100, 150, 200, 250, 300, 350, 400, 450, 500, 550, 600, 628, or 629 probes, the expression levels of the genes corresponding thereto may be measured. Furthermore, with the use of a combination of at least one of the 84 probes (No. 1 to No. 84) (SEQ ID NOs: 869-952) shown in FIG. 3 and at least one of the 629 probes (No. 85 to No. 713) (SEQ ID NOs: 953-1581) shown in FIG. 3, the expression levels of the genes corresponding to the probes may be measured.

Furthermore, with the use of at least one of 107 probes shown in FIG. 4 corresponding particularly to genes with expression levels that vary significantly from among the genes corresponding to the above 713 probes, the expression levels of the genes (described in the rightmost column in FIG. 4) corresponding to the probes may be measured. At this time, with the use of the 107 probes, specifically at least 1, 2, 3, 4, 5, 6, 7, 8, 9, 10, 20, 30, 40, 50, 60, 70, 80, 90, 100, 106, or 107 probes, the expression levels of the genes corresponding to the probes may be measured. Also, with the use of at least one of probes No. 1 to No. 6 (from among the 107 probes shown in FIG. 4) corresponding to genes that exhibit attenuated expression in gastric cancer patients compared with normal healthy subjects, the expression levels of the genes may be measured. With the use of, from among the 107 probes shown in FIG. 4, at least one of probes No. 7 to No. 107 corresponding to genes that exhibit enhanced expression in gastric cancer patients compared with normal healthy subjects, the expression levels of the genes may be measured. Furthermore, with the use of a combination of at least one of the probes No. 1 to No. 6 and at least one of the probes No. 7 to No. 107, the expression levels of the genes may be measured. At this time, 1, 2, 3, 4, 5, or 6 probes of the probes No. 1 to No. 6 may be used and at least 1, 2, 3, 4, 5, 6, 7, 8, 9, 10, 20, 30, 40, 50, 60, 70, 80, 90, or 100, or 101 probes of the probes No. 7 to No. 107 may be used.

The method for detecting colorectal cancer of the present invention comprises measuring the expression levels of genes in peripheral blood of a subject (described in the rightmost column in FIG. 5) using at least one of 771 probes shown in FIG. 5, wherein the genes correspond to the 771 probes. At this time, with the use of at least 1 to 770 probes from among the 771 probes shown in FIG. 5, specifically at least 1, 2, 3, 4, 5, 6, 7, 8, 9, 10, 50, 100, 150, 200, 250, 300, 350, 400, 450, 500, 550, 600, 650, 700, 750, 770, or 771 probes, the expression levels of the genes corresponding thereto may be measured. Also, with the use of at least one of probes corresponding to genes that exhibit attenuated expression in a group of colorectal cancer patients, the expression level of the gene corresponding thereto may be measured. Also, with the use of at least one of probes corresponding to genes that exhibit enhanced expression in a group of colorectal cancer patients, the expression level of the gene corresponding to the probe may be measured. Furthermore, with the use of a combination of at least one of probes corresponding to genes that exhibit attenuated expression in a group of colorectal cancer patients and at least one of probes corresponding to genes that exhibit enhanced expression in the group of colorectal cancer patients, the expression levels of the genes corresponding to the probes may be measured. Specifically, with the use of at least one of 125 probes (No. 1 to No. 125) (SEQ ID NOs: 1582-1706) shown in FIG. 5, the expression level of at least one of the genes corresponding to the probes may be measured. At this time, with the use of at least 1 to 124 probes from among the 125 probes, specifically at least 1, 2, 3, 4, 5, 6, 7, 8, 9, 10, 20, 30, 40, 50, 60, 70, 80, 90, 100, 110, 120, 124, or 125 probes, the expression levels of the genes corresponding thereto may be measured. Also, with the use of at least one of 646 probes (No. 126 to No. 771) (SEQ ID NOs: 1707-2352) shown in FIG. 5, the expression levels of the genes corresponding thereto may be measured. At this time, with the use of at least 1 to 645 probes from among the 646 probes, specifically at least 1, 2, 3, 4, 5, 6, 7, 8, 9, 10, 50, 100, 150, 200, 250, 300, 350, 400, 450, 500, 550, 600, 645, or 646 probes, the expression levels of the genes corresponding thereto may be measured. Furthermore, with the use of a combination of at least one of the 125 probes (No. 1 to No. 125) (SEQ ID NOs: 1582-1706) shown in FIG. 5 and at least one of the 646 probes (No. 126 to No. 771) (SEQ ID NOs: 1707-2352) shown in FIG. 5, the expression levels of the genes corresponding thereto may be measured.

Furthermore, with the use of at least one of 116 probes shown in FIG. 6 corresponding particularly to genes with expression levels that vary significantly from among the genes corresponding to the above 771 probes, the expression levels of the genes (described in the rightmost column in FIG. 6) corresponding to the probes may be measured. At this time, with the use of the 116 probes, specifically 1, 2, 3, 4, 5, 6, 7, 8, 9, 10, 20, 30, 40, 50, 60, 70, 80, 90, 100, 110, or 115, or 116 probes, the expression levels of the genes corresponding to the probes may be measured. Also, with the use of at least one of probes No. 1 to No. 9 (from among the 116 probes shown in FIG. 6) corresponding to genes that exhibit attenuated expression in colorectal cancer patients compared with normal healthy subjects, the expression levels of the genes may be measured. With the use of, from among the 116 probes shown in FIG. 6, at least one of probes No. 10 to No. 116 corresponding to genes that exhibit enhanced expression in colorectal cancer patients compared with normal healthy subjects, the expression levels of the genes may be measured. Furthermore, with the use of a combination of at least one of the probes No. 1 to No. 9 and at least one of the probes No. 10 to No. 116, the expression levels of the genes may be measured. At this time, 1, 2, 3, 4, 5, 6, 7, 8, or 9 probes of the probes No. 1 to No. 9 may be used and at least 1, 2, 3, 4, 5, 6, 7, 8, 9, 10, 20, 30, 40, 50, 60, 70, 80, 90, 100, or 109, or 110 probes of the probes No. 10 to No. 116 may be used.

The method for detecting pancreatic cancer of the present invention comprises measuring the expression levels of genes in peripheral blood of a subject (described in the rightmost column in FIG. 7) using at least one of 677 probes shown in FIG. 7, wherein the genes correspond to the 677 probes. At this time, with the use of at least 1 to 676 probes from among the 677 probes shown in FIG. 7, specifically at least 1, 2, 3, 4, 5, 6, 7, 8, 9, 10, 50, 100, 150, 200, 250, 300, 350, 400, 450, 500, 550, 600, 650, 676, or 677 probes, the expression levels of the genes corresponding thereto may be measured. Also, with the use of at least one of probes corresponding to genes that exhibit attenuated expression in a group of pancreatic cancer patients, the expression level of the gene corresponding thereto may be measured. Also, with the use of at least one of probes corresponding to genes that exhibit enhanced expression in a group of pancreatic cancer patients, the expression level of the gene corresponding to the probe may be measured. Furthermore, with the use of a combination of at least one of probes corresponding to genes that exhibit attenuated expression in a group of pancreatic cancer patients and at least one of probes corresponding to genes that exhibit enhanced expression in the group of pancreatic cancer patients, the expression levels of the genes corresponding to the probes may be measured. Specifically, with the use of at least one of 96 probes (No. 1 to No. 96) (SEQ ID NOs: 2353-2448) shown in FIG. 7, the expression level of at least one of the genes corresponding to the probes may be measured. At this time, with the use of at least 1 to 95 probes from among the 96 probes, specifically at least 1, 2, 3, 4, 5, 6, 7, 8, 9, 10, 20, 30, 40, 50, 60, 70, 80, 90, or 95, or 96 probes, the expression levels of the genes corresponding thereto may be measured. Also, with the use of at least one of 581 probes (No. 97 to No. 677) (SEQ ID NOs: 2449-3029) shown in FIG. 7, the expression levels of the genes corresponding thereto may be measured. At this time, with the use of at least 1 to 580 probes from among the 581 probes, specifically at least 1, 2, 3, 4, 5, 6, 7, 8, 9, 10, 50, 100, 150, 200, 250, 300, 350, 400, 450, 500, 550, or 580, or 581 probes, the expression levels of the genes corresponding thereto may be measured. Furthermore, with the use of a combination of at least one of the 96 probes (No. 1 to No. 96) (SEQ ID NOs: 2353-2448) shown in FIG. 7 and at least one of the 581 probes (No. 97 to No. 677) (SEQ ID NOs: 2449-3029) shown in FIG. 7, the expression levels of the genes corresponding thereto may be measured.

Furthermore, with the use of at least one of 61 probes shown in FIG. 8 corresponding particularly to genes with expression levels that vary significantly (from among the genes corresponding to the above 677 probes), the expression levels of the genes (described in the rightmost column in FIG. 8) corresponding to the probes may be measured. At this time, with the use of the 61 probes, specifically at least 1, 2, 3, 4, 5, 6, 7, 8, 9, 10, 20, 30, 40, 50, or 60, or 61 probes, the expression levels of the genes corresponding to the probes may be measured. Also, with the use of at least one of probes No. 1 to No. 6 (from among the 61 probes shown in FIG. 8) corresponding to genes that exhibit attenuated expression in pancreatic cancer patients compared with normal healthy subjects, the expression levels of the genes may be measured. With the use of, from among the 61 probes shown in FIG. 8, at least one of probes No. 7 to No. 61 corresponding to genes that exhibit enhanced expression in pancreatic cancer patients compared with normal healthy subjects, the expression levels of the genes may be measured. Furthermore, with the use of a combination of at least one of the probes No. 1 to No. 6 and at least one of the probes No. 7 to No. 61, the expression levels of the genes may be measured. At this time, 1, 2, 3, 4, 5, or 6 probes of the probes No. 1 to No. 6 may be used and 1, 2, 3, 4, 5, 6, 7, 8, 9, 10, 20, 30, 40, 50, or 54, or 55 probes of the probes No. 7 to No. 61 may be used.

The method for detecting biliary tract cancer of the present invention comprises measuring the expression levels of genes in peripheral blood of a subject (described in the rightmost column in FIG. 24) using at least one of 363 probes shown in FIG. 24 (FIG. 24-1 to FIG. 24-19), wherein the genes correspond to the 363 probes. At this time, with the use of at least 1 to 362 probes from among the 363 probes shown in FIG. 24, specifically at least 1, 2, 3, 4, 5, 6, 7, 8, 9, 10, 50, 100, 150, 200, 250, 300, 350, or 362, or 363 probes, the expression levels of the genes corresponding thereto may be measured. Also, with the use of at least one of probes corresponding to genes that exhibit attenuated expression in a group of biliary tract cancer patients, the expression level of the gene corresponding thereto may be measured. Also, with the use of at least one of probes corresponding to genes that exhibit enhanced expression in a group of biliary tract cancer patients, the expression level of the gene corresponding to the probe may be measured. Furthermore, with the use of a combination of at least one of probes corresponding to genes that exhibit attenuated expression in a group of biliary tract cancer patients and at least one of probes corresponding to genes that exhibit enhanced expression in the group of biliary tract cancer patients, the expression levels of the genes corresponding to the probes may be measured. Specifically, with the use of at least one of 98 probes (No. 1 to No. 98) (SEQ ID NOs: 3055-3152) shown in FIG. 24, the expression level of at least one of the genes corresponding to the probes may be measured. At this time, with the use of at least 1 to 97 probes from among the 98 probes, specifically at least 1, 2, 3, 4, 5, 6, 7, 8, 9, 10, 20, 30, 40, 50, 60, 70, 80, 90, or 97, or 98 probes, the expression levels of the genes corresponding thereto may be measured. Also, with the use of at least one of 265 probes (No. 99 to No. 363) (SEQ ID NOs: 3153-3417) shown in FIG. 24, the expression levels of the genes corresponding thereto may be measured. At this time, with the use of at least 1 to 264 probes from among the 265 probes, specifically at least 1, 2, 3, 4, 5, 6, 7, 8, 9, 10, 50, 100, 150, 200, 250, 264, or 265 probes, the expression levels of the genes corresponding thereto may be measured. Furthermore, with the use of a combination of at least one of the 98 probes (No. 1 to No. 98) (SEQ ID NOs: 3055-3152) shown in FIG. 24 and at least one of the 265 probes (No. 99 to No. 363) (SEQ ID NOs: 3153-3417) shown in FIG. 24, the expression levels of the genes corresponding thereto may be measured.

The method of the present invention enables identification of a patient with digestive organ cancer, gastric cancer, colorectal cancer, pancreatic cancer, or biliary tract cancer. Specifically, the presence of digestive organ cancer, gastric cancer, colorectal cancer, pancreatic cancer, or biliary tract cancer can be detected.

Subjects may exhibit unknown pathological conditions. When such a subject with unknown pathological conditions is used, whether the subject is normal or affected with digestive organ cancer, gastric cancer, colorectal cancer, pancreatic cancer, or biliary tract cancer can be determined and diagnosed.

In the present invention, the above determination of the pathological conditions of digestive organ cancer, gastric cancer, colorectal cancer, pancreatic cancer, or biliary tract cancer, prognostic prediction, and the like are broadly referred to as detection of digestive organ cancer, gastric cancer, colorectal cancer, pancreatic cancer, or biliary tract cancer.

Furthermore, the pathological conditions of a subject can be determined by obtaining the expression profiles of one or more genes corresponding to the above probes (specifically, 868 probes or 25 probes for digestive organ cancer, 713 probes for gastric cancer, 771 probes for colorectal cancer, 677 probes for pancreatic cancer, and 363 probes for biliary tract cancer) and then analyzing the expression profiles. If expression profiles obtained from a subject are analogous to expression profiles obtained from a digestive organ cancer, gastric cancer, colorectal cancer, pancreatic cancer, or biliary tract cancer patient, the subject can be determined as having digestive organ cancer, gastric cancer, colorectal cancer, pancreatic cancer, or biliary tract cancer. Also, expression profiles obtained from a subject are compared with expression profiles obtained from a normal subject and then evaluation and determination can be made based on a difference in expression profiles between the subject and the normal subject.

Gene expression profiling comprises recording the patterns of expression signals such as fluorescence intensities in the form of digital numerical values or color images. Gene expression profiles can be compared using pattern comparison software. Cox hazard analysis, discriminant analysis, and the like can be used herein. A discriminant analysis model is constructed in advance for evaluation and determination of pathological conditions, prediction of pathological conditions, or prognostic prediction, data concerning gene expression profiles obtained from a subject are input into the discriminant analysis model, and thus determination of pathological conditions, prediction of pathological conditions, or prognostic prediction can also be performed. For example, pathological conditions, prediction of pathological conditions, or prognostic prediction can be evaluated and determined by obtaining a discriminant via discriminant analysis, relating fluorescence intensities to pathological conditions, predicting pathological conditions, or conducting prognostic prediction, and then substituting the numerical value representing the expression signal of the subject into the discriminant.

The present invention encompasses an in vitro diagnostic or a kit for detecting digestive organ cancer, gastric cancer, colorectal cancer, pancreatic cancer, or biliary tract cancer, which contains: nucleotides consisting of the nucleotide sequences of genes with expression levels that vary in digestive organ cancer patients compared with normal healthy subjects, genes with expression levels that vary in gastric cancer patients compared with normal healthy subjects, genes with expression levels that vary in colorectal cancer patients compared with normal healthy subjects, genes with expression levels that vary in pancreatic cancer patients compared with normal healthy subjects, or genes with expression levels that vary in biliary tract cancer patients compared with normal healthy subjects for measurement of the expression levels of these genes, or nucleotides containing partial sequences thereof.

The reagent contains nucleotides consisting of the nucleotide sequences of the above genes or nucleotides containing partial sequences thereof as probes or primers. The reagent is also a substrate such as a microarray on which nucleotides consisting of the nucleotide sequences of the above genes or nucleotides containing partial sequences thereof have been immobilized.

For example, a reagent or a kit for detecting digestive organ cancer contains at least one of the above 868 or 25 probes that can be used for detection of digestive organ cancer and is capable of measuring the expression level of at least one of genes corresponding to the probes. Also, a reagent or a kit for detecting gastric cancer contains at least one of the above 713 probes that can be used for detection of gastric cancer and is capable of measuring the expression level of at least one of genes corresponding to the probes. Also, a reagent or a kit for detecting colorectal cancer contains at least one of the above 771 probes that can be used for detection of colorectal cancer and is capable of measuring the expression level of at least one of genes corresponding to the probes. Moreover, a reagent or a kit for detecting pancreatic cancer contains at least one of 677 probes that can be used for detection of pancreatic cancer, and is capable of measuring the expression level of at least one of genes corresponding to the probes. Furthermore, a reagent or a kit for detecting biliary tract cancer contains at least one of 363 probes that can be used for detection of biliary tract cancer and is capable of measuring the expression level of at least one of genes corresponding to the probes.

The present invention encompasses a system for detecting digestive organ cancer, gastric cancer, colorectal cancer, pancreatic cancer, or biliary tract cancer of a subject by the method for detecting digestive organ cancer, gastric cancer, colorectal cancer, pancreatic cancer, or biliary tract cancer of the present invention.

The system for detecting digestive organ cancer, gastric cancer, colorectal cancer, pancreatic cancer, or biliary tract cancer of the present invention comprises:

(a) a data input means for inputting data concerning the gene expression profiles of a subject (here, the "data concerning gene expression profiles to be input" refers to data representing the expression level of each gene, such as a numerical value for signals in each gene;

(b) a memory means for storing the thus constructed discriminant model;

(c) a data processing means for applying data input using the input means (a) to the discriminant model stored in the memory means (b), and then determining the pathological conditions of digestive organ cancer, gastric cancer, colorectal cancer, pancreatic cancer, or biliary tract cancer; and (d) a data output means for outputting data concerning the determination of predicted pathological conditions of digestive organ cancer, gastric cancer, colorectal cancer, pancreatic cancer, or biliary tract cancer, prediction of the pathological conditions, and prognostic prediction.

The data input means (a) contains a key board or an external memory device storing data, for example. The memory means (b) contains a hard disk, for example. The data processing means receives a discriminant model from the memory means and processing the input data, sends the processing result to the data output means, and then displaying the processing result with the data output means. The data processing means contains a central processing unit (CPU) and the like for processing data. Also, the output means contains a monitor, a printer, and the like for displaying the results.

The system of the present invention can be constructed using a commercially available personal computer and the like.

EXAMPLES

The present invention will be specifically described using the following examples, but the present invention is not limited to these examples.

Materials and experimental methods employed in the examples are as follows.

Object

Blood samples collected from patients diagnosed by a doctor as having digestive organ cancer, gastric cancer, colorectal cancer, pancreatic cancer, or biliary tract cancer were designated as a digestive organ cancer case, a gastric cancer case, a colorectal cancer case, a pancreatic cancer case, and a biliary tract cancer case, respectively. Regarding a control group, blood samples provided with the consent of patients who had received health checkups for residents held by local governments and consented to provide their blood were used herein. Blood samples were examined through a search for the following test items, and patients who exhibited normal values were designated as normal healthy subjects.

Test items: systolic blood pressure, diastolic blood pressure, number of erythrocytes, number of leukocytes, hemoglobin value, hematocrit value, liver functions (GOT, GPT, γ-GTP), renal functions (creatinine value), lipid metabolism (LDL cholesterol value, HDL cholesterol value, total cholesterol value), protein in urine, urinary blood Collection of Peripheral Blood:

Peripheral blood was collected from patients using PAXgene™ RNA blood collecting tube (Becton, Dickinson and Company, Japan, Medical Device Marketing Authorization No. (Iryo-kiki Seizo Hanbai Ninsho No.): 218AFBZX00014000).

RNA Extraction and Hybridization

RNA was extracted via a PAXgene™ RNA blood collecting tube according to protocols using a PAXgene Blood RNA Kit (QIAGEN GmbH, Hilden, Germany). RNA was amplified based on the thus extracted RNA using a QuickAmp Labeling Kit, 1 color (Agilent Technologies, Santa Clara, Calif.), and at the same time labeled with a Cy3 dye. The thus labeled RNA was mixed using a Gene Expression Hybridization Kit (Agilent Technologies, Santa Clara, Calif.), followed by hybridization to Whole Human Genome oligo DNA microarrays (Agilent Technologies, Santa Clara, Calif.). In addition, the process from RNA amplification to hybridization was performed according to experimental protocols disclosed by Agilent Technologies.

Image Analysis and Data Analysis of DNA Microarrays:

The fluorescence intensity of each spot on the oligo DNA microarrays was acquired using a DNA microarray scanner (Agilent Technologies, Santa Clara, Calif.). The thus acquired images were processed with Feature Extraction software (Agilent Technologies, Santa Clara, Calif.), so that the fluorescence intensity of each spot was quantitated. The fluorescence intensity of a probe at each spot was calculated by quantitation.

The numerical values of the fluorescence intensities of all probes on the microarrays were normalized using Gene-Spring GX (Agilent Technologies, Santa Clara, Calif.). A quality check was performed for the fluorescence intensity of each probe based on the thus normalized numerical value representing the enhanced or attenuated expression of each probe. Only probes that had passed the quality check were subjected as analytical objects to hierarchical clustering. Also, similarly, with the use of GeneSpring GX, genes with expression levels that were observed to differ between the digestive organ cancer patient group and the normal healthy subject group, were examined using Welch t-test as a statistic analysis tool. Candidate probes were extracted using the Benjamini and Hochberg False Discovery Rate as a multiple test and p<0.05 as significant value. Furthermore, similarly, with the use of GeneSpring GX, predictive determination was performed to determine if a subject belonged to a cancer case group or a normal healthy subject group (differing from the cancer case group or the normal healthy subject group used for extraction of candidate probes) using a class prediction tool and support vector machines for calculation.

The following results were obtained from the examples
1. Detection of Digestive Organ Cancer (1)
Hierarchical Clustering:

Hierarchical clustering was performed using a GeneSpring GX hierarchical clustering tool and 23352 probes that had passed a quality check. As shown in FIG. 9, 5 clusters were formed. In the 1st cluster, 3 out of 3 cases (100%) were digestive organ cancer cases. In the $2^{nd}$ cluster, 8 out of 9 cases (88.9%) were digestive organ cancer cases. In the $3^{rd}$ cluster, 5 out of 6 cases (83.3%) and in the $4^{th}$ cluster, 9 out of 10 cases (90.0%) were digestive organ cancer cases. In the $5^{th}$ cluster, 3 out of 4 cases (75.0%) were digestive organ cancer cases. Hence, digestive organ cancer cases and normal healthy subjects were separately clustered.

Genes with expression levels that were observed to differ between a digestive organ cancer case group and a normal healthy subject group:

Similarly, with the use of a GeneSpring GX Statistic Analysis tool, probes capable of discriminating between a digestive organ cancer case group and a normal healthy subject group were examined using the Benjamini and Hochberg false discovery rate for a multiple test and p<0.0005. As a result, the expression of 868 probes was observed to differ between the two groups.

Also, normalized numerical values for fluorescence intensities of the 868 probes were compared using a Fold Change tool between the digestive organ cancer case group and the normal healthy subject group. The expression of 555 probes was observed to be attenuated regardless of multiplying factor, and the expression of 313 probes was observed to be enhanced regardless of multiplying factor, in the digestive organ cancer case group, compared with normal healthy subjects. Also, the expression of 6 probes was observed to be attenuated at levels 0.4 times or less that of the normal healthy subject group and the expression of 15 probes was observed to be enhanced at levels 2.5 times or more that of the normal healthy subject group.

Hierarchical clustering with 868 probes corresponding to genes with expression levels that were observed to be attenuated or enhanced in digestive organ cancer cases compared with normal healthy subjects:

Hierarchical clustering was performed for subject cancer cases and normal healthy subjects using a total of 868 probes including the above 555 probes and 313 probes. As shown in FIG. 10, 3 clusters were formed. In the $1^{st}$ cluster, 14 out of 14 cases (100%) were digestive organ cancer cases. In the $2^{nd}$ cluster, 8 out of 8 cases (100%) were digestive organ cancer cases. In the $3^{rd}$ cluster, 8 out of 10 cases (80%) were normal healthy subject cases. Thus, digestive organ cancer cases and normal healthy subjects were separately clustered.

Predictive determination using 868 probes corresponding to genes with expression levels that were observed to be attenuated or enhanced in digestive organ cancer cases compared with normal healthy subjects:

Similarly with the use of a GeneSpring GX Class Prediction tool, a prediction model was prepared based on 868 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 39 out of 40 separately analyzed cancer cases were determined with the prediction model to be cancer cases and the probability that such cases had been properly diagnosed was 97.5%. Also, 9 out of 13 normal healthy subject cases were determined with prediction model to be normal healthy subjects, and the probability that such cases had been properly diagnosed was 69.2%. Altogether, 48 out of 53 such cases were correct answers. Thus, the percentage of cases determined correctly was 90.6% (48/53).

Hierarchical clustering with 21 probes corresponding to genes with expression levels that were observed to be attenuated at levels 0.4 times or less the normal healthy subject group or enhanced at levels 2.5 times or more the normal healthy subject group:

Hierarchical clustering was performed using a total of 21 probes including the above 6 probes and 15 probes for subject cancer cases and normal healthy subjects. As shown in FIG. 11, 3 clusters were formed. In the $1^{st}$ cluster, 17 out of 17 cases (100%) were digestive organ cancer cases. In the $2^{nd}$ cluster, 7 out of 9 cases (77.8%) were digestive organ cancer cases. In the $3^{rd}$ cluster, 6 out of 6 cases (100%) were normal healthy subject cases. Thus, digestive organ cancer cases and normal healthy subjects were separately clustered.

Predictive determination using 21 probes corresponding to genes with expression levels that were observed to be attenuated at levels 0.4 times or less the normal healthy subject group or enhanced at levels 2.5 times or more the normal healthy subject group:

Similarly, with the use of a GeneSpring GX Class Prediction tool, a prediction model was prepared based on 21 probes observed to exhibit differences in expression, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 37 out of 40 separately analyzed cancer cases were determined with the prediction model to be cancer cases and the probability that such cases had been properly diagnosed was 92.5%. Also, 12 out of 13 normal healthy subjects were determined with the prediction model to be normal healthy subjects, and the probability that such cases had been properly diagnosed was 92.3%. Altogether, 49 out of 53 such cases were correct answers. Thus, the percentage of cases determined correctly was 92.5% (49/53).

1-2. Detection of Digestive Organ Cancer (2)

In a manner similar to that in the above detection of digestive organ cancer (1), 39 cancer cases and 15 normal healthy subject cases were examined using a GeneSpring GX hierarchical clustering tool and 23278 probes that had passed a quality check. As shown in FIG. 22, 5 clusters were formed. In the $1^{st}$ cluster, 5 out of 5 cases (100%) were digestive organ cancer cases. In the $2^{nd}$ cluster, 29 out of 30 cases (96.7%) were digestive organ cancer cases. In the 3rd cluster, 1 out of 1 case (100%) and in the $4^{th}$ cluster, 6 out of 10 cases (60%) were digestive organ cancer cases. In the $5^{th}$ cluster, 8 out of 8 cases (100%) were normal healthy subject cases. Thus, the digestive organ cancer cases and the normal healthy subjects were separately clustered.

Furthermore, in a manner similar to that in the above detection of digestive organ cancer (1), probes capable of discriminating between a group of 39 digestive organ cancer cases and a group of 15 normal healthy subject cases were examined using a GeneSpring GX Statistic Analysis tool. Probes were extracted using Benjamini and Hochberg False Discovery Rate as a multiple test and $p<0.000005$. The normalized numerical values of fluorescence intensities of the thus extracted probes were compared between the group of digestive organ cancer cases and the group of normal healthy subjects using a Fold Change tool. Thus, the expression of 14 probes was observed to be attenuated at levels 0.33 times or less that of the normal healthy subject group and the expression of 11 probes was observed to be enhanced at levels 3 times or more that of the normal healthy subject group (FIG. 21, SEQ ID NOs: 3030-3054).

Hierarchical clustering with 25 probes corresponding to genes with expression levels that were observed to be attenuated or enhanced in digestive organ cancer cases compared with normal healthy subjects:

Hierarchical clustering was performed using a total of 25 probes including the above 14 probes and 11 probes for subject cancer cases and normal healthy subjects. As shown in FIG. 23, 3 clusters were formed. In the $1^{st}$ cluster, 31 out of 31 cases (100%) were digestive organ cancer cases. In the $2^{nd}$ cluster, 6 out of 6 cases (100%) were digestive organ cancer cases. In the $3^{rd}$ cluster, 15 out of cases (88.2%) were normal healthy subject cases. Thus, the digestive organ cancer cases and the normal healthy subjects were separately clustered.

Predictive determination using 25 probes corresponding to genes with expression levels that were observed to be attenuated or enhanced in digestive organ cancer cases compared with normal healthy subjects:

Similarly, with the use of a GeneSpring GX Class Prediction tool, a prediction model was prepared based on 25 probes observed to exhibit differences in expression, using Support Vector Machines. The prediction model was applied to cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 37 out of 37 separately analyzed cancer cases were determined with the prediction model to be cancer cases and the probability that such cases had been properly diagnosed was 100%. Also, 11 out of 15 normal healthy subjects were determined with the prediction model to be normal healthy subjects, and the probability that such cases had been properly diagnosed was 73.3%. Altogether, 48 out of 52 such cases were correct answers. Thus, the percentage of cases determined correctly was 92.3% (48/52).

2. Detection of Gastric Cancer

Hierarchical Clustering:

Hierarchical clustering was performed using a GeneSpring GX hierarchical clustering tool and 22155 probes that had passed a quality check. As shown in FIG. 12, 4 clusters were formed. In the 1st cluster, 6 out of 6 cases (100%) were gastric cancer cases. In the $2^{nd}$ cluster, 3 out of 4 cases (75%) were normal healthy subject cases. In the $3^{rd}$ cluster, 3 out of 4 cases (75%) and in the $4^{th}$ cluster, 2 out of 2 cases (100%) were normal healthy subject cases. Hence, gastric cancer cases and normal healthy subjects were separately clustered.

Genes with expression levels that were observed to differ between a gastric cancer case group and a normal healthy subject group:

Similarly, with the use of a GeneSpring GX Statistic Analysis tool, probes capable of discriminating between a gastric cancer case group and a normal healthy subject group were examined using the Benjamini and Hochberg false discovery rate for a multiple test and $p<0.05$. As a result, the expression of 3453 probes was observed to differ between the two groups.

Also, normalized numerical values for fluorescence intensities of the 3453 probes were compared using a Fold Change tool between the gastric cancer case group and the normal healthy subject group. The expression of 84 probes was observed to be attenuated in the gastric cancer case group at levels 0.5 times or less that of the normal healthy subject group and the expression of 629 probes was observed to be enhanced in the gastric cancer case group at levels 2 times or more that of the normal healthy subject group. Also, the expression of 6 probes was observed to be attenuated in the gastric cancer case group at levels 0.33 times or less that of the normal healthy subject group and the expression of 101 probes was observed to be enhanced in the gastric cancer case group at levels 3 times or more that of the normal healthy subject group.

Hierarchical clustering with 713 probes corresponding to genes with expression levels that were observed to be attenuated at levels 0.5 times or less or enhanced at levels 2 times or more that of the normal healthy subject group:

Hierarchical clustering was performed for subject cancer cases and normal healthy subjects using a total of 713 probes including the above 84 probes and 629 probes. As shown in FIG. 13, 2 clusters were formed, in which a cluster of cancer cases accounting for 100% and a cluster of normal healthy subject cases accounting for 100%.

Predictive determination using 713 probes corresponding to genes with expression levels that were observed to be attenuated at levels 0.5 times or less or enhanced at levels 2 times or more that of the normal healthy subject group:

Similarly with the use of a GeneSpring GX Class Prediction tool, a prediction model was prepared based on 713 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 7 out of 10 separately analyzed cancer cases were determined with the prediction model to be cancer cases and the probability that such cases had been properly diagnosed was 70%. Also, 13 out of 13 normal healthy subject cases were determined with prediction model to be normal healthy subject cases, and the probability that such cases had been properly diagnosed was 100%. Altogether, 20 out of 23 such cases were correct answers. Thus, the percentage of cases determined correctly was 87.0% (20/23).

Hierarchical clustering with 107 probes corresponding to genes with expression levels that were observed to be attenuated at levels 0.33 times or less or enhanced at levels 3 times or more that of the normal healthy subject group:

Hierarchical clustering was performed for subject cancer cases and normal healthy subjects using a total of 107 probes including the above 6 probes and 101 probes. As shown in FIG. 14, 2 clusters were formed, in which a cluster of cancer cases accounting for 100% and a cluster of normal healthy subject cases accounting for 100%.

Predictive determination using 107 probes corresponding to genes with expression levels that were observed to be attenuated at levels 0.33 times or less or enhanced at levels 3 times or more that of the normal healthy subject group:

Similarly with the use of a GeneSpring GX Class Prediction tool, a prediction model was prepared based on 107 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 8 out of 10 separately analyzed cancer cases were determined with the prediction model to be cancer cases and the probability that such cases had been properly diagnosed was 80%. Also, 13 out of 13 normal healthy subject cases were determined with prediction model to be normal healthy subject cases, and the probability that such cases had been properly diagnosed was 100%. Altogether, 21 out of 23 such cases were correct answers. Thus, the percentage of cases determined correctly was 91.3% (21/23).

3. Detection of Colorectal Cancer

Hierarchical Clustering:

Hierarchical clustering was performed using a GeneSpring GX hierarchical clustering tool and 22181 probes that had passed a quality check. As shown in FIG. 15, 3 clusters were formed. In the 1st cluster, 4 out of 5 cases (80%) were colorectal cancer cases. In the $2^{nd}$ cluster, 6 out of 7 cases (85.7%) were normal healthy subject cases. In the $3^{rd}$ cluster, 3 out of 4 cases (75%) were colorectal cancer cases. Hence, colorectal cancer cases and normal healthy subjects were separately clustered.

Also, normalized numerical values for fluorescence intensities of the 5267 probes were compared using a Fold Change tool between the colorectal cancer case group and the normal healthy subject group. The expression of 125 probes was observed to be attenuated in the large bowel case group at levels 0.5 times or less that of the normal healthy subject group and the expression of 646 probes was observed to be enhanced in the colorectal cancer case group at levels 2 times or more that of the normal healthy subject group. Also, the expression of 9 probes was observed to be attenuated in the colorectal cancer case group at levels 0.33 times or less that of the normal healthy subject group and the expression of 107 probes was observed to be enhanced in the colorectal cancer case group at levels 3 times or more that of the normal healthy subject group.

Hierarchical clustering with 771 probes corresponding to genes with expression levels that were observed to be attenuated at levels 0.5 times or less or enhanced at levels 2 times or more that of the normal healthy subject group:

Hierarchical clustering was performed for subject cancer cases and normal healthy subjects using a total of 771 probes including the above 125 probes and 646 probes. As shown in FIG. 16, 3 clusters were formed. In the $1^{st}$ cluster, 5 out of 5 cases (100%) were colorectal cancer cases. In the $2^{nd}$ cluster, 3 out of 5 cases (60.0%) were colorectal cancer cases. In the $3^{rd}$ cluster, 7 out of 7 cases (100%) were normal healthy subject cases.

Predictive determination using 771 probes corresponding to genes with expression levels that were observed to be attenuated at levels 0.5 times or less or enhanced at levels 2 times or more that of the normal healthy subject group:

Similarly with the use of a GeneSpring GX Class Prediction tool, a prediction model was prepared based on 771 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 9 out of 10 separately analyzed cancer cases were determined with the prediction model to be cancer cases and the probability that such cases had been properly diagnosed was 90%. Also, 13 out of 13 normal healthy subject cases were determined with prediction model to be normal healthy subject cases, and the probability that such cases had been properly diagnosed was 100%. Altogether, 22 out of 23 such cases were correct answers. Thus, the percentage of cases determined correctly was 95.7% (22/23).

Hierarchical clustering with 116 probes corresponding to genes with expression levels that were observed to be attenuated at levels 0.33 times or less or enhanced at levels 3 times or more that of the normal healthy subject group:

Hierarchical clustering was performed using a total of 116 probes including the above 9 probes and 107 probes for subject cancer cases and normal healthy subjects. As shown in FIG. 17, 3 clusters were formed. In the $1^{st}$ cluster, 5 out of 5 cases (100%) were colorectal cancer cases. In the $2^{nd}$ cluster, 3 out of 6 cases (50.0%) were colorectal cancer cases. In the $3^{rd}$ cluster, 5 out of 5 cases (100%) were normal healthy subject cases.

Predictive determination using 116 probes corresponding to genes with expression levels that were observed to be attenuated at levels 0.33 times or less or enhanced at levels 3 times or more that of the normal healthy subject group:

Similarly with the use of a GeneSpring GX Class Prediction tool, a prediction model was prepared based on 116 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 9 out of 10 separately analyzed cancer cases were determined with the prediction model to be cancer cases and the probability that such cases had been properly diagnosed was 90%. Also, 13 out of 13 normal healthy subject cases were determined with prediction model to be normal healthy subject cases, and the probability that such cases had been properly diagnosed was 100%. Altogether, 22 out of 23 such cases were correct answers. Thus, the percentage of cases determined correctly was 95.7% (22/23).

4. Detection of Pancreatic Cancer
Hierarchical Clustering:

Hierarchical clustering was performed using a GeneSpring GX hierarchical clustering tool and 22149 probes that had passed a quality check. As shown in FIG. 18, 3 clusters were formed. In the 1st cluster, 7 out of 7 cases (100%) were normal healthy subject cases. In the $2^{nd}$ cluster, 4 out of 5 cases (80%) were pancreatic cancer cases. In the $3^{rd}$ cluster, 4 out of 4 cases (100%) were pancreatic cancer cases. Hence, pancreatic cancer cases and normal healthy subjects were separately clustered.

Genes with expression levels that were observed to differ between a pancreatic cancer case group and a normal healthy subject group:

Similarly, with the use of a GeneSpring GX Statistic Analysis tool, probes capable of discriminating between a pancreatic cancer case group and a normal healthy subject group were examined using the Benjamini and Hochberg false discovery rate for a multiple test and p<0.05. As a result, the expression of 3301 probes was observed to differ between the two groups.

Also, normalized numerical values for fluorescence intensities of the 3301 probes were compared using a Fold Change tool between the pancreatic cancer case group and the normal healthy subject group. The expression of 96 probes was observed to be attenuated in the pancreatic cancer case group at levels 0.5 times or less that of the normal healthy subject group and the expression of 581 probes was observed to be enhanced in the pancreatic cancer case group at levels 2 times or more that of the normal healthy subject group. Also, the expression of 6 probes was observed to be attenuated in the pancreatic cancer case group at levels 0.33 times or less that of the normal healthy subject group and the expression of 55 probes was observed to be enhanced in the pancreatic cancer case group at levels 3 times or more that of the normal healthy subject group.

Hierarchical clustering with 677 probes corresponding to genes with expression levels that were observed to be attenuated at levels 0.5 times or less or enhanced at levels 2 times or more that of the normal healthy subject group:

Hierarchical clustering was performed for subject cancer cases and normal healthy subjects using a total of 677 probes including the above 96 probes and 581 probes. As shown in FIG. 19, 2 clusters were formed. In the $1^{st}$ cluster, 8 out of 9 cases (88.9%) were normal healthy subject cases. In the $2^{nd}$ cluster, 7 out of 7 cases (100%) were pancreatic cancer cases.

Predictive determination using 677 probes corresponding to genes with expression levels that were observed to be attenuated at levels 0.5 times or less or enhanced at levels 2 times or more that of the normal healthy subjects:

Similarly with the use of a GeneSpring GX Class Prediction tool, a prediction model was prepared based on 677 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 15 out of 20 separately analyzed cancer cases were determined with the prediction model to be pancreatic cancer cases and the probability that such cases had been properly diagnosed was 75%. Also, 13 out of 13 normal healthy subject cases were determined with prediction model to be normal healthy subject cases, and the probability that such cases had been properly diagnosed was 100%. Altogether, 28 out of 33 such cases were correct answers. Thus, the percentage of cases determined correctly was 84.8% (28/33).

Hierarchical clustering with 61 probes corresponding to genes with expression levels that were observed to be attenuated at levels 0.33 times or less or enhanced at levels 3 times or more that of the normal healthy subject group:

Hierarchical clustering was performed for subject cancer cases and normal healthy subjects using a total of 61 probes including the above 6 probes and 55 probes. As shown in FIG. 20, 2 clusters were formed. In the $1^{st}$ cluster, 8 out of 9 cases (88.9%) were normal healthy subject cases. In the $2^{nd}$ cluster, 7 out of 7 cases (100%) were pancreatic cancer cases.

Predictive determination using 61 probes corresponding to genes with expression levels that were observed to be attenuated at levels 0.33 times or less or enhanced at levels 3 times or more that of the normal healthy subjects:

Similarly with the use of a GeneSpring GX Class Prediction tool, a prediction model was prepared based on 61 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 15 out of 20 separately analyzed cancer cases were determined with the prediction model to be pancreatic cancer cases and the probability that such cases had been properly diagnosed was 75%. Also, 9 out of 13 normal healthy subject cases were determined with prediction model to be normal healthy subject cases, and the probability that such cases had been properly diagnosed was 69.2%. Altogether, 24 out of 33 such cases were correct answers. Thus, the percentage of cases determined correctly was 72.7% (24/33).

5. Detection of Biliary Tract Cancer
Hierarchical Clustering

Hierarchical clustering was performed using a GeneSpring GX hierarchical clustering tool and 22066 probes that had passed a quality check. As shown in FIG. 25, 3 clusters were formed. In the 1st cluster, 7 out of 7 cases (100%) were normal healthy subject cases. In the $2^{nd}$ cluster, 3 out of 3 cases (100%) were biliary tract cancer cases. In the $3^{rd}$ cluster, 5 out of 6 cases (83.3%) were biliary tract cancer cases. Hence, biliary tract cancer cases and normal healthy subjects were separately clustered.

Genes with expression levels that were observed to differ between a biliary tract cancer case group and a normal healthy subject group:

Similarly, with the use of a GeneSpring GX Statistic Analysis tool, probes capable of discriminating between a biliary tract cancer case group and a normal healthy subject group were examined using the Benjamini and Hochberg false discovery rate for a multiple test and p<0.05. As a result, the expression of 8090 probes was observed to differ between the two groups.

Also, normalized numerical values for fluorescence intensities of the 8090 probes were compared using a Fold Change tool between the biliary tract cancer case group and the normal healthy subject group. The expression of 98 probes was observed to be attenuated in the biliary tract cancer case group at levels 0.33 times or less that of the normal healthy subject group and the expression of 265 probes was observed to be enhanced in the biliary tract cancer case group at levels 3 times or more that of the normal healthy subject group.

Hierarchical clustering with 363 probes corresponding to genes with expression levels that were observed to be attenuated at levels 0.33 times or less or enhanced at levels 3 times or more that of the normal healthy subject group:

Hierarchical clustering was performed for subject cancer cases and normal healthy subjects using a total of 363 probes including the above 98 probes and 265 probes. As shown in FIG. 26, 2 clusters were formed. In the $1^{st}$ cluster, 7 out of 7 cases (100%) were normal healthy subject cases. In the $2^{nd}$ cluster, 8 out of 9 cases (88.9%) were biliary tract cancer cases.

Predictive determination using 363 probes corresponding to genes with expression levels that were observed to be attenuated at levels 0.33 times or less or enhanced at levels 3 times or more that of the normal healthy subjects:

Similarly with the use of a GeneSpring GX Class Prediction tool, a prediction model was prepared based on 363 probes with expression levels that were observed to differ, using Support Vector Machines. The prediction model was applied to a cancer case group and a normal healthy subject group (separate from the cancer case group and the normal healthy subject group used for probe extraction and preparation of the prediction model) for which image analysis and data analysis had been performed for DNA microarrays by similar procedures. Thus, the probability of determining cancer cases to be cancer cases and the probability of determining normal healthy subjects to be normal healthy subjects were found. As a result, 8 out of 8 separately analyzed cancer cases were determined with the prediction model to be cancer cases and the probability that such cases had been properly diagnosed was 100%. Also, 13 out of 13 normal healthy subject cases were determined with prediction model to be normal healthy subject cases, and the probability that such cases had been properly diagnosed was 100%. Altogether, 21 out of 21 such cases were correct answers. Thus, the percentage of cases determined correctly was 100% (21/21).

All publications, patents, and patent applications cited in this description are herein incorporated by reference in their entirety

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09512491B2). An electronic copy of the "Sequence Listing" will also be available from the USPTO upon request and payment of the fee set forth in 37 CFR 1.19(b)(3).

The invention claimed is:

1. A reagent consisting of:
a set of probes bound to a solid support
wherein the set of probes consists of SEQ ID NOs: 3055 to 3417.

2. The reagent of claim 1, wherein the reagent is a DNA microarray.

3. A method for detecting biliary tract cancer, in a subject, comprising
(i) measuring the expression of genes of the subject using the reagent of claim 1, to obtain an expression profile;
(ii) determining a difference in expression profiles between the subject and a normal subject;
(iii) detecting biliary tract cancer based on the difference in expression profiles between the subject and the normal subject; and
(iv) identifying that the subject has biliary tract cancer.

4. The method of claim 3, wherein the measuring step is conducted by contacting nucleic acid molecules extracted from a blood or tissue sample obtained from the subject, with the reagent, under conditions suitable for hybridizing the nucleic acid molecules of the subject, under stringent conditions, to the probes of the reagent.

5. The method of claim 3, wherein the genes of the subject are mRNA molecules extracted from peripheral blood obtained from the subject.

* * * * *